(12) United States Patent
Imaeda et al.

(10) Patent No.: US 8,329,691 B2
(45) Date of Patent: Dec. 11, 2012

(54) AMIDE COMPOUNDS AND USE OF THE SAME

(75) Inventors: Yasuhiro Imaeda, Ann Arbor, MI (US); Takanobu Kuroita, Osaka (JP); Yoshiyuki Fukase, Osaka (JP); Shinkichi Suzuki, Osaka (JP); Michiko Tawada, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 30 days.

(21) Appl. No.: 12/734,150

(22) PCT Filed: Oct. 14, 2008

(86) PCT No.: PCT/JP2008/068595
§ 371 (c)(1),
(2), (4) Date: Apr. 14, 2010

(87) PCT Pub. No.: WO2009/051112
PCT Pub. Date: Apr. 23, 2009

(65) Prior Publication Data
US 2010/0324010 A1   Dec. 23, 2010

(30) Foreign Application Priority Data
Oct. 15, 2007   (JP) ................ 2007-268100

(51) Int. Cl.
*A61K 31/5377* (2006.01)
*A61K 31/506* (2006.01)
*C07D 413/14* (2006.01)
*C07D 239/20* (2006.01)

(52) U.S. Cl. ............... 514/235.8; 514/256; 544/122; 544/242

(58) Field of Classification Search ............. 544/122, 544/242; 514/235.8, 256
See application file for complete search history.

(56) References Cited

U.S. PATENT DOCUMENTS

| | | | |
|---|---|---|---|
| 4,734,418 A * | 3/1988 | Yokoyama et al. ...... | 514/252.16 |
| 5,225,402 A | 7/1993 | Ogawa et al. | |
| 5,250,548 A | 10/1993 | Winn et al. | |
| 5,436,254 A | 7/1995 | Ogawa et al. | |
| 5,652,247 A | 7/1997 | Ogawa et al. | |
| 7,919,511 B2 | 4/2011 | Lu et al. | |
| 7,932,270 B2 | 4/2011 | Lu et al. | |
| 7,939,534 B2 | 5/2011 | Lu et al. | |
| 7,939,548 B2 * | 5/2011 | Lu et al. ............ | 514/334 |
| 2003/0032647 A1 | 2/2003 | Yamada et al. | |
| 2003/0229089 A1 | 12/2003 | Yamada et al. | |
| 2003/0229095 A1 | 12/2003 | Yamada et al. | |
| 2004/0142930 A1 | 7/2004 | Yamada et al. | |
| 2006/0089350 A1 | 4/2006 | Hochman et al. | |
| 2008/0027037 A1 | 1/2008 | Yamada et al. | |
| 2008/0132545 A1 | 6/2008 | Lu et al. | |
| 2008/0139575 A1 | 6/2008 | Lu et al. | |
| 2008/0146619 A1 | 6/2008 | Lu et al. | |
| 2009/0012126 A1 | 1/2009 | Lu et al. | |
| 2009/0156612 A1 | 6/2009 | Kuroita et al. | |
| 2009/0227560 A1 | 9/2009 | Kuroita et al. | |

FOREIGN PATENT DOCUMENTS

| | | |
|---|---|---|
| EP | 0 188 094 | 7/1986 |
| EP | 0 711 757 | 5/1996 |
| EP | 1 277 741 | 1/2003 |
| EP | 2 119 702 | 11/2009 |
| JP | 61-140568 | 6/1986 |
| JP | 3-173870 | 7/1991 |
| JP | 2002-12587 | 1/2002 |
| WO | 01/83460 | 11/2001 |
| WO | 02/20489 | 3/2002 |
| WO | 2004/054974 | 7/2004 |
| WO | 2004/080463 | 9/2004 |
| WO | 2005/023260 | 3/2005 |
| WO | 2006/018284 | 2/2006 |
| WO | 2007/006534 | 1/2007 |
| WO | 2007/047447 | 4/2007 |
| WO | 2007/077005 | 7/2007 |
| WO | 2007/094513 | 8/2007 |
| WO | 2007/118854 | 10/2007 |
| WO | 2008/016643 | 2/2008 |
| WO | 2008/053194 | 5/2008 |
| WO | 2008/093737 | 8/2008 |
| WO | 2008/123469 | 10/2008 |
| WO | 2008/139941 | 11/2008 |

(Continued)

OTHER PUBLICATIONS

CAplus Registry Data, RN 1005754-45-9, STN accessed Feb. 3, 2012.*

(Continued)

*Primary Examiner* — Joseph K. McKane
*Assistant Examiner* — Samantha Shterengarts
(74) *Attorney, Agent, or Firm* — Wenderoth, Lind & Ponack, L.L.P.

(57) ABSTRACT

A renin inhibitor comprising a compound represented by the formua:

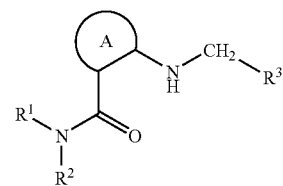

wherein each symbol is as defined in the description, or a salt thereof or a prodrug thereof. The compound of the present invention has a superior renin inhibitory activity, and thus is useful as an agent for the prophylaxis or treatment of hypertension, various organ damages attributable to hypertension and the like.

12 Claims, No Drawings

FOREIGN PATENT DOCUMENTS

| WO | 2009/001915 | 12/2008 |
| WO | 2009/154300 | 12/2009 |

OTHER PUBLICATIONS

Supplementary European Search Report issued May 27, 2011 in European Application No. 08839108.1.

International Search Report issued Dec. 16, 2008 in International (PCT) Application No. PCT/JP2008/068595.

J. R. Proudfoot et al., "Novel Non-Nucleoside Inhibitors of HIV-1 Reverse Transcriptase. 3. Dipyrido[2,3-*b*:2',3'-e]diazepinones", Journal of Medicinal Chemistry, vol. 38, No. 8, pp. 1406-1410, 1995.

* cited by examiner

AMIDE COMPOUNDS AND USE OF THE SAME

This application is a U.S. national stage of International Application No. PCT/JP2008/068595 filed Oct. 14, 2008.

TECHNICAL FIELD

The present invention relates to an amide compound and the like, which has a superior renin inhibitory activity and is useful as an agent for the prophylaxis or treatment of hypertension, various organ damages attributable to hypertension, and the like.

BACKGROUND OF THE INVENTION

Hypertension is one of representative lifestyle-related diseases. Hypertension which is left untreated for long time lays a heavy burden on the cardiovascular system and results in arteriosclerosis to progress, thus causing various disorders in important organs, such as cerebral hemorrhage, cerebral infarction, cardiac failure, angina pectoris, myocardial infarction, renal failure and the like. Accordingly, the purpose of treating hypertension lies not only in lowering the blood pressure, but also in improving and/or preventing disorders in important organs including brain, heart and kidney, by controlling the blood pressure. As a method of treating hypertension, there are available fundamental treatments based on improvement in the lifestyle, such as dietetic therapy, exercise therapy and the like, as well as an attempt to control the blood pressure by positive pharmaceutical intervention.

The renin-angiotensin (RA) system is a system of biosynthesis of angiotensin II (AII), which is a major vasopressor factor, and takes an important role in the control of the blood pressure and the amount of body fluid. AII exhibits a strong vasoconstrictive effect brought by the intervention of AII receptors on the cellular membrane, thus raising the blood pressure, and also promotes cellular propagation or production of extracellular matrix by directly acting on the AII receptors in the cardiac cells or renal cells. Therefore, drugs inhibiting increase in the activity of the RA system can be expected to have a blood pressure lowering action as well as a powerful organ protecting action, and thus active researches on such drugs have been conducted so far.

The method of inhibiting the AII action is broadly classified into methods of inhibiting the biosynthesis of AII and methods of inhibiting the binding of AII to AII receptors. For the drugs inhibiting the biosynthesis of AII, angiotensin converting enzyme (ACE) inhibitory drugs have been already put to practical use and are being confirmed to have a blood pressure lowering action as well as an effect for protecting various organs. However, since ACE is an enzyme identical to kininase II, which is a bradykinin degrading enzyme, ACE inhibitory drug inhibits the biosynthesis of AII as well as the degradation of bradykinin. As a result, ACE inhibitory drugs are believed to induce side effects such as dry cough, angioedema and the like, which are considered to be caused by accumulation of bradykinin.

As the drugs inhibiting the binding of AII to AII receptors, AII type 1 receptor blockers (ARB) have been developed. ARB has a merit in that it can inhibit, at the receptor level, the action of AII that is biosynthesized by not only ACE but also an enzyme other than ACE, such as chymase and the like. It is known that administration of ACE inhibitors and ARB increases the plasma renin activity (PRA) as a compensatory feedback effect, since these drugs act on a more peripheral region of the RA system.

Renin is an enzyme occupying a position at the uppermost stream of the RA system, and converts angiotensinogen to angiotensin I. A renin inhibitory drug inhibits the RA system by inhibiting the biosynthesis of AII in the same manner as the ACE inhibitory drugs do, and thus can be expected to have a blood pressure lowering action or an effect of protecting various organs. Since the renin inhibitory drug does not have influence on the metabolism of bradykinin, it is believed to have no risk of side effects such as dry cough and the like, that are observed with the ACE inhibitory drugs. Furthermore, while the ACE inhibitory drugs or ARB increase the PRA level, the renin inhibitory drugs are the only drugs that can reduce PRA.

As renin inhibitors, orally Administrable Aliskiren has been reported (Chem. Biol., 2000, vol. 7, pages 493-504; Hypertension, 2003, vol. 42, pages 1137-1143; J. Hypertens., 2005, vol. 23, pages 417-426 etc.).

Besides the above, the following compounds have been reported as renin inhibitors.

(1) A compound represented by the formula

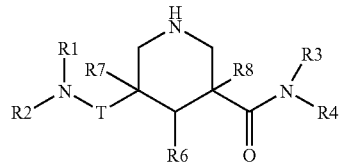

wherein R1 is hydrogen, unsubstituted or substituted alkyl, unsubstituted or substituted alkenyl, unsubstituted or substituted alkynyl, unsubstituted or substituted aryl, unsubstituted or substituted heterocyclyl, or unsubstituted or substituted cycloalkyl;

R2 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;

R3 is hydrogen, unsubstituted or substituted aryl, or unsubstituted or substituted alkyl;

R4 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl; or R3 and R4 may form together a 3- to 7-membered nitrogen containing saturated hydrocarbon ring which can be unsubstituted or substituted;

R6 is hydrogen, halo, unsubstituted alkyl or unsubstituted alkoxy;

R7 and R8 are independently of each other hydrogen or halo; and

T is methylene or carbonyl, or a salt thereof (see WO2007/077005).

(2) A compound represented by the formula

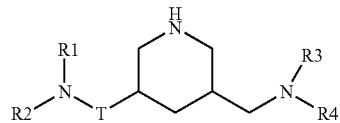

wherein R1 is hydrogen, unsubstituted or substituted alkyl, unsubstituted or substituted alkenyl, unsubstituted or substituted alkynyl, unsubstituted or substituted aryl, unsubstituted or substituted heterocyclyl, or unsubstituted or substituted cycloalkyl;

R2 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;

R3 is hydrogen, unsubstituted or substituted aryl, or unsubstituted or substituted alkyl;

R4 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl; or $R^3$ and $R^4$ may form together a 3- to 7-membered nitrogen containing saturated hydrocarbon ring which can be unsubstituted or substituted; and T is methylene or carbonyl, or a salt thereof (see WO2007/006534).

(3) A compound represented by the formula

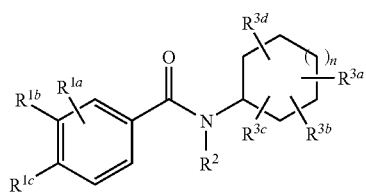

wherein $R^{1a}$ is a hydrogen atom, an optionally substituted $C_{1-6}$ alkyl group or the like; $R^{1b}$ is a substituted $C_{1-6}$ alkoxy group or the like; $R^{1b}$ is a hydrogen atom, an optionally substituted $C_{1-6}$ alkoxy group or the like; $R^2$ is a hydrogen atom, an optionally substituted $C_{1-6}$ alkyl group or the like; $R^{3a}$, $R^{3b}$, $R^{3c}$ and $R^{3d}$ are the same or different and each independently is a group: -A-B (wherein A is a single bond, —(CH$_2$)$_s$O—, —(CH$_2$)$_s$N(R$^4$)CO— etc., B is a hydrogen atom, an optionally substituted C$_{1-6}$ alkyl group etc.) or the like; $R^4$ is a hydrogen atom, an optionally substituted $C_{1-6}$ alkyl group or the like; s is 0 or the like; n is 1 or the like, or a pharmacologically acceptable salt, for example, a compound of the following formula (see WO2008/093737).

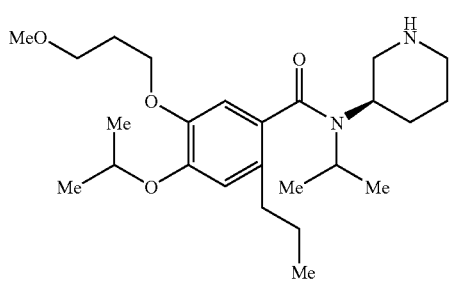

On the other hand, as an amide compound, the following compounds have been reported.

(4) In EP711757, for example, a compound having the following formula has been reported as an α1-adrenergic receptor antagonist:

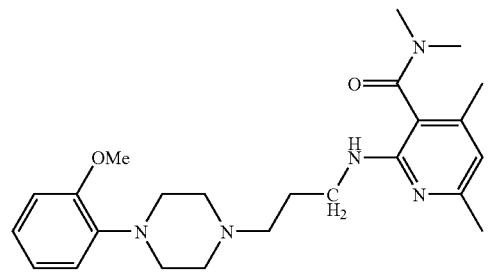

(5) In U.S. Pat. No. 5,250,548, for example, a compound having the following formula has been reported as an AII receptor antagonist:

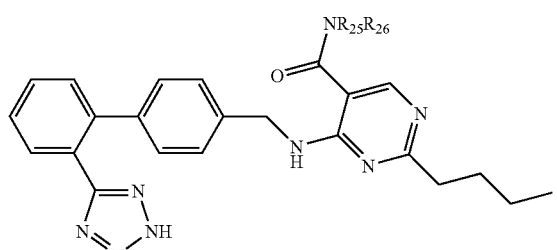

NR$_{25}$R$_{26}$: 1-morpholino (Ex. 24)
4-methoxymethoxy-1-piperidinyl (Ex. 25)
——N(CH$_3$)$_2$ (Ex. 26)

(6) In Journal of Medicinal Chemistry, 1995, vol. 38, pages 1406-1410, a compound having the following formula has been reported as an intermediate for an HIV-1 reverse transcriptase inhibitor:

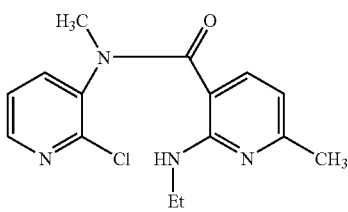

(7) In WO01/83460, for example, compounds having the following formulas have been reported as compounds having a cGMP-specific phosphodiesterase (PDE) inhibitory action (PDE V inhibitory action):

Ex. 461

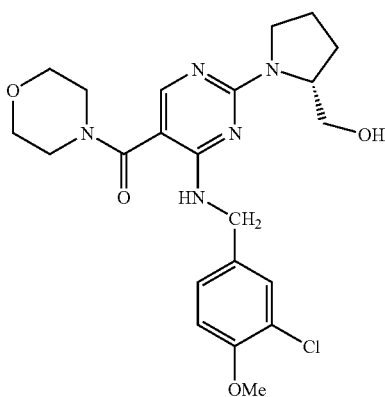

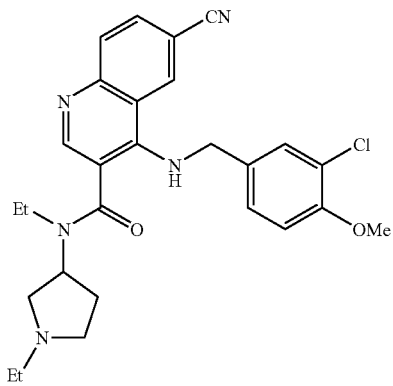

Ex. 474

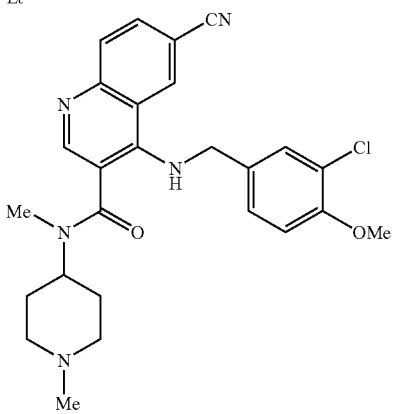

Ex. 475

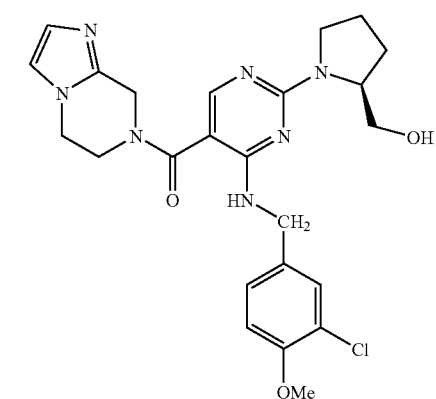

(8) In WO02/20489, for example, compounds having the following formulas have been reported as compounds having a PDE V inhibitory action:

However, these reports do not describe a renin inhibitory activity.

Other than the above, amide compounds having particular structures are disclosed as a cathepsin S inhibitor in WO2006/018284, as a kinase inhibitor in WO2004/080463, as a CNS disorder regulator in WO2007/047447, as a $Na^+$—$K^+$-$2Cl^-$ cotransporter antagonist in US2006/0089350, as a CCR5 antagonist in WO2004/054974, and as a glycine uptake inhibitor in WO2005/023260.

patent document 1: WO2007/077005
patent document 2: WO2007/006534
patent document 3: WO2008/093737
patent document 4: EP711757
patent document 5: U.S. Pat. No. 5,250,548
patent document 6: WO01/83460
patent document 7: WO02/20489
patent document 8: WO2006/018284
patent document 9: WO2004/080463
patent document 10: WO2007/047447
patent document 11: US2006/0089350
patent document 12: WO2004/054974
patent document 13: WO2005/023260
non-patent document 1: Journal of Medicinal Chemistry, 1995, vol. 38, pages 1406-1410

DISCLOSURE OF THE INVENTION

There is a demand on the development of a compound having a superior renin inhibitory activity, which is useful as a medicament (e.g., an agent for the prophylaxis or treatment of hypertension, various organ damages attributable to hypertension and the like, and the like), and a novel renin inhibitor.

The present inventors have conducted various studies and found that a compound represented by the following formula (I) and a salt thereof have a superior renin inhibitory activity and are useful as renin inhibitors, which resulted in the completion of the present invention. Of the compounds represented by the following formula (I) and salts thereof, compounds represented by the following formulas (A) and (B) and salts thereof are novel compounds.

The present invention relates to

[1] a renin inhibitor comprising a compound represented by the formula

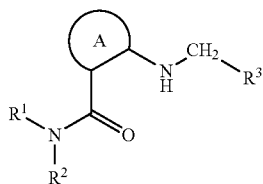

(I)

wherein $R^1$ and $R^2$ are each a hydrocarbon group optionally having substituent(s) or a heterocyclic group optionally having substituent(s), or $R^1$ and $R^2$ optionally form, together with the nitrogen atom bonded thereto, a nitrogen-containing heterocycle optionally having substituent(s), $R^3$ is a substituent, and ring A is a homocycle or heterocycle optionally having substituent(s), or a salt thereof [hereinafter sometimes to be abbreviated as compound (1)] or a prodrug thereof;

[2] a compound represented by the formula

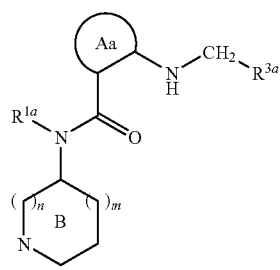

(A)

wherein $R^{1a}$ is alkyl optionally having substituent(s), $R^{3a}$ is a 5- or 6-membered aromatic group optionally having substituent(s), ring Aa is a homocycle or heterocycle optionally having substituent(s), ring B is a nitrogen-containing 5- to 7-membered ring optionally having substituent(s), and n and m are each an integer of 0 to 2, and the total of n and m is 1 to 3, or a salt thereof, excluding 4-[(3-chloro-4-methoxybenzyl)amino]-6-cyano-N-ethyl-N-(1-ethylpyrrolidin-3-yl)quinoline-3-carboxamide and 4-[(3-chloro-4-methoxybenzyl)amino]-6-cyano-N-methyl-N-(1-methylpiperidin-4-yl)quinoline-3-carboxamide [hereinafter sometimes to be abbreviated as compound (A)];

[3] the compound of the aforementioned [2], wherein $R^{1a}$ is $C_{1-6}$ alkyl;

[4] the compound of the aforementioned [2], wherein $R^{3a}$ is a 5-membered aromatic group optionally having substituent(s);

[5] the compound of the aforementioned [2], wherein ring Aa is a 5- or 6-membered aromatic heterocycle optionally having substituent(s);

[6] the compound of the aforementioned [2], wherein ring B is a ring represented by the formula

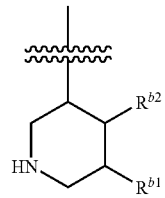

wherein $R^{b1}$ and $R^{b2}$ are each a hydrogen atom or a substituent, or $R^{b1}$ and $R^{b2}$ optionally form, together with the carbon atoms bonded thereto, a 5- to 7-membered ring optionally having substituent(s);

[7] the compound of the aforementioned [2], wherein $R^{1a}$ is $C_{1-6}$ alkyl, $R^{3a}$ is a 5-membered aromatic group optionally having substituent(s), ring Aa is a 5- or 6-membered aromatic heterocycle optionally having substituent(s), and ring B is a ring represented by the formula

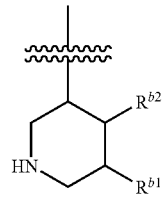

wherein $R^{b1}$ and $R^{b2}$ are each a hydrogen atom or a substituent, or $R^{b1}$ and $R^{b2}$ optionally form, together with the carbon atoms bonded thereto, a 5- to 7-membered ring optionally having substituent(s);

[8] a compound represented by the formula

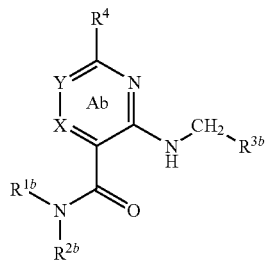

(B)

wherein $R^{1b}$ and $R^{2b}$ are each a hydrocarbon group optionally having substituent(s) or a heterocyclic group optionally having substituent(s), or $R^{1b}$ and $R^{2b}$ optionally form, together with the nitrogen atom bonded thereto, a nitrogen-containing heterocycle optionally having substituent(s), $R^{3b}$ is a substituent, excluding 2-(4-phenylpiperazin-1-yl)ethyl optionally having substituent(s) and biphenyl-4-yl having substituent(s), $R^4$ is a hydrocarbon group optionally having substituent(s), a heterocyclic group optionally having substituent(s), excluding a cyclic amino optionally having substituent(s), mercapto optionally having a substituent or acyl, X and Y are each C or N, and ring Ab is a nitrogen-containing 6-membered ring optionally having substituent(s) in addition to $R^4$, or a salt thereof, excluding N-(2-chloro-3-pyridinyl)-2-(ethylamino)-N,6-dimethyl-3-pyridinecarboxamide [hereinafter sometimes to be abbreviated as compound (B)];

[9] the compound of the aforementioned [8], wherein $R^{1b}$ and $R^{2b}$ are each a hydrocarbon group optionally having substituent(s) or pyrrolidinyl, imidazolidinyl, pyrazolidinyl, piperidinyl, piperazinyl, morpholinyl or thiomorpholinyl optionally having substituent(s);

[10] the compound of the aforementioned [8], wherein $R^{1b}$ and $R^{2b}$ form, together with the nitrogen atom bonded thereto, piperidine optionally having substituent(s) or piperazine optionally having substituent(s);

[11] the compound of the aforementioned [8], wherein $R^{3b}$ is (1) a 5- or 6-membered aromatic or nonaromatic heterocyclic group containing, as a ring-constituting atom besides carbon atom, 1 to 4 heteroatoms selected from an oxygen atom, a sulfur atom and a nitrogen atom, and optionally having 1 to 3 $C_{1-6}$ alkyl, (2) $C_{6-14}$ aryl, (3) $C_{3-10}$ cycloalkyl, (4) $C_{1-6}$ alkyl optionally having 1 to 3 $C_{1-6}$ alkoxy, or (5) $C_{1-6}$ alkoxy-carbonyl;

[12] the compound of the aforementioned [8], wherein $R^4$ is a hydrocarbon group optionally having substituent(s) or a heterocyclic group optionally having substituent(s), excluding a cyclic amino optionally having substituent(s);

[13] the compound of the aforementioned [8], wherein $R^4$ is a hydrocarbon group optionally having substituent(s);

[14] the compound of the aforementioned [8], wherein ring Ab is a ring represented by the formula

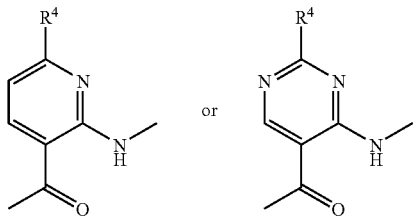

wherein $R^4$ is as defined in the aforementioned [8];

[15] the compound of the aforementioned [8], wherein $R^{1b}$ and $R^{2b}$ are each a hydrocarbon group optionally having substituent(s) or pyrrolidinyl, imidazolidinyl, pyrazolidinyl, piperidinyl, piperazinyl, morpholinyl or thiomorpholinyl optionally having substituent(s), $R^{3b}$ is (1) a 5- or 6-membered aromatic or nonaromatic heterocyclic group containing, as a ring-constituting atom besides carbon atom, 1 to 4 heteroatoms selected from an oxygen atom, a sulfur atom and a nitrogen atom, and optionally having 1 to 3 $C_{1-6}$ alkyl, (2) $C_{6-14}$ aryl, (3) $C_{3-10}$ cycloalkyl, (4) $C_{1-6}$ alkyl optionally having 1 to 3 $C_{1-6}$ alkoxy, or (5) $C_{1-6}$ alkoxy-carbonyl, $R^4$ is a hydrocarbon group optionally having substituent(s), and ring Ab is a ring represented by the formula

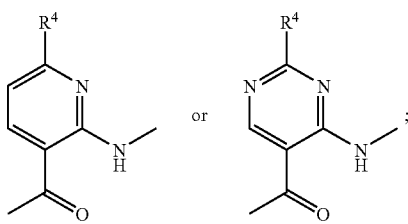

[16] 2-tert-butyl-N-[(3S,5R)-5-carbamoylpiperidin-3-yl]-4-[(furan-2-ylmethyl)amino]-N-(2-methylpropyl)pyrimidine-5-carboxamide or a salt thereof;

[17] 2-tert-butyl-4-[(3-methoxypropyl)amino]-N-(2-methylpropyl)-N-[(3S,5R)-5-(morpholin-4-ylcarbonyl)piperidin-3-yl]pyrimidine-5-carboxamide or a salt thereof;

[18] 2-tert-butyl-N-(2-methylpropyl)-N-[(3S,5R)-5-(morpholin-4-ylcarbonyl)piperidin-3-yl]-4-[(1,3-oxazol-2-ylmethyl)amino]pyrimidine-5-carboxamide or a salt thereof;

[19] a prodrug of the compound of the aforementioned [2] or [8];

[20] a medicament comprising the compound of the aforementioned [2] or [8] or a prodrug thereof;

[21] the medicament of the aforementioned [20], which is a renin inhibitor;

[22] the medicament of the aforementioned [20], which is an agent for the prophylaxis or treatment of hypertension; and

[23] the medicament of the aforementioned [20], which is an agent for the prophylaxis or treatment of various organ damages attributable to hypertension.

Furthermore, the present invention also relates to a compound represented by the formula (C)

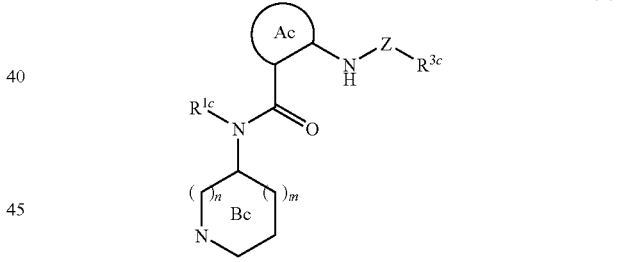

wherein $R^{1c}$ is alkyl optionally having substituent(s), $R^{3c}$ is a substituent, Z is $C_{2-6}$ alkylene optionally having substituent(s), $C_{2-6}$ alkenylene optionally having substituent(s) or $C_{2-6}$ alkynylene optionally having substituent(s), ring Ac is a homocycle or heterocycle optionally having substituent(s), ring Bc is a nitrogen-containing 5- to 7-membered ring optionally having substituent(s), and n and m are each an integer of 0 to 2, and the total of n and m is 1 to 3, or a salt thereof, excluding 4-{[(1R)-1-cyclohexylethyl]amino}-1-ethyl-N-methyl-N-(1-methylpiperidin-4-yl)-1H-pyrazolo[3,4-b]pyridine-5-carboxamide, 4-{[(1R)-1-cyclohexylethyl]amino}-N,1-diethyl-N-(1-ethylpyrrolidin-3-yl)-1H-pyrazolo[3,4-b]pyridine-5-carboxamide and N-(1-benzylpyrrolidin-3-yl)-4-{[(1R)-1-cyclohexylethyl]amino}-1-ethyl-N-methyl-1H-pyrazolo[3,4-b]pyridine-5-carboxamide [hereinafter sometimes to be abbreviated as compound (C)] and the like.

Compound (I), compound (A), compound (B) and compound (C) have a superior renin inhibitory activity, and thus they are useful as agents for the prophylaxis or treatment of hypertension, various organ damages attributable to hypertension, and the like.

Examples of the "halogen atom" in the present specification include fluorine, chlorine, bromine and iodine.

Examples of the "$C_{1-4}$ alkylenedioxy" in the present specification include methylenedioxy, ethylenedioxy, trimethylenedioxy and the like.

Examples of the "$C_{1-6}$ alkyl" in the present specification include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like.

Examples of the "$C_{1-6}$ alkoxy" in the present specification include methoxy, ethoxy, propoxy, isopropoxy, butoxy, isobutoxy, sec-butoxy, tert-butoxy and the like.

Examples of the "$C_{1-6}$ alkoxy-carbonyl" in the present specification include methoxycarbonyl, ethoxycarbonyl, propoxycarbonyl, tert-butoxycarbonyl and the like.

Examples of the "$C_{1-6}$ alkyl-carbonyl" in the present specification include acetyl, propanoyl, butanoyl, isobutanoyl, pentanoyl, isopentanoyl, hexanoyl and the like.

The "optionally halogenated" in the present specification means being optionally substituted by 1 to 5, preferably 1 to 3, halogen atoms.

Examples of the "hydrocarbon group" of the "hydrocarbon group optionally having substituent(s)" in the present specification include alkyl, alkenyl, alkynyl, alkylidene, cycloalkyl, cycloalkenyl, cycloalkadienyl, aryl, aralkyl, arylalkenyl, cycloalkylalkyl and the like. Preferred are $C_{1-10}$ alkyl, $C_{2-10}$ alkenyl, $C_{2-10}$ alkynyl, $C_{1-3}$ alkylidene, $C_{3-10}$ cycloalkyl, $C_{3-10}$ cycloalkenyl, $C_{4-10}$ cycloalkadienyl, $C_{6-14}$ aryl, $C_{7-16}$ aralkyl, $C_{8-13}$ arylalkenyl, $C_{3-10}$ cycloalkyl-$C_{1-6}$ alkyl and the like. The above-mentioned $C_{3-10}$ cycloalkyl, $C_{3-10}$ cycloalkenyl and $C_{4-10}$ cycloalkadienyl are each optionally condensed with a benzene ring.

Examples of the "$C_{1-10}$ alkyl" in the present specification include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like. Among these, $C_{1-6}$ alkyl is preferable.

Examples of the "$C_{2-10}$ alkenyl" in the present specification include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like. Among these, $C_{2-6}$ alkenyl is preferable.

Examples of the "$C_{2-10}$ alkynyl" in the present specification include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like. Among these, $C_{2-6}$ alkynyl is preferable.

Examples of the "$C_{1-3}$ alkylidene" in the present specification include methylene, ethylidene, propylidene, isopropylidene and the like.

Examples of the "$C_{3-10}$ cycloalkyl" in the present specification include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like. Among these, $C_{3-6}$ cycloalkyl is preferable. The above-mentioned $C_{3-10}$ cycloalkyl is optionally condensed with a benzene ring. Examples of the condensed group include indanyl, tetrahydronaphthyl, fluorenyl and the like.

Examples of the "$C_{3-10}$ cycloalkenyl" in the present specification include 2-cyclopenten-1-yl, 3-cyclopenten-1-yl, 2-cyclohexen-1-yl, 3-cyclohexen-1-yl and the like. The above-mentioned $C_{3-10}$ cycloalkenyl is optionally condensed with a benzene ring. Examples of the condensed group include indenyl and the like.

Examples of the "$C_{4-10}$ cycloalkadienyl" in the present specification include 2,4-cyclopentadien-1-yl, 2,4-cyclohexadien-1-yl, 2,5-cyclohexadien-1-yl and the like. The above-mentioned $C_{4-10}$ cycloalkadienyl is optionally condensed with a benzene ring.

Examples of the "$C_{6-14}$ aryl" in the present specification include phenyl, 1-naphthyl, 2-naphthyl, biphenylyl, 2-anthryl and the like. Among these, $C_{6-10}$ aryl is preferable, and phenyl is more preferable. The above-mentioned $C_{6-14}$ aryl is optionally condensed with $C_{3-10}$ cycloalkane (examples of the $C_{3-10}$ cycloalkane include rings corresponding to the above-mentioned $C_{3-10}$ cycloalkyl). Examples of the condensed group include tetrahydronaphthyl and the like.

Examples of the "$C_{7-16}$ aralkyl" in the present specification include benzyl, phenethyl, naphthylmethyl, biphenylylmethyl and the like.

Examples of the "$C_{8-13}$ arylalkenyl" in the present specification include styryl and the like.

Examples of the "$C_{3-10}$ cycloalkyl-$C_{1-6}$ alkyl" in the present specification include cyclopropylmethyl, cyclohexylmethyl and the like.

The "hydrocarbon group" of the "hydrocarbon group optionally having substituent(s)" optionally have substituent(s) (e.g., 1 to 5, preferably 1 to 3, substituents) at substitutable position(s). When the number of the substituents is two or more, respective substituents may be the same or different.

Examples of the "substituent" of the "hydrocarbon group optionally having substituent(s)" include the following substituents.

(1) halogen atom;
(2) nitro;
(3) cyano;
(4) hydroxy;
(5) $C_{1-6}$ alkoxy optionally having 1 to 3 halogen atoms;
(6) amino;
(7) mono- or di-$C_{1-6}$ alkylamino;
(8) $C_{7-16}$ aralkylamino;
(9) $C_{1-6}$ alkoxy-carbonylamino;
(10) $C_{7-16}$ aralkyloxy-carbonylamino;
(11) $C_{1-6}$ alkyl-carbonylamino;
(12) $C_{3-10}$ cycloalkyl-carbonylamino;
(13) $C_{1-6}$ alkylsulfonylamino;
(14) $C_{6-14}$ arylsulfonylamino;
(15) $C_{1-6}$ alkylaminocarbonylamino;
(16) $C_{6-14}$ arylaminocarbonylamino;
(17) $C_{1-6}$ alkyl-carbonyl;
(18) $C_{3-10}$ cycloalkyl-carbonyl;
(19) carboxy;
(20) $C_{1-6}$ alkoxy-carbonyl;
(21) carbamoyl;
(22) mono- or di-$C_{1-6}$ alkylcarbamoyl;
(23) $C_{7-16}$ aralkylcarbamoyl;
(24) mercapto;
(25) $C_{1-6}$ alkylthio;
(26) $C_{1-6}$ alkylsulfinyl;
(27) $C_{1-6}$ alkylsulfonyl;

(28) $C_{1-4}$ alkylenedioxy;
(29) $C_{1-6}$ alkyl optionally having 1 to 3 substituents selected from
  (a) a halogen atom,
  (b) hydroxy,
  (c) $C_{1-6}$ alkoxy,
  (d) $C_{6-14}$ aryl,
  (e) amino,
  (f) mono- or di-$C_{1-6}$ alkylamino,
  (g) $C_{7-16}$ aralkylamino,
  (h) $C_{1-6}$ alkoxy-carbonylamino,
  (i) $C_{1-6}$ alkyl-carbonyloxy,
  (j) $C_{1-6}$ alkylthio, and
  (k) $C_{1-6}$ alkylsulfonyl;
(30) $C_{6-14}$ aryl optionally having 1 to 3 halogen atoms;
(31) $C_{7-16}$ aralkyl;
(32) $C_{3-10}$ cycloalkyl and the like.

Examples of the "heterocyclic group" of the "heterocyclic group optionally having substituent(s)" in the present specification include an aromatic heterocyclic group and a nonaromatic heterocyclic group.

Examples of the "aromatic heterocyclic group" include a 4- to 7-membered (preferably 5- or 6-membered) monocyclic aromatic heterocyclic group containing, as a ring-constituting atom besides carbon atoms, 1 to 4 heteroatoms selected from an oxygen atom, a sulfur atom and a nitrogen atom, and a fused aromatic heterocyclic group. Examples of the fused aromatic heterocyclic group include a group derived from a fused ring wherein a ring corresponding to such 4- to 7-membered monocyclic aromatic heterocyclic group, and 1 or 2 rings selected from a 5- or 6-membered aromatic heterocycle containing 1 or 2 nitrogen atoms, a 5-membered aromatic heterocycle containing one sulfur atom and a benzene ring are condensed, and the like.

Examples of the "aromatic heterocyclic group" include 4- to 7-membered (preferably 5- or 6-membered) monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,2,4-thiadiazol-5-yl, 1,3,4-thiadiazol-2-yl), triazolyl (e.g., 1,2,4-triazol-1-yl, 1,2,4-triazol-3-yl, 1,2,3-triazol-1-yl, 1,2,3-triazol-4-yl), tetrazolyl (e.g., tetrazol-1-yl, tetrazol-5-yl), triazinyl (e.g., 1,3,5-triazin-2-yl, 1,3,5-triazin-4-yl, 1,2,3-triazin-4-yl, 1,2,4-triazin-3-yl) and the like;
fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like; and the like.

Examples of the "nonaromatic heterocyclic group" include a 4- to 7-membered (preferably 5- or 6-membered) monocyclic nonaromatic heterocyclic group containing, as a ring-constituting atom besides carbon atoms, 1 to 4 heteroatoms selected from an oxygen atom, a sulfur atom and a nitrogen atom, and a fused nonaromatic heterocyclic group. Examples of the fused nonaromatic heterocyclic group include a group derived from a fused ring wherein a ring corresponding to such 4- to 7-membered monocyclic nonaromatic heterocyclic group, and 1 or 2 rings selected from a 5- or 6-membered heterocycle containing 1 or 2 nitrogen atoms, a 5-membered heterocycle containing one sulfur atom and a benzene ring are condensed, and the like.

Examples of the "nonaromatic heterocyclic group" include 4- to 7-membered (preferably 5- or 6-membered) monocyclic nonaromatic heterocyclic groups such as pyrrolidinyl (e.g., 1-pyrrolidinyl, 2-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), 2-thioxo-1,3-oxazolidin-5-yl, pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-s thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like; fused nonaromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydrobenzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydrobenzofuran-3-yl), chromenyl (e.g., 4H-chromen-2-yl, 2H-chromen-3-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like; and the like.

The "heterocyclic group" optionally has substituent(s) (e.g., 1 to 5, preferably 1 to 3, substituents) at substitutable position(s). When the number of the substituents is two or more, respective substituents may be the same or different.

Examples of the "substituent" of the "heterocyclic group optionally having substituent(s)" include the following substituents.
(1) a halogen atom;
(2) nitro;
(3) cyano;
(4) hydroxy;
(5) $C_{1-6}$ alkoxy optionally having 1 to 3 halogen atoms;
(6) amino;
(7) mono- or di-$C_{1-6}$ alkylamino;
(8) $C_{7-16}$ aralkylamino;
(9) $C_{1-6}$ alkoxy-carbonylamino;
(10) $C_{7-16}$ aralkyloxy-carbonylamino;
(11) $C_{1-6}$ alkyl-carbonylamino;
(12) $C_{3-10}$ cycloalkyl-carbonylamino;
(13) $C_{1-6}$ alkylsulfonylamino;
(14) $C_{6-14}$ arylsulfonylamino;
(15) $C_{1-6}$ alkylaminocarbonylamino;
(16) $C_{6-14}$ arylaminocarbonylamino;
(17) $C_{1-6}$ alkyl-carbonyl;
(18) $C_{3-10}$ cycloalkyl-carbonyl;
(19) carboxy;
(20) $C_{1-6}$ alkoxy-carbonyl;
(21) a group represented by the formula: —CO—N($R^5$)($R^6$) wherein $R^5$ and $R^6$ are each a hydrogen atom or $C_{1-6}$ alkyl, or $R^5$ and $R^6$ optionally form, together with the nitrogen atom bonded thereto, a nitrogen-containing heterocycle optionally having substituent(s);
(22) $C_{7-16}$ aralkylcarbamoyl;
(23) mercapto;
(24) $C_{1-6}$ alkylthio;
(25) $C_{1-6}$ alkylsulfinyl;
(26) $C_{1-6}$ alkylsulfonyl;
(27) $C_{1-4}$ alkylenedioxy;
(28) $C_{1-6}$ alkyl optionally having 1 to 3 substituents selected from
   (a) a halogen atom,
   (b) hydroxy,
   (c) $C_{1-6}$ alkoxy,
   (d) $C_{6-14}$ aryl,
   (e) amino,
   (f) mono- or di-$C_{1-6}$ alkylamino,
   (g) $C_{7-16}$ aralkylamino,
   (h) $C_{1-6}$ alkoxy-carbonylamino,
   (i) $C_{1-6}$ alkyl-carbonyloxy,
   (j) $C_{1-6}$ alkylthio, and
   (k) $C_{1-6}$ alkylsulfonyl;
(29) $C_{6-14}$ aryl optionally having 1 to 3 halogen atoms;
(30) $C_{7-16}$ aralkyl;
(31) $C_{3-10}$ cycloalkyl and the like.

Examples of the "nitrogen-containing heterocycle" of the "nitrogen-containing heterocycle optionally having substituent(s)" formed by $R^5$ and $R^6$ together with the nitrogen atom bonded thereto include a 4- to 7-membered (preferably 5- to 7-membered) nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom. Examples of the nitrogen-containing heterocycle include azetidine, pyrrolidine, imidazolidine, pyrazolidine, piperidine, piperazine, morpholine, thiomorpholine and the like.

The "nitrogen-containing heterocycle" optionally forms a fused ring with a benzene ring, a cyclohexane ring or an oxazole ring, or optionally forms a spiro ring with a 1,3-dioxolane ring. Examples of the fused ring include 1,2,3,4-tetrahydroquinoline, 1,2,3,4-tetrahydroisoquinoline, 2,3-dihydro-1H-isoindole, 2,3-dihydro-1H-indole, decahydroquinoline, 4,5,6,7-tetrahydro[1,3]oxazolo[5,4-b]pyridine and the like. Examples of the spiro ring include 1,4-dioxa-8-azaspiro[4.5]decane and the like.

The "nitrogen-containing heterocycle", a fused ring thereof and a spiro ring thereof optionally have preferably 1 to 3, more preferably 1 or 2 substituents at substitutable position(s). When the number of substituents is two or more, the respective substituents may be the same or different. Examples of the substituent include the aforementioned groups exemplified as the substituents that the "hydrocarbon group" optionally has and the like. Preferable examples of the substituent include a halogen atom; hydroxy; $C_{1-6}$ alkoxy optionally having 1 to 3 halogen atoms; $C_{1-6}$ alkyl-carbonyl; $C_{1-6}$ alkoxy-carbonyl; $C_{1-6}$ alkyl optionally having 1 to 3 substituents selected from halogen atom, hydroxy and $C_{1-6}$ alkoxy; oxo; $C_{6-14}$ aryl (e.g., phenyl) optionally having 1 to 3 $C_{1-6}$ alkoxy; $C_{7-16}$ aralkyl (e.g., benzyl); $C_{6-14}$ aryloxy (e.g., phenoxy); $C_{7-16}$ aralkyloxy (e.g., benzyloxy); $C_{6-14}$ aryl-carbonyl (e.g., benzoyl); mono- or di-$C_{1-6}$ alkylsulfamoyl; $C_{1-6}$ alkylsulfonyl; a 5- or 6-membered heterocyclic group containing, as a ring-constituting atom besides carbon atom, 1 to 4 heteroatoms selected from an oxygen atom, a sulfur atom and a nitrogen atom (e.g., pyridyl, thiazolyl) and the like.

In the present specification, examples of the "homocycle or heterocycle" of the "homocycle or heterocycle optionally having substituent(s)" include (i) an aromatic heterocycle or a nonaromatic heterocycle containing, as a ring-constituting atom besides carbon atom, 1 to 3 heteroatoms selected from an oxygen atom, a sulfur atom and a nitrogen atom, (ii) cyclic hydrocarbon (homocycle) and the like.

Examples of the "aromatic heterocycle" include a 5- or 6-membered aromatic heterocycle containing, as a ring-constituting atom besides carbon atom, 1 to 3 heteroatoms selected from an oxygen atom, a sulfur atom and a nitrogen atom (e.g., pyrazole, pyridine, pyrimidine etc.) and the like. Preferable examples thereof include a 6-membered aromatic heterocycle containing, as a ring-constituting atom besides carbon atom, 1 or 2 nitrogen atoms (e.g., pyridine, pyrimidine etc.) and the like.

Examples of the "nonaromatic heterocycle" include a 5- to 9-membered (preferably 5- or 6-membered) nonaromatic heterocycle containing, as a ring-constituting atom besides carbon atom, 1 to 3 heteroatoms selected from an oxygen atom, a sulfur atom and a nitrogen atom and the like.

Examples of the "cyclic hydrocarbon" include 3- to 10-membered (preferably 5- to 9-membered, more preferably 5- or 6-membered) cyclic hydrocarbon and the like, with preference given to benzene, $C_{3-10}$ cycloalkene, $C_{3-10}$ cycloalkane and the like.

The above-mentioned "homocycle or heterocycle" optionally has substituent(s) (e.g., 1 to 5, preferably 1 to 3, substituents) at substitutable position(s). Examples of the substituent(s) include groups exemplified as the substituents that the "hydrocarbon group" optionally has and the like. When the number of substituents is two or more, the respective substituents may be the same or different.

Examples of the "$C_{2-6}$ alkylene" in the present specification include ethylene, trimethylene, tetramethylene, pentamethylene, hexamethylene, —CH($CH_3$)—, —C($CH_3$)$_2$—, —CH($CH_2CH_3$)—, —C($CH_2CH_3$)$_2$—, —CH($CH_3$)—$CH_2$—, —$CH_2$—CH($CH_3$)—, —C($CH_3$)$_2$—$CH_2$—, —$CH_2$—C($CH_3$)$_2$—, —CH($CH_3$)—($CH_2$)$_2$—, —$CH_2$—CH($CH_3$)—$CH_2$—, —($CH_2$)$_2$—CH($CH_3$)—, —C($CH_3$)$_2$—($CH_2$)$_2$—, —$CH_2$—C($CH_3$)$_2$—$CH_2$—($CH_2$)$_2$—C($CH_3$)$_2$— and the like.

Examples of the "$C_{2-6}$ alkenylene" in the present specification include —CH=CH—, —CH=CH—CH$_2$—, —CH$_2$—CH=CH—, —CH=CH—(CH$_2$)$_2$—, —CH$_2$—CH=CH—CH$_2$—, —(CH$_2$)$_2$—CH=CH—, —CH=CH—(CH$_2$)$_3$—, —CH$_2$—CH=CH—(CH$_3$)$_2$—, —(CH$_3$)$_2$—CH=CH—CH$_2$—, —(CH$_2$)$_3$—CH=CH—, —CH=CH—(CH$_2$)$_4$—, —CH$_2$—CH=CH—(CH$_2$)$_3$—, —(CH$_2$)$_2$—CH=CH—(CH$_2$)$_2$—, —(CH$_2$)$_3$—CH=CH—CH$_2$—, (CH$_2$)$_4$—CH=CH—, —C(CH$_3$)=CH—, —CH=C(CH$_3$)—, —CH(CH$_3$)—CH=CH—CH$_2$—, —CH$_2$—CH=CH—CH(CH$_3$)—, —CH=CH—CH=CH— and the like.

Examples of the "$C_{2-6}$ alkynylene" in the present specification include —C≡C—, —C≡C—CH$_2$—, —CH$_2$—C≡C—, —C≡C—(CH$_2$)$_2$—, —CH$_2$—C≡C—CH$_2$—, —(CH$_2$)$_2$—C≡C—, —C≡C—(CH$_2$)$_3$—, —CH$_2$—C≡C—(CH$_3$)$_2$—, —(CH$_3$)$_2$—C≡C—CH$_2$—, —(CH$_2$)$_3$—C≡C—, —C≡C—(CH$_2$)$_4$—, —CH$_2$—C≡C—(CH$_2$)$_3$—, —(CH$_2$)$_2$—C≡C—(CH$_2$)$_2$—, —(CH$_2$)$_3$—C≡C—CH$_2$—, —(CH$_2$)$_4$—C≡C—, —CH(CH$_3$)—C≡C—CH$_2$—, —CH$_2$—C≡C—CH(CH$_3$)— and the like.

The "$C_{2-6}$ alkylene", "$C_{2-6}$ alkenylene" and "$C_{2-6}$ alkynylene" of the "$C_{2-6}$ alkylene optionally having substituent(s)", "$C_{2-6}$ alkenylene optionally having substituent(s)" and "$C_{2-6}$ alkynylene optionally having substituent(s)" in the present specification optionally have substituent(s) (e.g., 1 to 3, preferably 1 or 2 substituents) at substitutable position(s). When the number of substituents is two or more, respective substituents may be the same or different. Examples thereof include the following substituents.

(1) oxo;
(2) halogen atom;
(3) nitro;
(4) cyano;
(5) hydroxy;
(6) $C_{1-6}$ alkoxy optionally having 1 to 3 halogen atoms;
(7) amino;
(8) mono- or di-$C_{1-6}$ alkylamino;
(9) $C_{7-16}$ aralkylamino;
(10) $C_{1-6}$ alkoxy-carbonylamino;
(11) $C_{1-6}$ alkyl-carbonylamino;
(12) $C_{1-6}$ alkyl-carbonyl;
(13) carboxy;
(14) $C_{1-6}$ alkoxy-carbonyl;
(15) carbamoyl;
(16) mono- or di-$C_{1-6}$ alkylcarbamoyl;
(17) mercapto;
(18) $C_{1-6}$ alkylthio;
(19) $C_{1-6}$ alkylsulfinyl;
(20) $C_{1-6}$ alkylsulfonyl and the like.

Examples of the "hydroxy optionally having a substituent" in the present specification include (1) hydroxy, or (2) hydroxy having, instead of the hydrogen atom of hydroxy, one group selected from, for example, the aforementioned "hydrocarbon group optionally having substituent(s)", the aforementioned "heterocyclic group optionally having substituent(s)", the groups exemplified as the substituents that the aforementioned "hydrocarbon group optionally having substituent(s)" may have and the like.

Examples of the "hydroxy optionally having a substituent" include hydroxy optionally having a substituent selected from $C_{1-10}$ alkyl optionally having substituent(s), $C_{2-10}$ alkenyl optionally having substituent(s), $C_{3-10}$ cycloalkyl optionally having substituent(s), $C_{3-10}$ cycloalkenyl optionally having substituent(s), $C_{6-14}$ aryl optionally having substituent(s), $C_{7-16}$ aralkyl optionally having substituent(s), $C_{8-13}$ arylalkenyl optionally having substituent(s), a heterocyclic group optionally having substituent(s), acyl and the like.

The aforementioned $C_{1-10}$ alkyl, $C_{2-10}$ alkenyl, $C_{3-10}$ cycloalkyl, $C_{3-10}$ cycloalkenyl, $C_{6-14}$ aryl, $C_{7-16}$ aralkyl and $C_{8-13}$ arylalkenyl each optionally have substituent(s) (preferably 1 to 3 substituents) at substitutable position(s). Examples of the substituent include groups similar to the substituents that the aforementioned "hydrocarbon group" optionally has. When the number of substituents is two or more, the respective substituents may be the same or different.

Examples of the "mercapto optionally having a substituent" in the present specification include (1) mercapto or (2) mercapto having, instead of the hydrogen atom of mercapto, one group selected from, for example, the aforementioned "hydrocarbon group optionally having substituent(s)", the aforementioned "heterocyclic group optionally having substituent(s)", the groups exemplified as the substituents that the aforementioned "hydrocarbon group optionally having substituent(s)" may have and the like.

Examples of the "mercapto optionally having a substituent" include mercapto optionally having a substituent selected from $C_{1-10}$ alkyl optionally having substituent(s), $C_{2-10}$ alkenyl optionally having substituent(s), $C_{3-10}$ cycloalkyl optionally having substituent(s), $C_{3-10}$ cycloalkenyl optionally having substituent(s), $C_{6-14}$ aryl optionally having substituent(s), $C_{7-16}$ aralkyl optionally having substituent(s), $C_{8-13}$ arylalkenyl optionally having substituent(s), a heterocyclic group optionally having substituent(s), acyl and the like.

The aforementioned $C_{1-10}$ alkyl, $C_{2-10}$ alkenyl, $C_{3-10}$ cycloalkyl, $C_{3-10}$ cycloalkenyl, $C_{6-14}$ aryl, $C_{7-16}$ aralkyl and $C_{8-13}$ arylalkenyl each optionally have substituent(s) (preferably 1 to 3 substituents) at substitutable position(s). Examples of the substituent include groups similar to the substituents that the aforementioned "hydrocarbon group" optionally has. When the number of substituents is two or more, the respective substituents may be the same or different.

Examples of the "acyl" in the present specification include a group represented by the formula: —COR$^A$, —CO—OR$^A$, —SO$_2$R$^A$, —SOR$^A$, —CO—NR$^{A\prime}$R$^{B\prime}$ or —CS—NR$^{A\prime}$R$^{B\prime}$ wherein R$^A$ is a hydrogen atom, a hydrocarbon group optionally having substituent(s) or a heterocyclic group optionally having substituent(s), and R$^{A\prime}$ and R$^{B\prime}$ are each a hydrogen atom, a hydrocarbon group optionally having substituent(s) or a heterocyclic group optionally having substituent(s), or R$^{A\prime}$ and R$^{B\prime}$ optionally form, together with the nitrogen atom bonded thereto, a nitrogen-containing heterocycle optionally having substituent(s) and the like.

Examples of the "nitrogen-containing heterocycle" of the "nitrogen-containing heterocycle optionally having substituent(s)" formed by R$^{A\prime}$ and R$^{B\prime}$ together with the nitrogen atom bonded thereto include a 5- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom. Examples of the nitrogen-containing heterocycle include pyrrolidine, imidazolidine, pyrazolidine, piperidine, piperazine, morpholine, thiomorpholine and the like.

The "nitrogen-containing heterocycle" optionally has substituent(s) (preferably 1 to 3, more preferably 1 or 2 substituents) at substitutable position(s). Examples of the substituent include groups exemplified as the substituents that the aforementioned "hydrocarbon group" optionally has and the like. When the number of substituents is two or more, the respective substituents may be the same or different.

Preferable examples of the "acyl" include
(1) formyl;
(2) carboxy;
(3) $C_{1-6}$ alkyl-carbonyl;
(4) $C_{1-6}$ alkoxy-carbonyl (e.g., methoxycarbonyl, ethoxycarbonyl, propoxycarbonyl, tert-butoxycarbonyl);
(5) a group represented by the formula: —CO—NR$^{A'}$R$^{B'}$ wherein R$^{A'}$ and R$^{B'}$ are each a hydrogen atom, a hydrocarbon group optionally having substituent(s) or a heterocyclic group optionally having substituent(s), or R$^{A'}$ and R$^{B'}$ optionally form, together with the nitrogen atom bonded thereto, a nitrogen-containing heterocycle optionally having substituent(s) and the like.

The definition of each symbol in the formulas (I), (A), (B) and (C) is explained in detail in the following.

$R^1$ and $R^2$

In the formula (I), $R^1$ and $R^2$ are each a hydrocarbon group optionally having substituent(s) or a heterocyclic group optionally having substituent(s), or $R^1$ and $R^2$ optionally form, together with the nitrogen atom bonded thereto, a nitrogen-containing heterocycle optionally having substituent(s).

Examples of the "hydrocarbon group" of the "hydrocarbon group optionally having substituent(s)" for $R^1$ or $R^2$ include alkyl, cycloalkyl, aralkyl, cycloalkylalkyl and the like. Preferable examples thereof include $C_{1-6}$ alkyl, $C_{3-10}$ cycloalkyl, $C_{7-16}$ aralkyl, $C_{3-10}$ cycloalkyl-$C_{1-6}$ alkyl and the like.

Examples of the "substituent" of the "hydrocarbon group optionally having substituent(s)" for $R^1$ or $R^2$ include 1 to 3 substituents selected from a halogen atom, cyano, hydroxy; amino; $C_{1-6}$ alkoxy-carbonyl; carbamoyl; $C_{1-6}$ alkylcarbamoyl optionally having 1 to 3 substituents selected from hydroxy and a heterocyclic group (preferably, 5- or 6-membered heterocyclic group containing, as a ring-constituting atom besides carbon atom, 1 to 4 heteroatoms selected from an oxygen atom, a sulfur atom and a nitrogen atom, e.g., pyridyl, morpholinyl); $C_{7-16}$ aralkylcarbamoyl (e.g., benzylcarbamoyl) and the like.

Examples of the "heterocyclic group" of the "heterocyclic group optionally having substituent(s)" for $R^1$ or $R^2$ include a 4- to 7-membered nonaromatic heterocyclic group containing, as a ring-constituting atom besides carbon atom, 1 to 4 heteroatoms selected from an oxygen atom, a sulfur atom and a nitrogen atom, and the like. Preferable examples thereof include a 5- to 7-membered nonaromatic heterocyclic group containing, as a ring-constituting atom besides carbon atom, 1 or 2 heteroatoms selected from an oxygen atom, a sulfur atom and a nitrogen atom (e.g., pyrrolidinyl, imidazolidinyl, pyrazolidinyl, piperidinyl, piperazinyl, morpholinyl, thiomorpholinyl) and the like. More preferably is piperidinyl.

The "heterocyclic group" optionally has substituent(s) (e.g., 1 to 5, preferably 1 to 3, substituents) at substitutable position(s). When the number of substituents is two or more, the respective substituents may be the same or different. Examples of the substituent include groups exemplified as the substituents of the aforementioned "heterocyclic group optionally having substituent(s)" and the like.

Preferable examples of the "substituent" of the "heterocyclic group optionally having substituent(s)" for $R^1$ or $R^2$ include
(1) $C_{1-6}$ alkyl optionally having 1 to 3 hydroxy;
(2) a group represented by the formula: —CO—N($R^5$)($R^6$) wherein $R^5$ and $R^6$ are each a hydrogen atom or $C_{1-6}$ alkyl, or $R^5$ and $R^6$ optionally form, together with the nitrogen atom bonded thereto, a nitrogen-containing heterocycle (preferably, 5- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom, for example, pyrrolidine, imidazolidine, pyrazolidine, piperidine, piperazine, morpholine, thiomorpholine) optionally having substituent(s) (e.g., 1 to 3 substituents selected from hydroxy and $C_{1-6}$ alkyl) and the like.

Examples of the "nitrogen-containing heterocycle" of the "nitrogen-containing heterocycle optionally having substituent(s)" formed by $R^1$ and $R^2$ together with the nitrogen atom bonded thereto include a 5- to 9-membered (preferably 5- to 7-membered, more preferably 5- or 6-membered) nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom.

Examples of the "nitrogen-containing heterocycle" include pyrrolidine, imidazolidine, pyrazolidine, piperidine, piperazine, morpholine, thiomorpholine, azepane, azocane, azonane, 1,4-diazepane and the like.

The "nitrogen-containing heterocycle" optionally has substituent(s) (e.g., 1 to 5, preferably 1 to 3, substituents) at substitutable position(s). When the number of substituents is two or more, the respective substituents may be the same or different. Examples of the substituent include groups exemplified as the substituents that the aforementioned "hydrocarbon group" optionally has and the like. Preferable examples of the substituent include 1 to 3 substituents selected from
(1) $C_{1-6}$ alkyl optionally having 1 to 3 substituents selected from
  (a) hydroxy,
  (b) $C_{1-6}$ alkoxy,
  (c) $C_{6-14}$ aryl (e.g., phenyl),
  (d) amino,
  (e) mono- or di-$C_{1-6}$ alkylamino,
  (f) $C_{7-16}$ aralkylamino (e.g., benzylamino), and
  (g) $C_{1-6}$ alkoxy-carbonylamino (e.g., tert-butoxycarbonylamino),
(2) $C_{6-14}$ aryl (e.g., phenyl) optionally having 1 to 3 halogen atoms,
(3) $C_{7-16}$ aralkyl (e.g., benzyl, phenethyl),
(4) $C_{3-10}$ cycloalkyl (e.g., cyclohexyl),
(5) amino,
(6) hydroxy,
(7) $C_{1-6}$ alkoxy-carbonyl (e.g., tert-butoxycarbonyl),
(8) carbamoyl
and the like.

$R^1$ and $R^2$ are preferably each
(1) $C_{1-6}$ alkyl optionally having 1 to 3 substituents selected from
  (a) a halogen atom,
  (b) cyano,
  (c) hydroxy,
  (d) amino,
  (e) $C_{1-6}$ alkoxy-carbonyl,
  (f) carbamoyl,
  (g) $C_{1-6}$ alkylcarbamoyl optionally having 1 to 3 substituents selected from hydroxy and a heterocyclic group (preferably, a 5- or 6-membered heterocyclic group containing, as a ring-constituting atom besides carbon atom, 1 to 4 heteroatoms selected from an oxygen atom, a sulfur atom and a nitrogen atom, e.g., pyridyl, morpholinyl), and
  (h) $C_{7-16}$ aralkylcarbamoyl (e.g., benzylcarbamoyl),
(2) $C_{3-10}$ cycloalkyl (e.g., cyclopropyl, cyclohexyl),
(3) $C_{7-16}$ aralkyl (e.g., benzyl), (4) C$_{3-10}$ cycloalkyl-C$_{1-6}$ alkyl (e.g., cyclopropylmethyl),
(5) a group represented by the formula

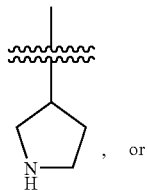

or
(6) a group represented by the formula

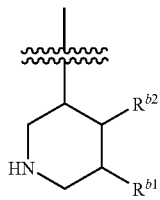

wherein R$^{b1}$ and R$^{b2}$ are each
(1') a hydrogen atom,
(2') cyano,
(3') C$_{1-6}$ alkyl optionally having 1 to 3 substituents selected from
  (a) hydroxy,
  (b) C$_{1-6}$ alkyl-carbonyloxy,
  (c) C$_{1-6}$ alkylthio, and
  (d) C$_{1-6}$ alkylsulfonyl,
(4') C$_{3-10}$ cycloalkyl (e.g., cyclohexyl) optionally having 1 to 3 hydroxy,
(5') C$_{7-16}$ aralkylamino (e.g., phenethylamino) optionally having 1 to 3 hydroxy,
(6') C$_{1-6}$ alkoxy-carbonylamino,
(7') C$_{7-16}$ aralkyloxy-carbonylamino (e.g., benzyloxycarbonylamino),
(8') C$_{1-6}$ alkyl-carbonylamino,
(9') C$_{3-10}$ cycloalkyl-carbonylamino (e.g., cyclohexylcarbonylamino) optionally having 1 to 3 substituents selected from hydroxy and C$_{1-6}$ alkoxy,
(10') C$_{1-6}$ alkylsulfonylamino,
(11') C$_{6-14}$ arylsulfonylamino (e.g., phenylsulfonylamino),
(12') C$_{1-6}$ alkylaminocarbonylamino,
(13') C$_{6-14}$ arylaminocarbonylamino (e.g., phenylaminocarbonylamino),
(14') C$_{1-6}$ alkyl-carbonyl,
(15') C$_{3-10}$ cycloalkyl-carbonyl (e.g., cyclopropylcarbonyl),
(16') carboxy,
(17') a group represented by the formula: —W$^1$—R$^7$
wherein W$^1$ is a bond, —CH$_2$—, —CH$_2$O—, —NHCO— or —NHSO$_2$—, and
R$^7$ is a 5- or 6-membered heterocyclic group containing, as a ring-constituting atom besides carbon atom, 1 to 4 heteroatoms selected from an oxygen atom, a sulfur atom and a nitrogen atom (e.g., imidazolyl, morpholinyl, pyridyl, tetrahydropyranyl, piperidinyl, tetrazolyl, 4,5-dihydro-1,2,4-oxadiazolyl, 1,2,4-triazolyl, 1,3,4-oxadiazolyl, 1,2,4-oxadiazolyl, imidazolidinyl, hexahydropyrimidinyl, pyrazolyl), the 5- or 6-membered heterocyclic group optionally has 1 to 3 substituents selected from
  (a) oxo,
  (b) C$_{1-6}$ alkyl optionally having 1 to 3 hydroxy,
  (c) C$_{6-14}$ aryl,
  (d) carbamoyl, and
  (e) C$_{1-6}$ alkoxy-carbonyl,
(18') C$_{1-6}$ alkoxy-carbonyl, or
(19') a group represented by the formula: —CO—N(R$^5$)(R$^6$) wherein R$^5$ and R$^6$ are each a hydrogen atom, C$_{1-6}$ alkyl or C$_{1-6}$ alkoxy, or
R$^5$ and R$^6$ optionally form, together with the nitrogen atom bonded thereto, a 4- to 7-membered (preferably 5- to 7-membered) nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom, said nonaromatic nitrogen-containing heterocycle optionally forms a fused ring with a benzene ring, a cyclohexane ring or an oxazole ring, or optionally forms a spiro ring with a 1,3-dioxolane ring (e.g., azetidine, pyrrolidine, imidazolidine, pyrazolidine, piperidine, piperazine, morpholine, thiomorpholine, 1,4-oxazepane, 1,2,3,4-tetrahydroquinoline, 1,2,3,4-tetrahydroisoquinoline, 2,3-dihydro-1H-isoindole, 2,3-dihydro-1H-indole, decahydroquinoline, 4,5,6,7-tetrahydro[1,3]oxazolo[5,4-b]pyridine, 1,4-dioxa-8-azaspiro[4.5]decane, 1,2,3,6-tetrahydropyridine), the 4- to 7-membered nonaromatic nitrogen-containing heterocycle, a fused ring thereof and a spiro ring thereof optionally have 1 to 3 substituents selected from
  (a) oxo,
  (b) a halogen atom,
  (c) C$_{1-6}$ alkyl optionally having 1 to 3 substituents selected from hydroxy and C$_{1-6}$ alkoxy,
  (d) C$_{6-14}$ aryl (e.g., phenyl) optionally having 1 to 3 C$_{1-6}$ alkoxy,
  (e) C$_{7-16}$ aralkyl (e.g., benzyl),
  (f) hydroxy,
  (g) C$_{1-6}$ alkoxy,
  (h) C$_{6-14}$ aryloxy (e.g., phenoxy),
  (i) C$_{7-16}$ aralkyloxy (e.g., benzyloxy),
  (j) C$_{1-6}$ alkyl-carbonyl,
  (k) C$_{6-14}$ aryl-carbonyl (e.g., benzoyl),
  (l) mono- or di-C$_{1-6}$ alkylsulfamoyl,
  (m) C$_{1-6}$ alkylsulfonyl, and
  (n) a 5- or 6-membered heterocyclic group containing, as a ring-constituting atom besides carbon atom, 1 to 4 heteroatoms selected from an oxygen atom, a sulfur atom and a nitrogen atom (e.g., pyridyl, thiazolyl), or R$^{b1}$ and R$^{b2}$ optionally form, together with the carbon atoms bonded thereto, a benzene ring or a cyclohexane ring, or R$^1$ and R$^2$ optionally form, together with the nitrogen atom bonded thereto, a 5- to 9-membered (preferably 5- to 7-membered, more preferably 5- or 6-membered) nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., pyrrolidine, imidazolidine, pyrazolidine, piperidine, piperazine, thiomorpholine, azepane, azocane, azonane, 1,4-diazepane), and optionally having 1 to 3 substituents selected from
(1) C$_{1-6}$ alkyl optionally having 1 to 3 substituents selected from
  (a) hydroxy,
  (b) C$_{1-6}$ alkoxy,
  (c) C$_{6-14}$ aryl (e.g., phenyl),
  (d) amino,
  (e) mono- or di-C$_{1-6}$ alkylamino, (f) $C_{7-16}$ aralkylamino (e.g., benzylamino), and
(g) $C_{1-6}$ alkoxy-carbonylamino (e.g., tert-butoxycarbonylamino),
(2) $C_{6-14}$ aryl (e.g., phenyl) optionally having 1 to 3 halogen atoms,
(3) $C_{7-16}$ aralkyl (e.g., benzyl, phenethyl),
(4) $C_{3-10}$ cycloalkyl (e.g., cyclohexyl),
(5) amino,
(6) hydroxy,
(7) $C_{1-6}$ alkoxy-carbonyl (e.g., tert-butoxycarbonyl), and
(8) carbamoyl.

$R^{1a}$ and Ring B

In the formula (A), $R^{1a}$ is alkyl optionally having substituent(s).

Examples of the "alkyl" of the "alkyl optionally having substituent(s)" for $R^{1a}$ include $C_{1-6}$ alkyl.

Examples of the "substituent" of the "alkyl optionally having substituent(s)" for $R^{1a}$ include 1 to 3 substituents selected from a halogen atom, cyano, hydroxy, $C_{3-10}$ cycloalkyl and the like.

As $R^{1a}$, preferred is $C_{1-6}$ alkyl optionally having $C_{3-10}$ cycloalkyl, more preferably, $C_{1-6}$ alkyl.

In the formula (A), ring B is a nitrogen-containing saturated or unsaturated 5- to 7-membered ring optionally having substituent(s). Preferred is a nitrogen-containing saturated 5- to 7-membered ring optionally having substituent(s). n and m are each an integer of 0 to 2, and the total of n and m is 1 to 3.

Examples of the combination of n and m include (n,m) of (0,1), (0,2), (1,0), (1,1), (1,2), (2,0) and (2,1). Among these, both n and m are preferably 1.

The "nitrogen-containing 5- to 7-membered ring" for ring B optionally has substituent(s) (preferably 1 to 3, more preferably 1 or 2 substituents) at substitutable position(s). When the number of substituents is two or more, the respective substituents may be the same or different. Examples of the substituent include groups exemplified as the substituents of the aforementioned "heterocyclic group optionally having substituent(s)" and the like.

As ring B,
(1) a ring represented by the formula

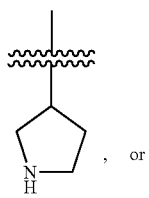

, or or
(2) a ring represented by the formula

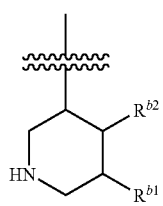

wherein $R^{b1}$ and $R^{b2}$ are each a hydrogen atom or a substituent, or $R^{b1}$ and $R^{b2}$ optionally form, together with the carbon atoms bonded thereto, a 5- to 7-membered ring optionally having substituent(s) is preferable.

Examples of the "substituent" for $R^{b1}$ or $R^{b2}$ include a halogen atom, cyano, a hydrocarbon group optionally having substituent(s), a heterocyclic group optionally having substituent(s), acyl, amino optionally having substituent(s) and the like.

Examples of the "hydrocarbon group" of the "hydrocarbon group optionally having substituent(s)" for $R^{b1}$ or $R^{b2}$ include $C_{1-6}$ alkyl.

The "hydrocarbon group" optionally has substituent(s) (e.g., 1 to 5, preferably 1 to 3, substituents) at substitutable position(s). When the number of substituents is two or more, the respective substituents may be the same or different. Examples of the substituent include groups exemplified as the substituents that the aforementioned "hydrocarbon group" optionally has and the like.

Examples of the "substituent" of the "hydrocarbon group optionally having substituent(s)" for $R^{b1}$ or $R^{b2}$ include 1 to 3 substituents selected from (1) a halogen atom; (2) nitro; (3) cyano; (4) hydroxy; (5) $C_{1-6}$ alkoxy optionally having 1 to 3 halogen atoms; (6) amino; (7) mono- or di-$C_{1-6}$ alkylamino; (8) $C_{7-16}$ aralkylamino; (9) $C_{1-6}$ alkoxy-carbonylamino; (10) $C_{1-6}$ alkyl-carbonylamino; (11) $C_{1-6}$ alkyl-carbonyl; (12) carboxy; (13) $C_{1-6}$ alkoxy-carbonyl; (14) carbamoyl; (15) mono- or di-$C_{1-6}$ alkylcarbamoyl; (16) mercapto; (17) $C_{1-6}$ alkylthio; (18) $C_{1-6}$ alkylsulfinyl; (19) $C_{1-6}$ alkylsulfonyl and the like.

Preferable examples of the "hydrocarbon group optionally having substituent(s)" for $R^{b1}$ or $R^{b2}$ include $C_{1-6}$ alkyl optionally having 1 to 3 substituents selected from (a) hydroxy, (b) $C_{1-6}$ alkyl-carbonyloxy, (c) $C_{1-6}$ alkylthio and (d) $C_{1-6}$ alkylsulfonyl.

Examples of the "heterocyclic group" of the "heterocyclic group optionally having substituent(s)" for $R^{b1}$ or $R^{b2}$ include a 5- to 7-membered aromatic heterocyclic group or nonaromatic heterocyclic group containing, as a ring-constituting atom besides carbon atom, 1 to 4 heteroatoms selected from an oxygen atom, a sulfur atom and a nitrogen atom and the like.

Examples of the "aromatic heterocyclic group" include a 5- or 6-membered aromatic heterocyclic group containing, as a ring-constituting atom besides carbon atom, 1 to 4 heteroatoms selected from an oxygen atom, a sulfur atom and a nitrogen atom (e.g., furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl, tetrazolyl, triazolyl, oxadiazolyl, thiadiazolyl) and the like.

Examples of the "nonaromatic heterocyclic group" include a 5- to 7-membered nonaromatic heterocyclic group containing, as a ring-constituting atom besides carbon atom, 1 to 3 heteroatoms selected from an oxygen atom, a sulfur atom and a nitrogen atom (e.g., pyrrolidinyl, piperidinyl, morpholinyl, thiomorpholinyl, piperazinyl, tetrahydrofuryl, 4,5-dihydro-1,2,4-oxadiazolyl) and the like.

The "heterocyclic group" optionally has substituent(s) (e.g., 1 to 5, preferably 1 to 3, substituents) at substitutable position(s). When the number of substituents is two or more, the respective substituents may be the same or different. Examples of the substituent include the groups exemplified as the substituents of the aforementioned "heterocyclic group optionally having substituent(s)" and the like. For example, 1 to 3 substituents selected from (a) oxo, (b) $C_{1-6}$ alkyl optionally having 1 to 3 hydroxy, (c) $C_{6-14}$ aryl and (d) carbamoyl can be mentioned.

Examples of the "acyl" for $R^{b1}$ or $R^{b2}$ include
(1) formyl;
(2) carboxy;

(3) $C_{1-6}$ alkyl-carbonyl;
(4) $C_{1-6}$ alkoxy-carbonyl (e.g., methoxycarbonyl, ethoxycarbonyl, propoxycarbonyl, tert-butoxycarbonyl);
(5) a group represented by the formula: —CO—N($R^5$)($R^6$) wherein $R^5$ and $R^6$ are each a hydrogen atom or $C_{1-6}$ alkyl, or $R^5$ and $R^6$ optionally form, together with the nitrogen atom bonded thereto, a 4- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., azetidine, pyrrolidine, piperidine, piperazine, morpholine, thiomorpholine), and optionally having 1 to 3 substituents selected from hydroxy and $C_{1-6}$ alkyl and the like.

Examples of the "amino optionally having substituent(s)" for $R^{b1}$ or $R^{b2}$ include
(1) $C_{1-6}$ alkoxy-carbonylamino,
(2) $C_{7-16}$ aralkyloxy-carbonylamino (e.g., benzyloxycarbonylamino),
(3) $C_{1-6}$ alkyl-carbonylamino,
(4) $C_{3-10}$ cycloalkyl-carbonylamino (e.g., cyclohexylcarbonylamino) optionally having 1 to 3 substituents selected from hydroxy and $C_{1-6}$ alkoxy and the like.

Examples of the "substituent" for $R^{b1}$ or $R^{b2}$ also include a group represented by the formula: —$W^2$—$R^8$ wherein $W^2$ is a bond, —$CH_2$—, —$CH_2O$— or —NHCO—, and
$R^8$ is a 5- or 6-membered heterocyclic group containing, as a ring-constituting atom besides carbon atom, 1 to 4 heteroatoms selected from an oxygen atom, a sulfur atom and a nitrogen atom (e.g., imidazolyl, morpholinyl, pyridyl, tetrahydropyranyl, piperidinyl, tetrazolyl, 4,5-dihydro-1,2,4-oxadiazolyl, 1,2,4-triazolyl, 1,3,4-oxadiazolyl, 1,2,4-oxadiazolyl), the 5- or 6-membered heterocyclic group optionally has 1 to 3 substituents selected from
(a) oxo,
(b) $C_{1-6}$ alkyl optionally having 1 to 3 hydroxy,
(c) $C_{6-14}$ aryl, and
(d) carbamoyl.

Examples of the "5- to 7-membered ring" of the "5- to 7-membered ring optionally having substituent(s)" formed by $R^{b1}$ and $R^{b2}$ together with the carbon atoms bonded thereto include (i) a 5- to 7-membered aromatic heterocycle or nonaromatic heterocycle containing, as a ring-constituting atom besides carbon atom, 1 to 3 heteroatoms selected from an oxygen atom, a sulfur atom and a nitrogen atom, (ii) 5- to 7-membered cyclic hydrocarbon and the like.

Examples of the "aromatic heterocycle" include a 5- or 6-membered aromatic heterocycle containing, as a ring-constituting atom besides carbon atom, 1 to 3 heteroatoms selected from an oxygen atom, a sulfur atom and a nitrogen atom (e.g., pyridine, pyrazine, pyrimidine, pyridazine, pyrrole, imidazole, pyrazole, triazole, thiophene, furan, thiazole, isothiazole, oxazole, isoxazole) and the like.

Examples of the "nonaromatic heterocycle" include a 5- to 7-membered (preferably 5- or 6-membered) nonaromatic heterocycle containing, as a ring-constituting atom besides carbon atom, 1 to 3 (preferably 1 or 2) heteroatoms selected from an oxygen atom, a sulfur atom and a nitrogen atom (e.g., tetrahydropyridine, dihydropyridine, tetrahydropyrazine, tetrahydropyrimidine, tetrahydropyridazine, dihydropyran, dihydropyrrole, dihydrothiophene, dihydrofuran, piperidine, piperazine, hexahydropyrimidine, hexahydropyridazine, tetrahydropyran, morpholine, pyrrolidine, pyrazoline, imidazolidine, thiazoline, isothiazoline, oxazoline, isoxazoline, pyrazolidine, tetrahydrothiophene, tetrahydrofuran, thiazolidine, oxazolidine) and the like.

Examples of the "5- to 7-membered cyclic hydrocarbon" include benzene, $C_{5-7}$ cycloalkene (e.g., cyclopentene, cyclohexene, cycloheptene), $C_{5-7}$ cycloalkane (e.g., cyclopentane, cyclohexane, cycloheptane) and the like.

The above-mentioned "5- to 7-membered ring" optionally has substituent(s) (e.g., 1 to 5, preferably 1 to 3, substituents) at substitutable position(s). When the number of substituents is two or more, the respective substituents may be the same or different. Examples of the substituent include groups exemplified as the substituents that the aforementioned "hydrocarbon group" optionally has and the like.

$R^{b1}$ and $R^{b2}$ are each preferably a hydrogen atom, a hydrocarbon group optionally having substituent(s) or acyl.

$R^{b1}$ and $R^{b2}$ are each more preferably a hydrogen atom, $C_{1-6}$ alkyl optionally having substituent(s) or acyl.

$R^{b1}$ and $R^{b2}$ are each still more preferably
(1) a hydrogen atom,
(2) $C_{1-6}$ alkyl optionally having 1 to 3 hydroxy,
(3) $C_{1-6}$ alkoxy-carbonyl, or
(4) a group represented by the formula: —CO—N($R^5$)($R^6$) wherein $R^5$ and $R^6$ are each a hydrogen atom or $C_{1-6}$ alkyl, or $R^5$ and $R^6$ optionally form, together with the nitrogen atom bonded thereto, a 5- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., pyrrolidine, piperidine, piperazine, morpholine, thiomorpholine), and optionally having 1 to 3 substituents selected from hydroxy and $C_{1-6}$ alkyl.

Particularly preferably, $R^{b2}$ is a hydrogen atom, and $R^{b1}$ is
(1) a hydrogen atom,
(2) cyano,
(3) $C_{1-6}$ alkyl optionally having 1 to 3 substituents selected from
(a) hydroxy,
(b) $C_{1-6}$ alkyl-carbonyloxy,
(c) alkylthio, and
(d) $C_{1-6}$ alkylsulfonyl,
(4) $C_{1-6}$ alkoxy-carbonylamino,
(5) $C_{7-16}$ aralkyloxy-carbonylamino (e.g., benzyloxycarbonylamino),
(6) $C_{1-6}$ alkyl-carbonylamino,
(7) $C_{3-10}$ cycloalkyl-carbonylamino (e.g., cyclohexylcarbonylamino) optionally having 1 to 3 substituents selected from hydroxy and $C_{1-6}$ alkoxy,
(8) a group represented by the formula: —$W^2$—$R^8$ wherein $W^2$ is a bond, —$CH_2$—, —$CH_2O$— or —NHCO—, and
$R^8$ is a 5- or 6-membered heterocyclic group containing, as a ring-constituting atom besides carbon atom, 1 to 4 heteroatoms selected from an oxygen atom, a sulfur atom and a nitrogen atom (e.g., imidazolyl, morpholinyl, pyridyl, tetrahydropyranyl, piperidinyl, tetrazolyl, 4,5-dihydro-1,2,4-oxadiazolyl, 1,2,4-triazolyl, 1,3,4-oxadiazolyl, 1,2,4-oxadiazolyl), the 5- or 6-membered heterocyclic group optionally has 1 to 3 substituents selected from
(a) oxo,
(b) $C_{1-6}$ alkyl optionally having 1 to 3 hydroxy,
(c) $C_{6-14}$ aryl, and
(d) carbamoyl,
(9) $C_{1-6}$ alkoxy-carbonyl, or
(10) a group represented by the formula: —CO—N($R^5$)($R^6$) wherein $R^5$ and $R^6$ are each a hydrogen atom or $C_{1-6}$ alkyl, or $R^5$ and $R^6$ optionally form, together with the nitrogen atom bonded thereto, a 4- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., azetidine, pyrrolidine, piperidine, piperazine, morpholine, thiomorpholine), and optionally having 1 to 3 substituents selected from hydroxy and $C_{1-6}$ alkyl, or $R^{b1}$ and $R^{b2}$ optionally form, together with the carbon atoms bonded thereto, a benzene ring or a cyclohexane ring.

Of these, further more preferably, $R^{b1}$ is (1) $C_{1-6}$ alkyl optionally having 1 to 3 hydroxy, (2) $C_{1-6}$ alkoxy-carbonyl, or (3) a group represented by the formula: —CO—N($R^5$)($R^6$) wherein $R^5$ and $R^6$ are each a hydrogen atom or $C_{1-6}$ alkyl, or $R^5$ and $R^6$ optionally form, together with the nitrogen atom bonded thereto, a 5- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., pyrrolidine, piperidine, piperazine, morpholine, thiomorpholine), and optionally having 1 to 3 substituents selected from hydroxy and $C_{1-6}$ alkyl, and $R^{b2}$ is a hydrogen atom.

$R^{1b}$ and $R^{2b}$

In the formula (B), $R^{1b}$ and $R^{2b}$ are each a hydrocarbon group optionally having substituent(s) or a heterocyclic group optionally having substituent(s), or $R^{1b}$ and $R^{2b}$ optionally form, together with the nitrogen atom bonded thereto, a nitrogen-containing heterocycle optionally having substituent(s).

Examples of the "hydrocarbon group" of the "hydrocarbon group optionally having substituent(s)" for $R^{1b}$ or $R^{2b}$ include alkyl, cycloalkyl, aralkyl, cycloalkyl and the like. Preferable examples thereof include $C_{1-6}$ alkyl, $C_{3-10}$ cycloalkyl, $C_{7-16}$ aralkyl, $C_{3-10}$ cycloalkyl-$C_{1-6}$ alkyl and the like.

Examples of the "substituent" of the "hydrocarbon group optionally having substituent(s)" for $R^{1b}$ or $R^{2b}$ include 1 to 3 substituents selected from (a) a halogen atom, (b) cyano, (c) hydroxy, (d) amino, (e) $C_{1-6}$ alkoxy-carbonyl, (f) carbamoyl, (g) $C_{1-6}$ alkylcarbamoyl optionally having 1 to 3 substituents selected from hydroxy and a heterocyclic group (preferably, a 5- or 6-membered heterocyclic group containing, as a ring-constituting atom besides carbon atom, 1 to 4 heteroatoms selected from an oxygen atom, a sulfur atom and a nitrogen atom, e.g., pyridyl, morpholinyl) and (h) $C_{7-16}$ aralkylcarbamoyl (e.g., benzylcarbamoyl).

Examples of the "heterocyclic group" of the "heterocyclic group optionally having substituent(s)" for $R^{1b}$ or $R^{2b}$ include a 4- to 7-membered nonaromatic heterocyclic group containing, as a ring-constituting atom besides carbon atom, 1 to 4 heteroatoms selected from an oxygen atom, a sulfur atom and a nitrogen atom, and the like. Preferable examples thereof include a 5- to 7-membered nonaromatic heterocyclic group containing, as a ring-constituting atom besides carbon atom, 1 or 2 heteroatoms selected from an oxygen atom, a sulfur atom and a nitrogen atom (e.g., pyrrolidinyl, imidazolidinyl, pyrazolidinyl, piperidinyl, piperazinyl, morpholinyl, thiomorpholinyl) and the like.

The "heterocyclic group" optionally has substituent(s) (e.g., 1 to 5, preferably 1 to 3, substituents) at substitutable position(s). Examples of the substituent include groups exemplified as the substituents of the aforementioned "heterocyclic group optionally having substituent(s)" and the like. When the number of substituents is two or more, the respective substituents may be the same or different.

Examples of the "heterocyclic group optionally having substituent(s)" for $R^{1b}$ or $R^{2b}$ include (1) a group represented by the formula

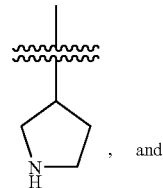
, and and (2) a group represented by the formula

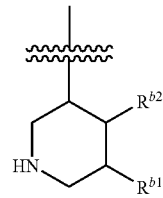

wherein $R^{b2}$ is a hydrogen atom, and $R^{b1}$ is (1') a hydrogen atom, (2') cyano, (3') $C_{1-6}$ alkyl optionally having 1 to 3 substituents selected from
  (a) hydroxy,
  (b) $C_{1-6}$ alkyl-carbonyloxy,
  (c) $C_{1-6}$ alkylthio, and
  (d) $C_{1-6}$ alkylsulfonyl, (4') $C_{3-10}$ cycloalkyl (e.g., cyclohexyl) optionally having 1 to 3 hydroxy, (5') $C_{7-16}$ aralkylamino (e.g., phenethylamino) optionally having 1 to 3 hydroxy, (6') $C_{1-6}$ alkoxy-carbonylamino, (7') $C_{7-16}$ aralkyloxy-carbonylamino (e.g., benzyloxycarbonylamino), (8') $C_{1-6}$ alkyl-carbonylamino, (9') $C_{3-10}$ cycloalkyl-carbonylamino (e.g., cyclohexylcarbonylamino) optionally having 1 to 3 substituents selected from hydroxy and $C_{1-6}$ alkoxy, (10') $C_{1-6}$ alkylsulfonylamino, (11') $C_{6-14}$ arylsulfonylamino (e.g., phenylsulfonylamino), (12') $C_{1-6}$ alkylaminocarbonylamino, (13') $C_{6-14}$ arylaminocarbonylamino (e.g., phenylaminocarbonylamino), (14') $C_{1-6}$ alkyl-carbonyl, (15') $C_{3-10}$ cycloalkyl-carbonyl (e.g., cyclopropylcarbonyl), (16') carboxy, (17') a group represented by the formula: —$W^1$—$R^7$
wherein $W^1$ is a bond, —$CH_2$—, —$CH_2O$—, —NHCO— or —$NHSO_2$—, and $R^7$ is a 5- or 6-membered heterocyclic group containing, as a ring-constituting atom besides carbon atom, 1 to 4 heteroatoms selected from an oxygen atom, a sulfur atom and a nitrogen atom (e.g., imidazolyl, morpholinyl, pyridyl, tetrahydropyranyl, piperidinyl, tetrazolyl, 4,5-dihydro-1,2,4-oxadiazolyl, 1,2,4-triazolyl, 1,3,4-oxadiazolyl, 1,2,4-oxadiazolyl, imidazolidinyl, hexahydropyrimidinyl, pyrazolyl), the 5- or 6-membered heterocyclic group optionally has 1 to 3 substituents selected from
(a) oxo,
(b) $C_{1-6}$ alkyl optionally having 1 to 3 hydroxy,
(c) $C_{6-14}$ aryl,
(d) carbamoyl, and
(e) $C_{1-6}$ alkoxy-carbonyl,
(18') $C_{1-6}$ alkoxy-carbonyl, or
(19') a group represented by the formula: —CO—N($R^6$)($R^6$) wherein $R^5$ and $R^6$ are each a hydrogen atom, $C_{1-6}$ alkyl or $C_{1-6}$ alkoxy, or
$R^5$ and $R^6$ optionally form, together with the nitrogen atom bonded thereto, a 4- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom, said 4- to 7-membered nonaromatic nitrogen-containing heterocycle optionally forms a fused ring with a benzene ring, a cyclohexane ring or an oxazole ring, or optionally forms a spiro ring with a 1,3-dioxolane ring (e.g., azetidine, pyrrolidine, piperidine, piperazine, morpholine, thiomorpholine, 1,4-oxazepane, 1,2,3,4-tetrahydroquinoline, 1,2,3,4-tetrahydroisoquinoline, 2,3-dihydro-1H-isoindole, 2,3-dihydro-1H-indole, decahydroquinoline, 4,5,6,7-tetrahydro[1,3]oxazolo[5,4-b]pyridine, 1,4-dioxa-8-azaspiro[4.5]decane, 1,2,3,6-tetrahydropyridine), the 4- to 7-membered nonaromatic nitrogen-containing heterocycle, a fused ring thereof and a spiro ring thereof optionally have 1 to 3 substituents selected from
(a) oxo,
(b) a halogen atom,
(c) $C_{1-6}$ alkyl optionally having 1 to 3 substituents selected from hydroxy and $C_{1-6}$ alkoxy,
(d) $C_{6-14}$ aryl (e.g., phenyl) optionally having 1 to 3 $C_{1-6}$ alkoxy,
(e) $C_{7-16}$ aralkyl (e.g., benzyl),
(f) hydroxy,
(g) $C_{1-6}$ alkoxy,
(h) $C_{6-14}$ aryloxy (e.g., phenoxy),
(i) $C_{7-16}$ aralkyloxy (e.g., benzyloxy),
(j) $C_{1-6}$ alkyl-carbonyl,
(k) $C_{6-14}$ aryl-carbonyl (e.g., benzoyl),
(l) mono- or di-$C_{1-6}$ alkylsulfamoyl,
(m) $C_{1-6}$ alkylsulfonyl, and
(n) a 5- or 6-membered heterocyclic group containing, as a ring-constituting atom besides carbon atom, 1 to 4 heteroatoms selected from an oxygen atom, a sulfur atom and a nitrogen atom (e.g., pyridyl, thiazolyl), or
$R^{b1}$ and $R^{b2}$ optionally form, together with the carbon atoms bonded thereto, a benzene ring or a cyclohexane ring.

Examples of the "nitrogen-containing heterocycle" of the "nitrogen-containing heterocycle optionally having substituent(s)" formed by $R^{1b}$ and $R^{2b}$ together with the nitrogen atom bonded thereto include a 5- to 9-membered (preferably 5- to 7-membered, more preferably 5- or 6-membered) nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom.

Examples of the "nitrogen-containing heterocycle" include pyrrolidine, imidazolidine, pyrazolidine, piperidine, piperazine, morpholine, thiomorpholine, azepane, azocane, azonane, 1,4-diazepane and the like. Preferred are piperidine and piperazine.

The "nitrogen-containing heterocycle" optionally has substituent(s) (e.g., 1 to 3, preferably 1 to 3 substituents) at substitutable position(s). When the number of substituents is two or more, the respective substituents may be the same or different. Examples of the substituent include groups similar to the substituents that the aforementioned "hydrocarbon group" optionally has. Examples of the substituent include 1 to 3 substituents selected from
(1) $C_{1-6}$ alkyl optionally having 1 to 3 substituents selected from
(a) hydroxy,
(b) $C_{1-6}$ alkoxy,
(c) $C_{6-14}$ aryl (e.g., phenyl),
(d) amino,
(e) mono- or di-$C_{1-6}$ alkylamino,
(f) $C_{7-16}$ aralkylamino (e.g., benzylamino), and
(g) $C_{1-6}$ alkoxy-carbonylamino (e.g., tert-butoxycarbonylamino),
(2) $C_{6-14}$ aryl (e.g., phenyl) optionally having 1 to 3 halogen atoms,
(3) $C_{7-16}$ aralkyl (e.g., benzyl, phenethyl),
(4) $C_{3-10}$ cycloalkyl (e.g., cyclohexyl),
(5) amino,
(6) hydroxy,
(7) $C_{1-6}$ alkoxy-carbonyl (e.g., tert-butoxycarbonyl), and
(8) carbamoyl.

Preferably, $R^{1b}$ and $R^{2b}$ form, together with the nitrogen atom bonded thereto, piperidine optionally having substituent(s) or piperazine optionally having substituent(s). Examples of the substituents that piperidine or piperazine optionally has include 1 to 3 substituents selected from
(1) $C_{1-6}$ alkyl selected from optionally having 1 to 3 substituents
(a) hydroxy,
(b) $C_{1-6}$ alkoxy,
(c) $C_{6-14}$ aryl (e.g., phenyl),
(d) amino,
(e) mono- or di-$C_{1-6}$ alkylamino,
(f) $C_{7-16}$ aralkylamino (e.g., benzylamino), and
(g) $C_{1-6}$ alkoxy-carbonylamino (e.g., tert-butoxycarbonylamino),
(2) $C_{6-14}$ aryl (e.g., phenyl) optionally having 1 to 3 halogen atoms,
(3) $C_{7-16}$ aralkyl (e.g., benzyl, phenethyl),
(4) $C_{3-10}$ cycloalkyl (e.g., cyclohexyl),
(5) amino,
(6) hydroxy,
(7) $C_{1-6}$ alkoxy-carbonyl (e.g., tert-butoxycarbonyl), and
(8) carbamoyl.

Preferably, $R^{1b}$ and $R^{2b}$ are each
(1) $C_{1-6}$ alkyl optionally having 1 to 3 substituents selected from
(a) a halogen atom,
(b) cyano,
(c) hydroxy,
(d) amino,
(e) $C_{1-6}$ alkoxy-carbonyl,
(f) carbamoyl,
(g) $C_{1-6}$ alkylcarbamoyl optionally having 1 to 3 substituents selected from hydroxy and a heterocyclic group (preferably, 5- or 6-membered heterocyclic group containing, as a ring-constituting atom besides carbon atom, 1 to 4 heteroatoms selected from an oxygen atom, a sulfur atom and a nitrogen atom, e.g., pyridyl, morpholinyl), and
(h) $C_{7-16}$ aralkylcarbamoyl (e.g., benzylcarbamoyl),
(2) $C_{3-10}$ cycloalkyl (e.g., cyclopropyl, cyclohexyl),
(3) $C_{7-16}$ aralkyl (e.g., benzyl), (4) $C_{3-10}$ cycloalkyl-$C_{1-6}$ alkyl (e.g., cyclopropylmethyl),
(5) a group represented by the formula

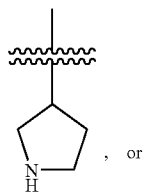

or
(6) a group represented by the formula

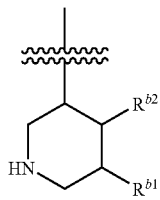

wherein $R^{b2}$ is a hydrogen atom, and
$R^{b1}$ is
(1') a hydrogen atom,
(2') cyano,
(3') $C_{1-6}$ alkyl optionally having 1 to 3 substituents selected from
 (a) hydroxy,
 (b) $C_{1-6}$ alkyl-carbonyloxy,
 (c) $C_{1-6}$ alkylthio, and
 (d) $C_{1-6}$ alkylsulfonyl,
(4') $C_{3-10}$ cycloalkyl (e.g., cyclohexyl) optionally having 1 to 3 hydroxy,
(5') $C_{7-16}$ aralkylamino (e.g., phenethylamino) optionally having 1 to 3 hydroxy,
(6') $C_{1-6}$ alkoxy-carbonylamino,
(7') $C_{7-16}$ aralkyloxy-carbonylamino (e.g., benzyloxycarbonylamino),
(8') $C_{1-6}$ alkyl-carbonylamino,
(9') $C_{3-10}$ cycloalkyl-carbonylamino (e.g., cyclohexylcarbonylamino) optionally having 1 to 3 substituents selected from hydroxy and $C_{1-6}$ alkoxy,
(10') $C_{1-6}$ alkylsulfonylamino,
(11') $C_{6-14}$ arylsulfonylamino (e.g., phenylsulfonylamino),
(12') $C_{1-6}$ alkylaminocarbonylamino,
(13') $C_{6-14}$ arylaminocarbonylamino (e.g., phenylaminocarbonylamino),
(14') $C_{1-6}$ alkyl-carbonyl,
(15') $C_{3-10}$ cycloalkyl-carbonyl (e.g., cyclopropylcarbonyl),
(16') carboxy,
(17') a group represented by the formula: —$W^1$—$R^7$
wherein $W^1$ is a bond, —$CH_2$—, —$CH_2O$—, —NHCO— or —$NHSO_2$—, and
$R^7$ is a 5- or 6-membered heterocyclic group containing, as a ring-constituting atom besides carbon atom, 1 to 4 heteroatoms selected from an oxygen atom, a sulfur atom and a nitrogen atom (e.g., imidazolyl, morpholinyl, pyridyl, tetrahydropyranyl, piperidinyl, tetrazolyl, 4,5-dihydro-1,2,4-oxadiazolyl, 1,2,4-triazolyl, 1,3,4-oxadiazolyl, 1,2,4-oxadiazolyl, imidazolidinyl, hexahydropyrimidinyl, pyrazolyl), the 5- or 6-membered heterocyclic group optionally has 1 to 3 substituents selected from
 (a) oxo,
 (b) $C_{1-6}$ alkyl optionally having 1 to 3 hydroxy,
 (c) $C_{6-14}$ aryl,
 (d) carbamoyl, and
 (e) $C_{1-6}$ alkoxy-carbonyl,
(18') $C_{1-6}$ alkoxy-carbonyl, or
(19') a group represented by the formula: —CO—N($R^5$)($R^6$) wherein $R^5$ and $R^6$ are each a hydrogen atom, $C_{1-6}$ alkyl or $C_{1-6}$ alkoxy, or
$R^5$ and $R^6$ optionally form, together with the nitrogen atom bonded thereto, a 4- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom, said 4- to 7-membered nonaromatic nitrogen-containing heterocycle optionally forms a fused ring with a benzene ring, a cyclohexane ring or an oxazole ring, or optionally forms a spiro ring with a 1,3-dioxolane ring (e.g., azetidine, pyrrolidine, piperidine, piperazine, morpholine, thiomorpholine, 1,4-oxazepane, 1,2,3,4-tetrahydroquinoline, 1,2,3,4-tetrahydroisoquinoline, 2,3-dihydro-1H-isoindole, 2,3-dihydro-1H-indole, decahydroquinoline, 4,5,6,7-tetrahydro[1,3]oxazolo[5,4-b]pyridine, 1,4-dioxa-8-azaspiro[4.5]decane, 1,2,3,6-tetrahydropyridine), said 4- to 7-membered nonaromatic nitrogen-containing heterocycle, a fused ring thereof and a spiro ring thereof optionally have 1 to 3 substituents selected from
 (a) oxo,
 (b) a halogen atom,
 (c) $C_{1-6}$ alkyl optionally having 1 to 3 substituents selected from hydroxy and $C_{1-6}$ alkoxy,
 (d) $C_{6-14}$ aryl (e.g., phenyl) optionally having 1 to 3 $C_{1-6}$ alkoxy,
 (e) $C_{7-16}$ aralkyl (e.g., benzyl),
 (f) hydroxy,
 (g) $C_{1-6}$ alkoxy,
 (h) $C_{6-14}$ aryloxy (e.g., phenoxy),
 (i) $C_{7-16}$ aralkyloxy (e.g., benzyloxy),
 (j) $C_{1-6}$ alkyl-carbonyl,
 (k) $C_{6-14}$ aryl-carbonyl (e.g., benzoyl),
 (l) mono- or di-$C_{1-6}$ alkylsulfamoyl,
 (m) $C_{1-6}$ alkylsulfonyl, and
 (n) a 5- or 6-membered heterocyclic group containing, as a ring-constituting atom besides carbon atom, 1 to 4 heteroatoms selected from an oxygen atom, a sulfur atom and a nitrogen atom (e.g., pyridyl, thiazolyl), or
$R^{b1}$ and $R^{b2}$ optionally form, together with the carbon atoms bonded thereto, a benzene ring or a cyclohexane ring, or
$R^{1b}$ and $R^{2b}$ optionally form, together with the nitrogen atom bonded thereto, a 5- to 9-membered (preferably 5- to 7-membered, more preferably 5- or 6-membered) nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., pyrrolidine, piperidine, piperazine, morpholine, thiomorpholine, azepane, azocane, azonane, 1,4-diazepane), and optionally having 1 to 3 substituents selected from
(1) $C_{1-6}$ alkyl optionally having 1 to 3 substituents selected from
 (a) hydroxy,
 (b) $C_{1-6}$ alkoxy,
 (c) $C_{6-14}$ aryl (e.g., phenyl),
 (d) amino,
 (e) mono- or di-$C_{1-6}$ alkylamino, (f) $C_{7-16}$ aralkylamino (e.g., benzylamino), and
(g) $C_{1-6}$ alkoxy-carbonylamino (e.g., tert-butoxycarbonylamino),
(2) $C_{6-14}$ aryl (e.g., phenyl) optionally having 1 to 3 halogen atoms,
(3) $C_{7-16}$ aralkyl (e.g., benzyl, phenethyl),
(4) $C_{3-10}$ cycloalkyl (e.g., cyclohexyl),
(5) amino,
(6) hydroxy,
(7) $C_{1-6}$ alkoxy-carbonyl (e.g., tert-butoxycarbonyl), and
(8) carbamoyl.

More preferably, $R^{1b}$ and $R^{2b}$ are each
(1) $C_{1-6}$ alkyl optionally having 1 to 3 substituents selected from cyano and hydroxy,
(2) $C_{3-10}$ cycloalkyl, or
(3) $C_{7-16}$ aralkyl, or $R^{1b}$ and $R^{2b}$ optionally form, together with the nitrogen atom bonded thereto, a 5- to 9-membered (preferably 5- to 7-membered, more preferably 5- or 6-membered) nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., pyrrolidine, imidazolidine, pyrazolidine, piperidine, piperazine, morpholine, thiomorpholine, azepane, azocane, azonane, 1,4-diazepane), and optionally having 1 to 3 substituents selected from
(1) $C_{1-6}$ alkyl optionally having 1 to 3 substituents selected from
  (a) hydroxy,
  (b) $C_{1-6}$ alkoxy,
  (c) $C_{6-14}$ aryl (e.g., phenyl),
  (d) amino,
  (e) mono- or di-$C_{1-6}$ alkylamino,
  (f) $C_{7-16}$ aralkylamino (e.g., benzylamino), and
  (g) $C_{1-6}$ alkoxy-carbonylamino (e.g., tert-butoxycarbonylamino),
(2) $C_{6-14}$ aryl (e.g., phenyl) optionally having 1 to 3 halogen atoms,
(3) $C_{7-16}$ aralkyl (e.g., benzyl, phenethyl),
(4) $C_{3-10}$ cycloalkyl (e.g., cyclohexyl),
(5) amino,
(6) hydroxy,
(7) $C_{1-6}$ alkoxy-carbonyl (e.g., tert-butoxycarbonyl), and
(8) carbamoyl.

$R^{1c}$ and Ring Bc

In the formula (C), $R^{1c}$ is alkyl optionally having substituent(s).

Examples of the "alkyl" of the "alkyl optionally having substituent(s)" for $R^{1c}$ include $C_{1-6}$ alkyl.

Examples of the "substituent" of the "alkyl optionally having substituent(s)" for $R^{1c}$ include 1 to 3 substituents selected from a halogen atom, cyano, hydroxy and the like.

As $R^{1c}$, preferred is $C_{1-6}$ alkyl.

In the formula (C), ring Bc is a nitrogen-containing saturated or unsaturated 5- to 7-membered ring optionally having substituent(s). Preferred is a nitrogen-containing saturated 5- to 7-membered ring optionally having substituent(s). n and m are each an integer of 0 to 2, and the total of n and m is 1 to 3.

Examples of the combination of n and m include (n,m) of (0,1), (0,2), (1,0), (1,1), (1,2), (2,0) and (2,1). Among these, both n and m are preferably 1.

The "nitrogen-containing 5- to 7-membered ring" for ring Bc optionally has substituent(s) (preferably 1 to 3, more preferably 1 or 2 substituents) at substitutable position(s). When the number of substituents is two or more, the respective substituents may be the same or different. Examples of the substituent include groups exemplified as the substituents of the aforementioned "heterocyclic group optionally having substituent(s)" and the like.

As ring Bc, a ring represented by the formula

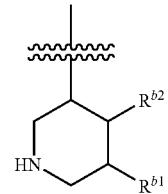

wherein $R^{b1}$ and $R^{b2}$ are each a hydrogen atom or a substituent, or $R^{b1}$ and $R^{b2}$ optionally form, together with the carbon atoms bonded thereto, a 5- to 7-membered ring optionally having substituent(s) is preferable.

Preferable examples of $R^{b1}$ and $R^{b2}$ in ring Bc include those similar to the preferable examples of $R^{b1}$ and $R^{b2}$ in the aforementioned ring B.

In ring Bc, $R^{b1}$ and $R^{b2}$ are each preferably a hydrogen atom, a hydrocarbon group optionally having substituent(s) or acyl.

$R^{b1}$ and $R^{b2}$ are each more preferably a hydrogen atom, $C_{1-6}$ alkyl optionally having substituent(s) or acyl.

$R^{b1}$ and $R^{b2}$ are each further preferably
(1) a hydrogen atom,
(2) $C_{1-6}$ alkyl optionally having 1 to 3 hydroxy,
(3) $C_{1-6}$ alkoxy-carbonyl, or
(4) a group represented by the formula: —CO—N($R^5$)($R^6$)
wherein $R^5$ and $R^6$ are each a hydrogen atom or $C_{1-6}$ alkyl, or $R^5$ and $R^6$ optionally form, together with the nitrogen atom bonded thereto, a 5- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., pyrrolidine, piperidine, piperazine, morpholine, thiomorpholine), and optionally having 1 to 3 substituents selected from hydroxy and $C_{1-6}$ alkyl.

Particularly preferably,
$R^{b1}$ is
(1) $C_{1-6}$ alkyl optionally having 1 to 3 hydroxy,
(2) $C_{1-6}$ alkoxy-carbonyl, or
(3) a group represented by the formula: —CO—N($R^5$)($R^6$)
wherein $R^5$ and $R^6$ are each a hydrogen atom or $C_{1-6}$ alkyl, or $R^5$ and $R^6$ optionally form, together with the nitrogen atom bonded thereto, a 5- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., pyrrolidine, piperidine, piperazine, morpholine, thiomorpholine), and optionally having 1 to 3 substituents selected from hydroxy and $C_{1-6}$ alkyl, and $R^{b2}$ is a hydrogen atom.

$R^3$, $R^{3a}$, $R^{3b}$, Z and $R^3$

In the formula (I), $R^3$ is a substituent.

Examples of the "substituent" for $R^3$ include a hydrocarbon group optionally having substituent(s), a heterocyclic group optionally having substituent(s), acyl and the like.

Examples of the "hydrocarbon group" of the "hydrocarbon group optionally having substituent(s)" for $R^3$ include alkyl, cycloalkyl, aryl and the like. Preferable examples thereof include $C_{1-6}$ alkyl, $C_{3-10}$ cycloalkyl, $C_{6-14}$ aryl and the like.

Examples of the "substituent" of the "hydrocarbon group optionally having substituent(s)" for $R^3$ include 1 to 3 substituents selected from a halogen atom; cyano; hydroxy; $C_{1-6}$ alkoxy optionally having 1 to 3 halogen atoms; mercapto; $C_{1-6}$ alkylthio; $C_{1-6}$ alkylsulfinyl; $C_{1-6}$ alkylsulfonyl and the like.

Examples of the "heterocyclic group" of the "heterocyclic group optionally having substituent(s)" for $R^3$ include a 5- to 7-membered aromatic heterocyclic group or nonaromatic heterocyclic group containing, as a ring-constituting atom besides carbon atom, 1 to 4 heteroatoms selected from an oxygen atom, a sulfur atom and a nitrogen atom and the like.

Examples of the "aromatic heterocyclic group" include a 5- or 6-membered aromatic heterocyclic group containing, as a ring-constituting atom besides carbon atom, 1 to 4 heteroatoms selected from an oxygen atom, a sulfur atom and a nitrogen atom (e.g., furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl) and the like.

Examples of the "nonaromatic heterocyclic group" include a 5- to 7-membered nonaromatic heterocyclic group containing, as a ring-constituting atom besides carbon atom, 1 to 4 heteroatoms selected from an oxygen atom, a sulfur atom and a nitrogen atom (e.g., pyrrolidinyl, piperidinyl, morpholinyl, thiomorpholinyl, piperazinyl, tetrahydrofuryl) and the like.

The "heterocyclic group" optionally has substituent(s) (e.g., 1 to 5, preferably 1 to 3, substituents) at substitutable position(s). When the number of substituents is two or more, the respective substituents may be the same or different. Examples of the substituent include groups exemplified as the substituents of the aforementioned "heterocyclic group optionally having substituent(s)" and the like.

Preferable examples of the "substituent" of the "heterocyclic group optionally having substituent(s)" for $R^3$ include 1 to 3 substituents selected from (1) a halogen atom; (2) nitro; (3) cyano; (4) hydroxy; (5) $C_{1-6}$ alkoxy; (6) amino; (7) mono- or di-$C_{1-6}$ alkylamino; (8) $C_{7-16}$ aralkylamino; (9) $C_{1-6}$ alkoxy-carbonylamino; (10) $C_{1-6}$ alkyl-carbonylamino; (11) $C_{1-6}$ alkyl-carbonyl; (12) carboxy; (13) $C_{1-6}$ alkoxy-carbonyl; (14) carbamoyl; (15) mono- or di-$C_{1-6}$ alkylcarbamoyl; (16) mercapto; (17) $C_{1-6}$ alkylthio; (18) $C_{1-6}$ alkylsulfinyl; (19) $C_{1-6}$ alkylsulfonyl; (20) $C_{1-6}$ alkyl optionally having 1 to 3 halogen atoms and the like.

Examples of the "acyl" for $R^3$ include
(1) formyl;
(2) carboxy;
(3) $C_{1-6}$ alkyl-carbonyl;
(4) $C_{1-6}$ alkoxy-carbonyl (e.g., methoxycarbonyl, ethoxycarbonyl, propoxycarbonyl, tert-butoxycarbonyl);
(5) a group represented by the formula: —CO—NR$^{A'}$R$^{B'}$
wherein R$^{A'}$ and R$^{B'}$ are each a hydrogen atom, a hydrocarbon group optionally having substituent(s) or a heterocyclic group optionally having substituent(s), or R$^{A'}$ and R$^{B'}$ optionally form, together with the nitrogen atom bonded thereto, a nitrogen-containing heterocycle optionally having substituent(s) and the like.

$R^3$ is preferably
(1) a heterocyclic group optionally having substituent(s),
(2) $C_{6-14}$ aryl optionally having substituent(s),
(3) $C_{3-10}$ cycloalkyl optionally having substituent(s),
(4) $C_{1-6}$ alkyl optionally having substituent(s),
(5) $C_{1-6}$ alkoxy-carbonyl and the like.

$R^3$ is more preferably
(1) a 5- or 6-membered aromatic or nonaromatic heterocyclic group containing, as a ring-constituting atom besides carbon atom, 1 to 4 heteroatoms selected from an oxygen atom, a sulfur atom and a nitrogen atom (e.g., furyl, thienyl, oxazolyl, pyridyl, tetrahydrofuryl), and optionally having 1 to 3 $C_{1-6}$ alkyl,
(2) $C_{6-14}$ aryl,
(3) $C_{3-10}$ cycloalkyl,
(4) $C_{1-6}$ alkyl optionally having 1 to 3 substituents selected from $C_{1-6}$ alkoxy and $C_{1-6}$ alkylthio, or
(5) $C_{1-6}$ alkoxy-carbonyl and the like.

In the formula (A), $R^{3a}$ is a 5- or 6-membered aromatic group optionally having substituent(s).

Examples of the "5- or 6-membered aromatic group" of the "5- or 6-membered aromatic group optionally having substituent(s)" for $R^{3a}$ include (i) a 5- or 6-membered aromatic heterocyclic group containing, as a ring-constituting atom besides carbon atom, 1 to 4 heteroatoms selected from an oxygen atom, a sulfur atom and a nitrogen atom, (ii) phenyl and the like.

Examples of the "5- or 6-membered aromatic group" include a 5-membered aromatic heterocyclic group such as furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,2,4-thiadiazol-5-yl, 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl) and the like; and a 6-membered aromatic heterocyclic group such as pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), triazinyl (e.g., 1,3,5-triazin-2-yl, 1,3,5-triazin-4-yl, 1,2,3-triazin-4-yl, 1,2,4-triazin-3-yl) and the like. Preferably is a 5-membered aromatic heterocyclic group, more preferably furyl, thienyl, oxazolyl and the like.

Examples of the "substituent" of the "5- or 6-membered aromatic group optionally having substituent(s)" for $R^{3a}$ include 1 to 3 substituents selected from (1) a halogen atom; (2) nitro; (3) cyano; (4) hydroxy; (5) $C_{1-6}$ alkoxy; (6) amino; (7) mono- or di-$C_{1-6}$ alkylamino; (8) $C_{7-16}$ aralkylamino; (9) $C_{1-6}$ alkoxy-carbonylamino; (10) $C_{1-6}$ alkyl-carbonylamino; (11) $C_{1-6}$ alkyl-carbonyl; (12) carboxy; (13) $C_{1-6}$ alkoxy-carbonyl; (14) carbamoyl; (15) mono- or di-$C_{1-6}$ alkylcarbamoyl; (16) mercapto; (17) $C_{1-6}$ alkylthio; (18) $C_{1-6}$ alkylsulfinyl; (19) $C_{1-6}$ alkylsulfonyl; (20) $C_{1-6}$ alkyl optionally having 1 to 3 halogen atoms and the like.

As $R^{3a}$, preferred is a 5- or 6-membered aromatic heterocyclic group containing, as a ring-constituting atom besides carbon atom, 1 to 4 heteroatoms selected from an oxygen atom, a sulfur atom and a nitrogen atom (e.g., furyl, oxazolyl, thienyl, pyridyl), or phenyl.

As $R^{3a}$, more preferred is a 5-membered aromatic heterocyclic group containing, as a ring-constituting atom besides carbon atom, 1 to 4 heteroatoms selected from an oxygen atom, a sulfur atom and a nitrogen atom (e.g., furyl, oxazolyl, thienyl).

Among these, preferred as $R^{3a}$ is furyl, thienyl or oxazolyl, each of which optionally has substituent(s), more preferred is furyl, thienyl or oxazolyl optionally having 1 to 3 $C_{1-6}$ alkyl, further preferred is furyl optionally having 1 to 3 $C_{1-6}$ alkyl, and particularly preferred is unsubstituted furyl.

In the formula (B), $R^{3b}$ is a substituent excluding 2-(4-phenylpiperazin-1-yl)ethyl optionally having substituent(s) and biphenyl-4-yl having substituent(s).

Examples of the "substituent" for $R^{3b}$ include a hydrocarbon group optionally having substituent(s), a heterocyclic group optionally having substituent(s), acyl and the like.

Examples of the "hydrocarbon group" of the "hydrocarbon group optionally having substituent(s)" for $R^{3b}$ include alkyl, cycloalkyl, aryl and the like. Preferable examples thereof include $C_{1-6}$ alkyl, $C_{3-10}$ cycloalkyl, $C_{6-14}$ aryl and the like.

Examples of the "substituent" of the "hydrocarbon group optionally having substituent(s)" for $R^{3b}$ include 1 to 3 substituents selected from a halogen atom; cyano; hydroxy; $C_{1-6}$ alkoxy optionally having 1 to 3 halogen atoms; mercapto; $C_{1-6}$ alkylthio; $C_{1-6}$ alkylsulfinyl; $C_{1-6}$ alkylsulfonyl and the like.

Examples of the "heterocyclic group" of the "heterocyclic group optionally having substituent(s)" for $R^{3b}$ include a 5- to 7-membered aromatic heterocyclic group or nonaromatic heterocyclic group containing, as a ring-constituting atom besides carbon atom, 1 to 4 heteroatoms selected from an oxygen atom, a sulfur atom and a nitrogen atom and the like.

Examples of the "aromatic heterocyclic group" include a 5- or 6-membered aromatic heterocyclic group containing, as a ring-constituting atom besides carbon atom, 1 to 4 heteroatoms selected from an oxygen atom, a sulfur atom and a nitrogen atom (e.g., furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl) and the like.

Examples of the "nonaromatic heterocyclic group" include a 5- to 7-membered nonaromatic heterocyclic group containing, as a ring-constituting atom besides carbon atom, 1 to 4 heteroatoms selected from an oxygen atom, a sulfur atom and a nitrogen atom (e.g., pyrrolidinyl, piperidinyl, morpholinyl, thiomorpholinyl, piperazinyl, tetrahydrofuryl) and the like.

The "heterocyclic group" optionally has substituent(s) (e.g., 1 to 5, preferably 1 to 3, substituents) at substitutable position(s). When the number of substituents is two or more, the respective substituents may be the same or different. Examples of the substituent include groups exemplified as the substituents of the aforementioned "heterocyclic group optionally having substituent(s)" and the like.

Preferable examples of the "substituent" of the "heterocyclic group optionally having substituent(s)" for $R^{3b}$ include 1 to 3 substituents selected from (1) a halogen atom; (2) nitro; (3) cyano; (4) hydroxy; (5) $C_{1-6}$ alkoxy; (6) amino; (7) mono- or di-$C_{1-6}$ alkylamino; (8) $C_{7-16}$ aralkylamino; (9) $C_{1-6}$ alkoxy-carbonylamino; (10) $C_{1-6}$ alkyl-carbonylamino; (11) $C_{1-6}$ alkyl-carbonyl; (12) carboxy; (13) $C_{1-6}$ alkoxy-carbonyl; (14) carbamoyl; (15) mono- or di-$C_{1-6}$ alkylcarbamoyl; (16) mercapto; (17) $C_{1-6}$ alkylthio; (18) $C_{1-6}$ alkylsulfinyl; (19) $C_{1-6}$ alkylsulfonyl; (20) $C_{1-6}$ alkyl optionally having 1 to 3 halogen atoms and the like.

Examples of the "acyl" for $R^{3b}$ include
(1) formyl;
(2) carboxy;
(3) $C_{1-6}$ alkyl-carbonyl;
(4) $C_{1-6}$ alkoxy-carbonyl (e.g., methoxycarbonyl, ethoxycarbonyl, propoxycarbonyl, tert-butoxycarbonyl);
(5) a group represented by the formula: —CO—NR$^{A'}$R$^{B'}$
wherein R$^{A'}$ and R$^{B'}$ are each a hydrogen atom, a hydrocarbon group optionally having substituent(s) or a heterocyclic group optionally having substituent(s), or R$^{A'}$ and R$^{B'}$ optionally form, together with the nitrogen atom bonded thereto, a nitrogen-containing heterocycle optionally having substituent(s) and the like.

As $R^{3b}$, preferred is
(1) a 5- or 6-membered aromatic or nonaromatic heterocyclic group containing, as a ring-constituting atom besides carbon atom, 1 to 4 heteroatoms selected from an oxygen atom, a sulfur atom and a nitrogen atom (e.g., furyl, thienyl, oxazolyl, pyridyl, tetrahydrofuryl), and optionally having 1 to 3 $C_{1-6}$ alkyl,
(2) $C_{6-14}$ aryl (e.g., phenyl),
(3) $C_{3-10}$ cycloalkyl (e.g., cyclopropyl),
(4) $C_{1-6}$ alkyl optionally having 1 to 3 substituents selected from
  (a) hydroxy,
  (b) $C_{1-6}$ alkoxy,
  (c) $C_{1-6}$ alkylthio,
  (d) $C_{1-6}$ alkylsulfinyl, and
  (e) $C_{1-6}$ alkylsulfonyl, or
(5) $C_{1-6}$ alkoxy-carbonyl.

As $R^{3b}$, more preferred is
(1) a 5- or 6-membered aromatic or nonaromatic heterocyclic group containing, as a ring-constituting atom besides carbon atom, 1 to 4 heteroatoms selected from an oxygen atom, a sulfur atom and a nitrogen atom (e.g., furyl, thienyl, oxazolyl, pyridyl, tetrahydrofuryl), and optionally having 1 to 3 $C_{1-6}$ alkyl,
(2) $C_{6-14}$ aryl (e.g., phenyl),
(3) $C_{3-10}$ cycloalkyl (e.g., cyclopropyl),
(4) $C_{1-6}$ alkyl optionally having 1 to 3 $C_{1-6}$ alkoxy,
(5) $C_{1-6}$ alkoxy-carbonyl and the like.

As $R^{3b}$, more preferred is a 5-membered aromatic group optionally having substituent(s). Examples of the "5-membered aromatic group optionally having substituent(s)" for $R^{3b}$ include groups exemplified as the "5-membered aromatic group optionally having substituent(s)" for $R^{1a}$ and the like.

Among these, preferred as $R^{3b}$ is furyl, thienyl or oxazolyl, each of which optionally has substituent(s), more preferred is furyl, thienyl or oxazolyl optionally having 1 to 3 $C_{1-6}$ alkyl, further preferred is furyl optionally having 1 to 3 $C_{1-6}$ alkyl, and particularly preferred is unsubstituted furyl.

In the formula (C), $R^{3c}$ is a substituent.

Examples of the "substituent" for $R^{3c}$ include a hydrocarbon group optionally having substituent(s), a heterocyclic group optionally having substituent(s), hydroxy optionally having a substituent, mercapto optionally having a substituent, acyl and the like.

Examples of the "hydrocarbon group" of the "hydrocarbon group optionally having substituent(s)" for $R^{3c}$ include alkyl, cycloalkyl, aryl and the like. Preferred are $C_{1-6}$ alkyl, $C_{3-10}$ cycloalkyl, $C_{6-14}$ aryl and the like.

Examples of the "substituent" of the "hydrocarbon group optionally having substituent(s)" for $R^{3c}$ include 1 to 3 substituents selected from a halogen atom; cyano; hydroxy; $C_{1-6}$ alkoxy optionally having 1 to 3 halogen atoms; mercapto; $C_{1-6}$ alkylthio and the like.

Examples of the "heterocyclic group" of the "heterocyclic group optionally having substituent(s)" for $R^{3c}$ include a 5- to 7-membered aromatic heterocyclic group or nonaromatic heterocyclic group containing, as a ring-constituting atom besides carbon atom, 1 to 4 heteroatoms selected from an oxygen atom, a sulfur atom and a nitrogen atom and the like.

Examples of the "aromatic heterocyclic group" include a 5- or 6-membered aromatic heterocyclic group containing, as a ring-constituting atom besides carbon atom, 1 to 4 heteroatoms selected from an oxygen atom, a sulfur atom and a nitrogen atom (e.g., furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl) and the like.

Examples of the "nonaromatic heterocyclic group" include a 5- to 7-membered nonaromatic heterocyclic group containing, as a ring-constituting atom besides carbon atom, 1 to 4 heteroatoms selected from an oxygen atom, a sulfur atom and a nitrogen atom (e.g., pyrrolidinyl, piperidinyl, morpholinyl, thiomorpholinyl, piperazinyl, tetrahydrofuryl) and the like.

The "heterocyclic group" optionally has substituent(s) (e.g., 1 to 5, preferably 1 to 3, substituents) at substitutable position(s). When the number of substituents is two or more, the respective substituents may be the same or different. Examples of the substituent include groups exemplified as the substituents of the aforementioned "heterocyclic group optionally having substituent(s)" and the like.

Preferable examples of the "substituent" of the "heterocyclic group optionally having substituent(s)" for $R^{3c}$ include 1 to 3 substituents selected from (1) a halogen atom; (2) nitro; (3) cyano; (4) hydroxy; (5) $C_{1-6}$ alkoxy; (6) amino; (7) mono- or di-$C_{1-6}$ alkylamino; (8) $C_{7-16}$ aralkylamino; (9) $C_{1-6}$ alkoxy-carbonylamino; (10) $C_{1-6}$ alkyl-carbonylamino; (11) $C_{1-6}$ alkyl-carbonyl; (12) carboxy; (13) $C_{1-6}$ alkoxy-carbonyl; (14) carbamoyl; (15) mono- or di-$C_{1-6}$ alkylcarbamoyl; (16) mercapto; (17) $C_{1-6}$ alkylthio; (18) $C_{1-6}$ alkylsulfinyl; (19) $C_{1-6}$ alkylsulfonyl; (20) $C_{1-6}$ alkyl optionally having 1 to 3 halogen atoms and the like.

Examples of the "hydroxy optionally having a substituent" for $R^{3c}$ include hydroxy optionally having a substituent selected from $C_{1-6}$ alkyl optionally having substituent(s), $C_{2-6}$ alkenyl optionally having substituent(s), $C_{3-10}$ cycloalkyl optionally having substituent(s), $C_{3-10}$ cycloalkenyl optionally having substituent(s), $C_{6-14}$ aryl optionally having substituent(s), $C_{7-16}$ aralkyl optionally having substituent(s) and the like. The aforementioned $C_{1-6}$ alkyl, $C_{2-6}$ alkenyl, $C_{3-10}$ cycloalkyl, $C_{3-10}$ cycloalkenyl, $C_{6-14}$ aryl and $C_{7-16}$ aralkyl optionally have 1 to 3 substituents selected from a halogen atom; cyano; hydroxy; $C_{1-6}$ alkoxy optionally having 1 to 3 halogen atoms; mercapto; $C_{1-6}$ alkylthio and the like. Preferable examples of the "hydroxy optionally having a substituent" for $R^{3c}$ include $C_{1-6}$ alkoxy.

Examples of the "mercapto optionally having a substituent" for $R^{3c}$ include mercapto optionally having a substituent selected from $C_{1-6}$ alkyl optionally having substituent(s), $C_{2-6}$ alkenyl optionally having substituent(s), $C_{3-10}$ cycloalkyl optionally having substituent(s), $C_{3-10}$ cycloalkenyl optionally having substituent(s), $C_{6-14}$ aryl optionally having substituent(s), $C_{7-16}$ aralkyl optionally having substituent(s) and the like. The aforementioned $C_{1-6}$ alkyl, $C_{2-6}$ alkenyl, $C_{3-10}$ cycloalkyl, $C_{3-10}$ cycloalkenyl, $C_{6-14}$ aryl and $C_{7-16}$ aralkyl optionally have 1 to 3 substituents selected from a halogen atom; cyano; hydroxy; $C_{1-6}$ alkoxy optionally having 1 to 3 halogen atoms; mercapto; $C_{1-6}$ alkylthio and the like. Preferable examples of the "mercapto optionally having a substituent" for $R^{3c}$ include $C_{1-6}$ alkylthio.

Examples of the "acyl" for $R^{3c}$ include
(1) formyl;
(2) carboxy;
(3) $C_{1-6}$ alkyl-carbonyl;
(4) $C_{1-6}$ alkoxy-carbonyl (e.g., methoxycarbonyl, ethoxycarbonyl, propoxycarbonyl, tert-butoxycarbonyl);
(5) a group represented by the formula: —CO—NR$^{A'}$R$^{B'}$ wherein R$^{A'}$ and R$^{B'}$ are each a hydrogen atom, a hydrocarbon group optionally having substituent(s) or a heterocyclic group optionally having substituent(s), or R$^{A'}$ and R$^{B'}$ optionally form, together with the nitrogen atom bonded thereto, a nitrogen-containing heterocycle optionally having substituent(s) and the like.

As $R^{3c}$, preferred is
(1) hydroxy optionally having a substituent,
(2) mercapto optionally having a substituent and the like.

As $R^{3c}$, more preferred is
(1) $C_{1-6}$ alkoxy,
(2) $C_{1-6}$ alkylthio and the like.

In the formula (C), Z is $C_{2-6}$ alkylene optionally having substituent(s), $C_{2-6}$ alkenylene optionally having substituent(s) or $C_{2-6}$ alkynylene optionally having substituent(s).

Examples of the "substituent" of the "$C_{2-6}$ alkylene optionally having substituent(s)", "$C_{2-6}$ alkenylene optionally having substituent(s)" or "$C_{2-6}$ alkynylene optionally having substituent(s)" for Z include 1 to 3 (preferably 1 or 2) substituents selected from oxo; a halogen atom; nitro; cyano; hydroxy; $C_{1-6}$ alkoxy optionally having 1 to 3 halogen atoms; amino and the like.

As Z, preferred is $C_{2-6}$ alkylene optionally having substituent(s), more preferred is $C_{2-6}$ alkylene (e.g., ethylene, trimethylene) optionally having 1 or 2 substituents selected from oxo and hydroxy, and further preferred is $C_{2-6}$ alkylene (e.g., ethylene, trimethylene).

Ring A, Ring Aa, Ring Ab and Ring Ac

In the formula (I), the formula (A) and the formula (C), ring A, ring Aa and ring Ac are each a homocycle or heterocycle optionally having substituent(s).

Examples of the "homocycle or heterocycle" of the "homocycle or heterocycle optionally having substituent(s)" for ring A, ring Aa or ring Ac include (i) an aromatic heterocycle or nonaromatic heterocycle containing, as a ring-constituting atom besides carbon atom, 1 to 3 heteroatoms selected from an oxygen atom, a sulfur atom and a nitrogen atom, (ii) cyclic hydrocarbon (homocycle) and the like.

Examples of the "aromatic heterocycle" include a 5- or 6-membered aromatic heterocycle containing, as a ring-constituting atom besides carbon atom, 1 to 3 heteroatoms selected from an oxygen atom, a sulfur atom and a nitrogen atom (e.g., pyrazole, pyridine, pyrimidine) and the like. Preferable examples thereof include a 6-membered aromatic heterocycle containing, as a ring-constituting atom besides carbon atom, 1 or 2 nitrogen atoms (e.g., pyridine, pyrimidine) and the like. The "aromatic heterocycle" is optionally fused with $C_{5-7}$ cycloalkene (e.g., cyclopentene, cyclohexene, cycloheptene) or heterocycle (e.g., thiophene).

Examples of the "nonaromatic heterocycle" include a 5- to 9-membered (preferably 5- or 6-membered) nonaromatic heterocycle containing, as a ring-constituting atom besides carbon atom, 1 to 3 heteroatoms selected from an oxygen atom, a sulfur atom and a nitrogen atom and the like.

Examples of the "cyclic hydrocarbon" include 3- to 10-membered (preferably, 5- to 9-membered, more preferably 5- or 6-membered) cyclic hydrocarbon and the like, with preference given to benzene, $C_{3-10}$ cycloalkene, $C_{3-10}$ cycloalkane and the like.

The above-mentioned "homocycle or heterocycle" optionally has substituent(s) (e.g., 1 to 3, preferably 1 or 2 substituents) at substitutable position(s). When the number of substituents is two or more, the respective substituents may be the same or different. Examples of the substituent include groups exemplified as the substituents that the aforementioned "hydrocarbon group" optionally has and the like. Preferable examples of the substituent include 1 to 3 (preferably 1 or 2) substituents selected from (1) a halogen atom, (2) hydroxy, (3) $C_{1-6}$ alkoxy, (4) $C_{1-6}$ alkyl optionally having 1 to 3 halogen atoms, (5) $C_{6-14}$ aryl (e.g., phenyl), (6) $C_{3-10}$ cycloalkyl (e.g., cyclopropyl), (7) a 5- or 6-membered aromatic heterocyclic group containing, as a ring-constituting atom besides carbon atom, 1 to 3 heteroatoms selected from an oxygen atom, a sulfur atom and a nitrogen atom (e.g., thienyl), (8) $C_{1-6}$ alkylthio and the like, more preferably 1 to 3 (preferably 1 or 2) $C_{1-6}$ alkyl optionally having 1 to 3 halogen atoms.

Examples of the "heterocycle" of the "heterocycle optionally having substituent(s)" for ring A, ring Aa or ring Ac include heterocycles represented by the formulas

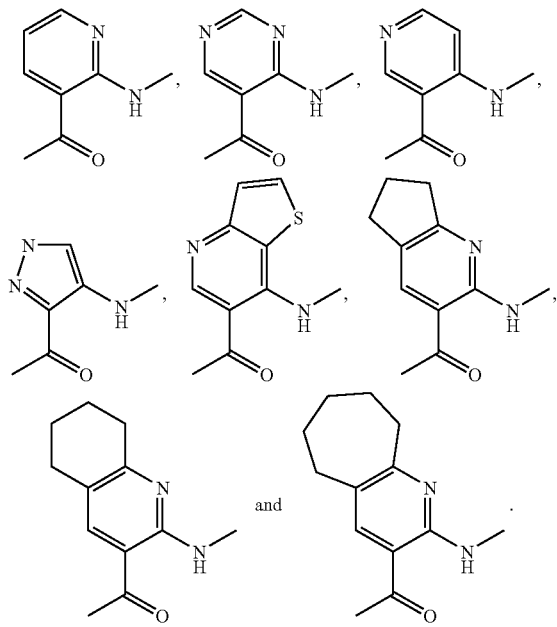

These heterocycles optionally have 1 to 3 substituents selected from
(1) a halogen atom,
(2) $C_{1-6}$ alkyl optionally having 1 to 3 halogen atoms,
(3) $C_{6-14}$ aryl (e.g., phenyl),
(4) $C_{3-10}$ cycloalkyl (e.g., cyclopropyl),
(5) a 5- or 6-membered aromatic heterocyclic group containing, as a ring-constituting atom besides carbon atom, 1 to 3 heteroatoms selected from an oxygen atom, a sulfur atom and a nitrogen atom (e.g., thienyl), and
(6) $C_{1-6}$ alkylthio.

As ring Aa, preferred is a 5- or 6-membered aromatic heterocycle optionally having substituent(s).

Examples of the "5- or 6-membered aromatic heterocycle" of the "5- or 6-membered aromatic heterocycle optionally having substituent(s)" for ring Aa include a 5- or 6-membered aromatic heterocycle containing, as a ring-constituting atom besides carbon atom, 1 to 3 heteroatoms selected from an oxygen atom, a sulfur atom and a nitrogen atom (e.g., pyrazole, pyridine, pyrimidine) and the like. Preferable examples thereof include a 6-membered aromatic heterocycle containing, as a ring-constituting atom besides carbon atom, 1 or 2 nitrogen atoms (e.g., pyridine, pyrimidine) and the like.

Examples of the "substituent" of the "5- or 6-membered aromatic heterocycle optionally having substituent(s)" for ring Aa include
(1) a hydrocarbon group optionally having substituent(s),
(2) a heterocyclic group optionally having substituent(s),
(3) mercapto optionally having a substituent,
(4) acyl and the like.

As ring Aa, more preferred is a heterocycle represented by the formula

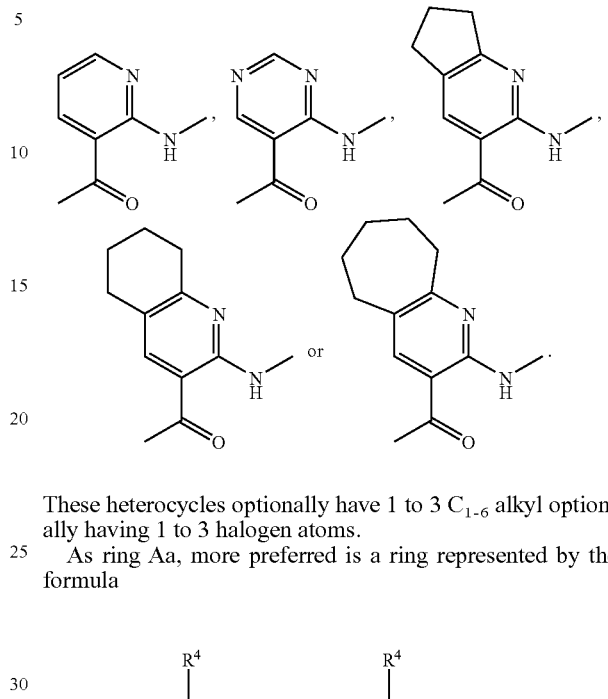

These heterocycles optionally have 1 to 3 $C_{1-6}$ alkyl optionally having 1 to 3 halogen atoms.

As ring Aa, more preferred is a ring represented by the formula

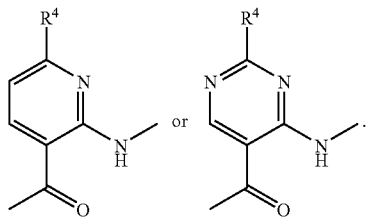

As ring Aa, particularly preferred is a ring represented by the formula

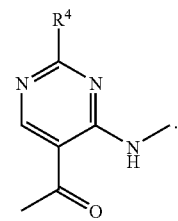

As $R^4$ in compound (A), preferred is
(1) a hydrocarbon group optionally having substituent(s),
(2) a heterocyclic group optionally having substituent(s),
(3) mercapto optionally having a substituent and the like.
As $R^4$ in compound (A), more preferred is
(1) $C_{1-6}$ alkyl optionally having 1 to 3 halogen atoms,
(2) $C_{6-14}$ aryl,
(3) $C_{3-10}$ cycloalkyl,
(4) a 5- or 6-membered aromatic heterocyclic group containing, as a ring-constituting atom besides carbon atom, 1 to 3 heteroatoms selected from an oxygen atom, a sulfur atom and a nitrogen atom (e.g., thienyl),
(5) $C_{1-6}$ alkylthio and the like.
As $R^4$ in compound (A), further preferred is $C_{1-6}$ alkyl optionally having 1 to 3 halogen atoms, and particularly preferred is $C_{1-6}$ alkyl.

In the formula (B), X and Y are each C or N, and ring Ab is a nitrogen-containing 6-membered ring optionally having substituent(s) in addition to $R^4$.

X is preferably C.

ring Ab optionally has substituent(s) (preferably 1 or 2 substituents) at substitutable position(s) in addition to $R^4$. Examples of the substituent include a halogen atom, hydroxy, $C_{1-6}$ alkoxy, $C_{1-6}$ alkyl and the like. Preferable examples of the substituent include 1 or 2 substituents selected from a halogen atom and $C_{1-6}$ alkyl, and more preferred is $C_{1-6}$ alkyl.

As ring Ab, preferred is a ring represented by the formula

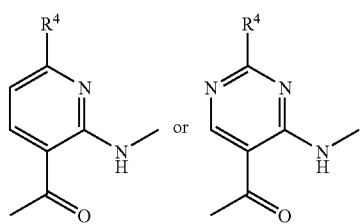

wherein $R^4$ is a hydrocarbon group optionally having substituent(s), a heterocyclic group optionally having substituent(s) excluding a cyclic amino optionally having substituent(s), mercapto optionally having a substituent or acyl.

In compound (B), $R^4$ is preferably (1) a hydrocarbon group optionally having substituent(s), (2) an aromatic heterocyclic group optionally having substituent(s), (3) mercapto optionally having a substituent and the like.

In compound (B), $R^4$ is more preferably (1) $C_{1-6}$ alkyl optionally having 1 to 3 halogen atoms, (2) $C_{6-14}$ aryl, (3) $C_{3-10}$ cycloalkyl, (4) a 5- or 6-membered aromatic heterocyclic group containing, as a ring-constituting atom besides carbon atom, 1 to 3 heteroatoms selected from an oxygen atom, a sulfur atom and a nitrogen atom (e.g., thienyl), (5) $C_{1-6}$ alkylthio and the like.

Ring Ac is preferably a 5- or 6-membered aromatic ring optionally having substituent(s).

Examples of the "5- or 6-membered aromatic ring" of the "5- or 6-membered aromatic ring optionally having substituent(s)" for ring Ac include (i) 5- or 6-membered aromatic heterocycle containing, as a ring-constituting atom besides carbon atom, 1 to 3 heteroatoms selected from an oxygen atom, a sulfur atom and a nitrogen atom, (ii) benzene and the like. Preferred is a 6-membered aromatic ring containing, as a ring-constituting atom besides carbon atom, 1 or 2 nitrogen atoms (e.g., pyridine, pyrimidine) and the like.

Examples of the "substituent" of the "5- or 6-membered aromatic ring optionally having substituent(s)" for ring Ac include (1) a hydrocarbon group optionally having substituent(s), (2) a heterocyclic group optionally having substituent(s), (3) mercapto optionally having a substituent, (4) acyl and the like.

Ring Ac is more preferably a ring represented by the formula

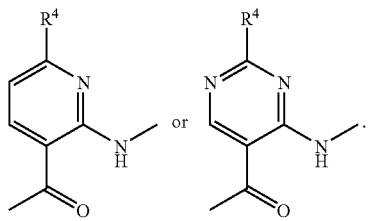

Ring Ac is further preferably a ring represented by the formula

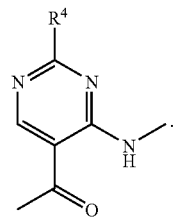

$R^4$ in compound (C) is preferably (1) a hydrocarbon group optionally having substituent(s), (2) a heterocyclic group optionally having substituent(s), (3) mercapto optionally having a substituent and the like.

$R^4$ in compound (C) is more preferably (1) $C_{1-6}$ alkyl optionally having 1 to 3 halogen atoms, (2) $C_{6-14}$ aryl, (3) $C_{3-10}$ cycloalkyl, (4) a 5- or 6-membered aromatic heterocyclic group containing, as a ring-constituting atom besides carbon atom, 1 to 3 heteroatoms selected from an oxygen atom, a sulfur atom and a nitrogen atom (e.g., thienyl), (5) $C_{1-6}$ alkylthio and the like.

$R^4$ in compound (C) is further preferably $C_{1-6}$ alkyl optionally having 1 to 3 halogen atoms, and particularly preferably $C_{1-6}$ alkyl.

Preferable examples of compound (1) are as described below.

[Compound I-1]

A compound represented by the formula (I) wherein $R^1$ and $R^2$ are each (1) $C_{1-6}$ alkyl optionally having 1 to 3 substituents selected from cyano and hydroxy, (2) $C_{3-10}$ cycloalkyl (e.g., cyclopropyl, cyclohexyl), (3) $C_{7-16}$ aralkyl (e.g., benzyl), or (4) a group represented by the formula

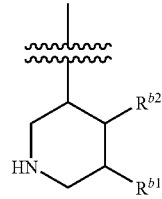

wherein $R^{b1}$ and $R^{b2}$ are each (1) a hydrogen atom, (2) $C_{1-6}$ alkyl optionally having 1 to 3 hydroxy, (3) $C_{1-6}$ alkoxy-carbonyl, or
(4) a group represented by the formula: —CO—N($R^6$)($R^6$)
wherein $R^5$ and $R^6$ are each a hydrogen atom or $C_{1-6}$ alkyl, or $R^5$ and $R^6$ optionally form, together with the nitrogen atom bonded thereto, a 5- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., pyrrolidine, piperidine, piperazine, morpholine, thiomorpholine), and optionally having 1 to 3 substituents selected from hydroxy and $C_{1-6}$ alkyl, or $R^1$ and $R^2$ optionally form, together with the nitrogen atom bonded thereto, a 5- to 9-membered (preferably 5- to 7-membered, more preferably 5- or 6-membered) nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., pyrrolidine, piperidine, piperazine, morpholine, thiomorpholine, azepane, azocane, azonane, 1,4-diazepane), and optionally having 1 to 3 substituents selected from
(1) $C_{1-6}$ alkyl optionally having 1 to 3 substituents selected from
 (a) hydroxy,
 (b) $C_{1-6}$ alkoxy,
 (c) $C_{6-14}$ aryl (e.g., phenyl),
 (d) amino,
 (e) mono- or di-$C_{1-6}$ alkylamino,
 (f) $C_{7-16}$ aralkylamino (e.g., benzylamino), and
 (g) $C_{1-6}$ alkoxy-carbonylamino (e.g., tert-butoxycarbonylamino),
(2) $C_{6-14}$ aryl (e.g., phenyl) optionally having 1 to 3 halogen atoms,
(3) $C_{7-16}$ aralkyl (e.g., benzyl, phenethyl),
(4) $C_{3-10}$ cycloalkyl (e.g., cyclohexyl),
(5) amino,
(6) hydroxy,
(7) $C_{1-6}$ alkoxy-carbonyl (e.g., tert-butoxycarbonyl), and
(8) carbamoyl;
$R^3$ is
(1) a 5- or 6-membered aromatic or nonaromatic heterocyclic group containing, as a ring-constituting atom besides carbon atom, 1 to 4 heteroatoms selected from an oxygen atom, a sulfur atom and a nitrogen atom (e.g., furyl, thienyl, oxazolyl, pyridyl, tetrahydrofuryl), and optionally having 1 to 3 $C_{1-6}$ alkyl,
(2) $C_{6-14}$ aryl (e.g., phenyl),
(3) $C_{3-10}$ cycloalkyl (e.g., cyclopropyl),
(4) $C_{1-6}$ alkyl optionally having 1 to 3 substituents selected from $C_{1-6}$ alkoxy and $C_{1-6}$ alkylthio, or
(5) $C_{1-6}$ alkoxy-carbonyl; and
ring A is a ring represented by the formula

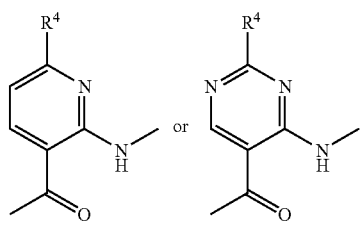

wherein $R^4$ is
(1) $C_{1-6}$ alkyl optionally having 1 to 3 halogen atoms,
(2) $C_{6-14}$ aryl (e.g., phenyl),
(3) $C_{3-10}$ cycloalkyl (e.g., cyclopropyl),
(4) a 5- or 6-membered aromatic heterocyclic group containing, as a ring-constituting atom besides carbon atom, 1 to 3 heteroatoms selected from an oxygen atom, a sulfur atom and a nitrogen atom (e.g., thienyl), or
(5) $C_{1-6}$ alkylthio, and ring A optionally further has 1 or 2 $C_{1-6}$ alkyl in addition to $R^4$, or a salt thereof.
[Compound I-2]
A compound represented by the formula (I)
wherein $R^1$ and $R^2$ are each
(1) $C_{1-6}$ alkyl optionally having 1 to 3 substituents selected from
 (a) a halogen atom,
 (b) cyano,
 (c) hydroxy,
 (d) amino,
 (e) $C_{1-6}$ alkoxy-carbonyl,
 (f) carbamoyl,
 (g) $C_{1-6}$ alkylcarbamoyl optionally having 1 to 3 substituents selected from hydroxy and a heterocyclic group (preferably a 5- or 6-membered heterocyclic group containing, as a ring-constituting atom besides carbon atom, 1 to 4 heteroatoms selected from an oxygen atom, a sulfur atom and a nitrogen atom, e.g., pyridyl, morpholinyl), and
 (h) $C_{7-16}$ aralkylcarbamoyl (e.g., benzylcarbamoyl),
(2) $C_{3-10}$ cycloalkyl (e.g., cyclopropyl, cyclohexyl),
(3) $C_{7-16}$ aralkyl (e.g., benzyl),
(4) $C_{3-10}$ cycloalkyl-$C_{1-6}$ alkyl (e.g., cyclopropylmethyl),
(5) a group represented by the formula

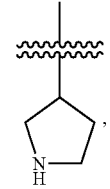

or
(6) a group represented by the formula

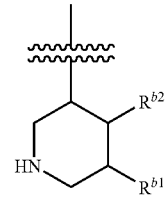

wherein $R^{b2}$ is a hydrogen atom, and
$R^{b1}$ is
(1') a hydrogen atom,
(2') cyano,
(3') $C_{1-6}$ alkyl optionally having 1 to 3 substituents selected from
 (a) hydroxy,
 (b) $C_{1-6}$ alkyl-carbonyloxy,
 (c) $C_{1-6}$ alkylthio, and
 (d) $C_{1-6}$ alkylsulfonyl,
(4') $C_{3-10}$ cycloalkyl (e.g., cyclohexyl) optionally having 1 to 3 hydroxy, (5') C$_{7-16}$ aralkylamino (e.g., phenethylamino) optionally having 1 to 3 hydroxy,
(6') C$_{1-6}$ alkoxy-carbonylamino,
(7') C$_{7-16}$ aralkyloxy-carbonylamino (e.g., benzyloxycarbonylamino),
(8') C$_{1-6}$ alkyl-carbonylamino,
(9') C$_{3-10}$ cycloalkyl-carbonylamino (e.g., cyclohexylcarbonylamino) optionally having 1 to 3 substituents selected from hydroxy and C$_{1-6}$ alkoxy,
(10') C$_{1-6}$ alkylsulfonylamino,
(11') C$_{6-14}$ arylsulfonylamino (e.g., phenylsulfonylamino),
(12') C$_{1-6}$ alkylaminocarbonylamino,
(13') C$_{6-14}$ arylaminocarbonylamino (e.g., phenylaminocarbonylamino),
(14') C$_{1-6}$ alkyl-carbonyl,
(15') C$_{3-10}$ cycloalkyl-carbonyl (e.g., cyclopropylcarbonyl),
(16') carboxy,
(17') a group represented by the formula: —W$^1$—R$^7$
wherein W$^1$ is a bond, —CH$_2$—, —CH$_2$O—, —NHCO— or —NHSO$_2$—, and
R$^7$ is a 5- or 6-membered heterocyclic group containing, as a ring-constituting atom besides carbon atom, 1 to 4 heteroatoms selected from an oxygen atom, a sulfur atom and a nitrogen atom (e.g., imidazolyl, morpholinyl, pyridyl, tetrahydropyranyl, piperidinyl, tetrazolyl, 4,5-dihydro-1,2,4-oxadiazolyl, 1,2,4-triazolyl, 1,3,4-oxadiazolyl, 1,2,4-oxadiazolyl, imidazolidinyl, hexahydropyrimidinyl, pyrazolyl), said 5- or 6-membered heterocyclic group optionally has 1 to 3 substituents selected from
(a) oxo,
(b) C$_{1-6}$ alkyl optionally having 1 to 3 hydroxy,
(c) C$_{6-14}$ aryl,
(d) carbamoyl, and
(e) C$_{1-6}$ alkoxy-carbonyl,
(18') C$_{1-6}$ alkoxy-carbonyl, or
(19') a group represented by the formula: —CO—N(R$^5$)(R$^6$)
wherein R$^5$ and R$^6$ are each a hydrogen atom, C$_{1-6}$ alkyl or C$_{1-6}$ alkoxy, or
R$^5$ and R$^6$ optionally form, together with the nitrogen atom bonded thereto, a 4- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom, said 4- to 7-membered nonaromatic nitrogen-containing heterocycle optionally forms a fused ring with a benzene ring, a cyclohexane ring or an oxazole ring, or optionally forms a spiro ring with a 1,3-dioxolane ring (e.g., azetidine, pyrrolidine, piperidine, piperazine, morpholine, thiomorpholine, 1,4-oxazepane, 1,2,3,4-tetrahydroquinoline, 1,2,3,4-tetrahydroisoquinoline, 2,3-dihydro-1H-isoindole, 2,3-dihydro-1H-indole, decahydroquinoline, 4,5,6,7-tetrahydro[1,3]oxazolo[5,4-b]pyridine, 1,4-dioxa-8-azaspiro[4.5]decane, 1,2,3,6-tetrahydropyridine), said 4- to 7-membered nonaromatic nitrogen-containing heterocycle, a fused ring thereof and a spiro ring thereof optionally have 1 to 3 substituents selected from
(a) oxo,
(b) a halogen atom,
(c) C$_{1-6}$ alkyl optionally having 1 to 3 substituents selected from hydroxy and C$_{1-6}$ alkoxy,
(d) C$_{6-14}$ aryl (e.g., phenyl) optionally having 1 to 3 C$_{1-6}$ alkoxy,
(e) C$_{7-16}$ aralkyl (e.g., benzyl),
(f) hydroxy,
(g) C$_{1-6}$ alkoxy,
(h) C$_{6-14}$ aryloxy (e.g., phenoxy),
(i) C$_{7-16}$ aralkyloxy (e.g., benzyloxy),
(j) C$_{1-6}$ alkyl-carbonyl,
(k) C$_{6-14}$ aryl-carbonyl (e.g., benzoyl),
(l) mono- or di-C$_{1-6}$ alkylsulfamoyl,
(m) C$_{1-6}$ alkylsulfonyl, and
(n) a 5- or 6-membered heterocyclic group containing, as a ring-constituting atom besides carbon atom, 1 to 4 heteroatoms selected from an oxygen atom, a sulfur atom and a nitrogen atom (e.g., pyridyl, thiazolyl), or R$^{b1}$ and R$^{b2}$ optionally form, together with the carbon atoms bonded thereto, a benzene ring or a cyclohexane ring, or R$^1$ and R$^2$ optionally form, together with the nitrogen atom bonded thereto, a 5- to 9-membered (preferably 5- to 7-membered, more preferably 5- or 6-membered) nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., pyrrolidine, piperidine, piperazine, morpholine, thiomorpholine, azepane, azocane, azonane, 1,4-diazepane), and optionally having 1 to 3 substituents selected from (1) C$_{1-6}$ alkyl optionally having 1 to 3 substituents selected from
(a) hydroxy,
(b) C$_{1-6}$ alkoxy,
(c) C$_{6-14}$ aryl (e.g., phenyl),
(d) amino,
(e) mono- or di-C$_{1-6}$ alkylamino,
(f) C$_{7-16}$ aralkylamino (e.g., benzylamino), and
(g) C$_{1-6}$ alkoxy-carbonylamino (e.g., tert-butoxycarbonylamino),
(2) C$_{6-14}$ aryl (e.g., phenyl) optionally having 1 to 3 halogen atoms,
(3) C$_{7-16}$ aralkyl (e.g., benzyl, phenethyl),
(4) C$_{3-10}$ cycloalkyl (e.g., cyclohexyl),
(5) amino,
(6) hydroxy,
(7) C$_{1-6}$ alkoxy-carbonyl (e.g., tert-butoxycarbonyl), and
(8) carbamoyl;

R$^3$ is
(1) a 5- or 6-membered aromatic or nonaromatic heterocyclic group containing, as a ring-constituting atom besides carbon atom, 1 to 4 heteroatoms selected from an oxygen atom, a sulfur atom and a nitrogen atom (e.g., furyl, thienyl, oxazolyl, pyridyl, tetrahydrofuryl), and optionally having 1 to 3 C$_{1-6}$ alkyl,
(2) C$_{6-14}$ aryl (e.g., phenyl),
(3) C$_{3-10}$ cycloalkyl (e.g., cyclopropyl),
(4) C$_{1-6}$ alkyl optionally having 1 to 3 substituents selected from
(a) hydroxy,
(b) C$_{1-6}$ alkoxy,
(c) C$_{1-6}$ alkylthio,
(d) C$_{1-6}$ alkylsulfinyl, and
(e) C$_{1-6}$ alkylsulfonyl, or (5) $C_{1-6}$ alkoxy-carbonyl; and ring A is a heterocycle represented by the formula

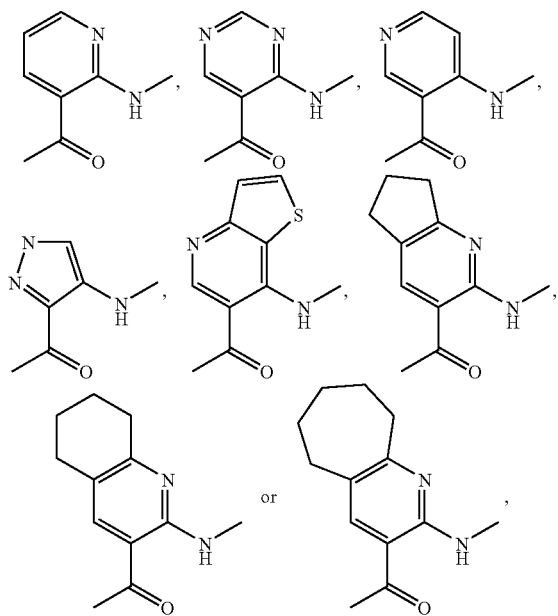

said heterocycle optionally has 1 to 3 substituents selected from
(1) a halogen atom,
(2) $C_{1-6}$ alkyl optionally having 1 to 3 halogen atoms,
(3) $C_{6-14}$ aryl (e.g., phenyl),
(4) $C_{3-10}$ cycloalkyl (e.g., cyclopropyl),
(5) a 5- or 6-membered aromatic heterocyclic group containing, as a ring-constituting atom besides carbon atom, 1 to 3 heteroatoms selected from an oxygen atom, a sulfur atom and a nitrogen atom (e.g., thienyl), and
(6) $C_{1-6}$ alkylthio, or a salt thereof.

Preferable examples of compound (A) are as described below.

[Compound A-1]

A compound of the formula (A)
wherein $R^{1a}$ is $C_{1-6}$ alkyl;
$R^{3a}$ is a 5- or 6-membered aromatic group optionally having substituent(s);
ring Aa is a 5- or 6-membered aromatic ring optionally having substituent(s); and
ring B is a ring represented by the formula

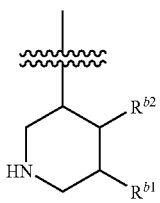

wherein $R^{b1}$ and $R^{b2}$ are each a hydrogen atom or a substituent, or $R^{b1}$ and $R^{b2}$ optionally form, together with the carbon atoms bonded thereto, a 5- to 7-membered ring optionally having substituent(s), or a salt thereof.

[Compound A-2]

A compound represented by the formula (A)
wherein $R^{1a}$ is $C_{1-6}$ alkyl;
$R^{3a}$ is a 5-membered aromatic heterocyclic group containing, as a ring-constituting atom besides carbon atom, 1 to 4 heteroatoms selected from an oxygen atom, a sulfur atom and a nitrogen atom (e.g., furyl), or phenyl;
ring Aa is a ring represented by the formula

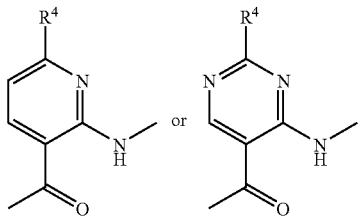

wherein $R^4$ is $C_{1-6}$ alkyl; and
ring B is a ring represented by the formula

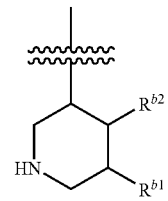

wherein $R^{b1}$ and $R^{b2}$ are each
(1) a hydrogen atom,
(2) $C_{1-6}$ alkyl optionally having 1 to 3 hydroxy,
(3) $C_{1-6}$ alkoxy-carbonyl, or
(4) a group represented by the formula: —CO—N($R^5$)($R^6$)
wherein $R^5$ and $R^6$ are each a hydrogen atom or $C_{1-6}$ alkyl, or $R^5$ and $R^6$ optionally form, together with the nitrogen atom bonded thereto, a 5- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., pyrrolidine, piperidine, piperazine, morpholine, thiomorpholine), and optionally having 1 to 3 substituents selected from hydroxy and $C_{1-6}$ alkyl, or a salt thereof.

[Compound A-3]

A compound represented by the formula (A)
wherein $R^{1a}$ is $C_{1-6}$ alkyl optionally having $C_{3-10}$ cycloalkyl;
$R^{3a}$ is a 5- or 6-membered aromatic heterocyclic group containing, as a ring-constituting atom besides carbon atom, 1 to 4 heteroatoms selected from an oxygen atom, a sulfur atom and a nitrogen atom (e.g., furyl, oxazolyl, thienyl, pyridyl), or phenyl;
ring Aa is a heterocycle represented by the formula

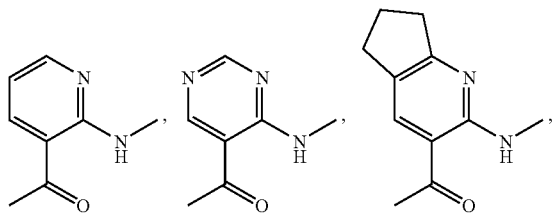

-continued

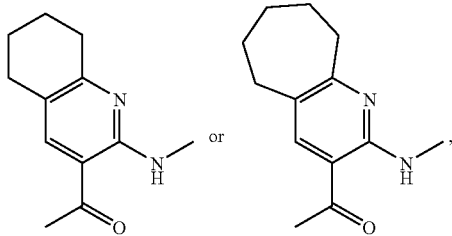

said heterocycle optionally has 1 to 3 $C_{1-6}$ alkyl optionally having 1 to 3 halogen atoms; and
ring B is
(1) a ring represented by the formula

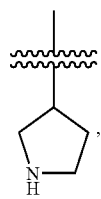

or
(2) a ring represented by the formula

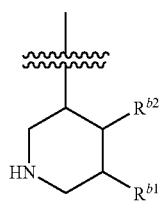

wherein $R^{b2}$ is a hydrogen atom, and
$R^{b1}$ is
(1') a hydrogen atom,
(2') cyano,
(3') $C_{1-6}$ alkyl optionally having 1 to 3 substituents selected from
  (a) hydroxy,
  (b) $C_{1-6}$ alkyl-carbonyloxy,
  (c) $C_{1-6}$ alkylthio, and
  (d) $C_{1-6}$ alkylsulfonyl,
(4') $C_{1-6}$ alkoxy-carbonylamino,
(5') $C_{7-16}$ aralkyloxy-carbonylamino (e.g., benzyloxycarbonylamino),
(6') $C_{1-6}$ alkyl-carbonylamino,
(7') $C_{3-10}$ cycloalkyl-carbonylamino (e.g., cyclohexylcarbonylamino) optionally having 1 to 3 substituents selected from hydroxy and $C_{1-6}$ alkoxy,
(8') a group represented by the formula: —$W^2$—$R^8$
wherein $W^2$ is a bond, —$CH_2$—, —$CH_2O$— or —NHCO—, and
$R^8$ is a 5- or 6-membered heterocyclic group containing, as a ring-constituting atom besides carbon atom, 1 to 4 heteroatoms selected from an oxygen atom, a sulfur atom and a nitrogen atom (e.g., imidazolyl, morpholinyl, pyridyl, tetrahydropyranyl, piperidinyl, tetrazolyl, 4,5-dihydro-1,2,4-oxadiazolyl, 1,2,4-triazolyl, 1,3,4-oxadiazolyl, 1,2,4-oxadiazolyl), said 5- or 6-membered heterocyclic group optionally has 1 to 3 substituents selected from
  (a) oxo,
  (b) $C_{1-6}$ alkyl optionally having 1 to 3 hydroxy,
  (c) $C_{6-14}$ aryl, and
  (d) carbamoyl,
(9') $C_{1-6}$ alkoxy-carbonyl, or
(10') a group represented by the formula: —CO—N($R^5$)($R^6$)
wherein $R^5$ and $R^6$ are each a hydrogen atom or $C_{1-6}$ alkyl, or
$R^5$ and $R^6$ optionally form, together with the nitrogen atom bonded thereto, a 4- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., azetidine, pyrrolidine, piperidine, piperazine, morpholine, thiomorpholine), and optionally having 1 to 3 substituents selected from hydroxy and $C_{1-6}$ alkyl, or
$R^{b1}$ and $R^{b2}$ optionally form, together with the carbon atoms bonded thereto, a benzene ring or a cyclohexane ring, or a salt thereof.

[Compound A-4]
A compound represented by the formula (A)
wherein $R^{1a}$ is $C_{1-6}$ alkyl;
$R^{1a}$ is a 5-membered aromatic heterocyclic group containing, as a ring-constituting atom besides carbon atom, 1 to 4 heteroatoms selected from an oxygen atom, a sulfur atom and a nitrogen atom (e.g., furyl, oxazolyl, thienyl); ring Aa is a ring represented by the formula

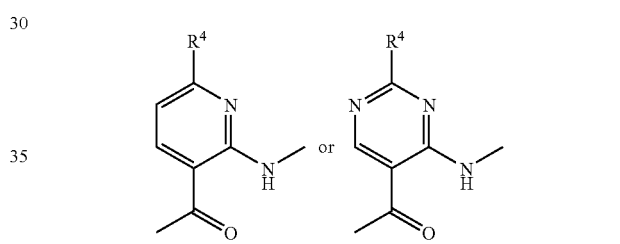

wherein $R^4$ is $C_{1-6}$ alkyl optionally having 1 to 3 halogen atoms; and
ring B is a ring represented by the formula

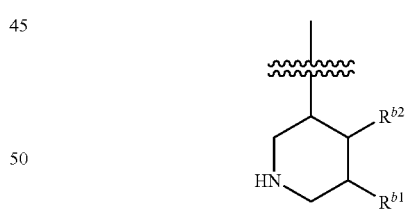

wherein $R^{b2}$ is a hydrogen atom, and
$R^{b1}$ is
(1) a hydrogen atom,
(2) cyano,
(3) $C_{1-6}$ alkyl optionally having 1 to 3 substituents selected from
  (a) hydroxy,
  (b) $C_{1-6}$ alkyl-carbonyloxy,
  (c) $C_{1-6}$ alkylthio, and
  (d) $C_{1-6}$ alkylsulfonyl,
(4) $C_{1-6}$ alkoxy-carbonylamino,
(5) $C_{7-16}$ aralkyloxy-carbonylamino (e.g., benzyloxycarbonylamino),
(6) $C_{1-6}$ alkyl-carbonylamino, (7) $C_{3-10}$ cycloalkyl-carbonylamino (e.g., cyclohexylcarbonylamino) optionally having 1 to 3 substituents selected from hydroxy and $C_{1-6}$ alkoxy,
(8) a group represented by the formula: —$W^2$—$R^8$
wherein $W^2$ is a bond, —$CH_2$—, —$CH_2O$— or —NHCO—, and
$R^8$ is a 5- or 6-membered heterocyclic group containing, as a ring-constituting atom besides carbon atom, 1 to 4 heteroatoms selected from an oxygen atom, a sulfur atom and a nitrogen atom (e.g., imidazolyl, morpholinyl, pyridyl, tetrahydropyranyl, piperidinyl, tetrazolyl, 4,5-dihydro-1,2,4-oxadiazolyl, 1,2,4-triazolyl, 1,3,4-oxadiazolyl, 1,2,4-oxadiazolyl), said 5- or 6-membered heterocyclic group optionally has 1 to 3 substituents selected from
  (a) oxo,
  (b) $C_{1-6}$ alkyl optionally having 1 to 3 hydroxy,
  (c) $C_{6-14}$ aryl, and
  (d) carbamoyl,
(9) $C_{1-6}$ alkoxy-carbonyl, or
(10) a group represented by the formula: —CO—N($R^5$)($R^6$)
wherein $R^5$ and $R^6$ are each a hydrogen atom or $C_{1-6}$ alkyl, or
$R^5$ and $R^6$ optionally form, together with the nitrogen atom bonded thereto, a 4- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., azetidine, pyrrolidine, piperidine, piperazine, morpholine, thiomorpholine), and optionally having 1 to 3 substituents selected from hydroxy and $C_{1-6}$ alkyl, or
$R^{b1}$ and $R^{b2}$ optionally form, together with the carbon atoms bonded thereto, a benzene ring or a cyclohexane ring, or a salt thereof.

[Compound A-5]
A compound represented by the formula (A)
wherein $R^{1a}$ is $C_{1-6}$ alkyl;
$R^{3a}$ is a 5-membered aromatic heterocyclic group containing, as a ring-constituting atom besides carbon atom, 1 to 4 heteroatoms selected from an oxygen atom, a sulfur atom and a nitrogen atom (e.g., furyl, oxazolyl, thienyl); ring Aa is a ring represented by the formula

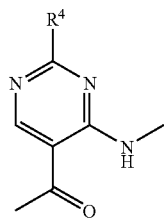

wherein $R^4$ is $C_{1-6}$ alkyl; and
ring B is a ring represented by the formula

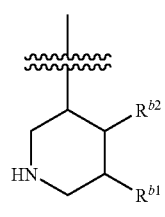

wherein $R^{b2}$ is a hydrogen atom, and
$R^{b1}$ is a group represented by the formula: —CO—N($R^5$)($R^6$)
wherein $R^5$ and $R^6$ are each a hydrogen atom or $C_{1-6}$ alkyl, or $R^5$ and $R^6$ optionally form, together with the nitrogen atom bonded thereto, a 4- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., azetidine, pyrrolidine, piperidine, piperazine, morpholine, thiomorpholine), and optionally having 1 to 3 substituents selected from hydroxy and $C_{1-6}$ alkyl, or a salt thereof.

Preferable examples of compound (B) are as described below.
[Compound B-1]
A compound represented by the formula (B)
wherein $R^{1b}$ and $R^{2b}$ form, together with the nitrogen atom bonded thereto, piperidine optionally having substituent(s) or piperazine optionally having substituent(s);
$R^{3b}$ is furyl, thienyl or oxazolyl, each of which optionally has substituent(s); and
m ring Ab is a ring represented by the formula

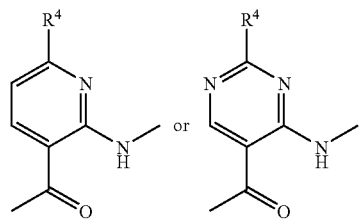

wherein $R^4$ is a hydrocarbon group optionally having substituent(s) or a heterocyclic group optionally having substituent(s), excluding a cyclic amino optionally having substituent(s), or a salt thereof.

[Compound B-2]
A compound represented by the formula (B)
wherein $R^{1b}$ and $R^{2b}$ are each
(1) $C_{1-6}$ alkyl optionally having 1 to 3 substituents selected from cyano and hydroxy,
(2) $C_{3-10}$ cycloalkyl (e.g., cyclopropyl, cyclohexyl), or
(3) $C_{7-16}$ aralkyl (e.g., benzyl), or
$R^{1b}$ and $R^{2b}$ optionally form, together with the nitrogen atom bonded thereto, a 5- to 9-membered (preferably 5- to 7-membered, more preferably 5- or 6-membered) nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., pyrrolidine, piperidine, piperazine, morpholine, thiomorpholine, azepane, azocane, azonane, 1,4-diazepane), and optionally having 1 to 3 substituents selected from
(1) $C_{1-6}$ alkyl optionally having 1 to 3 substituents selected from
  (a) hydroxy,
  (b) $C_{1-6}$ alkoxy,
  (c) $C_{6-14}$ aryl (e.g., phenyl),
  (d) amino,
  (e) mono- or di-$C_{1-6}$ alkylamino,
  (f) $C_{7-16}$ aralkylamino (e.g., benzylamino), and
  (g) $C_{1-6}$ alkoxy-carbonylamino (e.g., tert-butoxycarbonylamino), (2) C$_{6-14}$ aryl (e.g., phenyl) optionally having 1 to 3 halogen atoms,
(3) C$_{7-16}$ aralkyl (e.g., benzyl, phenethyl),
(4) C$_{3-10}$ cycloalkyl (e.g., cyclohexyl),
(5) amino,
(6) hydroxy,
(7) C$_{1-6}$ alkoxy-carbonyl (e.g., tert-butoxycarbonyl), and
(8) carbamoyl;

R$^{3b}$ is
(1) a 5- or 6-membered aromatic or nonaromatic heterocyclic group containing, as a ring-constituting atom besides carbon atom, 1 to 4 heteroatoms selected from an oxygen atom, a sulfur atom and a nitrogen atom (e.g., furyl, thienyl, oxazolyl, pyridyl, tetrahydrofuryl), and optionally having 1 to 3 C$_{1-6}$ alkyl,
(2) C$_{6-14}$ aryl (e.g., phenyl),
(3) C$_{3-10}$ cycloalkyl (e.g., cyclopropyl),
(4) C$_{1-6}$ alkyl optionally having 1 to 3 C$_{1-6}$ alkoxy, or
(5) C$_{1-6}$ alkoxy-carbonyl;

R$^4$ is
(1) C$_{1-6}$ alkyl optionally having 1 to 3 halogen atoms,
(2) C$_{6-14}$ aryl (e.g., phenyl),
(3) C$_{3-10}$ cycloalkyl (e.g., cyclopropyl),
(4) a 5- or 6-membered aromatic heterocyclic group containing, as a ring-constituting atom besides carbon atom, 1 to 3 heteroatom selected from an oxygen atom, a sulfur atom and a nitrogen atom (e.g., thienyl), or
(5) C$_{1-6}$ alkylthio;

X is C;
Y is C or N; and
ring Ab is a nitrogen-containing 6-membered ring optionally further having 1 or 2 C$_{1-6}$ alkyl in addition to R$^4$, or a salt thereof.

[Compound B-3]
A compound represented by the formula (B) wherein R$^{1b}$ and R$^{2b}$ are each
(1) C$_{1-6}$ alkyl optionally having 1 to 3 substituents selected from
  (a) a halogen atom,
  (b) cyano,
  (c) hydroxy,
  (d) amino,
  (e) C$_{1-6}$ alkoxy-carbonyl,
  (f) carbamoyl,
  (g) C$_{1-6}$ alkylcarbamoyl optionally having 1 to 3 substituents selected from hydroxy and a heterocyclic group (preferably a 5- or 6-membered heterocyclic group containing, as a ring-constituting atom besides carbon atom, 1 to 4 heteroatoms selected from an oxygen atom, a sulfur atom and a nitrogen atom, e.g., pyridyl, morpholinyl), and
  (h) C$_{7-16}$ aralkylcarbamoyl (e.g., benzylcarbamoyl),
(2) C$_{3-10}$ cycloalkyl (e.g., cyclopropyl, cyclohexyl),
(3) C$_{7-16}$ aralkyl (e.g., benzyl),
(4) C$_{3-10}$ cycloalkyl-C$_{1-6}$ alkyl (e.g., cyclopropylmethyl),
(5) a group represented by the formula

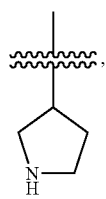

, or
(6) a group represented by the formula

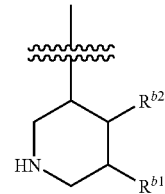

wherein R$^{b2}$ is a hydrogen atom, and
R$^{b1}$ is
(1') a hydrogen atom,
(2') cyano,
(3') C$_{1-6}$ alkyl optionally having 1 to 3 substituents selected from
  (a) hydroxy,
  (b) C$_{1-6}$ alkyl-carbonyloxy,
  (c) C$_{1-6}$ alkylthio, and
  (d) C$_{1-6}$ alkylsulfonyl,
(4') C$_{3-10}$ cycloalkyl (e.g., cyclohexyl) optionally having 1 to 3 hydroxy,
(5') C$_{7-16}$ aralkylamino (e.g., phenethylamino) optionally having 1 to 3 hydroxy,
(6') C$_{1-6}$ alkoxy-carbonylamino,
(7') C$_{7-16}$ aralkyloxy-carbonylamino (e.g., benzyloxycarbonylamino),
(8') C$_{1-6}$ alkyl-carbonylamino,
(9') C$_{3-10}$ cycloalkyl-carbonylamino (e.g., cyclohexylcarbonylamino) optionally having 1 to 3 substituents selected from hydroxy and C$_{1-6}$ alkoxy,
(10') C$_{1-6}$ alkylsulfonylamino,
(11') C$_{6-14}$ arylsulfonylamino (e.g., phenylsulfonylamino),
(12') C$_{1-6}$ alkylaminocarbonylamino,
(13') C$_{6-14}$ arylaminocarbonylamino (e.g., phenylaminocarbonylamino),
(14') C$_{1-6}$ alkyl-carbonyl,
(15') C$_{3-10}$ cycloalkyl-carbonyl (e.g., cyclopropylcarbonyl),
(16') carboxy,
(17') a group represented by the formula: —W$^1$—R$^7$
wherein W$^1$ is a bond, —CH$_2$—, —CH$_2$O—, —NHCO— or —NHSO$_2$—, and
R$^7$ is a 5- or 6-membered heterocyclic group containing, as a ring-constituting atom besides carbon atom, 1 to 4 heteroatoms selected from an oxygen atom, a sulfur atom and a nitrogen atom (e.g., imidazolyl, morpholinyl, pyridyl, tetrahydropyranyl, piperidinyl, tetrazolyl, 4,5-dihydro-1,2,4-oxadiazolyl, 1,2,4-triazolyl, 1,3,4-oxadiazolyl, 1,2,4oxadiazolyl, imidazolidinyl, hexahydropyrimidinyl, pyrazolyl), said 5- or 6-membered heterocyclic group optionally has 1 to 3 substituents selected from
  (a) oxo,
  (b) C$_{1-6}$ alkyl optionally having 1 to 3 hydroxy,
  (c) C$_{6-14}$ aryl,
  (d) carbamoyl, and
  (e) C$_{1-6}$ alkoxy-carbonyl,
(18') C$_{1-6}$ alkoxy-carbonyl, or
(19') a group represented by the formula: —CO—N(R$^6$)(R$^6$)
wherein R$^5$ and R$^6$ are each a hydrogen atom, C$_{1-6}$ alkyl or C$_{1-6}$ alkoxy, or
R$^5$ and R$^6$ optionally form, together with the nitrogen atom bonded thereto, a 4- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom, said 4- to 7-membered nonaromatic nitrogen-containing heterocycle optionally forms a fused ring with a benzene ring, a cyclohexane ring or an oxazole ring, or optionally forms a spiro ring with a 1,3-dioxolane ring (e.g., azetidine, pyrrolidine, piperidine, piperazine, morpholine, thiomorpholine, 1,4-oxazepane, 1,2,3,4-tetrahydroquinoline, 1,2,3,4-tetrahydroisoquinoline, 2,3-dihydro-1H-isoindole, 2,3-dihydro-1H-indole, decahydroquinoline, 4,5,6,7-tetrahydro[1,3]oxazolo[5,4-b]pyridine, 1,4-dioxa-8-azaspiro[4.5]decane, 1,2,3,6-tetrahydropyridine), said 4- to 7-membered nonaromatic nitrogen-containing heterocycle, a fused ring thereof and a spiro ring thereof optionally have 1 to 3 substituents selected from
(a) oxo,
(b) a halogen atom,
(c) $C_{1-6}$ alkyl optionally having 1 to 3 substituents selected from hydroxy and $C_{1-6}$ alkoxy,
(d) $C_{6-14}$ aryl (e.g., phenyl) optionally having 1 to 3 $C_{1-6}$ alkoxy,
(e) $C_{7-16}$ aralkyl (e.g., benzyl),
(f) hydroxy,
(g) $C_{1-6}$ alkoxy,
(h) $C_{6-14}$ aryloxy (e.g., phenoxy),
(i) $C_{7-16}$ aralkyloxy (e.g., benzyloxy),
(j) $C_{1-6}$ alkyl-carbonyl,
(k) $C_{6-14}$ aryl-carbonyl (e.g., benzoyl),
(l) mono- or di-$C_{1-6}$ alkylsulfamoyl,
(m) $C_{1-6}$ alkylsulfonyl, and
(n) a 5- or 6-membered heterocyclic group containing, as a ring-constituting atom besides carbon atom, 1 to 4 heteroatoms selected from an oxygen atom, a sulfur atom and a nitrogen atom (e.g., pyridyl, thiazolyl), or
$R^{b1}$ and $R^{b2}$ optionally form, together with the carbon atoms bonded thereto, a benzene ring or a cyclohexane ring, or
$R^{1b}$ and $R^{2b}$ optionally form, together with the nitrogen atom bonded thereto, a 5- to 9-membered (preferably 5- to 7-membered, more preferably 5- or 6-membered) nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., pyrrolidine, piperidine, piperazine, morpholine, thiomorpholine, azepane, azocane, azonane, 1,4-diazepane), and optionally having 1 to 3 substituents selected from
(1) $C_{1-6}$ alkyl optionally having 1 to 3 substituents selected from
(a) hydroxy,
(b) $C_{1-6}$ alkoxy,
(c) $C_{6-14}$ aryl (e.g., phenyl),
(d) amino,
(e) mono- or di-$C_{1-6}$ alkylamino,
(f) $C_{7-16}$ aralkylamino (e.g., benzylamino), and
(g) $C_{1-6}$ alkoxy-carbonylamino (e.g., tert-butoxycarbonylamino),
(2) $C_{6-14}$ aryl (e.g., phenyl) optionally having 1 to 3 halogen atoms,
(3) $C_{7-16}$ aralkyl (e.g., benzyl, phenethyl),
(4) $C_{3-10}$ cycloalkyl (e.g., cyclohexyl),
(5) amino,
(6) hydroxy,
(7) $C_{1-6}$ alkoxy-carbonyl (e.g., tert-butoxycarbonyl), and
(8) carbamoyl;
$R^{3b}$ is
(1) a 5- or 6-membered aromatic or nonaromatic heterocyclic group containing, as a ring-constituting atom besides carbon atom, 1 to 4 heteroatoms selected from an oxygen atom, a sulfur atom and a nitrogen atom (e.g., furyl, thienyl, oxazolyl, pyridyl, tetrahydrofuryl), and optionally having 1 to 3 $C_{1-6}$ alkyl,
(2) $C_{6-14}$ aryl (e.g., phenyl),
(3) $C_{3-10}$ cycloalkyl (e.g., cyclopropyl),
(4) $C_{1-6}$ alkyl optionally having 1 to 3 substituents selected from
(a) hydroxy,
(b) $C_{1-6}$ alkoxy,
(c) $C_{1-6}$ alkylthio,
(d) $C_{1-6}$ alkylsulfinyl, and
(e) $C_{1-6}$ alkylsulfonyl, or
(5) $C_{1-6}$ alkoxy-carbonyl;
$R^4$ is
(1) $C_{1-6}$ alkyl optionally having 1 to 3 halogen atoms,
(2) $C_{6-14}$ aryl (e.g., phenyl),
(3) $C_{3-10}$ cycloalkyl (e.g., cyclopropyl),
(4) a 5- or 6-membered aromatic heterocyclic group containing, as a ring-constituting atom besides carbon atom, 1 to 3 heteroatoms selected from an oxygen atom, a sulfur atom and a nitrogen atom (e.g., thienyl), or
(5) $C_{1-6}$ alkylthio;
X is C;
Y is C or N; and
ring Ab is a nitrogen-containing 6-membered ring optionally further having, in addition to $R^4$, 1 or 2 substituents selected from a halogen atom and $C_{1-6}$ alkyl, or a salt thereof.
[Compound B-4]
A compound represented by the formula (B) wherein $R^{1b}$ is
(1) $C_{1-6}$ alkyl optionally having 1 to 3 halogen atoms,
(2) $C_{3-10}$ cycloalkyl (e.g., cyclopropyl, cyclohexyl),
(3) $C_{7-16}$ aralkyl (e.g., benzyl), or
(4) $C_{3-10}$ cycloalkyl-$C_{1-6}$ alkyl (e.g., cyclopropylmethyl);
$R^{2b}$ is a group represented by the formula

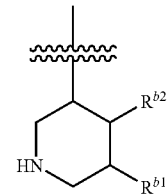

wherein $R^{b2}$ is a hydrogen atom, and
$R^{b1}$ is
(1') a hydrogen atom,
(2') cyano,
(3') $C_{1-6}$ alkyl optionally having 1 to 3 substituents selected from
(a) hydroxy,
(b) $C_{1-6}$ alkyl-carbonyloxy,
(c) $C_{1-6}$ alkylthio, and
(d) $C_{1-6}$ alkylsulfonyl,
(4') $C_{3-10}$ cycloalkyl (e.g., cyclohexyl) optionally having 1 to 3 hydroxy,
(5') $C_{7-16}$ aralkylamino (e.g., phenethylamino) optionally having 1 to 3 hydroxy,
(6') $C_{1-6}$ alkoxy-carbonylamino,
(7') $C_{7-16}$ aralkyloxy-carbonylamino (e.g., benzyloxycarbonylamino),
(8') $C_{1-6}$ alkyl-carbonylamino, (9') C$_{3-10}$ cycloalkyl-carbonylamino (e.g., cyclohexylcarbonylamino) optionally having 1 to 3 substituents selected from hydroxy and C$_{1-6}$ alkoxy,
(10') C$_{1-6}$ alkylsulfonylamino,
(11') C$_{6-14}$ arylsulfonylamino (e.g., phenylsulfonylamino),
(12') C$_{1-6}$ alkylaminocarbonylamino,
(13') C$_{6-14}$ arylaminocarbonylamino (e.g., phenylaminocarbonylamino),
(14') C$_{1-6}$ alkyl-carbonyl,
(15') C$_{3-10}$ cycloalkyl-carbonyl (e.g., cyclopropylcarbonyl),
(16') carboxy,
(17') a group represented by the formula: —W$^1$—R$^7$
wherein W$^1$ is a bond, —CH$_2$—, —CH$_2$O—, —NHCO— or —NHSO$_2$—, and
R$^7$ is a 5- or 6-membered heterocyclic group containing, as a ring-constituting atom besides carbon atom, 1 to 4 heteroatoms selected from an oxygen atom, a sulfur atom and a nitrogen atom (e.g., imidazolyl, morpholinyl, pyridyl, tetrahydropyranyl, piperidinyl, tetrazolyl, 4,5-dihydro-1,2,4-oxadiazolyl, 1,2,4-triazolyl, 1,3,4-oxadiazolyl, 1,2,4-oxadiazolyl, imidazolidinyl, hexahydropyrimidinyl, pyrazolyl), said 5- or 6-membered heterocyclic group optionally has 1 to 3 substituents selected from
(a) oxo,
(b) C$_{1-6}$ alkyl optionally having 1 to 3 hydroxy,
(c) C$_{6-14}$ aryl,
(d) carbamoyl, and
(e) C$_{1-6}$ alkoxy-carbonyl,
(18') C$_{1-6}$ alkoxy-carbonyl, or
(19') a group represented by the formula: —CO—N(R$^5$)(R$^6$)
wherein R$^5$ and R$^6$ are each a hydrogen atom, C$_{1-6}$ alkyl or C$_{1-6}$ alkoxy, or
R$^5$ and R$^6$ optionally form, together with the nitrogen atom bonded thereto, a 4- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom, said 4- to 7-membered nonaromatic nitrogen-containing heterocycle optionally forms a fused ring with a benzene ring, a cyclohexane ring or an oxazole ring, or optionally forms a spiro ring with a 1,3-dioxolane ring (e.g., azetidine, pyrrolidine, piperidine, piperazine, morpholine, thiomorpholine, 1,4-oxazepane, 1,2,3,4-tetrahydroquinoline, 1,2,3,4-tetrahydroisoquinoline, 2,3-dihydro-1H-isoindole, 2,3-dihydro-1H-indole, decahydroquinoline, 4,5,6,7-tetrahydro[1,3]oxazolo[5,4-b]pyridine, 1,4-dioxa-8-azaspiro[4.5]decane, 1,2,3,6-tetrahydropyridine), said 4- to 7-membered nonaromatic nitrogen-containing heterocycle, a fused ring thereof and a spiro ring thereof optionally have 1 to 3 substituents selected from
(a) oxo,
(b) a halogen atom,
(c) C$_{1-6}$ alkyl optionally having 1 to 3 substituents selected from hydroxy and C$_{1-6}$ alkoxy,
(d) C$_{6-14}$ aryl (e.g., phenyl) optionally having 1 to 3 C$_{1-6}$ alkoxy,
(e) C$_{7-16}$ aralkyl (e.g., benzyl),
(f) hydroxy,
(g) C$_{1-6}$ alkoxy,
(h) C$_{6-14}$ aryloxy (e.g., phenoxy),
(i) C$_{7-16}$ aralkyloxy (e.g., benzyloxy),
(j) C$_{1-6}$ alkyl-carbonyl,
(k) C$_{6-14}$ aryl-carbonyl (e.g., benzoyl),
(l) mono- or di-C$_{1-6}$ alkylsulfamoyl,
(m) C$_{1-6}$ alkylsulfonyl, and
(n) a 5- or 6-membered heterocyclic group containing, as a ring-constituting atom besides carbon atom, 1 to 4 heteroatoms selected from an oxygen atom, a sulfur atom and a nitrogen atom (e.g., pyridyl, thiazolyl), or
R$^{b1}$ and R$^{b2}$ optionally form, together with the carbon atoms bonded thereto, a benzene ring or a cyclohexane ring;
R$^{3b}$ is
(1) a 5- or 6-membered aromatic or nonaromatic heterocyclic group containing, as a ring-constituting atom besides carbon atom, 1 to 4 heteroatoms selected from an oxygen atom, a sulfur atom and a nitrogen atom (e.g., furyl, thienyl, oxazolyl, pyridyl, tetrahydrofuryl), and optionally having 1 to 3 C$_{1-6}$ alkyl,
(2) C$_{6-14}$ aryl (e.g., phenyl),
(3) C$_{3-10}$ cycloalkyl (e.g., cyclopropyl),
(4) C$_{1-6}$ alkyl optionally having 1 to 3 substituents selected from
(a) hydroxy,
(b) C$_{1-6}$ alkoxy,
(c) C$_{1-6}$ alkylthio,
(d) C$_{1-6}$ alkylsulfinyl, and
(e) C$_{1-6}$ alkylsulfonyl, or
(5) C$_{1-6}$ alkoxy-carbonyl;
R$^4$ is
(1) C$_{1-6}$ alkyl optionally having 1 to 3 halogen atoms,
(2) C$_{6-14}$ aryl (e.g., phenyl), or
(3) C$_{3-10}$ cycloalkyl (e.g., cyclopropyl); and ring Ab is a ring represented by the formula

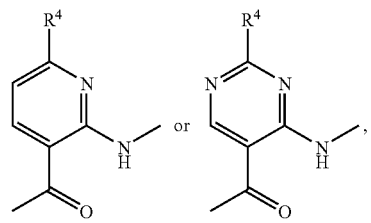

or a salt thereof.
[Compound B-5]
A compound represented by the formula (B)
wherein R$^{1b}$ and R$^{2b}$ form, together with the nitrogen atom bonded thereto, a 5- to 9-membered (preferably 5- to 7-membered, more preferably 5- or 6-membered) nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., pyrrolidine, piperidine, piperazine, morpholine, thiomorpholine, azepane, azocane, azonane, 1,4-diazepane), and optionally having 1 to 3 substituents selected from
(1) C$_{1-6}$ alkyl optionally having 1 to 3 substituents selected from
(a) hydroxy,
(b) C$_{1-6}$ alkoxy,
(c) C$_{6-14}$ aryl (e.g., phenyl),
(d) amino,
(e) mono- or di-C$_{1-6}$ alkylamino,
(f) C$_{7-16}$ aralkylamino (e.g., benzylamino), and
(g) C$_{1-6}$ alkoxy-carbonylamino (e.g., tert-butoxycarbonylamino),
(2) C$_{6-14}$ aryl (e.g., phenyl) optionally having 1 to 3 halogen atoms,
(3) C$_{7-16}$ aralkyl (e.g., benzyl, phenethyl),
(4) C$_{3-10}$ cycloalkyl (e.g., cyclohexyl), (5) amino,
(6) hydroxy,
(7) $C_{1-6}$ alkoxy-carbonyl (e.g., tert-butoxycarbonyl), and
(8) carbamoyl;
$R^{3b}$ is
(1) a 5- or 6-membered aromatic or nonaromatic heterocyclic group containing, as a ring-constituting atom besides carbon atom, 1 to 4 heteroatoms selected from an oxygen atom, a sulfur atom and a nitrogen atom (e.g., furyl, thienyl, oxazolyl, pyridyl, tetrahydrofuryl), and optionally having 1 to 3 $C_{1-6}$ alkyl,
(2) $C_{6-14}$ aryl (e.g., phenyl),
(3) $C_{3-10}$ cycloalkyl (e.g., cyclopropyl),
(4) $C_{1-6}$ alkyl optionally having 1 to 3 $C_{1-6}$ alkoxy, or
(5) $C_{1-6}$ alkoxy-carbonyl;
$R^4$ is
(1) $C_{1-6}$ alkyl optionally having 1 to 3 halogen atoms,
(2) $C_{6-14}$ aryl (e.g., phenyl), or
(3) $C_{3-10}$ cycloalkyl (e.g., cyclopropyl); and
ring Ab is a ring represented by the formula

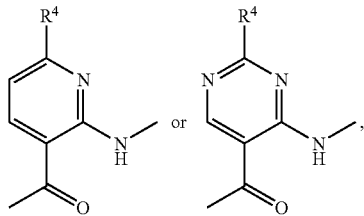

or a salt thereof.
[Compound B-6]
A compound represented by the formula

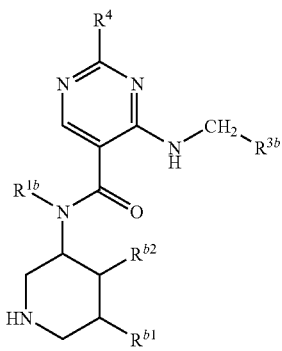

wherein $R^{1b}$ is $C_{1-6}$ alkyl optionally having 1 to 3 halogen atoms;
$R^{b2}$ is a hydrogen atom,
$R^{b1}$ is
(1) a hydrogen atom,
(2) cyano,
(3) $C_{1-6}$ alkyl optionally having 1 to 3 substituents selected from
  (a) hydroxy,
  (b) $C_{1-6}$ alkyl-carbonyloxy,
  (c) $C_{1-6}$ alkylthio, and
  (d) $C_{1-6}$ alkylsulfonyl,
(4) $C_{3-10}$ cycloalkyl (e.g., cyclohexyl) optionally having 1 to 3 hydroxy,
(5) $C_{7-16}$ aralkylamino (e.g., phenethylamino) optionally having 1 to 3 hydroxy,
(6) $C_{1-6}$ alkoxy-carbonylamino,
(7) $C_{7-16}$ aralkyloxy-carbonylamino (e.g., benzyloxycarbonylamino),
(8) $C_{1-6}$ alkyl-carbonylamino,
(9) $C_{3-10}$ cycloalkyl-carbonylamino (e.g., cyclohexylcarbonylamino) optionally having 1 to 3 substituents selected from hydroxy and $C_{1-6}$ alkoxy,
(10) $C_{1-6}$ alkylsulfonylamino,
(11) $C_{6-14}$ arylsulfonylamino (e.g., phenylsulfonylamino),
(12) $C_{1-6}$ alkylaminocarbonylamino,
(13) $C_{6-14}$ arylaminocarbonylamino (e.g., phenylaminocarbonylamino),
(14) $C_{1-6}$ alkyl-carbonyl,
(15) $C_{3-10}$ cycloalkyl-carbonyl (e.g., cyclopropylcarbonyl),
(16) carboxy,
(17) a group represented by the formula: —$W^1$—$R^7$
wherein $W^1$ is a bond, —$CH_2$—, —$CH_2O$—, —NHCO— or —$NHSO_2$—, and
$R^7$ is a 5- or 6-membered heterocyclic group containing, as a ring-constituting atom besides carbon atom, 1 to 4 heteroatoms selected from an oxygen atom, a sulfur atom and a nitrogen atom (e.g., imidazolyl, morpholinyl, pyridyl; tetrahydropyranyl, piperidinyl, tetrazolyl, 4,5-dihydro-1,2,4-oxadiazolyl, 1,2,4-triazolyl, 1,3,4-oxadiazolyl, 1,2,4-oxadiazolyl, imidazolidinyl, hexahydropyrimidinyl, pyrazolyl), said 5- or 6-membered heterocyclic group optionally has 1 to 3 substituents selected from
  (a) oxo,
  (b) $C_{1-6}$ alkyl optionally having 1 to 3 hydroxy,
  (c) $C_{6-14}$ aryl,
  (d) carbamoyl, and
  (e) $C_{1-6}$ alkoxy-carbonyl,
(18) $C_{1-6}$ alkoxy-carbonyl, or
(19) a group represented by the formula: —CO—N($R^5$)($R^6$)
wherein $R^5$ and $R^6$ are each a hydrogen atom, $C_{1-6}$ alkyl or $C_{1-6}$ alkoxy, or
$R^5$ and $R^6$ optionally form, together with the nitrogen atom bonded thereto, a 4- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., azetidine, pyrrolidine, piperidine, piperazine, morpholine, thiomorpholine, 1,4-oxazepane), said 4- to 7-membered nonaromatic nitrogen-containing heterocycle optionally has 1 to 3 substituents selected from,
  (a) oxo,
  (b) a halogen atom,
  (c) $C_{1-6}$ alkyl optionally having 1 to 3 substituents selected from hydroxy and $C_{1-6}$ alkoxy,
  (d) $C_{6-14}$ aryl (e.g., phenyl) optionally having 1 to 3 $C_{1-6}$ alkoxy,
  (e) $C_{7-16}$ aralkyl (e.g., benzyl),
  (f) hydroxy,
  (g) $C_{1-6}$ alkoxy,
  (h) $C_{6-14}$ aryloxy (e.g., phenoxy),
  (i) $C_{7-16}$ aralkyloxy (e.g., benzyloxy),
  (j) $C_{1-6}$ alkyl-carbonyl,
  (k) $C_{6-14}$ aryl-carbonyl (e.g., benzoyl),
  (l) mono- or di-$C_{1-6}$ alkylsulfamoyl,
  (m) $C_{1-6}$ alkylsulfonyl, and
  (n) a 5- or 6-membered heterocyclic group containing, as a ring-constituting atom besides carbon atom, 1 to 4 heteroatoms selected from an oxygen atom, a sulfur atom and a nitrogen atom (e.g., pyridyl, thiazolyl);

$R^{3b}$ is
(1) a 5- or 6-membered aromatic or nonaromatic heterocyclic group containing, as a ring-constituting atom besides carbon atom, 1 to 4 heteroatoms selected from an oxygen atom, a sulfur atom and a nitrogen atom (e.g., furyl, thienyl, oxazolyl, pyridyl, tetrahydrofuryl), and optionally having 1 to 3 $C_{1-6}$ alkyl, or
(2) $C_{1-6}$ alkyl optionally having 1 to 3 $C_{1-6}$ alkoxy; and
$R^4$ is $C_{1-6}$ alkyl optionally having 1 to 3 halogen atoms, or a salt thereof.

[Compound B-7]

A compound represented by the formula

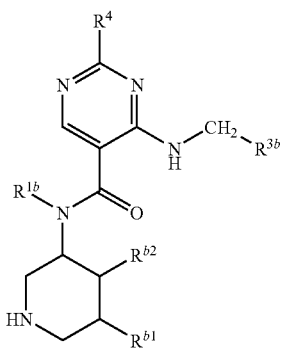

wherein $R^{1b}$ is $C_{1-6}$ alkyl optionally having 1 to 3 halogen atoms;
$R^{b2}$ is a hydrogen atom,
$R^{b1}$ is a group represented by the formula: —CO—N($R^5$)($R^6$) wherein $R^5$ and $R^6$ are each a hydrogen atom, $C_{1-6}$ alkyl or $C_{1-6}$ alkoxy, or
$R^5$ and $R^6$ optionally form, together with the nitrogen atom bonded thereto, a 4- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., azetidine, pyrrolidine, piperidine, piperazine, morpholine, thiomorpholine, 1,4-oxazepane), said 4- to 7-membered nonaromatic nitrogen-containing heterocycle optionally has 1 to 3 substituents selected from
(a) oxo,
(b) a halogen atom,
(c) $C_{1-6}$ alkyl optionally having 1 to 3 substituents selected from hydroxy and $C_{1-6}$ alkoxy,
(d) $C_{6-14}$ aryl (e.g., phenyl) optionally having 1 to 3 $C_{1-6}$ alkoxy,
(e) $C_{7-16}$ aralkyl (e.g., benzyl),
(f) hydroxy,
(g) $C_{1-6}$ alkoxy,
(h) $C_{6-14}$ aryloxy (e.g., phenoxy),
(i) $C_{7-16}$ aralkyloxy (e.g., benzyloxy),
(j) $C_{1-6}$ alkyl-carbonyl,
(k) $C_{6-14}$ aryl-carbonyl (e.g., benzoyl),
(l) mono- or di-$C_{1-6}$ alkylsulfamoyl,
(m) $C_{1-6}$ alkylsulfonyl, and
(n) a 5- or 6-membered heterocyclic group containing, as a ring-constituting atom besides carbon atom, 1 to 4 heteroatoms selected from an oxygen atom, a sulfur atom and a nitrogen atom (e.g., pyridyl, thiazolyl);
$R^{3b}$ is
(1) a 5- or 6-membered aromatic or nonaromatic heterocyclic group containing, as a ring-constituting atom besides carbon atom, 1 to 4 heteroatoms selected from an oxygen atom, a sulfur atom and a nitrogen atom (e.g., furyl, thienyl, oxazolyl, pyridyl, tetrahydrofuryl), and optionally having 1 to 3 $C_{1-6}$ alkyl, or
(2) $C_{1-6}$ alkyl optionally having 1 to 3 $C_{1-6}$ alkoxy; and
$R^4$ is $C_{1-6}$ alkyl optionally having 1 to 3 halogen atoms, or a salt thereof.

Preferable examples of compound (C) are as described below.

[Compound C-1]

A compound represented by the formula (C) wherein $R^{1b}$ is $C_{1-6}$ alkyl;
$R^3$ is $C_{1-6}$ alkoxy or $C_{1-6}$ alkylthio;
Z is $C_{2-6}$ alkylene;
ring Ac is a ring represented by the formula

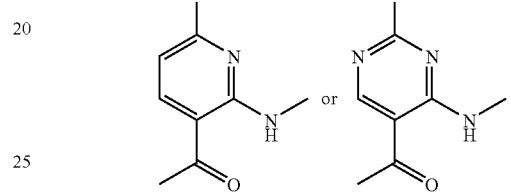

wherein $R^4$ is $C_{1-6}$ alkyl; and
ring B is a ring represented by the formula

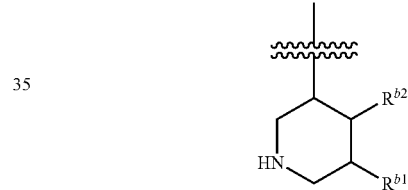

wherein $R^{b1}$ and $R^{b2}$ are each
(1) a hydrogen atom,
(2) $C_{1-6}$ alkyl optionally having 1 to 3 hydroxy,
(3) $C_{1-6}$ alkoxy-carbonyl, or
(4) a group represented by the formula: —CO—N($R^5$)($R^6$) wherein $R^5$ and $R^6$ are each a hydrogen atom or $C_{1-6}$ alkyl, or
$R^5$ and $R^6$ optionally form, together with the nitrogen atom bonded thereto, a 5- to 7-membered nonaromatic nitrogen-containing heterocycle containing, as a ring-constituting atom besides carbon atom, one nitrogen atom, and optionally further containing 1 or 2 heteroatoms selected from an oxygen atom, a sulfur atom and a nitrogen atom (e.g., pyrrolidine, piperidine, piperazine, morpholine, thiomorpholine), and optionally having 1 to 3 substituents selected from hydroxy and $C_{1-6}$ alkyl, or a salt thereof.

Examples of the salt of compound (1) (including compound (A), compound (B) and compound (C), hereinafter the same) include metal salts, ammonium salts, salts with organic bases, salts with inorganic acids, salts with organic acids, salts with basic or acidic amino acids, and the like.

Preferable examples of the metal salt include alkali metal salts such as sodium salt, potassium salt and the like; alkaline earth metal salts such as calcium salt, magnesium salt, barium salt and the like; aluminum salt and the like.

Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N-dibenzylethylenediamine or the like.

Preferable examples of the salt with inorganic acid include a salt with hydrochloric acid, hydrobromic acid, nitric acid, sulfuric acid, phosphoric acid or the like.

Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid or the like.

Preferable examples of the salt with basic amino acid include a salt with arginine, lysine, ornithine or the like.

Preferable examples of the salt with acidic amino acid include a salt with aspartic acid, glutamic acid or the like.

Of these, a pharmaceutically acceptable salt is preferable. When the compound has an acidic functional group, examples thereof include inorganic salts such as alkali metal salts (e.g., sodium salt, potassium salt, etc.), alkaline earth metal salts (e.g., calcium salt, magnesium salt, barium salt, etc.) and the like, ammonium salts, and the like. When the compound has a basic functional group, examples thereof include salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like.

The production methods of compound (I) are shown in the following.

Compound (I) is obtained by, for example, a method shown in the following reaction scheme or a method analogous thereto, or the like.

Each of compounds (II)-(LI) shown in the reaction scheme may form a salt. Examples of the salt include salts similar to the salts of compound (I).

The compound obtained in each step can also be used for the next reaction directly as the reaction mixture or as a crude product. In addition, it can also be isolated from the reaction mixture according to a conventional method, and can be isolated and purified by a known method such as phase transfer, concentration, solvent extraction, fractional distillation, pH conversion, crystallization, recrystallization, chromatography and the like.

The schematic drawings of the reaction scheme are shown in the following.

Each symbol of the compounds in the schemes is as defined above. R is $C_{1-4}$ alkyl, Q is a hydrogen atom or an alkali metal atom, LG is a leaving group (e.g., chloro group, bromo group, iodo group etc.), and PG is an N-protecting group (e.g., benzyl, tert-butoxycarbonyl, benzyloxycarbonyl etc.). Ring Bb is a nitrogen-containing 5- to 7-membered ring optionally having substituent(s).

(Reaction 1)

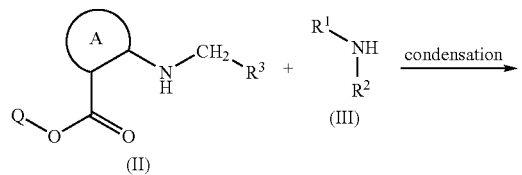

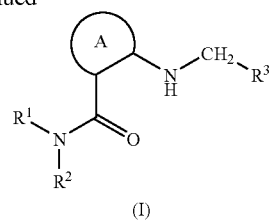

Compound (I) can be produced by a condensation reaction of compound (II) and compound (III).

Compound (II) can be produced by a method known per se, for example, the method described in J. Med. Chem., 1993, vol. 36, pages 2676-2688 and the like, or a method analogous thereto.

As compound (III), a commercially available product may be used, or it can be produced by a method known per se, for example, the method described in J. Am. Chem. Soc., 1948, vol. 70, page 4009 and the like, or a method analogous thereto.

When Q is a hydrogen atom, the condensation reaction is performed according to a conventional peptide synthesis technique, for example, an acid chloride method, an acid anhydride method, a mixed anhydride method, a method of using N,N'-dicyclohexylcarbodiimide (DCC), an active ester method, a method of using N,N'-carbonyldiimidazole (CDI), a method of using diethyl phosphorocyanidate (DEPC), a method of using N-ethyl-N'-(3-dimethylaminopropyl)carbodiimide hydrochloride (WSC.HCl) and 1-hydroxybenzotriazole (HOBt), or the like. Compound (III) is used in an amount of about 1 to 2 mol, is preferably about 1.0 to 1.1 mol, per 1 mol of compound (II). The reagent for the aforementioned methods is used in an amount of about 1 mol to a large excess, preferably about 1.1 to 5 mol, per 1 mol of compound (II). The reaction temperature is generally −10° C. to 80° C., preferably 0° C. to 30° C.

When Q is an alkali metal atom, the condensation reaction is advantageously performed according to a method using WSC.HCl and HOBt. Compound (III) is used in an amount of about 1 to 2 mol, preferably about 1.0 to 1.1 mol, per 1 mol of compound (II). WSC.HCl is used in an amount of about 1 to 4 mol, preferably about 1.5 to 2.5 mol, per 1 mol of compound (II). HOBt is used in an amount of about 1 to 8 mol, preferably about 2.5 to 5.0 mol, per 1 mol of compound (II). The reaction temperature is generally −10° C. to 100° C., preferably 40° C. to 70° C.

In all cases, the condensation reaction is preferably performed in a solvent. Examples of the solvent to be used include halogenated hydrocarbons such as dichloromethane, chloroform, carbon tetrachloride, 1,2-dichloroethane and the like, ethers such as diethyl ether, tetrahydrofuran, dioxane and the like, amides such as N,N-dimethylformamide, N,N-dimethylacetamide and the like, dimethyl sulfoxide, pyridine, acetonitrile and a mixed solvent thereof.

While the reaction time varies depending on the reagent and solvent to be used, it is generally 30 min to 3 days, preferably 30 min to 15 hr.

Compound (I) can also be produced by performing, when desired in addition to the above-mentioned reaction, known hydrolysis reaction, acylation reaction, alkylation reaction, amination reaction, oxidation-reduction reaction, cyclization reaction, carbon chain extension reaction, substituent exchange reaction and the like, each singly or in combination of multiple operations.

When compound (I) is obtained as a free compound, it can be converted to an object salt by a method known per se or a method analogous thereto. When compound (I) is obtained as a salt, it can be converted to a free form or other object salt by a method known per se or a method analogous thereto.

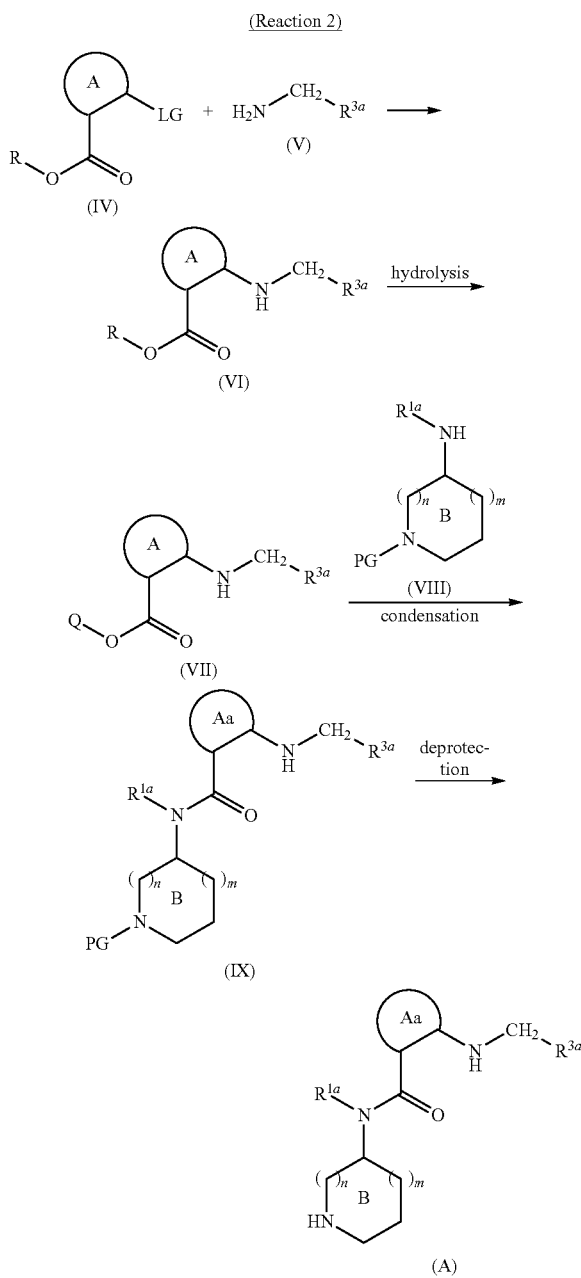

(Reaction 2)

Compound (VI) can be produced by reacting compound (IV) with compound (V).

As compound (IV), a commercially available product may be used, or it can be produced by a method known per se, for example, the method described in Bioorg. Med. Chem. Lett., 2000, vol. 10, pages 1645-1648 and the like, or a method analogous thereto.

As compound (V), a commercially available product may be used, or it can be produced by a method known per se, for example, the method described in Bioorg. Med. Chem. Lett., 2004, vol. 14, pages 2543-2546 and the like, or a method analogous thereto.

Compound (VI) can be produced according to a method known per se, for example, the method described in J. Med. Chem., 1993, vol. 36, pages 2676-2688 and the like, or a method analogous thereto.

This reaction is more advantageously performed in the presence of a base. As the base in this step, tertiary amine such as triethylamine, diisopropylethylamine and the like, or an inorganic base such as sodium hydrogen carbonate, potassium hydrogen carbonate and the like is preferable. The amount of the base to be used is about 1 mol to a large excess, preferably 1 to 5 mol, per 1 mol of compound (IV).

This reaction is advantageously performed using a solvent inert to the reaction. While the solvent is not particularly limited as long as the reaction proceeds, for example, solvents such as alcohols (e.g., 2-propanol and the like), highly polar solvents (e.g., N,N-dimethylformamide, dimethyl sulfoxide and the like), hydrocarbons (e.g., benzene, toluene, cyclohexane, hexane and the like), ethers (e.g., diethyl ether, tetrahydrofuran, dioxane and the like) and the like, a mixed solvent thereof and the like are preferable.

While the reaction time varies depending on the reagent and solvent to be used, it is generally 30 min to 48 hr, preferably 30 min to 15 hr.

The reaction temperature is generally 0° C. to 200° C., preferably 20° C. to 120° C.

Compound (VII) can be produced by a known hydrolysis, for example, alkaline hydrolysis or acid hydrolysis to compound (VI).

The reaction is more advantageously performed under alkali conditions. As the alkali in this step, alkali metal hydroxide such as lithium hydroxide, sodium hydroxide, potassium hydroxide and the like is preferable. The amount of the alkali to be used is about 1 mol to a large excess, preferably 1 to 5 mol, per 1 mol of compound (VI).

This reaction is advantageously performed using a solvent inert to the reaction. While the solvent is not particularly limited as long as the reaction proceeds, for example, solvents such as alcohols (e.g., methanol, ethanol, propanol and the like), hydrocarbons (e.g., benzene, toluene, cyclohexane, hexane and the like), halogenated hydrocarbons (e.g., dichloromethane, chloroform, carbon tetrachloride, 1,2-dichloroethane and the like), ethers (e.g., diethyl ether, tetrahydrofuran, dioxane and the like) and the like, a mixed solvent thereof and the like are preferable.

While the reaction time varies depending on the reagent and solvent to be used, it is generally 30 min to 24 hr, preferably 30 min to 8 hr.

The reaction temperature is generally 0° C. to 150° C., preferably 20° C. to 80° C.

After the reaction, the reaction mixture is neutralized by the addition of a mineral acid (e.g., hydrochloric acid, sulfuric acid etc.), an organic acid (e.g., acetic acid etc.) or an ion exchange resin to give carboxylic acid (VII) in a free form (in this case, Q is hydrogen atom). Moreover, the reaction mixture may be directly concentrated to give compound (VII) as an alkali metal salt of carboxylic acid (in this case, Q is alkali metal atom such as lithium, sodium, potassium and the like).

Compound (IX) can be produced by a condensation reaction of compound (VII) and compound (VIII).

As compound (VIII), a commercially available product may be used, or it can be produced by a method known per se, for example, the method described in Bioorg. Med. Chem. Lett., 2005, vol. 15, pages 833-838, or EP1757582 and the like, or a method analogous thereto.

When Q is a hydrogen atom, the condensation reaction is performed according to a conventional peptide synthesis technique, for example, an acid chloride method, an acid anhydride method, a mixed anhydride method, a method using N,N'-dicyclohexylcarbodiimide (DCC), an active ester method, a method using N,N'-carbonyldiimidazole (CDI), a method using diethyl phosphorocyanidate (DEPC), a method using N-ethyl-N'-(3-dimethylaminopropyl)carbodiimide hydrochloride (WSC.HCl) and 1-hydroxybenzotriazole (HOBt) and the like. Compound (VIII) is used in an amount of about 1 to 2 mol, preferably about 1.0 to 1.1 mol, per 1 mol of compound (VII). The reagent to be used in the above-mentioned method is used in an amount of about 1 mol to a large excess, preferably about 1.1 to 5 mol, per 1 mol of compound (VII). The reaction temperature is generally −10° C. to 80° C., preferably 0° C. to 30° C.

When Q is an alkali metal atom, the condensation reaction is advantageously performed by a method using WSC.HCl and HOBt. Compound (VIII) is used in an amount of about 1 to 2 mol, preferably about 1.0 to 1.1 mol, per 1 mol of compound (VII). WSC.HCl is used in an amount of about 1 to 4 mol, preferably about 1.5 to 2.5 mol, per 1 mol of compound (VII). HOBt is used in an amount of about 1 to 8 mol, preferably about 2.5 to 5.0 mol, per 1 mol of compound (VII). The reaction temperature is generally −10° C. to 100° C., preferably 40° C. to 70° C.

In all cases, the condensation reaction is preferably performed in a solvent. Examples of the solvent to be used include the above-mentioned halogenated hydrocarbons, the above-mentioned ethers, amides such as N,N-dimethylformamide, N,N-dimethylacetamide, N-methylpyrrolidone and the like, dimethyl sulfoxide, pyridine, acetonitrile and a mixed solvent thereof.

While the reaction time varies depending on the reagent and solvent to be used, it is generally 30 min to 3 days, preferably 30 min to 15 hr.

Compound (IX) can also be produced by performing, when desired in addition to the above-mentioned reaction, known hydrolysis reaction, acylation reaction, alkylation reaction, amination reaction, oxidation-reduction reaction, cyclization reaction, carbon chain extension reaction, substituent exchange reaction and the like, each singly or in combination of multiple operations.

Compound (A) can be produced by removing the N-protecting group PG of compound (IX). In addition, in each of the aforementioned reactions, when the starting compound has an amino group, a carboxyl group or a hydroxyl group as a substituent, a protecting group generally used in peptide chemistry and the like may be introduced into these groups. By removing the protecting group as necessary after the reaction, the objective compound can be obtained. Introduction or removal of these protective groups may be performed according to a method known per se, for example, the method disclosed in Theodora W. Greene and Peter G. M. Wuts, "Protective Groups in Organic Synthesis, 3rd Ed.", Wiley-Interscience (1999), or the like.

Examples of the amino-protecting group include a formyl group; a $C_{1-6}$ alkyl-carbonyl group, a phenylcarbonyl group, a $C_{1-6}$ alkoxy-carbonyl group, an allyloxycarbonyl (Alloc) group, a phenyloxycarbonyl group, a fluorenylmethyloxycarbonyl (Fmoc) group, a $C_{7-10}$ aralkyl-carbonyl group (e.g., benzylcarbonyl and the like), a $C_{7-10}$ aralkyloxy-carbonyl group (e.g., benzyloxycarbonyl (Cbz) and the like), a $C_{7-10}$ aralkyl group (e.g., benzyl and the like), a trityl group, a phthaloyl group, a dithiasuccinoyl group, a N,N-dimethylaminomethylene group, each optionally having substituent(s), and the like. As the substituent(s), for example, a phenyl group, a halogen atom, a $C_{1-6}$ alkyl-carbonyl group, a $C_{1-6}$ alkoxy group optionally substituted by halogen atom(s) (e.g., methoxy, ethoxy, trifluoromethoxy and the like), a nitro group and the like can be used. The number of the substituent(s) is 1 to 3.

Examples of the carboxyl-protecting group include a $C_{1-6}$ alkyl group, an allyl group, a benzyl group, a phenyl group, a trityl group, a trialkylsilyl group, each optionally having substituent(s), and the like. As the substituent(s), for example, a halogen atom, a formyl group, a $C_{1-6}$ alkyl-carbonyl group, a $C_{1-6}$ alkoxy group optionally substituted by halogen atom(s) (e.g., methoxy, ethoxy, trifluoromethoxy and the like), a nitro group and the like can be used. The number of the substituent(s) is 1 to 3.

Examples of the hydroxy-protecting group include a $C_{1-6}$ alkyl group, a $C_{7-20}$ aralkyl group (e.g., benzyl, trityl and the like), a formyl group, a $C_{1-6}$ alkyl-carbonyl group, a benzoyl group, a $C_{7-10}$ aralkyl-carbonyl group (e.g., benzylcarbonyl and the like), a 2-tetrahydropyranyl group, a tetrahydrofuranyl group, a trialkylsilyl group (e.g., trimethylsilyl, tert-butyldimethylsilyl, diisopropylethylsilyl and the like), each optionally having substituent(s), and the like. As the substituent(s), for example, a halogen atom, a $C_{1-6}$ alkyl group, a phenyl group, a $C_{7-10}$ aralkyl group (e.g., benzyl and the like), a $C_{1-6}$ alkoxy group, a nitro group and the like can be used. The number of the substituent(s) is 1 to 4.

When compound (A) is obtained as a free compound, it can be converted to an object salt by a method known per se or a method analogous thereto. When compound (A) is obtained as a salt, it can be converted to a free compound or other object salt by a method known per se or a method analogous thereto.

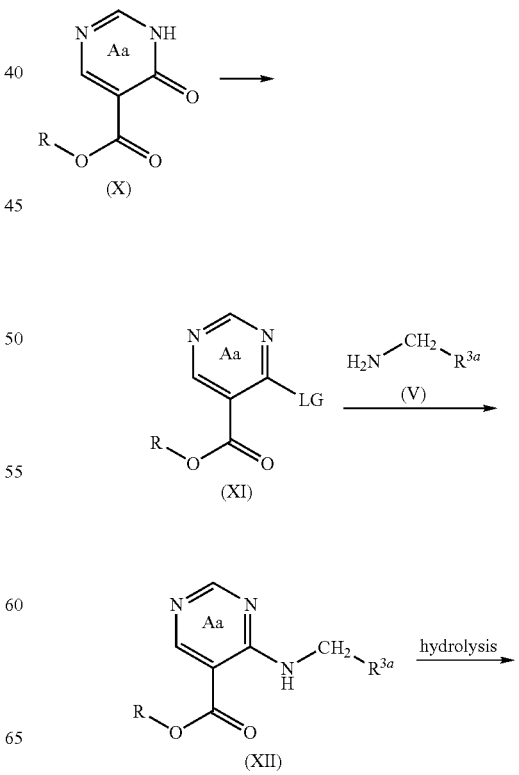

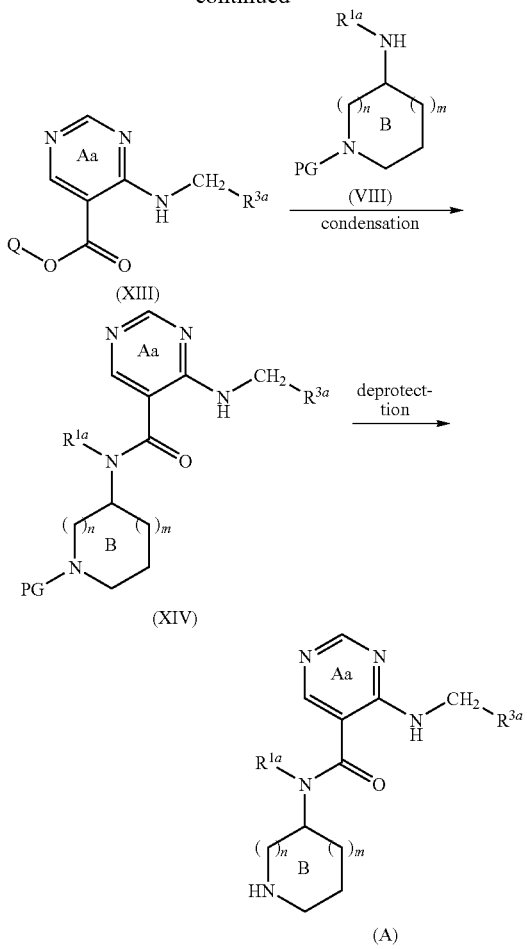

This method is used for the production of compound (A) wherein ring Aa is a pyrimidine ring.

As compound (X), a commercially available product may be used, or it can be produced by a method known per se, for example, the method described in J. Med. Chem., 2000, vol. 43, pages 3995-4004 and the like, or a method analogous thereto.

As compound (XI) having a substitutable leaving group LG, a commercially available product may be used, or it can be produced using compound (X) as a starting material by a method known per se, for example, the method described in Bioorg. Med. Chem. Lett., 2000, vol. 10, pages 1645-1648 and the like, or a method analogous thereto. Preferable examples of the reagent in the step include phosphorus oxychloride, phosphorus oxybromide, thionyl chloride and the like.

The amount of the reagent to be used is about 1 mol to a large excess, per 1 mol of compound (X).

This reaction is advantageously performed using a solvent inert to the reaction or without solvent. While the solvent is not particularly limited as long as the reaction proceeds, for example, solvents such as hydrocarbons (e.g., benzene, toluene, cyclohexane, hexane and the like), halogenated hydrocarbons (e.g., dichloromethane, chloroform, carbon tetrachloride, 1,2-dichloroethane and the like), ethers (e.g., diethyl ether, tetrahydrofuran, dioxane and the like) and the like, a mixed solvent thereof and the like are preferable.

While the reaction time varies depending on the reagent to be used, it is generally 30 min to 24 hr, preferably 30 min to 8 hr.

The reaction temperature is generally 0° C. to 150° C., preferably 20° C. to 130° C.

Compound (XII) can be produced by reacting compound (XI) with compound (V).

As compound (V), a commercially available product may be used, or it can be produced by a method known per se, for example, the method described in Bioorg. Med. Chem. Lett., 2004, vol. 14, pages 2543-2546 and the like, or a method analogous thereto.

Compound (XII) can be produced by a method known per se, for example, the method described in J. Med. Chem., 1993, vol. 36, pages 2676-2688 and the like, or a method analogous thereto.

This reaction is more advantageously performed in the presence of a base. As the base in this step, tertiary amine such as triethylamine, diisopropylethylamine and the like, or an inorganic base such as sodium hydrogen carbonate, potassium hydrogen carbonate and the like is preferable. The amount of the base to be used is about 1 mol to a large excess, preferably 1 to 5 mol, per 1 mol of compound (XI).

This reaction is advantageously performed using a solvent inert to the reaction. While the solvent is not particularly limited as long as the reaction proceeds, for example, solvents such as alcohols (e.g., 2-propanol and the like), amides (e.g., N,N-dimethylformamide, N,N-dimethylacetamide, N-methylpyrrolidone and the like), hydrocarbons (e.g., benzene, toluene, cyclohexane, hexane and the like), ethers (e.g., diethyl ether, tetrahydrofuran, dioxane and the like), dimethyl sulfoxide and the like, a mixed solvent thereof and the like are preferable.

While the reaction time varies depending on the reagent and solvent to be used, it is generally 30 min to 48 hr, preferably 30 min to 15 hr.

The reaction temperature is generally 0° C. to 200° C., preferably 20° C. to 120° C.

Compound (XIII) can be produced by known hydrolysis, for example, alkaline hydrolysis or acid hydrolysis to compound (XII).

The reaction is more advantageously performed under the alkaline conditions. As the alkali in this step, alkali metal hydroxide such as lithium hydroxide, sodium hydroxide, potassium hydroxide and the like is preferable. The amount of the alkali to be used is about 1 mol to a large excess, preferably 1 to 5 mol, per 1 mol of compound (XII).

This reaction is advantageously performed using a solvent inert to the reaction. While the solvent is not particularly limited as long as the reaction proceeds, for example, solvents such as alcohols (e.g., methanol, ethanol, propanol and the like), hydrocarbons (e.g., benzene, toluene, cyclohexane, hexane and the like), halogenated hydrocarbons (e.g., dichloromethane, chloroform, carbon tetrachloride, 1,2-dichloroethane and the like), ethers (e.g., diethyl ether, tetrahydrofuran, dioxane and the like) and the like, a mixed solvent thereof and the like are preferable.

While the reaction time varies depending on the reagent and solvent to be used, it is generally 30 min to 24 hr, preferably 30 min to 8 hr.

The reaction temperature is generally 0° C. to 150° C., preferably 20° C. to 80° C.

After the reaction, the reaction mixture is neutralized by the addition of a mineral acid (e.g., hydrochloric acid, sulfuric acid etc.), an organic acid (e.g., acetic acid etc.) or an ion exchange resin to give carboxylic acid (XIII) in a free form (in this case, Q is a hydrogen atom). Moreover, the reaction mixture may be directly concentrated to give compound (XIII) as an alkali metal salt of carboxylic acid (in this case, Q is an alkali metal atom such as lithium, sodium, potassium and the like).

Compound (XIV) can be produced by a condensation reaction of compound (XIII) and compound (VIII).

As compound (VIII), a commercially available product may be used, or it can be produced by a method known per se, for example, the method described in Bioorg. Med. Chem. Lett., 2005, vol. 15, pages 833-838, or EP1757582 and the like, or a method analogous thereto.

When Q is a hydrogen atom, the condensation reaction is performed by a conventional peptide synthesis technique, for example, an acid chloride method, an acid anhydride method, a mixed anhydride method, a method using N,N'-dicyclohexylcarbodiimide (DCC), an active ester method, a method using N,N'-carbonyldiimidazole (CDI), a method using diethyl phosphorocyanidate (DEPC), a method using N-ethyl-N'-(3-dimethylaminopropyl)carbodiimide hydrochloride (WSC.HCl) and 1-hydroxybenzotriazole (HOBt) and the like. Compound (VIII) is used in an amount of about 1 to 2 mol, preferably about 1.0 to 1.1 mol, per 1 mol of compound (XIII). The reagent to be used in the above-mentioned method is used in an amount of about 1 mol to a large excess, preferably about 1.1 to 5 mol, per 1 mol of compound (XIII). The reaction temperature is generally $-10°$ C. to $80°$ C., preferably $0°$ C. to $30°$ C.

When Q is an alkali metal atom, the condensation reaction is advantageously performed by a method using WSC.HCl and HOBt. Compound (VIII) is used in an amount of about 1 to 2 mol, preferably about 1.0 to 1.1 mol, per 1 mol of compound (XIII). WSC.HCl is used in an amount of about 1 to 4 mol, preferably about 1.5 to 2.5 mol, per 1 mol of compound (XIII). HOBt is used in an amount of about 1 to 8 mol, preferably about 2.5 to 5.0 mol, per 1 mol of compound (XIII). The reaction temperature is generally $-10°$ C. to $100°$ C., preferably $40°$ C., to $70°$ C.

In all cases, the condensation reaction is preferably performed in a solvent. Examples of the solvent to be used include the above-mentioned halogenated hydrocarbons, the above-mentioned ethers, amides such as N,N-dimethylformamide, N,N-dimethylacetamide, N-methylpyrrolidone and the like, dimethyl sulfoxide, pyridine, acetonitrile and a mixed solvent thereof.

While the reaction time varies depending on the reagent and solvent to be used, it is generally 30 min to 3 days, preferably 30 min to 15 hr.

Compound (XIV) can also be produced by performing, when desired in addition to the above-mentioned reaction, known hydrolysis reaction, acylation reaction, alkylation reaction, amination reaction, oxidation-reduction reaction, cyclization reaction, carbon chain extension reaction, substituent exchange reaction and the like, each singly or in combination of multiple operations.

Compound (A) is produced by removing the N-protecting group PG of compound (XIV). Moreover, when the starting material compound has an amino group, a carboxyl group or a hydroxyl group as a substituent in each of the above-mentioned reactions, these groups are optionally protected by a protecting group generally used in the peptide chemistry and the like. In this case, the object compound can be obtained by removing the protecting group as necessary after the reaction. These protecting groups can be introduced or removed by a method known per se, for example, the method described in Theodora W. Greene and Peter G. M. Wuts, "Protective Groups in Organic Synthesis, $3^{rd}$ Ed.", Wiley-Interscience (1999) and the like.

Examples of the amino-protecting group include a formyl group; a $C_{1-6}$ alkyl-carbonyl group, a phenylcarbonyl group, a $C_{1-6}$ alkoxy-carbonyl group, an allyloxycarbonyl (Alloc) group, a phenyloxycarbonyl group, a fluorenylmethyloxycarbonyl (Fmoc) group, a $C_{7-10}$ aralkyl-carbonyl group (e.g., benzylcarbonyl etc.), a $C_{7-10}$ aralkyloxy-carbonyl group (e.g., benzyloxycarbonyl (Cbz) etc.), a $C_{7-10}$ aralkyl group (e.g., benzyl etc.), a trityl group, a phthaloyl group, a dithiasuccinoyl group, a N,N-dimethylaminomethylene group, each of which optionally having substituent(s), and the like. Here, as the substituent(s), a phenyl group, a halogen atom, a $C_{1-6}$ alkyl-carbonyl group, a $C_{1-6}$ alkoxy group optionally substituted by halogen atom(s) (e.g., methoxy, ethoxy, trifluoromethoxy etc.), a nitro group and the like can be used. The number of the substituent(s) is 1 to 3.

Examples of the carboxyl-protecting group include a $C_{1-6}$ alkyl group, an allyl group, a benzyl group, a phenyl group, a trityl group, a trialkylsilyl group each of which optionally having substituent(s), and the like. Here, as the substituent(s), a halogen atom, a formyl group, a $C_{1-6}$ alkyl-carbonyl group, a $C_{1-6}$ alkoxy group optionally substituted by halogen atom(s) (e.g., methoxy, ethoxy, trifluoromethoxy etc.), a nitro group and the like can be used. The number of the substituent(s) is 1 to 3.

Examples of the hydroxy-protecting group include a $C_{1-6}$ alkyl group, a $C_{7-20}$ aralkyl group (e.g., benzyl, trityl etc.), a formyl group, a $C_{1-6}$ alkyl-carbonyl group, a benzoyl group, a $C_{7-10}$ aralkyl-carbonyl group (e.g., benzylcarbonyl etc.), a 2-tetrahydropyranyl group, a tetrahydrofuranyl group, a trialkylsilyl group (e.g., trimethylsilyl, tert-butyldimethylsilyl, diisopropylethylsilyl etc.), each of which optionally having substituent(s), and the like. Here, as the substituent(s), a halogen atom, a $C_{1-6}$ alkyl group, a phenyl group, a $C_{7-10}$ aralkyl group (e.g., benzyl etc.), a $C_{1-6}$ alkoxy group, a nitro group and the like can be used. The number of the substituent(s) is 1 to 4.

When compound (A) is obtained as a free compound, it can be converted to an object salt by a method known per se or a method analogous thereto. When compound (A) is obtained as a salt, it can be converted to a free form or other object salt by a method known per se or a method analogous thereto.

(Reaction 4)

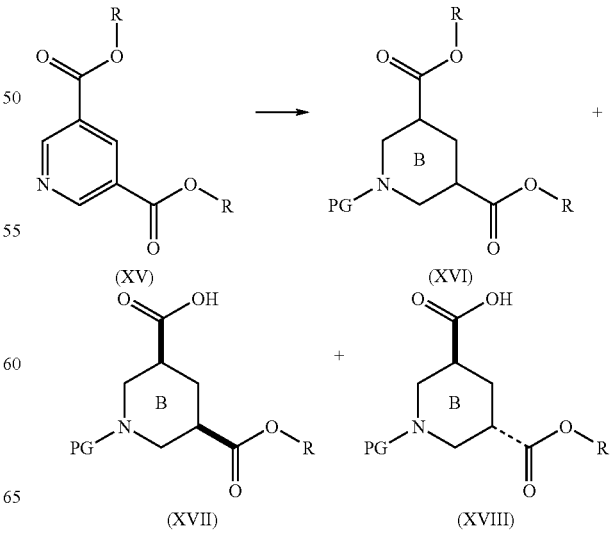

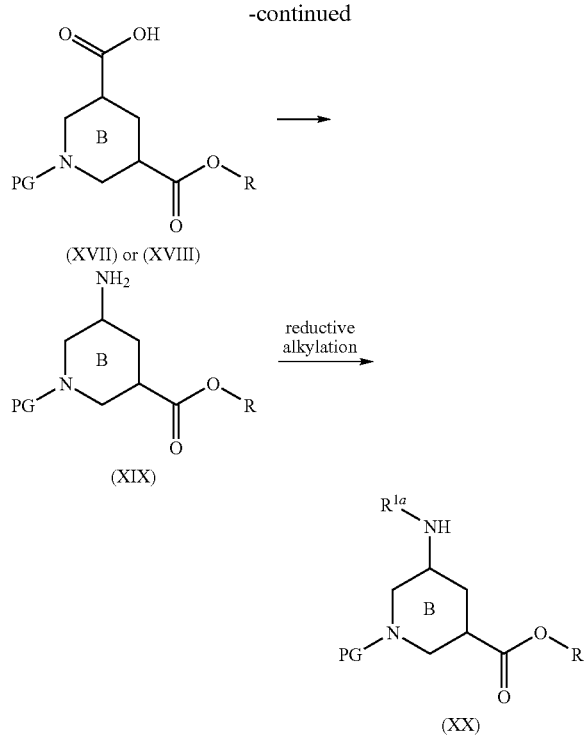

This method is used for the production of a compound wherein compound (VIII) has a structure shown by compound (XX).

Compound (XV) can be produced by a method known per se, for example, U.S. Pat. No. 6,018,046 and the like, or a method analogous thereto.

Compounds (XVI), (XVII) and (XVIII) can be each produced by subjecting compound (XV) to a known reduction reaction, for example, catalytic hydrogen reduction reaction in the presence of a metal catalyst and the like, and successively introducing the PG group (protecting group) by a known reaction.

The catalytic hydrogen reduction reaction and the subsequent introduction of the protecting group (PG group) can be performed by a known method, for example, the method described in Tetrahedron Lett., 1994, vol. 35, pages 4515-4518, or Tetrahedron: Asymmetry., 2003, vol. 14, pages 1541-1545, or Tetrahedron Lett., 2003, vol. 44, pages 1611-1614 and the like, or a method analogous thereto.

The catalytic hydrogen reduction reaction is more advantageously performed under the acidic conditions. As the acid in this step, a mineral acid such as hydrochloric acid and the like, an organic acid such as acetic acid etc., and the like are preferable. The amount of the acid to be used is about 1 mol to a large excess, per 1 mol of compound (XV).

As the metal catalyst to be used in the catalytic hydrogen reduction reaction, for example, rhodium carbon, platinum oxide, palladium-carbon, rhodium-platinum oxide alloy and the like are preferable. The amount of the catalyst to be used is about 0.01 g to 1 g, preferably about 0.05 g to 0.3 g, per 1 g of compound (XV).

The catalytic hydrogen reduction reaction is advantageously performed using a solvent inert to the reaction. While the solvent is not particularly limited as long as the reaction proceeds, for example, organic acids such as acetic acid and the like, mineral acids such as hydrochloric acid and the like, alcohols such as methanol, ethanol, propanol and the like, hydrocarbons such as benzene, toluene, cyclohexane, hexane and the like, ethers such as diethyl ether, tetrahydrofuran, dioxane and the like, esters such as ethyl acetate and the like, highly polar solvent such as N,N-dimethylformamide, N-methylpyrrolidone and the like, a mixed solvent thereof and the like are preferable.

While the reaction time varies depending on the reagent and solvent to be used, it is generally 30 min to 60 hr, preferably 30 min to 30 hr.

The reaction temperature is generally 0° C. to 150° C., preferably 20° C. to 70° C.

After the reduction reaction, the reaction mixture is neutralized by the addition of an inorganic base (e.g., sodium hydroxide, potassium carbonate etc.), an organic base (e.g., triethylamine etc.) and the like and the reaction mixture is directly concentrated, or the reaction mixture is directly concentrated and the concentrate is neutralized by the addition of an inorganic base (e.g., sodium hydroxide, potassium carbonate etc.), an organic base (e.g., triethylamine etc.) and the like, and then a protecting group (PG group) is introduced, whereby compounds (XVI), (XVII) and (XVIII) can be respectively produced. The protecting group (PG group) may be introduced by a method known per se, for example, the method described in Theodora W. Greene and Peter G. M. Wuts, "Protective Groups in Organic Synthesis, 3$^{rd}$ Ed.", Wiley-Interscience (1999) and the like.

Compound (XVII) can be separated from a mixture of compounds (XVI), (XVII) and (XVIII) by a known purification method, for example, silica gel column chromatography, recrystallization, high pressure liquid chromatography and the like.

Compound (XVII) can also be produced by a method known per se, for example, the method described in WO97/18813 and the like, or a method analogous thereto.

Compound (XIX) is produced by a rearrangement reaction (e.g., Curtius rearrangement and the like) of compound (XVII) or compound (XVIII).

Compound (XIX) can be produced by a method known per se, for example, the method described in U.S. Pat. No. 5,817,678 and the like, or a method analogous thereto.

Compound (XX) can be produced by a reaction to introduce substituent R$^{1a}$ into the amino group of compound (XIX) (e.g., reductive alkylation).

Compound (XX) can be produced by a known method, for example, Bioorg. Med. Chem. Lett., 2005, vol. 15, pages 833-838, or a method analogus thereto.

(Reaction 5)

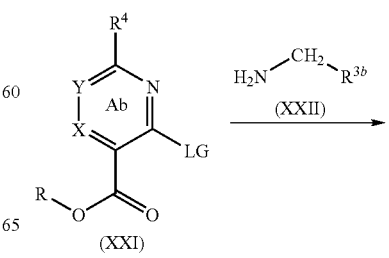

-continued

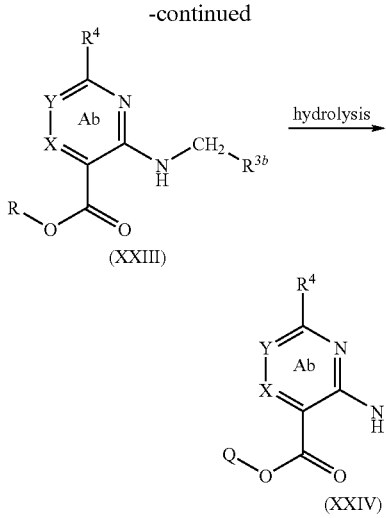

Compound (XXIII) can be produced by reacting compound (XXI) with compound (XXII).

Compound (XXIII) can be produced under the conditions similar to those used for the production of compound (VI) and according to a method known per se, for example, the method described in J. Med. Chem., 1993, vol. 36, pages 2676-2688 and the like, or a method analogous thereto.

Compound (XXIV) can be produced by subjecting compound (XXIII) to known hydrolysis, for example, alkaline hydrolysis or acid hydrolysis.

Compound (XXIV) can be produced under the conditions similar to those used for the production of compound (XIII) and by performing known hydrolysis, for example, alkaline hydrolysis or acid hydrolysis.

(Reaction 6)

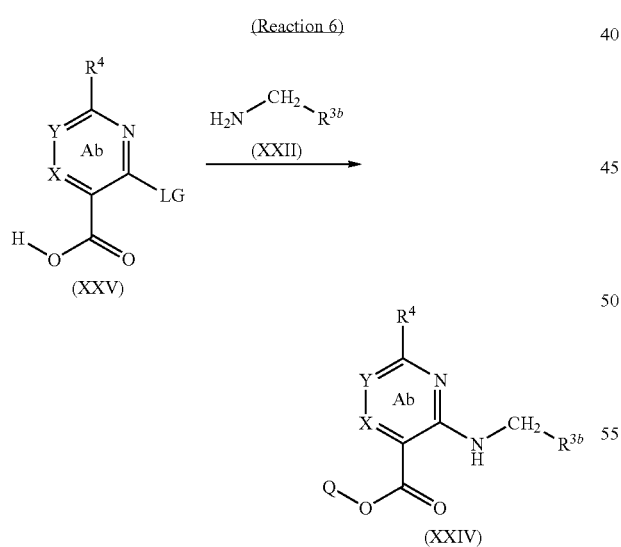

Compound (XXIV) can be produced by reacting compound (XXV) with compound (XXII).

As compound (XXV), a commercially available product may be used, or it can be produced by a method known per se, for example, the method described in U.S. Pat. No. 3,928,366 and the like, or a method analogous thereto.

Compound (XXIV) can be produced by a known method, for example, the method described in Heterocycles, 1994, vol. 38, pages 529-540 and the like, or a method analogous thereto.

(Reaction 7)

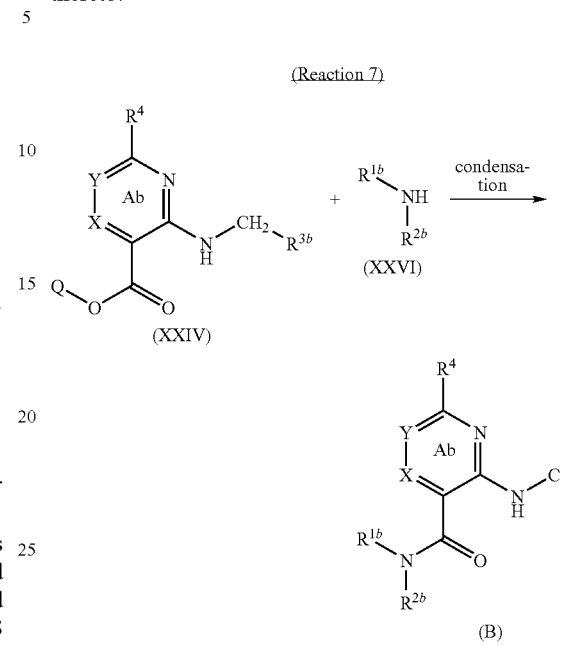

Compound (B) can be produced by a condensation reaction of compound (XXIV) with compound (XXVI).

As compound (XXVI), a commercially available product may be used, or it can be produced by a method known per se, for example, the method described in J. Am. Chem. Soc., 1948, vol. 70, page 4009 and the like, or a method analogous thereto.

The condensation reaction can be performed by a method according to the conditions used in compound (I).

Compound (B) can also be produced by performing, when desired in addition to the above-mentioned reaction, known hydrolysis reaction, acylation reaction, alkylation reaction, amination reaction, oxidation-reduction reaction, cyclization reaction, carbon chain extension reaction, substituent exchange reaction and the like, each singly or in combination of multiple operations.

When compound (B) is obtained as a free compound, it can be converted to an object salt by a method known per se or a method analogous thereto. When compound (B) is obtained as a salt, it can be converted to a free form or other object salt by a method known per se or a method analogous thereto.

(Reaction 8)

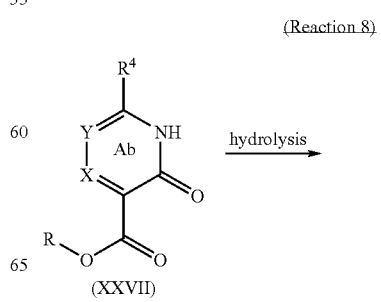

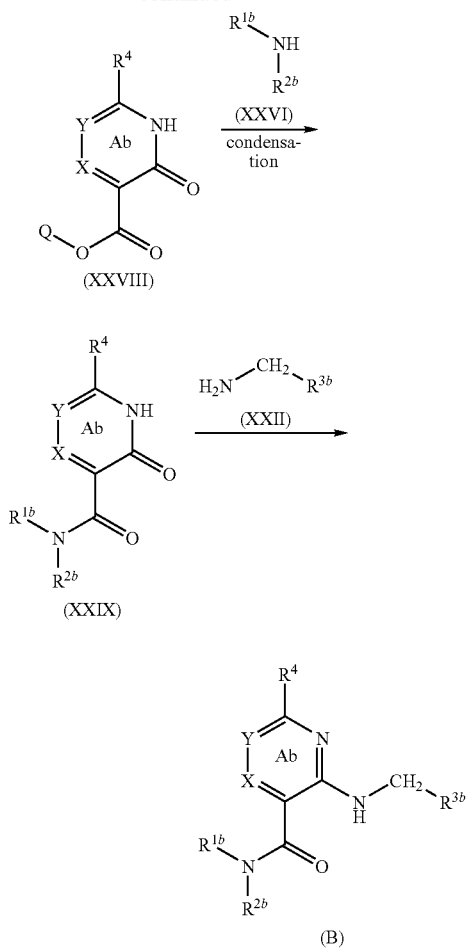

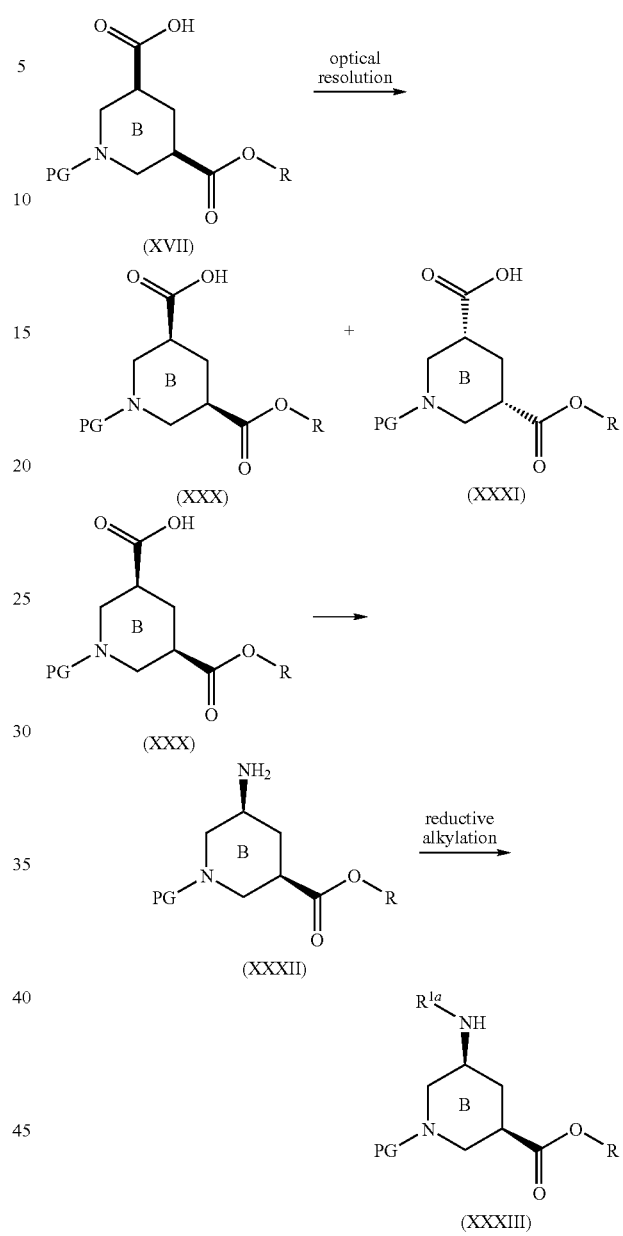

(Reaction 9)

Compound (XXVIII) can be produced by subjecting compound (XXVII) to known hydrolysis, for example, alkaline hydrolysis or acid hydrolysis. For example, the reaction can be performed by a method according to hydrolysis conditions similar to those employed for compound (VI).

Compound (XXIX) can be produced by a condensation reaction of compound (XXVIII) with compound (XXVI). For example, the reaction can be performed by a method according to conditions similar to those employed for the production of compound (I).

Compound (B) can be produced by reacting compound (XXIX) with (XXII) according to the method described in Org. Lett., 2006, vol. 11, pages 2425-2428 and the like, or a method analogous thereto.

Compound (B) can also be produced by performing, when desired in addition to the above-mentioned reaction, known hydrolysis reaction, acylation reaction, alkylation reaction, amination reaction, oxidation-reduction reaction, cyclization reaction, carbon chain extension reaction, substituent exchange reaction and the like, each singly or in combination of multiple operations.

When compound (B) is obtained as a free compound, it can be converted to an object salt by a method known per se or a method analogous thereto. When compound (B) is obtained as a salt, it can be converted to a free form or other object salt by a method known per se or a method analogous thereto.

This method is used for the production of a compound wherein compound (VIII) has a structure shown by compound (XXXIII).

Compound (XXX) can be separated from compound (XVII), which is a mixture of compounds (XXX) and (XXXI), according to a known purification method, for example, diastereomeric salt method, optically active column chromatography and the like.

Compound (XXX) can also be produced by a method known per se, for example, the method described in Tetrahedron Lett., 2003, vol. 44, pages 1611-1614 and the like, or a method analogous thereto.

Compound (XXXII) is produced by a rearrangement reaction (e.g., Curtius rearrangement and the like) of compound (XXX).

Compound (XXXII) can be produced by a known method, for example, the method described in Tetrahedron Lett., 2003, vol. 44, pages 1611-1614 and the like, or a method analogous thereto.

Compound (XXXIII) can be produced by a reaction to introduce substituent R$^{1a}$ into the amino group of compound (XXXII) (e.g., reductive alkylation).

Compound (XXXIII) can be produced by a known method, for example, Bioorg. Med. Chem. Lett., 2005, vol. 15, pages 833-838, or a method analogous thereto.

(Reaction 10)

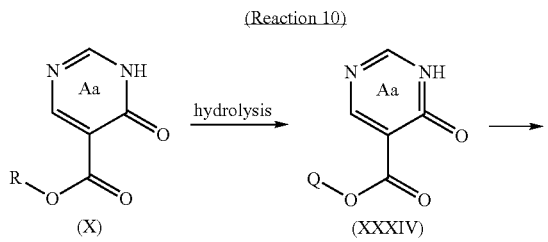

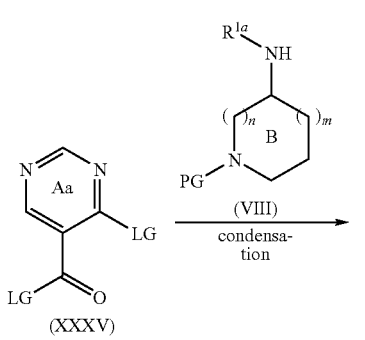

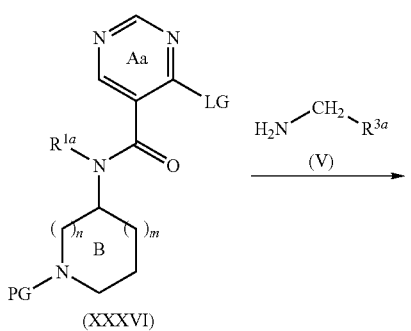

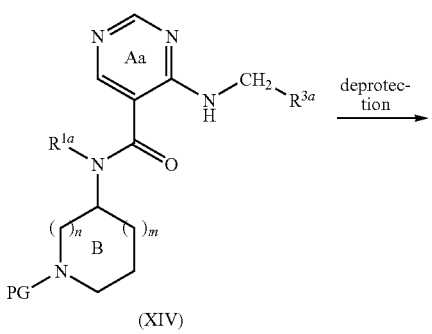

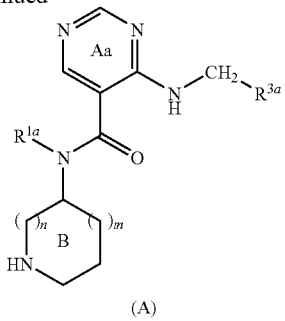

(A)

This method is used for the production of compound (A) wherein ring Aa is a pyrimidine ring.

Compound (XXXIV) can be produced by subjecting compound (X) to known hydrolysis, for example, alkaline hydrolysis or acid hydrolysis. For example, the reaction can be performed by a method according to hydrolysis conditions similar to those employed for hydrolysis of compound (XII).

Compound (XXXV) having a substitutable leaving group LG can be produced by using compound (XXXIV) as a starting material and according to a method known per se, for example, the method described in J. Med. Chem., 2000, vol. 43, pages 3995-4004 and the like, or a method analogous thereto. As the reagent in this step, phosphorus oxychloride, phosphorus oxybromide, thionyl chloride and the like are preferable.

The amount of the reagent to be used is about 1 mol to a large excess, per 1 mol of compound (XXXIV).

This reaction is advantageously performed using a solvent inert to the reaction or without solvent. While the solvent is not particularly limited as long as the reaction proceeds, for example, solvents such as hydrocarbons (e.g., benzene, toluene, cyclohexane, hexane and the like), halogenated hydrocarbons (e.g., dichloromethane, chloroform, carbon tetrachloride, 1,2-dichloroethane and the like), ethers (e.g., diethyl ether, tetrahydrofuran, dioxane and the like) and the like, a mixed solvent thereof and the like are preferable.

While the reaction time varies depending on the reagent to be used, it is generally 30 min to 24 hr, preferably 30 min to 8 hr.

The reaction temperature is generally 0° C. to 150° C., preferably 20° C. to 130° C.

Compound (XXXVI) can be produced by a condensation reaction of compound (XXXV) with compound (VIII). For example, the reaction can be performed by a method according to conditions similar to those employed for the production of compound (IX).

Compound (XIV) can be produced by reacting compound (XXXVI) with compound (V) and by a method according to conditions similar to those employed for the production of compound (XII).

Compound (A) is produced by removing the N-protecting group PG of compound (XIV). Moreover, when the starting material compound has an amino group, a carboxyl group or a hydroxyl group as a substituent in each of the above-mentioned reactions, these groups are optionally protected by a protecting group generally used in the peptide chemistry and the like. In this case, the object compound can be obtained by removing the protecting group as necessary after the reaction. These protecting groups can be introduced or removed by a method known per se, for example, the method described in Theodora W. Greene and Peter G. M. Wuts, "Protective Groups in Organic Synthesis, 3${}^{rd}$ Ed.", Wiley-Interscience (1999) and the like.

When compound (A) is obtained as a free compound, it can be converted to an object salt by a method known per se or a method analogous thereto. When compound (A) is obtained as a salt, it can be converted to a free form or other object salt by a method known per se or a method analogous thereto.

(Reaction 11)

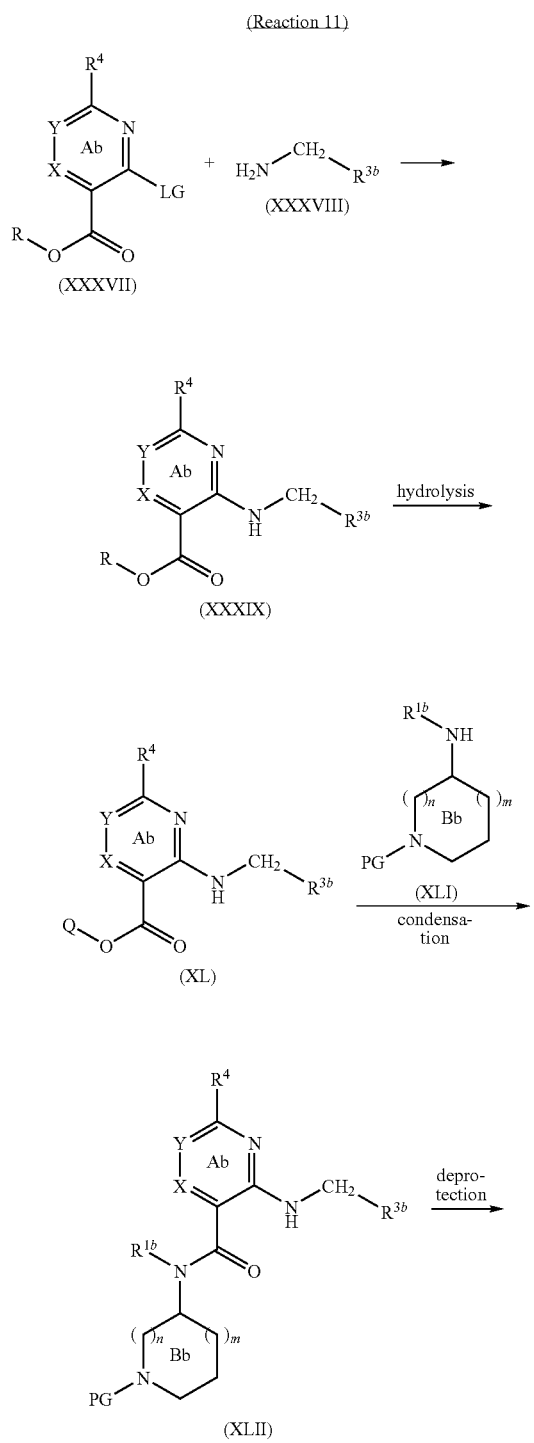

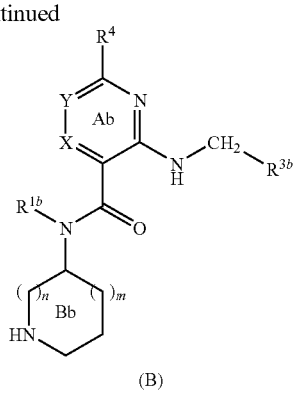

This method is used for the production of compound (B) wherein $R^{2b}$ is a nitrogen-containing 5- to 7-membered ring optionally having substituent(s).

Compound (XXXIX) can be produced by reacting compound (XXXVII) with compound (XXXVIII) and by a method according to conditions similar to those employed for the production of compound (VI).

As compound (XXXVII), a commercially available product may be used, or it can be produced by a method known per se, for example, the method described in Bioorg. Med. Chem. Lett., 2000, vol. 10, pages 1645-1648 and the like, or a method analogous thereto.

As compound (XXXVIII), a commercially available product may be used, or it can be produced by a method known per se, for example, the method described in J. Org. Chem., 1970, vol. 35, pages 340-344 and the like, or a method analogous thereto.

Compound (XL) can be produced by subjecting compound (XXXIX) to known hydrolysis, for example, alkaline hydrolysis or acid hydrolysis. For example, the reaction can be performed by a method according to hydrolysis conditions similar to those employed for compound (VI).

Compound (XLII) can be produced by a condensation reaction of compound (XL) with compound (XLI). For example, the reaction can be performed by a method according to conditions similar to those employed for the production of compound (IX).

As compound (XLI), a commercially available product may be used, or it can produced by a method according to conditions similar to those employed for the production of compound (VIII).

Compound (B) is produced by removing the N-protecting group PG of compound (XLII). Moreover, when the starting material compound has an amino group, a carboxyl group or a hydroxyl group as a substituent in each of the above-mentioned reactions, these groups are optionally protected by a protecting group generally used in the peptide chemistry and the like. In this case, the object compound can be obtained by removing the protecting group as necessary after the reaction. These protecting groups can be introduced or removed by a method according to conditions similar to those employed for the production of compound (A).

When compound (B) is obtained as a free compound, it can be converted to an object salt by a method known per se or a method analogous thereto. When compound (B) is obtained as a salt, it can be converted to a free form or other object salt by a method known per se or a method analogous thereto.

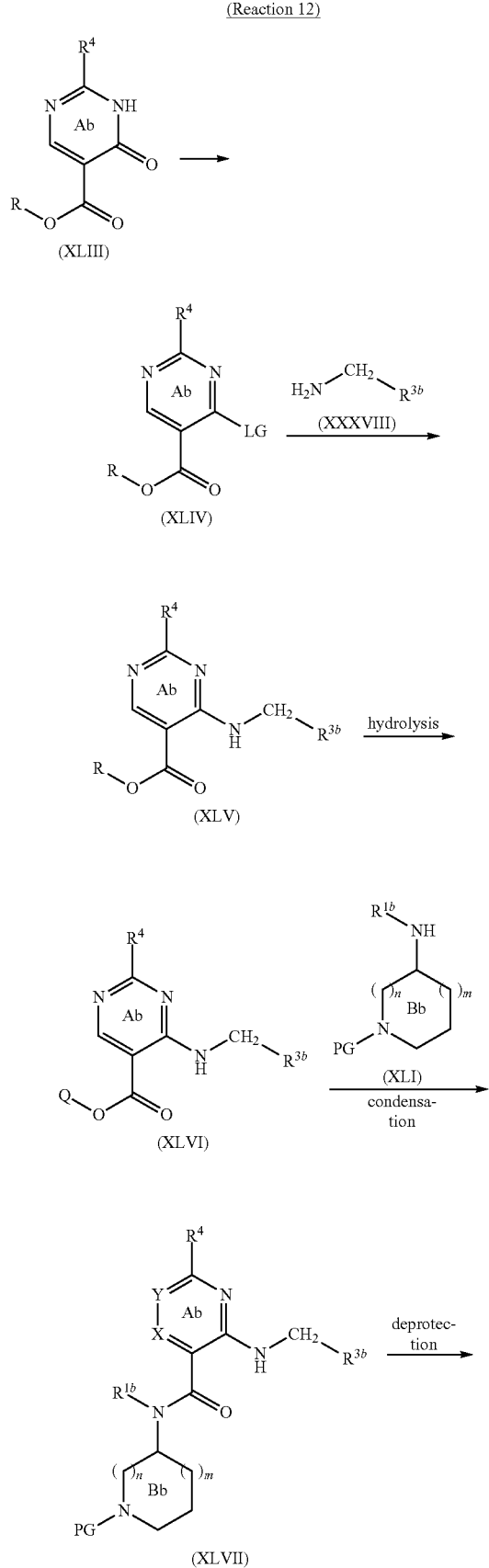

This method is used for the production of compound (B) wherein ring Ab is a pyrimidine ring and $R^{2b}$ is a nitrogen-containing 5- to 7-membered ring optionally having substituent(s).

As compound (XLIV), a commercially available product may be used, or it can be produced using compound (XLIII) as starting material and by a method according to conditions similar to those employed for the production of compound (XI).

Compound (XLV) can be produced by reacting compound (XLIV) with compound (XXXVIII) and by a method according to conditions similar to those employed for the production of compound (XII).

Compound (XLVI) can be produced by subjecting compound (XLV) to known hydrolysis, for example, alkaline hydrolysis or acid hydrolysis. For example, the reaction can be performed by a method according to hydrolysis conditions similar to those employed for compound (XII).

Compound (XLVII) can be produced by a condensation reaction of compound (XLVI) with compound (XLI). For example, the reaction can be performed by a method according to conditions similar to those employed for the production of compound (IX).

Compound (B) is produced by removing the N-protecting group PG of compound (XLVII). Moreover, when the starting material compound has an amino group, a carboxyl group or a hydroxyl group as a substituent in each of the above-mentioned reactions, these groups are optionally protected by a protecting group generally used in the peptide chemistry and the like. In this case, the object compound can be obtained by removing the protecting group as necessary after the reaction. These protecting groups can be introduced or removed by a method according to conditions similar to those employed for the production of compound (A).

When compound (B) is obtained as a free compound, it can be converted to an object salt by a method known per se or a method analogous thereto. When compound (B) is obtained as a salt, it can be converted to a free form or other object salt by a method known per se or a method analogous thereto.

(Reaction 13)

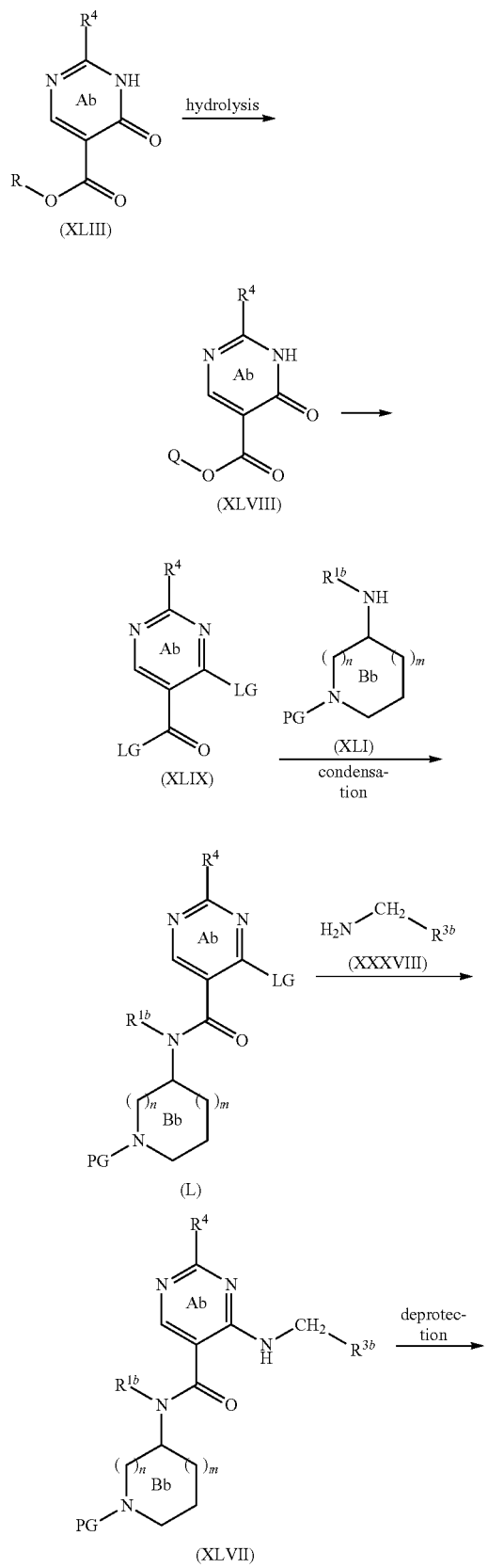

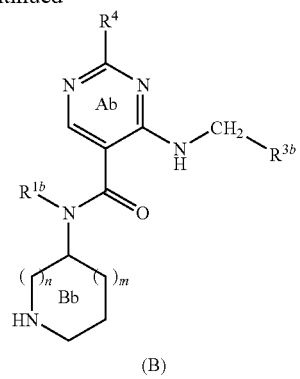

(B)

This method is used for the production of compound (B) wherein ring Ab is a pyrimidine ring and $R^{2b}$ is a nitrogen-containing 5- to 7-membered ring optionally having substituent(s).

Compound (XLVIII) can be produced by subjecting compound (XLIII) to known hydrolysis, for example, alkaline hydrolysis or acid hydrolysis. For example, the reaction can be performed by a method according to hydrolysis conditions similar to those employed for compound (XII).

Compound (XLIX) having a substitutable leaving group LG can be produced by using compound (XLVIII) as a starting material and by a method according to conditions similar to those employed for the production of compound (XXXV).

Compound (L) can be produced by a condensation reaction of compound (XLIX) with compound (XLI). For example, the reaction can be performed by a method according to conditions similar to those employed for the production of compound (IX).

Compound (XLVII) can be produced by reacting compound (L) with compound (XXXVIII) and by a method according to conditions similar to those employed for the production of compound (XII).

Compound (B) is produced by removing the N-protecting group PG of compound (XLVII). Moreover, when the starting material compound has an amino group, a carboxyl group or a hydroxyl group as a substituent in each of the above-mentioned reactions, these groups are optionally protected by a protecting group generally used in the peptide chemistry and the like. In this case, the object compound can be obtained by removing the protecting group as necessary after the reaction. These protecting groups can be introduced or removed by a method according to conditions similar to those employed for the production of compound (A).

When compound (B) is obtained as a free compound, it can be converted to an object salt by a method known per se or a method analogous thereto. When compound (B) is obtained as a salt, it can be converted to a free form or other object salt by a method known per se or a method analogous thereto.

(Reaction 14)

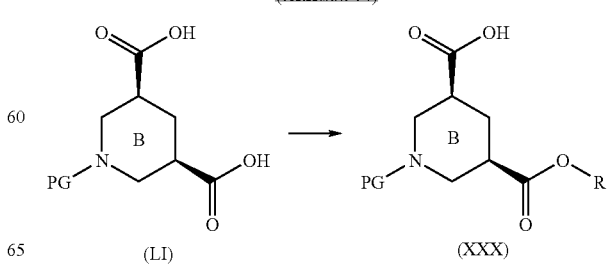

Compound (LI) can also be produced by a method known per se, for example, the method described in Tetrahedron Lett., 2003, vol. 44, pages 1611-1614 and the like, or a method analogous thereto.

Compound (XXX) can be produced by a known asymmetric esterification reaction and using compound (LI).

Compound (XXX) can also be produced by a known method, for example, the method described in J. Am. Chem. Soc., 2000, vol. 122, pages 9542-9543 and the like, or a method analogous thereto.

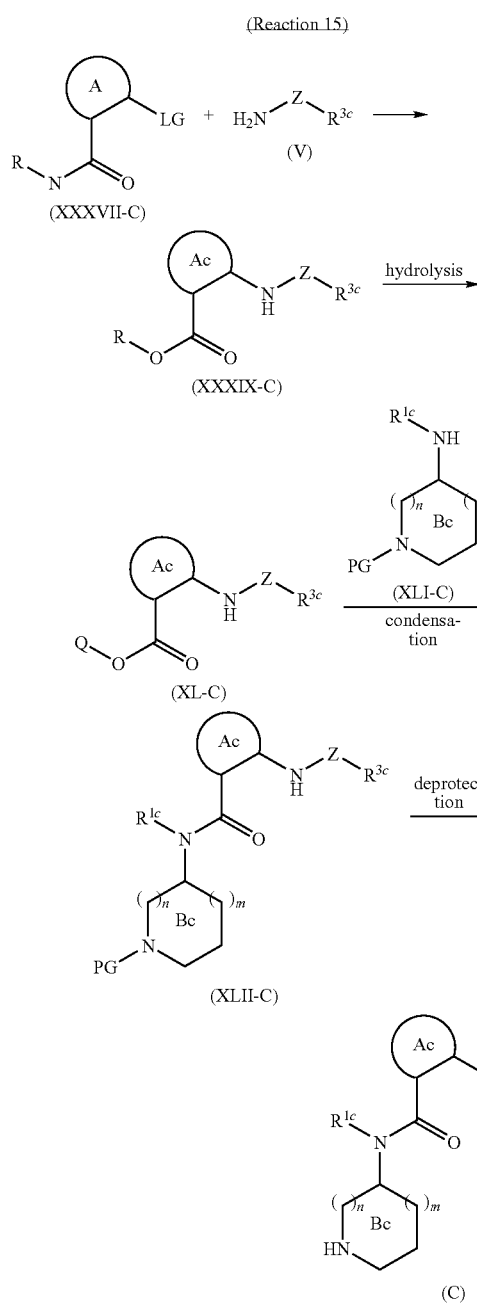

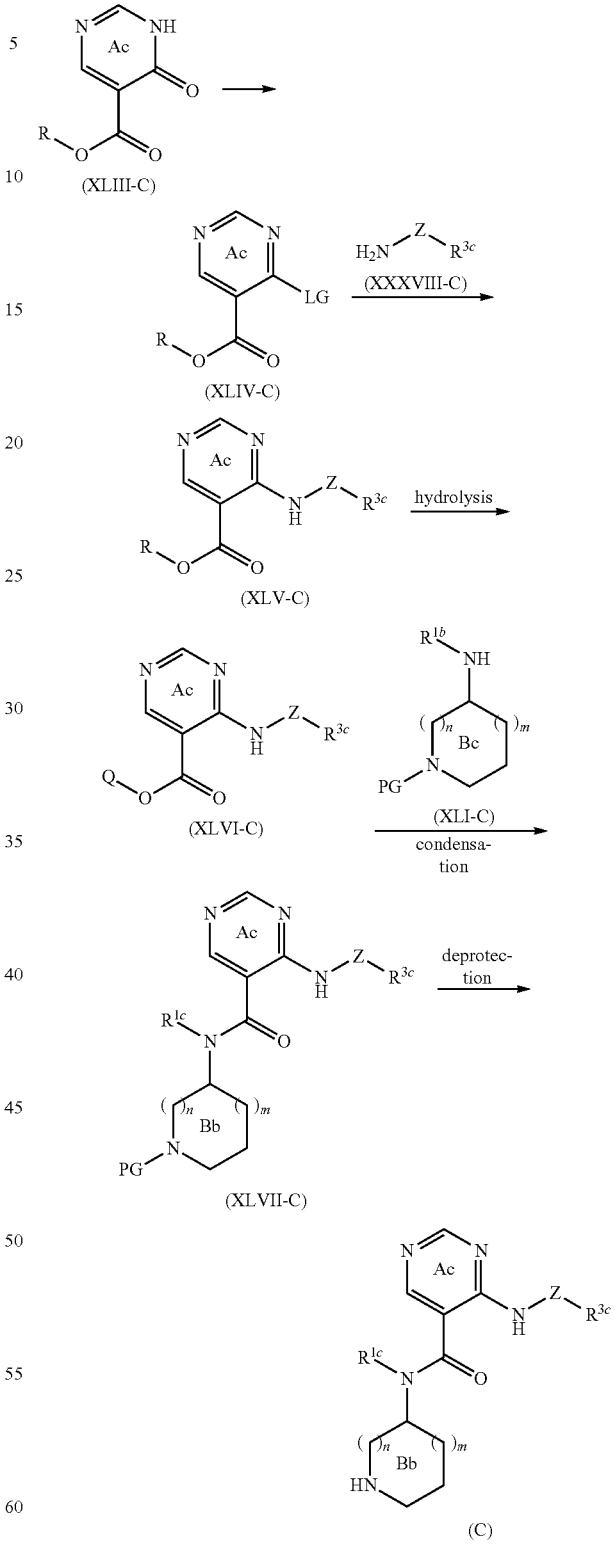

This method is used for the production of compound (C). The reaction in each step can be performed according to conditions similar to those employed for the production of compound (B) in reaction 11.

This method is used for the production of compound (C) wherein ring Ac is a pyrimidine ring. The reaction in each step can be performed according to conditions similar to those employed for the production of compound (B) in reaction 12.

(Reaction 17)

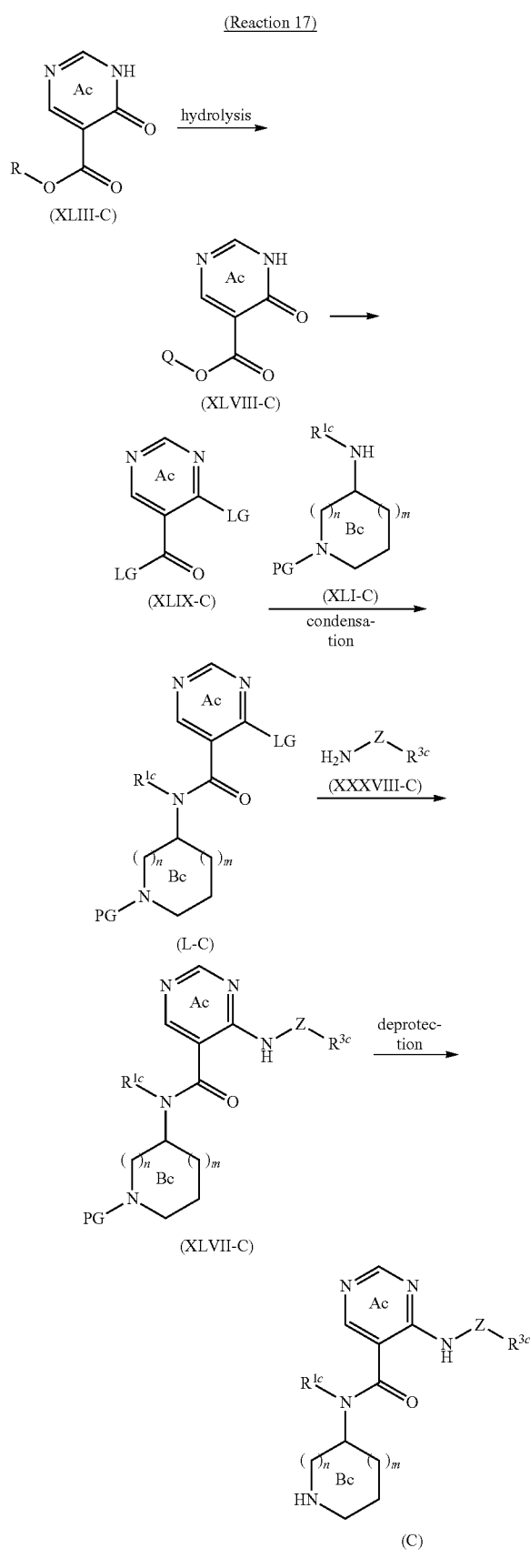

This method is used for the production of compound (C) wherein ring Ac is a pyrimidine ring. The reaction in each step can be performed according to conditions similar to those employed for the production of compound (B) in reaction 13.

Compound (I) (including compound (A), compound (B) and compound (C), hereinafter the same) may be used as a prodrug. A prodrug of compound (I) means a compound which is converted to compound (I) with a reaction due to an enzyme, gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

Examples of a prodrug of compound (I) include a compound wherein an amino group of compound (I) is acylated, alkylated or phosphorylated (e.g., compound wherein amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated, and the like); a compound wherein a hydroxy group of compound (I) is acylated, alkylated, phosphorylated or borated (e.g., a compound wherein a hydroxy group of compound (I) is acetylated, palmitoylated, propanoylated, pivaloylated, succinylated, fumarylated, alanylated or dimethylaminomethylcarbonylated, and the like); a compound wherein a carboxyl group of compound (I) is esterified or amidated (e.g., a compound wherein a carboxyl group of compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated, and the like) and the like. These compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

When compound (I) has an isomer such as optical isomer, stereoisomer, positional isomer, rotational isomer and the like, any isomers and a mixture thereof are encompassed in compound (I). For example, when compound (I) has an optical isomer, an optical isomer resolved from a racemate is also encompassed in compound (I). Such isomer can be obtained as a single product by a synthesis method, a separation method (e.g., concentration, solvent extraction, column chromatography, recrystallization etc.), optical resolution method (e.g., fractional recrystallization, chiral column method, diastereomer method etc.) and the like known per se.

Compound (I) may be a crystal, and both a single crystal and crystal mixtures are encompassed in compound (I). Crystals can be produced by crystallization according to crystallization methods known per se.

Compound (I) may be a solvate (e.g., hydrate etc.) or a non-solvate (e.g., non-hydrate etc.), both of which are encompassed in compound (I).

A compound labeled with an isotope (e.g., $^3H$, $^{14}C$, $^{35}S$, $^{125}I$ and the like) and the like is also encompassed in compound (I).

Deuterium-converted compound wherein $^1H$ has been converted to $^2H(D)$ are also encompassed in the compound (I).

Compound (I) or its prodrug, or salts thereof (hereinafter, sometimes to be abbreviated to as a compound of the present invention) exhibit superior renin inhibitory activity. They have low toxicity (e.g., acute toxicity, chronic toxicity, genetic toxicity, reproductive toxicity, cardiac toxicity, drug interaction, carcinogenicity, etc.) and high water-solubility, and are excellent in the aspects of stability, pharmacokinetics (absorption, distribution, metabolism, excretion, etc.) and efficacy, thus being useful as medicine.

The compound of the present invention acts as a renin inhibitory drug in mammals (e.g., mouse, rat, hamster, rabbit, cat, dog, cattle, sheep, monkey, human, etc.), and is useful as a drug inhibiting the RA system by inhibiting the biosynthesis of AII, and is useful as an agent for the prophylaxis or treatment of various diseases caused by the RA system.

Examples of such diseases include hypertension (e.g., essential hypertension, renal vascular hypertension, renoparenchymal hypertension, primary aldosteronism, Cushing's syndrome etc.), blood pressure circadian rhythm abnormality, heart diseases (e.g., cardiac hypertrophy, acute heart failure, chronic heart failure including congestive heart failure, failure of expansion, cardiac myopathy, angina pectoris, myocarditis, atrial fibrillation, arrhythmia, tachycardia, cardiac infraction etc.), cerebrovascular disorders (e.g., asymptomatic cerebrovascular disorder, transient ischemic attack, apoplexy, cerebrovascular dementia, hypertensive encephalopathy, cerebral infarction etc.), cerebral edema, cerebral circulatory disorder, recurrence and sequela of cerebrovascular disorders (e.g., neurotic symptom, psychic symptom, subjective symptom, disorder in daily living activities etc.), ischemic peripheral circulation disorder, myocardial ischemia, venous insufficiency, progression of cardiac insufficiency after myocardial infarction, renal diseases (e.g., nephritis, glomerulonephritis, glomerulosclerosis, renal failure, nephrotic syndrome, thrombotic vasculopathy, complication of dialysis, organ damage including nephropathy by radiation irradiation etc.), arteriosclerosis including atherosclerosis (e.g., aneurysm, coronary sclerosis, cerebral arteriosclerosis, peripheral arterial sclerosis etc.), vascular hypertrophy, vascular hypertrophy or obliteration and organ damages after intervention (e.g., percutaneous transluminal coronary angioplasty, stenting, coronary angioscopy, intravascular ultrasound, dounce thrombolytic therapy etc.), vascular re-obliteration and restenosis after bypass surgery, polycythemia, hypertension, organ damage and vascular hypertrophy after transplantation, rejection after transplantation, ocular diseases (e.g., glaucoma, ocular hypertension etc.), thrombosis, multiple organ disorder, endothelial dysfunction, hypertensive tinnitus, other cardiovascular diseases (e.g., deep vein thrombosis, obstructive peripheral circulatory disorder, arteriosclerosis obliterans, thromboangiitis obliterans, ischemic cerebral circulatory disorder, Raynaud's disease, Buerger's disease etc.), metabolic and/or nutritional disorders (e.g., diabetes, impaired glucose tolerance, insulin resistance, hyperinsulinemia, diabetic nephropathy, diabetic retinopathy, diabetic neuropathy, obesity, hyperlipidemia, hypercholesterolemia, hyperuricacidemia, hyperkalemia, hypernatremia etc.), metabolic syndrome, nerve degeneration diseases (e.g., Alzheimer's disease, Parkinson's disease, Creutzfeldt-Jakob disease, multiple sclerosis, amyotrophic lateral sclerosis, AIDS encephalopathy etc.), central nervous system disorders (e.g., damages such as cerebral hemorrhage and cerebral infarction, and sequela and complication thereof, head injury, spinal injury, cerebral edema, sensory malfunction, sensory functional disorder, autonomic nervous system disorder, autonomic nervous system malfunction etc.), dementia, migraine, defects of memory, disorder of consciousness, amnesia, anxiety symptom, catatonic symptom, discomfort mental state, sleep disorder, insomnia, psychopathies (e.g., depression, epilepsy, alcoholism etc.), inflammatory diseases (e.g., arthritis such as rheumatoid arthritis, osteoarthritis, rheumatoid myelitis, periostitis etc.; inflammation after operation or injury; remission of swelling; pharyngitis; cystitis; pneumonia; atopic dermatitis; inflammatory intestinal diseases such as Crohn's disease, ulcerative colitis etc.; meningitis; inflammatory ocular disease; inflammatory pulmonary diseases such as pneumonia, pulmonary silicosis, pulmonary sarcoidosis, pulmonary tuberculosis etc.), allergic diseases (e.g., allergic rhinitis, conjunctivitis, gastrointestinal allergy, pollinosis, anaphylaxis etc.), chronic obstructive pulmonary disease, interstitial pneumonia, pneumocystis carinni pneumonia, collagen diseases (e.g., systemic lupus erythematodes, scleroderma, polyarteritis etc.), hepatic diseases (e.g., hepatitis including chronic hepatitis, hepatic cirrhosis etc.), portal hypertension, digestive system disorders (e.g., gastritis, gastric ulcer, gastric cancer, gastric disorder after operation, dyspepsia, esophageal ulcer, pancreatitis, colon polyp, cholelithiasis, hemorrhoidal disease, varices ruptures of esophagus and stomach etc.), blood and/or myelopoietic diseases (e.g., erythrocytosis, vascular purpura, autoimmune hemolytic anemia, disseminated intravascular coagulation syndrome, multiple myelopathy etc.), bone diseases (e.g., fracture, refracture, osteoporosis, osteomalacia, Paget's disease of bone, sclerosing myelitis, rheumatoid arthritis, joint tissue dysfunction and the like caused by osteoarthritis of the knee and diseases similar to these), solid tumor, tumors (e.g., malignant melanoma, malignant lymphoma, cancer of digestive organs (e.g., stomach, intestine etc.) etc.), cancer and cachexia following cancer, metastasis cancer, endocrinopathy (e.g., Addison's disease, pheochromocytoma etc.), urinary organ and/or male genital diseases (e.g., cystitis, benign prostatic hyperplasia, prostatic cancer, sex infectious disease etc.), female disorders (e.g., climacteric disorder, gestosis, endometriosis, hysteromyoma, ovarian disease, breast disease, sex infectious disease etc.), disease relating to environment and occupational factors (e.g., radiation hazard, hazard by ultraviolet, infrared or laser beam, altitude sickness etc.), respiratory diseases (e.g., cold syndrome, pneumonia, asthma, pulmonary hypertension, pulmonary thrombosis and pulmonary embolism etc.), infectious diseases (e.g., viral infectious diseases with cytomegalovirus, influenza virus, herpes virus etc., rickettsiosis, bacterial infectious disease etc.), toxemias (e.g., sepsis, septic shock, endotoxin shock, Gram-negative sepsis, toxic shock syndrome etc.), otorhinolaryngological diseases (e.g., Meniere's syndrome, tinnitus, dysgeusia, vertigo, disequilibrium, dysphagia etc.), skin diseases (e.g., keloid, hemangioma, psoriasis etc.), intradialytic hypotension, myasthenia gravis, systemic diseases such as chronic fatigue syndrome and the like.

The compound of the present invention can be used in combination with an existing hypertension therapeutic drug such as an ACE inhibitor (captopril, enalapril maleate, alacepril, delapril hydrochloride, imidapril hydrochloride, quinapril hydrochloride, cilazapril, temocapril hydrochloride, trandolapril, benazepril hydrochloride, perindopril, lisinopril, etc.), ARB (losartan potassium, candesartan cilexetil, valsartan, TAK-536, TAK-491, irbesartan, telmisartan, eprosartan, olmesartan medoxomil, etc.), an aldosterone receptor antagonist (spironolactone, eplerenone, etc.), a Ca-ion channel inhibitor (verapamil hydrochloride, diltiazem hydrochloride, nifedipine, amlodipine hydrochloride, azelnidipine, aranidipine, efonidipine hydrochloride, cilnidipine, nicardipine hydrochloride, nisoldipine, nitrendipine, nilvadipine, barnidipine hydrochloride, felodipine, benidipine hydrochloride, manidipine hydrochloride, etc.), diuretic (trichlormethiazide, hydrochlorothiazide, benzylhydrochlorothiazide, indapamide, tripamide, meticrane, mefruside, furosemide, triamterene, chlorthalidone etc.), a β-blocker (propranolol hydrochloride, atenolol, metoprolol tartrate, bisoprolol fumarate, etc.), an α,β-blocker (carvedilol, etc.), and the like.

Moreover, the compound of the present invention can be also used in combination with an antithrombotic drug such as heparin sodium, heparin calcium, warfarin calcium (Warfarin), a blood coagulation factor Xa inhibitor, drug having a function of balance correction in the coagulation-fibrinolysis system, an oral thrombin inhibitor, a thrombolytic drug (tPA, urokinase, etc.), an antiplatelet drug [aspirin, sulfinpyrazone (Anturane), dipyridamol (Persantine), ticlopidine hydrochloride (Panaldine), clopidogrel, cilostazol (Pletal), GPIIb/IIIa antagonist (ReoPro, etc.)], and the like. Also, the compound can be used in combination with a lipid lowering drug or a cholesterol lowering drug. Examples thereof include a squalene synthase inhibitor (lapaquistat acetate etc.), fibrates (clofibrate, benzafibrate, gemfibrozil, etc.), nicotinic acid, its derivatives and analogs (acipimox, probucol, etc.), a bile acid binding resin (cholestyramine, colestipol, etc.), an omega-3 polyunsaturated fatty acid (EPA (eicosapentaenoic acid), DHA (docosahexaenoic acid), or a mixture thereof etc.), a compound inhibiting cholesterol absorption (sitosterol, neomycin, etc.), and a squalene epoxidase inhibitor (NB-598 and its analogs, etc.). Furthermore, other possible combination components are an oxidosqualene-lanosterol cyclase, for example, a decalin derivative, an azadecalin derivative, an indane derivative and the like. Combination with a HMG-CoA reductase (3-hydroxy-3-methylglutaryl coenzyme A reductase) inhibitor (atorvastatin calcium hydrate, pravastatin sodium, simvastatin, itavastatin, lovastatin, fluvastatin, etc.) is also possible.

The compound of the present invention can also be used in combination with a therapeutic drug for diabetes or a therapeutic drug for diabetic complications. For example, the compound of the present invention can be used in combination with an insulin preparation, an insulin sensitizer [pioglitazone hydrochloride, rosiglitazone, etc.], an α-glucosidase inhibitor [voglibose, acarbose, miglitol, emiglitate etc.], biguanide [phenformin, metformin, buformine etc.], insulin secretagogue [tolbutamide, glibenclamide, gliclazide, nateglinide, mitiglinide, glimepiride etc.], a dipeptidylpeptidase IV inhibitor [Alogliptin benzoate, Vidagliptin (LAF237), P32/98, Saxagliptin (BMS-477118) etc.], Kinedak, Penfill, Humulin, Euglucon, Glimicron, Daonil, Novolin, Monotard, Glucobay, Dimelin, Rastinon, Bacilcon, Deamelin S, Iszilin family, or the like.

In addition, the compound can be also used together with other pharmaceutical components, including a bone disease medicine, a myocardial protective drug, a coronary artery disease medicine, a chronic cardiac failure medicine, a hypothyroidism medicine, a nephrotic syndrome medicine, a chronic renal failure medicine, a gynecological disease medicine, an infection medicine, or the like.

The administration mode may be exemplified by (1) administration of a single preparation obtained by simultaneously formulating the compound of the present invention and the combination drug, (2) simultaneous administration through the same administration route of two preparations obtained by separately formulating the compound of the present invention and the combination drug, (3) administration with a time interval through the same administration route of two preparations obtained by separately formulating the compound of the present invention and the combination drug, (4) simultaneous administration through different administration routes of two preparations obtained by separately formulating the compound of the present invention and the combination drug, (5) administration with a time interval through different administration routes of two preparations obtained by separately formulating the compound of the present invention and the combination drug (e.g., administration in order of the compound of the present invention and then the combination drug, or administration in the reverse order), or the like. The amount of the combination drug to be administered can be appropriately selected with reference to the clinically used dosage. The mixing ratio of the compound of the present invention and the combination drug can be appropriately selected in accordance with the subject of administration, administration route, disease to be treated, symptoms, combination, and the like.

The compound of the present invention can be also used in combination with, for example, gene therapy involving VEGF, TNFα or the like, or therapeutic methods involving various antibody medicines or the like.

The compound of the present invention can be safely administered individually, or according to ordinary methods (e.g., methods described in the Japanese Pharmacopeia, etc.), as a pharmaceutical composition mixed with pharmaceutically acceptable carriers, for example, a tablet (including a sugar-coated tablet and a film-coated tablet), a film, a powder, a granule, a capsule, a liquid, an emulsion, a suspension, an injectable preparation, a suppository, a sustained release preparation, a patch and the like, either orally or parenterally (e.g., topical, rectal, intravenous administration, etc.).

The dosage form of the aforementioned pharmaceutical preparation may be exemplified by oral preparations such as a tablet (including a sublingual tablet and a buccal disintegration tablet), a film (including a buccal disintegration film), a capsule (including a soft capsule and a microcapsule), a granule, a powder, a troche, a syrup, an emulsion, a suspension and the like; and parenteral preparations such as an injectable preparation (e.g., a subcutaneous injectable preparation, an intravenous injectable preparation, intramuscular injectable preparation, intraperitoneal injectable preparation, a drip infusion), external preparation (e.g., a percutaneous preparation, an ointment), a suppository (e.g., a rectal suppository, a vaginal suppository), a pellet, a transnasal preparation, a transpulmonary preparation (inhalant), an eye drop and the like.

These preparations may be controlled release preparations such as a rapid release preparation, a sustained release preparation and the like (e.g., a sustained release microcapsule).

The content of the compound of the present invention in the pharmaceutical composition is about 0.01 to 100% by weight of the entire composition.

The amount of administration of the compound of the present invention may vary depending on the subject of administration, administration route, subject disease or the like; however, in the case of administering orally to an adult as a hypertension medicine, the amount of administration is about 0.0005 to 2 mg/kg of body weight, preferably about 0.001 to 1 mg/kg of body weight, and more preferably about 0.001 to 0.5 mg/kg of body weight, in terms of compound (I), the active ingredient, possibly once to several times a day.

The aforementioned pharmaceutically acceptable carrier may be exemplified by various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Further, if necessary, additives such as preservative, antioxidant, colorant, sweetening agent, adsorbing agent, wetting agent and the like can be also used.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoic acid esters, chlorobutanol, benzyl alcohol, phenethyl alcohol, dehydroacetic acid, sorbic acid and the like.

Examples of the antioxidant include sulfites, ascorbic acid, α-tocopherol and the like.

Examples of the colorant include water-soluble Food coal tar dyes (e.g., Food dyes such as Food Red No. 2 and No. 3, Food Yellow No. 4 and No. 5, Food Blue No. 1 and No. 2, and the like), water-insoluble lake dyes (e.g., aluminum salts of the aforementioned water-soluble Food coal tar dyes), natural dyes (e.g., β-carotene, chlorophyll, ferric oxide red) and the like.

Examples of the sweetening agent include saccharin sodium, dipotassium glycyrrhizinate, aspartame, stevia and the like.

EXAMPLES

The present invention is explained in detail in the following by referring to Reference Examples, Examples, Preparation Examples and Experimental Examples, which are not to be construed as limitative. Of the synthesis starting materials used in Reference Examples and Examples, synthesis methods of known compounds are omitted.

"Room temperature" in the following Reference Examples and Examples represents a temperature of about 10° C. to about 35° C., and "%" represents weight % unless otherwise stated. Provided that, yield represents mol/mol %.

$^{1}$H-NMR spectra were measured with a Varian MERCURY 300 (300 MHz) spectrometer or a BRUKER ADVANCE 300 (300 MHz) spectrometer using tetramethylsilane as an internal standard. All of the δ values are represented in ppm.

LC/MS spectra were measured under the following conditions.

Equipment: Agilent 1100 HPLC (Gilson 215 autosampler)/Waters ZQ, or Waters 2795/ZQ
Column: Capcell Pak C18 UG120 (1.5 mmID×35 mL, S-3 μm), manufactured by Shiseido Co., Ltd.
Solvent: Solution A (0.05% trifluoroacetic acid-containing water), Solution B (0.04% trifluoroacetic acid-containing water)
Gradient cycle: 0.00 min (A/B=90/10), 2.00 min (A/B=5/95), 2.75 min (A/B=5/95), 2.76 min (A/B=90/10), 3.45 min (A/B=90/10)
Flow rate: 0.5 ml/min
Detection: UV (220 nm)
Mass spectrum: electrospray ionization (ESI)

Reverse-phase preparative HPLC was performed on a YMC CombiPrep ODS-A (20 mmID×50 mL, S-5 μm) column using a Gilson UniPoint system, and eluted with 0.1% trifluoroacetic acid-containing acetonitrile/water (10:90-100:0) at a flow rate of 25 ml/min.

The microwave reactor used was Discover of CEM.

Other symbols used in the present text indicate the following meanings.

s: singlet, d: doublet, t: triplet, q: quartet, dd: double doublet, dt: double triplet, td: triple doublet, dq: double quartet, tq: triple quartet, ddd: double double doublet, dddd: double double double doublet, m: multiplet, br: broad.
DMF: N,N-dimethylformamide, DMSO: dimethyl sulfoxide, THF: tetrahydrofuran, DMA: N,N-dimethylacetamide.
HOBt: 1-hydroxybenzotriazole monohydrate, WSC.HCl: 1-ethyl-3-[3-(dimethylamino)propyl]carbodiimide hydrochloride, BOP reagent: benzotriazol-1-yloxytris(dimethylamino)phosphonium hexafluorophosphate, Z-chloride: benzyloxycarbonyl chloride,
TFA: trifluoroacetic acid.
Boc: tert-butoxycarbonyl.

When relative configuration is known but absolute configuration is not, the chiral atom is shown by R*, S*.

Reference Example 1 ethyl 2-tert-butyl-6-oxo-1,6-dihydropyrimidine-5-carboxylate

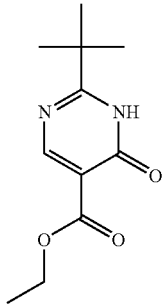

To a solution of diethyl 2,2-dimethylpropanimidamide hydrochloride (1.36 g) and (ethoxymethylene)malonate (2.16 g) in ethanol (100 ml) was added 20% sodium ethoxide-ethanol solution (6.8 g) under ice-cooling, and the mixture was stirred at 80° C. for 5 hr. The reaction mixture was concentrated under reduced pressure, 1 M hydrochloric acid (10 ml) was added under ice-cooling, and the mixture was extracted with ethyl acetate. The extract was concentrated under reduced pressure, hexane was added to the residue, and the precipitate was collected by filtration to give the object compound (1.65 g) as a powder.

MS (ESI+, m/e) 225 (M+1)

$^1$H-NMR (CDCl$_3$) δ 1.33-1.41 (3H, m), 1.43 (9H, s), 4.32-4.41 (2H, m), 8.72 (1H, s).

By a method similar to that of Reference Example 1, the following compounds (Reference Examples 2 to 7) were obtained.

Reference Example 2 ethyl 2-isopropyl-6-oxo-1,6-dihydropyrimidine-5-carboxylate

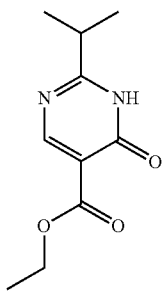

MS (ESI+, m/e) 211 (M+1)

Reference Example 3 ethyl 2-cyclopropyl-6-oxo-,6-dihydropyrimidine-5-carboxylate

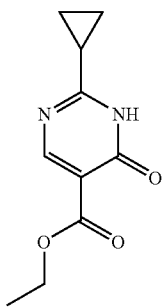

MS (ESI+, m/e) 209 (M+1)

Reference Example 4 ethyl 6-oxo-2-phenyl-1,6-dihydropyrimidine-5-carboxylate

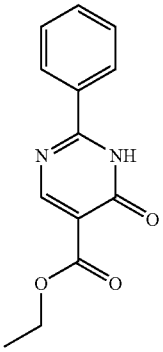

$^1$H-NMR (DMSO-d$_6$) δ 1.29 (3H, t), 4.26 (2H, q), 7.52-7.70 (3H, m), 8.17 (2H, d), 8.64 (1H, s), 13.20 (1H, br s).

Reference Example 5 ethyl 2-methyl-6-oxo-1,6-dihydropyrimidine-5-carboxylate

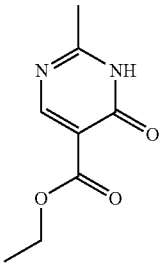

$^1$H-NMR (DMSO-d$_6$) δ 1.25 (3H, t), 2.34 (3H, s), 4.21 (2H, q), 8.41 (1H, s), 12.94 (1H, br s).

Reference Example 6 ethyl 2-ethyl-6-oxo-1,6-dihydropyrimidine-5-carboxylate

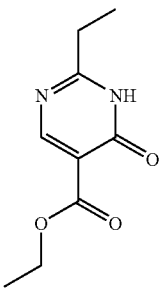

$^1$H-NMR (DMSO-d$_6$) δ 1.18 (3H, t), 1.25 (3H, t), 2.60 (2H, q), 4.21 (2H, q), 8.45 (1H, s), 12.90 (1H, br s).

Reference Example 7 ethyl 6-oxo-2-(2-thienyl)-1,6-dihydropyrimidine-5-carboxylate

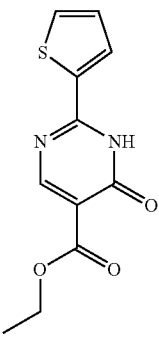

MS (ESI+, m/e) 251 (M+1)

Reference Example 8 ethyl 4-methyl-6-oxo-2-(trifluoromethyl)-1,6-dihydropyrimidine-5-carboxylate

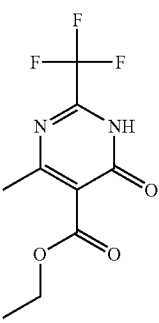

Trifluoroacetamidine (2.47 g) and diethyl ethylidenemalonate (3.64 ml) were dissolved in ethanol (50 ml) and the mixture was stirred at 90° C. overnight. The reaction mixture was concentrated under reduced pressure, and the residue was dissolved in water. The mixture was adjusted to pH 4 with 1 M hydrochloric acid, and extracted with ethyl acetate. The extract was washed with water and saturated brine, dried over anhydrous sodium sulfate, and concentrated under reduced pressure. The obtained residue was purified by silica gel column chromatography, and the obtained oil (570 mg) was dissolved in carbon tetrachloride (45 ml). N-Bromosuccinimide (381 mg), 2,2'-azobis(2-methylpropionitrile) (16 mg) and potassium carbonate (2.90 g) were added and the mixture was heated under reflux for 30 min. The reaction mixture was cooled to room temperature, and water was added. The aqueous layer was separated, adjusted to pH 3 with 1 M hydrochloric acid, and extracted with ethyl acetate. The extract was washed with saturated brine, dried over anhydrous sodium sulfate, and concentrated under reduced pressure. The obtained residue was purified by silica gel column chromatography to give the object compound (313 mg) as a powder.

$^1$H-NMR (CDCl$_3$) δ 1.49 (3H, t), 2.85 (3H, s), 4.22-4.42 (1H, m), 4.55 (2H, q).

Reference Example 9

2-[(2-furylmethyl)amino]-6-methylnicotinic acid

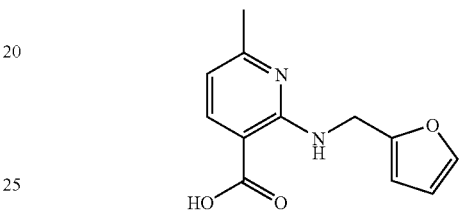

2-Chloro-6-methylnicotinic acid (1.72 g) and furfurylamine (1.94 g) were dissolved in 1-methylpyrrolidin-2-one (25 ml), and the mixture was stirred at 150° C. overnight. The reaction mixture was concentrated under reduced pressure, and the residue was purified by silica gel column chromatography. The fraction eluted with ethyl acetate-hexane (1:4-1:0) was concentrated under reduced pressure, and the precipitate was collected by filtration to give the object compound (838 mg) as a powder.

$^1$H-NMR (CDCl$_3$) δ 2.45 (3H, s), 4.78 (2H, s), 6.26 (1H, d), 6.32 (1H, dd), 6.46 (1H, d), 7.33-7.40 (1H, m), 8.05-8.14 (2H, m).

By a method similar to that of Reference Example 9, the following compounds (Reference Examples 10 and 11) were obtained.

Reference Example 10

6-methyl-2-{[(5-methyl-2-furyl)methyl]amino}nicotinic acid

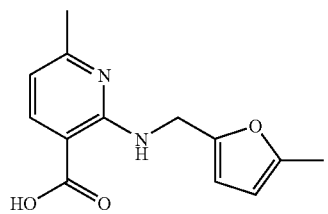

$^1$H-NMR (CDCl$_3$) δ 2.28 (3H, s), 2.44 (3H, s), 4.71 (2H, s), 5.89 (1H, d), 6.13 (1H, d), 6.45 (1H, d), 7.97-8.07 (2H, m).

Reference Example 11

6-methyl-2-[(2-thienylmethyl)amino]nicotinic acid

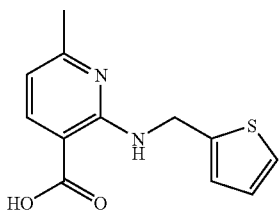

¹H-NMR (CDCl₃) δ 2.47 (3H, s), 4.94 (2H, d), 6.47 (1H, d), 6.94 (1H, dd), 7.03 (1H, d), 7.19 (1H, d), 8.05 (1H, d), 8.13 (s, 1H)

Reference Example 12

4-[(2-furylmethyl)amino]-2-(methylthio)pyrimidine-5-carboxylic acid

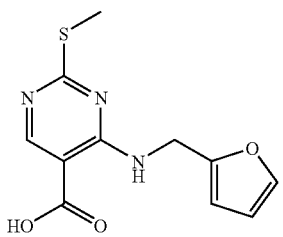

To a solution of ethyl 4-chloro-2-(methylthio)pyrimidine-5-carboxylate (1.71 g) in 2-propanol (10 ml) were added furfurylamine (714 mg) and diisopropylethylamine (950 mg), and the mixture was stirred at room temperature for 10 min. The reaction mixture was poured into 2% aqueous sodium hydrogen carbonate, and the mixture was extracted with ethyl acetate. The extract was dried over anhydrous magnesium sulfate, and the solvent was evaporated under reduced pressure. Ethyl acetate was added to the residue, and the precipitate was collected by filtration. The precipitate was dissolved in ethanol (10 ml), 2 M aqueous sodium hydroxide solution (10 ml) was added and the mixture was stirred at room temperature for 5 hr. The reaction mixture was adjusted to pH 3 with 1 M hydrochloric acid, and the precipitated crystals were collected by filtration to give the object compound (1.75 g) as a powder.

¹H-NMR (DMSO-d₆) δ 2.48 (3H, s), 4.72 (2H, d), 6.30 (1H, d), 6.39-6.45 (1H, m), 7.60 (1H, d), 8.54 (1H, s), 8.74 (1H, t), 13.34 (1H, s).

By a method similar to that of Reference Example 12, the following compounds (Reference Examples 13 to 20) were obtained.

Reference Example 13

4-(benzylamino)-2-(methylthio)pyrimidine-5-carboxylic acid

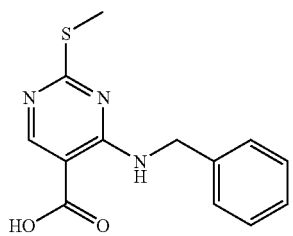

¹H-NMR (DMSO-d₆) δ 2.40 (3H, s), 4.71 (2H, d), 7.23-7.28 (1H, m), 7.30-7.35 (4H, m), 8.53 (1H, s), 8.90 (1H, t), 13.28 (1H, s).

Reference Example 14

4-[(2-furylmethyl)amino]-2-(trifluoromethyl)pyrimidine-5-carboxylic acid

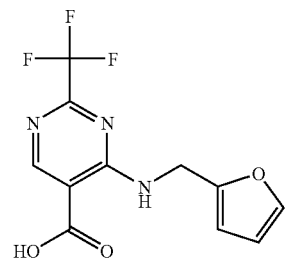

MS (ESI+, m/e) 288 (M+1)

Reference Example 15

4-(benzylamino)-2-(trifluoromethyl)pyrimidine-5-carboxylic acid

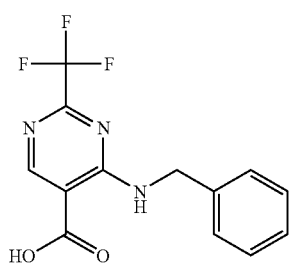

¹H-NMR (CDCl₃) δ 4.82 (2H, d), 7.28-7.41 (5H, m), 8.65 (1H, br s), 9.01 (1H, s).

Reference Example 16

4-[(1,3-oxazol-2-ylmethyl)amino]-2-(trifluoromethyl)pyrimidine-5-carboxylic acid

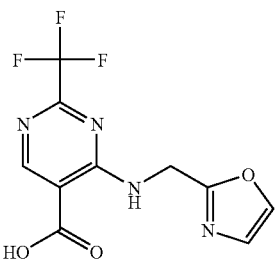

¹H-NMR (CDCl₃) δ 4.95 (2H, s), 7.10 (1H, d), 7.66 (1H, d), 8.99 (1H, s).

Reference Example 17

4-[(tetrahydrofuran-2-ylmethyl)amino]-2-(trifluoromethyl)pyrimidine-5-carboxylic acid

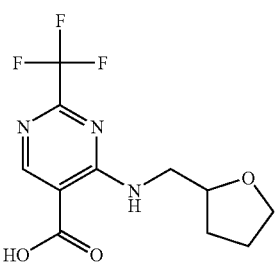

¹H-NMR (DMSO-d₆) δ 1.48-1.65 (1H, m), 1.77-2.00 (3H, m), 3.53 (1H, dd), 3.58-3.72 (2H, m), 3.78 (1H, t), 4.05 (1H, dd), 8.79-8.90 (2H, m), 13.99 (1H, br s).

Reference Example 18

4-[(2-ethoxyethyl)amino]-2-(trifluoromethyl)pyrimidine-5-carboxylic acid

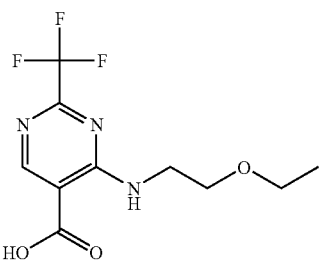

¹H-NMR (DMSO-d₆) δ 1.11 (3H, t), 3.48 (2H, q), 3.57 (2H, d), 3.67 (2H, q), 8.83 (1H, s), 8.84-8.91 (1H, m), 13.94 (1H, br s).

Reference Example 19

4-[(3-methoxypropyl)amino]-2-(trifluoromethyl)pyrimidine-5-carboxylic acid

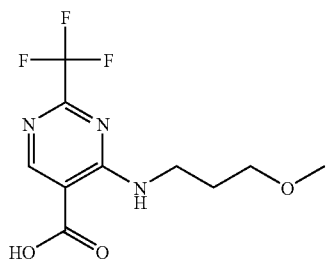

¹H-NMR (DMSO-d₆) δ 1.77-1.87 (2H, m), 3.24 (3H, s), 3.41 (2H, t), 3.57 (2H, q), 8.81 (1H, s), 8.88 (1H, t), 13.87 (1H, br s).

Reference Example 20

4-(butylamino)-2-(trifluoromethyl)pyrimidine-5-carboxylic acid

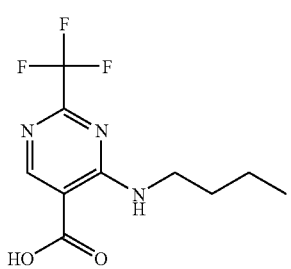

¹H-NMR (DMSO-d₆) δ 0.86-0.94 (3H, m), 1.23-1.39 (2H, m), 1.51-1.62 (2H, m), 3.51 (2H, q), 8.76 (1H, t), 8.81 (1H, s), 13.90 (1H, br s).

Reference Example 21

2-tert-butyl-4-[(2-furylmethyl)amino]pyrimidine-5-carboxylic acid

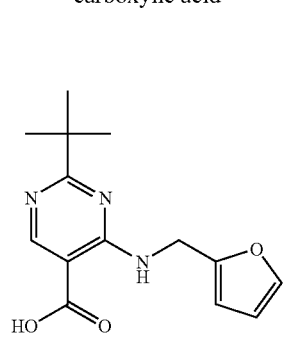

Ethyl 2-tert-butyl-6-oxo-1,6-dihydropyrimidine-5-carboxylate (2.90 g) was suspended in phosphorus oxychloride (9.6 g), and the suspension was stirred at 100° C. for 2 hr. Phosphorus oxychloride was evaporated under reduced pressure, and the mixture was cooled to 0° C. and neutralized with saturated aqueous sodium hydrogen carbonate and water. The mixture was extracted with ethyl acetate. The extract was washed with saturated brine, dried over anhydrous sodium sulfate, and concentrated under reduced pressure. The obtained residue was dissolved in 2-propanol (10 ml), and furfurylamine (1.20 ml) and diisopropylethylamine (2.26 ml) were added. The mixture was stirred at 100° C. for 15 hr and concentrated under reduced pressure. Saturated aqueous sodium hydrogen carbonate was added, and the mixture was extracted with ethyl acetate. The extract was washed with saturated brine, dried over anhydrous sodium sulfate, and concentrated under reduced pressure. The obtained residue was purified by silica gel chromatography, and the fraction eluted with ethyl acetate-hexane (1:5) was concentrated under reduced pressure. The obtained residue was dissolved in ethanol (15 ml) and THF (5 ml), 2 M aqueous sodium hydroxide solution (15 ml) was added and the mixture was stirred at room temperature for 15 hr. The reaction mixture was concentrated under reduced pressure and the aqueous layer was adjusted to pH 3 with 1 M hydrochloric acid. The precipitate was collected by filtration and washed with water to give the object compound (3.30 g) as a powder.

$^1$H-NMR (DMSO-$d_6$) δ 1.32 (9H, s), 4.77 (2H, d), 6.32 (1H, s), 6.40 (1H, s), 7.60 (1H, s), 8.68 (1H, s), 8.99 (1H, s).

By a method similar to that of Reference Example 21, the following compounds (Reference Examples 22 to 32) were obtained.

Reference Example 22

4-[(2-furylmethyl)amino]-2-isopropylpyrimidine-5-carboxylic acid

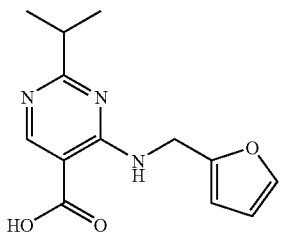

$^1$H-NMR (DMSO-$d_6$) δ 1.23 (6H, d), 2.94-3.09 (1H, m), 4.78 (2H, d), 6.33 (1H, d), 6.41 (1H, s), 7.60 (1H, s), 8.70 (1H, s), 9.09 (1H, s).

Reference Example 23

2-cyclopropyl-4-[(2-furylmethyl)amino]pyrimidine-5-carboxylic acid

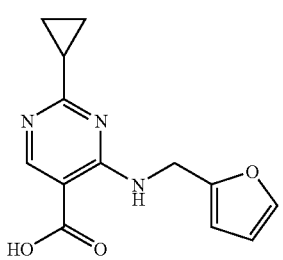

$^1$H-NMR (DMSO-$d_6$) δ 1.08-1.29 (4H, m), 2.16-2.29 (1H, m), 4.73 (2H, d), 6.31 (1H, d), 6.42 (1H, t), 7.60 (1H, t), 8.67 (1H, s), 9.40 (1H, s).

Reference Example 24

4-[(2-furylmethyl)amino]-2-phenylpyrimidine-5-carboxylic acid

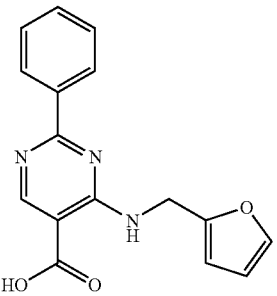

$^1$H-NMR (CDCl$_3$) δ 4.86 (2H, d), 6.36-6.42 (2H, m), 7.48-7.61 (4H, m), 8.42 (2H, dd), 8.72 (1H, s), 8.86 (1H, s).

Reference Example 25

4-[(2-furylmethyl)amino]-2-methylpyrimidine-5-carboxylic acid

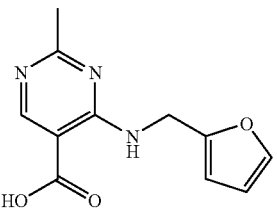

MS (ESI+, m/e) 234 (M+1)

Reference Example 26

2-ethyl-4-[(2-furylmethyl)amino]pyrimidine-5-carboxylic acid

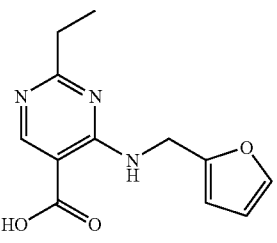

MS (ESI+, m/e) 248 (M+1)

Reference Example 27

4-[(2-furylmethyl)amino]-2-(2-thienyl)pyrimidine-5-carboxylic acid

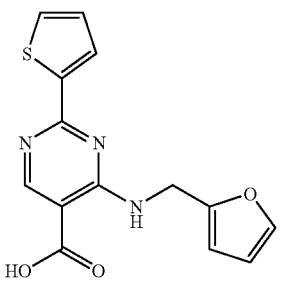

MS (ESI+, m/e) 302 (M+1)

Reference Example 28

2-isopropyl-4-[(tetrahydrofuran-2-ylmethyl)amino]pyrimidine-5-carboxylic acid

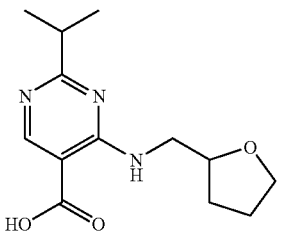

$^1$H-NMR (DMSO-$d_6$) δ 1.25 (6H, d), 1.59 (1H, td), 1.78-2.00 (3H, m), 3.03 (1H, dt), 3.55-3.83 (4H, m), 3.99-4.13 (1H, m), 8.69 (1H, s), 9.10 (1H, br s).

Reference Example 29

4-[(2-ethoxyethyl)amino]-2-isopropylpyrimidine-5-carboxylic acid

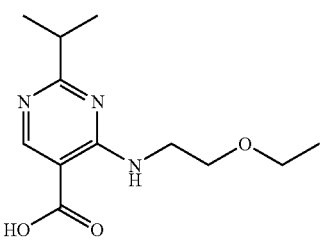

$^1$H-NMR (DMSO-$d_6$) δ 1.12 (3H, t), 1.26 (6H, d), 2.98-3.17 (1H, m), 3.49 (2H, q), 3.59 (2H, t), 3.77 (2H, q), 8.70 (1H, s), 9.34 (1H, br s).

Reference Example 30

2-isopropyl-4-[(3-methoxypropyl)amino]pyrimidine-5-carboxylic acid

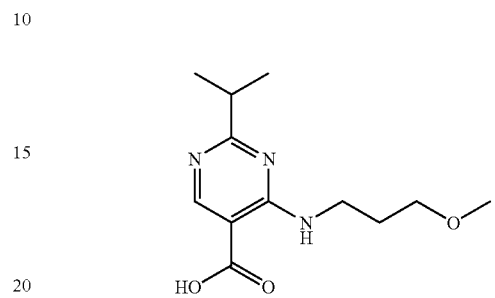

$^1$H-NMR (DMSO-$d_6$) δ 1.25 (6H, d), 1.78-1.88 (2H, m), 2.96-3.17 (1H, m), 3.16-3.31 (3H, m), 3.41 (2H, t), 3.63 (2H, q), 8.65 (1H, s), 9.09 (1H, br s).

Reference Example 31

4-(butylamino)-2-isopropylpyrimidine-5-carboxylic acid

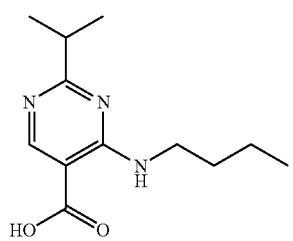

$^1$H-NMR (DMSO-$d_6$) δ 0.91 (3H, t), 1.21 (6H, d), 1.26-1.41 (2H, m), 1.50-1.70 (2H, m), 2.85-2.98 (1H, m), 3.42-3.57 (2H, m), 8.42 (1H, br s), 8.62 (1H, s), 13.21 (1H, br s).

Reference Example 32

4-[(2-furylmethyl)amino]-6-methyl-2-(trifluoromethyl)pyrimidine-5-carboxylic acid

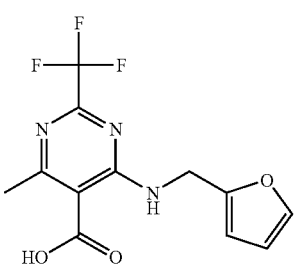

MS (ESI+, m/e) 302 (M+1)

Reference Example 33 dimethylpyridine-3,5-dicarboxylate

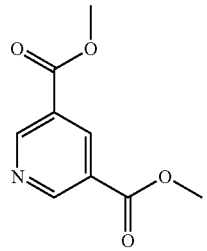

Pyridine-3,5-dicarboxylic acid (100 g) was suspended in methanol (1000 ml), and thionyl chloride (130 ml) was added dropwise at room temperature. The reaction mixture was stirred with heating to reflux for 3 hr. The mixture was allowed to cool to room temperature, and concentrated under reduced pressure. The residue was diluted with water, and the mixture was extracted with ethyl acetate. The aqueous layer was neutralized with 8 M aqueous sodium hydroxide solution, and the mixture was extracted with ethyl acetate. The extract was washed successively with saturated aqueous sodium hydrogen carbonate solution and saturated brine, and dried over anhydrous sodium sulfate. The solvent was evaporated under reduced pressure to give the object compound (117 g) as a powder.

$^1$H-NMR (CDCl$_3$) δ 4.00 (6H, s), 8.88 (1H, t), 9.37 (2H, d).

Reference Example 34

(3R*,5S*)-1-(tert-butoxycarbonyl)-5-(methoxycarbonyl)piperidine-3-carboxylic acid

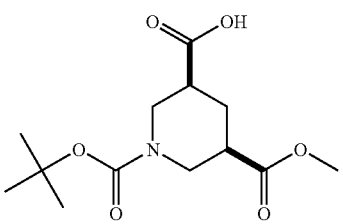

Dimethylpyridine-3,5-dicarboxylate (55 g) was dissolved in methanol (500 ml) and 6 M hydrochloric acid (70 ml), and rhodium-carbon (5.5 g) was added. The reaction mixture was stirred under pressurized hydrogen atmosphere (5 atm) at room temperature for 3 hr and then at 50° C. for 12 hr. The mixture was allowed to cool to room temperature, the rhodium catalyst was filtered off, and the filtrate was concentrated under reduced pressure. The residue was dissolved in ethanol (300 ml), and triethylamine (60 ml) and di-t-butyl dicarbonate (68 g) were successively added under ice-cooling. The reaction mixture was stirred at room temperature for 12 hr, and concentrated under reduced pressure. The residue was dissolved in 0.5 M hydrochloric acid, and the mixture was extracted with ethyl acetate. The extract was washed with saturated brine, and dried over anhydrous sodium sulfate. The solvent was evaporated under reduced pressure and the residue was purified by silica gel column chromatography. The fraction eluted with hexane-ethyl acetate (7:1-1:4) was concentrated under reduced pressure. The residue was diluted with ethyl acetate, and the precipitate was collected by filtration and washed with ethyl acetate to give the object compound (15.6 g) as a powder.

$^1$H-NMR (CDCl$_3$) δ 1.47 (9H, s), 1.72 (1H, d), 2.41-2.63 (3H, m), 2.72 (2H, br s), 3.71 (3H, s), 4.38 (2H, d).

Reference Example 35

1-tert-butyl 3-methyl (3R*,5S*)-5-aminopiperidine-1,3-dicarboxylate

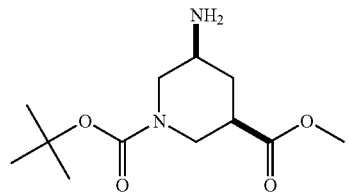

(3R*,5S*)-1-(tert-Butoxycarbonyl)-5-(methoxycarbonyl)piperidine-3-carboxylic acid (575 mg) was suspended in toluene (10 ml), diphenylphosphoryl azide (0.52 ml) and triethylamine (0.34 ml) were added and the mixture was stirred at 80° C. for 2 hr. The reaction mixture was cooled to room temperature, benzyl alcohol (0.52 ml) and triethylamine (0.34 ml) were added and the mixture was stirred at 80° C. for 2 hr. The reaction mixture was washed with water, 5% aqueous citric acid solution, saturated aqueous sodium hydrogen carbonate and saturated brine in this order, and dried over anhydrous sodium sulfate, and the solvent was evaporated under reduced pressure. The residue was purified by silica gel column chromatography, and the fraction eluted with ethyl acetate-hexane (1:4) was concentrated under reduced pressure. The obtained residue was dissolved in methanol (5 ml), 10% palladium-carbon (50% containing water) (70 mg) was added, and the mixture was subjected to catalytic reduction at ambient temperature under a hydrogen atmosphere (1 atm) for 12 hr. The catalyst was filtered off, and the filtrate was concentrated under reduced pressure to give the object compound (370 mg) as an oil.

$^1$H-NMR (CDCl$_3$) δ 1.22-1.43 (4H, m), 1.46 (9H, s), 2.27-2.79 (4H, m), 3.70 (3H, s), 4.13 (2H, br s).

Reference Example 36

1-tert-butyl 3-methyl (3R*,5S*)-5-(isobutylamino)piperidine-1,3-dicarboxylate

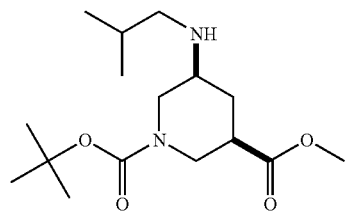

1-tert-Butyl 3-methyl (3R*,5S*)-5-aminopiperidine-1,3-dicarboxylate (370 mg) was dissolved in methanol (10 ml), isobutyraldehyde (0.137 ml), acetic acid (85 μl) and sodium triacetoxyborohydride (759 mg) were added and the mixture was stirred at room temperature for 1 hr. The reaction mixture was concentrated under reduced pressure, and the concentrated solution was basified with aqueous sodium hydrogen carbonate and extracted with ethyl acetate. The extract was dried over anhydrous sodium sulfate, and the solvent was evaporated under reduced pressure to give the object compound (439 mg) as an oil.

$^1$H-NMR (CDCl$_3$) δ 0.90 (6H, d), 1.17-1.41 (3H, m), 1.46 (9H, s), 1.69 (1H, dt), 2.30 (2H, dd), 2.47 (2H, d), 2.52 (1H, dt), 2.74 (1H, br s), 3.69 (3H, s), 4.26 (2H, br s).

Reference Example 37

1-tert-butyl 3-methyl (3R*,5S*)-5-[({2-tert-butyl-4-[(2-furylmethyl)amino]pyrimidin-5-yl}carbonyl)(isobutyl)amino]piperidine-1,3-dicarboxylate

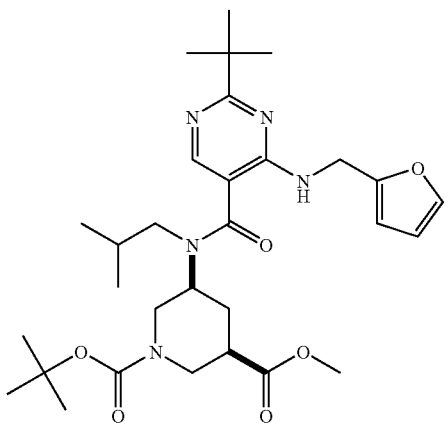

2-tert-Butyl-4-[(2-furylmethyl)amino]pyrimidine-5-carboxylic acid (385 mg) was suspended in toluene (10 ml), thionyl chloride (0.255 ml) and DMF (1 drop) were added and the mixture was stirred at 80° C. for 2 hr. The reaction mixture was cooled to room temperature, and concentrated under reduced pressure, and the residue was subjected to azeotropic distillation with toluene. The obtained residue was dissolved in acetonitrile (5 ml), the mixture was added to a solution of 1-tert-butyl 3-methyl (3R*,5S*)-5-(isobutylamino)piperidine-1,3-dicarboxylate (440 mg) and triethylamine (0.488 ml) in acetonitrile (5 ml), and the mixture was stirred at room temperature for 1 hr. The reaction mixture was concentrated under reduced pressure and diluted with water, and the mixture was extracted with ethyl acetate. The extract was washed with saturated aqueous sodium hydrogen carbonate and saturated brine, and dried over anhydrous sodium sulfate. The solvent was evaporated under reduced pressure. The residue was purified by silica gel column chromatography, and the fraction eluted with ethyl acetate-hexane (1:20-1:4) was concentrated under reduced pressure to give the object compound (363 mg).

MS (ESI+, m/e) 572 (M+1)

Reference Example 38

(3R*,5S*)-1-(tert-butoxycarbonyl)-5-[({2-tert-butyl-4-[(2-furylmethyl)amino]pyrimidin-5-yl}carbonyl)(isobutyl)amino]piperidine-3-carboxylic acid

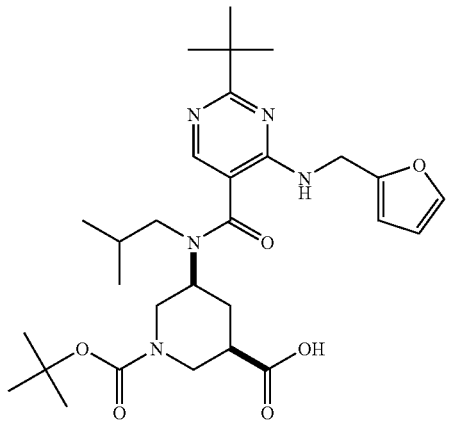

1-tert-Butyl 3-methyl (3R*,5S*)-5-[({2-tert-butyl-4-[(2-furylmethyl)amino]pyrimidin-5-yl}carbonyl)(isobutyl)amino]piperidine-1,3-dicarboxylate (250 mg) was dissolved in 2 M aqueous sodium hydroxide solution (1 ml) and methanol (2 ml), and the mixture was stirred at room temperature for 15 hr. The reaction mixture was concentrated under reduced pressure, and the residue was diluted with water. The mixture was adjusted to pH 3 with 1 M hydrochloric acid, and the precipitate was collected by filtration to give the object compound (205 mg) as a powder.

MS (ESI+, m/e) 558 (M+1)

Reference Example 39 tert-butyl (3R*,5S*)-3-(aminocarbonyl)-5-[({2-tert-butyl-4-[(2-furylmethyl)amino]pyrimidin-5-yl}carbonyl)(isobutyl)amino]piperidine-1-carboxylate

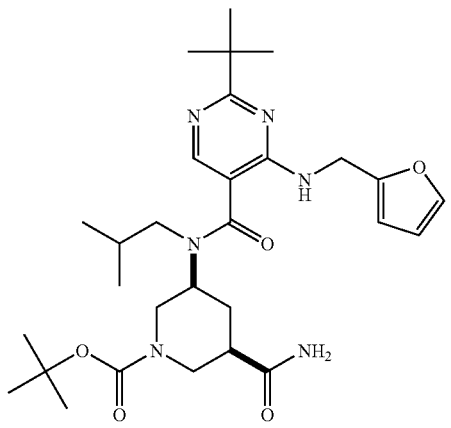

A solution of (3R*,5S*)-1-(tert-butoxycarbonyl)-5-[({2-tert-butyl-4-[(2-furylmethyl)amino]pyrimidin-5-yl} carbonyl)(isobutyl)amino]piperidine-3-carboxylic acid (1.03 g), 1H-1,2,3-benzotriazol-1-ol ammoniate (420 mg), WSC.HCl (530 mg) and triethylamine (520 µl) in 1,2-dichloroethane (16 ml) was stirred at room temperature for 24 hr. The mixture was poured into water and the mixture was extracted with ethyl acetate. The extract was washed with saturated brine, and dried over anhydrous magnesium sulfate. The solvent was evaporated under reduced pressure and the residue was purified by silica gel column chromatography. The fraction eluted with ethyl acetate-hexane (1:9-1:0) was concentrated under reduced pressure to give the object compound (944 mg).

MS (ESI+, m/e) 557 (M+1)

Reference Example 40 tert-butyl (3R*,5S*)-3-[({2-tert-butyl-4-[(2-furylm-ethyl)amino]pyrimidin-5-yl}carbonyl)(isobutyl)amino]-5-[(4-hydroxy-4-methylpiperidin-1-yl)carbonyl]piperidine-1-carboxylate

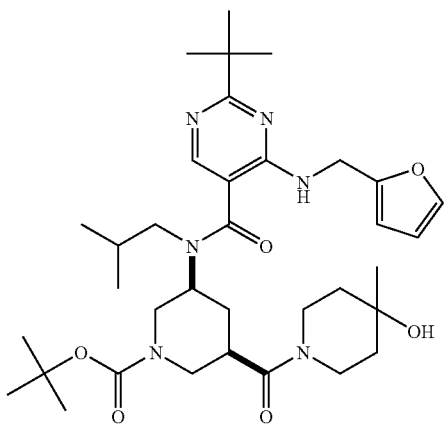

(3R*,5S*)-1-(tert-Butoxycarbonyl)-5-[({2-tert-butyl-4-[(2-furylmethyl)amino]pyrimidin-5-yl}carbonyl)(isobutyl)amino]piperidine-3-carboxylic acid (100 mg), HOBt (41 mg) and WSC.HCl (52 mg) were dissolved in acetonitrile (3 ml), 4-methylpiperidin-4-ol monohydrochloride (27 mg) and triethylamine (75 µl) were added and the mixture was stirred at room temperature for 15 hr. The reaction mixture was concentrated, the residue was diluted with water, and the mixture was extracted with ethyl acetate. The extract was washed with saturated brine, and dried over anhydrous sodium sulfate. The solvent was evaporated under reduced pressure and the residue was purified by silica gel column chromatography. The fraction eluted with ethyl acetate-hexane (1:5-3:1) was concentrated under reduced pressure to give the object compound (110 mg).

MS (ESI+, m/e) 655 (M+1)

Reference Example 41 tert-butyl (3R*,5S*)-3-[({2-tert-butyl-4-[(2-furylm-ethyl)amino]pyrimidin-5-yl}carbonyl)(isobutyl)amino]-5-(1-hydroxy-1-methylethyl)piperidine-1-carboxylate

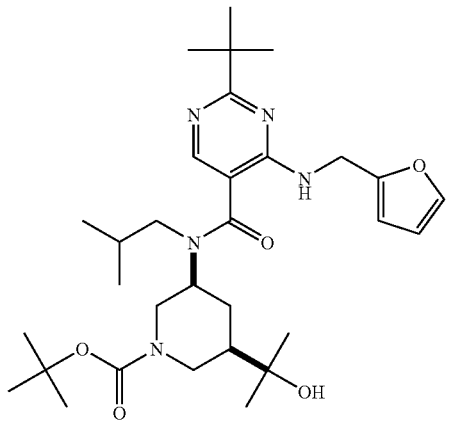

1-tert-Butyl 3-methyl (3R*,5S*)-5-[({2-tert-butyl-4-[(2-furylmethyl)amino]pyrimidin-5-yl}carbonyl)(isobutyl)amino]piperidine-1,3-dicarboxylate (280 mg) was dissolved in THF (5 ml), 1 M methylmagnesium bromide in THF solution (2.45 ml) was added and the mixture was stirred at room temperature for 15 hr. Aqueous ammonium chloride solution was added to the reaction mixture, and the mixture was extracted with ethyl acetate. The extract was washed with saturated brine, dried over anhydrous sodium sulfate, and concentrated under reduced pressure. The residue was purified by silica gel column chromatography, and the fraction eluted with ethyl acetate-hexane (1:9-1:2) was concentrated under reduced pressure to give the object compound (280 mg).

MS (ESI+, m/e) 572 (M+1)

Reference Example 42

(3S,5R)-1-(tert-butoxycarbonyl)-5-(methoxycarbonyl)piperidine-3-carboxylic acid

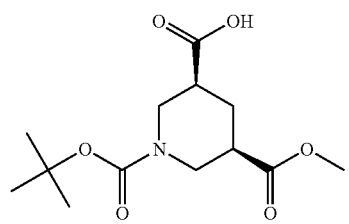

A mixture of (3R*,5S*)-1-(tert-butoxycarbonyl)-5-(methoxycarbonyl)piperidine-3-carboxylic acid (6.16 g), (S)-(−)-1-phenylethylamine (2.60 g) and ethanol (24 ml) was dissolved by heating to 70° C. and recrystallization was conducted. The precipitated crystals were collected by filtration, dissolved again in ethanol (7 ml) and recrystallization was carried out. The precipitated crystals were collected by filtration, and suspended in water. The suspension was acidified with saturated aqueous potassium hydrogen sulfate solution, and the mixture was extracted three times with ethyl acetate. The extract was washed with saturated brine, and dried over anhydrous magnesium sulfate. The solvent was evaporated under reduced pressure to give the object compound (915 mg) as a powder.

specific optical rotation $[\alpha]_D^{20}$:−6.2° (after drying, 20.12 mg, methanol, 2 ml, 100 mm)

$^1$H-NMR (DMSO-$d_6$) δ1.39 (9H, s), 1.52 (1H, q), 2.18-2.54 (3H, m), 2.55-2.78 (2H, m), 3.63 (3H, s), 4.03-4.23 (2H, m), 12.51 (1H, br s).

Reference Example 43

1-tert-butyl 3-methyl (3R,5S)-5-aminopiperidine-1,3-dicarboxylate

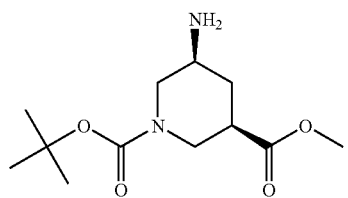

(3S,5R)-1-(tert-Butoxycarbonyl)-5-(methoxycarbonyl)piperidine-3-carboxylic acid (2.83 g) was suspended in toluene (36 ml), diphenylphosphoryl azide (2.60 ml) and triethylamine (1.70 ml) were added and the mixture was stirred at 100° C. for 1 hr. The reaction mixture was cooled to room temperature, benzyl alcohol (1.53 ml) and triethylamine (7.00 ml) were added and the mixture was stirred at 80° C. for 3 hr. The reaction mixture was concentrated, and the residue was dissolved in ethyl acetate. The mixture was washed with water, 0.5 M hydrochloric acid, saturated aqueous sodium hydrogen carbonate and saturated brine in this order, and dried over anhydrous magnesium sulfate. The solvent was evaporated under reduced pressure and the residue was purified by silica gel column chromatography. The fraction eluted with ethyl acetate-hexane (1:3-3:1) was concentrated under reduced pressure. The obtained residue was dissolved in methanol (60 ml), 10% palladium-carbon (50% containing water) (150 mg) was added, and the mixture was subjected to catalytic reduction at ambient temperature under a hydron atmosphere (1 atm) for 5 hr. The catalyst was filtered off, and the filtrate was concentrated under reduced pressure to give the object compound (1.83 g) as an oil.

$^1$H-NMR (CDCl$_3$) δ 1.22-1.43 (4H, m), 1.46 (9H, s), 2.27-2.79 (4H, m), 3.70 (3H, s), 4.13 (2H, br s).

Reference Example 44

1-tert-butyl 3-methyl (3R,5S)-5-(isobutylamino)piperidine-1,3-dicarboxylate

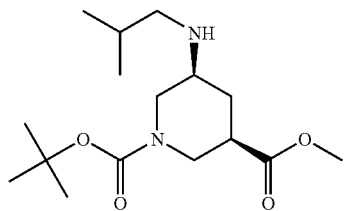

1-tert-Butyl 3-methyl (3R,5S)-5-aminopiperidine-1,3-dicarboxylate (1.83 g), isobutyraldehyde (0.78 ml) and acetic acid (0.49 ml) were dissolved in methanol (50 ml), and the mixture was stirred at room temperature for 30 min. Sodium triacetoxyborohydride (3.80 g) was added to the reaction mixture, and the mixture was stirred at room temperature for 7 hr. The reaction mixture was concentrated under reduced pressure, the concentrated solution was basified with aqueous sodium hydrogen carbonate, and the mixture was extracted with ethyl acetate. The extract was washed with water and saturated brine, and dried over anhydrous magnesium sulfate. The solvent was evaporated under reduced pressure and the residue was purified by silica gel column chromatography. The fraction eluted with ethyl acetate-hexane (1:1) to ethyl acetate 100% to ethyl acetate-methanol (9:1) was concentrated under reduced pressure to give the object compound (1.42 g) as an oil.

$^1$H-NMR (CDCl$_3$) δ 0.90 (6H, d), 1.22-1.38 (3H, m), 1.46 (9H, s), 1.69 (1H, dt), 2.23-2.39 (2H, m), 2.44-2.59 (1H, m), 2.47 (2H, d), 2.74 (1H, br s), 3.69 (3H, s), 4.18-4.34 (2H, m).

Reference Example 45

2-tert-butyl-6-oxo-1,6-dihydropyrimidine-5-carboxylic acid

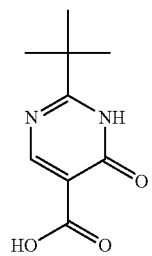

Ethyl 2-tert-butyl-6-oxo-1,6-dihydropyrimidine-5-carboxylate (43.9 g) was dissolved in ethanol (200 ml), 2 M aqueous sodium hydroxide solution (330 ml) was added and the mixture was stirred at room temperature for 40 hr. The reaction mixture was concentrated under reduced pressure, and the aqueous layer was adjusted to pH 8 with 6 M hydrochloric acid. The mixture was concentrated under reduced pressure, and subjected to azeotropic distillation with 2-propanol. The residue was suspended in acetone, and insoluble powder was collected by filtration. The obtained powder was suspended in 1 M hydrochloric acid and the suspension was adjusted to pH 3. The suspesion was concentrated under reduced pressure. The residue was subjected to azeotropic distillation with 2-propanol, and suspended in acetone. The insoluble material was filtered off and the filtrate was concentrated under reduced pressure to give the object compound (32.8 g) as a powder.

$^1$H-NMR (DMSO-$d_6$) δ 1.45 (9H, s), 8.99 (1H, s), 10.59 (1H, br s), 12.47 (1H, br s).

Reference Example 46

1-tert-butyl 3-methyl (3R,5S)-5-{[(2-tert-butyl-4-chloropyrimidin-5-yl)carbonyl](isobutyl)amino}piperidine-1,3-dicarboxylate

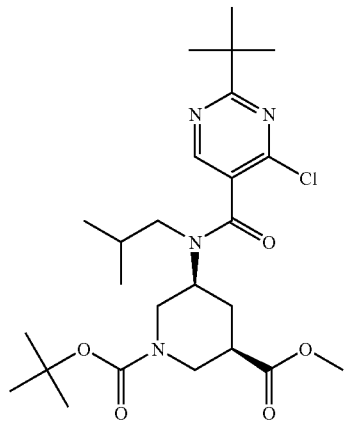

2-tert-Butyl-6-oxo-1,6-dihydropyrimidine-5-carboxylic acid (3.25 g) was dissolved in THF (60 ml), thionyl chloride (4.3 ml) and DMF (5 drops) were added and the mixture was stirred with heating to reflux for 2.5 hr. The reaction mixture was cooled to room temperature, and concentrated under reduced pressure, and the residue was subjected to azeotropic distillation with toluene. The obtained residue was suspended in THF (50 ml), a solution of 1-tert-butyl 3-methyl (3R,5S)-5-(isobutylamino)piperidine-1,3-dicarboxylate (4.13 g) and diisopropylethylamine (9.15 ml) in THF (50 ml) was added and the mixture was stirred at room temperature for 8 hr. The reaction mixture was concentrated under reduced pressure, and diluted with water, and the mixture was extracted with ethyl acetate. The extract was washed with saturated brine, and dried over anhydrous magnesium sulfate. The solvent was evaporated under reduced pressure and the residue was purified by silica gel column chromatography. The fraction eluted with ethyl acetate-hexane (1:19-2:3) was concentrated under reduced pressure to give the object compound (6.29 g).

MS (ESI+, m/e) 511 (M+1)

By a method similar to that of Reference Example 46, the following compound (Reference Example 47) was obtained.

Reference Example 47

1-tert-butyl 3-methyl (3R*,5S*)-5-{[(2-tert-butyl-4-chloropyrimidin-5-yl)carbonyl](isobutyl)amino}piperidine-1,3-dicarboxylate

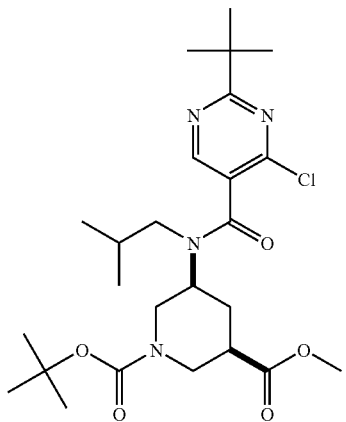

MS (ESI+, m/e) 511 (M+1)

Reference Example 48

1-tert-butyl 3-methyl (3R,5S)-5-[({2-tert-butyl-4-[(3-methoxypropyl)amino]pyrimidin-5-yl}carbonyl)(isobutyl)amino]piperidine-1,3-dicarboxylate

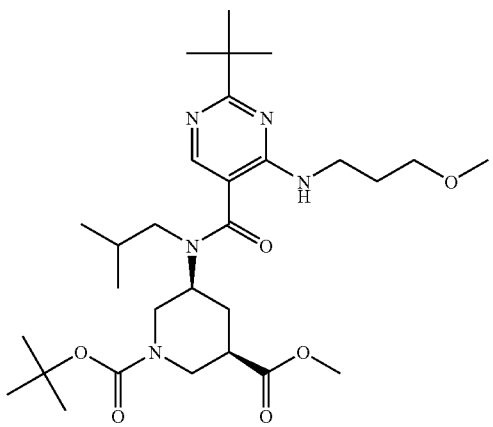

To a solution of 1-tert-butyl 3-methyl (3R,5S)-5-{([(2-tert-butyl-4-chloropyrimidin-5-yl)carbonyl](isobutyl)amino}piperidine-1,3-dicarboxylate (2.98 g) and diisopropylethylamine (3.0 ml) in DMF (60 ml) was added 3-methoxypropylamine (1.19 ml), and the mixture was stirred at 80° C. for 1.5 hr. The reaction mixture was concentrated under reduced pressure, saturated aqueous sodium hydrogen carbonate was added, and the mixture was extracted with ethyl acetate. The extract was dried over anhydrous magnesium sulfate, and concentrated under reduced pressure. The obtained residue was purified by silica gel chromatography, and the fraction eluted with hexane to ethyl acetate-hexane (1:2) was concentrated under reduced pressure to give the object compound (3.15 g).

MS (ESI+, m/e) 564 (M+1)

Reference Example 49

(3R,5S)-1-(tert-butoxycarbonyl)-5-[({2-tert-butyl-4-[(3-methoxypropyl)amino]pyrimidin-5-yl}carbonyl)(isobutyl)amino]piperidine-3-carboxylic acid

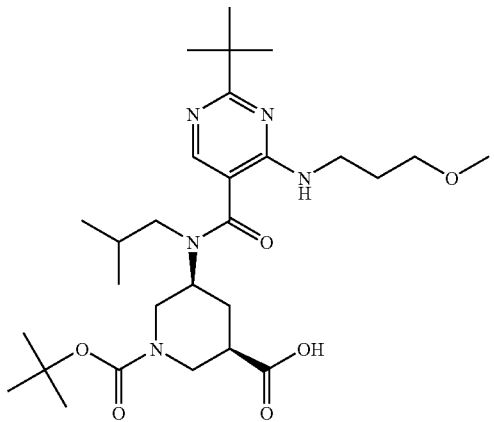

1-tert-Butyl 3-methyl (3R,5S)-5-[({2-tert-butyl-4-[(3-methoxypropyl)amino]pyrimidin-5-yl}carbonyl)(isobutyl)amino]piperidine-1,3-dicarboxylate (1.08 g) was dissolved in methanol (25 ml) and THF (12 ml), 2 M aqueous sodium hydroxide solution (4.79 ml) was added and the mixture was stirred at room temperature for 2 hr. The reaction mixture was concentrated under reduced pressure, the residue was diluted with saturated aqueous ammonium chloride solution, and the mixture was extracted with ethyl acetate. The extract was dried over anhydrous magnesium sulfate, and concentrated under reduced pressure to give the object compound (1.05 g).

MS (ESI+, m/e) 550 (M+1)

Reference Example 50 tert-butyl (3S,5R)-3-[({2-tert-butyl-4-[(3-methoxypropyl)amino]pyrimidin-5-yl}carbonyl)(isobutyl)amino]-5-(morpholin-4-ylcarbonyl)piperidine-1-carboxylate

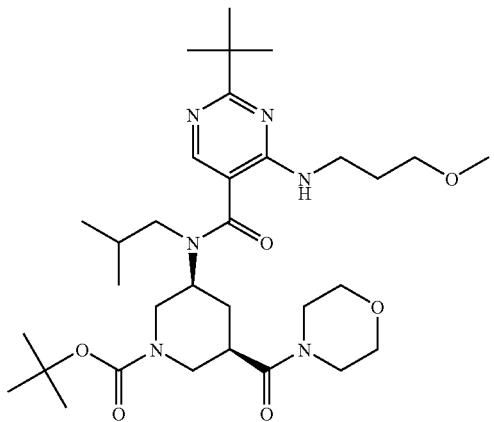

(3R,5S)-1-(tert-Butoxycarbonyl)-5-[({2-tert-butyl-4-[(3-methoxypropyl)amino]pyrimidin-5-yl}carbonyl)(isobutyl)amino]piperidine-3-carboxylic acid (110 mg), morpholine (52 μl) and diisopropylethylamine (140 μl) were dissolved in DMF (8 ml), BOP reagent (265 mg) was added and the mixture was stirred at room temperature for 1.5 hr. The reaction mixture was diluted with saturated aqueous sodium hydrogen carbonate, and the mixture was extracted with ethyl acetate. The extract was dried over anhydrous magnesium sulfate, and the solvent was evaporated under reduced pressure. The residue was purified by silica gel column chromatography, and the fraction eluted with ethyl acetate-hexane (1:9) to ethyl acetate was concentrated under reduced pressure to give the object compound (105 mg).

MS (ESI+, m/e) 619 (M+1)

Example 1

Method A

3-[(2-ethylpiperidin-1-yl)carbonyl]-N-(2-furylmethyl)-6-methylpyridin-2-amine

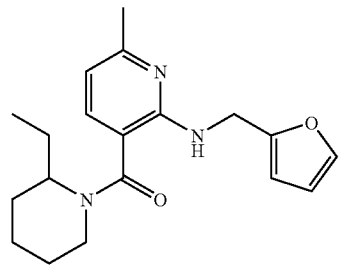

To a solution of 2-[(2-furylmethyl)amino]-6-methylnicotinic acid (65.0 mg) and 2-ethylpiperidine (47.5 mg) in DMF (2.8 ml) were added HOBt (45.9 mg) and WSC.HCl (65.2 mg), and the mixture was stirred at room temperature overnight. The reaction mixture was poured into 2% aqueous sodium hydrogen carbonate and the mixture was extracted with ethyl acetate. The extract was dried over anhydrous magnesium sulfate, and the solvent was evaporated under reduced pressure. The residue was subjected to silica gel column chromatography, and the fraction eluted with ethyl acetate-hexane (0:1-3:7) was concentrated under reduced pressure to give the object compound (81.8 mg).

$^1$H-NMR (CDCl$_3$) δ 0.81 (3H, s), 1.38-1.62 (4H, m), 1.65-1.80 (4H, m), 2.41 (3H, s), 2.83-2.97 (3H, m), 4.65 (2H, d), 5.80 (1H, s), 6.22 (1H, d), 6.26-6.34 (1H, m), 6.43 (1H, d), 7.19 (1H, d), 7.33 (1H, s).

Example 2

Method B

N-(2-furylmethyl)-3-{[(2R)-2-(methoxymethyl)pyrrolidin-1-yl]carbonyl}-6-methylpyridin-2-amine trifluoroacetate

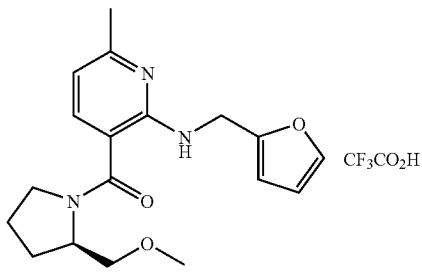

To a solution of 2-[(2-furylmethyl)amino]-6-methylnicotinic acid (13.9 mg) and (2R)-2-(methoxymethyl)pyrrolidine (8.3 mg) in DMF (1.0 ml) was added a solution of HOBt (9.7 mg) and WSC.HCl (13.8 mg) in DMF (0.5 ml), and the mixture was stirred at room temperature overnight. The reaction mixture was poured into 2% aqueous sodium hydrogen carbonate, the mixture was extracted with ethyl acetate, and the extract was concentrated by a nitrogen gas blower. The residue was subjected to reversed-phase preparative HPLC, and the object fraction was concentrated by a nitrogen gas blower to give the object compound (12.2 mg).

MS (ESI+, m/e) 330 (M+1)

Example 3

Method C

[(2R)-1-({2-[(2-furylmethyl)amino]-6-methylpyridin-3-yl}carbonyl)pyrrolidin-2-yl](diphenyl)methanol

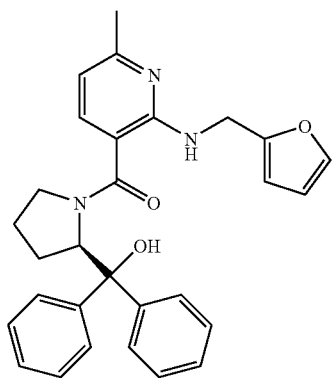

To a solution of 2-[(2-furylmethyl)amino]-6-methylnicotinic acid (13.9 mg) and diphenyl(pyrrolidin-2-yl)methanol (18.2 mg) in DMF (1.0 ml) was added a solution of HOBt (9.7 mg) and WSC.HCl (13.8 mg) in DMF (0.5 ml), and the mixture was stirred at room temperature overnight. The reaction mixture was poured into 2% aqueous sodium hydrogen carbonate, the mixture was extracted with ethyl acetate, and the extract was concentrated by a nitrogen gas blower. The residue was subjected to reversed-phase preparative HPLC, and the object fraction was passed through MP-CO3 resin (manufactured by Polymer Laboratories) to remove trifluoroacetic acid. The obtained solution was concentrated by a nitrogen gas blower to give the object compound (10.6 mg).

MS (ESI+, m/e) 468 (M+1)

Example 4

Method D

5-[(2-ethylpiperazin-1-yl)carbonyl]-N-(2-furylmethyl)-2-isopropylpyrimidin-4-amine dihydrochloride

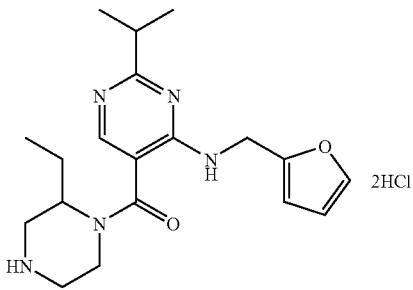

tert-Butyl 3-ethyl-4-({4-[(2-furylmethyl)amino]-2-isopropylpyrimidin-5-yl}carbonyl)piperazine-1-carboxylate (100 mg) was dissolved in 4 M hydrogen chloride-ethyl acetate solution (3 ml), and the mixture was stirred at room temperature for 15 hr. The reaction mixture was concentrated under reduced pressure, ethyl acetate was added and the precipitate was collected by filtration to give the object compound (74 mg).

MS (ESI+, m/e) 358 (M+1)

Example 5

Method E

5-[(3-aminopyrrolidin-1-yl)carbonyl]-N-(2-furylmethyl)-2-(methylthio)pyrimidin-4-amine

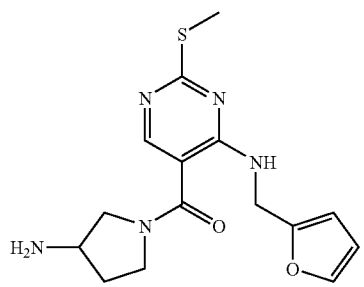

To a solution of 4-[(2-furylmethyl)amino]-2-(methylthio)pyrimidine-5-carboxylic acid (19.1 mg) and tert-butyl pyrrolidin-3-ylcarbamate (13.4 mg) in DMF (1.0 ml) was added a solution of HOBt (9.7 mg) and WSC.HCl (13.8 mg) in DMF (0.5 ml), and the mixture was stirred at room temperature overnight. The reaction mixture was poured into 2% aqueous sodium hydrogen carbonate, the mixture was extracted with ethyl acetate, and the extract was concentrated by a nitrogen gas blower. The residue was purified by reversed-phase preparative HPLC, and the object fraction was concentrated by a nitrogen gas blower. The residue was dissolved in trifluoroacetic acid/acetonitrile solution (20% (V/V), 1.0 ml), and the mixture was stirred at room temperature for 3 hr. The reaction mixture was passed through a column of MP-TsOH resin (manufactured by Argonaut) to fix the object compound on the resin, and the resin was washed with methanol (6 ml). 2 M Ammonia-methanol solution (6 ml) was passed through the column, and the eluate was concentrated by a nitrogen gas blower to give the object compound (6.3 mg).

MS (ESI+, m/e) 334 (M+1)

Example 6

Method F

N-(cyclopropylmethyl)-5-[(2-ethylpiperidin-1-yl)carbonyl]-2-isopropylpyrimidin-4-amine trifluoroacetate

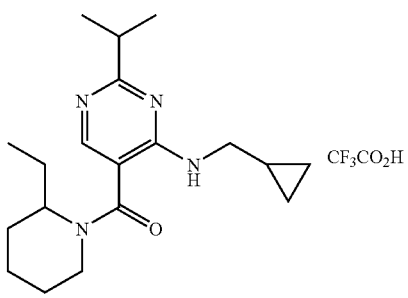

To ethyl 2-isopropyl-6-oxo-1,6-dihydropyrimidine-5-carboxylate (250 mg) was added 6 M hydrochloric acid (5 ml), and the mixture was stirred at room temperature for 3 hr. The reaction mixture was concentrated under reduced pressure and the obtained residue was dissolved in DMF (5 ml). Triethylamine (146 mg), 2-ethylpiperidine (163 mg), HOBt (194 mg) and WSC.HCl (275 mg) were added and the mixture was stirred at room temperature overnight. The reaction mixture was poured into 2% aqueous sodium hydrogen carbonate, the mixture was extracted with ethyl acetate, and the extract was concentrated by a nitrogen gas blower. The residue was subjected to silica gel column chromatography, and the fraction eluted with methanol-ethyl acetate (0:1-1:9) was concentrated under reduced pressure. The residue was dissolved in acetonitrile (10 ml). A solution of benzotriazol-1-yloxytris(dimethylamino)phosphonium hexafluorophosphate (35.0 mg) in acetonitrile (0.5 ml) and a solution of triethylamine (9.1 mg) in acetonitrile (0.5 ml) were added to the solution (0.5 ml), and the mixture was stirred at room temperature for 20 min. A solution of 1-cyclopropylmethanamine (6.4 mg) in acetonitrile (0.5 ml) was added and the mixture was stirred at 70° C. overnight. The reaction mixture was poured into 2% aqueous sodium hydrogen carbonate, the mixture was extracted with ethyl acetate, and the extract was concentrated by a nitrogen gas blower. The residue was purified by reversed-phase preparative HPLC, and the object fraction was concentrated by a nitrogen gas blower to give the object compound (15.8 mg).

MS (ESI+, m/e) 331 (M+1)

By a method similar to that of the above-mentioned Example 1 (Method A) to Example 6 (Method F), the compounds of Examples 7 to 92 below were obtained. The respective compounds were isolated and purified as necessary by a known means such as phase transfer, pH conversion, solvent extraction, silica gel column chromatography, reversed-phase preparative HPLC and the like. The final products were isolated as a free form as in Method A and the like, or as trifluoroacetate by concentrating the object fraction of reversed-phase preparative HPLC as in Method B and the like, or as hydrochloride by treating with 4 M hydrogen chloride-ethyl acetate solution as in Method D and the like.

Example 7

3-(azepan-1-ylcarbonyl)-N-(2-furylmethyl)-6-methylpyridin-2-amine

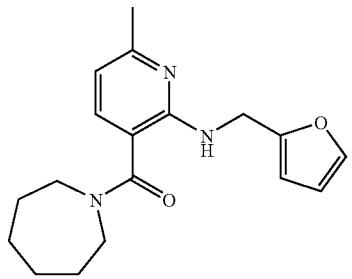

$^1$H-NMR (CDCl$_3$) δ 1.55-1.86 (8H, m), 2.41 (3H, s), 3.52 (4H, s), 4.65 (2H, d), 5.81 (1H, t), 6.23 (1H, d), 6.27-6.34 (1H, m), 6.43 (1H, d), 7.22 (1H, d), 7.34 (1H, d).

Example 8

N-(2-furylmethyl)-2-phenyl-5-(piperidin-1-ylcarbonyl)pyrimidin-4-amine

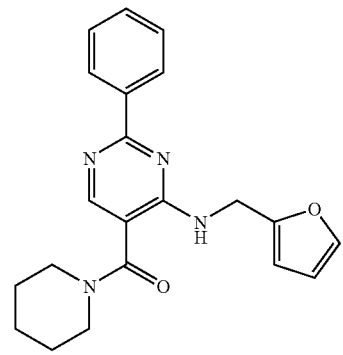

MS (ESI+, m/e) 363 (M+1)

127

Example 9

5-[(2-ethylpiperidin-1-yl)carbonyl]-N-(2-furylmethyl)-2-phenylpyrimidin-4-amine

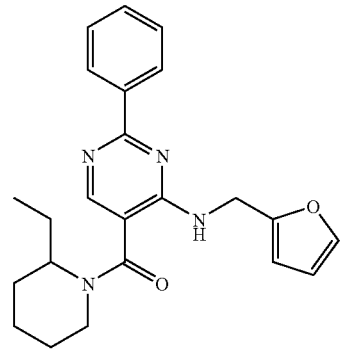

MS (ESI+, m/e) 391 (M+1)

Example 10

1-({4-[(2-furylmethyl)amino]-2-phenylpyrimidin-5-yl}carbonyl)piperidin-3-ol

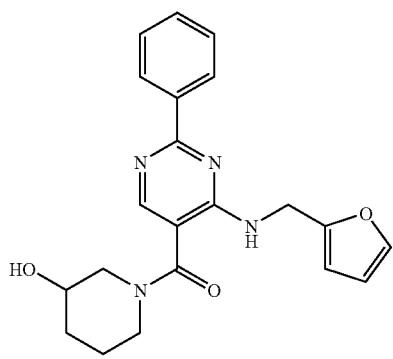

MS (ESI+, m/e) 379 (M+1)

Example 11

1-({4-[(2-furylmethyl)amino]-2-phenylpyrimidin-5-yl}carbonyl)piperidin4-ol

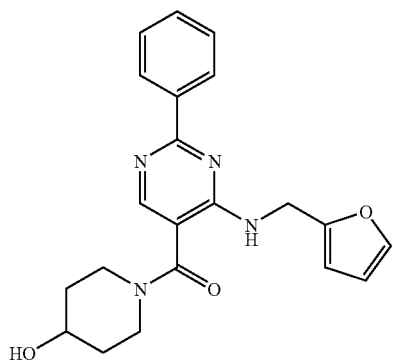

MS (ESI+, m/e) 379 (M+1)

128

Example 12

5-[(2-ethylpiperidin-1-yl)carbonyl]-N-(2-furylmethyl)-2-(trifluoromethyl)pyrimidin-4-amine

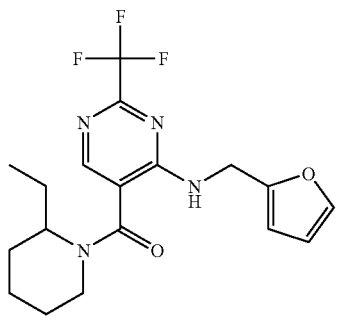

MS (ESI+, m/e) 383 (M+1)

Example 13

5-[(2-ethylpiperidin-1-yl)carbonyl]-N-(2-furylmethyl)-2-methylpyrimidin-4-amine

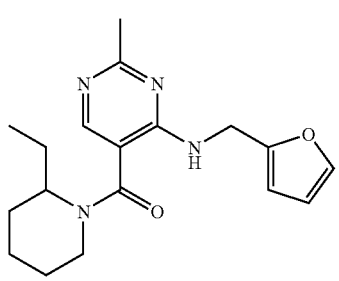

MS (ESI+, m/e) 329 (M+1)

Example 14

2-ethyl-5-[(2-ethylpiperidin-1-yl)carbonyl]-N-(2-furylmethyl)pyrimidin-4-amine

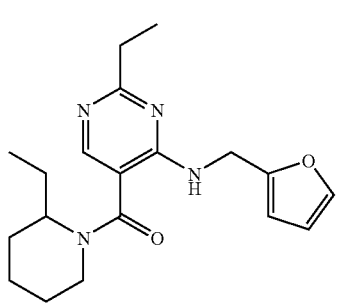

MS (ESI+, m/e) 343 (M+1)

Example 15

5-[(2-ethylpiperidin-1-yl)carbonyl]-N-(2-furylmethyl)-2-(2-thienyl)pyrimidin-4-amine

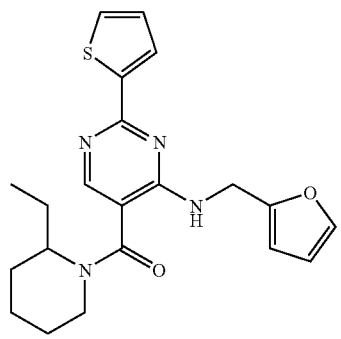

MS (ESI+, m/e) 397 (M+1)

Example 16

N-(2-furylmethyl)-5-[(2-methylpiperidin-1-yl)carbonyl]-2-(trifluoromethyl)pyrimidin-4-amine

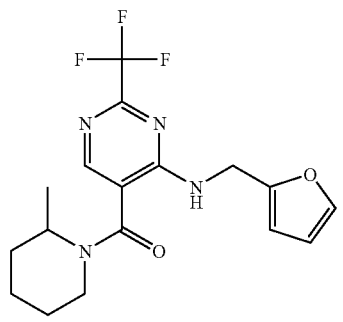

MS (ESI+, m/e) 369 (M+1)

Example 17

N-benzyl-5-[(2-ethylpiperidin-1-yl)carbonyl]-2-(trifluoromethyl)pyrimidin-4-amine

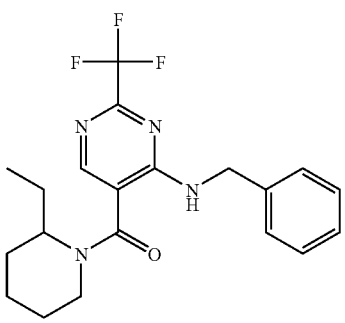

MS (ESI+, m/e) 393 (M+1)

Example 18

5-[(2-ethylpiperidin-1-yl)carbonyl]-N-(2-furylmethyl)-6-methyl-2-(trifluoromethyl)pyrimidin-4-amine

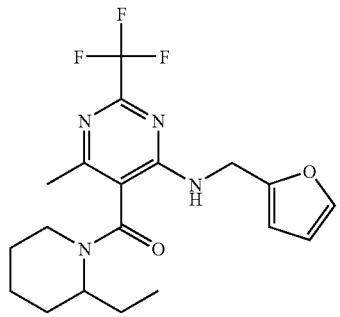

MS (ESI+, m/e) 397 (M+1)

Example 19

5-[(2-ethylpiperidin-1-yl)carbonyl]-N-(2-furylmethyl)-2-isopropylpyrimidin-4-amine

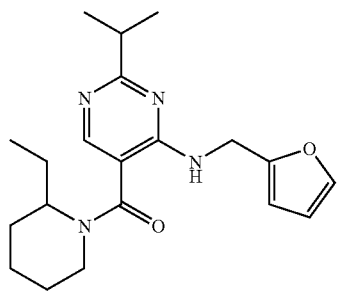

MS (ESI+, m/e) 357 (M+1)

Example 20

2-cyclopropyl-5-[(2-ethylpiperidin-1-yl)carbonyl]-N-(2-furylmethyl)pyrimidin-4-amine

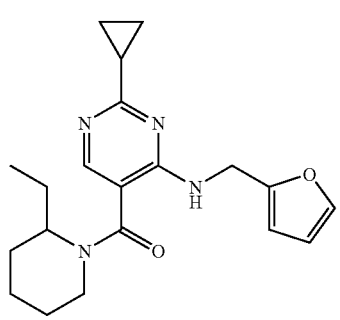

MS (ESI+, m/e) 355 (M+1)

Example 21

2-tert-butyl-5-[(2-ethylpiperidin-1-yl)carbonyl]-N-(2-furylmethyl)pyrimidin-4-amine

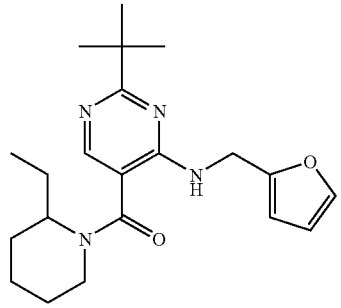

MS (ESI+, m/e) 371 (M+1)

Example 22

5-[(2-ethylpiperidin-1-yl)carbonyl]-N-(2-furylmethyl)-2-(methylthio)pyrimidin-4-amine

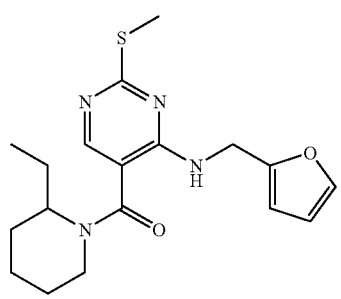

MS (ESI+, m/e) 361 (M+1)

Example 23

5-[(2-ethylpiperidin-1-yl)carbonyl]-N-(1,3-oxazol-2-ylmethyl)-2-(trifluoromethyl)pyrimidin-4-amine

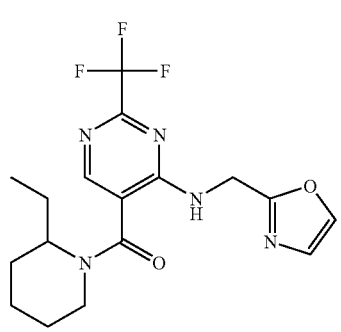

MS (ESI+, m/e) 384 (M+1)

Example 24

N-(2-furylmethyl)-5-[(2-propylpiperidin-1-yl)carbonyl]-2-(trifluoromethyl)pyrimidin-4-amine

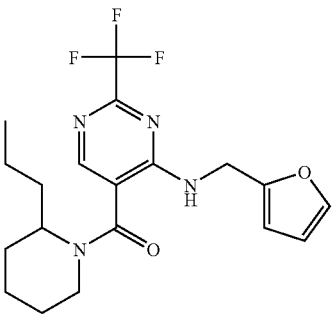

MS (ESI+, m/e) 397 (M+1)

Example 25 tert-butyl 3-ethyl-4-{[4-[(2-furylmethyl)amino]-2-(trifluoromethyl)pyrimidin-5-yl]carbonyl}piperazine-1-carboxylate

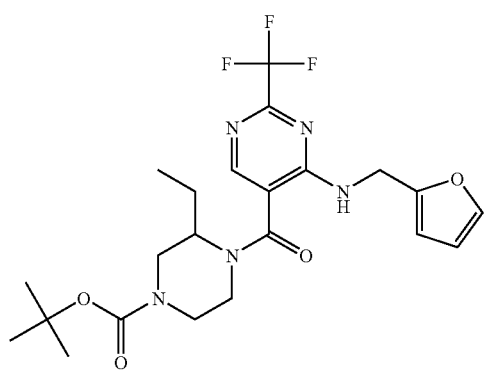

MS (ESI+, m/e) 484 (M+1)

Example 26 tert-butyl 3-ethyl-4-({4-[(2-furylmethyl)amino]-2-isopropylpyrimidin-5-yl}carbonyl)piperazine-1-carboxylate

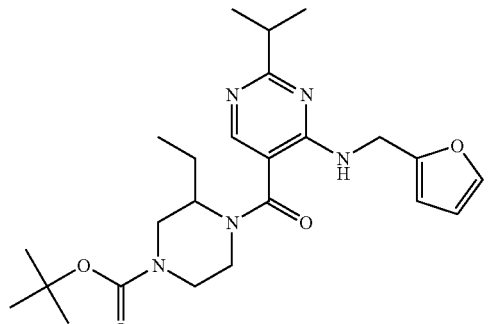

MS (ESI+, m/e) 458 (M+1)

Example 27 tert-butyl {[1-({4-[(2-furylmethyl)amino]-2-isopropylpyrimidin-5-yl}carbonyl)piperidin-2-yl]methyl}carbamate

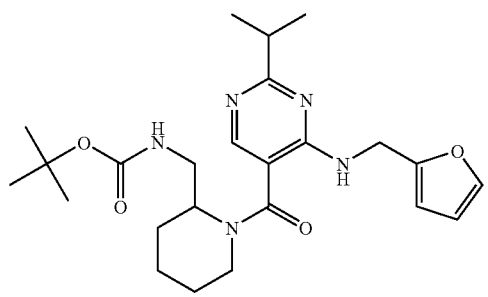

MS (ESI+, m/e) 458 (M+1)

Example 28 tert-butyl {[1-({2-tert-butyl-4-[(2-furylmethyl)amino]pyrimidin-5-yl}carbonyl)piperidin-4-yl]methyl}carbamate

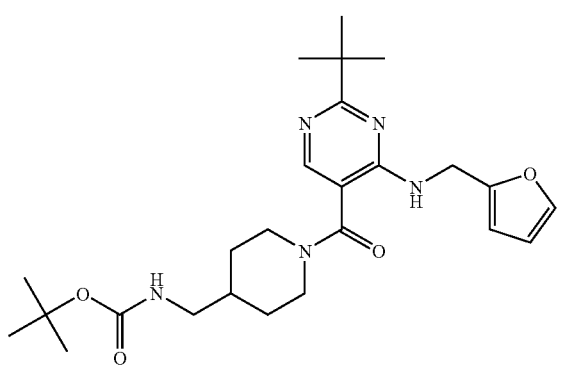

MS (ESI+, m/e) 472 (M+1)

Example 29

1-({2-[(2-furylmethyl)amino]-6-methylpyridin-3-yl}carbonyl)-4-phenylpiperidin-4-ol trifluoroacetate

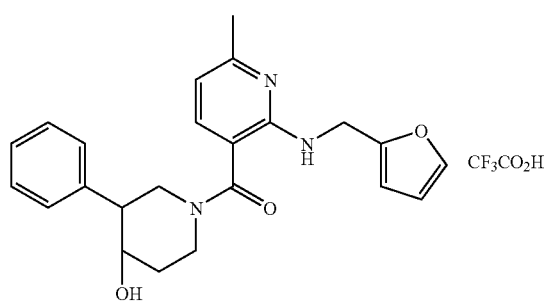

MS (ESI+, m/e) 392 (M+1)

Example 30

N-(2-furylmethyl)-2-(methylthio)-5-{[2-(2-phenylethyl)pyrrolidin-1-yl]carbonyl}pyrimidin-4-amine trifluoroacetate

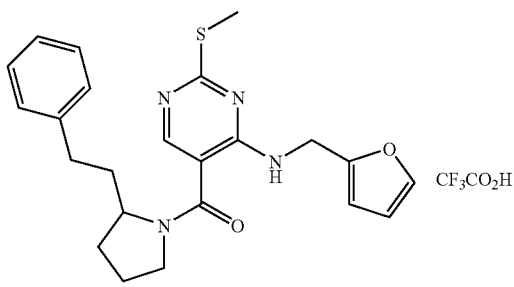

MS (ESI+, m/e) 423 (M+1)

Example 31

N-(2-furylmethyl)-5-[(2-isobutylpyrrolidin-1-yl)carbonyl]-2-(methylthio)pyrimidin-4-amine trifluoroacetate

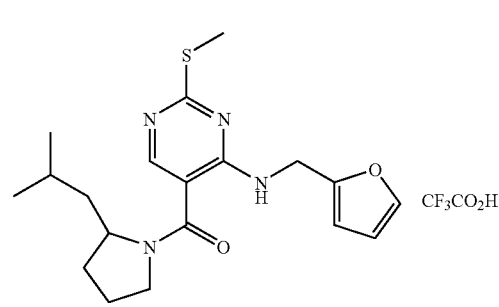

MS (ESI+, m/e) 375 (M+1)

Example 32

N-benzyl-5-[(2-isobutylpyrrolidin-1-yl)carbonyl]-2-(methylthio)pyrimidin-4-amine trifluoroacetate

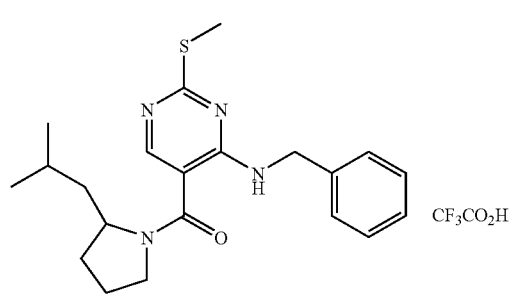

MS (ESI+, m/e) 385 (M+1)

Example 33

3-[(2-ethylpiperidin-1-yl)carbonyl]-6-methyl-N-[(5-methyl-2-furyl)methyl]pyridin-2-amine trifluoroacetate

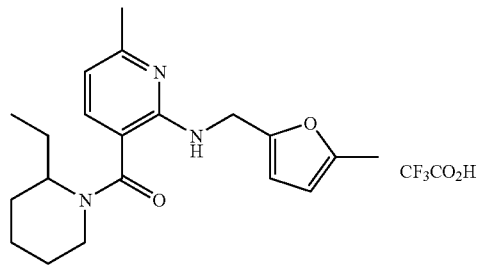

MS (ESI+, m/e) 342 (M+1)

Example 34

3-[(2-ethylpiperidin-1-yl)carbonyl]-6-methyl-N-(2-thienylmethyl)pyridin-2-amine trifluoroacetate

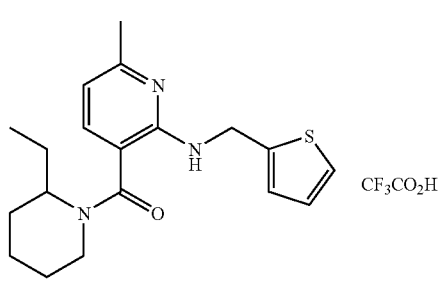

MS (ESI+, m/e) 344 (M+1)

Example 35

2-tert-butyl-N-(2-furylmethyl)-5-[(4-methylpiperazin-1-yl)carbonyl]pyrimidin-4-amine bis(trifluoroacetate)

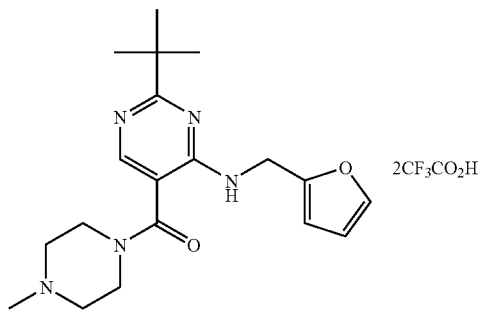

MS (ESI+, m/e) 358 (M+1)

Example 36

1-({2-tert-butyl-4-[(2-furylmethyl)amino]pyrimidin-5-yl}carbonyl)-4-methylpiperidin-4-ol trifluoroacetate

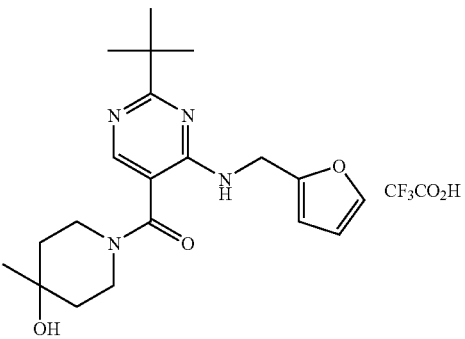

MS (ESI+, m/e) 373 (M+1)

Example 37

1-({2-tert-butyl-4-[(2-furylmethyl)amino]pyrimidin-5-yl}carbonyl)piperidine-4-carboxamide trifluoroacetate

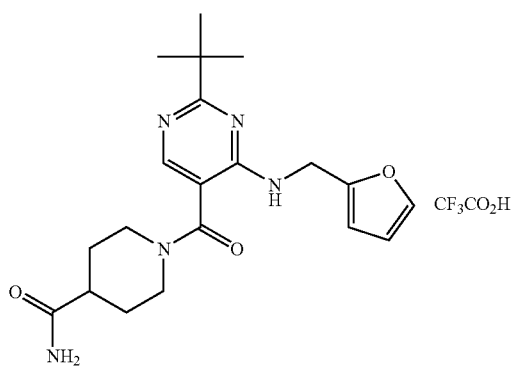

MS (ESI+, m/e) 386 (M+1)

Example 38

1-({2-tert-butyl-4-[(2-furylmethyl)amino]pyrimidin-5-yl}carbonyl)piperidine-3-carboxamide trifluoroacetate

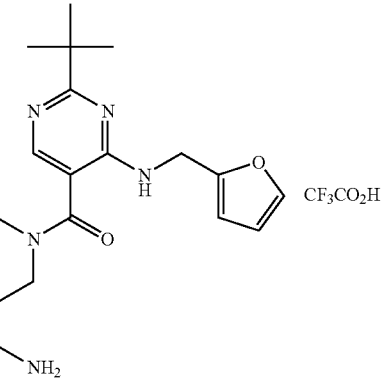

MS (ESI+, m/e) 386 (M+1)

Example 39

2-tert-butyl-N,N-diethyl-4-[(2-furylmethyl)amino]pyrimidine-5-carboxamide trifluoroacetate

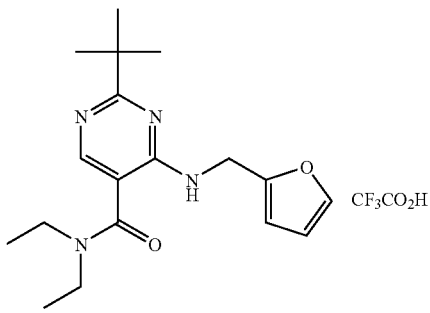

MS (ESI+, m/e) 331 (M+1)

Example 40

5-(perhydroazocin-1-ylcarbonyl)-2-tert-butyl-N-(2-furylmethyl)pyrimidin-4-amine trifluoroacetate

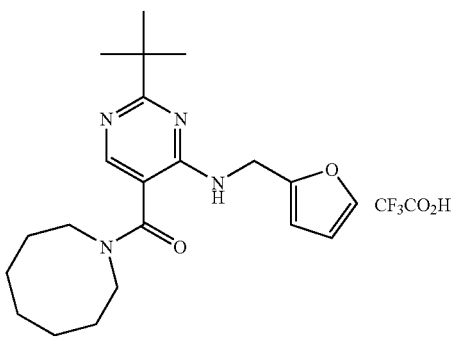

MS (ESI+, m/e) 371 (M+1)

Example 41

2-tert-butyl-N-cyclohexyl-4-[(2-furylmethyl)amino]-N-methylpyrimidine-5-carboxamide trifluoroacetate

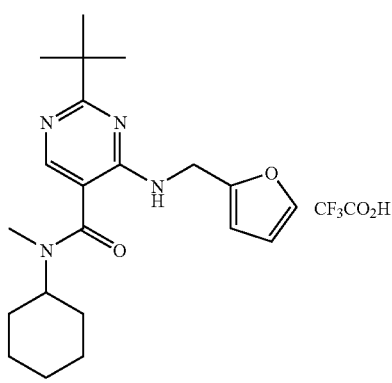

MS (ESI+, m/e) 371 (M+1)

Example 42

2-tert-butyl-5-{[4-(4-chlorophenyl)piperazin-1-yl]carbonyl}-N-(2-furylmethyl)pyrimidin-4-amine bis(trifluoroacetate)

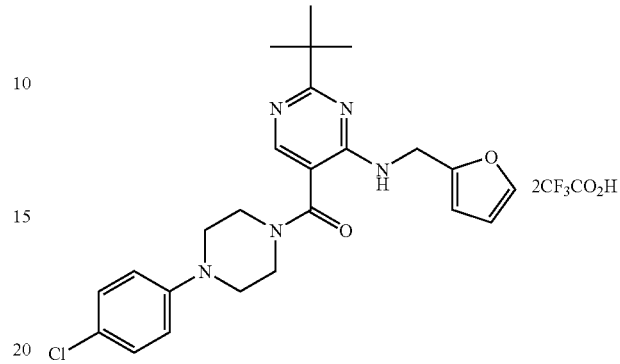

MS (ESI+, m/e) 454 (M+1)

Example 43

2-tert-butyl-N-(2-furylmethyl)-5-{[4-(2-phenylethyl)piperazin-1-yl]carbonyl}pyrimidin-4-amine bis(trifluoroacetate)

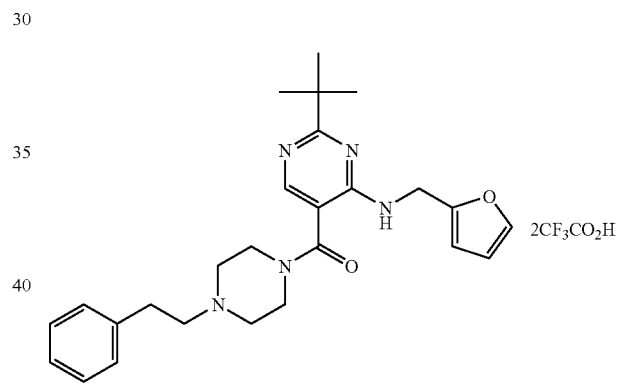

MS (ESI+, m/e) 448 (M+1)

Example 44

5-[(4-benzylpiperidin-1-yl)carbonyl]-2-tert-butyl-N-(2-furylmethyl)pyrimidin-4-amine trifluoroacetate

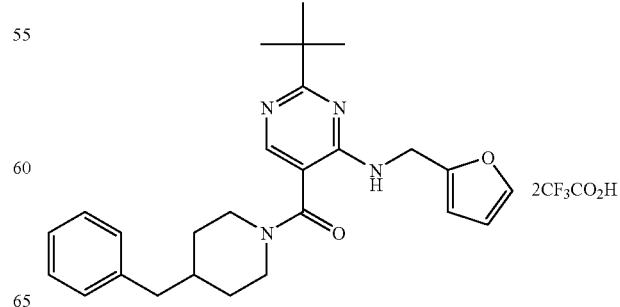

MS (ESI+, m/e) 433 (M+1)

Example 45

2-tert-butyl-N-(2-furylmethyl)-5-[(3-phenylthiomorpholin-4-yl)carbonyl]pyrimidin-4-amine trifluoroacetate

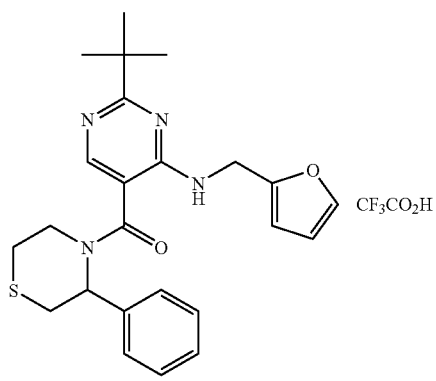

MS (ESI+, m/e) 437 (M+1)

Example 46

5-[(2-benzylpyrrolidin-1-yl)carbonyl]-2-tert-butyl-N-(2-furylmethyl)pyrimidin-4-amine triuoroacetate

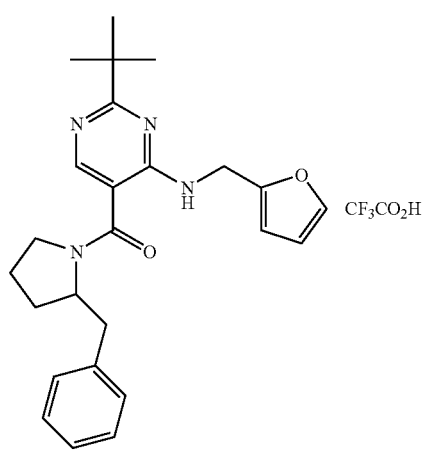

MS (ESI+, m/e) 419 (M+1)

Example 47

2-tert-butyl-N-(2-furylmethyl)-5-{[2-(2-phenylethyl)pyrrolidin-1-yl]carbonyl}pyrimidin-4-amine trifluoroacetate

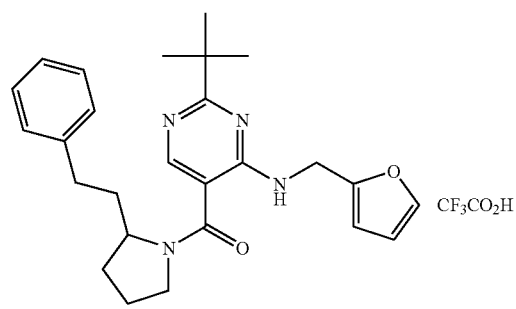

MS (ESI+, m/e) 433 (M+1)

Example 48

2-tert-butyl-5-[(2-cyclohexylpyrrolidin-1-yl)carbonyl]-N-(2-furylmethyl)pyrimidin-4-amine trifluoroacetate

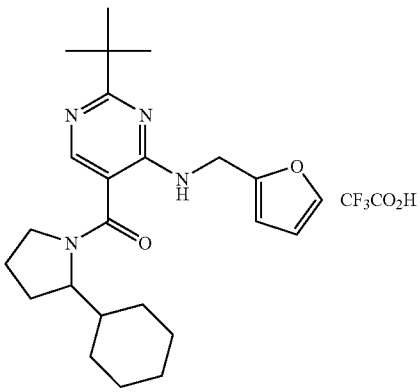

MS (ESI+, m/e) 411 (M+1)

Example 49

2-tert-butyl-N-(2-furylmethyl)-5-[(2-isopropylpyrrolidin-1-yl)carbonyl]pyrimidin-4-amine trifluoroacetate

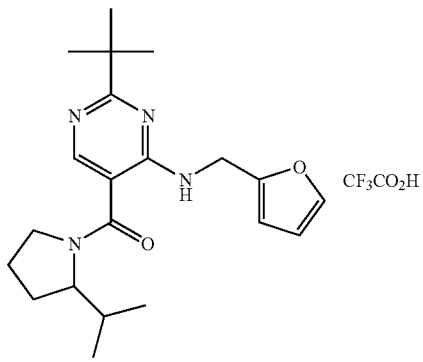

MS (ESI+, m/e) 371 (M+1)

Example 50

2-tert-butyl-N-(2-furylmethyl)-5-[(2-isobutylpyrrolidin-1-yl)crbonyl]pyrimidin-4-amine trifluoroacetate

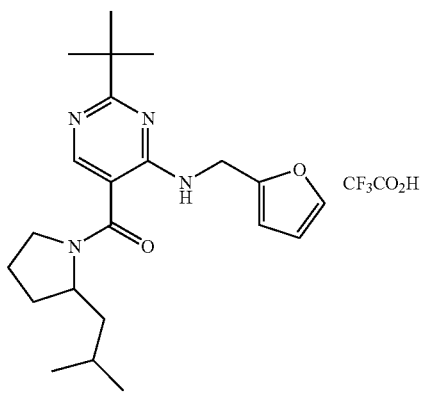

MS (ESI+, m/e) 385 (M+1)

Example 51

[1-({2-tert-butyl-4-[(2-furylmethyl)amino]pyrimidin-5-yl}carbonyl)piperidin-4-yl]methanol trifluoroacetate

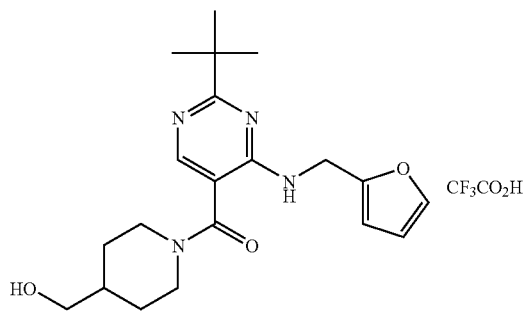

MS (ESI+, m/e) 373 (M+1)

Example 52

5-(perhydroazonin-1-ylcarbonyl)-2-tert-butyl-N-(2-furylmethyl)pyrimidin-4-amine trifluoroacetate

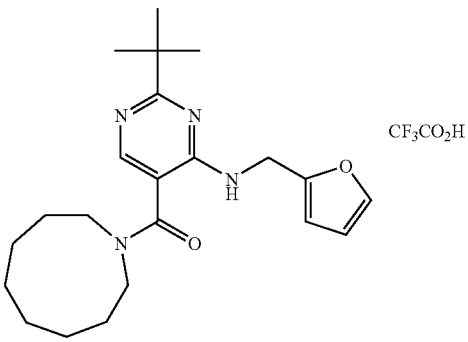

MS (ESI+, m/e) 385 (M+1)

Example 53

N-benzyl-2-tert-butyl-4-[(2-furylmethyl)amino]-N-isopropylpyrimidine-5-carboxamide trifluoroacetate

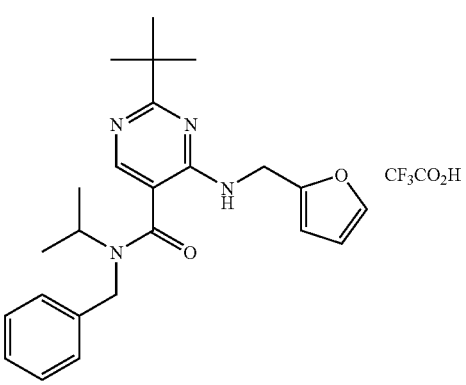

MS (ESI+, m/e) 407 (M+1)

Example 54

2-tert-butyl-4-[(2-furylmethyl)amino]-N-(2-hydroxyethyl)-N-isopropylpyrimidine-5-carboxamide trifluoroacetate

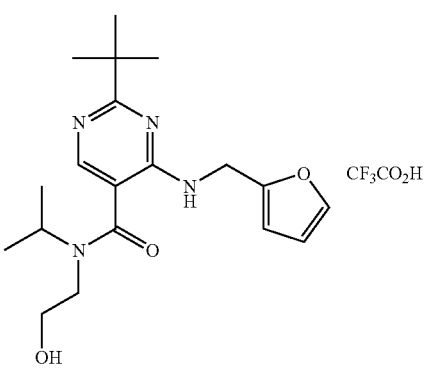

MS (ESI+, m/e) 361 (M+1)

Example 55

2-tert-butyl-N-(2-cyanoethyl)-N-cyclopropyl-4-[(2-furylmethyl)amino]pyrimidine-5-carboxamide trifluoroacetate

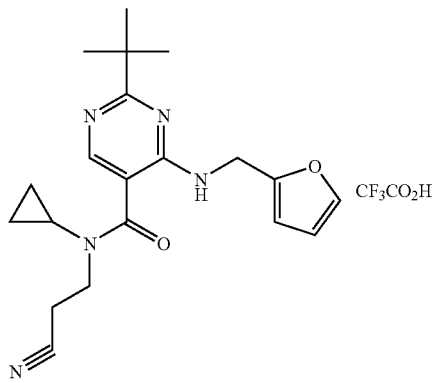

MS (ESI+, m/e) 368 (M+1)

Example 56

5-[(2-ethylpiperazin-1-yl)carbonyl]-N-(2-furylmethyl)-2-(trifluoromethyl)pyrimidin-4-amine bis(trifluoroacetate)

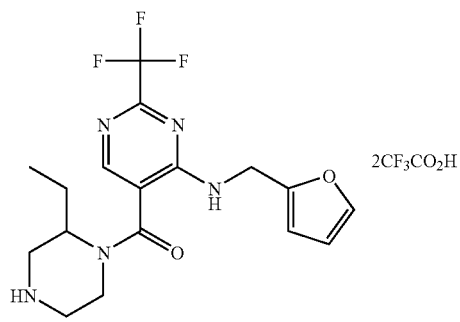

MS (ESI+, m/e) 384 (M+1)

Example 57

5-{[2-(aminomethyl)piperidin-1-yl]carbonyl}-N-(2-furylmethyl)-2-isopropylpyrimidin-4-amine dihydrochloride

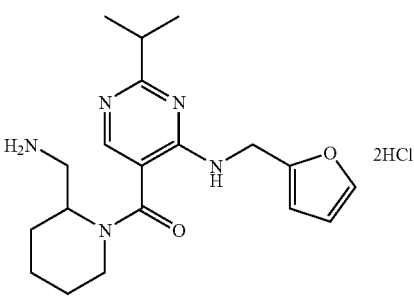

MS (ESI+, m/e) 358 (M+1)

Example 58

5-{[4-(aminomethyl)piperidin-1-yl]carbonyl}-2-tert-butyl-N-(2-furylmethyl)pyrimidin-4-amine dihydrochloride

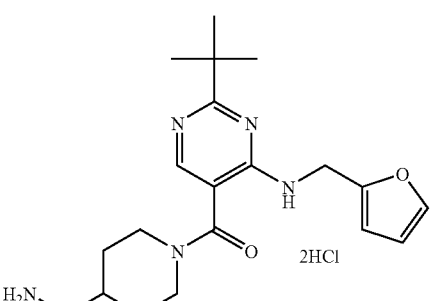

MS (ESI+, m/e) 372 (M+1)

Example 59

2-tert-butyl-N-(2-furylmethyl)-5-({4-[(methylamino)methyl]piperidin-1-yl}carbonyl)pyrimidin-4-amine dihydrochloride

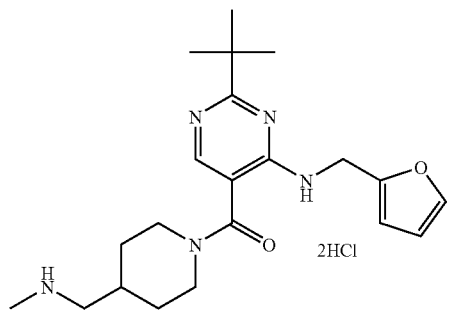

MS (ESI+, m/e) 386 (M+1)

Example 60

5-({4-[(benzylamino)methyl]piperidin-1-yl}carbonyl)-2-tert-butyl-N-(2-furylmethyl)pyrimidin-4-amine dihydrochloride

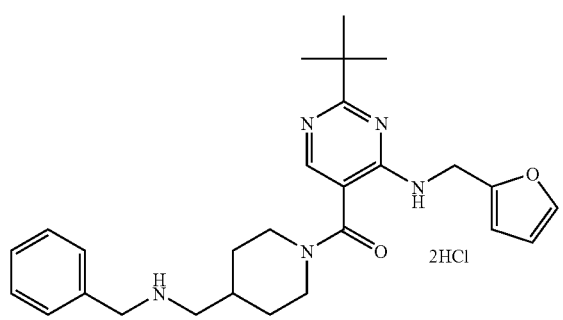

MS (ESI+, m/e) 462 (M+1)

Example 61

N-(2-furylmethyl)-2-(methylthio)-5-(piperazin-1-ylcarbonyl)pyrimidin-4-amine

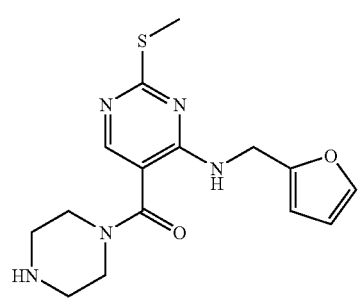

MS (ESI+, m/e) 334 (M+1)

Example 62

5-{[4-(aminomethyl)piperidin-1-yl]carbonyl}-N-(2-furylmethyl)-2-isopropylpyrimidin-4-amine

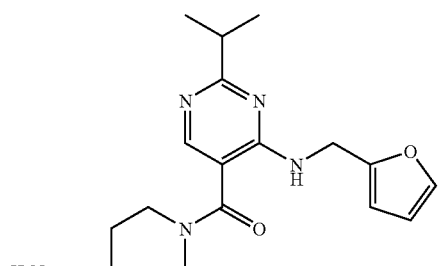

MS (ESI+, m/e) 358 (M+1)

Example 63

N-(2-furylmethyl)-2-isopropyl-5-({4-[(methylamino)methyl]piperidin-1-yl}carbonyl)pyrimidin-4-amine

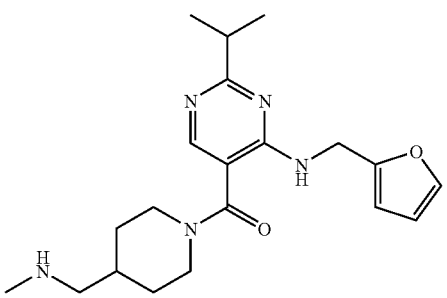

MS (ESI+, m/e) 372 (M+1)

Example 64

5-{[4-(aminomethyl)piperidin-1-yl]carbonyl}-2-cyclopropyl-N-(2-furylmethyl)pyrimidin-4-amine

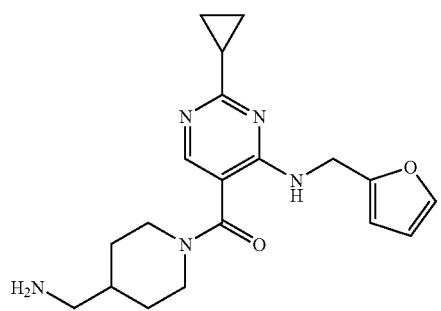

MS (ESI+, m/e) 356 (M+1)

Example 65

2-cyclopropyl-N-(2-furylmethyl)-5-({4-[(methylamino)methyl]piperidin-1-yl}carbonyl)pyrimidin-4-amine

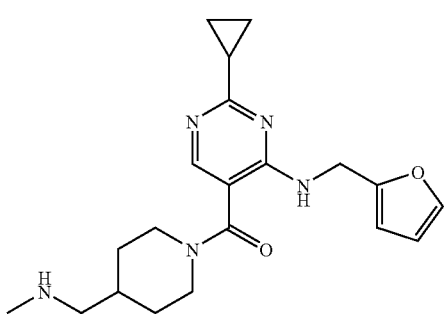

MS (ESI+, m/e) 370 (M+1)

Example 66

2-tert-butyl-N-(2-furylmethyl)-5-(piperazin-1-ylcarbonyl)pyrimidin-4-amine

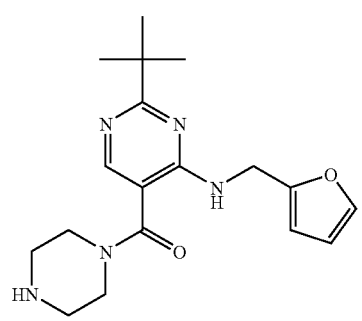

MS (ESI+, m/e) 344 (M+1)

Example 67

5-[(4-aminopiperidin-1-yl)carbonyl]-2-tert-butyl-N-(2-furylmethyl)pyrimidin-4-amine

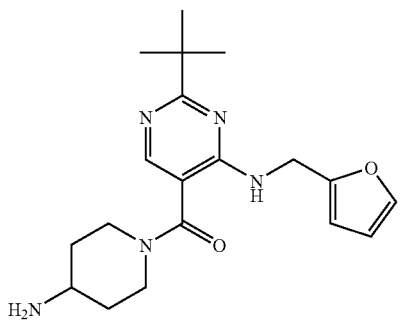

MS (ESI+, m/e) 358 (M+1)

Example 68

2-tert-butyl-N-(2-furylmethyl)-5-[(2-phenylpiperazin-1-yl)carbonyl]pyrimidin-4-amine

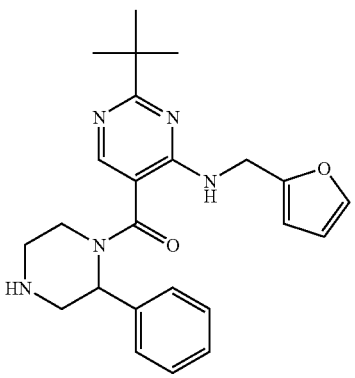

MS (ESI+, m/e) 420 (M+1)

Example 69

2-tert-butyl-5-(1,4-diazepan-1-ylcarbonyl)-N-(2-furylmethyl)pyrimidin-4-amine

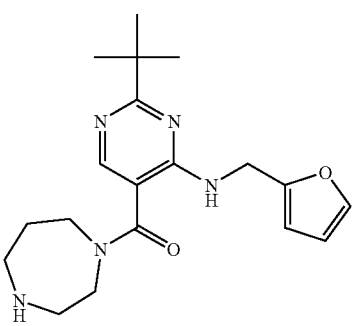

MS (ESI+, m/e) 358 (M+1)

Example 70

5-{[4-(2-aminoethyl)piperazin-1-yl]carbonyl}-2-tert-butyl-N-(2-furylmethyl)pyrimidin-4-amine

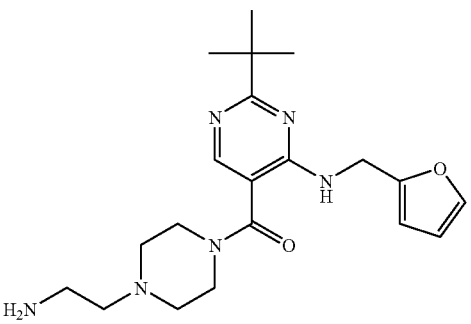

MS (ESI+, m/e) 387 (M+1)

Example 71

5-{[4-(aminomethyl)piperidin-1-yl]carbonyl}-2-tert-butyl-N-(2-furylmethyl)pyrimidin-4-amine

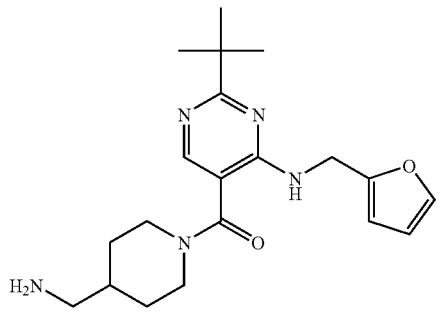

MS (ESI+, m/e) 372 (M+1)

Example 72

5-{[3-(aminomethyl)piperidin-1-yl]carbonyl}-2-tert-butyl-N-(2-furylmethyl)pyrimidin-4-amine

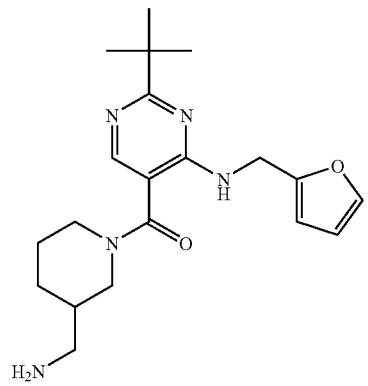

MS (ESI+, m/e) 372 (M+1)

Example 73

2-tert-butyl-N-(2-furylmethyl)-5-({4-[(methylamino)methyl]piperidin-1-yl}carbonyl)pyrimidin-4-amine

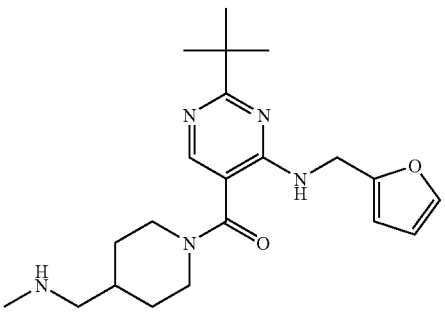

MS (ESI+, m/e) 386 (M+1)

Example 74

5-{[4-(aminomethyl)piperidin-1-yl]carbonyl}-N-(2-furylmethyl)-2-(trifluoromethyl)pyrimidin-4-amine

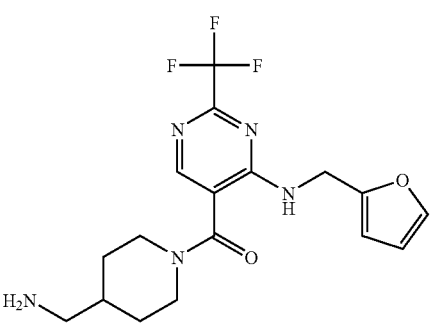

MS (ESI+, m/e) 384 (M+1)

Example 75

N-(2-furylmethyl)-5-({4-[(methylamino)methyl]piperidin-1-yl}carbonyl)-2-(trifluoromethyl)pyrimidin-4-amine

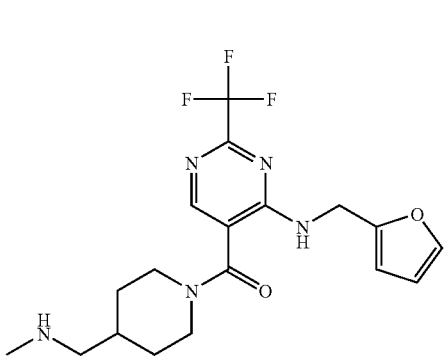

MS (ESI+, m/e) 398 (M+1)

Example 76

5-[(3-aminopyrrolidin-1-yl)carbonyl]-2-tert-butyl-N-(2-furylmethyl)pyrimidin-4-amine

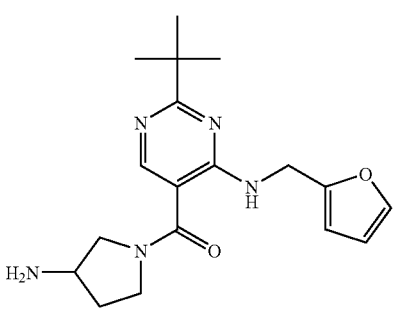

MS (ESI+, m/e) 344 (M+1)

Example 77

5-[(3-aminopiperidin-1-yl)carbonyl]-2-tert-butyl-N-(2-furylmethyl)pyrimidin-4-amine

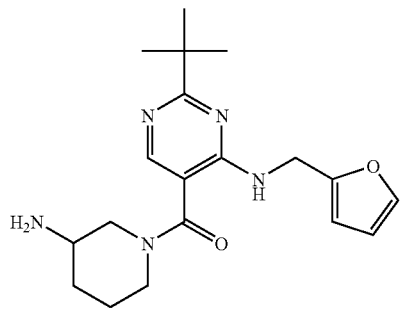

MS (ESI+, m/e) 358 (M+1)

Example 78

2-tert-butyl-5-[(2-ethylpiperazin-1-yl)carbonyl]-N-(2-furylmethyl)pyrimidin-4-amine

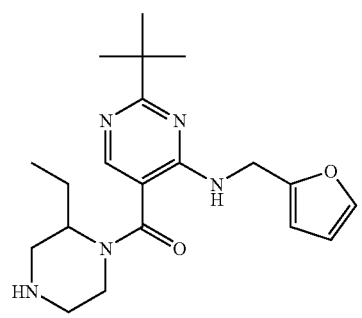

MS (ESI+, m/e) 372 (M+1)

Example 79

5-[(3-aminopiperidin-1-yl)carbonyl]-N-(2-furylmethyl)-2-(2-thienyl)pyrimidin-4-amine

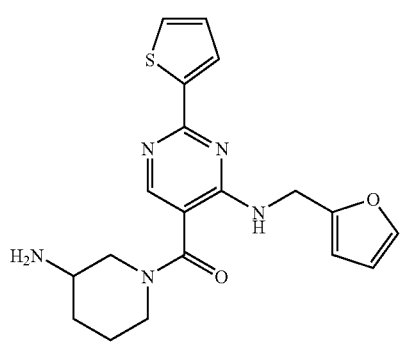

MS (ESI+, m/e) 384 (M+1)

Example 80

5-[(4-aminopiperidin-1-yl)carbonyl]-N-(tetrahydrofuran-2-ylmethyl)-2-(trifluoromethyl)pyrimidin-4-amine

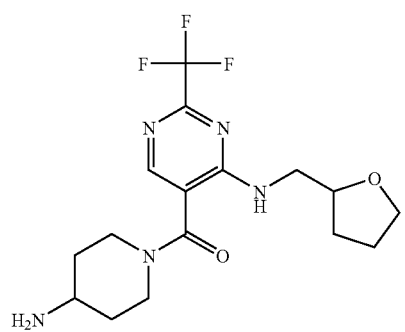

MS (ESI+, m/e) 374 (M+1)

Example 81

5-[(4-aminopiperidin-1-yl)carbonyl]-2-isopropyl-N-(tetrahydrofuran-2-ylmethyl)pyrimidin-4-amine

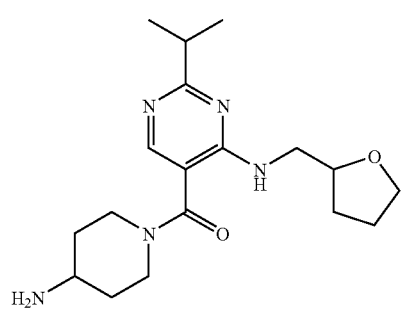

MS (ESI+, m/e) 348 (M+1)

Example 82

5-[(4-aminopiperidin-1-yl)carbonyl]-N-(2-ethoxyethyl)-2-(trifluoromethyl)pyrimidin-4-amine

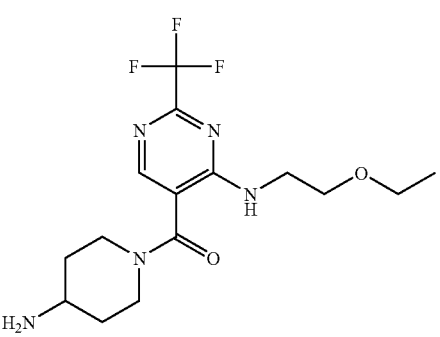

MS (ESI+, m/e) 362 (M+1)

Example 83

5-[(4-aminopiperidin-1-yl)carbonyl]-N-(2-ethoxy-ethyl)-2-isopropylpyrimidin-4-amine

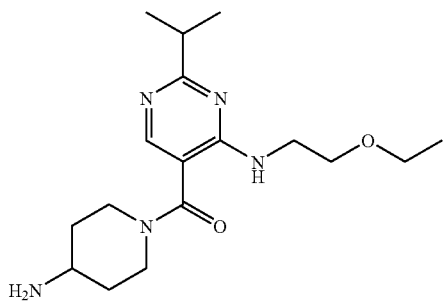

MS (ESI+, m/e) 336 (M+1)

Example 84

5-[(4-aminopiperidin-1-yl)carbonyl]-N-(3-methoxypropyl)-2-(trifluoromethyl)pyrimidin-4-amine

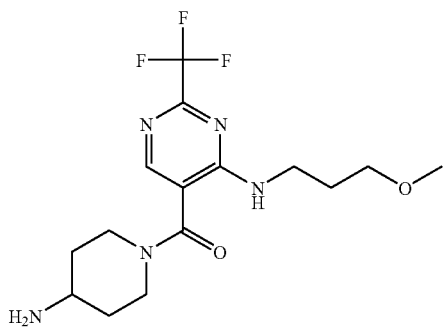

MS (ESI+, m/e) 362 (M+1)

Example 85

5-[(4-aminopiperidin-1-yl)carbonyl]-2-isopropyl-N-(3-methoxypropyl)pyrimidin-4-amine

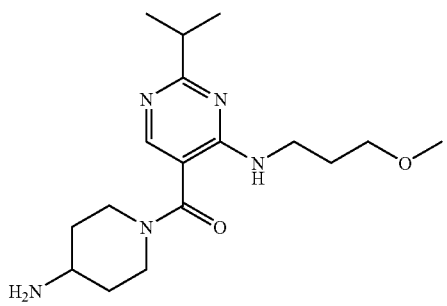

MS (ESI+, m/e) 336 (M+1)

Example 86

5-[(4-aminopiperidin-1-yl)carbonyl]-N-butyl-2-(trifluoromethyl)pyrimidin-4-amine

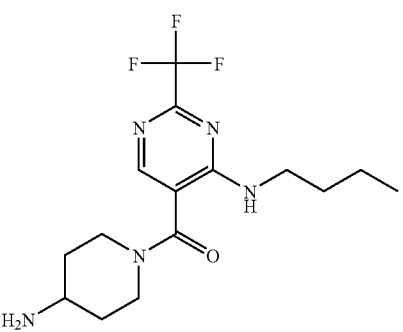

MS (ESI+, m/e) 346 (M+1)

Example 87

5-[(4-aminopiperidin-1-yl)carbonyl]-N-butyl-2-isopropylpyrimidin-4-amine

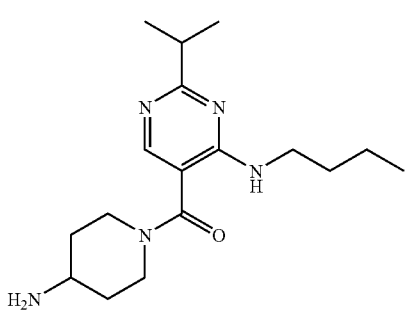

MS (ESI+, m/e) 320 (M+1)

Example 88

N-isobutyl-2-isopropyl-5-(piperazin-1-ylcarbonyl)pyrimidin-4-amine

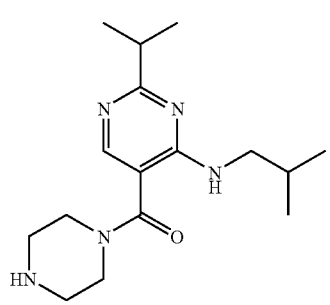

MS (ESI+, m/e) 306 (M+1)

Example 89 methyl N-[2-isopropyl-5-(piperazin-1-ylcarbonyl)pyrimidin-4-yl]glycinate

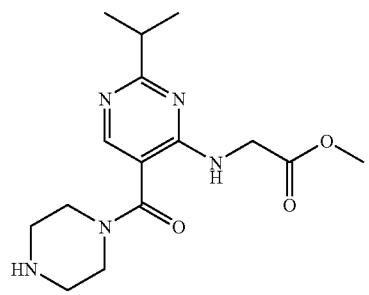

MS (ESI+, m/e) 322 (M+1)

Example 90

2-isopropyl-5-(piperazin-1-ylcarbonyl)-N-(pyridin-3-ylmethyl)pyrimidin-4-amine

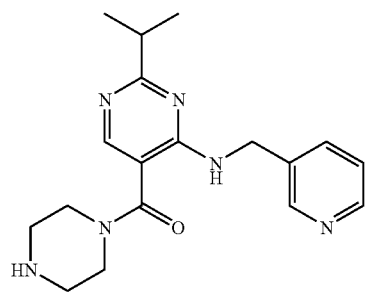

MS (ESI+, m/e) 341 (M+1)

Example 91

2-isopropyl-5-(piperazin-1-ylcarbonyl)-N-(pyridin-2-ylmethyl)pyrimidin-4-amine

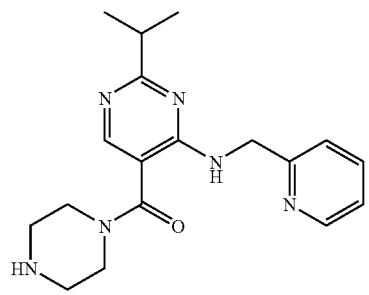

MS (ESI+, m/e) 341 (M+1)

Example 92

2-isopropyl-5-(piperazin-1-ylcarbonyl)-N-(pyridin-4-ylmethyl)pyrimidin-4-amine

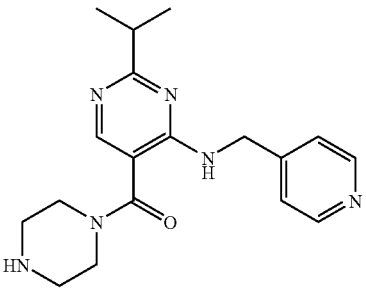

MS (ESI+, m/e) 341 (M+1)

Example 93

Method G

N-[(3R*,5S*)-5-(aminocarbonyl)piperidin-3-yl]-2-tert-butyl-4-[(2-furylmethyl)amino]-N-isobutylpyrimidine-5-carboxamide dihydrochloride

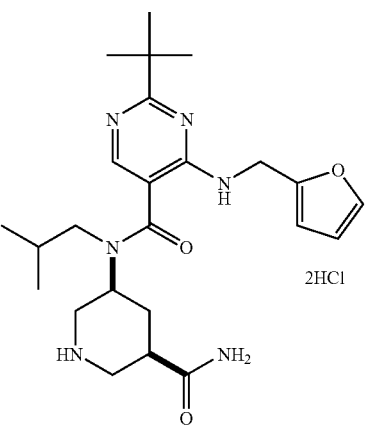

tert-Butyl (3R*,5S*)-3-(aminocarbonyl)-5-[({2-tert-butyl-4-[(2-furylmethyl)amino]pyrimidin-5-yl}carbonyl)(isobutyl)amino]piperidine-1-carboxylate (230 mg) was dissolved in 1 M hydrogen chloride-ethyl acetate (4 ml), and the mixture was stirred at room temperature for 2 hr. The reaction mixture was concentrated, ethyl acetate was added and the precipitate was collected by filtration and washed with ethyl acetate to give the object compound (218 mg).

MS (ESI+, m/e) 457 (M+1)

Example 94

Method H 2-tert-butyl-4-[(2-furylmethyl)amino]-N-{(3R*,5S*)-5-[(4-hydroxy-4-methylpiperidin-1-yl)carbonyl]piperidin-3-yl}-N-isobutylpyrimidine-5-carboxamide dihydrochloride

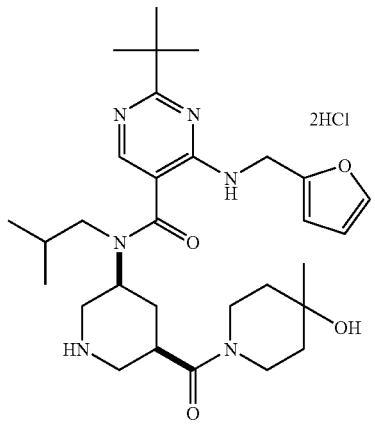

tert-Butyl (3R*,5S*)-3-[({2-tert-butyl-4-[(2-furylmethyl)amino]pyrimidin-5-yl}carbonyl)(isobutyl)amino]-5-[(4-hydroxy-4-methylpiperidin-1-yl)carbonyl]piperidine-1-carboxylate (110 mg) was dissolved in 2 M hydrogen chloride-ethyl acetate (2 ml), and the mixture was stirred at room temperature for 2 hr. The reaction mixture was concentrated, ethyl acetate-hexane was added and the precipitate was collected by filtration and washed with ethyl acetate-hexane to give the object compound (104 mg).

MS (ESI+, m/e) 555 (M+1)

By a method similar to that of the above-mentioned Example 93 (Method G) and Example 94 (Method H), the compounds of Examples 95 and 96 below were obtained. The respective compounds were isolated and purified as necessary by a known means such as phase transfer, pH conversion, solvent extraction, silica gel column chromatography, reversed-phase preparative HPLC and the like. The final products were isolated as hydrochloride as in Method G and Method H by treating with a hydrogen chloride-ethyl acetate solution.

Example 95

2-tert-butyl-4-[(2-furylmethyl)amino]-N-[(3R*,5S*)-5-(1-hydroxy-1-methylethyl)piperidin-3-yl]-N-isobutylpyrimidine-5-carboxamide dihydrochlorde

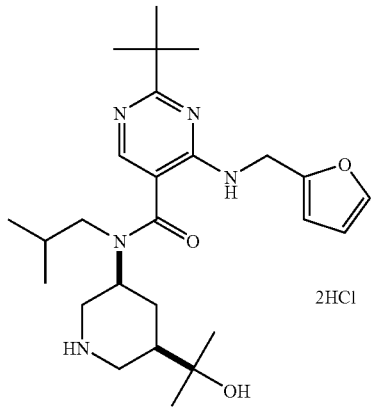

MS (ESI+, m/e) 472 (M+1)

Example 96 methyl (3R,5S)-5-[({2-tert-butyl-4-[(3-methoxypropyl)amino]pyrimidin-5-yl}carbonyl)(isobutyl)amino]piperidine-3-carboxylate dihydrochloride

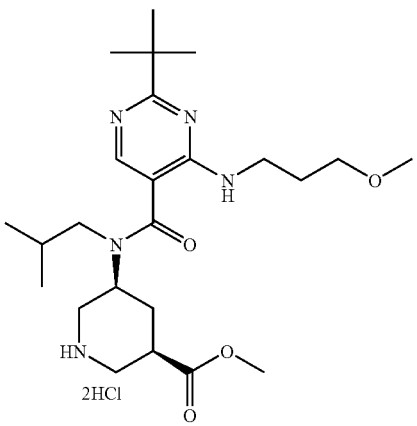

MS (ESI+, m/e) 464 (M+1)

Example 97

2-tert-butyl-4-[(3-methoxypropyl)amino]-N-(2-methylpropyl)-N-[(3S,5R)-5-(morpholin-4-ylcarbonyl)piperidin-3-yl]pyrimidine-5-carboxamide dihydrochloride

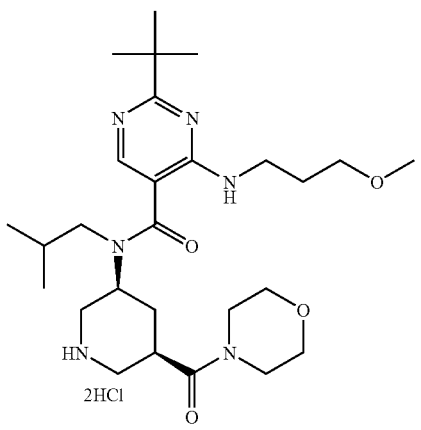

tert-Butyl (3S,5R)-3-[({2-tert-butyl-4-[(3-methoxypropyl)amino]pyrimidin-5-yl}carbonyl)(isobutyl)amino]-5-(morpholin-4-ylcarbonyl)piperidine-1-carboxylate (105 mg) is was dissolved in 1 M hydrogen chloride-ethyl acetate (6 ml), and the mixture was stirred at room temperature for 13 hr. The reaction mixture was concentrated to give the object compound (93 mg).

MS (ESI+, m/e) 519 (M+1)

Example 98

Method I methyl (3R*,5S*)-5-[[(2-tert-butyl-4-{[3-(methylthio)propyl]amino}pyrimidin-5-yl)carbonyl](isobutyl)amino]piperidine-3-carboxylate

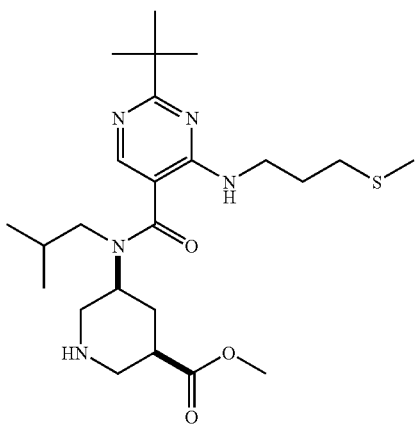

To a solution of 1-tert-butyl 3-methyl (3R*,5S*)-5-{[(2-tert-butyl-4-chloropyrimidin-5-yl)carbonyl](isobutyl)amino}piperidine-1,3-dicarboxylate (51.1% mg) and diisopropylethylamine (38 mg) in DMF (0.5 ml) was added a solution of 3-methylthiopropylamine (21 mg) in DMF (0.5 ml), and the mixture was stirred at 80° C. overnight. To the reaction mixture was added 2% aqueous sodium hydrogen carbonate and the mixture was extracted with ethyl acetate, and the extract was concentrated by a nitrogen gas blower. The residue was purified by reversed-phase preparative HPLC, and the object fraction was concentrated by a nitrogen gas blower. The residue was dissolved in trifluoroacetic acid/acetonitrile solution (20% (V/V), 1.0 ml), and the mixture was stirred at room temperature for 6 hr. The reaction mixture was concentrated by a nitrogen gas blower. The residue was neutralized with triethylamine (1 ml), saturated aqueous sodium hydrogen carbonate was added, and the mixture was extracted with ethyl acetate. The extract was concentrated by a nitrogen gas blower. The residue was purified by reversed-phase preparative HPLC, and the object fraction was concentrated by a nitrogen gas blower to give the object compound (6.4 mg).

MS (ESI+, m/e) 480 (M+1)

By a method similar to that of the above-mentioned Example 98 (Method I), the compound of Example 99 below was obtained. The compounds were isolated and purified as necessary by a known means such as phase transfer, pH conversion, solvent extraction, silica gel column chromatography, reversed-phase preparative HPLC and the like. The final products were isolated as a free form.

Example 99 methyl (3R*,5S*)-5-[{[4-(benzylamino)-2-tert-butylpyrimidin-5-yl]carbonyl}(isobutyl)amino]piperidine-3-carboxylate

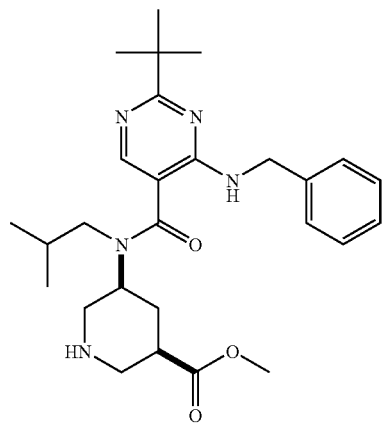

MS (ESI+, m/e) 482 (M+1)

Reference Example 51

(3R*,5S*)-1-(tert-butoxycarbonyl)-5-(methoxycarbonyl)piperidine-3-carboxylic acid, (3R*,5R*)-1-(tert-butoxycarbonyl)-5-(methoxycarbonyl)piperidine-3-carboxylic acid and 1-tert-butyl 3,5-dimethyl piperidine-1,3,5-tricarboxlate

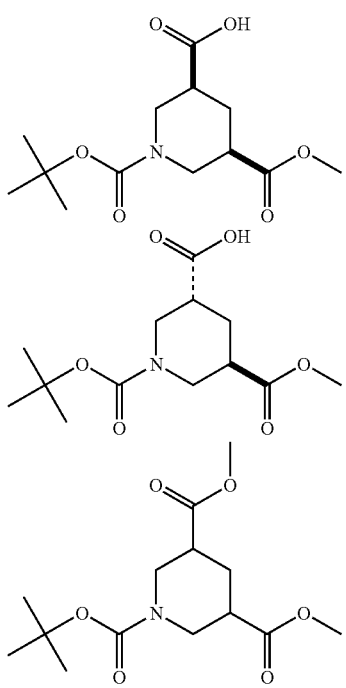

Dimethylpyridine-3,5-dicarboxylate (55 g) was dissolved in methanol (500 ml) and 6 M hydrochloric acid (70 ml), and rhodium-carbon (5.5 g) was added. The reaction mixture was stirred under pressurized hydrogen atmosphere (5 atm) at room temperature for 3 hr, and thereafter at 50° C. for 12 hr. The mixture was allowed to cool to room temperature, the rhodium catalyst was filtered off, and the filtrate was concentrated under reduced pressure. The residue was dissolved in ethanol (300 ml) and, under ice-cooling, triethylamine (60 ml) and di-tert-butyl dicarbonate (68 g) were successively added. The reaction mixture was stirred at room temperature for 12 hr, and concentrated under reduced pressure. The residue was dissolved in 0.5 M hydrochloric acid, and the mixture was extracted with ethyl acetate. The extract was washed with saturated brine, and dried over anhydrous sodium sulfate. The solvent was evaporated under reduced pressure and the residue was purified by silica gel column chromatography. The fraction eluted with hexane-ethyl acetate (7:1-1:4) was obtained. The less polar fraction was concentrated under reduced pressure to give 1-tert-butyl 3,5-dimethyl piperidine-1,3,5-tricarboxylate (22.2 g). The more polar fraction was concentrated under reduced pressure, and the residue was diluted with ethyl acetate. The precipitate was collected by filtration and washed with ethyl acetate to give (3R*,5S*)-1-(tert-butoxycarbonyl)-5-(methoxycarbonyl)piperidine-3-carboxylic acid (15.6 g) as a powder. The filtrate was concentrated under reduced pressure to give a mixture (8.9 g) of (3R*,5S*)-1-(tert-butoxycarbonyl)-5-(methoxycarbonyl)piperidine-3-carboxylic acid and (3R*,5R*)-1-(tert-butoxycarbonyl)-5-(methoxycarbonyl)piperidine-3-carboxylic acid.

(3R*,5S*)-1-(tert-butoxycarbonyl)-5-(methoxycarbonyl)piperidine-3-carboxylic acid $^1$H-NMR (CDCl$_3$) δ 1.47 (9H, s), 1.72 (1H, d), 2.41-2.63 (3H, m), 2.72 (2H, br s), 3.71 (3H, s), 4.38 (2H, d).

Mixture of (3R*,5S*)-1-(tert-butoxycarbonyl)-5-(methoxycarbonyl)piperidine-3-carboxylic acid and (3R*,5R*)-1-(tert-butoxycarbonyl)-5-(methoxycarbonyl)piperidine-3-carboxylic acid $^1$H-NMR (CDCl$_3$) δ 1.33-1.50 (9H, m), 1.60-1.82 (1H, m), 1.96-2.22 (1H, m), 2.41-2.58 (2H, m), 2.62-2.91 (2H, m), 3.34-3.91 (1H, m), 3.71 (3H, s), 4.37 (1H, br s), 7.55-8.47 (1H, m).

1-tert-butyl 3,5-dimethyl piperidine-1,3,5-tricarboxylate $^1$H-NMR (CDCl$_3$) δ 1.36-1.50 (2H, m), 1.46 (7H, m), 1.62-1.76 (1H, m), 1.99-2.16 (1H, m), 2.38-2.55 (2H, m), 2.61-2.75 (1H, m), 2.81 (1H, t), 3.39-3.60 (1H, m), 3.64-3.81 (6H, m), 4.35 (1H, br s).

Reference Example 52

(3R,5S)-1-(tert-butoxycarbonyl)piperidine-3,5-dicarboxylic acid

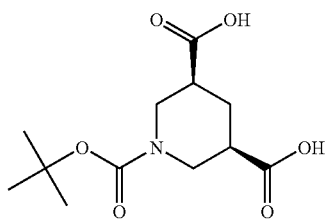

Dimethylpyridine-3,5-dicarboxylate (50 g) was dissolved in acetic acid (300 ml), 5% rhodium carbon (5 g) was added, and the mixture was stirred under pressurized hydrogen atmosphere (5 atm) at 50° C. for 15 hr. The reaction mixture was allowed to cool to room temperature, the rhodium catalyst was filtered off, and the filtrate was concentrated under reduced pressure. The residue was dissolved in ethanol (300 ml) and, under ice-cooling, triethylamine (107 ml) and di-tert-butyl dicarbonate (67 g) were successively added. The reaction mixture was stirred at room temperature for 15 hr, and concentrated under reduced pressure. The residue was dissolved in water, and the mixture was adjusted to pH 3 with 6 M hydrochloric acid. The mixture was extracted with ethyl acetate. The ethyl acetate extract layer was washed with saturated brine, and dried over anhydrous sodium sulfate. The solvent was evaporated under reduced pressure. The residue was dissolved in methanol (250 ml), and 8 N aqueous sodium hydroxide solution (128 ml) was added dropwise at room temperature. The reaction mixture was stirred at room temperature for 24 hr, and methanol was evaporated under reduced pressure. The concentrated solution was diluted with saturated aqueous sodium hydrogen carbonate solution (100 ml) and washed twice with diethyl ether. The basic aqueous layer was acidified (pH 3) with 6 M hydrochloric acid. The precipitated powder was collected by filtration, washed with water, and air-dried. The obtained powder (55 g) was dissolved in methanol (200 ml) by heating and the mixture was concentrated under reduced pressure until the amount of methanol became half. Water (50 ml) was added, and the mixture was stood at room temperature overnight. The precipitated white powder was collected by filtration, washed with cold methanol/water=2/1 (200 ml) and air-dried to give the object compound (38 g) as a powder.

$^1$H-NMR (CDCl$_3$) δ 1.47 (9H, s), 1.72 (1H, d), 2.41-2.63 (3H, m), 2.72 (2H, br s), 3.71 (3H, s), 4.38 (2H, d).

Reference Example 53

(3S,5R)-1-(tert-butoxycarbonyl)-5-(methoxycarbonyl)piperidine-3-carboxylic acid

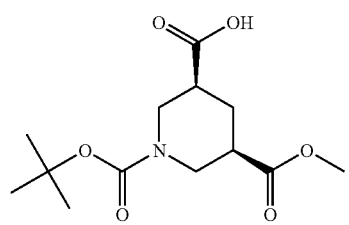

(3R,5S)-1-(tert-Butoxycarbonyl)piperidine-3,5-dicarboxylic acid (222 g) was suspended in acetic anhydride (2 L), and the suspension was heated under reflux for 3 hr. The reaction mixture was concentrated under reduced pressure. Toluene (200 ml) was added and the mixture was concentrated under reduced pressure. This operation was repeated twice. The obtained residue and quinidine (142 g) were dissolved in THF (900 ml), and the mixture was cooled to −40° C. A solution of methanol (161 ml) in THF (100 ml) was added dropwise over 30 min, and the mixture was stirred at the same temperature for 7 hr. THF (about 700 ml) was evaporated under reduced pressure, ethyl acetate was added, and the mixture was washed with 2 N hydrochloric acid. The aqueous layer was extracted with ethyl acetate, the organic layer was combined and the mixture was washed successively with 2 N hydrochloric acid and saturated brine, and dried over anhydrous magnesium sulfate. The solvent was concentrated under reduced pressure and the obtained residue (106 g) was suspended in ethanol (410 ml). (R)-(+)-1-Phenylethylamine (45 g) was added, and the mixture was dissolved by heating to 75° C. The hot ethanol solution was rapidly filtered, and the filtrate was allowed to stand at room temperature for 12 hr. The resulting colorless crystals were collected by filtration, washed with ethyl acetate-hexane, and then with hexane and air-dried. The obtained solid was suspended in water (490 ml). Saturated aqueous potassium hydrogen sulfate solution (490 ml) was added and the mixture was extracted 3 times with ethyl acetate. The organic layer was washed with saturated brine, dried over anhydrous magnesium sulfate and concentrated to dryness to give the object compound (148 g) as a solid.

$^1$H-NMR (DMSO-$d_6$) δ1.39 (9H, s), 1.52 (1H, q), 2.18-2.54 (3H, m), 2.55-2.78 (2H, m), 3.63 (3H, s), 4.03-4.23 (2H, m), 12.51 (1H, br s).

Reference Example 54

1-(tert-butoxycarbonyl)-5-(methoxycarbonyl)piperidine-3-carboxyl acid

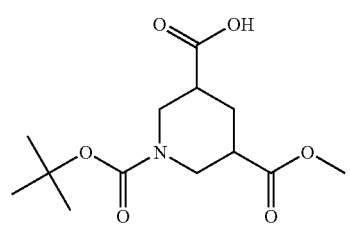

1-tert-Butyl 3,5-dimethyl piperidine-1,3,5-tricarboxylate (75 g) was dissolved in methanol (375 ml), and 2 M aqueous sodium hydroxide solution (125 ml) was added dropwise at room temperature. The reaction mixture was stirred at room temperature for 14 hr, and methanol was evaporated under reduced pressure. The concentrated solution was diluted with saturated aqueous sodium hydrogen carbonate solution (100 ml) and washed twice with ethyl acetate. The basic aqueous layer was acidified (pH 2) with 6 M hydrochloric acid, and the mixture was extracted with ethyl acetate. The extract was dried over anhydrous magnesium sulfate, and the solvent was evaporated under reduced pressure to give the object compound (71 g).

$^1$H-NMR (CDCl$_3$) δ 1.33-1.50 (9H, m), 1.60-1.82 (1H, m), 1.96-2.22 (1H, m), 2.41-2.58 (2H, m), 2.62-2.91 (2H, m), 3.34-3.91 (1H, m), 3.71 (3H, s), 4.37 (1H, br s), 7.55-8.47 (1H, m).

By a method similar to that of Reference Example 43, the following compound (Reference Example 55) was obtained.

Reference Example 55

1-tert-butyl 3-methyl 5-aminopiperidine-1,3-dicarboxylate

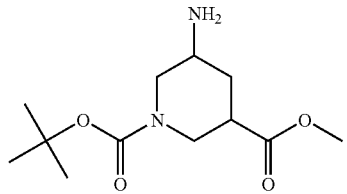

$^1$H-NMR (CDCl$_3$) δ 1.19-1.41 (3H, m), 1.46-1.50 (9H, m), 1.82-2.78 (4H, m), 3.49 (1H, m), 3.64-3.73 (3H, m), 4.15 (2H, br s).

By a method similar to that of Reference Example 44, the following compound (Reference Example 56) was obtained.

Reference Example 56

1-tert-butyl 3-methyl 5-[(2-methylpropyl)amino]piperidine-1,3-dicarboxylate

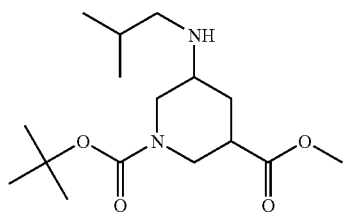

$^1$H-NMR (CDCl$_3$) δ 0.93-1.09 (2H, m), 1.02 (4H, d), 1.45 (9H, d), 2.05 (3H, s), 2.65-2.79 (2H, m), 2.83-2.98 (1H, m), 3.25 (1H, dd), 3.49 (2H, s), 3.58-3.75 (3H, m), 3.94 (1H, d).

Reference Example 57

1-tert-butyl 3-methyl (3R,5S)-5-{[(benzyloxy)carbonyl]amino}piperidine-1,3-dicarboxylate

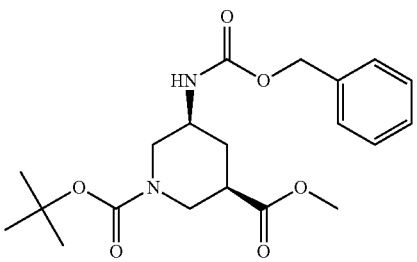

(3S,5R)-1-(tert-Butoxycarbonyl)-5-(methoxycarbonyl)piperidine-3-carboxylic acid (2.83 g) was suspended in toluene (36 ml), diphenylphosphoryl azide (2.60 ml) and triethylamine (1.70 ml) were added, and the mixture was stirred at 100° C. for 1 hr. The reaction mixture was cooled to room temperature, benzyl alcohol (1.53 ml) and triethylamine (7.00 ml) were added and the mixture was stirred at 80° C. for 3 hr. The reaction mixture was concentrated, and the residue was dissolved in ethyl acetate, washed with water, 0.5 M hydrochloric acid, saturated aqueous sodium hydrogen carbonate and saturated brine in this order, and dried over anhydrous magnesium sulfate. The solvent was evaporated under reduced pressure. The residue was subjected to silica gel column chromatography, and the fraction eluted with ethyl acetate-hexane (1:3-3:1) was concentrated under reduced pressure to give the object compound (2.78 g) as an oil.

MS (ESI+, m/e) 393 (M+1)

Reference Example 58

(3R,5S)-5-{[(benzyloxy)carbonyl]amino}-1-(tert-butoxycarbonyl)piperidine-3-carboxylic acid

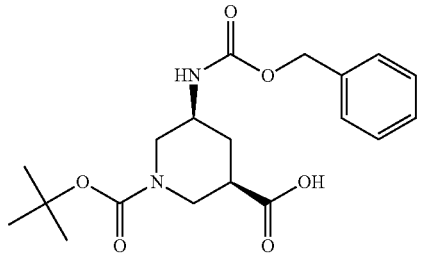

To a solution of 1-tert-butyl 3-methyl (3R,5S)-5-{[(benzyloxy)carbonyl]amino}piperidine-1,3-dicarboxylate (115 g) in methanol (700 ml) was added 1 M aqueous sodium hydroxide solution (350 ml) under ice-cooling, and the mixture was stirred at room temperature for 12 hr. The reaction mixture was concentrated under reduced pressure to about 1/3 volume, and the residual aqueous solution was washed with ethyl acetate-hexane (1:1, 600 ml). The aqueous layer was neutralized with 1 M hydrochloric acid, and the mixture was extracted with ethyl acetate. The extract was washed with saturated brine, and dried over anhydrous magnesium sulfate. The solvent was evaporated under reduced pressure to give the object compound (98.5 g).

$^1$H-NMR (DMSO-$d_6$) δ 1.33 (1H, br s), 1.40 (9H, s), 2.09 (1H, d), 2.36-2.52 (3H, m), 3.93-4.09 (2H, m), 5.03 (2H, s), 7.28-7.43 (5H, m), 12.52 (1H, br s).

Reference Example 59 tert-butyl (3S,5R)-3-{[(benzyloxy)carbonyl]amino}-5-(morpholin-4-ylcarbonyl)piperidine-1-carboxylate

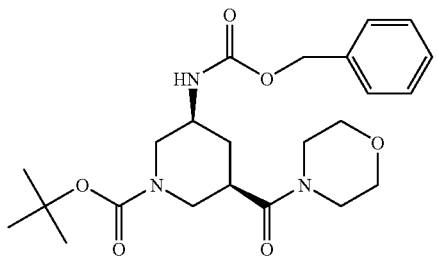

(3R,5S)-5-{[(Benzyloxy)carbonyl]amino}-1-(tert-butoxycarbonyl)piperidine-3-carboxylic acid (49.2 g), morpholine (11.4 ml), 1H-benzotriazol-1-ol (10.0 g) and triethylamine (40 ml) were dissolved in DMF (250 ml), WSC.HCl (30.0 g) was added and the mixture was stirred at room temperature for 4 days. The reaction mixture was poured into water, and the mixture was extracted with ethyl acetate. The extract was washed successively with saturated aqueous sodium hydrogen carbonate solution and saturated brine, and dried over anhydrous magnesium sulfate. The solvent was evaporated under reduced pressure to give the object compound (62.9 g).

$^1$H-NMR (CDCl$_3$) δ 1.46 (9H, s), 1.69 (2H, br s), 2.04 (1H, s), 2.73 (2H, br s), 2.79-2.96 (1H, m), 3.52-3.65 (6H, m), 3.69 (2H, d), 3.67 (1H, br s), 4.04 (1H, d), 5.09 (2H, s), 5.40 (1H, br s), 7.25-7.41 (5H, m).

Reference Example 60 tert-butyl (3S,5R)-3-[(2-methylpropyl)amino]-5-(morpholin-4-ylcarbonyl)piperidine-1arboxylate

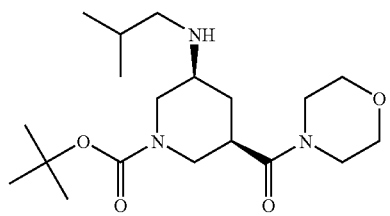

tert-Butyl (3S,5R)-3-{[(benzyloxy)carbonyl]amino}-5-(morpholin-4-ylcarbonyl)piperidine-1-carboxylate (58 g) and palladium(II) hydroxide-carbon (5 g) were suspended in methanol (400 ml), and the suspension was stirred under a hydrogen atmosphere (1 atm) at room temperature for 16 hr. The palladium catalyst was filtered off, and the filtrate was concentrated under reduced pressure. The obtained residue and acetic acid (8.8 ml) were dissolved in methanol (400 ml), 2-methylpropanal (14.0 ml) was added and the mixture was stirred at room temperature for 1 hr. Sodium triacetoxyborohydride (40.4 g) was added to the reaction mixture, and the mixture was stirred at room temperature for 2 hr. The reaction mixture was concentrated under reduced pressure, the concentrated solution was basified with 3.5 M aqueous potassium carbonate solution, and the mixture was extracted with ethyl acetate. The extract was washed with water and saturated brine, and dried over anhydrous magnesium sulfate. The solvent was evaporated under reduced pressure. The residue was subjected to silica gel column chromatography, and the fraction eluted with ethyl acetate-hexane (1:5) to ethyl acetate 100% to ethyl acetate-methanol (9:1) was concentrated under reduced pressure to give the object compound (33.3 g).

$^1$H-NMR (CDCl$_3$) δ 0.90 (6H, d), 1.46 (9H, s), 1.54 (1H, d), 1.69 (1H, dt), 1.96-2.12 (2H, m), 2.23-2.37 (1H, m), 2.47 (3H, d), 2.66 (1H, d), 3.61 (1H, br s), 3.55 (2H, d), 3.69 (5H, ddd), 4.01-4.46 (2H, m).

Reference Example 61 tert-butyl (3S)-3-[(2-methylpropyl)amino]piperidine-1-carboxylate

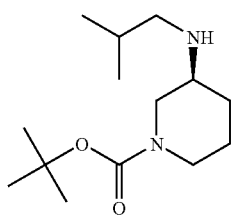

tert-Butyl (3S)-3-aminopiperidine-1-carboxylate (5.0 g), isobutyraldehyde (2.66 ml) and acetic acid (1.72 ml) were dissolved in methanol (100 ml), and the mixture was stirred at room temperature for 10 min. To the reaction mixture was added sodium triacetoxyborohydride (13.2 g) and the mixture was stirred at room temperature for 30 min. The reaction mixture was basified with aqueous sodium hydrogen carbonate, and the mixture was extracted with ethyl acetate. The extract was washed with saturated brine, and dried over anhydrous magnesium sulfate. The solvent was evaporated under reduced pressure. A part of the residue was subjected to silica gel column chromatography, and the fraction eluted with ethyl acetate-hexane (35:65) was concentrated under reduced pressure to give the object compound (3.04 g) as an oil.

$^1$H-NMR (CDCl$_3$) δ 0.79-1.15 (8H, m), 1.16-1.36 (1H, m), 1.36-1.56 (11H, m), 1.58-1.80 (2H, m), 1.80-2.00 (1H, m), 2.35-2.60 (3H, m), 2.74-2.99 (1H, m), 3.68-3.91 (1H, m).

MS (ESI+, m/e) 257 (M+1)

By a method similar to that of Reference Example 61, the following compounds (Reference Examples 62 and 63) were obtained.

Reference Example 62 tert-butyl (3R)-3-[(2-methylpropyl)amino]piperidine-1-carboxylate

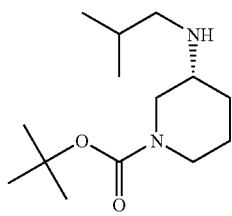

$^1$H-NMR (CDCl$_3$) δ 0.79-1.15 (8H, m), 1.16-1.36 (1H, m), 1.36-1.56 (11H, m), 1.58-1.80 (2H, m), 1.80-2.00 (1H, m), 2.35-2.60 (3H, m), 2.74-2.99 (1H, m), 3.68-3.91 (1H, m).

Reference Example 63 tert-butyl 3-[(2-methylpropyl)amino]pyrrolidine-1-carboxylate

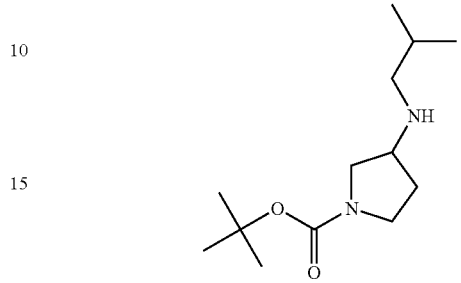

$^1$H-NMR (CDCl$_3$) δ 0.77-1.15 (8H, m), 1.16-1.37 (1H, m), 1.36-1.56 (9H, m), 1.61-1.81 (2H, m), 1.83-2.02 (1H, m), 2.34-2.59 (3H, m), 2.76-3.00 (1H, m), 3.70-3.95 (1H, m).

Reference Example 64 tert-butyl 3-(propylamino)piperidine-1-carboxylate

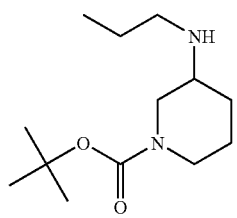

tert-Butyl 3-piperidone-1-carboxylate (1.99 g), propylamine (0.82 ml) and acetic acid (0.57 ml) were dissolved in methanol (50 ml), and the mixture was stirred at room temperature for 1 hr. To the reaction mixture was added sodium triacetoxyborohydride (4.23 g) and the mixture was stirred at room temperature for 15 hr. The reaction mixture was basified with aqueous sodium hydrogen carbonate, and the mixture was extracted with ethyl acetate. The extract was washed with saturated brine, and dried over anhydrous sodium sulfate. The solvent was evaporated under reduced pressure. The residue was dissolved in THF (20 ml), 2 M aqueous sodium hydroxide solution (3 ml) was added, Z-chloride (2.86 ml) was added dropwise, and the mixture was stirred at room temperature for 15 hr. To the reaction mixture was added ethyl acetate, and the organic layer was separated, washed with water and saturated brine, and dried over anhydrous sodium sulfate. The solvent was evaporated under reduced pressure. The residue was subjected to silica gel column chromatography, the fraction eluted with ethyl acetate-hexane (1:9-1:4) was concentrated under reduced pressure and the obtained residue was dissolved in ethanol (30 ml). 10% Palladium carbon (50% containing water, 0.20 g) was added, and the mixture was stirred under a hydrogen atmosphere (1 atm) at room temperature for 16 hr. The palladium catalyst was filtered off, and the filtrate was concentrated under reduced pressure to give the object compound (2.42 g) as an oil.

¹H-NMR (CDCl₃) δ 0.92 (3H, t), 1.26 (1H, dd), 1.37-1.58 (2H, m), 1.46 (9H, s), 1.67 (1H, td), 1.78 (1H, br s), 1.91 (1H, dd), 2.44-2.76 (4H, m), 2.87 (1H, br s), 3.79 (2H, d).

By a method similar to that of Reference Example 64, the following compounds (Reference Examples 65 to 67) were obtained.

Reference Example 65 tert-butyl 3-(cyclopropylmethylamino)piperidine-1-carboxylate

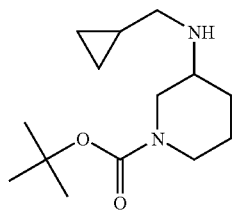

¹H-NMR (CDCl₃) δ 0.06-0.17 (2H, m), 0.41-0.54 (2H, m), 0.94 (1H, dddd), 1.28 (1H, dd), 1.46 (9H, s), 1.60-1.77 (3H, m), 1.91 (1H, dd), 2.45-2.78 (3H, m), 2.77-3.08 (1H, m), 3.78 (1H, dt), 4.00 (1H, br s).

Reference Example 66 tert-butyl 3-[(2-methylpropyl)amino]piperidine-1-carboxylate

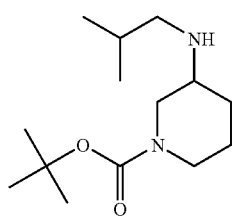

¹H-NMR (CDCl₃) δ 0.90 (6H, d), 1.22-1.40 (3H, m), 1.46 (9H, s), 1.55-1.78 (2H, m), 1.90 (1H, d), 2.45 (3H, dd), 2.87 (1H, br s), 3.54-4.24 (2H, m).

Reference Example 67 tert-butyl 3-(butylamino)piperidine-1-carboxylate


¹H-NMR (CDCl₃) δ 0.91 (3H, t), 1.20-1.42 (4H, m), 1.42-1.52 (3H, m), 1.46 (9H, s), 1.67 (1H, td), 1.78-2.04 (1H, m), 2.47-2.79 (3H, m), 2.87 (1H, br s), 3.79 (1H, d), 4.04 (1H, br s).

By a method similar to that of Example 1, the following compounds (Reference Examples 68 and 69) were obtained.

Reference Example 68 tert-butyl 3-[({2-tert-butyl-4-[(furan-2-ylmethyl)amino]pyrimidin-5-yl}carbonyl)(propyl)amino]piperidine-1-carboxylate

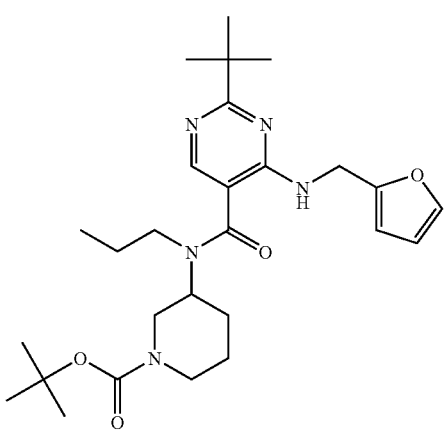

MS (ESI+, m/e) 500 (M+1)

Reference Example 69 tert-butyl 3-[({2-tert-butyl-4-[(furan-2-ylmethyl)amino]pyrimidin-5-yl}carbonyl)(cyclopropylmethyl)amino]piperidine-1-carboxylate

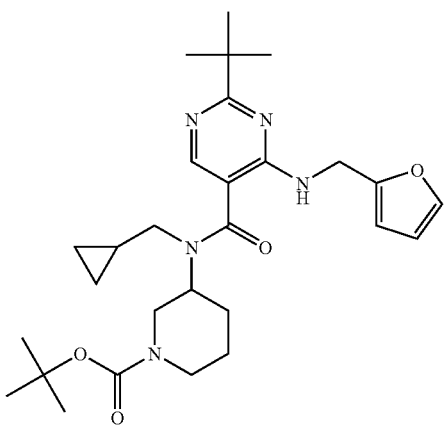

MS (ESI+, m/e) 512 (M+1)

By a method similar to that of Reference Example 37, the following compounds (Reference Examples 70 to 74) were obtained.

Reference Example 70 tert-butyl 3-[({2-tert-butyl-4-[(furan-2-ylmethyl)amino]pyrimidin-5-yl}carbonyl)(2-methylpropyl)amino]piperidine-1-carboxylate

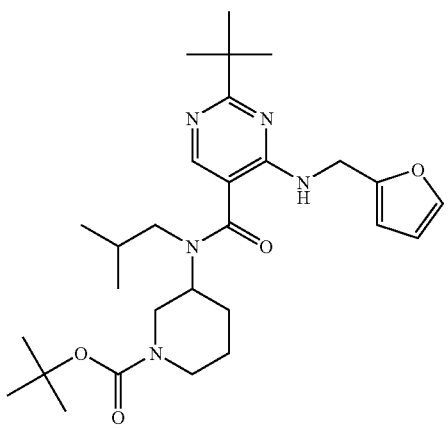

MS (ESI+, m/e) 514 (M+1)

Reference Example 71 tert-butyl 3-[butyl({2-tert-butyl-4-[(furan-2-ylmethyl)amino]pyrimidin-5-yl}carbonyl)amino]piperidine-1-carboxylate

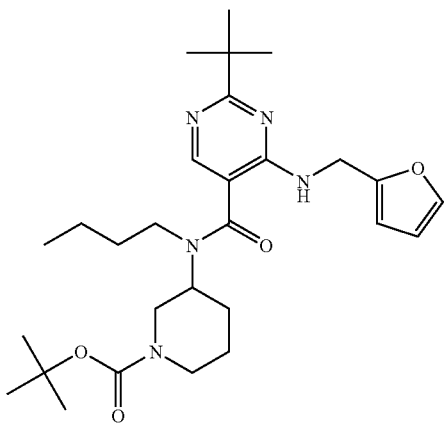

MS (ESI+, m/e) 514 (M+1)

Reference Example 72 tert-butyl (3R)-3-[({2-tert-butyl-4-[(furan-2-ylmethyl)amino]pyrimidin-5-yl}carbonyl)(2-methylpropyl)amino]piperidine-1-carboxyate

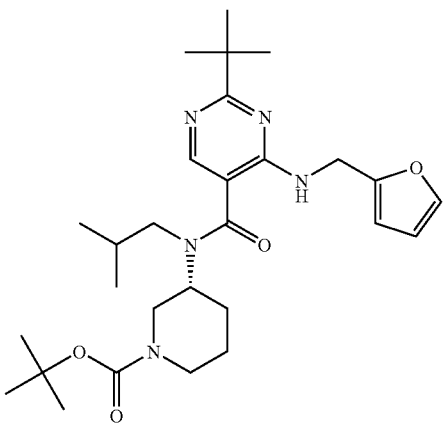

MS (ESI+, m/e) 514 (M+1)

Reference Example 73 tert-butyl (3S)-3-[({2-tert-butyl-4-[(furan-2-ylmethyl)amino]pyrimidin-5-yl}carbonyl)(2-methylpropyl)amino]piperidine-1-carboxylate

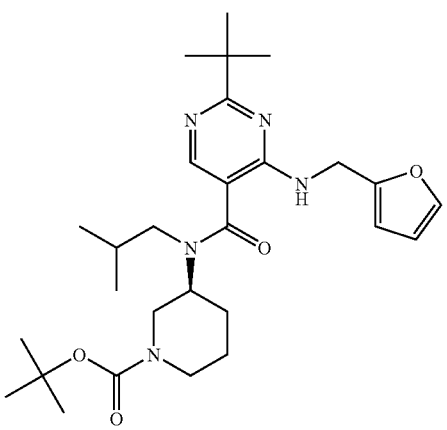

MS (ESI+, m/e) 514 (M+1)

Reference Example 74 tert-butyl 3-[({2-tert-butyl-4-[(furan-2-ylmethyl)amino]pyrimidin-5-yl}carbonyl)(2-methylpropyl)amino]pyrrolidine-1-carboxylate

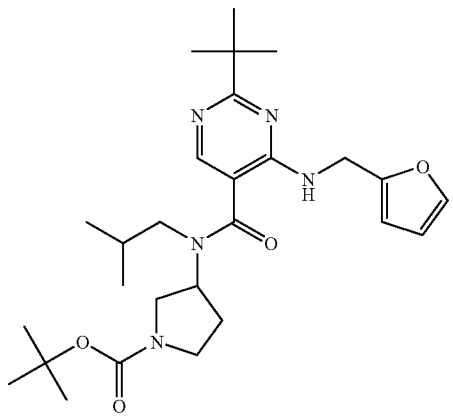

MS (ESI+, m/e) 500 (M+1)

Reference Example 75

1-tert-butyl 3-methyl (3R,5S)-5-[({2-tert-butyl-4-[(1,3-oxazol-2-ylmethyl)amino]pyrimidin-5-yl}carbonyl)(2-methylpropyl)amino]piperidine-1,3-dicarboxylate

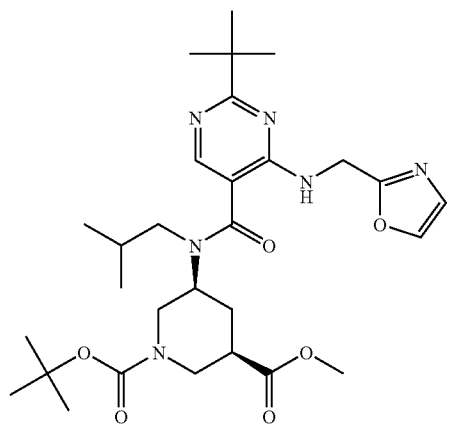

To a solution of 1-tert-butyl 3-methyl (3R,5S)-5-{[(2-tert-butyl-4-chloropyrimidin-5-yl)carbonyl](isobutyl)amino}piperidine-1,3-dicarboxylate (0.55 g) and diisopropylethylamine (0.87 ml) in 2-propanol (5 ml) was added 2-oxazolylmethylamine hydrochloride (0.34 g), and the mixture was stirred at 80° C. for 15 hr. The reaction mixture was concentrated under reduced pressure, saturated aqueous sodium hydrogen carbonate was added, and the mixture was extracted with ethyl acetate. The extract was dried over anhydrous sodium sulfate and concentrated under reduced pressure. The obtained residue was subjected to silica gel chromatography, and the fraction eluted with hexane to ethyl acetate-hexane (1:2) was concentrated under reduced pressure to give the object compound (525 mg).

MS (ESI+, m/e) 573 (M+1)

Reference Example 76

(3R,5S)-1-(tert-butoxycarbonyl)-5-[({2-tert-butyl-4-[(1,3-oxazol-2-ylmethyl)amino]pyrimidin-5-yl}carbonyl)(2-methylpropyl)amino]piperidine-3-carboxylic acid

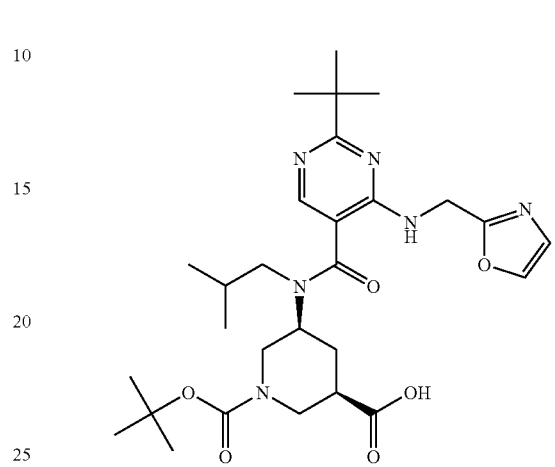

1-tert-Butyl 3-methyl (3R,5S)-5-[({2-tert-butyl-4-[(1,3-oxazol-2-ylmethyl)amino]pyrimidin-5-yl}carbonyl) (2-methylpropyl)amino]piperidine-1,3-dicarboxylate (0.26 g) was dissolved in methanol (3 ml), 2 M aqueous sodium hydroxide solution (1.0 ml) was added and the mixture was stirred at room temperature for 2 hr. The reaction mixture was concentrated under reduced pressure, the residue was diluted with saturated aqueous ammonium chloride solution, and the mixture was extracted with ethyl acetate. The extract was dried over anhydrous sodium sulfate and concentrated under reduced pressure to give the object compound (0.25 g).

MS (ESI+, m/e) 559 (M+1)

Reference Example 77 tert-butyl (3S,5R)-3-[({2-tert-butyl-4-[(1,3-oxazol-2-ylmethyl)amino]pyrimidin-5-yl}carbonyl)(2-methylpropyl)amino]-5-(morpholin-4-ylcarbonyl)piperidine-1-carboxylate

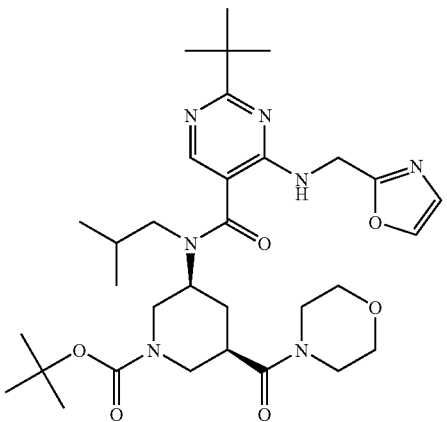

(3R,5S)-1-(tert-Butoxycarbonyl)-5-[({2-tert-butyl-4-[(1,3-oxazol-2-ylmethyl)amino]pyrimidin-5-yl}carbonyl)(2-methylpropyl)amino]piperidine-3-carboxylic acid (125 mg), HOBt (52 mg) and WSC.HCl (64 mg) were dissolved in acetonitrile (3 ml), morpholine (20 μl) and triethylamine (94 μl) were added and the mixture was stirred at room temperature for 15 hr. The reaction mixture was diluted with saturated aqueous sodium hydrogen carbonate, and the mixture was extracted with ethyl acetate. The extract was washed with saturated brine, and dried over anhydrous sodium sulfate. The solvent was evaporated under reduced pressure and the residue was purified by silica gel column chromatography. The fraction eluted with ethyl acetate-hexane (1:9) to ethyl acetate was concentrated under reduced pressure to give the object compound (110 mg).

MS (ESI+, m/e) 628 (M+1)

By a method similar to that of Reference Example 75, the following compound (Reference Example 78) was obtained.

Reference Example 78

1-tert-butyl 3-methyl (3R,5S)-5-[({[4-(benzylamino)-2-tert-butylpyrimidin-5-yl]carbonyl}(2-methylpropyl)amino]piperidine-1,3-dicarboxylate

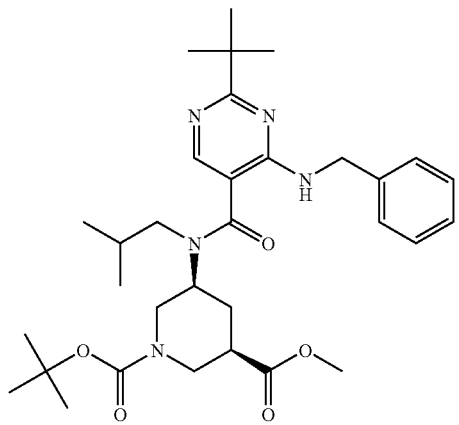

MS (ESI+, m/e) 582 (M+1)

By a method similar to that of Reference Example 76, the following compound (Reference Example 79) was obtained.

Reference Example 79

(3R,5S)-5-[{[4-(benzylamino)-2-tert-butylpyrimidin-5-yl]carbonyl}(2-methylpropyl)amino]-1-(tert-butoxycarbonyl)piperidine-3-carboxylic acid

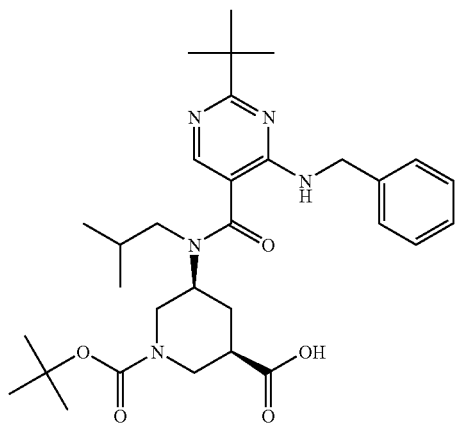

MS (ESI+, m/e) 568 (M+1)

By a method similar to that of Reference Example 77, the following compound (Reference Example 80) was obtained.

Reference Example 80 tert-butyl (3S,5R)-3-[{[4-(benzylamino)-2-tert-butylpyrimidin-5-yl]carbonyl}(2-methylpropyl)amino]-5-(morpholin-4-ylcarbonyl)piperidine-1-carboxylate

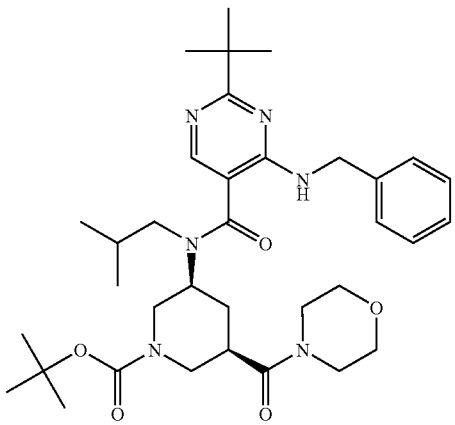

MS (ESI+, m/e) 637 (M+1)

By a method similar to that of the above-mentioned Example 93 (Method G) and Example 94 (Method H), the compounds of Examples 100 to 107 below were obtained. The respective compounds were isolated and purified as necessary by a known means such as phase transfer, pH conversion, solvent extraction, silica gel column chromatography, reversed-phase preparative HPLC and the like. The final products were isolated as hydrochloride as in Method G and Method H by treating with a hydrogen chloride-ethyl acetate solution.

Example 100

2-tert-butyl-4-[(furan-2-ylmethyl)amino]-N-piperidin-3-yl-N-propylpyrimidine-5-carboxamide dihydrochloride

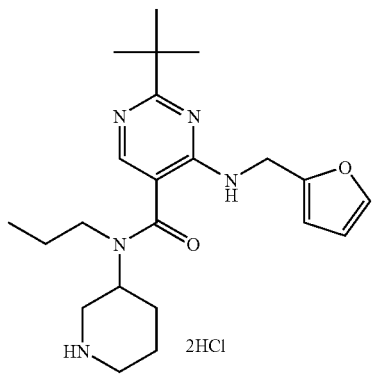

MS (ESI+, m/e) 473 (M+1)

Example 101

2-tert-butyl-N-(cyclopropylmethyl)-4-[(furan-2-ylmethyl)amino]-N-piperidin-3-ylpyrimidine-5-carboxamide dihydrochloride

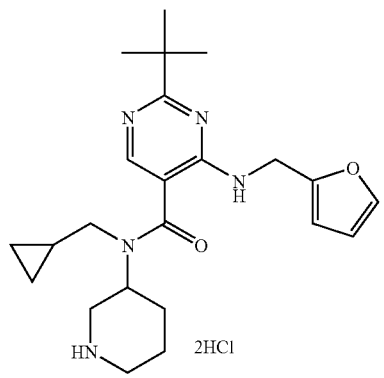

MS (ESI+, m/e) 485 (M+1)

Example 102

2-tert-butyl-4-[(furan-2-ylmethyl)amino]-N-(2-methylpropyl)-N-piperidin-3-ylpyrimidine-5-carboxamide dihydrochloride

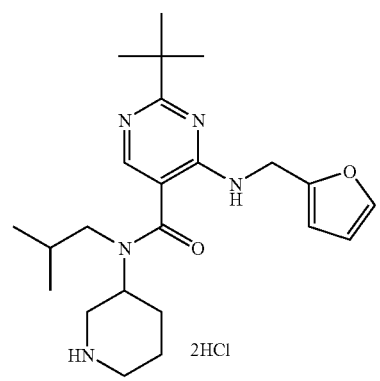

MS (ESI+, m/e) 487 (M+1)

Example 103

N-butyl-2-tert-butyl-4-[(furan-2-ylmethyl)amino]-N-piperidin-3-ylpyrimidine-5-carboxamide dihydrochloride

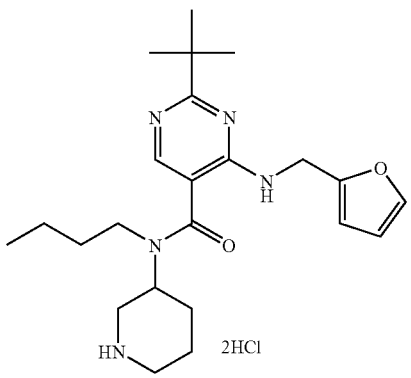

MS (ESI+, m/e) 487 (M+1)

Example 104

2-tert-butyl-4-[(furan-2-ylmethyl)amino]-N-(2-methylpropyl)-N-[(3R)-piperidin-3-yl]pyrimidine-5-carboxamide dihydrochloride

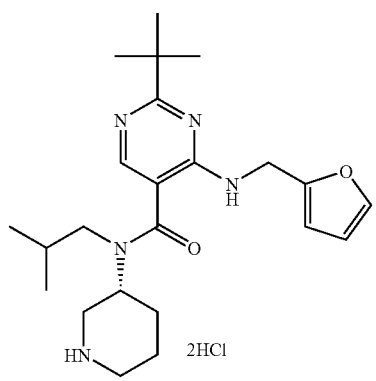

MS (ESI+, m/e) 487 (M+1)

Example 105

2-tert-butyl-4-[(furan-2-ylmethyl)amino]-N-(2-methylpropyl)-N-[(3S)-piperidin-3-yl]pyrimidine-5-carboxamide dihydrochloride

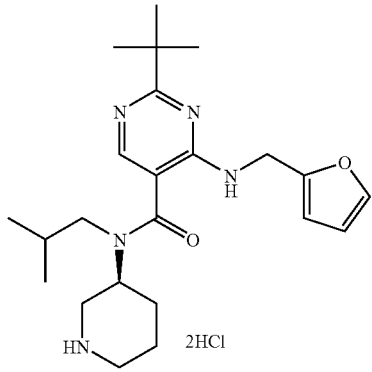

MS (ESI+, m/e) 487 (M+1)

Example 106

2-tert-butyl-4-[(furan-2-ylmethyl)amino]-N-(2-methylpropyl)-N-pyrrolidin-3-ylpyrimidine-5-carboxamide dihydrochloride

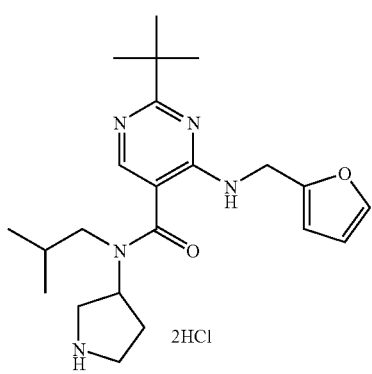

MS (ESI+, m/e) 473 (M+1)

Example 107

4-(benzylamino)-2-tert-butyl-N-(2-methylpropyl)-N-[(3S,5R)-5-(morpholin-4-ylcarbonyl)piperidin-3-yl]pyrimidine-5-carboxamide dihydrochloride

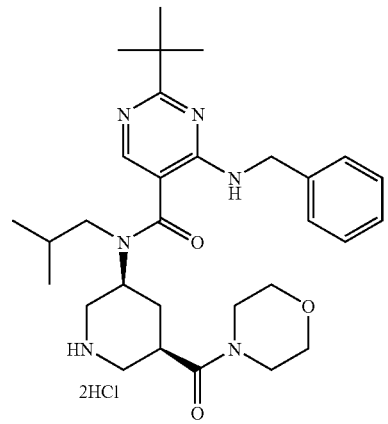

MS (ESI+, m/e) 610 (M+1)

Example 108

2-tert-butyl-N-(2-methylpropyl)-N-[(3S,5R)-5-(morpholin-4-ylcarbonyl)piperidin-3-yl]-4-[(1,3-oxazol-2-ylmethyl)amino]pyrimidine-5-carboxamide dihydrochloride

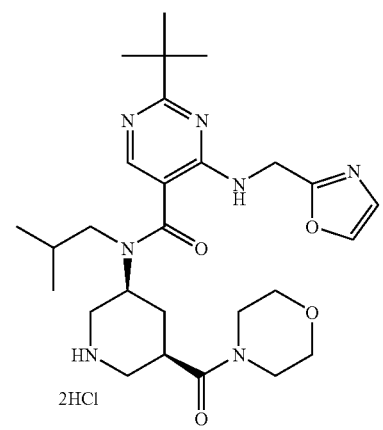

tert-Butyl (3S,5R)-3-[({2-tert-butyl-4-[(1,3-oxazol-2-ylmethyl)amino]pyrimidin-5-yl}carbonyl)(2-methylpropyl)amino]-5-(morpholin-4-ylcarbonyl)piperidine-1-carboxylate (108 mg) was dissolved in 2 M hydrogen chloride-ethyl acetate (2 ml), and the mixture was stirred at room temperature for 16 hr. The reaction mixture was concentrated, ethyl acetate was added and the precipitate was collected by filtration and washed with ethyl acetate to give the object compound (85 mg).

MS (ESI+, m/e) 528 (M+1)

Example 109

2-tert-butyl-N-(2-methylpropyl)-N-[(3S,5R)-5-(morpholin-4-ylcarbonyl)piperidin-3-yl]-4-[(1,3-oxazol-2-ylmethyl)amino]pyrimidine-5-carboxamide sulfate

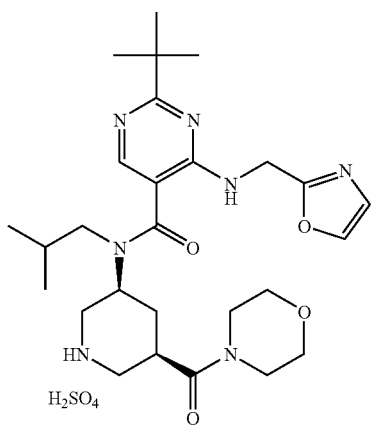

tert-Butyl (3S,5R)-3-[({2-tert-butyl-4-[(1,3-oxazol-2-ylmethyl)amino]pyrimidin-5-yl}carbonyl)(2-methylpropyl)amino]-5-(morpholin-4-ylcarbonyl)piperidine-1-carboxylate (108 mg) was dissolved in 2 M hydrogen chloride-ethyl acetate (2 ml), and the mixture was stirred at room temperature for 16 hr. The reaction mixture was basified with saturated sodium hydrogen carbonate solution, and the mixture was extracted with ethyl acetate. The extract was dried over sodium sulfate and concentrated under reduced pressure. The residue was dissolved in ethanol (3 ml), concentrated sulfuric acid (10 μl) was added and the mixture was concentrated under reduced pressure. Ethyl acetate (5 ml) and ethanol (0.1 ml) were added to the residue and the mixture was heated to 90° C. Ethanol was added and a homogeneous solution was cooled to room temperature. The precipitate was collected by filtration to give the object compound (40 mg).

MS (ESI+, m/e) 528 (M+1)

Reference Example 81 sodium 2-oxocyclohexylidenemethanolate

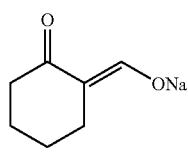

Cyclohexanone (30 ml) and ethyl formate (24 ml) were dissolved in diethyl ether (150 ml), sodium ethoxide (21 g) was added under ice-cooling, and the reaction mixture was stirred at room temperature for 10 hr. Insoluble material was collected by filtration, and washed with diethyl ether to give the object compound (49.2 g) as a solid.

$^1$H-NMR (D$_2$O) δ 1.47-1.61 (4H, m), 2.06-2.16 (2H, m), 2.10 (2H, d), 8.98 (1H, s).

By a method similar to that of Reference Example 81, the following compound (Reference Example 82) was obtained.

Reference Example 82 sodium 3,3-dimethyl-2-oxocyclopentylidenemethanolate

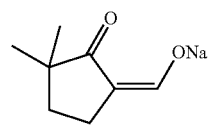

$^1$H-NMR (D$_2$O) δ 0.91 (6H, s), 1.58 (2H, t), 2.25 (2H, t), 8.63 (1H, s).

Reference Example 83

8a-hydroxy-2-oxo-1,2,3,5,6,7,8,8a-octahydroquinoline-3-carbonitrile

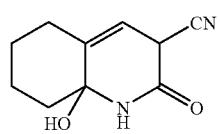

Sodium 2-oxocyclohexylidenemethanolate (15 g), 2-cyanoacetamide (4.3 g) and piperidine (1.0 ml) were suspended in water (35 ml), and the mixture was stirred at 40° C. for 4 days. Insoluble material was filtered off, and the filtrate was concentrated under reduced pressure. The residue was suspended in methanol, and insoluble material was filtered off. The filtrate was concentrated under reduced pressure to give the object compound (21.4 g).

MS (ESI+, m/e) 193 (M+1)

By a method similar to that of Reference Example 83, the following compound (Reference Example 84) was obtained.

Reference Example 84

7a-hydroxy-7,7-dimethyl-2-oxo-2,3,5,6,7,7a-hexahydro-1H-cyclopenta[b]pyridine-3-carbonitrile

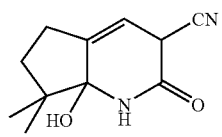

MS (ESI+, m/e) 207 (M+1)

Reference Example 85

2-hydroxy-5,6,7,8-tetrahydroquinoline-3-carboxylic acid

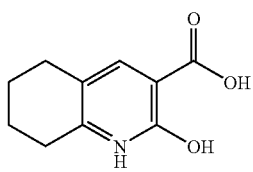

8a-Hydroxy-2-oxo-1,2,3,5,6,7,8,8a-octahydroquinoline-3-carbonitrile (20.5 g) was suspended in concentrated hydrochloric acid (100 ml), and the mixture was stirred with heating to reflux for 12 hr. The reaction mixture was cooled to room temperature, and insoluble material was filtered off. The filtrate was applied to DIAION (registered trademark) HP-20 (manufactured by Mitsubishi Chemical Corporation), and washed with water and the fraction eluted with acetone was concentrated under reduced pressure to give the object compound (11.5 g).

MS (ESI+, m/e) 222 (M+1)

By a method similar to that of Reference Example 85, the following compound (Reference Example 86) was obtained.

Reference Example 86

2-hydroxy-7,7-dimethyl-6,7-dihydro-5H-cyclopenta[b]pyridine-3-carboxylic acid

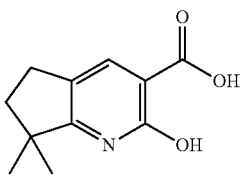

MS (ESI+, m/e) 208 (M+1)

Reference Example 87 ethyl 2-hydroxy-5,6,7,8-tetrahydroquinoline-3-carboxylate

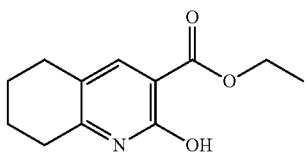

2-Hydroxy-7,7-dimethyl-6,7-dihydro-5H-cyclopenta[b]pyridine-3-carboxylic acid (11.0 g) was dissolved in ethanol (100 ml), sulfuric acid (3.4 ml) was added and the mixture was stirred with heating to reflux for 12 hr. The reaction mixture was concentrated under reduced pressure to a half volume, the residue was basified with 8 M aqueous sodium hydroxide solution, and the mixture was extracted with ethyl acetate. The extract was washed successively with 1 M aqueous sodium hydroxide solution and saturated brine, and dried over anhydrous magnesium sulfate. The solvent was evaporated under reduced pressure. The residue was subjected to silica gel column chromatography, and the fraction eluted with ethyl acetate-hexane (50:50-85:15) was concentrated under reduced pressure to give the object compound (3.45 g).

$^1$H-NMR (CDCl$_3$) δ 1.38 (3H, t), 1.79 (4H, dd), 2.55 (2H, t), 2.77 (2H, t), 4.36 (2H, q), 7.99 (1H, s).

By a method similar to that of Reference Example 87, the following compound (Reference Example 88) was obtained.

Reference Example 88 ethyl 2-hydroxy-7,7-dimethyl-6,7-dihydro-5H-cyclopenta[b]pyridine-3-carboxylate

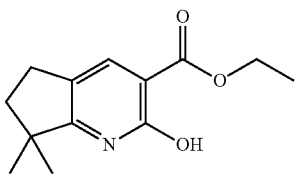

$^1$H-NMR (CDCl$_3$) δ 1.30 (6H, s), 1.40 (3H, t), 1.98 (2H, t), 2.78 (1H, t), 4.12 (1H, d), 4.40 (2H, q), 8.01 (1H, s).

MS (ESI+, m/e) 236 (M+1)

Reference Example 89 ethyl 2-chloro-5,6,7,8-tetrahydroquinoline-3-carboxylate

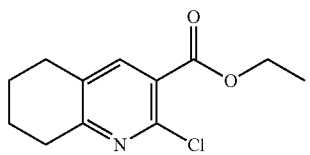

Ethyl 2-hydroxy-5,6,7,8-tetrahydroquinoline-3-carboxylate (3.40 g) was dissolved in phosphorus oxychloride (30 ml), and the mixture was stirred with heating to reflux for 10 hr. The reaction mixture was concentrated under reduced pressure, saturated aqueous sodium hydrogen carbonate solution was added to the residue, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane (50:50-100:0) was concentrated under reduced pressure to give the object compound (3.68 g).

MS (ESI+, m/e) 240 (M+1)

By a method similar to that of Reference Example 89, the following compound (Reference Example 90) was obtained.

Reference Example 90 ethyl 2-chloro-7,7-dimethyl-6,7-dihydro-5H-cyclopenta[b]pyridine-3-carboxylate

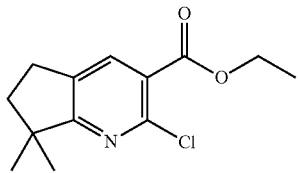

MS (ESI+, m/e) 254 (M+1)

Reference Example 91 ethyl 2-[(furan-2-ylmethyl)amino]-5,6,7,8-tetrahydroquinoline-3-carboxylate

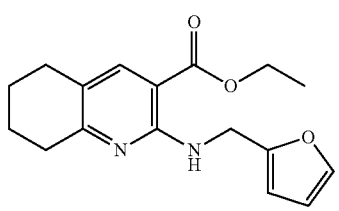

A mixture of ethyl 2-chloro-5,6,7,8-tetrahydroquinoline-3-carboxylate (500 mg) and furfurylamine (3.0, ml) was stirred in a sealed tube at 130° C. for 12 hr. The reaction mixture was subjected to silica gel column chromatography, and the fraction eluted with ethyl acetate-hexane (10:90-50:50) was concentrated under reduced pressure to give the object compound (683 mg).

MS (ESI+, m/e) 301 (M+1)

By a method similar to that of Reference Example 91, the following compound (Reference Example 92) was obtained.

Reference Example 92 ethyl 2-[(furan-2-ylmethyl)amino]-7,7-dimethyl-6,7-dihydro-5H-cyclopenta[b]pyridine-3-carboxylate

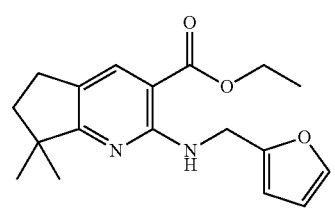

MS (ESI+, m/e) 315 (M+1)

Reference Example 93

2-[(furan-2-ylmethyl)amino]-5,6,7,8-tetrahydroquinoline-3-carboxyli acid

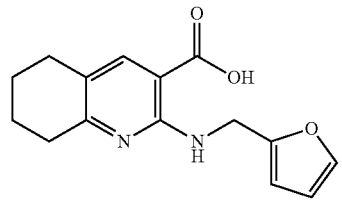

To a solution of ethyl 2-[(furan-2-ylmethyl)amino]-5,6,7,8-tetrahydroquinoline-3-carboxylate (600 mg) in ethanol (4 ml)-water (4 ml) was added 8 M aqueous sodium hydroxide solution (1.25 ml), and the mixture was stirred at 80° C. for 10 hr. The reaction mixture was concentrated under reduced pressure to about 1/3 volume, and neutralized with 1 M hydrochloric acid, and the mixture was extracted with ethyl acetate. The extract was washed with saturated brine and dried over anhydrous magnesium sulfate. The solvent was evaporated under reduced pressure to give the object compound (522 mg).

MS (ESI+, m/e) 273 (M+1)

By a method similar to that of Reference Example 93, the following compound (Reference Example 94) was obtained.

Reference Example 94

2-[(furan-2-ylmethyl)amino]-7,7-dimethyl-6,7-dihydro-5H-cyclopenta[b]pyridine-3-carboxylic acid

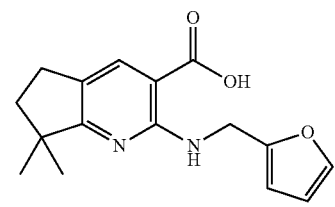

MS (ESI+, m/e) 287 (M+1)

Reference Example 95 tert-butyl 3-[({2-[(furan-2-ylmethyl)amino]-5,6,7,8-tetrahydroquinolin-3-yl}carbonyl)(2-methylpropyl)amino]piperidine-1-carboxylate

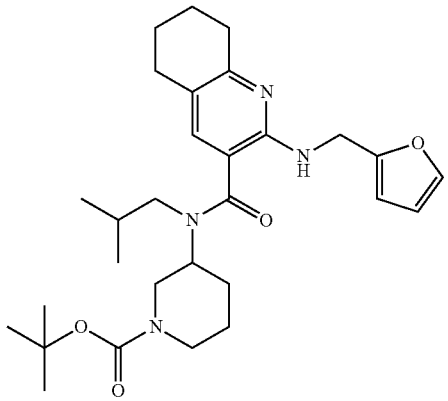

2-[(Furan-2-ylmethyl)amino]-5,6,7,8-tetrahydroquinoline-3-carboxylic acid (520 mg) was suspended in toluene (5 ml), thionyl chloride (0.42 ml) and DMF (5 drops) were added and the mixture was stirred at 80° C. for 30 min. The reaction mixture was cooled to room temperature, and concentrated under reduced pressure, and the residue was subjected to azeotropic distillation with toluene. The obtained residue was suspended in THF (5 ml), a solution of tert-butyl 3-[(2-methylpropyl)amino]piperidine-1-carboxylate (490 mg) and triethylamine (1.5 ml) in THF (2 ml) was added, and the mixture was stirred at room temperature for 12 hr. The reaction mixture was concentrated under reduced pressure, and diluted with 10% aqueous citric acid solution, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane (10:90-80:20) was concentrated under reduced pressure to give the object compound (29 mg).

MS (ESI+, m/e) 459 (M+1)

Reference Example 96 tert-butyl 3-[({2-[(furan-2-ylmethyl)amino]-7,7-dimethyl-6,7-dihydro-5H-cyclopenta[b]pyridin-3-yl}carbonyl)(2-methylpropyl)amino]piperidine-1-carboxylate

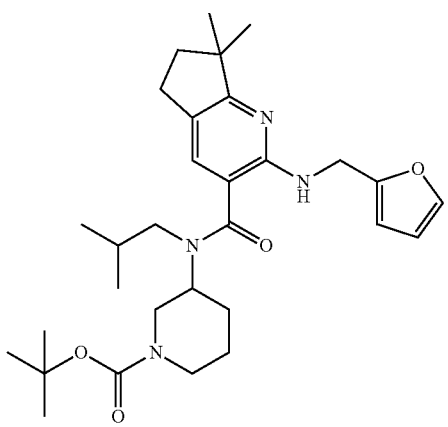

2-[(Furan-2-ylmethyl)amino]-7,7-dimethyl-6,7-dihydro-5H-cyclopenta[b]pyridine-3-carboxylic acid (390 mg), tert-butyl 3-[(2-methylpropyl)amino]piperidine-1-carboxylate (350 mg) and N,N-diisopropylethylamine (1.2 ml) were dissolved in 1,2-dichloroethane (10 ml), chloro-N,N,N',N'-tetramethylformamidinium hexafluorophosphate (540 mg) was added and the mixture was stirred at room temperature for 18 hr. The reaction mixture was diluted with saturated aqueous sodium hydrogen carbonate solution and the mixture was extracted with ethyl acetate. The extract was washed with saturated brine and dried over anhydrous magnesium sulfate. The solvent was evaporated under reduced pressure. The residue was subjected to silica gel column chromatography, and the fraction eluted with ethyl acetate-hexane (5:95-100:10) was concentrated under reduced pressure to give the object compound (123 mg).

MS (ESI+, m/e) 525 (M+1)

Reference Example 97

2-hydroxy-8,8-dimethyl-5,6,7,8-tetrahydroquinoline-3-carboxylic acid

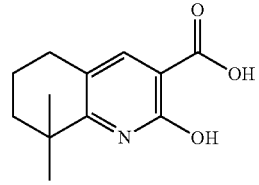

2,2-Dimethylcyclohexanone (3.0 g) and ethyl formate (24 ml) were dissolved in diethyl ether (20 ml), sodium ethoxide (1.75 g) was added under ice-cooling, and the reaction mixture was stirred at room temperature for 3 days, and concentrated under reduced pressure. The residue was dissolved in water (50 ml), 2-cyanoacetamide (1.80 g) and piperidine (0.20 ml) were added, and the mixture was stirred at 40° C. for 16 hr. Insoluble material was filtered off, and the filtrate was concentrated under reduced pressure. The residue was suspended in 4 M aqueous sodium hydroxide solution (100 ml), and the suspension was stirred at 90° C. for 14 hr. The reaction mixture was ice-cooled, neutralized with 6 M hydrochloric acid, and concentrated under reduced pressure. The residue was suspended in ethanol, insoluble material was filtered off, and the filtrate was concentrated under reduced pressure to give the object compound (2.47 g).

MS (ESI+, m/e) 222 (M+1)

By a method similar to that of Reference Example 97, the following compounds (Reference Examples 98 and 99) were obtained.

Reference Example 98

2-hydroxy-5,5,7-trimethyl-6,7-dihydro-5H-cyclopenta[b]pyridine-3-carboxylic acid

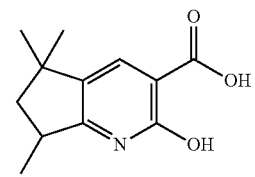

MS (ESI+, m/e) 222 (M+1)

Reference Example 99

2-hydroxy-6,7,8,9-tetrahydro-5H-cyclohepta[b]pyridine-3-carboxylic acid

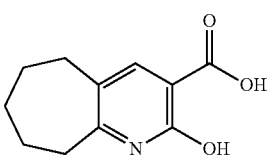

MS (ESI+, m/e) 208 (M+1)

By a method similar to that of Reference Example 87, the following compounds (Reference Examples 100 to 102) were obtained.

Reference Example 100 ethyl 2-hydroxy-8,8-dimethyl-5,6,7,8-tetrahydroquinoline-3-carboxylate

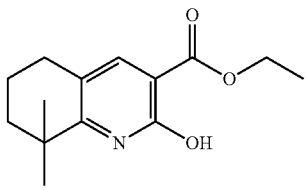

MS (ESI+, m/e) 250 (M+1)

Reference Example 101 ethyl 2-hydroxy-5,5,7-trimethyl-6,7-dihydro-5H-cyclopenta[b]pyridine-3-carboxylate

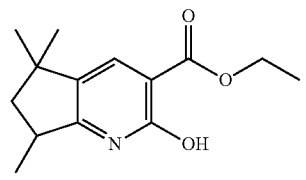

MS (ESI+, m/e) 250 (M+1)

Reference Example 102 ethyl 2-hydroxy-6,7,8,9-tetrahydro-5H-cyclohepta[b]pyridine-3-carboxylate

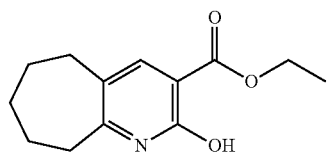

MS (ESI+, m/e) 236 (M+1)

By a method similar to that of Reference Example 89, the following compounds (Reference Examples 103 to 105) were obtained.

Reference Example 103 ethyl 2-chloro-8,8-dimethyl-5,6,7,8-tetrahydroquinoline-3-carboxylate

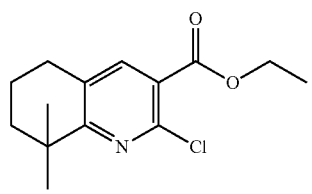

MS (ESI+, m/e) 268 (M+1)

Reference Example 104 ethyl 2-chloro-5,5,7-trimethyl-6,7-dihydro-5H-cyclopenta[b]pyridine-3-carboxylate

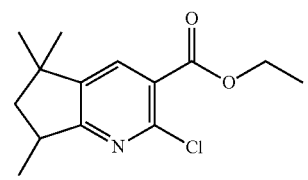

MS (ESI+, m/e) 268 (M+1)

Reference Example 105 ethyl 2-chloro-6,7,8,9-tetrahydro-5H-cyclohepta[b]pyridine-3-carboxylate

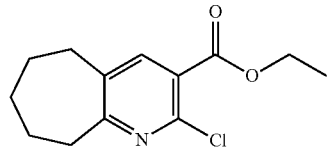

MS (ESI+, m/e) 254 (M+1)

By a method similar to that of Reference Example 91, the following compounds (Reference Examples 106 to 108) were obtained.

Reference Example 106 ethyl 2-[(furan-2-ylmethyl)amino]-8,8-dimethyl-5,6,7,8-tetrahydroquinoline-3-carboxylate

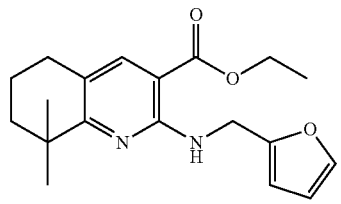

MS (ESI+, m/e) 329 (M+1)

Reference Example 107 ethyl 2-[(furan-2-ylmethyl)amino]-5,5,7-trimethyl-6,7-dihydro-5H-cyclopenta[b]pyridine-3-carboxylate

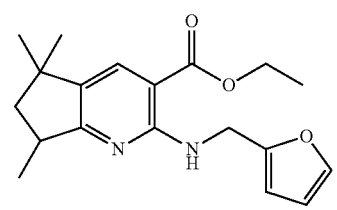

MS (ESI+, m/e) 329 (M+1)

Reference Example 108 ethyl 2-[(furan-2-ylmethyl)amino]-6,7,8,9-tetrahydro-5H-cyclohepta[b]pyridine-3-carboxylate

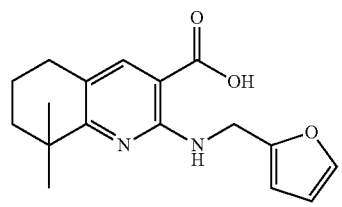

MS (ESI+, m/e) 315 (M+1)

By a method similar to that of Reference Example 93, the following compounds (Reference Examples 109 to 111) were obtained.

Reference Example 109

2-[(furan-2-ylmethyl)amino]-8,8-dimethyl-5,6,7,8-tetrahydroquinoline-3-carboxylic acid

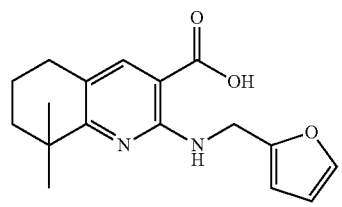

MS (ESI+, m/e) 301 (M+1)

Reference Example 110

2-[(furan-2-ylmethyl)amino]-5,5,7-trimethyl-6,7-dihydro-5H-cyclopenta[b]pyridine-3-carboxylic acid

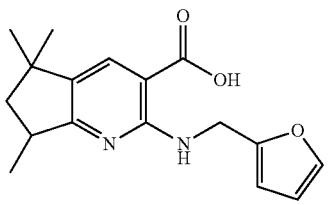

MS (ESI+, m/e) 301 (M+1)

Reference Example 111

2-[(furan-2-ylmethyl)amino]-6,7,8,9-tetrahydro-5H-cyclohepta[b]pyridine-3-carboxylic acid

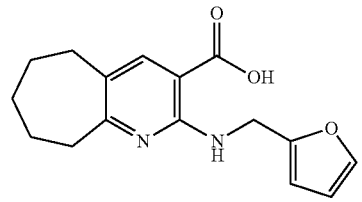

MS (ESI+, m/e) 287 (M+1)

By a method similar to that of Reference Example 96, the following compounds (Reference Examples 112 to 114) were obtained.

Reference Example 112 tert-butyl 3-[({2-[(furan-2-ylmethyl)amino]-8,8-dimethyl-5,6,7,8-tetrahydroquinolin-3-yl}carbonyl)(2-methylpropyl)amino]piperidine-1-carboxylate

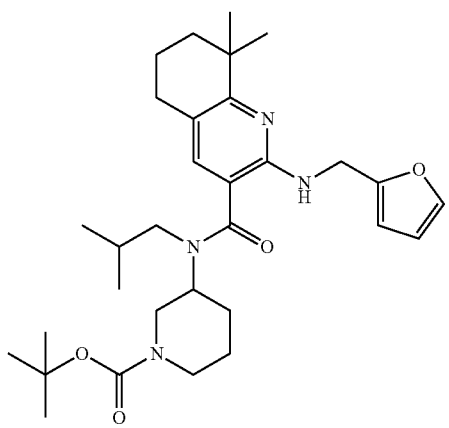

MS (ESI+, m/e) 539 (M+1)

Reference Example 113 tert-butyl 3-[({2-[(furan-2-ylmethyl)amino]-5,5,7-trimethyl-6,7-dihydro-5H-cyclopenta[b]pyridin-3-yl}carbonyl)(2-methylpropyl)amino]piperidine-1-carboxylate

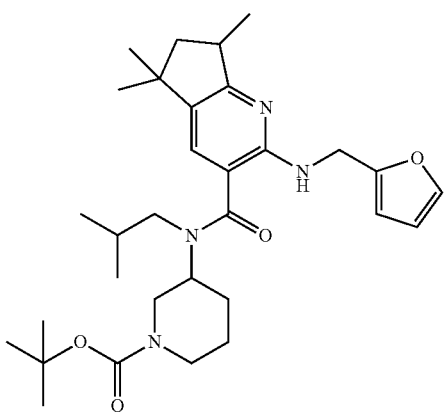

MS (ESI+, m/e) 539 (M+1)

Reference Example 114 tert-butyl 3-[({2-[(furan-2-ylmethyl)amino]-6,7,8,9-tetrahydro-5H-cyclohepta[b]pyridin-3-yl}carbonyl)(2-methylpropyl)amino]piperidine-1-carboxylate

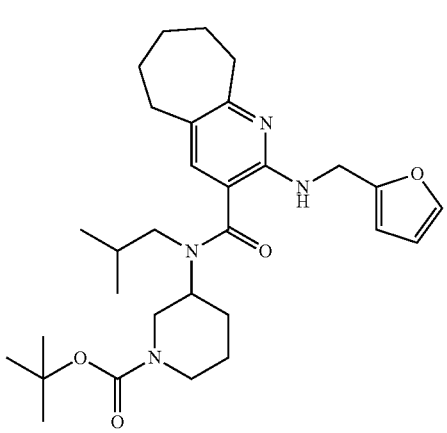

MS (ESI+, m/e) 525 (M+1)

Reference Example 115

1-tert-butyl 3-methyl 5-{[(benzyloxy)carbonyl](2-methylpropyl)amino}piperidine-1,3-dicarboxylate

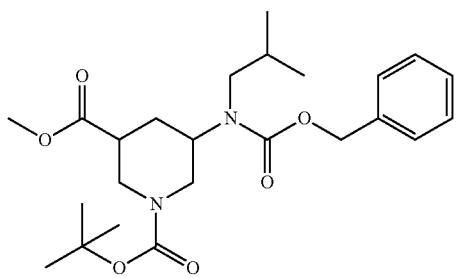

1-tert-Butyl 3-methyl 5-[(2-methylpropyl)amino]piperidine-1,3-dicarboxylate (13.7 g) was dissolved in ethyl acetate (250 ml)-1 M aqueous sodium hydroxide solution (55 ml)-water (200 ml), benzyl chlorocarbonate (7.5 ml) was added under ice-cooling, and the reaction mixture was stirred at room temperature for 3 days. The reaction mixture was diluted with water, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane (5:95-50:50) was concentrated under reduced pressure to give the object compound (9.87 g).

MS (ESI+, m/e) 449 (M+1)

Reference Example 116 tert-butyl 3-{[(benzyloxy)carbonyl](2-methylpropyl)amino}-5-(hydroxymethyl)piperidine-1-carboxylate

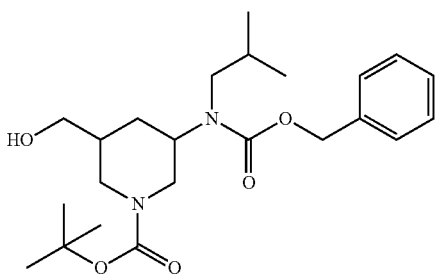

A solution of 1-tert-butyl 3-methyl 5-{[(benzyloxy)carbonyl](2-methylpropyl)amino}piperidine-1,3-dicarboxylate (13.0 g) in THF (100 ml) was added to a solution of calcium chloride (6.5 g) and sodium borohydride (4.5 g) in ethanol (100 ml) under ice-cooling, and the mixture was stirred at room temperature for 2 hr. The reaction mixture was adjusted to pH 4 with 10% aqueous citric acid solution, and concentrated under reduced pressure to a half volume. The residue was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane (5:95-80:20) was concentrated under reduced pressure to give the object compound (8.04 g).

MS (ESI+, m/e) 421 (M+1)

Reference Example 117 tert-butyl 3-[(acetyloxy)methyl]-5-{[(benzyloxy)carbonyl] (2-methylpropyl)amino}piperidine-1-carboxylate

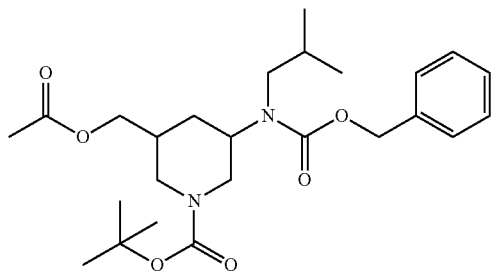

To a solution of tert-butyl 3-{[(benzyloxy)carbonyl](2-methylpropyl)amino}-5-(hydroxymethyl)piperidine-1-carboxylate (4.6 g) and triethylamine (2.3 ml) in ethyl acetate (25 ml) was added acetyl chloride (0.94 ml) under ice-cooling, and the mixture was stirred at room temperature for 5 hr. The reaction mixture was diluted with saturated aqueous sodium hydrogen carbonate solution, and the mixture was extracted with ethyl acetate. The extract was washed with saturated brine and dried over anhydrous magnesium sulfate, and the solvent was evaporated under reduced pressure to give the object compound (5.09 g).

MS (ESI+, m/e) 463 (M+1)

Reference Example 118 tert-butyl 3-[(acetyloxy)methyl]-5-[(2-methylpropyl)amino]piperidine-1-carboxylate

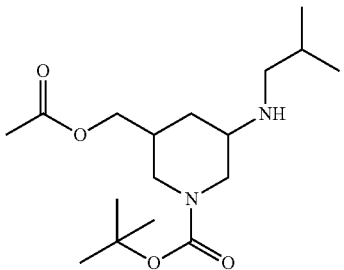

tert-Butyl 3-[(acetyloxy)methyl]-5-{[(benzyloxy)carbonyl](2-methylpropyl)amino}piperidine-1-carboxylate (5.0 g) and palladium(II) hydroxide-carbon (500 mg) were suspended in methanol (100 ml), and the mixture was stirred under a hydrogen atmosphere (1 atm) at room temperature for 8 hr. The palladium catalyst was filtered off, and the filtrate was concentrated under reduced pressure to give the object compound (3.50 g).

$^1$H-NMR (CDCl$_3$) δ 0.91 (6H, d), 1.46 (9H, s), 1.69 (4H, dd), 2.01-2.18 (4H, m), 2.25-2.42 (2H, m), 2.47 (1H, dd), 2.75 (1H, br s), 3.73 (1H, s), 3.86-4.02 (2H, m).

Reference Example 119 tert-butyl 3-[(acetyloxy)methyl]-5-[({2-tert-butyl-4-[(furan-2-ylmethyl)amino]pyrimidin-5-yl}carbonyl)(2-methylpropyl)amino]piperidine-1-carboxylate

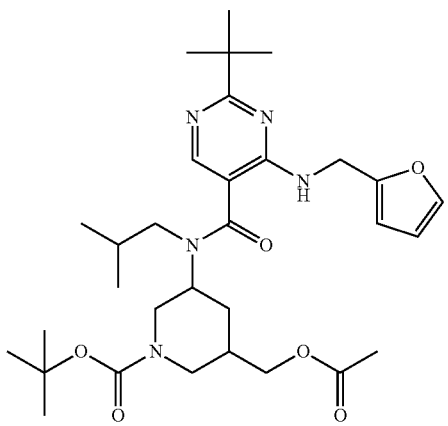

2-tert-Butyl-4-[(2-furylmethyl)amino]pyrimidine-5-carboxylic acid (1.00 g) was dissolved in toluene (20 ml), thionyl chloride (0.66 ml) and DMF (5 drops) were added and the mixture was stirred at 90° C. for 2 hr. The reaction mixture was cooled to room temperature, and concentrated under reduced pressure, and the residue was subjected to azeotropic distillation with toluene. The obtained residue was suspended in THF (10 ml), a solution of tert-butyl [(acetyloxy)methyl]-5-[(2-methylpropyl)amino]piperidine-1-carboxylate (1.00 g) and triethylamine (1.55 ml) in THF (10 ml)-1,2-dichloroethane (10 ml) was added and the mixture was stirred at room temperature for 3 hr. The reaction mixture was concentrated under reduced pressure, and diluted with water, and the mixture was extracted with ethyl acetate. The extract was washed successively with 1 M hydrochloric acid and saturated brine, and dried over anhydrous magnesium sulfate. The solvent was evaporated under reduced pressure. The residue was subjected to silica gel column chromatography, and the fraction eluted with ethyl acetate-hexane (5:95-70:30) was concentrated under reduced pressure to give the object compound (863 mg).

MS (ESI+, m/e) 586 (M+1)

Reference Example 120 tert-butyl 3-[({2-tert-butyl-4-[(furan-2-ylmethyl)amino]pyrimidin-5-yl}carbonyl)(2-methylpropyl)amino]-5-(hydroxymethyl)piperidine-1-carboxylate

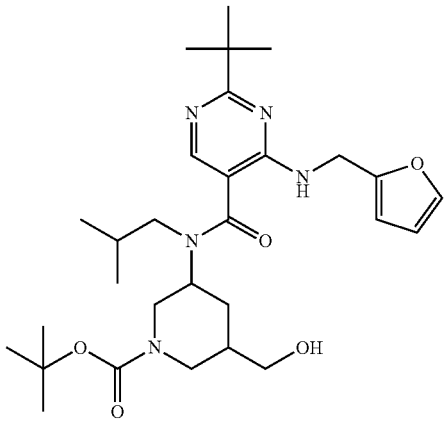

To a solution of tert-butyl 3-[(acetyloxy)methyl]-5-[({2-tert-butyl-4-[(furan-2-ylmethyl)amino]pyrimidin-5-yl}carbonyl)(2-methylpropyl)amino]piperidine-1-carboxylate (780 mg) in methanol (10 ml)-water (9 ml) was added 8 M aqueous sodium hydroxide solution (0.83 ml), and the mixture was stirred at 70° C. for 7 hr and extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane (5:95-100:0) was concentrated under reduced pressure to give the object compound (709 mg).

MS (ESI+, m/e) 544 (M+1)

Reference Example 121 tert-butyl 3-[({2-tert-butyl-4-[(furan-2-ylmethyl)amino]pyrimidin-5-yl}carbonyl)(2-methylpropyl)amino]-5-{[(methylsulfonyl)oxy]methyl}piperidine-1-carboxylate

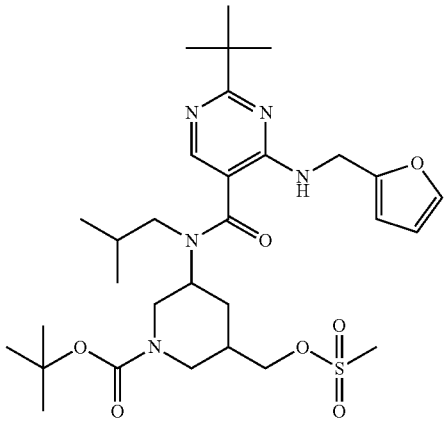

To a solution of tert-butyl 3-[({2-tert-butyl-4-[(furan-2-ylmethyl)amino]pyrimidin-5-yl}carbonyl)(2-methylpropyl)amino]-5-(hydroxymethyl)piperidine-1-carboxylate (570 mg) and triethylamine (0.25 ml) in THF (10 ml) was added methanesulfonyl chloride (0.1 ml) under ice-cooling, and the mixture was stirred at room temperature 1 hr. Triethylamine (0.25 ml) and methanesulfonyl chloride (0.1 ml) were further added, and the mixture was stirred at room temperature for 30 min. The reaction mixture was diluted with water, and the mixture was extracted with ethyl acetate. The extract was washed with saturated brine, and dried over anhydrous magnesium sulfate and the solvent was evaporated under reduced pressure to give the object compound (624 mg).

MS (ESI+, m/e) 622 (M+1)

Reference Example 122 tert-butyl 3-[({2-tert-butyl-4-[(furan-2-ylmethyl)amino]pyrimidin-5-yl}carbonyl)(2-methylpropyl)amino]-5-(1H-imidazol-1-ylmethyl)piperidine-1-carboxylate

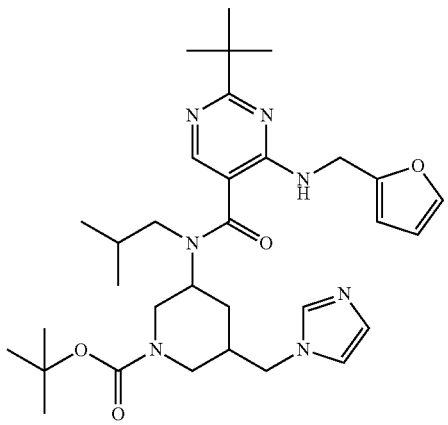

tert-Butyl 3-[({2-tert-butyl-4-[(furan-2-ylmethyl)amino]pyrimidin-5-yl}carbonyl)(2-methylpropyl)amino]-5-{[(methylsulfonyl)oxy]methyl}piperidine-1-carboxylate (100 mg) and imidazole (30 mg) were dissolved in N,N-dimethylacetamide (4 ml), cesium carbonate (130 mg) was added and the mixture was stirred at 60° C. for 1 day. The reaction mixture was diluted with saturated aqueous sodium hydrogen carbonate solution, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane (10:90-100:0) was concentrated under reduced pressure to give the object compound (43.1 mg).

MS (ESI+, m/e) 594 (M+1)

By a method similar to that of Reference Example 122, the following compounds (Reference Examples 123 and 124) were obtained.

Reference Example 123 tert-butyl 3-[({2-tert-butyl-4-[(furan-2-ylmethyl)amino]pyrimidin-5-yl}carbonyl)(2-methylpropyl)amino]-5-[(pyridin-2-yloxy)methyl]piperidine-1-carboxylate

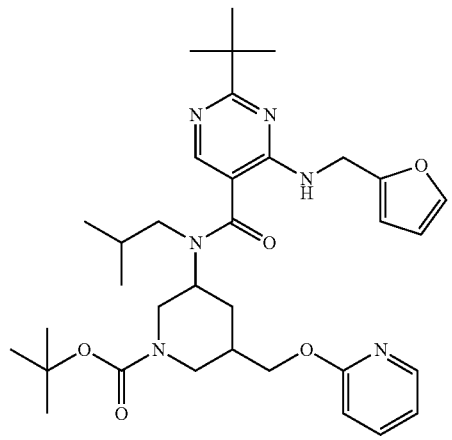

MS (ESI+, m/e) 621 (M+1)

Reference Example 124 tert-butyl 3-[({2-tert-butyl-4-[(furan-2-ylmethyl)amino]pyrimidin-5-yl}carbonyl)(2-methylpropyl)amino]-5-[(ethylsulfanyl)methyl]piperidine-1-carboxylate

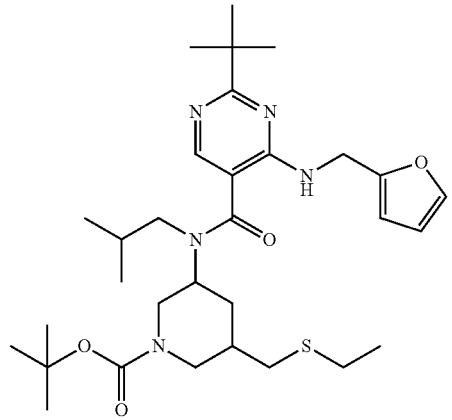

MS (ESI+, m/e) 588 (M+1)

Reference Example 125 tert-butyl (3S*,5R*)-3-[({2-tert-butyl-4-[(furan-2-ylmethyl)amino]pyrimidin-5-yl}carbonyl)(2-methylpropyl)amino]-5-[(ethylsulfonyl)methyl]piperidine-1-carboxylate and tert-butyl (3S*,5S*)-3-[({2-tert-butyl-4-[(furan-2-ylmethyl)amino]pyrimidin-5-yl}carbonyl)(2-methylpropyl)amino]-5-[(ethylsulfonyl)methyl]piperidine-1-carboxylate

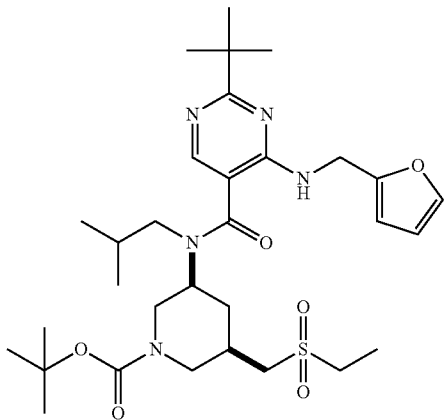

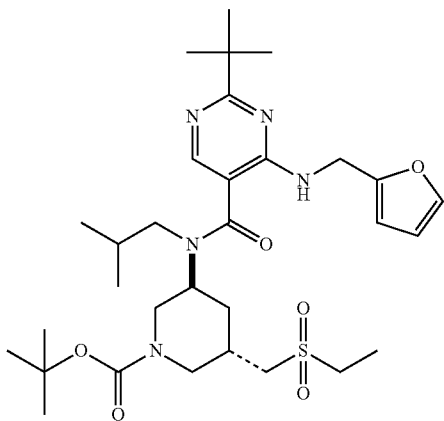

tert-Butyl 3-[({2-tert-butyl-4-[(furan-2-ylmethyl)amino]pyrimidin-5-yl}carbonyl)(2-methylpropyl)amino]-5-[(ethylsulfanyl)methyl]piperidine-1-carboxylate (110 mg) was dissolved in dichloromethane (3 ml), 3-chloroperbenzoic acid (65% contained, 125 mg) was added, and the mixture was stirred at room temperature for 2 hr. The reaction mixture was diluted with saturated aqueous sodium hydrogen carbonate solution, and the mixture was extracted with ethyl acetate. The extract was washed with saturated brine, and dried over anhydrous magnesium sulfate. The solvent was evaporated under reduced pressure. The residue was subjected to silica gel column chromatography, and eluted with ethyl acetate-hexane (5:95-70:30). A more polar fraction was concentrated under reduced pressure to give tert-butyl (3S*,5R*)-3-[({2-tert-butyl-4-[(furan-2-ylmethyl)amino]pyrimidin-5-yl}carbonyl)(2-methylpropyl)amino]-5-[(ethylsulfonyl)methyl]piperidine-1-carboxylate (70.8 mg), and a less polar fraction was concentrated under reduced pressure to give tert-butyl (3S*,5S*)-3-[({2-tert-butyl-4-[(furan-2-ylmethyl)amino]pyrimidin-5-yl}carbonyl)(2-methylpropyl)amino]-5-[(ethylsulfonyl)methyl]piperidine-1-carboxylate (49.4 mg).

tert-butyl (3S*,5R*)-3-[({2-tert-butyl-4-[(furan-2-ylmethyl)amino]pyrimidin-5-yl}carbonyl)(2-methylpropyl)amino]-5-[(ethylsulfonyl)methyl]piperidine-1-carboxylate MS (ESI+, m/e) 620 (M+1)

tert-butyl (3S*,5S*)-3-[({2-tert-butyl-4-[(furan-2-ylmethyl)amino]pyrimidin-5-yl}carbonyl)(2-methylpropyl)amino]-5-[(ethylsulfonyl)methyl]piperidine-1-carboxylate MS (ESI+, m/e) 620 (M+1)

Reference Example 126 tert-butyl 3-[({2-tert-butyl-4-[(furan-2-ylmethyl)amino]pyrimidin-5-yl}carbonyl)(2-methylpropyl)amino]-5-formylpiperidine-1-carboxylate

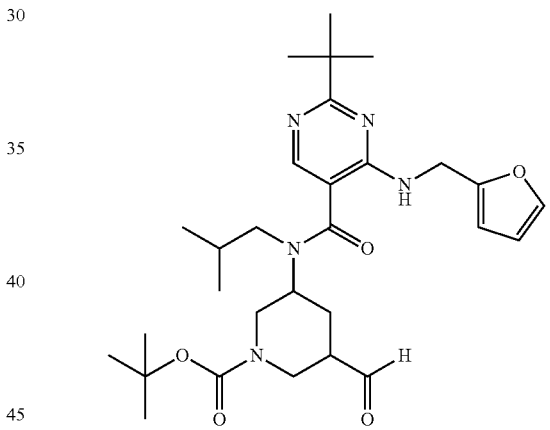

To a solution of tert-butyl 3-[({2-tert-butyl-4-[(furan-2-ylmethyl)amino]pyrimidin-5-yl}carbonyl)(2-methylpropyl)amino]-5-(hydroxymethyl)piperidine-1-carboxylate (420 mg) and triethylamine (0.87 ml) in DMSO (6 ml) was added dropwise a solution of sulfur trioxide pyridine complex (500 mg) in DMSO (5 ml) at room temperature, and the mixture was stirred at room temperature for 10 hr. The reaction mixture was diluted with water, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane (5:95-70:30) was concentrated under reduced pressure to give the object compound (382 mg).

MS (ESI+, m/e) 542 (M+1)

Reference Example 127 tert-butyl (3S*,5S*)-3-[({2-tert-butyl-4-[(furan-2-ylmethyl)amino]pyrimidin-5-yl}carbonyl)(2-methylpropyl)amino]-5-(morpholin-4-ylmethyl)piperidine-1-carboxylate and tert-butyl (3S*,5R*)-3-[({2-tert-butyl-4-[(furan-2-s ylmethyl)amino]pyrimidin-5-yl}carbonyl)(2-methylpropyl)amino]-5-(morpholin-4-ylmethyl)piperidine-1-carboxylate

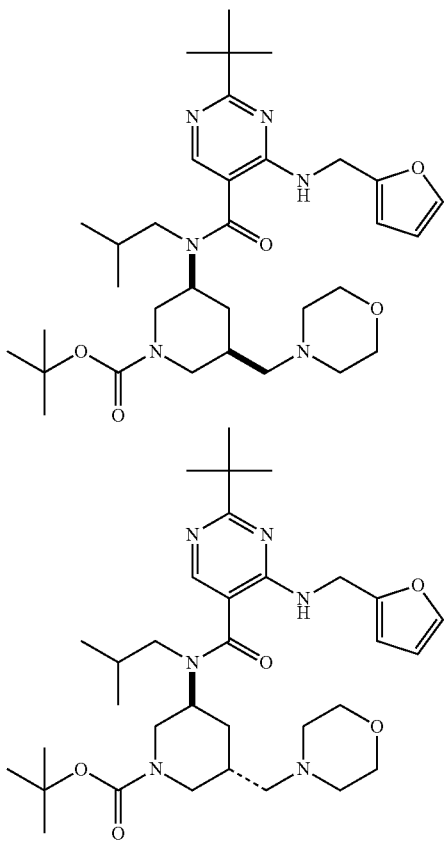

tert-Butyl 3-[({2-tert-butyl-4-[(furan-2-ylmethyl)amino]pyrimidin-5-yl}carbonyl) (2-methylpropyl)amino]-5-formylpiperidine-1-carboxylate (90 mg) and acetic acid (0.5 ml) were dissolved in 1,2-dichloroethane (4 ml), sodium triacetoxyborohydride (90 mg) was added and the mixture was stirred at room temperature for 7 hr. The reaction mixture was concentrated under reduced pressure, and the concentrated solution was basified with aqueous sodium hydrogen carbonate, and the mixture was extracted with ethyl acetate. The extract was washed with water and saturated brine, and dried over anhydrous magnesium sulfate. The solvent was evaporated under reduced pressure. The residue was subjected to silica gel column chromatography, and eluted with ethyl acetate-hexane (10:90-100:0). A more polar fraction was concentrated under reduced pressure to give tert-butyl (3S*,5S*)-3-[({2-tert-butyl-4-[(furan-2-ylmethyl)amino]pyrimidin-5-yl}carbonyl)(2-methylpropyl)amino]-5-(morpholin-4-ylmethyl)piperidine-1-carboxylate (33.6 mg), and a less polar fraction was concentrated under reduced pressure to give tert-butyl (3S*,5R*)-3-[({2-tert-butyl-4-[(furan-2-ylmethyl)amino]pyrimidin-5-yl}carbonyl)(2-methylpropyl) amino]-5-(morpholin-4-ylmethyl)piperidine-1-carboxylate (45.5 mg).

tert-butyl (3S*,5S*)-3-[({2-tert-butyl-4-[(furan-2-ylmethyl)amino]pyrimidin-5-yl}carbonyl)(2-methylpropyl)amino]-5-(morpholin-4-ylmethyl)piperidine-1-carboxylate MS (ESI+, m/e) 613 (M+1)

tert-butyl (3S*,5R*)-3-[({2-tert-butyl-4-[(furan-2-ylmethyl)amino]pyrimidin-5-yl}carbonyl)(2-methylpropyl)amino]-5-(morpholin-4-ylmethyl)piperidine-1-carboxylate MS (ESI+, m/e) 613 (M+1)

By a method similar to that of Reference Example 40, the following compound (Reference Example 128) was obtained.

Reference Example 128 tert-butyl (3S*,5R*)-3-[({2-tert-butyl-4-[(furan-2-ylmethyl)amino]pyrimidin-5-yl}carbonyl)(2-methylpropyl)amino]-5-[(3-hydroxyazetidin-1-yl)carbonyl]piperidine-1-carboxylate

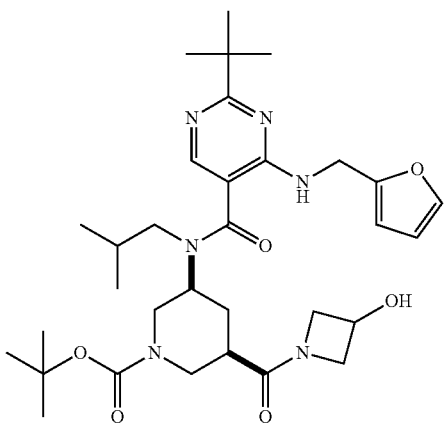

MS (ESI+, m/e) 613 (M+1)

Reference Example 129 tert-butyl (3S*,5R*)-3-[({2-tert-butyl-4-[(furan-2-ylmethyl)amino]pyrimidin-5-yl}carbonyl)(2-methylpropyl)amino]-5-cyanopiperidine-1-carboxylate

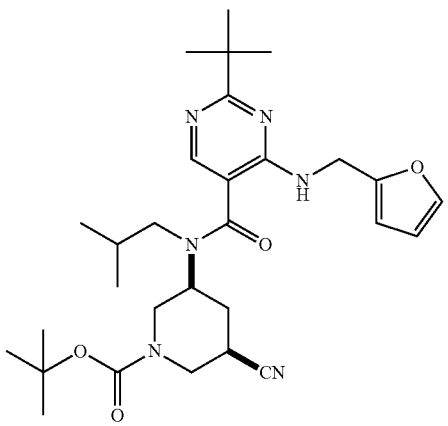

tert-Butyl (3R*,5S*)-3-(aminocarbonyl)-5-[({2-tert-butyl-4-[(2-furylmethyl)amino]pyrimidin-5-yl}carbonyl)(isobutyl)amino]piperidine-1-carboxylate (469 mg) was dissolved in pyridine (5 ml), trifluoroacetic anhydride (0.25 ml) was added under ice-cooling, and the mixture was stirred at room temperature for 11 hr. The reaction mixture was concentrated under reduced pressure, and the residue was diluted with ethyl acetate. The solution was washed successively with 1 M hydrochloric acid and saturated brine, and dried over anhydrous magnesium sulfate. The solvent was evaporated under reduced pressure. The residue was subjected to silica gel column chromatography, and the fraction eluted with ethyl acetate-hexane (5:95-80:20) was concentrated under reduced pressure to give the object compound (402 mg).

MS (ESI+, m/e) 539 (M+1)

Reference Example 130 tert-butyl (3S*,5R*)-3-[({2-tert-butyl-4-[(furan-2-ylmethyl)amino]pyrimidin-5-yl}carbonyl)(2-methylpropyl)amino]-5-(2H-tetrazol-5-yl)piperidine-1-carboxylate

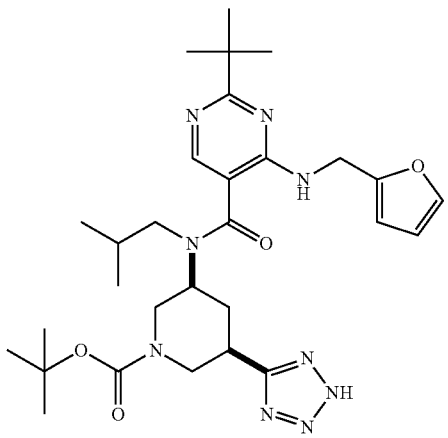

To tert-butyl (3S*,5R*)-3-[({2-tert-butyl-4-[(furan-2-ylmethyl)amino]pyrimidin-5-yl}carbonyl)(2-methylpropyl)amino]-5-cyanopiperidine-1-carboxylate (120 mg) were added azido(trimethyl)silane (55 mg) and dibutyl(oxo)stannane (5 mg), and the mixture was stirred with heating to reflux for 1 day. The reaction mixture was concentrated under reduced pressure, and the residue was subjected to silica gel column chromatography, and the fraction eluted with ethyl acetate-hexane (10:90-100:0) was concentrated under reduced pressure to give the object compound (75.5 mg).

MS (ESI+, m/e) 582 (M+1)

Reference Example 131 tert-butyl (3S*,5R*)-3-[({2-tert-butyl-4-[(furan-2-ylmethyl)amino]pyrimidin-5-yl}carbonyl)(2-methylpropyl)amino]-5-(5-oxo-4,5-dihydro-1,2,4-oxadiazol-3-yl)piperidine-1-carboxylate

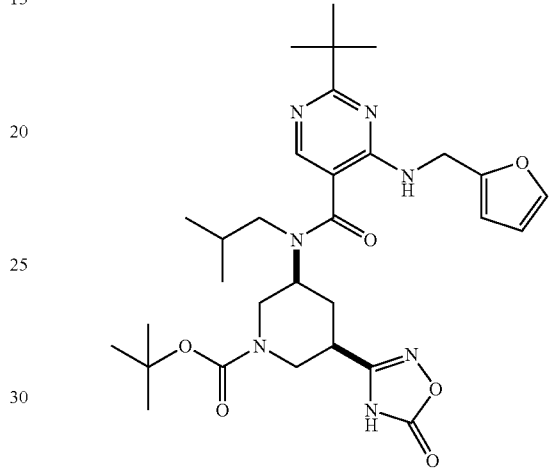

Hydroxylamine hydrochloride (35 mg) was dissolved in THF (3 ml)-methanol (3 ml), triethylamine (0.07 ml) was added, and the mixture was stirred at room temperature for 1 hr. A solution of tert-butyl (3S*,5R*)-3-[({2-tert-butyl-4-[(furan-2-ylmethyl)amino]pyrimidin-5-yl}carbonyl)(2-methylpropyl)amino]-5-(2H-tetrazol-5-yl)piperidine-1-carboxylate (120 mg) in THF (3 ml) was further added, and the mixture was stirred at 60° C. for 3 hr. The reaction mixture was allowed to cool to room temperature, and diluted with water, and the mixture was extracted with ethyl acetate. The extract was dried over anhydrous magnesium sulfate, and concentrated under reduced pressure, and the residue was dissolved in tetrahydrofuran (5 ml). 1,1'-Carbonylbis(1H-imidazole) (72 mg) and 1,8-diazabicyclo[5.4.0]undec-7-ene (0.066 ml) were added and the mixture was stirred at room temperature for 30 min. The reaction mixture was concentrated under reduced pressure, diluted with ethyl acetate, washed with 0.5 M hydrochloric acid and saturated brine, and dried over anhydrous magnesium sulfate. The solution was concentrated under reduced pressure, and the residue was subjected to silica gel chromatography. The fraction eluted with ethyl acetate-hexane (10:95) to ethyl acetate was concentrated under reduced pressure to give the object compound (26.1 mg).

MS (ESI+, m/e) 598 (M+1)

Reference Example 132 tert-butyl (3S*,5R*)-3-[({2-tert-butyl-4-[(furan-2-ylmethyl)amino]pyrimidin-5-yl}carbonyl)(2-methylpropyl)amino]-5-(1,2,4-oxadiazol-3-yl)piperidine-1-carboxylate

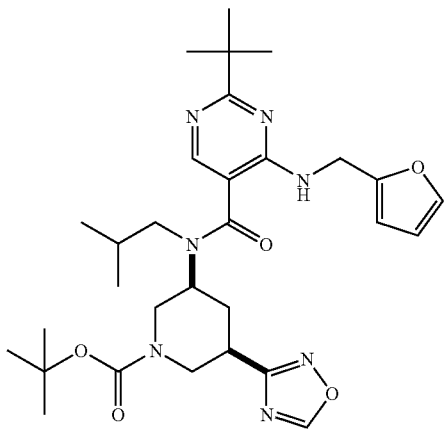

Hydroxylamine hydrochloride (35 mg) was dissolved in THF (3 ml)-methanol (3 ml), triethylamine (0.07 ml) was added, and the mixture was stirred at room temperature for 1 hr. A solution of tert-butyl (3S*,5R*)-3-[({2-tert-butyl-4-[(furan-2-ylmethyl)amino]pyrimidin-5-yl}carbonyl)(2-methylpropyl)amino]-5-(2H-tetrazol-5-yl)piperidine-1-carboxylate (120 mg) in THF (3 ml) was further added, and the mixture was stirred at 60° C. for 3 hr. The reaction mixture was allowed to cool to room temperature, and diluted with water, and the mixture was extracted with ethyl acetate. The extract was dried over anhydrous magnesium sulfate, and concentrated under reduced pressure. The obtained residue was dissolved in trimethyl orthoformate (5 ml), 4-methylbenzenesulfonic acid (20 mg) was added and the mixture was stirred at 100° C. for 10 hr. The reaction mixture was concentrated under reduced pressure, and the residue was subjected to silica gel chromatography. The fraction eluted with ethyl acetate-hexane (5:95-50:50) was concentrated under reduced pressure to give the object compound (72.6 mg).
MS (ESI+, m/e) 582 (M+1)

Reference Example 133 tert-butyl (3S*,5R*)-3-[({2-tert-butyl-4-[(furan-2-ylmethyl)amino]pyrimidin-5-yl}carbonyl)(2-methylpropyl)amino]-5-(5-methyl-1,3,4-oxadiazol-2-yl)piperidine-1-carboxylate

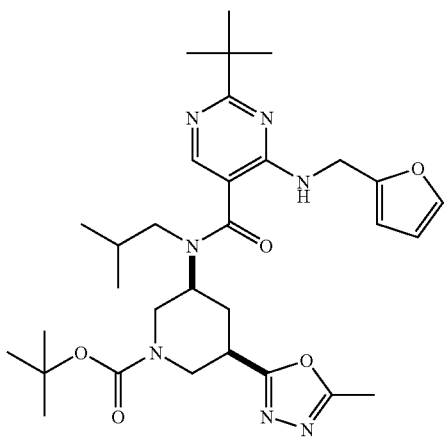

(3R*,5S*)-1-(tert-Butoxycarbonyl)-5-[({2-tert-butyl-4-[(2-furylmethyl)amino]pyrimidin-5-yl}carbonyl)(isobutyl)amino]piperidine-3-carboxylic acid (120 mg) and 5-methyl-1H-tetrazole (22 mg) were suspended in toluene (3 ml), DCC (60 mg) was added and the mixture was stirred at 100° C. for 14 hr. The reaction mixture was cooled to room temperature, and concentrated under reduced pressure. The residue was subjected to silica gel column chromatography, and the fraction eluted with ethyl acetate-hexane (5:95-75:25) was concentrated under reduced pressure to give the object compound (74.7 mg).
MS (ESI+, m/e) 596 (M+1)

By a method similar to that of Reference Example 133, the following compound (Reference Example 134) was obtained.

Reference Example 134 tert-butyl (3S*,5R*)-3-[({2-tert-butyl-4-[(furan-2-ylmethyl)amino]pyrimidin-5-yl}carbonyl)(2-methylpropyl)amino]-5-(5-phenyl-1,3,4-oxadiazol-2-yl)piperidine-1-carboxylate

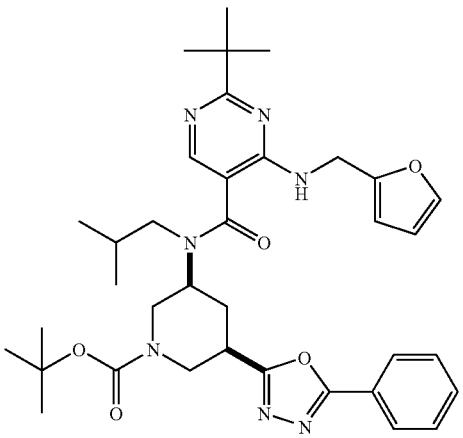

MS (ESI+, m/e) 658 (M+1)

Reference Example 135

1-tert-butyl 3-methyl (3S,5R)-5-[({2-tert-butyl-4-[(furan-2-ylmethyl)amino]pyrimidin-5-yl}carbonyl)(2-methylpropyl)amino]piperidine-1,3-dicarboxylate and 1-tert-butyl 3-methyl (3R,5S)-5-[({2-tert-butyl-4-[(furan-2-ylmethyl)amino]pyrimidin-5-yl}carbonyl)(2-methylpropyl)amino]piperidine-1,3-dicarboxylate

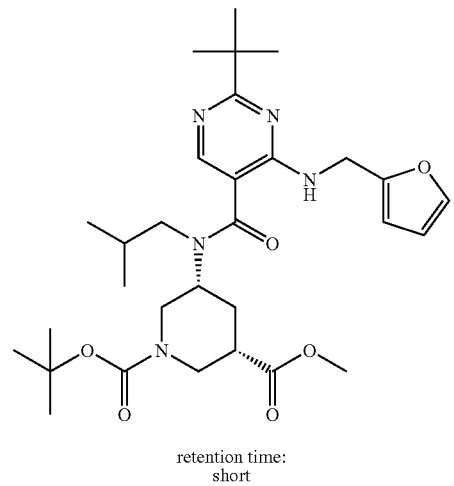

retention time: short

-continued

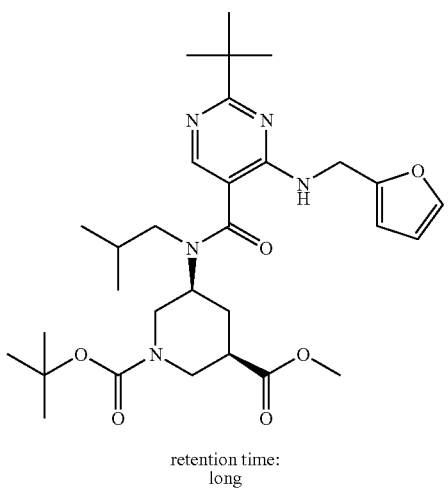

retention time:
long 1-tert-Butyl 3-methyl (3R*,5S*)-5-[({2-tert-butyl-4-[(2-furylmethyl)amino]pyrimidin-5-yl}carbonyl)(isobutyl)amino]piperidine-1,3-dicarboxylate (3.00 g) was optically resolved by normal phase chiral HPLC under the following conditions.

Column: CHIRALPAK AD 50 mmID×500 mL
Mobile phase: hexane-ethanol (97:3)
Flow rate: 85 ml/min
Temperature: 30° C.
Detection: UV (220 nm)
Injection amount (concentration): 100 mg/load (5 mg/ml)

By a method similar to that of Reference Example 38, the following compounds (Reference Examples 136 and 137) were obtained.

Reference Example 136

(3R,5S)-1-(tert-butoxycarbonyl)-5-[({2-tert-butyl-4-[(furan-2-ylmethyl)amino]pyrimidin-5-yl}carbonyl)(2-methylpropyl)amino]piperidine-3-carboxylic acid

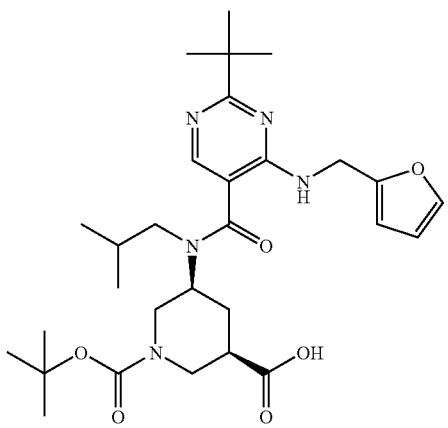

MS (ESI+, m/e) 558 (M+1)

Reference Example 137

(3S,5R)-1-(tert-butoxycarbonyl)-5-[({2-tert-butyl-4-[(furan-2-ylmethyl)amino]pyrimidin-5-yl}carbonyl)(2-methylpropyl)amino]piperidine-3-carboxylic acid

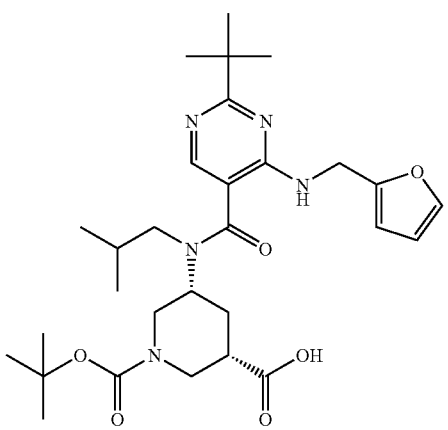

MS (ESI+, m/e) 558 (M+1)

By a method similar to that of Reference Example 39, the following compounds (Reference Examples 138 and 139) were obtained.

Reference Example 138 tert-butyl (3S,5R)-3-[({2-tert-butyl-4-[(furan-2-ylmethyl)amino]pyrimidin-5-yl}carbonyl)(2-methylpropyl)amino]-5-carbamoylpiperidine-1-carboxylate

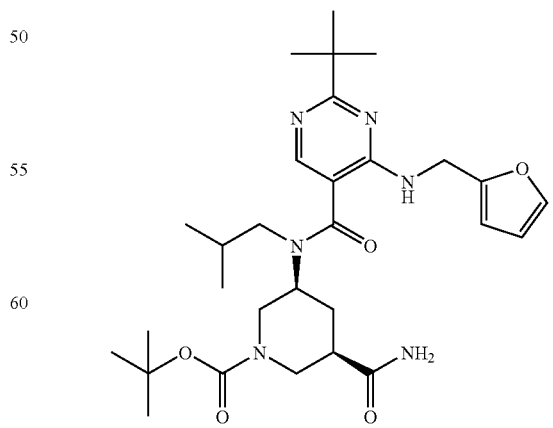

MS (ESI+, m/e) 557 (M+1)

Reference Example 139 tert-butyl (3R,5S)-3-[({2-tert-butyl-4-[(furan-2-ylmethyl)amino]pyrimidin-5-yl}carbonyl)(2-methylpropyl)amino]-5-carbamoylpiperidine-1-carboxylate

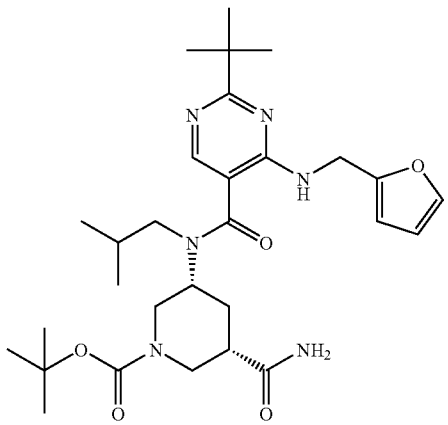

MS (ESI+, m/e) 557 (M+1)

Reference Example 140 tert-butyl (3S,5R)-3-[({2-tert-butyl-4-[(furan-2-ylmethyl)amino]pyrimidin-5-yl}carbonyl)(2-methylpropyl)amino]-5-[(methoxycarbonyl)amino]piperidine-1-carboxylate

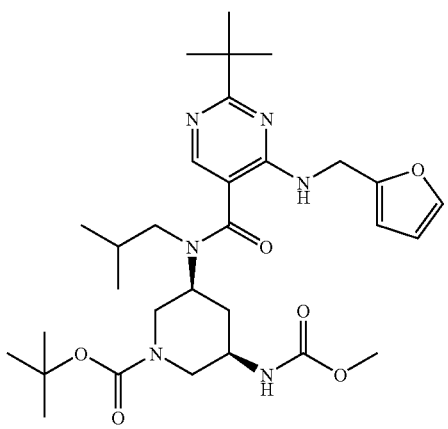

(3R,5S)-1-(tert-Butoxycarbonyl)-5-[({2-tert-butyl-4-[(furan-2-ylmethyl)amino]pyrimidin-5-yl}carbonyl)(2-methylpropyl)amino]piperidine-3-carboxylic acid (100 mg) was suspended in toluene (5 ml), diphenylphosphoryl azide (60 μl) and triethylamine (40 μl) were added and the mixture was stirred at 100° C. for 2 hr. The reaction mixture was cooled to room temperature, methanol (40 μl) and triethylamine (140 μl) to were added and the mixture was stirred at 80° C. for 4 hr. The reaction mixture was washed with water, 5% aqueous citric acid solution, saturated aqueous sodium hydrogen carbonate and saturated brine in this order, and dried over anhydrous sodium sulfate. The solvent was evaporated under reduced pressure. The residue was subjected to silica gel column chromatography, and the fraction eluted with ethyl acetate-hexane (5:95-65:35) was concentrated under reduced pressure to give the object compound (24.2 mg).

MS (ESI+, m/e) 587 (M+1)

By a method similar to that of Reference Example 140, the following compounds (Reference Examples 141 and 142) were obtained.

Reference Example 141 tert-butyl (3R,5S)-3-{[(benzyloxy)carbonyl]amino}-5-[({2-tert-butyl-4-[(furan-2-ylmethyl)amino]pyrimidin-5-yl}carbonyl)(2-methylpropyl)amino]piperidine-1-carboxylate

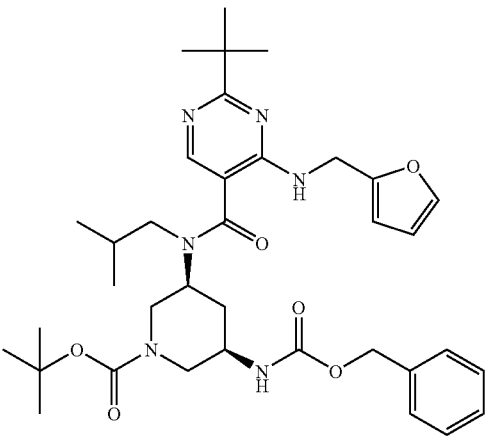

MS (ESI+, m/e) 663 (M+1)

Reference Example 142 tert-butyl (3S,5R)-3-[({2-tert-butyl-4-[(furan-2-ylmethyl)amino]pyrimidin-5-yl}carbonyl)(2-methylpropyl)amino]-5-{[(2,2,2-trichloroethoxy)carbonyl]amino}piperidine-1-carboxylate

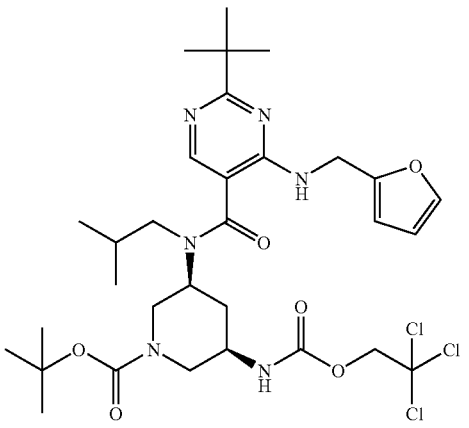

MS (ESI+, m/e) 705 (M+1)

Reference Example 143 tert-butyl (3S,5R)-3-[({2-tert-butyl-4-[(furan-2-ylmethyl)amino]pyrimidin-5-yl}carbonyl)(2-methylpropyl)amino]-5-[(morpholin-4-ylcarbonyl)amino]piperidine-1-carboxylate

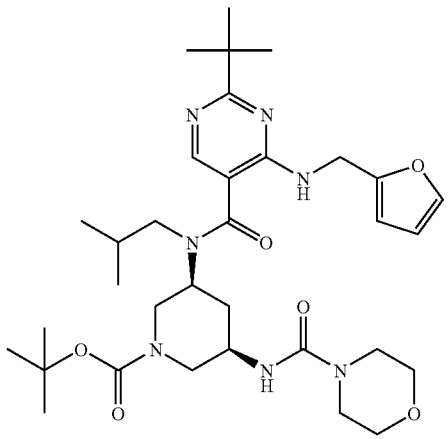

tert-Butyl (3S,5R)-3-[({2-tert-butyl-4-[(furan-2-ylmethyl)amino]pyrimidin-5-yl}carbonyl)(2-methylpropyl)amino]-5-{[(2,2,2-trichloroethoxy)carbonyl]amino}piperidine-1-carboxylate (98.0 mg) and N,N-diisopropylethylamine (120 μl) were dissolved in N,N-dimethylacetamide (3 ml), morpholine (20 μl) was added, and the mixture was stirred at 80° C. for 1 day. The reaction mixture was diluted with 1 M hydrochloric acid, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane (10:90-100:0) was concentrated under reduced pressure to give the object compound (12.7 mg).

MS (ESI+, m/e) 642 (M+1)

Reference Example 144 tert-butyl (3R,5S)-3-amino-5-[({2-tert-butyl-4-[(furan-2-ylmethyl)amino]pyrimidin-5-yl}carbonyl)(2-methylpropyl)amino]piperidine-1-carboxylate

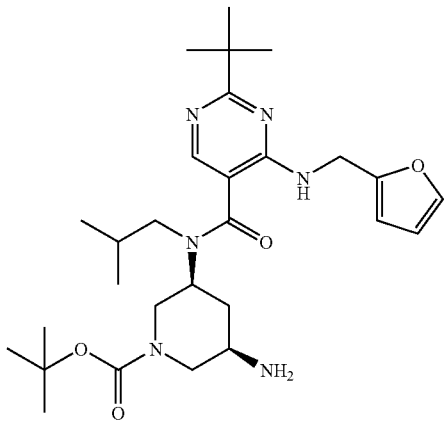

To a solution of tert-butyl (3S,5R)-3-[({2-tert-butyl-4-[(furan-2-ylmethyl)amino]pyrimidin-5-yl}carbonyl)(2-methylpropyl)amino]-5-{[2,2,2-trichloroethoxy)carbonyl]amino}piperidine-1-carboxylate (312 mg) in ethanol (5 ml) was added 4 M aqueous sodium hydroxide solution (3 ml), and the mixture was stirred at 80° C. for 1 day. The reaction mixture was diluted with water, and the mixture was extracted with ethyl acetate. The extract was washed with saturated brine, and dried over anhydrous magnesium sulfate, and the solvent was evaporated under reduced pressure to give the object compound (211 mg).

MS (ESI+, m/e) 529 (M+1)

Reference Example 145 tert-butyl (3R,5S)-3-(acetylamino)-5-[({2-tert-butyl-4-[(furan-2-ylmethyl)aino]pyrimidin-5-yl}carbonyl)(2-methylpropyl)amino]piperidine-1-carboxylate

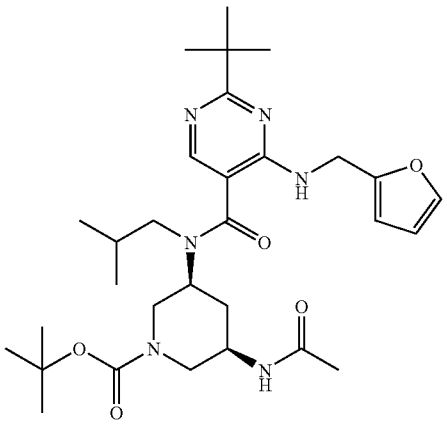

To a solution of tert-butyl (3R,5S)-3-amino-5-[({2-tert-butyl-4-[(furan-2-ylmethyl)amino]pyrimidin-5-yl}carbonyl)(2-methylpropyl)amino]piperidine-1-carboxylate (70 mg) in 1,2-dichloroethane (3 ml) were successively added triethylamine (55 μl) and acetic anhydride (35 μl), and the mixture was stirred at room temperature for 3 hr. The reaction mixture was acidified with 1 M hydrochloric acid, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane-methanol (50:50:0-85:0:15) was concentrated under reduced pressure to give the object compound (28.5 mg).

MS (ESI+, m/e) 571 (M+1)

215

By a method similar to that of Reference Example 40, the following compounds (Reference Examples 146 and 147) were obtained.

Reference Example 146 tert-butyl (3S,5R)-3-[({2-tert-butyl-4-[(furan-2-ylmethyl)amino]pyrimidin-5-yl}carbonyl)(2-methylpropyl)amino]-5-[(tetrahydro-2H-pyran-4-ylcarbonyl)amino]piperidine-1-carboxylate

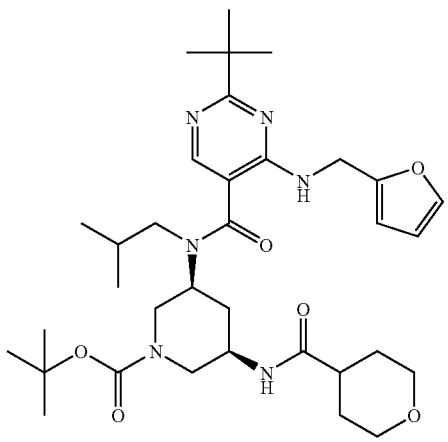

MS (ESI+, m/e) 641 (M+1)

Reference Example 147 tert-butyl (3S,5R)-3-[({2-tert-butyl-4-[(furan-2-ylmethyl)amino]pyrimidin-5-yl}carbonyl)(2-methylpropyl)amino]-5-({[4-(hydroxymethyl)tetrahydro-2H-pyran-4-yl]carbonyl}amino)piperidine-1-carboxylate

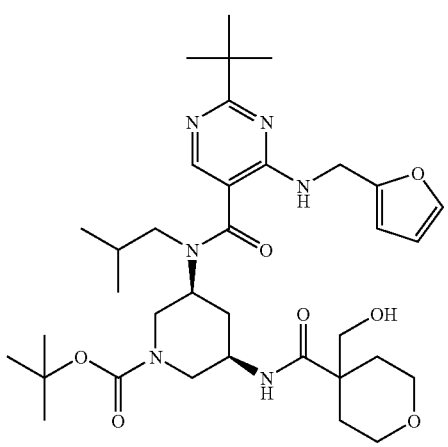

MS (ESI+, m/e) 671 (M+1)

216

Reference Example 148 tert-butyl (3S,5R)-3-[({2-tert-butyl-4-[(furan-2-ylmethyl)amino]pyrimidin-5-yl}carbonyl)(2-methylpropyl)amino]-5-(1H-1,2,4-triazol-3-yl)piperidine-1-carboxylate

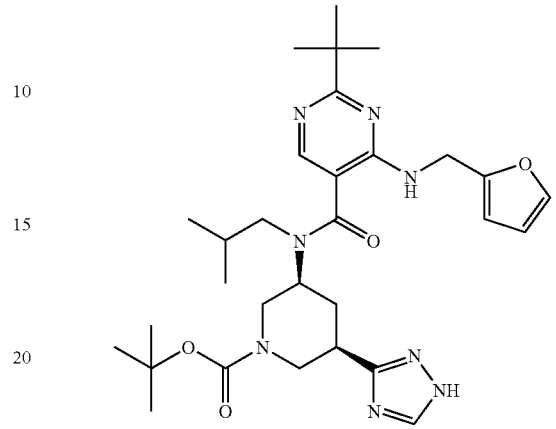

tert-Butyl (3R,5S)-3-[({2-tert-butyl-4-[(furan-2-ylmethyl)amino]pyrimidin-5-yl}carbonyl)(2-methylpropyl)amino]-5-carbamoylpiperidine-1-carboxylate (83.0 mg) was dissolved in N,N-dimethylformamide dimethyl acetal (2.5 ml), and the mixture was stirred at 100° C. for 4 hr. The reaction mixture was concentrated under reduced pressure, and the residue was dissolved in acetic acid (5 ml). Hydrazine monohydrate (20 μl) was added and the mixture was stirred at 80° C. for 2 hr. The reaction mixture was concentrated under reduced pressure, the residue was diluted with 1 M aqueous sodium hydroxide solution, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate to ethyl acetate-methanol (9:1) was concentrated under reduced pressure to give the object compound (50.0 mg).

MS (ESI+, m/e) 581 (M+1)

By a method similar to that of Reference Example 48, the following compounds (Reference Examples 149 and 150) were obtained.

Reference Example 149

1-tert-butyl 3-methyl (3R,5S)-5-[{[2-tert-butyl-4-(pentylamino)pyrimidin-5-yl]carbonyl}(2-methylpropyl)amino]piperidine-1,3-dicarboxylate

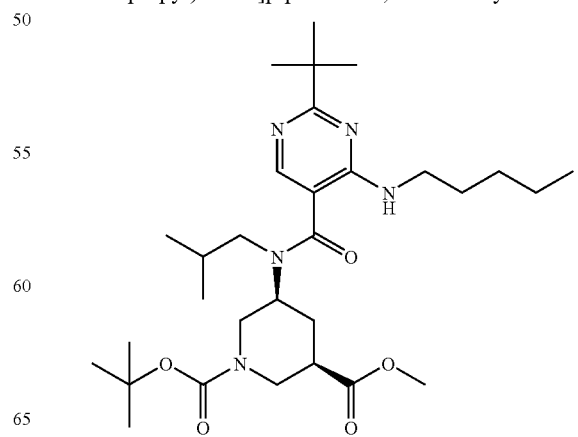

MS (ESI+, m/e) 562 (M+1)

Reference Example 150

1-tert-butyl 3-methyl (3R,5S)-5-{[(2-tert-butyl-4-{[3-(methylsulfanyl)propyl]amino}pyrimidin-5-yl)carbonyl](2-methylpropyl)amino}piperidine-1,3-dicarboxylate

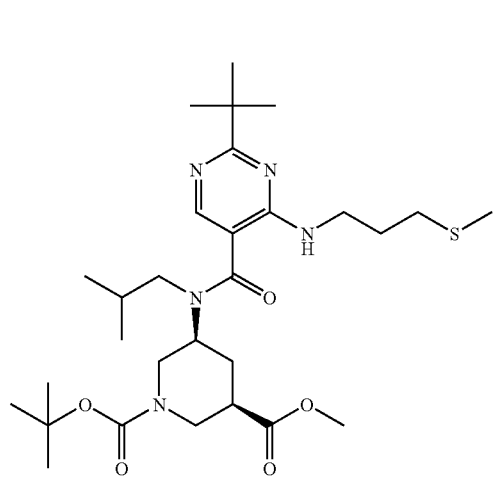

MS (ESI+, m/e) 580 (M+1)

By a method similar to that of Reference Example 38, the following compounds (Reference Examples 151 and 152) were obtained.

Reference Example 151

(3R,5S)-1-(tert-butoxycarbonyl)-5-[{[2-tert-butyl-4-(pentylamino)pyrimidin-5-yl]carbonyl}(2-methylpropyl)amino]piperidine-3-carboxylic acid

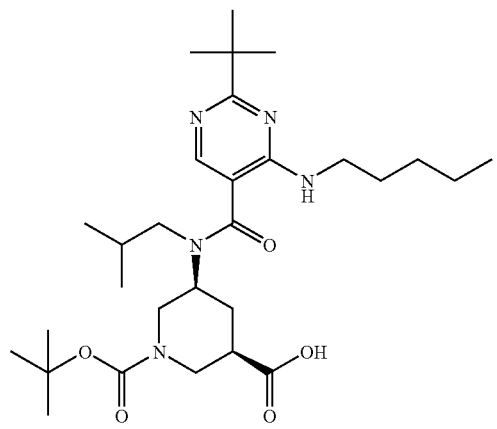

MS (ESI+, m/e) 548 (M+1)

Reference Example 152

(3R,5S)-1-(tert-butoxycarbonyl)-5-{[(2-tert-butyl-4-{[3-(methylsulfanyl)propyl]amino}pyrimidin-5-yl)carbonyl](2-methylpropyl)amino}piperidine-3-carboxylic acid

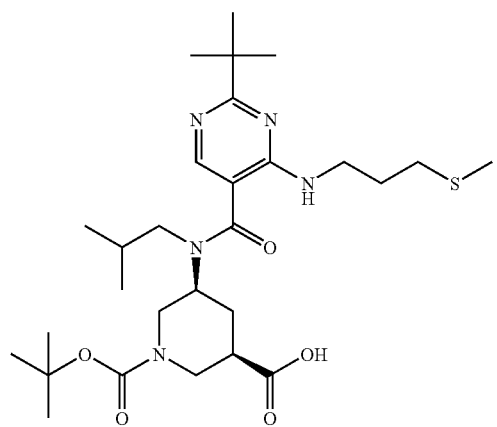

MS (ESI+, m/e) 566 (M+1)

By a method similar to that of Reference Example 50, the following compounds (Reference Examples 153 to 156) were obtained.

Reference Example 153 tert-butyl (3S,5R)-3-[{[2-tert-butyl-4-(pentylamino)pyrimidin-5-yl]carbonyl}(2-methylpropyl)amino]-5-carbamoylpiperidine-1-carboxylate

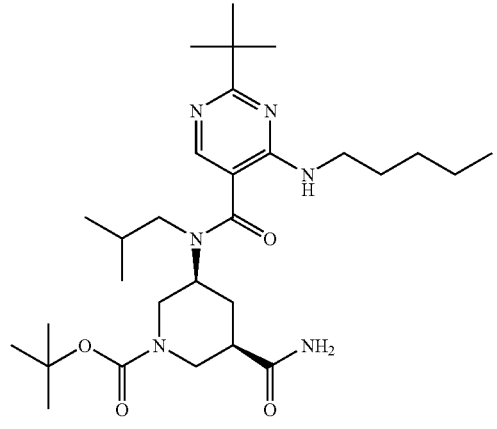

MS (ESI+, m/e) 547 (M+1)

Reference Example 154 tert-butyl (3S,5R)-3-[{[2-tert-butyl-4-(pentylamino)pyrimidin-5-yl]carbonyl}(2-methylpropyl)amino]-5-(morpholin-4-ylcarbonyl)piperidine-1-carboxylate

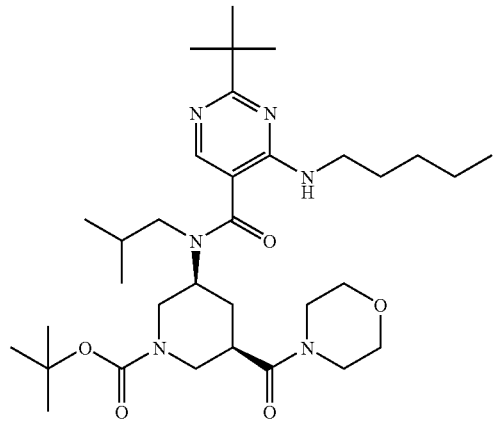

MS (ESI+, m/e) 617 (M+1)

Reference Example 155 tert-butyl (3S,5R)-3-{[(2-tert-butyl-4-{[3-(methylsulfanyl)propyl]amino}pyrimidin-5-yl)carbonyl](2-methylpropyl)amino}-5-carbamoylpiperidine-1-carboxylate

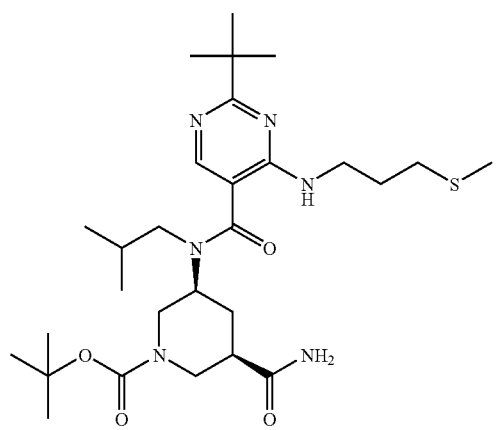

MS (ESI+, m/e) 565 (M+1)

Reference Example 156 tert-butyl (3S,5R)-3-{[(2-tert-butyl-4-{[3-(methylsulfanyl)propyl]amino}pyrimidin-5-yl)carbonyl](2-methylpropyl)amino}-5-(morpholin-4-ylcarbonyl)piperidine-1-carboxylate

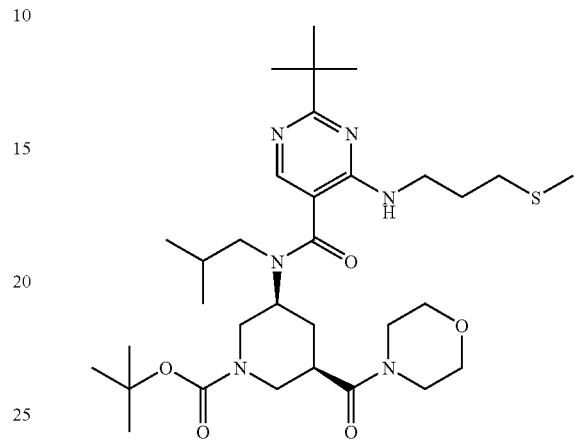

MS (ESI+, m/e) 635 (M+1)

Reference Example 157

1-tert-butyl 3-methyl (3R,5S)-5-{[(2-tert-butyl-4-{[3-(methylsulfinyl)propyl]amino}pyrimidin-5-yl)carbonyl](2-methylpropyl)amino}piperidine-1,3-dicarboxylate

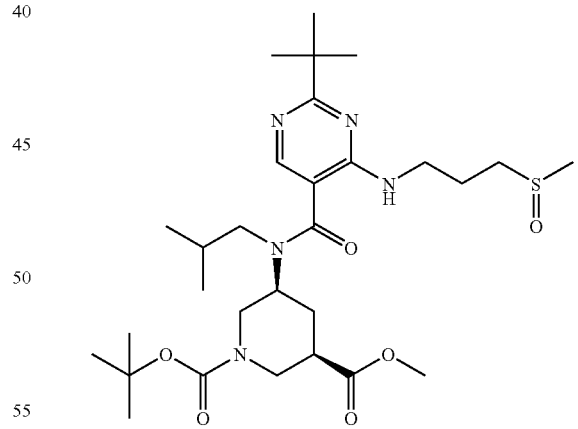

1-tert-Butyl 3-methyl (3R,5S)-5-{[(2-tert-butyl-4-{[3-(methylsulfanyl)propyl]amino}pyrimidin-5-yl)carbonyl](2-methylpropyl)amino}piperidine-1,3-dicarboxylate (150 mg) was dissolved in 1,2-dichloroethane (3 ml), 3-chloroperbenzoic acid (65% contained, 70 mg) was added, and the mixture was stirred at room temperature for 2 hr. The reaction mixture was diluted with saturated aqueous sodium hydrogen carbonate solution, and the mixture was extracted with ethyl acetate. The extract was washed with saturated brine, and dried over anhydrous magnesium sulfate. The solvent was evaporated under reduced pressure. The residue was subjected to silica gel column chromatography, eluted with ethyl acetate-hexane (10:90-85:15) and concentrated under reduced pressure to give the object compound (113 mg).

MS (ESI+, m/e) 596 (M+1)

By a method similar to that of Reference Example 38, the following compound (Reference Example 158) was obtained.

Reference Example 158

(3R,5S)-1-(tert-butoxycarbonyl)-5-{[(2-tert-butyl-4-{[3-(methylsulfinyl)propyl]amino}pyrimidin-5-yl)carbonyl](2-methylpropyl)amino}piperidine-3-carboxylic acid

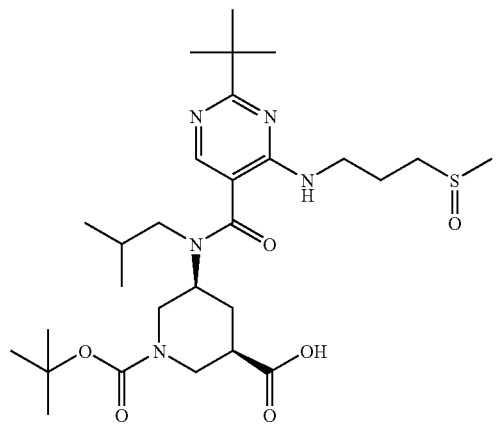

MS (ESI+, m/e) 582 (M+1)

By a method similar to that of Reference Example 50, the following compound (Reference Example 159) was obtained.

Reference Example 159 tert-butyl (3S,5R)-3-{[(2-tert-butyl-4-{[3-(methylsulfinyl)propyl]amino}pyrimidin-5-yl)carbonyl](2-methylpropyl)amino}-5-(morpholin-4-ylcarbonyl)piperidine-1-carboxylate

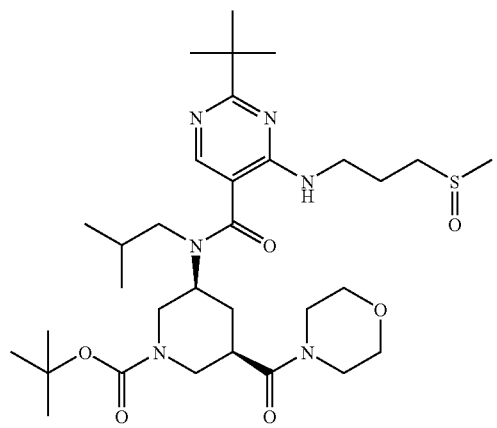

MS (ESI+, m/e) 651 (M+1)

By a method similar to that of Reference Example 148, the following compound (Reference Example 160) was obtained.

Reference Example 160 tert-butyl (3S,5R)-3-{[(2-tert-butyl-4-{[3-(methylsulfanyl)propyl]amino}pyrimidin-5-yl)carbonyl](2-methylpropyl)amino}-5-(4H-1,2,4-triazol-3-yl)piperidine-1-carboxylate

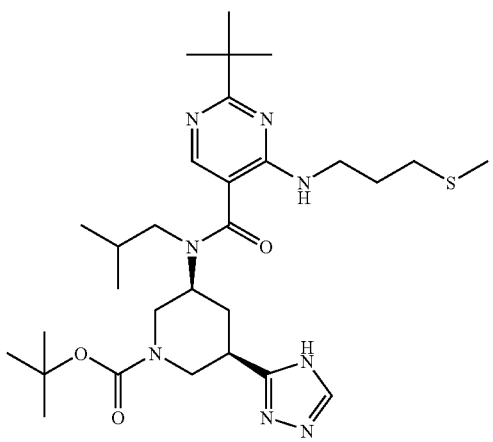

MS (ESI+, m/e) 589 (M+1)

By a method similar to that of Reference Example 40, the following compounds (Reference Examples 161 to 163) were obtained.

Reference Example 161 tert-butyl (3S,5R)-3-[({2-tert-butyl-4-[(furan-2-ylmethyl)amino]pyrimidin-5-yl}carbonyl)(2-methylpropyl)amino]-5-{[(4-hydroxycyclohexyl)carbonyl]amino}piperidine-1-carboxylate

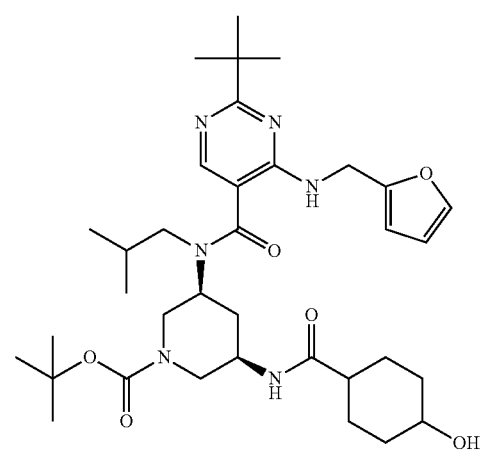

MS (ESI+, m/e) 655 (M+1)

Reference Example 162 tert-butyl (3S,5R)-3-[({2-tert-butyl-4-[(furan-2-ylmethyl)amino]pyrimidin-5-yl}carbonyl)(2-methylpropyl)amino]-5-{[(4-methoxycyclohexyl)carbonyl]amino}piperidine-1-carboxylate

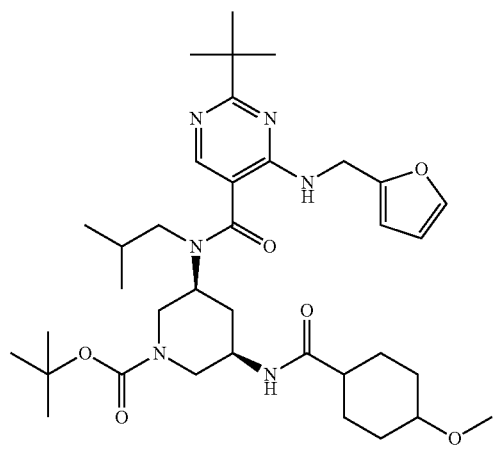

MS (ESI+, m/e) 669 (M+1)

Reference Example 163 tert-butyl (3S,5R)-3-[({2-tert-butyl-4-[(furan-2-ylmethyl)amino]pyrimidin-5-yl}carbonyl)(2-methylpropyl)amino]-5-{[(1-carbamoylpiperidin-4-yl)carbonyl]amino}piperidine-1-carboxylate

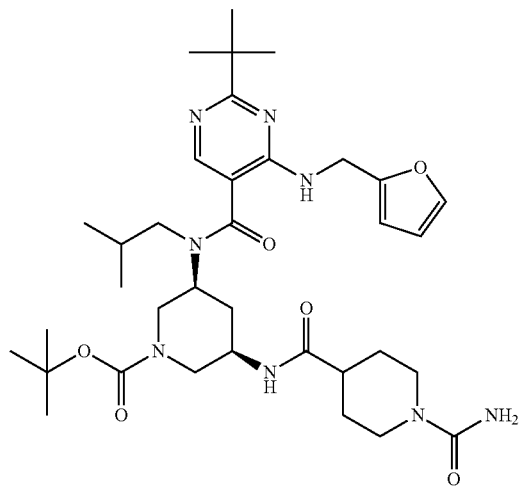

MS (ESI+, m/e) 683 (M+1)

By a method similar to that of Reference Example 140, the following compound (Reference Example 164) was obtained.

Reference Example 164 tert-butyl (3S,5R)-3-{[(2-tert-butyl-4-{[3-(methylsulfanyl)propyl]amino}pyrimidin-5-yl)carbonyl](2-methylpropyl)amino}-5-{[(2,2,2-trichloroethoxy)carbonyl]amino}piperidine-1-carboxylate

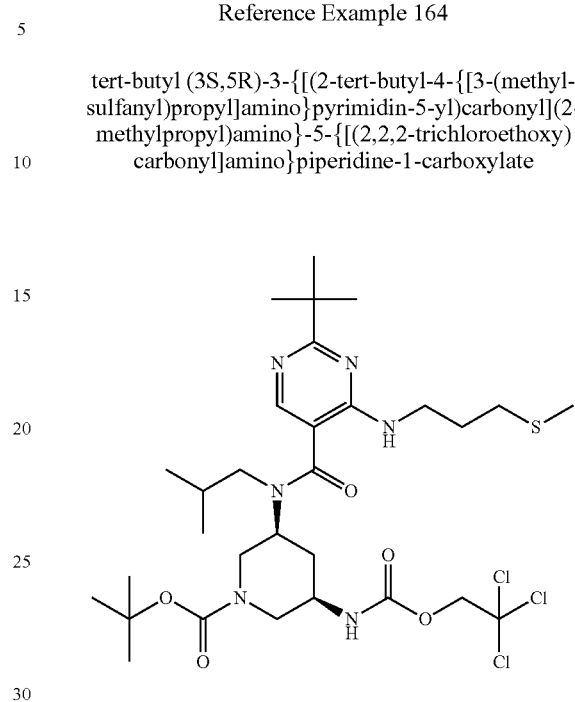

MS (ESI+, m/e) 713 (M+1)

By a method similar to that of Reference Example 144, the following compound (Reference Example 165) was obtained.

Reference Example 165 tert-butyl (3R,5S)-3-amino-5-{[(2-tert-butyl-4-{[3-(methylsulfanyl)propyl]amino}pyrimidin-5-yl)carbonyl](2-methylpropyl)amino}piperidine-1-carboxylate

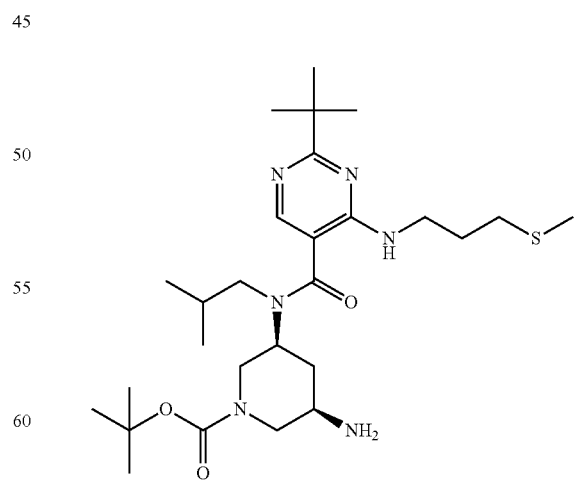

MS (ESI+, m/e) 537 (M+1)

Reference Example 166 tert-butyl (3S,5R)-3-{[(2-tert-butyl-4-{[3-(methyl-sulfanyl)propyl]amino}pyrimidin-5-yl)carbonyl](2-methylpropyl)amino}-5-(2-oxoimidazolidin-1-yl)piperidine-1-carboxylate

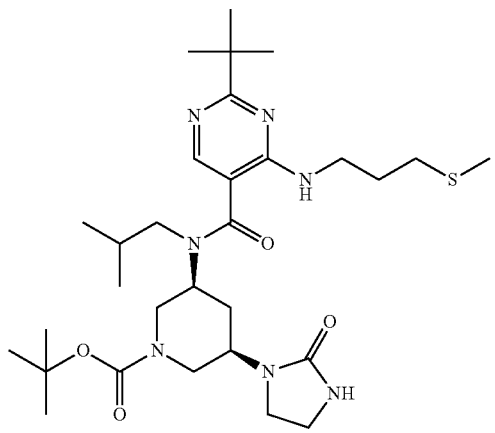

tert-Butyl (3R,5S)-3-amino-5-{[(2-tert-butyl-4-{[3-(methylsulfanyl)propyl]amino}pyrimidin-5-yl)carbonyl](2-methylpropyl)amino}piperidine-1-carboxylate (124 mg) was dissolved in THF (4 ml), chloroethyl isocyanate (24 µl) was added, and the mixture was stirred at room temperature for 1 hr. Potassium tert-butoxide (40 mg) was added and the reaction mixture was stirred at room temperature for 7 hr and further at 60° C. for 5 hr. The reaction mixture was diluted with water, and the mixture was extracted with ethyl acetate. The extract was washed with saturated brine, and dried over anhydrous magnesium sulfate. The solvent was evaporated under reduced pressure. The residue was subjected to silica gel column chromatography, eluted with ethyl acetate-hexane (10:90-100:0) and concentrated under reduced pressure to give the object compound (70.3 mg).

MS (ESI+, m/e) 606 (M+1)

By a method similar to that of Reference Example 48, the following compounds (Reference Examples 167 and 168) were obtained.

Reference Example 167

1-tert-butyl 3-methyl (3R,5S)-5-{[(2-tert-butyl-4-{[2-(methylsulfanyl)ethyl]amino}pyrimidin-5-yl)carbonyl](2-methylpropyl)amino}piperidine-1,3-dicarboxylate

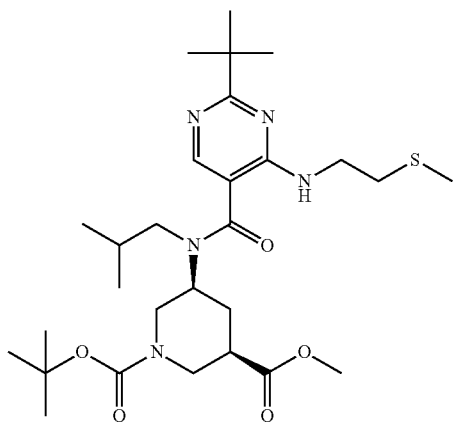

MS (ESI+, m/e) 566 (M+1)

Reference Example 168

1-tert-butyl 3-methyl (3R,5S)-5-{[(2-tert-butyl-4-{[2-(ethylsulfanyl)ethyl]amino}pyrimidin-5-yl)carbonyl](2-methylpropyl)amino}piperidine-1,3-dicarboxylate

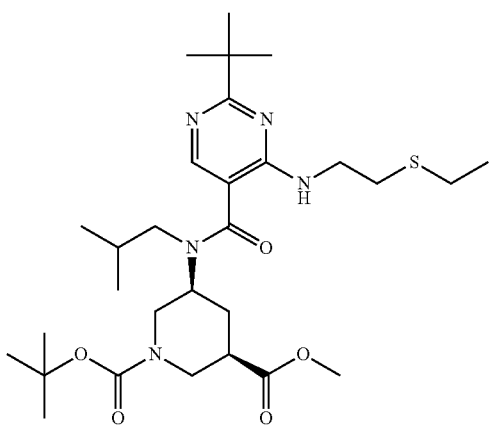

MS (ESI+, m/e) 580 (M+1)

By a method similar to that of Reference Example 125, the following compound (Reference Example 169) was obtained.

Reference Example 169

1-tert-butyl 3-methyl (3R,5S)-5-{[(2-tert-butyl-4-{[3-(methylsulfonyl)propyl]amino}pyrimidin-5-yl)carbonyl](2-methylpropyl)amino}piperidine-1,3-dicarboxylate

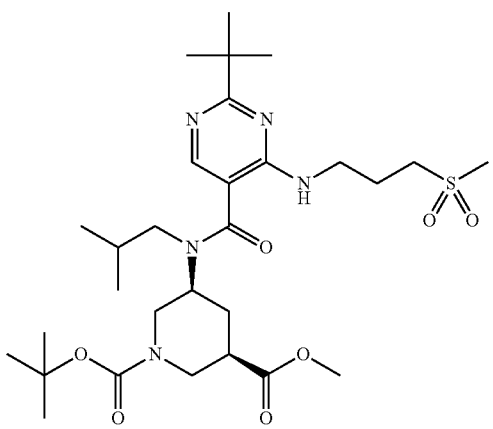

MS (ESI+, m/e) 612 (M+1)

By a method similar to that of Reference Example 38, the following compounds (Reference Examples 170 to 172) were obtained.

Reference Example 170

(3R,5S)-1-(tert-butoxycarbonyl)-5-{[(2-tert-butyl-4-{[2-(methylsulfanyl)ethyl]amino}pyrimidin-5-yl)carbonyl](2-methylpropyl)amino}piperidine-3-carboxylic acid

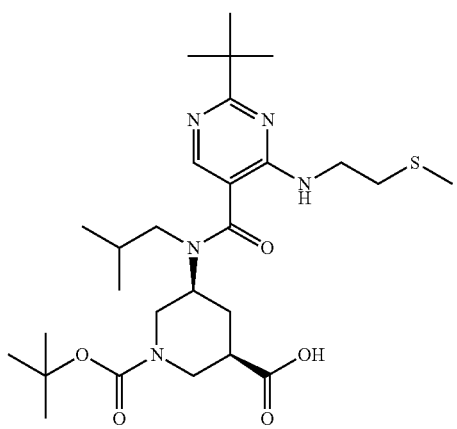

MS (ESI+, m/e) 552 (M+1)

Reference Example 171

(3R,5S)-1-(tert-butoxycarbonyl)-5-{[(2-tert-butyl-4-{[2-(ethylsulfanyl)ethyl]amino}pyrimidin-5-yl)carbonyl](2-methylpropyl)amino}piperidine-3-carboxylic acid

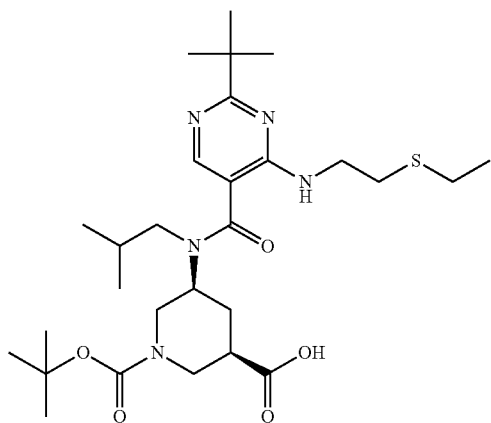

MS (ESI+, m/e) 566 (M+1)

Reference Example 172

(3R,5S)-1-(tert-butoxycarbonyl)-5-{[(2-tert-butyl-4-{[3-(methylsulfonyl)propyl]amino}pyrimidin-5-yl)carbonyl](2-methylpropyl)amino}piperidine-3-carboxylic acid

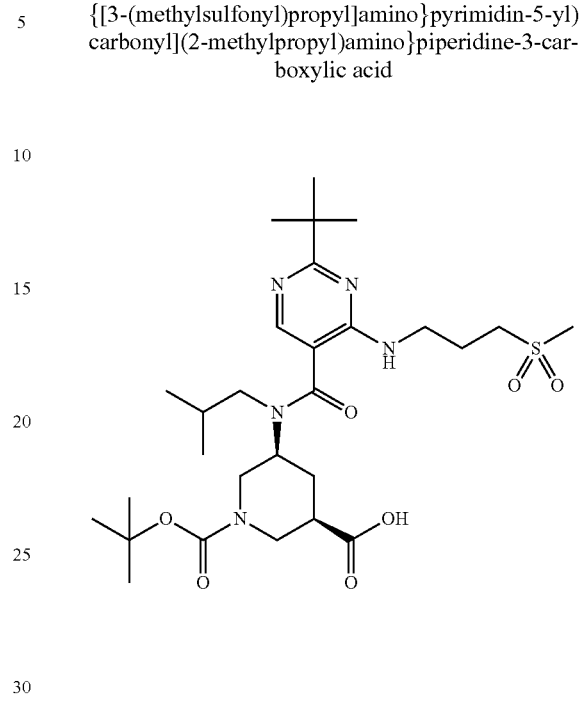

MS (ESI+, m/e) 598 (M+1)

By a method similar to that of Reference Example 50, the following compounds (Reference Examples 173 to 175) were obtained.

Reference Example 173 tert-butyl (3S,5R)-3-{[(2-tert-butyl-4-{[2-(methylsulfanyl)ethyl]amino}pyrimidin-5-yl)carbonyl](2-methylpropyl)amino}-5-(morpholin-4-ylcarbonyl)piperidine-1-carboxylate

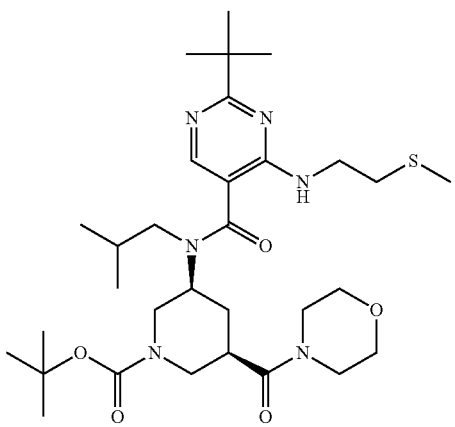

MS (ESI+, m/e) 621 (M+1)

Reference Example 174 tert-butyl (3S,5R)-3-{[(2-tert-butyl-4-{[2-(ethylsulfanyl)ethyl]amino}pyrimidin-5-yl)carbonyl](2-methylpropyl)amino}-5-(morpholin-4-ylcarbonyl)piperidine-1-carboxylate

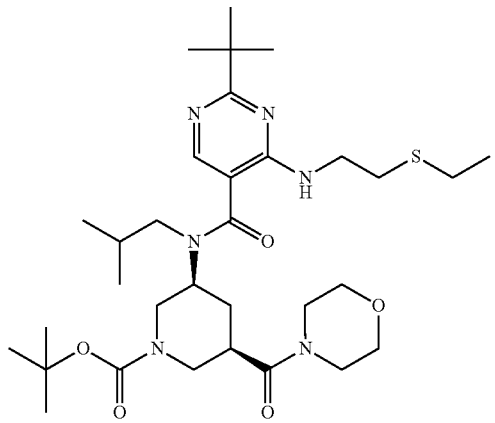

MS (ESI+, m/e) 635 (M+1)

Reference Example 175 tert-butyl (3S,5R)-3-{[(2-tert-butyl-4-{[3-(methylsulfonyl)propyl]amino}pyrimidin-5-yl)carbonyl](2-methylpropyl)amino}-5-(morpholin-4-ylcarbonyl)piperidine-1-carboxylate

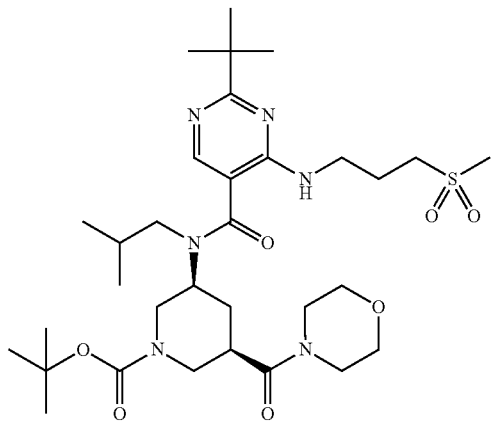

MS (ESI+, m/e) 667 (M+1)

Reference Example 176 tert-butyl (3S,5R)-3-{[(2-tert-butyl-4-{[3-(methylsulfanyl)propyl]amino}pyrimidin-5-yl)carbonyl](2-methylpropyl)amino}-5-[(ethoxycarbonyl)amino]piperidine-1-carboxylate

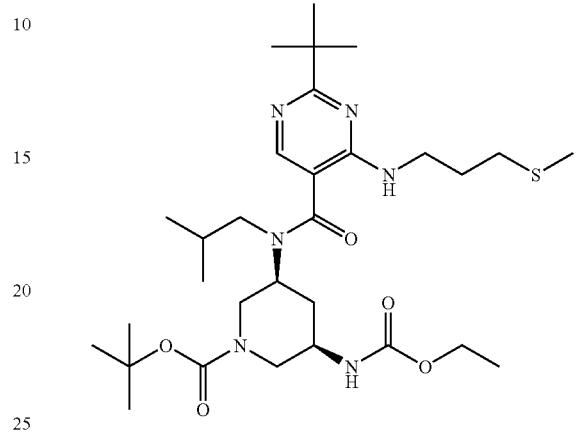

To a solution of tert-butyl (3S,5R)-3-{[(2-tert-butyl-4-{[3-(methylsulfanyl)propyl]amino}pyrimidin-5-yl)carbonyl](2-methylpropyl)amino}-5-{[(2,2,2-trichloroethoxy)carbonyl]amino}piperidine-1-carboxylate (1.12 g) in ethanol (10 ml) was added 4 M aqueous sodium hydroxide solution (10 ml), and the mixture was stirred at 80° C. for 12 hr. The reaction mixture was diluted with water, and the mixture was extracted with ethyl acetate. The extract was washed with saturated brine, and dried over anhydrous magnesium sulfate. The solvent was evaporated under reduced pressure. The residue was subjected to silica gel column chromatography, eluted with ethyl acetate-hexane (10:90-85:15) and concentrated under reduced pressure to give the object compound (119 mg).

MS (ESI+, m/e) 609 (M+1)

Reference Example 177 tert-butyl (3S,5R)-3-{[(2-tert-butyl-4-{[3-(methylsulfanyl)propyl]amino}pyrimidin-5-yl)carbonyl](2-methylpropyl)amino}-5-[(methylsulfonyl)amino]piperidine-1-carboxylate

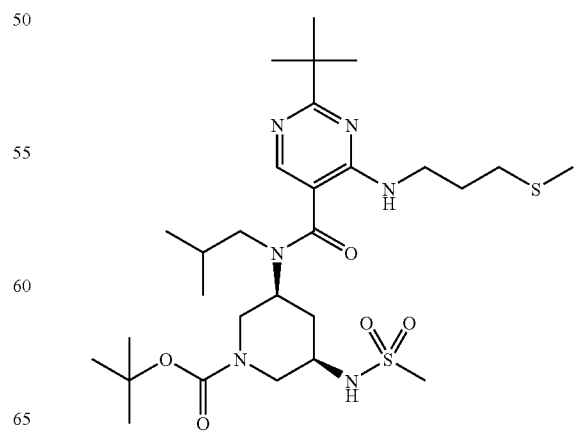

231

To a solution of tert-butyl (3R,5S)-3-amino-5-{[(2-tert-butyl-4-{[3-(methylsulfanyl)propyl]amino}pyrimidin-5-yl)carbonyl](2-methylpropyl)amino}piperidine-1-carboxylate (100 mg) in 1,2-dichloroethane (4 ml) were successively added triethylamine (40 μl) and methanesulfonyl chloride (18 μl), and the mixture was stirred at room temperature for 3 hr. The reaction mixture was diluted with water, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane (10:90-100:0) was concentrated under reduced pressure to give the object compound (51.7 mg).

MS (ESI+, m/e) 615 (M+1)

By a method similar to that of Reference Example 177, the following compounds (Reference Examples 178 and 179) were obtained.

Reference Example 178 tert-butyl (3S,5R)-3-{[(2-tert-butyl-4-{[3-(methylsulfanyl)propyl]amino}pyrimidin-5-yl)carbonyl](2-methylpropyl)amino}-5-[(phenylsulfonyl)amino]piperidine-1-carboxylate

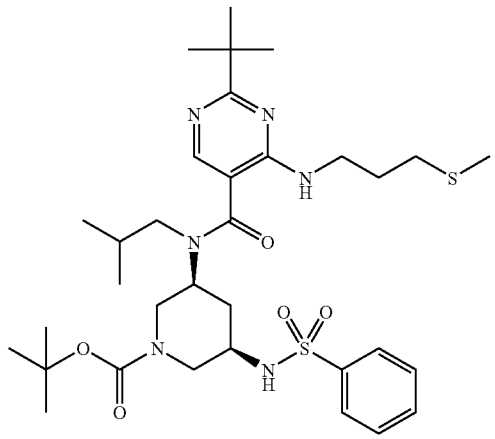

MS (ESI+, m/e) 677 (M+1)

Reference Example 179 tert-butyl (3S,5R)-3-{[(2-tert-butyl-4-{[3-(methylsulfanyl)propyl]amino}pyrimidin-5-yl)carbonyl](2-methylpropyl)amino}-5-[(morpholin-4-ylsulfonyl)amino]piperidine-1-carboxylate

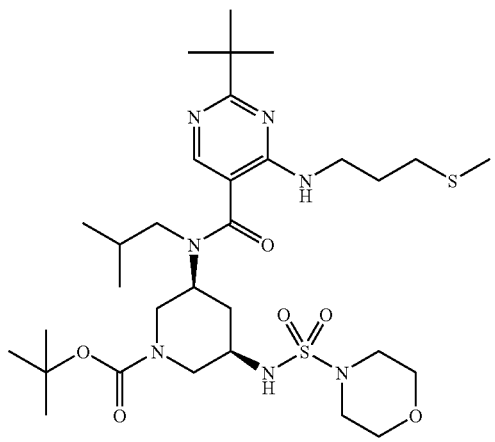

MS (ESI+, m/e) 686 (M+1)

Reference Example 180 tert-butyl (3S,5R)-3-{[(2-tert-butyl-4-{[3-(methylsulfanyl)propyl]amino}pyrimidin-5-yl)carbonyl](2-methylpropyl)amino}-5-[(ethylcarbamoyl)amino]piperidine-1-carboxylate

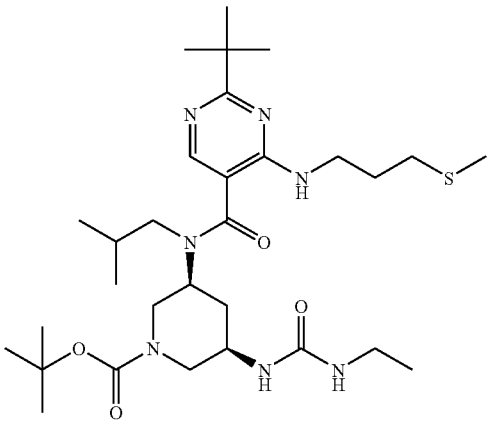

To a solution of tert-butyl (3R,5S)-3-amino-5-{[(2-tert-butyl-4-{[3-(methylsulfanyl)propyl]amino}pyrimidin-5-yl)carbonyl](2-methylpropyl)amino}piperidine-1-carboxylate (97 mg) and N,N-dimethylpyridin-4-amine (33 mg) in 1,2-dichloroethane (4 ml) was added a solution of 4-nitrophenyl chlorocarbonate (55 mg) in 1,2-dichloroethane (1 ml) under ice-cooling and the mixture was stirred at room temperature for 1 hr. Ethylamine (2 M solution in THF, 450 μl) was added, and the reaction mixture was stirred at room temperature for 2 hr. The reaction mixture was diluted with saturated aqueous sodium hydrogen carbonate solution, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane (10:90-100:0) was concentrated under reduced pressure to give the object compound (95.9 mg).

MS (ESI+, m/e) 608 (M+1)

By a method similar to that of Reference Example 180, the following compound (Reference Example 181) was obtained.

Reference Example 181 tert-butyl (3S,5R)-3-{[(2-tert-butyl-4-{[3-(methylsulfanyl)propyl]amino}pyrimidin-5-yl)carbonyl](2-methylpropyl)amino}-5-[(phenylcarbamoyl)amino]piperidine-1-carboxylate

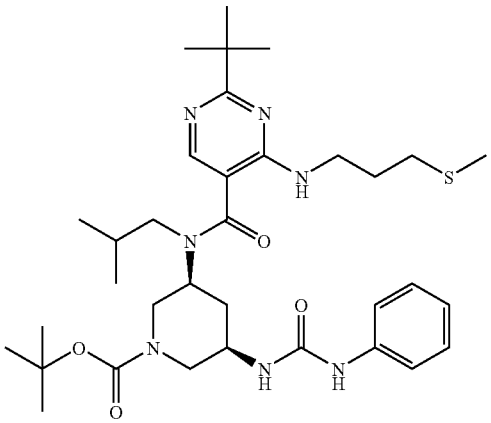

MS (ESI+, m/e) 656 (M+1)

Reference Example 182 tert-butyl (3S,5R)-3-{[(2-tert-butyl-4-{[3-(methylsulfanyl)propyl]amino}pyrimidin-5-yl)carbonyl](2-methylpropyl)amino}-5-(2-oxotetrahydropyrimidin-1(2H)-yl)piperidine-1-carboxylate

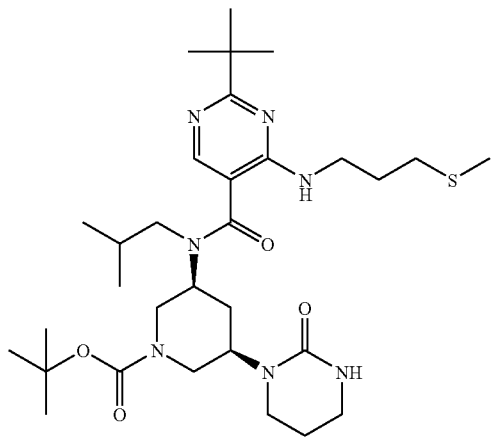

tert-Butyl (3R,5S)-3-amino-5-{[(2-tert-butyl-4-{[3-(methylsulfanyl)propyl]amino}pyrimidin-5-yl)carbonyl](2-methylpropyl)amino}piperidine-1-carboxylate (97 mg) was dissolved in 1,2-dichloroethane (2 ml)-THF (2 ml), chloropropyl isocyanate (25 µl) was added, and the mixture was stirred at room temperature for 1 hr. Potassium tert-butoxide (30 mg) was added and the reaction mixture was stirred at room temperature for 8 hr, and further at 60° C. for 12 hr. The reaction mixture was diluted with water, and the mixture was extracted with ethyl acetate. The extract was washed with saturated brine, and dried over anhydrous magnesium sulfate. The solvent was evaporated under reduced pressure. The residue was dissolved in THF (4 ml), sodium hydride (50% contained, 26 mg) was added under ice-cooling, and the mixture was stirred under ice-cooling for 4 hr. The reaction mixture was diluted with water, and the mixture was extracted with ethyl acetate. The extract was washed with saturated brine, and dried over anhydrous magnesium sulfate. The solvent was evaporated under reduced pressure. The residue was subjected to silica gel column chromatography, eluted with ethyl acetate-methanol (100:0-90:10) and concentrated under reduced pressure to give the object compound (103 mg).

MS (ESI+, m/e) 620 (M+1)

By a method similar to that of Reference Example 44, the following compound (Reference Example 183) was obtained.

Reference Example 183

1-tert-butyl 3-methyl (3R,5S)-5-[(3,3,3-trifluoropropyl)amino]piperidine-1,3-dicarboxylate

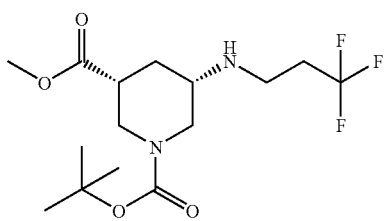

MS (ESI+, m/e) 355 (M+1)

By a method similar to that of Reference Example 46, the following compound (Reference Example 184) was obtained.

Reference Example 184

1-tert-butyl 3-methyl (3R,5S)-5-{[(2-tert-butyl-4-chloropyrimidin-5-yl)carbonyl](3,3,3-trifluoropropyl)amino}piperidine-1,3-dicarboxylate

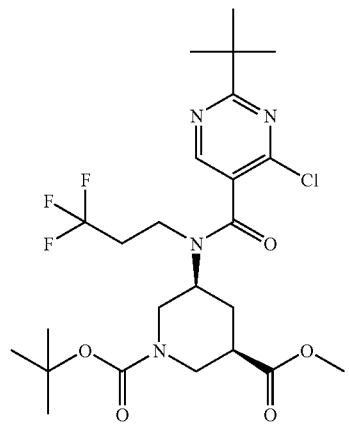

MS (ESI+, m/e) 551 (M+1)

By a method similar to that of Reference Example 48, the following compound (Reference Example 185) was obtained.

Reference Example 185

1-tert-butyl 3-methyl (3R,5S)-5-[({2-tert-butyl-4-[(3-methoxypropyl)amino]pyrimidin-5-yl}carbonyl)(3,3,3-trifluoropropyl)amino]piperidine-1,3-dicarboxylate

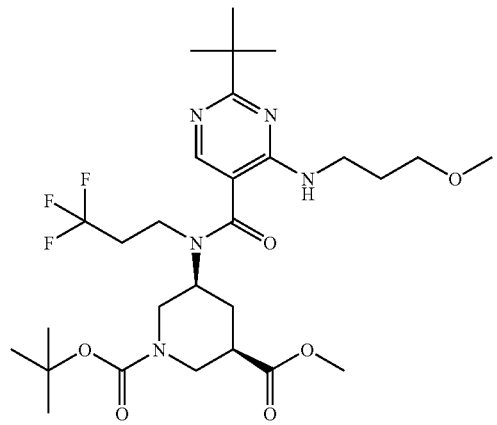

MS (ESI+, m/e) 604 (M+1)

By a method similar to that of Reference Example 38, the following compound (Reference Example 186) was obtained.

Reference Example 186

(3R,5S)-1-(tert-butoxycarbonyl)-5-[({2-tert-butyl-4-[(3-methoxypropyl)amino]pyrimidin-5-yl}carbonyl)(3,3,3-trifluoropropyl)amino]piperidine-3-carboxylic acid

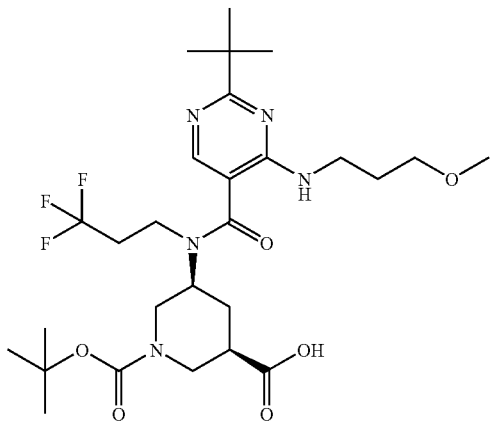

MS (ESI+, m/e) 590 (M+1)

By a method similar to that of Reference Example 50, the following compound (Reference Example 187) was obtained.

Reference Example 187 tert-butyl (3S,5R)-3-[({2-tert-butyl-4-[(3-methoxypropyl)amino]pyrimidin-5-yl}carbonyl)(3,3,3-trifluoropropyl)amino]-5-(morpholin-4-ylcarbonyl)piperidine-1-carboxylate

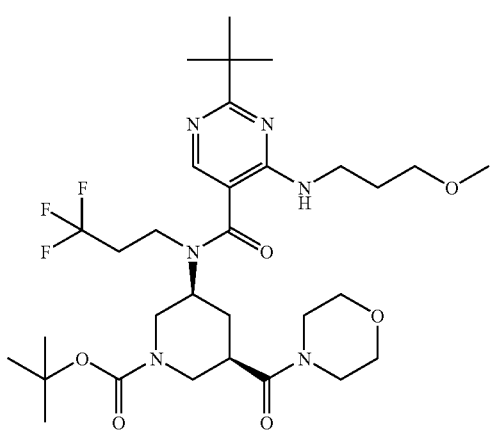

MS (ESI+, m/e) 659 (M+1)

Reference Example 188

(3R,5S)-5-{[(benzyloxy)carbonyl]amino}-1-(tert-butoxycarbonyl)piperidine-3-carboxylic acid

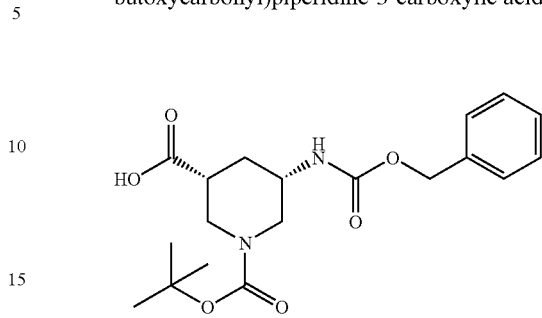

To a solution of 1-tert-butyl 3-methyl (3R,5S)-5-{[(benzyloxy)carbonyl]amino}piperidine-1,3-dicarboxylate (115 g) in methanol (700 ml) was added 1 M aqueous sodium hydroxide solution (350 ml) under ice-cooling and the mixture was stirred at room temperature for 12 hr. The reaction mixture was concentrated under reduced pressure to about 1/3 volume, and the residual aqueous solution was washed with ethyl acetate-hexane (1:1, 600 ml). The aqueous layer was neutralized with 1 M hydrochloric acid, and the mixture was extracted with ethyl acetate. The extract was washed with saturated brine and dried over anhydrous magnesium sulfate. The solvent was evaporated under reduced pressure to give the object compound (98.5 g).

$^1$H-NMR (DMSO-$d_6$) δ 1.33 (1H, br s), 1.40 (9H, s), 2.09 (1H, d), 2.36-2.52 (3H, m), 3.93-4.09 (2H, m), 5.03 (2H, s), 7.28-7.43 (5H, m), 12.52 (1H, br s).

Reference Example 189 tert-butyl (3S,5R)-3-{[(benzyloxy)carbonyl]amino}-5-(3-ethoxy-3-oxopropanoyl)piperidine-1-carboxylate

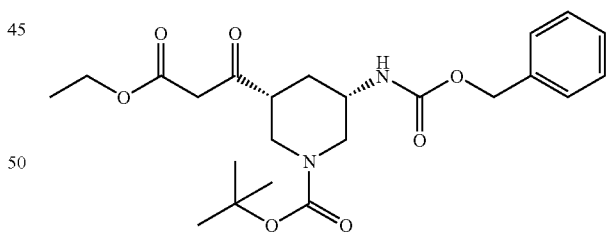

To a solution of (3R,5S)-5-{[(benzyloxy)carbonyl]amino}-1-(tert-butoxycarbonyl)piperidine-3-carboxylic acid (2.25 g) in THF (60 ml) was added 1,1'-carbonylbis(1H-imidazole) (1.20 g) and the mixture was stirred at room temperature for 2 hr. (3-Ethoxy-3-oxopropanoyl)potassium (1.26 g) and magnesium chloride (700 mg) were added and the reaction mixture was stirred with heating to reflux for 4 hr. After cooling to room temperature, the reaction mixture was diluted with 1 M hydrochloric acid, and the mixture was extracted with ethyl acetate. The extract was washed successively with 3.5 M aqueous potassium carbonate solution and saturated brine and dried over anhydrous magnesium sulfate. The solvent was evaporated under reduced pressure. The residue was subjected to silica gel column chromatography, eluted with ethyl acetate-hexane (10:90-80:20) and concentrated under reduced pressure to give the object compound (460 mg).

MS (ESI+, m/e) 449 (M+1)

Reference Example 190 tert-butyl (3S,5R)-3-{[(benzyloxy)carbonyl]amino}-5-[4-(ethoxycarbonyl)-1-methyl-1H-pyrazol-5-yl]piperidine-1-carboxylate

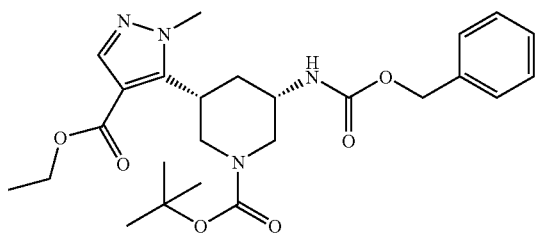

A mixture of tert-butyl (3S,5R)-3-{[(benzyloxy)carbonyl]amino}-5-(3-ethoxy-3-oxopropanoyl)piperidine-1-carboxylate (2.25 g) obtained in Reference Example 189 and N,N-dimethylformamide dimethyl acetal (7 ml) was stirred at 100° C. for 7 hr, and concentrated under reduced pressure. The residue was dissolved in ethanol (16 ml), methylhydrazine (250 mg) was added and the mixture was stirred at room temperature for 14 hr. The reaction mixture was concentrated under reduced pressure. Saturated brine was added and the mixture was extracted with ethyl acetate. The extract was dried over anhydrous magnesium sulfate. The solvent was evaporated under reduced pressure. The residue was subjected to silica gel column chromatography, eluted with ethyl acetate-hexane (10:90-100:0) and concentrated under reduced pressure to give the object compound (436 mg).

MS (ESI+, m/e) 487 (M+1)

By a method similar to that of Reference Example 43, the following compound (Reference Example 191) was obtained.

Reference Example 191 tert-butyl (3S,5R)-3-amino-5-[4-(ethoxycarbonyl)-1-methyl-1H-pyrazol-5-yl]piperidine-1-carboxylate

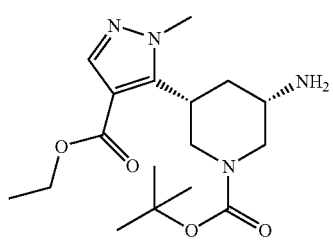

MS (ESI+, m/e) 353 (M+1)

By a method similar to that of Reference Example 44, the following compound (Reference Example 192) was obtained.

Reference Example 192 tert-butyl (3R,5S)-3-[4-(ethoxycarbonyl)-1-methyl-1H-pyrazol-5-yl]-5-[(2-methylpropyl)amino]piperidine-1-carboxylate

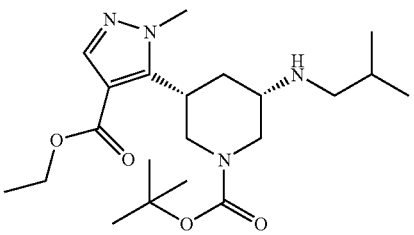

MS (ESI+, m/e) 409 (M+1)

By a method similar to that of Reference Example 46, the following compound (Reference Example 193) was obtained.

Reference Example 193 tert-butyl (3S,5R)-3-{[(2-tert-butyl-4-chloropyrimidin-5-yl)carbonyl](2-methylpropyl)amino}-5-[4-(ethoxycarbonyl)-1-methyl-1H-pyrazol-5-yl]piperidine-1-carboxylate

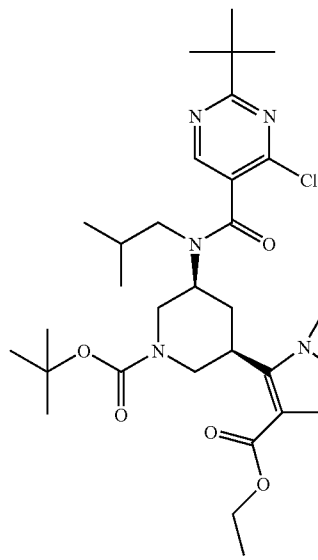

MS (ESI+, m/e) 606 (M+1)

By a method similar to that of Reference Example 48, the following compound (Reference Example 194) was obtained.

Reference Example 194 tert-butyl (3S,5R)-3-[({2-tert-butyl-4-[(3-methoxypropyl)amino]pyrimidin-5-yl}carbonyl)(2-methylpropyl)amino]-5-[4-(ethoxycarbonyl)-1-methyl-1H-pyrazol-5-yl]piperidine-1-carboxylate

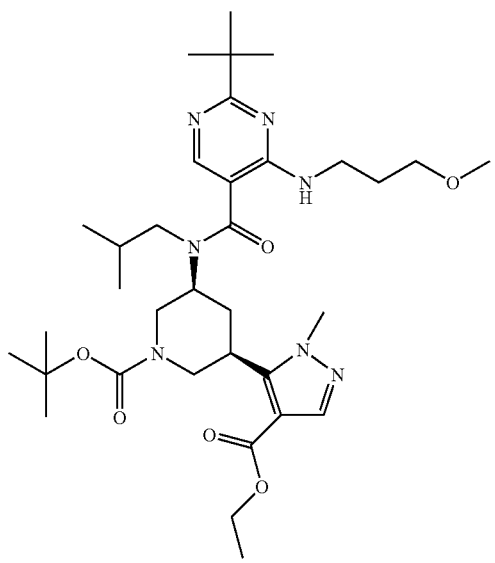

MS (ESI+, m/e) 658 (M+1)

Reference Example 195 benzyl (3S,5R)-3-[({2-tert-butyl-4-[(3-methoxypropyl)amino]pyrimidin-5-yl}carbonyl)(2-methylpropyl)amino]-5-{[(2,2,2-trichloroethoxy)carbonyl]amino}piperidine-1-carboxylate

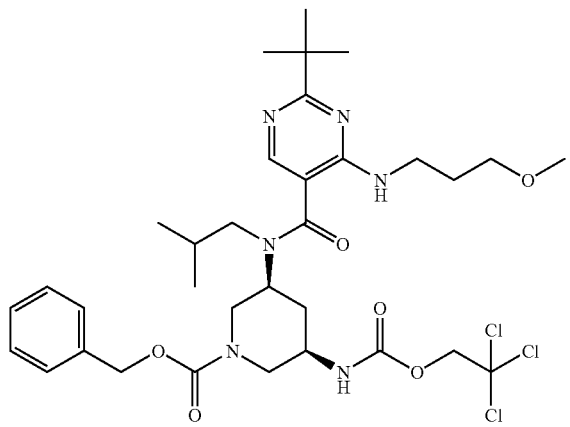

A solution of tert-butyl (3S,5R)-3-[({2-tert-butyl-4-[(3-methoxypropyl)amino]pyrimidin-5-yl}carbonyl)(2-methylpropyl)amino]-5-{[(2,2,2-trichloroethoxy)carbonyl]amino}piperidine-1-carboxylate (1.00 g) in 1 M hydrogen chloride-ethyl acetate (30 ml) was stirred at room temperature for 1 day, and concentrated under reduced pressure. The residue was suspended in THF (20 ml), triethylamine (500 μl) and benzyl chlorocarbonate (250 μl) were successively added under ice-cooling, and the mixture was stirred at room temperature for 3 days. The reaction mixture was diluted with water, and the mixture was extracted with ethyl acetate. The extract was washed with saturated brine and dried over anhydrous magnesium sulfate. The solvent was evaporated under reduced pressure. The residue was subjected to silica gel column chromatography, eluted with ethyl acetate-hexane (10:90-80:20) and concentrated under reduced pressure to give the object compound (550 mg).

MS (ESI+, m/e) 731 (M+1)

Reference Example 196 benzyl (3R,5S)-3-amino-5-[({2-tert-butyl-4-[(3-methoxypropyl)amino]pyrimidin-5-yl}carbonyl)(2-methylpropyl)amino]piperidine-1-carboxylate

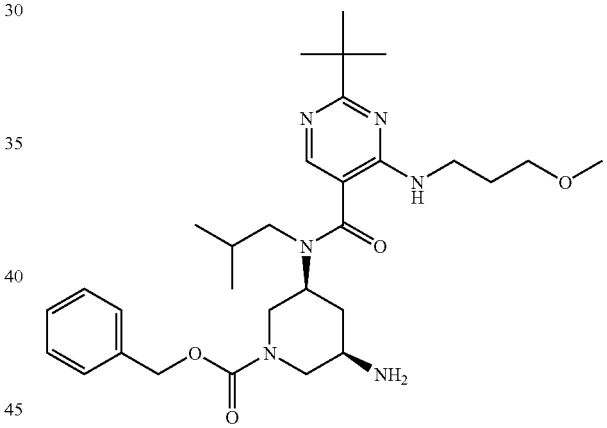

To a solution of benzyl (3S,5R)-3-[({2-tert-butyl-4-[(3-methoxypropyl)amino]pyrimidin-5-yl}carbonyl)(2-methylpropyl)amino]-5-{[(2,2,2-trichloroethoxy)carbonyl]amino}piperidine-1-carboxylate (550% mg) in acetic acid (14 ml) was added zinc-copper couple (200 mg) and the mixture was stirred at room temperature for 3 hr. Insoluble material was filtered off through celite, and the filtrate was concentrated under reduced pressure. Toluene was added to the residue, and the mixture was concentrated under reduced pressure. The obtained residue was diluted with saturated aqueous sodium hydrogen carbonate solution and the mixture was extracted with ethyl acetate. The extract was washed with saturated brine and dried over anhydrous magnesium sulfate. The solvent was evaporated under reduced pressure to give the object compound (420 mg).

MS (ESI+, m/e) 555 (M+1)

Reference Example 197 benzyl (3S,5R)-3-[({2-tert-butyl-4-[(3-methoxypropyl)amino]pyrimidin-5-yl}carbonyl)(2-methylpropyl)amino]-5-[(2-hydroxy-2-phenylethyl)amino]piperidine-1-carboxylate

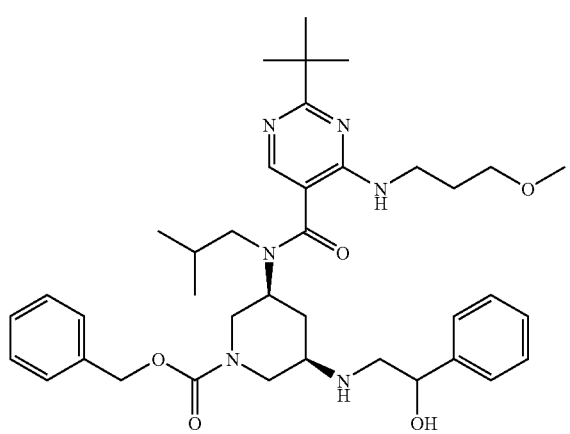

Benzyl (3R,5S)-3-amino-5-[({2-tert-butyl-4-[(3-methoxypropyl)amino]pyrimidin-5-yl}carbonyl)(2-methylpropyl)amino]piperidine-1-carboxylate (100 mg) and 2-phenyloxirane (55 μl) were dissolved in acetonitrile (5 ml), and lithium perchlorate (55 mg) was added. The mixture was stirred at room temperature for 3 days and thereafter stirred at 80° C. for 7 hr. The reaction mixture was concentrated under reduced pressure. The residue was subjected to silica gel column chromatography, eluted with ethyl acetate-hexane-methanol (10:90:0-100:0:0-85:0:15) and concentrated under reduced pressure to give the object compound (53.2 mg).

MS (ESI+, m/e) 675 (M+1)

By a method similar to that of Reference Example 115, the following compound (Reference Example 198) was obtained.

Reference Example 198

1-tert-butyl 3-methyl (3R,5S)-5-{[(benzyloxy)carbonyl](2-methylpropyl)amino}piperidine-1,3-dicarboxylate

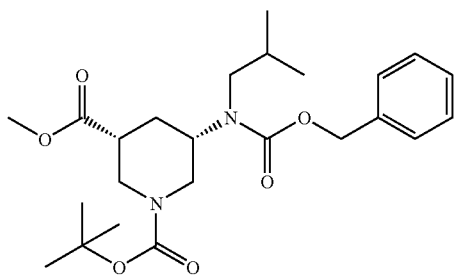

MS (ESI+, m/e) 449 (M+1)

Reference Example 199

1-tert-butyl 3-methyl (5S)-5-{[(benzyloxy)carbonyl](2-methylpropyl)amino}-3-methylpiperidine-1,3-dicarboxylate

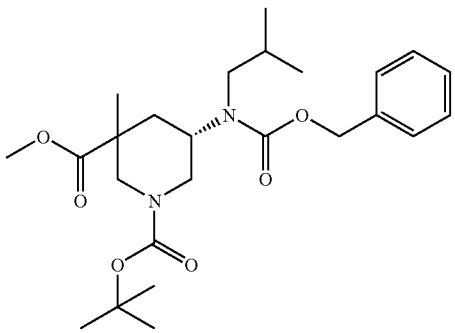

1-tert-Butyl 3-methyl (3R,5S)-5-{[(benzyloxy)carbonyl](2-methylpropyl)amino}piperidine-1,3-dicarboxylate (430 mg) and iodomethane (90 μl) were dissolved in DMF (5 ml), sodium hydride (50% contained, 70 mg) was added under ice-cooling, and the mixture was stirred at room temperature for 10 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure to give the object compound (500 mg).

MS (ESI+, m/e) 463 (M+1)

By a method similar to that of Reference Example 118, the following compound (Reference Example 200) was obtained.

Reference Example 200

1-tert-butyl 3-methyl (5S)-3-methyl-5-[(2-methylpropyl)amino]piperidine-1,3-dicarboxylate

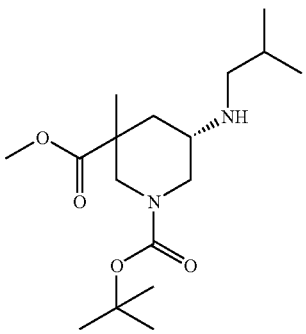

MS (ESI+, m/e) 329 (M+1)

By a method similar to that of Reference Example 46, the following compound (Reference Example 201) was obtained.

Reference Example 201

1-tert-butyl 3-methyl (5S)-5-{[(2-tert-butyl-4-chloro-pyrimidin-5-yl)carbonyl](2-methylpropyl)amino}-3-methylpiperidine-1,3-dicarboxylate

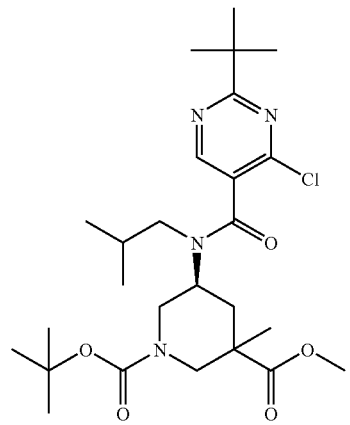

MS (ESI+, m/e) 526 (M+1)

By a method similar to that of Reference Example 48, the following compound (Reference Example 202) was obtained.

Reference Example 202

1-tert-butyl 3-methyl (5S)-5-[({2-tert-butyl-4-[(3-methoxypropyl)amino]pyrimidin-5-yl}carbonyl)(2-methylpropyl)amino]-3-methylpiperidine-1,3-dicarboxylate

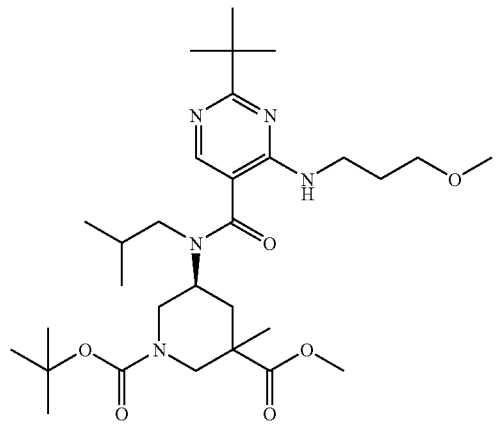

MS (ESI+, m/e) 578 (M+1)

By a method similar to that of Reference Example 38, the following compound (Reference Example 203) was obtained.

Reference Example 203

(5S)-1-(tert-butoxycarbonyl)-5-[({2-tert-butyl-4-[(3-methoxypropyl)amino]pyrimidin-5-yl}carbonyl)(2-methylpropyl)amino]-3-methylpiperidine-3-carboxylic acid

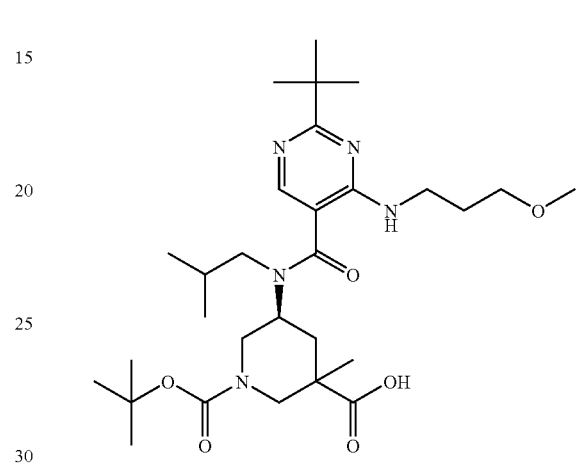

MS (ESI+, m/e) 564 (M+1)

By a method similar to that of Reference Example 50, the following compound (Reference Example 204) was obtained.

Reference Example 204 tert-butyl (5S)-5-[({2-tert-butyl-4-[(3-methoxypropyl)amino]pyrimidin-5-yl}carbonyl)(2-methylpropyl)amino]-3-methyl-3-(morpholin-4-ylcarbonyl)piperidine-1-carboxylate

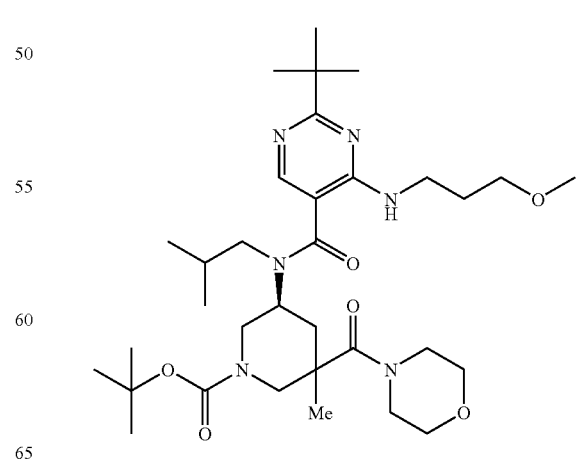

MS (ESI+, m/e) 633 (M+1)

By a method similar to that of Reference Example 91, the following compound (Reference Example 205) was obtained.

Reference Example 205 ethyl 2-[(3-methoxypropyl)amino]-7,7-dimethyl-6,7-dihydro-5H-cyclopenta[b]pyridine-3-carboxylate

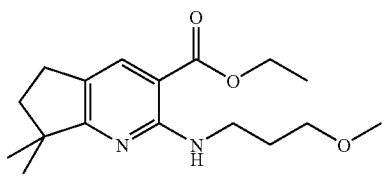

MS (ESI+, m/e) 307 (M+1)

By a method similar to that of Reference Example 93, the following compound (Reference Example 206) was obtained.

Reference Example 206

2-[(3-methoxypropyl)amino]-7,7-dimethyl-6,7-dihydro-5H-cyclopenta[b]pyridine-3-carboxylic acid

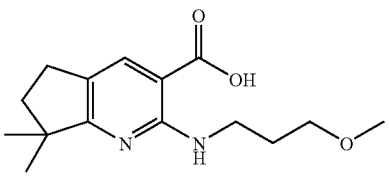

MS (ESI+, m/e) 279 (M+1)

Reference Example 207

(3R,5S)-5-{[(benzyloxy)carbonyl]amino}-1-(tert-butoxycarbonyl)piperidine-3-carboxylic acid

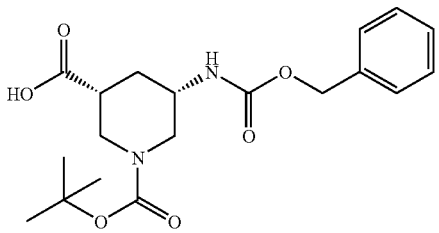

To a solution of 1-tert-butyl 3-methyl (3R,5S)-5-{[(benzyloxy)carbonyl]amino}piperidine-1,3-dicarboxylate (115 g) in methanol (700 ml) was added 1 M aqueous sodium hydroxide solution (350 ml) under ice-cooling and the mixture was stirred at room temperature for 12 hr. The reaction mixture was concentrated under reduced pressure to about 1/3 volume, and the residual aqueous solution was washed with ethyl acetate-hexane (1:1, 600 ml). The aqueous layer was neutralized with 1 M hydrochloric acid and the mixture was extracted with ethyl acetate. The extract was washed with saturated brine and dried over anhydrous magnesium sulfate. The solvent was evaporated under reduced pressure to give the object compound (98.5 g).

$^1$H-NMR (DMSO-$d_6$) δ 1.33 (1H, br s), 1.40 (9H, s), 2.09 (1H, d), 2.36-2.52 (3H, m), 3.93-4.09 (2H, m), 5.03 (2H, s), 7.28-7.43 (5H, m), 12.52 (1H, br s).

Reference Example 208 tert-butyl (3S,5R)-3-{[(benzyloxy)carbonyl]amino}-5-(morpholin-4-ylcarbonyl)piperidine-1-carboxylate

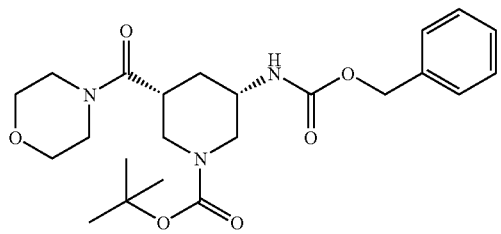

(3R,5S)-5-{[(Benzyloxy)carbonyl]amino}-1-(tert-butoxycarbonyl)piperidine-3-carboxylic acid (49.2 g), morpholine (11.4 ml), 1H-benzotriazol-1-ol (10.0 g) and triethylamine (40 ml) were dissolved in DMF (250 ml), WSC.HCl (30.0 g) was added and the mixture was stirred at room temperature for 4 days. The reaction mixture was poured into water, and the mixture was extracted with ethyl acetate. The extract was washed successively with saturated aqueous sodium hydrogen carbonate solution and saturated brine, and dried over anhydrous magnesium sulfate. The solvent was evaporated under reduced pressure to give the object compound (62.9 g).

$^1$H-NMR (CDCl$_3$) δ 1.46 (9H, s), 1.69 (2H, br s), 2.04 (1H, s), 2.73 (2H, br s), 2.79-2.96 (1H, m), 3.52-3.65 (6H, m), 3.69 (2H, d), 3.67 (1H, br s), 4.04 (1H, d), 5.09 (2H, s), 5.40 (1H, br s), 7.25-7.41 (5H, m).

Reference Example 209 tert-butyl (3S,5R)-3-[(2-methylpropyl)amino]-5-(morpholin-4-ylcarbonyl)piperidine-1-carboxylate

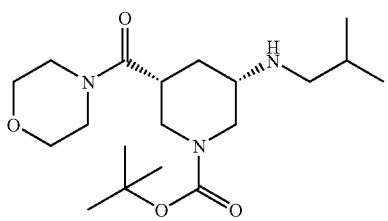

tert-Butyl (3S,5R)-3-{[(benzyloxy)carbonyl]amino}-5-(morpholin-4-ylcarbonyl)piperidine-1-carboxylate (58 g) and palladium(II) hydroxide-carbon (5 g) were suspended in methanol (400 ml), and the mixture was stirred at room temperature for 16 hr under a hydrogen atmosphere (1 atm). The palladium catalyst was filtered off, and the filtrate was concentrated under reduced pressure. The obtained residue and acetic acid (8.8 ml) were dissolved in methanol (400 ml), 2-methylpropanal (14.0 ml) was added and the mixture was stirred at room temperature for 1 hr. Sodium triacetoxyborohydride (40.4 g) was added to the reaction mixture and the mixture was stirred at room temperature for 2 hr. The reaction mixture was concentrated under reduced pressure, and the concentrated solution was basified with 3.5 M aqueous potassium carbonate solution, and the mixture was extracted with ethyl acetate. The extract was washed with water and saturated brine, and is dried over anhydrous magnesium sulfate. The solvent was evaporated under reduced pressure. The residue was subjected to silica gel column chromatography, and the fraction eluted with ethyl acetate-hexane (1:5) to ethyl acetate 100% to ethyl acetate-methanol (9:1) was concentrated under reduced pressure to give the object compound (33.3 g).

$^1$H-NMR (CDCl$_3$) δ 0.90 (6H, d), 1.46 (9H, s), 1.54 (1H, d), 1.69 (1H, dt), 1.96-2.12 (2H, m), 2.23-2.37 (1H, m), 2.47 (3H, d), 2.66 (1H, d), 3.61 (1H, br s), 3.55 (2H, d), 3.69 (5H, ddd), 4.01-4.46 (2H, m).

Reference Example 210 tert-butyl (3S,5R)-3-[({2-[(3-methoxypropyl)amino]-7,7-dimethyl-6,7-dihydro-5H-cyclopenta[b]pyridin-3-yl}carbonyl)(2-methylpropyl)amino]-5-(morpholin-4-ylcarbonyl)piperidine-1-carboxylate

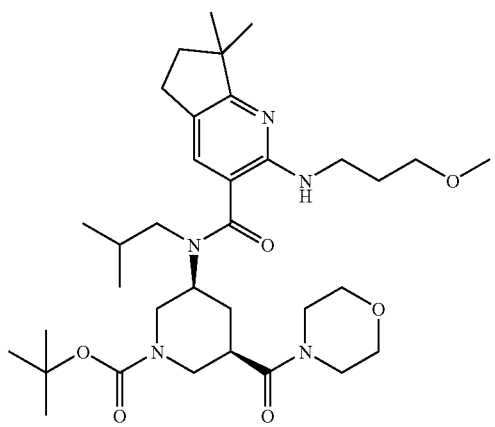

2-[(3-Methoxypropyl)amino]-7,7-dimethyl-6,7-dihydro-5H-cyclopenta[b]pyridine-3-carboxylic acid (190 mg), tert-butyl (3S,5R)-3-[(2-methylpropyl)amino]-5-(morpholin-4-ylcarbonyl)piperidine-1-carboxylate (255 mg) obtained in Reference Example 209 and N,N-diisopropylethylamine (180 μl) were dissolved in 1,2-dichloroethane (6 ml), chloro-N,N,N',N'-tetramethylformamidinium hexafluorophosphate (230 mg) was added and the mixture was stirred at room temperature for 3 days. The reaction mixture was diluted with saturated aqueous sodium hydrogen carbonate solution and the mixture was extracted with ethyl acetate. The extract was washed with saturated brine and dried over anhydrous magnesium sulfate. The solvent was evaporated under reduced pressure. The residue was subjected to silica gel column chromatography, and the fraction eluted with ethyl acetate-hexane (10:90-100:0) was concentrated under reduced pressure to give the object compound (210 mg).

MS (ESI+, m/e) 630 (M+1)

Example 110

Method J

2-[(furan-2-ylmethyl)amino]-N-(2-methylpropyl)-N-piperidin-3-yl-5,6,7,8-tetrahydroquinoline-3-carboxamide dihydrochloride

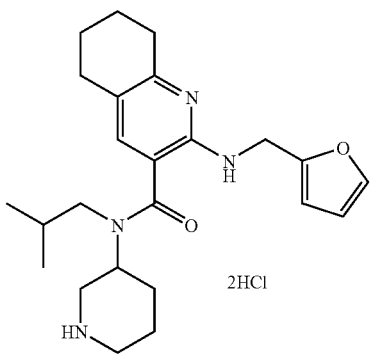

tert-Butyl 3-[({2-[(furan-2-ylmethyl)amino]-5,6,7,8-tetrahydroquinolin-3-yl}carbonyl)(2-s methylpropyl)amino]piperidine-1-carboxylate (25.0 mg) was dissolved in 1 M hydrogen chloride-ethyl acetate (3 ml), and the mixture was stirred at room temperature for 1 hr. The reaction mixture was concentrated, and the obtained residue was subjected to reversed-phase preparative HPLC. The fraction containing the object compound was diluted with 3.5 M aqueous potassium carbonate solution, and the mixture was extracted with ethyl acetate. The extract was washed with saturated brine, and dried over anhydrous magnesium sulfate. The solvent was evaporated under reduced pressure. The residue was dissolved in 1 M hydrogen chloride-ethyl acetate (1 ml), and concentrated under reduced pressure to give the object compound (20.7 mg).

MS (ESI+, m/e) 411 (M+1)

By a method similar to that of the above-mentioned Example 110 (Method J), the compounds of Examples 111 to 158 below were obtained. The respective compounds were isolated and purified as necessary by a known means such as phase transfer, pH conversion, solvent extraction, silica gel column chromatography, reversed-phase preparative HPLC and the like. The final products were isolated as hydrochloride as in Method J by treating with a hydrogen chloride-ethyl acetate solution.

Example 111

2-[(furan-2-ylmethyl)amino]-7,7-dimethyl-N-(2-methylpropyl)-N-piperidin-3-yl-6,7-dihydro-5H-cyclopenta[b]pyridine-3-carboxamide dihydrochloride

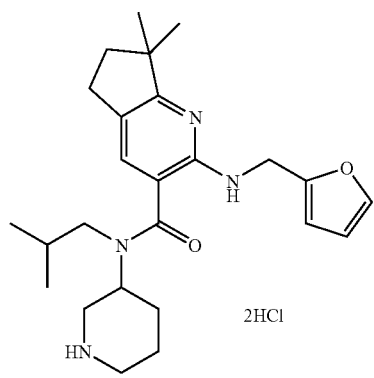

MS (ESI+, m/e) 425 (M+1)

Example 112

2-[(furan-2-ylmethyl)amino]-N-(2-methylpropyl)-N-piperidin-3-yl-6,7,8,9-tetrahydro-5H-cyclohepta[b]pyridine-3-carboxamide dihydrochloride

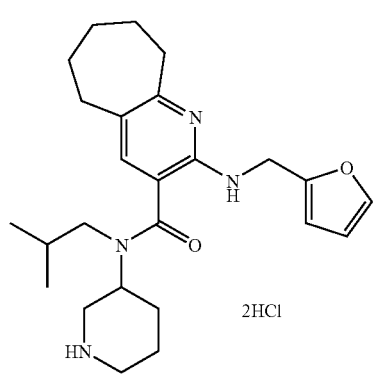

MS (ESI+, m/e) 425 (M+1)

Example 113

2-[(furan-2-ylmethyl)amino]-8,8-dimethyl-N-(2-methylpropyl)-N-piperidin-3-yl-5,6,7,8-tetrahydroquinoline-3-carboxamide dihydrochloride

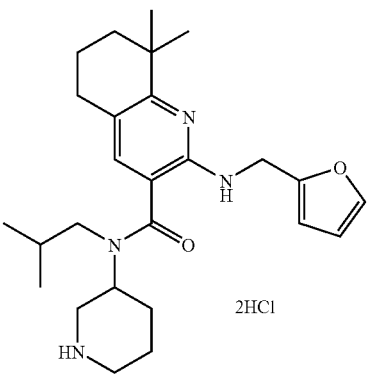

MS (ESI+, m/e) 439 (M+1)

Example 114

2-[(furan-2-ylmethyl)amino]-5,5,7-trimethyl-N-(2-methylpropyl)-N-piperidin-3-yl-6,7-dihydro-5H-cyclopenta[b]pyridine-3-carboxamide dihydrochloride

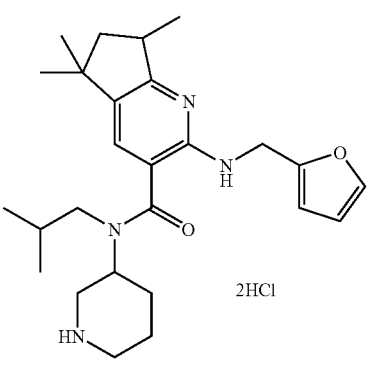

MS (ESI+, m/e) 439 (M+1)

Example 115

{5-[({2-tert-butyl-4-[(furan-2-ylmethyl)amino]pyrimidin-5-yl}carbonyl)(2-methylpropyl)amino]piperidin-3-yl}methyl acetate dihydrochloride

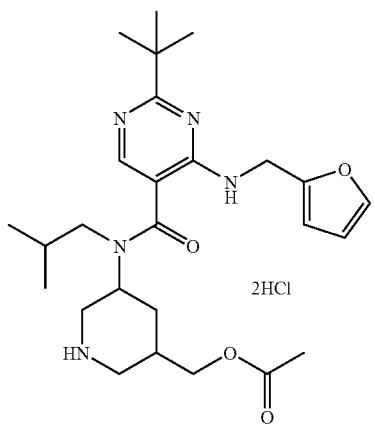

MS (ESI+, m/e) 486 (M+1)

Example 116

2-tert-butyl-4-[(furan-2-ylmethyl)amino]-N-[5-(1H-imidazol-1-ylmethyl)piperidin-3-yl]-N-(2-methylpropyl)pyrimidine-5-carboxamide dihydrochloride

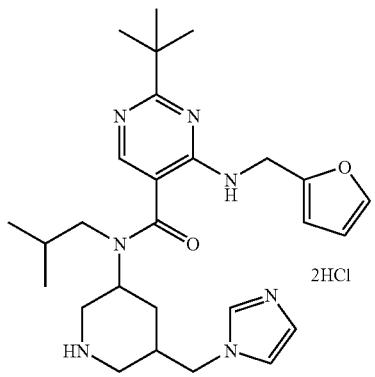

MS (ESI+, m/e) 494 (M+1)

Example 117

2-tert-butyl-N-[(3S*,5R*)-5-cyanopiperidin-3-yl]-4-[(furan-2-ylmethyl)amino]-N-(2-methylpropyl)pyrimidine-5-carboxamide dihydrochloride

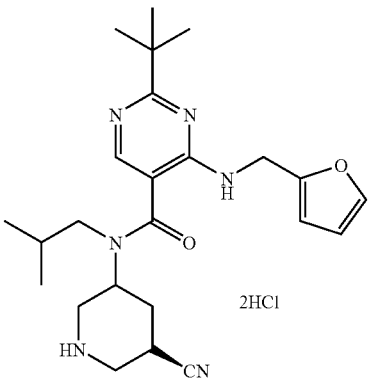

MS (ESI+, m/e) 439 (M+1)

Example 118

2-tert-butyl-4-[(furan-2-ylmethyl)amino]-N-(2-methylpropyl)-N-[(3S*,5R*)-5-(2H-tetrazol-5-yl)piperidin-3-yl]pyrimidine-5-carboxamide dihydrochloride

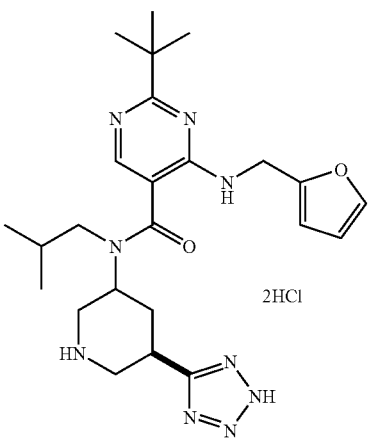

MS (ESI+, m/e) 482 (M+1)

Example 119

2-tert-butyl-4-[(furan-2-ylmethyl)amino]-N-(2-methylpropyl)-N-[(3S*,5R*)-5-(5-oxo-4,5-dihydro-1,2,4-oxadiazol-3-yl)piperidin-3-yl]pyrimidine-5-carboxamide dihydrochloride

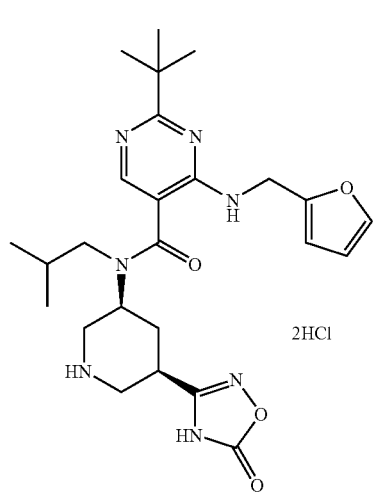

MS (ESI+, m/e) 498 (M+1)

Example 120

2-tert-butyl-N-{5-[(ethylsulfanyl)methyl]piperidin-3-yl}-4-[(furan-2-ylmethyl)amino]-N-(2-methylpropyl)pyrimidine-5-carboxamide dihydrochloride

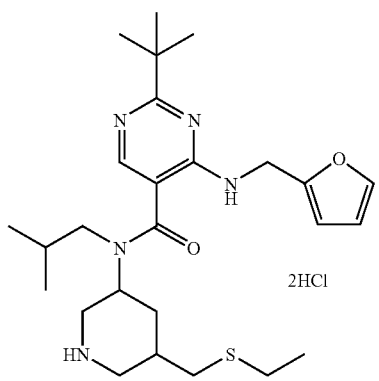

MS (ESI+, m/e) 488 (M+1)

Example 121

2-tert-butyl-4-[(furan-2-ylmethyl)amino]-N-(2-methylpropyl)-N-{5-[(pyridin-2-yloxy)methyl]piperidin-3-yl}pyrimidine-5-carboxamide trihydrochloride

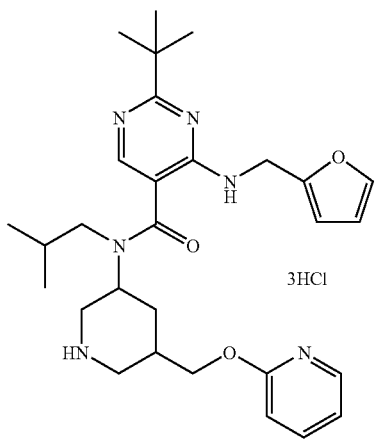

MS (ESI+, m/e) 521 (M+1)

Example 122

2-tert-butyl-4-[(furan-2-ylmethyl)amino]-N-(2-methylpropyl)-N-[(3S*,5R*)-5-(morpholin-4-ylmethyl)piperidin-3-yl]pyrimidine-5-carboxamide trihydrochloride

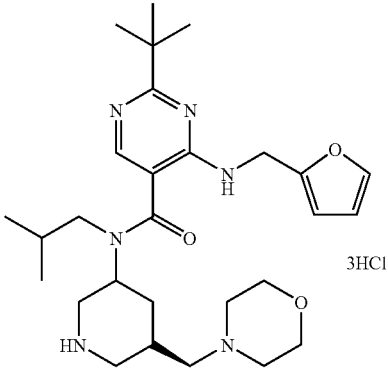

MS (ESI+, m/e) 513 (M+1)

Example 123

2-tert-butyl-4-[(furan-2-ylmethyl)amino]-N-(2-methylpropyl)-N-[(3S*,5S*)-5-(morpholin-4-ylmethyl)piperidin-3-yl]pyrimidine-5-carboxamide trihydrochloride

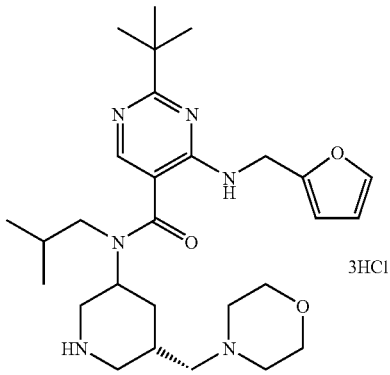

MS (ESI+, m/e) 513 (M+1)

Example 124

2-tert-butyl-N-{(3S*,5R*)-5-[(ethylsulfonyl)methyl]piperidin-3-yl}-4-[(furan-2-ylmethyl)amino]-N-(2-methylpropyl)pyrimidine-5-carboxamide dihydrochloride

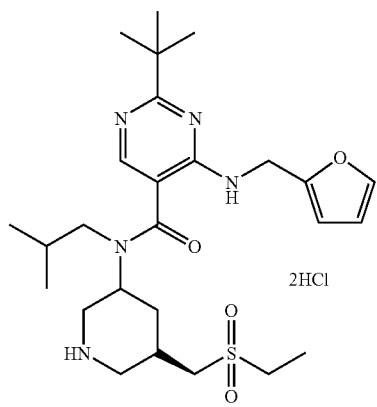

MS (ESI+, m/e) 520 (M+1)

Example 125

2-tert-butyl-N-{(3S*,5S*)-5-[(ethylsulfonyl)methyl]piperidin-3-yl}-4-[(furan-2-ylmethyl)amino]-N-(2-methylpropyl)pyrimidine-5-carboxamide dihydrochloride

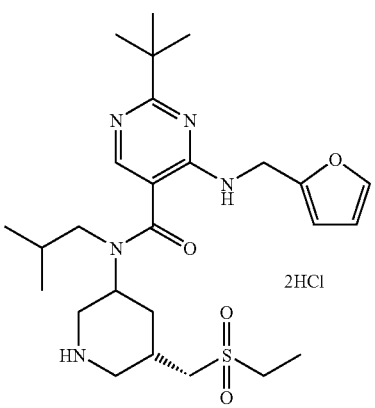

MS (ESI+, m/e) 520 (M+1)

Example 126

2-tert-butyl-4-[(furan-2-ylmethyl)amino]-N-{(3S*,5R*)-5-[(3-hydroxyazetidin-1-yl)carbonyl]piperidin-3-yl}-N-(2-methylpropyl)pyrimidine-5-carboxamide dihydrochloride

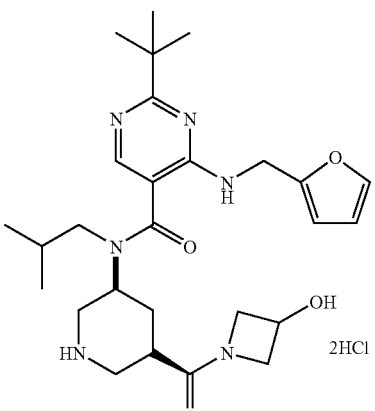

MS (ESI+, m/e) 513 (M+1)

257

Example 127 methyl {(3R,5S)-5-[({2-tert-butyl-4-[(furan-2-ylmethyl)amino]pyrimidin-5-yl}carbonyl)(2-methylpropyl)amino]piperidin-3-yl}carbamate dihydrochloride

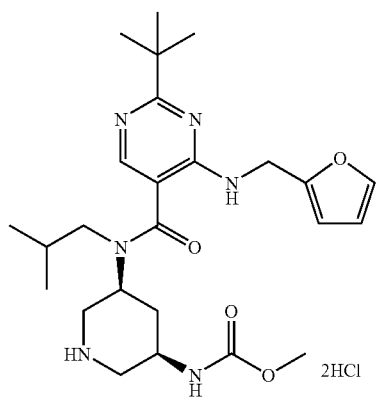

MS (ESI+, m/e) 487 (M+1)

Example 128

2-tert-butyl-4-[(furan-2-ylmethyl)amino]-N-(2-methylpropyl)-N-[(3S,5R)-5-(1H-1,2,4-triazol-3-yl)piperidin-3-yl]pyrimidine-5-carboxamide dihydrochloride

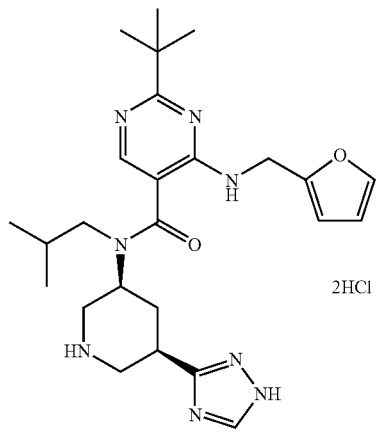

MS (ESI+, m/e) 481 (M+1)

258

Example 129 benzyl {(3R,5S)-5-[({2-tert-butyl-4-[(furan-2-ylmethyl)amino]pyrimidin-5-yl}carbonyl)(2-methylpropyl)amino]piperidin-3-yl}carbamate dihydrochloride

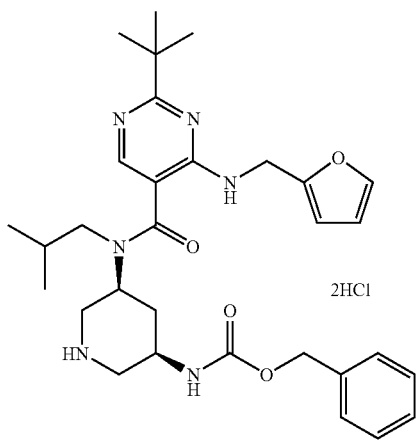

MS (ESI+, m/e) 563 (M+1)

Example 130

N-{(3R,5S)-5-[({2-tert-butyl-4-[(furan-2-ylmethyl)amino]pyrimidin-5-yl}carbonyl)(2-methylpropyl)amino]piperidin-3-yl}morpholine-4-carboxamide dihydrochloride

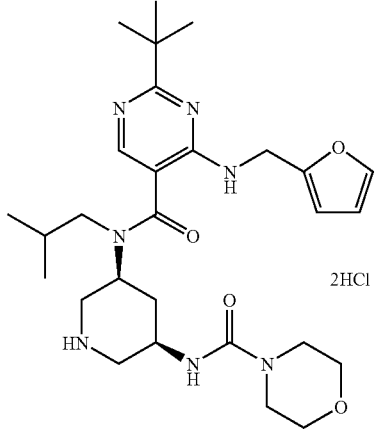

MS (ESI+, m/e) 542 (M+1)

Example 131

2-tert-butyl-N-[(3R,5S)-5-carbamoylpiperidin-3-yl]-
4-[(furan-2-ylmethyl)amino]-N-(2-methylpropyl)
pyrimidine-5-carboxamide dihydrochloride

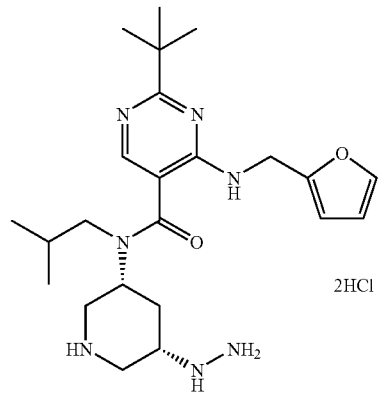

MS (ESI+, m/e) 457 (M+1)

Example 132

2-tert-butyl-N-[(3S,5R)-5-carbamoylpiperidin-3-yl]-
4-[(furan-2-ylmethyl)amino]-N-(2-methylpropyl)
pyrimidine-5-carboxamide dihydrochloride

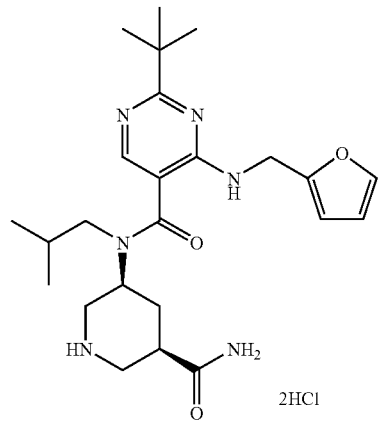

MS (ESI+, m/e) 457 (M+1)

Example 133

N-[(3S,5R)-5-(acetylamino)piperidin-3-yl]-2-tert-
butyl-4-[(furan-2-ylmethyl)amino]-N-(2-methylpro-
pyl)pyrimidine-5-carboxamide dihydrochloride

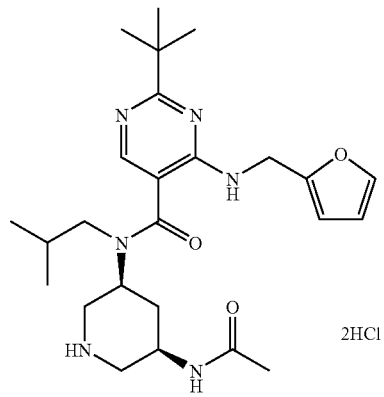

MS (ESI+, m/e) 471 (M+1)

Example 134

2-tert-butyl-4-[(furan-2-ylmethyl)amino]-N-(2-meth-
ylpropyl)-N-{(3S,5R)-5-[(tetrahydro-2H-pyran-4-
ylcarbonyl)amino]piperidin-3-yl}pyrimidine-5-car-
boxamide dihydrochloride

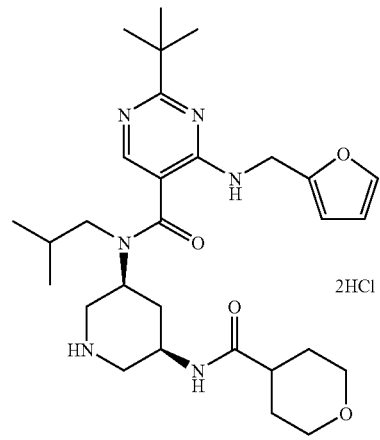

MS (ESI+, m/e) 541 (M+1)

Example 135

N-{(3R,5S)-5-[({2-tert-butyl-4-[(furan-2-ylmethyl)amino]pyrimidin-5-yl}carbonyl)(2-methylpropyl)amino]piperidin-3-yl}piperidine-1,4-dicarboxamide dihydrochloride

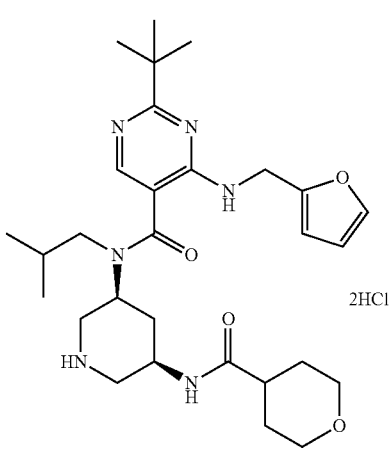

MS (ESI+, m/e) 583 (M+1)

Example 136 methyl (3R,5S)-5-{[(2-tert-butyl-4-{[3-(methylsulfanyl)propyl]amino}pyrimidin-5-yl)carbonyl](2-methylpropyl)amino}piperidine-3-carboxylate dihydrochloride

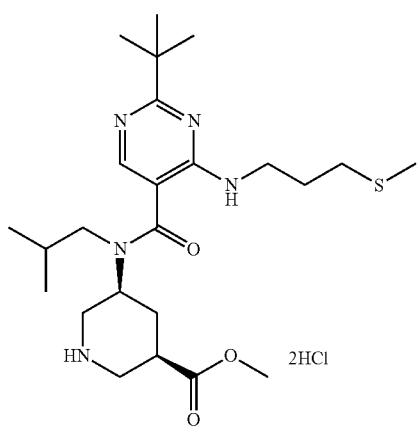

MS (ESI+, m/e) 480 (M+1)

Example 137

2-tert-butyl-N-[(3S,5R)-5-carbamoylpiperidin-3-yl]-N-(2-methylpropyl)-4-{[3-(methylsulfanyl)propyl]amino}pyrimidine-5-carboxamide dihydrochloride

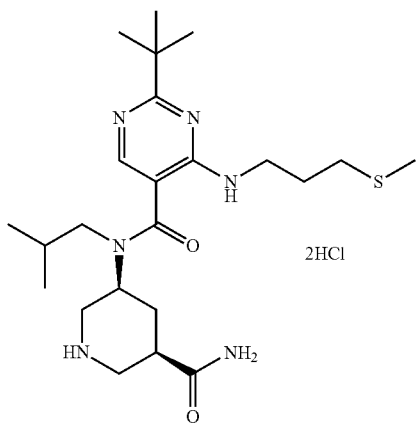

MS (ESI+, m/e) 465 (M+1)

Example 138

2-tert-butyl-N-(2-methylpropyl)-4-{[3-(methylsulfanyl)propyl]amino}-N-[(3S,5R)-5-(morpholin-4-ylcarbonyl)piperidin-3-yl]pyrimidine-5-carboxamide dihydrochloride

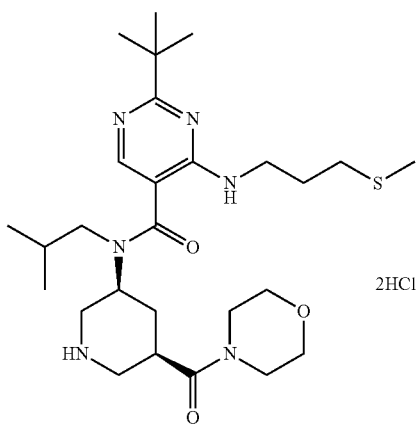

MS (ESI+, m/e) 535 (M+1)

Example 139

2-tert-butyl-N-[(3S,5R)-5-carbamoylpiperidin-3-yl]-N-(2-methylpropyl)-4-(pentylamino)pyrimidine-5-carboxamide dihydrochloride

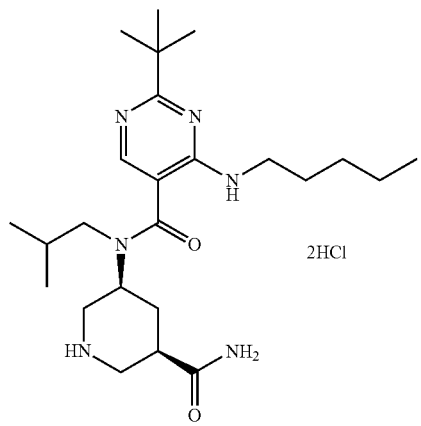

MS (ESI+, m/e) 447 (M+1)

Example 140

2-tert-butyl-N-(2-methylpropyl)-N-[(3S,5R)-5-(morpholin-4-ylcarbonyl)piperidin-3-yl]-4-(pentylamino)pyrimidine-5-carboxamide dihydrochloride

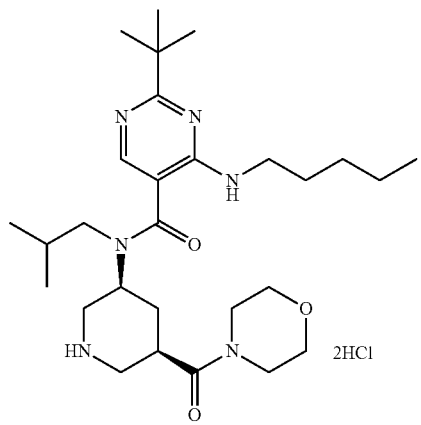

MS (ESI+, m/e) 517 (M+1)

Example 141

2-tert-butyl-N-(2-methylpropyl)-4-{[3-(methylsulfanyl)propyl]amino}-N-[(3S,5R)-5-(4H-1,2,4-triazol-3-yl)piperidin-3-yl]pyrimidine-5-carboxamide dihydrochloride

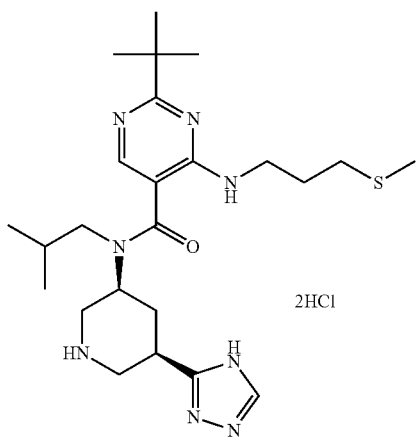

MS (ESI+, m/e) 489 (M+1)

Example 142

2-tert-butyl-N-(2-methylpropyl)-4-{[3-(methylsulfanyl)propyl]amino}-N-[(3S,5R)-5-(2-oxoimidazolidin-1-yl)piperidin-3-yl]pyrimidine-5-carboxamide dihydrochloride

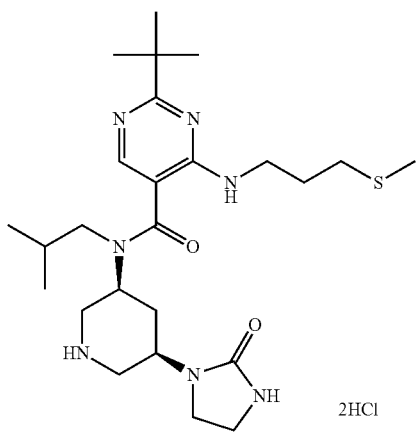

MS (ESI+, m/e) 506 (M+1)

Example 143

2-tert-butyl-N-(2-methylpropyl)-4-{[2-(methylsulfanyl)ethyl]amino}-N-[(3S,5R)-5-(morpholin-4-ylcarbonyl)piperidin-3-yl]pyrimidine-5-carboxamide dihydrochloride

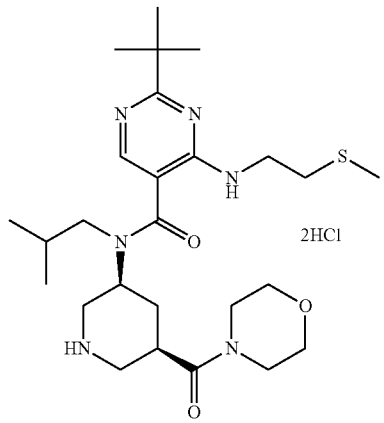

MS (ESI+, m/e) 521 (M+1)

Example 144

2-tert-butyl-4-{[2-(ethylsulfanyl)ethyl]amino}-N-(2-methylpropyl)-N-[(3S,5R)-5-(morpholin-4-ylcarbonyl)piperidin-3-yl]pyrimidine-5-carboxamide dihydrochloride

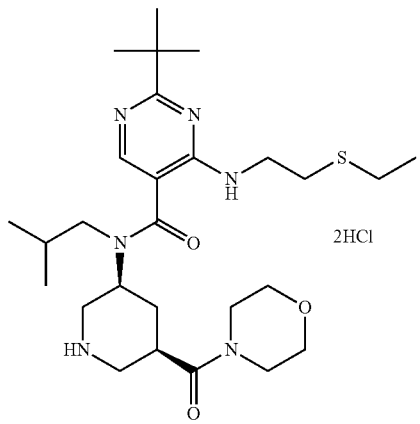

MS (ESI+, m/e) 535 (M+1)

Example 145

2-tert-butyl-N-(2-methylpropyl)-4-{[3-(methylsulfonyl)propyl]amino}-N-[(3S,5R)-5-(morpholin-4-ylcarbonyl)piperidin-3-yl]pyrimidine-5-carboxamide dihydrochloride

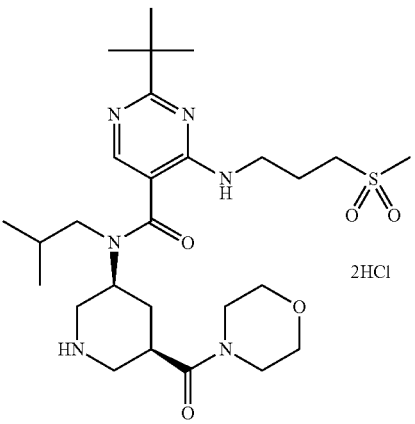

MS (ESI+, m/e) 567 (M+1)

Example 146 ethyl [(3R,5S)-5-{[(2-tert-butyl-4-{[3-(methylsulfanyl)propyl]amino}pyrimidin-5-yl)carbonyl](2-methylpropyl)amino}piperidin-3-yl]carbamate dihydrochloride

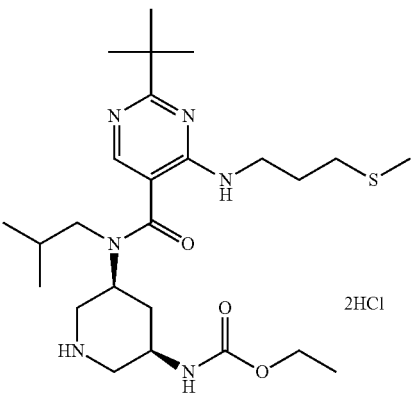

MS (ESI+, m/e) 509 (M+1)

Example 147

2-tert-butyl-N-(2-methylpropyl)-4-{[3-(methylsulfa-nyl)propyl]amino}-N-{(3S,5R)-5-[(methylsulfonyl)amino]piperidin-3-yl}pyrimidine-5-carboxamide dihydrochloride

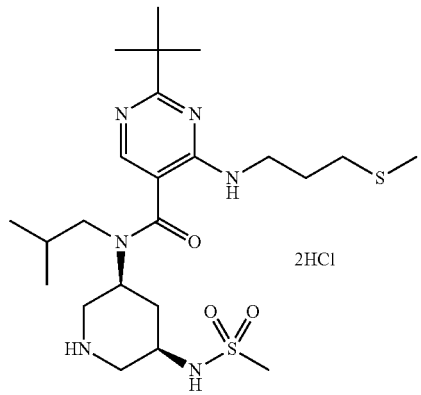

MS (ESI+, m/e) 515 (M+1)

Example 148

2-tert-butyl-N-(2-methylpropyl)-4-{[3-(methylsulfa-nyl)propyl]amino}-N-{(3S,5R)-5-[(phenylsulfonyl)amino]piperidin-3-yl}pyrimidine-5-carboxamide dihydrochloride

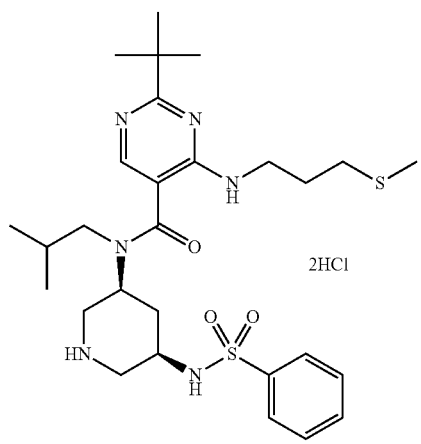

MS (ESI+, m/e) 577 (M+1)

Example 149

2-tert-butyl-N-(2-methylpropyl)-4-{[3-(methylsulfa-nyl)propyl]amino}-N-{(3S,5R)-5-[(morpholin-4-ylsulfonyl)amino]piperdin-3-yl}pyrimidine-5-carboxamide dihydrochloride

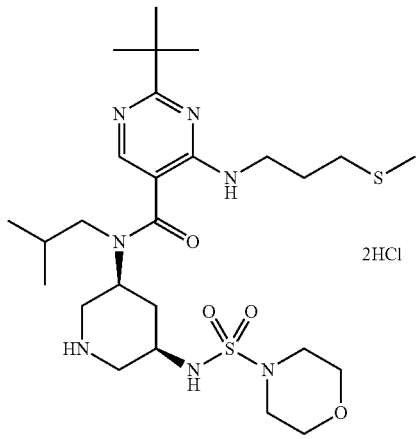

MS (ESI+, m/e) 586 (M+1)

Example 150

2-tert-butyl-N-{(3S,5R)-5-[(ethylcarbamoyl)amino]piperidin-3-yl}-N-(2-methylpropyl)-4-{[3-(methylsulfanyl)propyl]amino}pyrimidine-5-carboxamide dihydrochloride

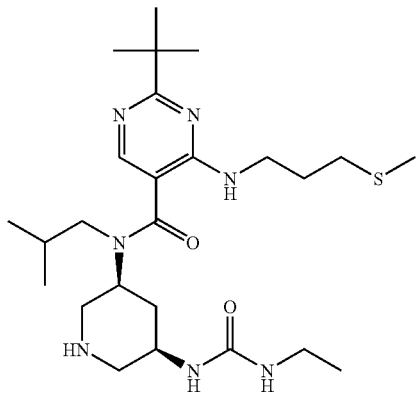

MS (ESI+, m/e) 508 (M+1)

Example 151

2-tert-butyl-N-(2-methylpropyl)-4-{[3-(methylsulfanyl)propyl]amino}-N-{(3S,5R)-5-[(phenylcarbamoyl)amino]piperidin-3-yl}pyrimidine-5-carboxamide dihydrochloride

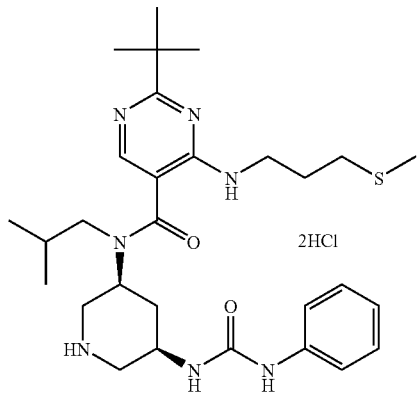

MS (ESI+, m/e) 556 (M+1)

Example 152

2-tert-butyl-N-(2-methylpropyl)-4-{[3-(methylsulfanyl)propyl]amino}-N-[(3S,5R)-5-(2-oxotetrahydropyrimidin-1(2H)-yl)piperidin-3-yl]pyrimidine-5-carboxamide dihydrochloride

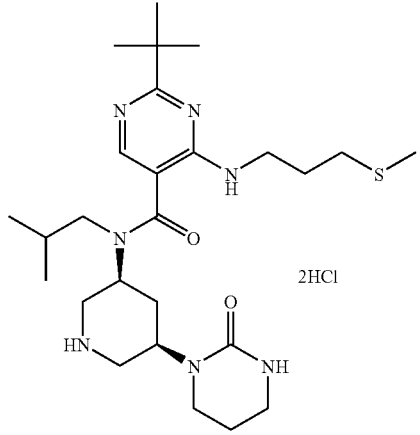

MS (ESI+, m/e) 520 (M+1)

Example 153 methyl (3S,5R)-5-[({2-tert-butyl-4-[(furan-2-ylmethyl)amino]pyrimidin-5-yl}carbonyl)(2-methylpropyl)amino]piperidine-3-carboxylate dihydrochloride

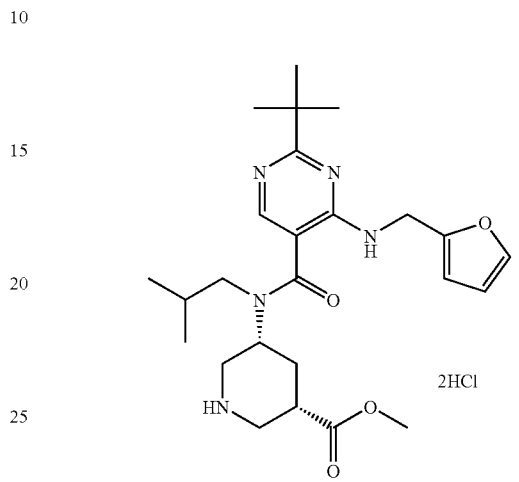

MS (ESI+, m/e) 472 (M+1)

Example 154 methyl (3R,5S)-5-[({2-tert-butyl-4-[(furan-2-ylmethyl)amino]pyrimidin-5-yl}carbonyl)(2-methylpropyl)amino]piperidine-3-carboxylate dihydrochloride

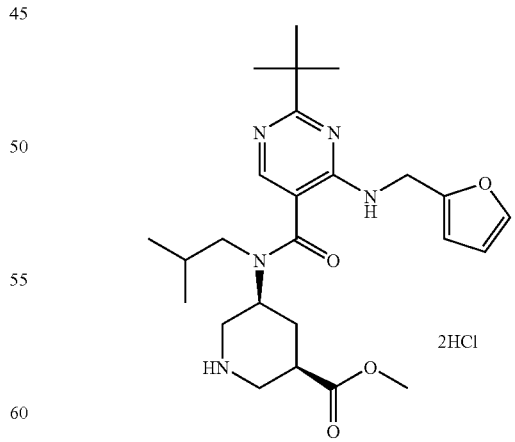

MS (ESI+, m/e) 472 (M+1)

Example 155 ethyl 5-{(3R,5S)-5-[({2-tert-butyl-4-[(3-methoxypropyl)amino]pyrimidin-5-yl}carbonyl)(2-methylpropyl)amino]piperidin-3-yl}-1-methyl-1H-pyrazole-4-carboxylate dihydrochloride

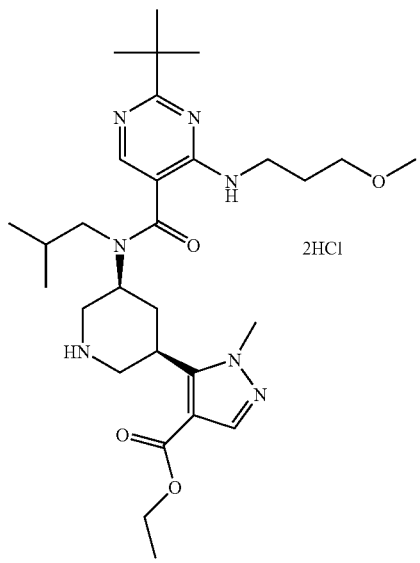

MS (ESI+, m/e) 558 (M+1)

Example 156

2-tert-butyl-4-[(3-methoxypropyl)amino]-N-[(3S,5R)-5-(morpholin-4-ylcarbonyl)piperidin-3-yl]-N-(3,3,3-trifluoropropyl)pyrimidine-5-carboxamide dihydrochloride

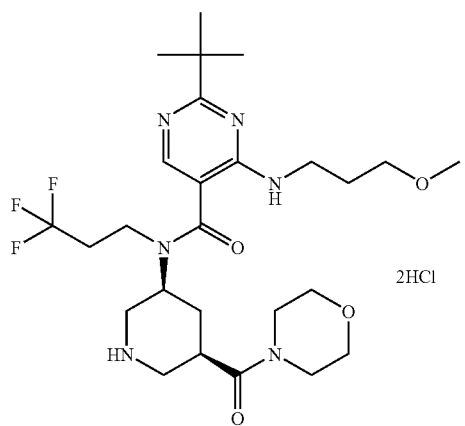

MS (ESI+, m/e) 559 (M+1)

Example 157

2-tert-butyl-4-[(3-methoxypropyl)amino]-N-[(3S)-5-methyl-5-(morpholin-4-ylcarbonyl)piperidin-3-yl]-N-(2-methylpropyl)pyrimidine-5-carboxamide dihydrochloride

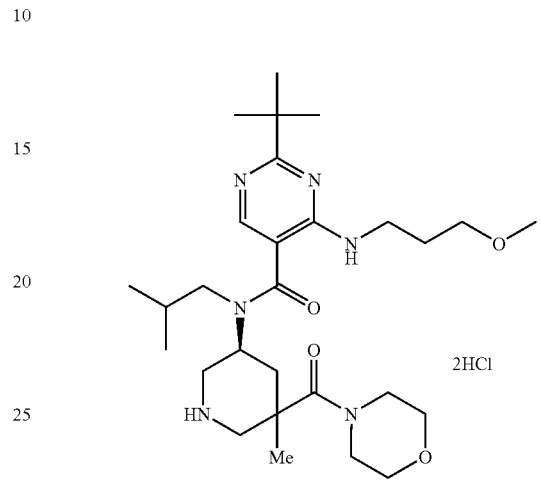

MS (ESI+, m/e) 533 (M+1)

Example 158

2-[(3-methoxypropyl)amino]-7,7-dimethyl-N-(2-methylpropyl)-N-[(3S,5R)-5-(morpholin-4-ylcarbonyl)piperidin-3-yl]-6,7-dihydro-5H-cyclopenta[b]pyridine-3-carboxamide dihydrochloride

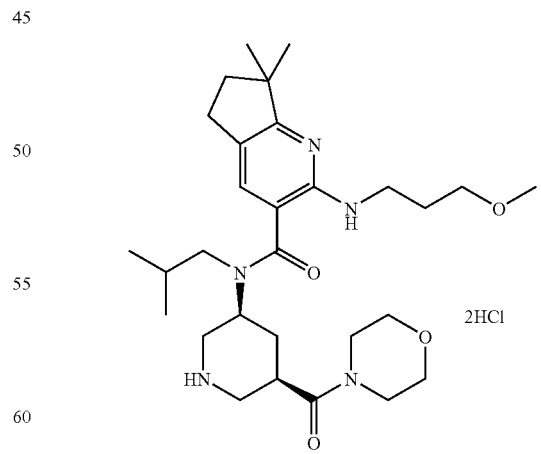

MS (ESI+, m/e) 530 (M+1)

Example 159

Method K 2-tert-butyl-4-[(furan-2-ylmethyl)amino]-N-[5-(hydroxymethyl)piperidin-3-yl]-N-(2-methylpropyl)pyrimidine-5-carboxamide

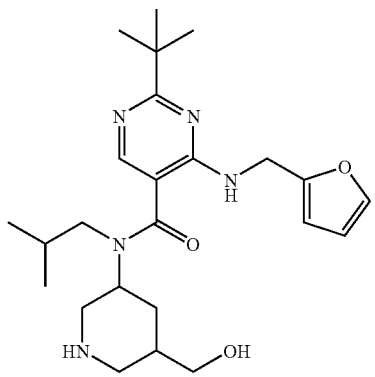

tert-Butyl 3-[({2-tert-butyl-4-[(furan-2-ylmethyl)amino]pyrimidin-5-yl}carbonyl)(2-methylpropyl)amino]-5-(hydroxymethyl)piperidine-1-carboxylate (50.0 mg) was dissolved in trifluoroacetic acid (50% 1,2-dichloroethane solution, 4 ml), and the mixture was stirred at room temperature for 1 hr. The reaction mixture was basified with saturated aqueous potassium carbonate solution, and the mixture was extracted with ethyl acetate. The extract was washed with saturated brine and dried over anhydrous magnesium sulfate. The solvent was evaporated under reduced pressure. The residue was subjected to silica gel column chromatography, and the fraction eluted with ethyl acetate-hexane-methanol (50:50:0-100:0:0-85:0:15) was concentrated under reduced pressure to give the object compound (24.4 mg).

MS (ESI+, m/e) 444 (M+1)

By a method similar to that of the above-mentioned Example 159 (Method K), the compounds of Examples 160 to 166 below were obtained. The respective compounds were isolated and purified as necessary by a known means such as phase transfer, pH conversion, solvent extraction, silica gel column chromatography, reversed-phase preparative HPLC and the like.

Example 160

2-tert-butyl-4-[(furan-2-ylmethyl)amino]-N-[(3S*,5R*)-5-(5-methyl-1,3,4-oxadiazol-2-yl)piperidin-3-yl]-N-(2-methylpropyl)pyrimidine-5-carboxamide

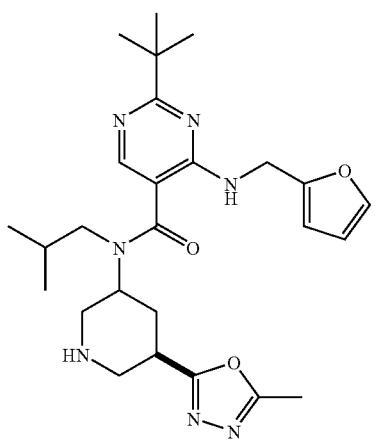

MS (ESI+, m/e) 496 (M+1)

Example 161

2-tert-butyl-4-[(furan-2-ylmethyl)amino]-N-(2-methylpropyl)-N-[(3S*,5R*)-5-(5-phenyl-1,3,4-oxadiazol-2-yl)piperidin-3-yl]pyrimidine-5-carboxamide

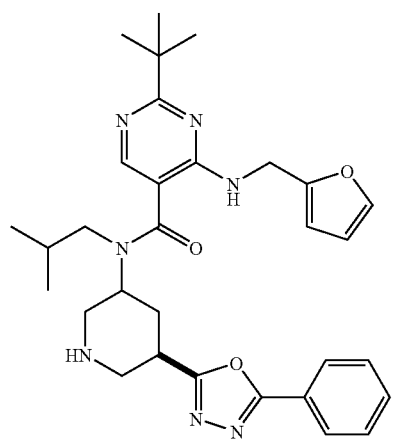

MS (ESI+, m/e) 558 (M+1)

Example 162

2-tert-butyl-4-[(furan-2-ylmethyl)amino]-N-(2-methylpropyl)-N-[(3S*,5R*)-5-(1,2,4-oxadiazol-3-yl)piperidin-3-yl]pyrimidine-5-carboxamide

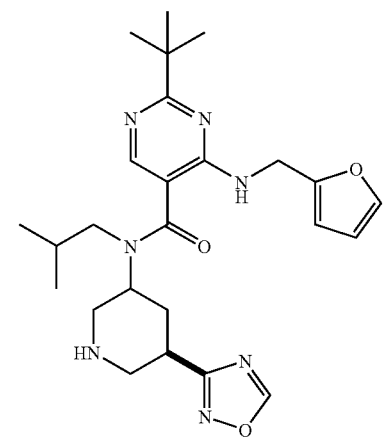

MS (ESI+, m/e) 482 (M+1)

Example 163

2-tert-butyl-4-[(furan-2-ylmethyl)amino]-N-[(3S,5R)-5-({[4-(hydroxymethyl)tetrahydro-2H-pyran-4-yl]carbonyl}amino)piperidin-3-yl]-N-(2-methylpropyl)pyrimidine-5-carboxamide

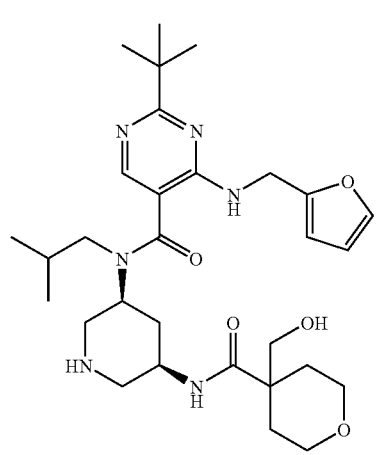

MS (ESI+, m/e) 571 (M+1)

Example 164

2-tert-butyl-4-[(furan-2-ylmethyl)amino]-N-[(3S,5R)-5-{[(4-hydroxycyclohexyl)carbonyl]amino}piperidin-3-yl]-N-(2-methylpropyl)pyrimidine-5-carboxamide

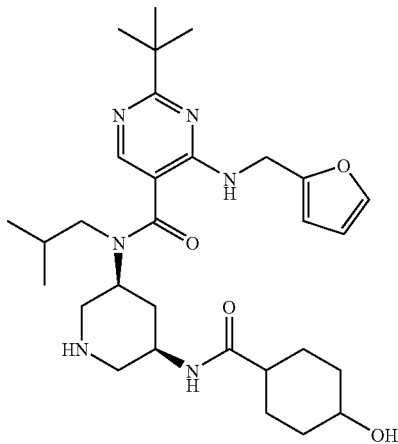

MS (ESI+, m/e) 555 (M+1)

Example 165

2-tert-butyl-4-[(furan-2-ylmethyl)amino]-N-[(3S,5R)-5-{[(4-methoxycyclohexyl)carbonyl]amino}piperidin-3-yl]-N-(2-methylpropyl)pyrimidine-5-carboxamide

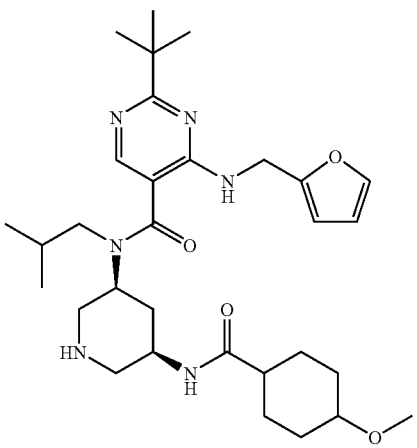

MS (ESI+, m/e) 569 (M+1)

Example 166

2-tert-butyl-N-(2-methylpropyl)-4-{[3-(methylsulfinyl)propyl]amino}-N-[(3S,5R)-5-(morpholin-4-ylcarbonyl)piperidin-3-yl]pyrimidine-5-carboxamide

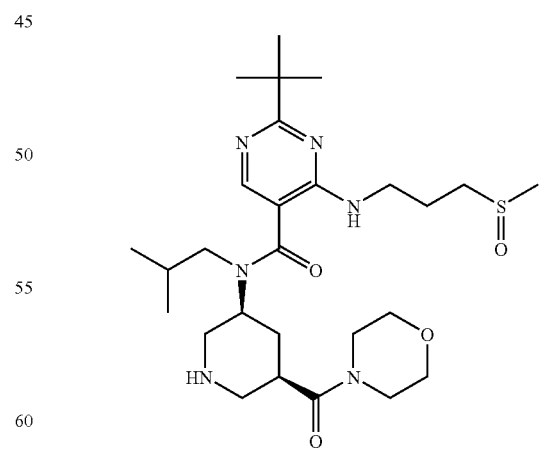

MS (ESI+, m/e) 551 (M+1)

Example 167

Method L 2-tert-butyl-N-{(3S,5R)-5-[(2-hydroxy-2-phenyl-ethyl)amino]piperidin-3-yl}-4-[(3-methoxypropyl)amino]-N-(2-methylpropyl)pyrimidine-5-carboxamide trihydrochloride

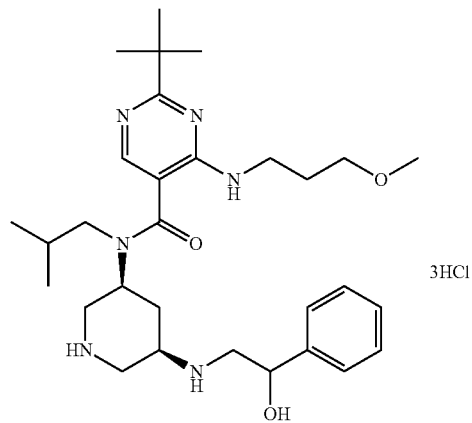

Benzyl (3S,5R)-3-[({2-tert-butyl-4-[(3-methoxypropyl)amino]pyrimidin-5-yl}carbonyl)(2-methylpropyl)amino]-5-[(2-hydroxy-2-phenylethyl)amino]piperidine-1-carboxylate (53.2 mg) was dissolved in ethanol (3 ml), 4 M aqueous sodium hydroxide solution (3 ml) was added and the mixture was stirred at 70° C. for 12 hr. After cooling to room temperature, the reaction mixture was diluted with water and the mixture was extracted with ethyl acetate. The extract was washed with saturated brine and dried over anhydrous magnesium sulfate. The solvent was evaporated under reduced pressure. The residue was dissolved in 1 M hydrogen chloride-ethyl acetate (3 ml), and concentrated under reduced pressure to give the object compound (46.7 mg).

MS (ESI+, m/e) 541 (M+1)

By a method similar to that of Reference Example 50, the following compounds (Reference Examples 211A and 211B) were obtained.

Reference Example 211A tert-butyl (3R*,5S*)-3-[({2-tert-butyl-4-[(furan-2-ylmethyl)amino]pyrimidin-5-yl}carbonyl)(2-methylpropyl)amino]-5-(morpholin-4-ylcarbonyl)piperidine-1-carboxylate

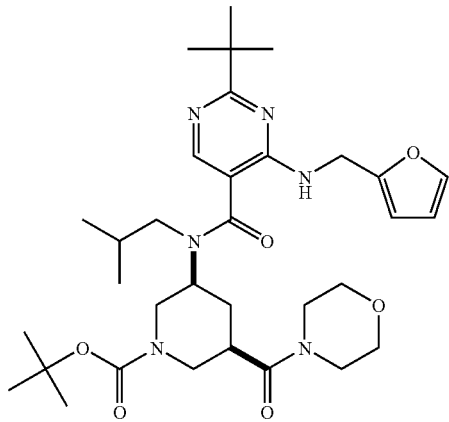

MS (ESI+, m/e) 627 (M+1)

Reference Example 211B tert-butyl (3R*,5R*)-3-[({2-tert-butyl-4-[(furan-2-ylmethyl)amino]pyrimidin-5-yl}carbonyl)(2-methylpropyl)amino]-5-(morpholin-4-ylcarbonyl)piperidine-1-carboxylate

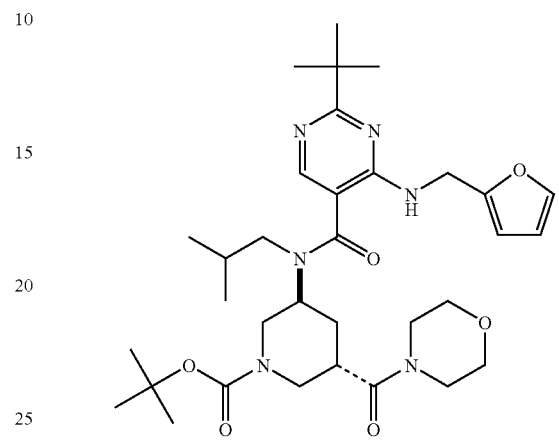

MS (ESI+, m/e) 627 (M+1)

By a method similar to that of the above-mentioned Example 93 (Method G) and Example 94 (Method H), the compounds of Examples 168 to 171 below were obtained. The respective compounds were isolated and purified as necessary by a known means such as phase transfer, pH conversion, solvent extraction, silica gel column chromatography, reversed-phase preparative HPLC and the like. The final products were isolated as hydrochloride as in Method G and Method H by treating with a hydrogen chloride-ethyl acetate solution.

Example 168 methyl (3R*,5S*)-5-[{[2-tert-butyl-4-(furan-2-ylmethyl)aminopyrimidin-5-yl]carbonyl}(isobutyl)amino]piperidine-3-carboxylate dihydrochloride

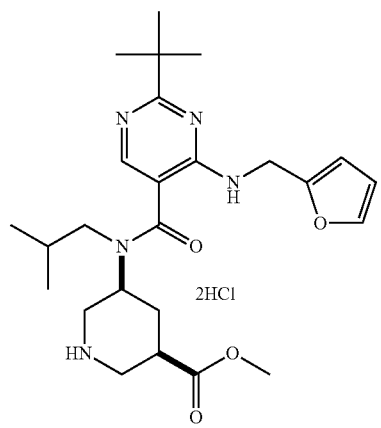

MS (ESI+, m/e) 472 (M+1)

Example 169 methyl (3R*,5R*)-5-[{[2-tert-butyl-4-(furan-2-ylmethyl)aminopyrimidin-5-yl]carbonyl}(isobutyl)amino]piperidine-3-carboxylate dihydrochloride

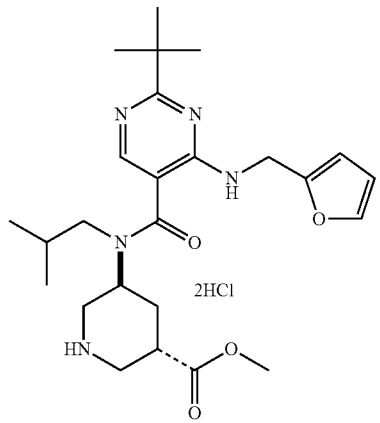

MS (ESI+, m/e) 472 (M+1)

Example 170

2-tert-butyl-4-[(furan-2-ylmethyl)amino]-N-(2-methylpropyl)-N-[(3R*,5S*)-5-(morpholin-4-ylcarbonyl)piperidin-3-yl]pyrimidine-5-carboxamide dihydrochloride

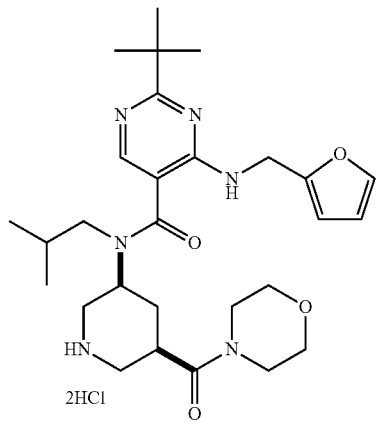

MS (ESI+, m/e) 527 (M+1)

Example 171

2-tert-butyl-4-[(furan-2-ylmethyl)amino]-N-(2-methylpropyl)-N-[(3R*,5R*)-5-(morpholin-4-ylcarbonyl)piperidin-3-yl]pyrimidine-5-carboxamide dihydrochloride

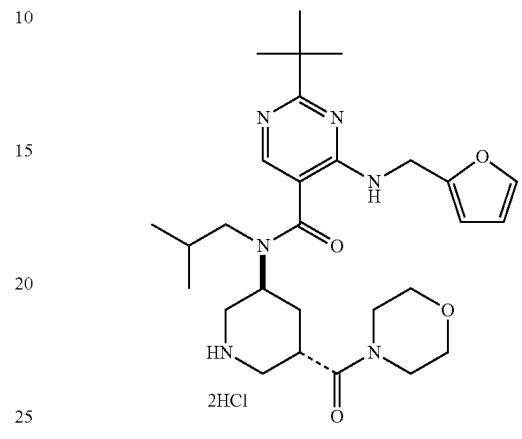

MS (ESI+, m/e) 527 (M+1)

Reference Example 212 tert-butyl 3-[{[2-amino-4-(trifluoromethyl)phenyl]carbonyl}(2-methylpropyl)amino]piperidine-1-carboxylate

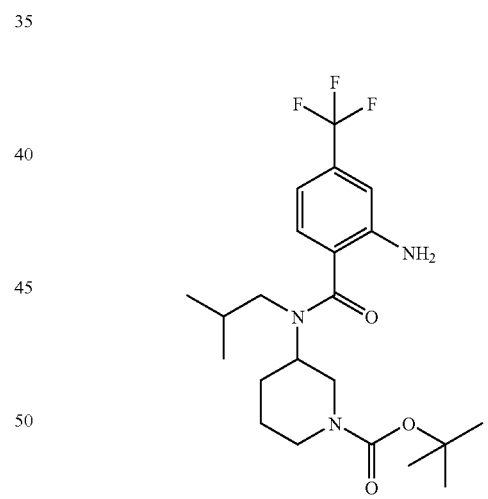

2-amino-4-(trifluoromethyl)benzoic acid (0.32 g) and tert-butyl 3-[(2-methylpropyl)amino]piperidine-1-carboxylate (0.4 g) were dissolved in 1,2-dichloroethane (20 ml), diethyl phosphorocyanidate (0.31 g) was added and the mixture was stirred at 70° C. overnight. The reaction mixture was poured into water, and the mixture was extracted with ethyl acetate. The extract was washed with saturated brine, and dried over anhydrous magnesium sulfate. The solvent was evaporated under reduced pressure, and the residue was subjected to silica gel column chromatography, and the fraction eluted with ethyl acetate-hexane (0:10-1:1) was concentrated under reduced pressure to give the object compound (0.33 g).

MS (ESI+, m/e) 444 (M+1)

Reference Example 213 ethyl 5-[(3-methoxypropyl)amino]-1-phenyl-1H-pyrazole-4-carboxylate

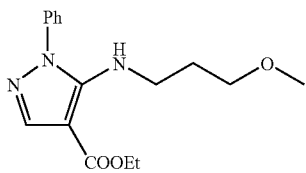

Ethyl 5-amino-1-phenyl-1H-pyrazole-4-carboxylate (1.26 g) was dissolved in DMF (10 ml), NaH (0.25 g) was added under ice-cooling, and the mixture was stirred at room temperature for 30 min. 1-Bromo-3-methoxypropane (0.83 g) was added to the reaction mixture under ice-cooling, and the mixture was stirred at 60° C. for 1 hr. The reaction mixture was concentrated, and the residue was subjected to silica gel column chromatography, and the fraction eluted with ethyl acetate-hexane (0:10-4:6) was concentrated under reduced pressure to give the object compound (1.1 g).

MS (ESI+, m/e) 304 (M+1)

Reference Example 214 methyl 2-cyano-3-[(2,2-dimethylpropanoyl)amino]-3-(methylsulfanyl)prop-2-enoate

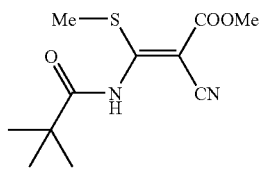

Methyl 2-cyano-3,3-bis(methylsulfanyl)prop-2-enoate (4.06 g) and 2,2-dimethylpropanamide (2.02 g) were dissolved in DMA (200 ml), and sodium hydride (1.92 g) was added under ice-cooling. The mixture was stirred at room temperature overnight, and poured into ice. The mixture was acidified with 1 N aqueous hydrochloric acid solution. The precipitated crystals were collected by filtration, and dried to give the object compound (2.4 g).

MS (ESI+, m/e) 257 (M+1)

Reference Example 215

2-tert-butyl-4-[(3-methoxypropyl)amino]-6-oxo-1,6-dihydropyrimidine-5-carboxylic acid

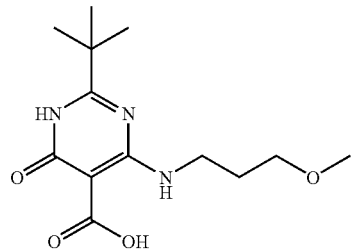

Methyl 2-cyano-3-[(2,2-dimethylpropanoyl)amino]-3-(methylsulfanyl)prop-2-enoate (2.0 g) was dissolved in 3-methoxypropan-1-amine (1.4 g), and the mixture was stirred at 80° C. for 1 hr. Methanol (10 ml) was added to the reaction mixture, and the mixture was refluxed overnight. The solvent was concentrated under reduced pressure, and the residue was subjected to silica gel column chromatography. The fraction eluted with ethyl acetate-hexane (0:10→6:4) was concentrated under reduced pressure, and the fraction eluted with ethyl acetate was concentrated under reduced pressure. The residue (1.0 g) was dissolved in methanol (10 ml), lithium hydroxide (0.42 g) and water (2 ml) were added, and the mixture was stirred at 70° C. for 6 hr. The reaction mixture was allowed to cool to room temperature, acidified with 6 N aqueous hydrochloric acid solution, and extracted with ethyl acetate. The extract was washed with saturated brine, and dried over anhydrous magnesium sulfate. The solvent was evaporated under reduced pressure to give the object compound (0.51 g).

MS (ESI+, m/e) 284 (M+1)

Reference Example 216 tert-butyl (3R,5S)-3-(1-hydroxycyclohexyl)-5-[(2-methylpropyl)amino]piperidine-1-carboxylate

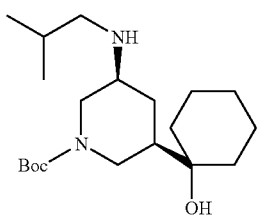

1-tert-Butyl 3-methyl (3R,5S)-5-[(2-methylpropyl)amino] piperidine-1,3-dicarboxylate (3.0 g) was dissolved in THF (30 ml), a solution (15.2 ml) of 3 M pentamethylenebis(magnesium bromide) in THF was added dropwise under ice-cooling, and the mixture was stirred at room temperature for 3 hr. 2 N Aqueous ammonium chloride solution (50 ml) was added to the reaction solution under ice-cooling, and the mixture was extracted with ethyl acetate, and dried over anhydrous magnesium sulfate. The solvent was evaporated under reduced pressure. The residue was subjected to basic silica gel column chromatography, and the fraction eluted with ethyl acetate-hexane (0:10→10:0) was concentrated under reduced pressure to give the object compound (1.3 mg).

MS (ESI+, m/e) 315 (M+1)

Example 172

2-[(furan-2-ylmethyl)amino]-N-(2-methylpropyl)-N-piperidin-3-yl-4-(trifluoromethyl)benzamide

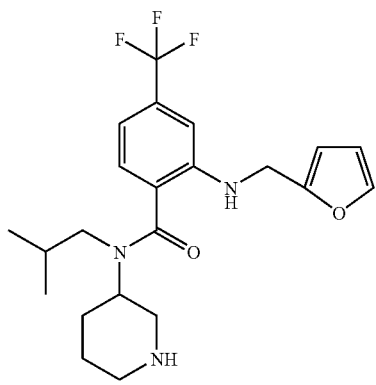

2-Furaldehyde (0.20 g) and tert-butyl 3-[{[2-amino-4-(trifluoromethyl)phenyl]carbonyl}(2-methylpropyl)amino]piperidine-1-carboxylate (0.33 g) were dissolved in acetic acid (5.0 ml), sodium triacetoxyborohydride (0.31 g) was added and the mixture was stirred at room temperature overnight. The reaction mixture was basified with saturated aqueous sodium hydrogen carbonate, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane (0:10→10:0) was concentrated under reduced pressure. The residue was dissolved in trifluoroacetic acid (2 ml), and the mixture was stirred for 30 min. The reaction mixture was concentrated and purified by HPLC to give the object compound (12.2 mg).

MS (ESI+, m/e) 424 (M+1)

Example 173

5-[(3-methoxypropyl)amino]-N-(2-methylpropyl)-N-[(3S,5R)-5-(morpholin-4-ylcarbonyl)piperidin-3-yl]-1-phenyl-1H-pyrazole-4-carboxamide dihydrochloride

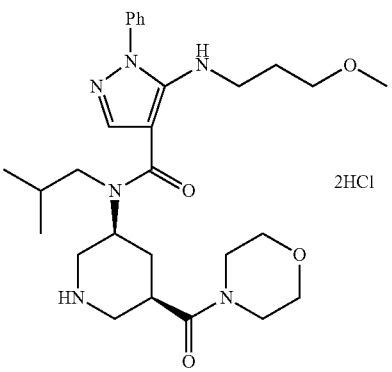

Ethyl 5-[(3-methoxypropyl)amino]-1-phenyl-1H-pyrazole-4-carboxylate (500 mg) was dissolved in methanol (10 ml), 4 N aqueous sodium hydroxide solution was added, and the mixture was stirred at 80° C. for 3 hr. The reaction mixture was allowed to cool to room temperature, acidified with 6 N aqueous hydrochloric acid solution, and extracted with ethyl acetate. The extract was washed with saturated brine, and dried over anhydrous magnesium sulfate. The solvent was evaporated under reduced pressure. The residue was dissolved in dichloromethane (10 ml), tert-butyl (3S,5R)-3-[(2-methylpropyl)amino]-5-(morpholin-4-ylcarbonyl)piperidine-1-carboxylate (540 mg) and N,N-diisopropylethylamine (940 ml) were added, chloro-N,N,N',N'-tetramethylformamidinium hexafluorophosphate (610 mg) was added with stirring and the mixture was stirred at room temperature for 3 hr. The reaction mixture was concentrated, and the residue was subjected to silica gel column chromatography, and the fraction eluted with ethyl acetate-hexane (0:10-10:0) was concentrated under reduced pressure. The residue was dissolved in 4 N hydrogen chloride-ethyl acetate (1 ml), and the mixture was stirred at room temperature for 0.5 hr. The reaction mixture was concentrated to give the object compound (73.6 mg).

MS (ESI+, m/e) 527 (M+1)

Example 174

2-tert-butyl-4-[(3-methoxypropyl)amino]-N-(2-methylpropyl)-N-[(3S,5R)-5-(morpholin-4-ylcarbonyl)piperidin-3-yl]-6-oxo-1,6-dihydropyrimidine-5-carboxamide

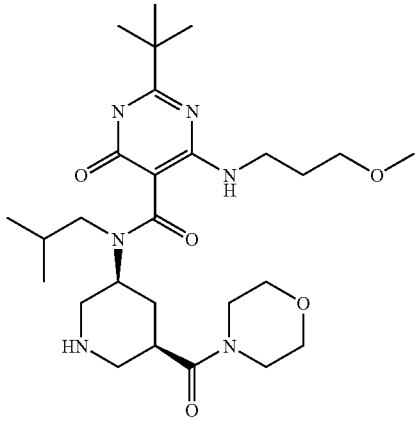

2-tert-Butyl-4-[(3-methoxypropyl)amino]-6-oxo-1,6-dihydropyrimidine-5-carboxylic acid (280 mg), tert-butyl (3S,5R)-3-[(2-methylpropyl)amino]-5-(morpholin-4-ylcarbonyl)piperidine-1-carboxylate (250 mg) and N,N-diisopropylethylamine (640 mg) were dissolved in 1,2-dichloroethane (10 ml), chloro-N,N,N',N'-tetramethylformamidinium hexafluorophosphate (420 mg) was added and the mixture was stirred at room temperature for 3 hr. The reaction mixture was concentrated, and diluted with aqueous calcium carbonate solution, and the mixture was extracted with ethyl acetate. The extract was washed with saturated brine, and dried over anhydrous magnesium sulfate. The solvent was evaporated under reduced pressure. The residue was dissolved in TFA (1 ml), and the mixture was stirred at room temperature for 0.5 hr. The reaction mixture was concentrated and purified by HPLC to give the object compound (15.8 mg).

MS (ESI+, m/e) 535 (M+1)

Example 175

2-tert-butyl-4-chloro-6-[(3-methoxypropyl)amino]-N-(2-methylpropyl)-N-[(3S,5R)-5-(morpholin-4-ylcarbonyl)piperidin-3-yl]pyrimidine-5-carboxamide dihydrochlorde

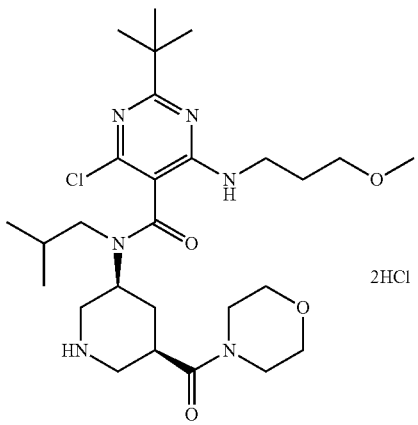

2-tert-Butyl-4-[(3-methoxypropyl)amino]-6-oxo-1,6-dihydropyrimidine-5-carboxylic acid (230 mg) was dissolved in toluene (10 ml), thionyl chloride (0.12 ml) was added, and the mixture was refluxed for 2 hr. The solvent was evaporated under reduced pressure. The residue was dissolved in 1,2-dichloroethane (5 ml), and the solution was added under ice-cooling to a solution of tert-butyl (3S,5R)-3-[(2-methylpropyl)amino]-5-(morpholin-4-ylcarbonyl)piperidine-1-carboxylate (210 mg) and N,N-diisopropylethylamine (520 mg) in 1,2-dichloroethane (10 ml), and the reaction mixture was stirred at room temperature for 1 hr. The reaction mixture was concentrated, and diluted with aqueous calcium carbonate solution, and the mixture was extracted with ethyl acetate. The extract was washed with saturated brine, and dried over anhydrous magnesium sulfate. The solvent was evaporated under reduced pressure. The residue was subjected to silica gel column chromatography, ethyl acetate-hexane (0:10-10:0) was passed, and the fraction eluted with methanol-ethyl acetate (0:10-3:7) was concentrated under reduced pressure. The residue was dissolved in 4 N hydrogen chloride-ethyl acetate (1 ml), and the mixture was stirred at room temperature for 0.5 hr. The reaction mixture was concentrated to give the object compound (73.6 mg).
MS (ESI+, m/e) 553 (M+1)

Example 176

2-tert-butyl-N-[(3S,5R)-5-(1-hydroxycyclohexyl)piperidin-3-yl]-4-[(3-methoxypropyl)amino]-N-(2-methylpropyl)pyrimidine-5-carboxamide dihydrochloride

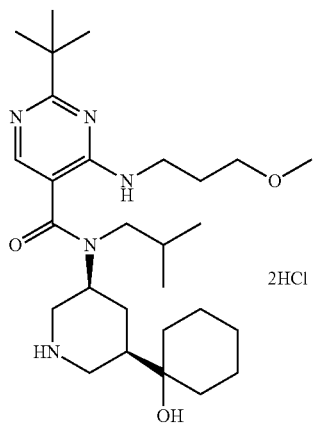

tert-Butyl (3R,5S)-3-(1-hydroxycyclohexyl)-5-[(2-methylpropyl)amino]piperidine-1-carboxylate (0.92 g) and N,N-diisopropylethylamine (1.0 g) were dissolved in 1,2-dichloroethane (10 ml), 2-tert-butyl-4-[(3-methoxypropyl)amino]pyrimidine-5-carbonyl chloride (0.74 g) was added under ice-cooling, and the mixture was stirred at room temperature for 3 hr. The reaction mixture was concentrated, and diluted with aqueous calcium carbonate solution, and the mixture was extracted with ethyl acetate. The extract was washed with saturated brine, and dried over anhydrous magnesium sulfate. The solvent was evaporated under reduced pressure. The residue was dissolved in 4 N hydrogen chloride-ethyl acetate (1 ml), and the mixture was stirred at room temperature for 0.5 hr. The reaction mixture was concentrated and purified by HPLC. The concentrate was dissolved in 4 N hydrogen chloride-ethyl acetate (1 ml) and concentrated to give the object compound (5.9 mg).
MS (ESI+, m/e) 504 (M+1)

Reference Example 217

1-tert-butyl 3-methyl (3R*,5S*)-5-[({2-tert-butyl-4-[(3-methoxypropyl)amino]pyrimidin-5-yl}carbonyl)(2-methylpropyl)amino]piperidine-1,3-dicarboxylate

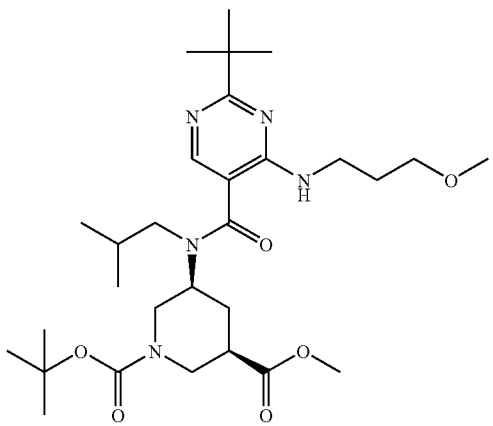

1-tert-Butyl 3-methyl (3R*,5S*)-5-{[(2-tert-butyl-4-chloropyrimidin-5-yl)carbonyl](2-methylpropyl)amino}piperidine-1,3-dicarboxylate (2.46 g) and diisopropylethylamine (1.38 ml) were dissolved in N,N-dimethylformamide (50 ml), 3-methoxypropan-1-amine (990 μl) was added and the mixture was stirred at 80° C. for 30 min. The reaction mixture was concentrated under reduced pressure, saturated aqueous sodium hydrogen carbonate was added, and the mixture was extracted with ethyl acetate. The extract was dried over anhydrous magnesium sulfate and the solvent was evaporated under reduced pressure. The residue was subjected to silica gel column chromatography, and the fraction eluted with hexane to ethyl acetate-hexane (35:65) was concentrated under reduced pressure to give the object compound (2.47 g).
MS (ESI+, m/e) 564 (M+1)

Reference Example 218

(3R*,5S*)-1-(tert-butoxycarbonyl)-5-[({2-tert-butyl-4-[(3-methoxypropyl)amino]pyrimidin-5-yl}carbonyl)(2-methylpropyl)amino]piperidine-3-carboxylic acid

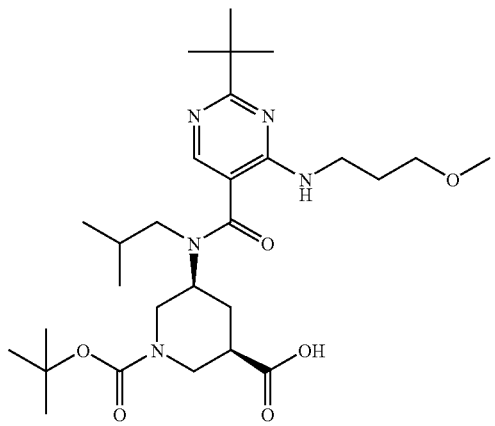

1-tert-Butyl 3-methyl (3R*,5S*)-5-[({2-tert-butyl-4-[(3-methoxypropyl)amino]pyrimidin-5-yl}carbonyl)(2-methylpropyl)amino]piperidine-1,3-dicarboxylate (304 mg) was dissolved in tetrahydrofuran-methanol (1:2, 12 ml), 2 M aqueous sodium hydroxide solution (1.35 ml) was added and the mixture was stirred for 2 hr. The reaction mixture was concentrated under reduced pressure, and diluted with saturated aqueous ammonium chloride solution, and the mixture was extracted with ethyl acetate. The extract was dried over anhydrous magnesium sulfate, and the solvent was evaporated under reduced pressure to give the object compound (287 mg).

MS (ESI+, m/e) 550 (M+1)

Reference Example 219 tert-butyl (3S*,5R*)-3-[({2-tert-butyl-4-[(3-methoxypropyl)amino]pyrimidin-5-yl}carbonyl)(2-methylpropyl)amino]-5-(morpholin-4-ylcarbonyl)piperidine-1-carboxylate

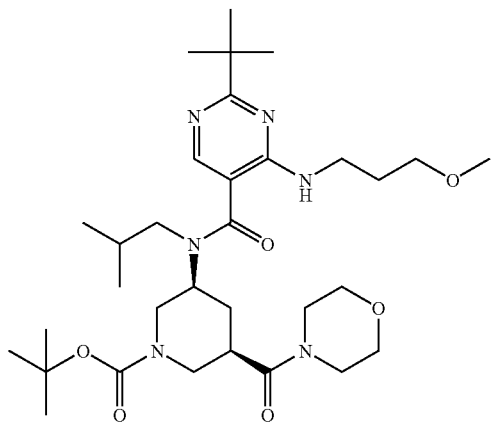

(3R*,5S*)-1-(tert-Butoxycarbonyl)-5-[({2-tert-butyl-4-[(3-methoxypropyl)amino]pyrimidin-5-yl}carbonyl)(2-s methylpropyl)amino]piperidine-3-carboxylic acid (125 mg), morpholine (59 μl) and diisopropylethylamine (160 μl) were dissolved in DMF (10 ml), BOP reagent (300 mg) was added and the mixture was stirred at room temperature for 1 hr. The reaction mixture was diluted with saturated aqueous sodium hydrogen carbonate, and the mixture was extracted with ethyl acetate. The extract was dried over anhydrous magnesium sulfate and the solvent was evaporated under reduced pressure. The residue was subjected to silica gel column chromatography, and the fraction eluted with ethyl acetate-hexane (1:9) to ethyl acetate was concentrated under reduced pressure to give the object compound (109 mg).

MS (ESI+, m/e) 619 (M+1)

Reference Example 220 tert-butyl (3S*,5R*)-3-[({2-tert-butyl-4-[(3-methoxypropyl)amino]pyrimidin-5-yl}carbonyl)(2-methylpropyl)amino]-5-carbamoylpiperidine-1-carboxylate

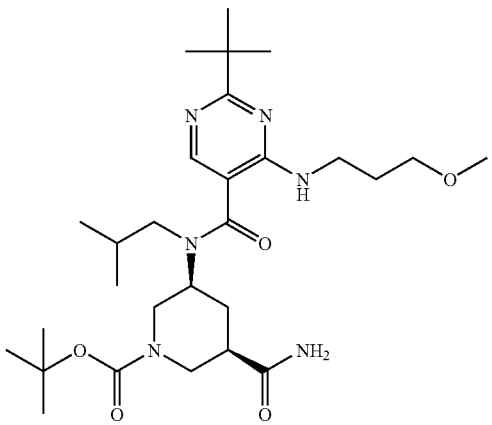

A solution of (3R*,5S*)-1-(tert-butoxycarbonyl)-5-[({2-tert-butyl-4-[(3-methoxypropyl)amino]pyrimidin-5-yl}carbonyl)(2-methylpropyl)amino]piperidine-3-carboxylic acid (160 mg), 1H-1,2,3-benzotriazol-1-ol ammoniate (133 mg), WSC.HCl (167 mg) and triethylamine (165 μl) in 1,2-dichloroethane (8 ml) was stirred at room temperature for 14 hr. The reaction mixture was concentrated under reduced pressure, and diluted with saturated aqueous sodium hydrogen carbonate, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with acetic acid was concentrated under reduced pressure to give the object compound (130 mg).

MS (ESI+, m/e) 549 (M+1)

Example 177 methyl (3R*,5S*)-5-[({2-tert-butyl-4-[(3-methoxypropyl)amino]pyrimidin-5-yl}carbonyl)(2-methylpropyl)amino]piperidine-3-carboxylate dihydrochloride

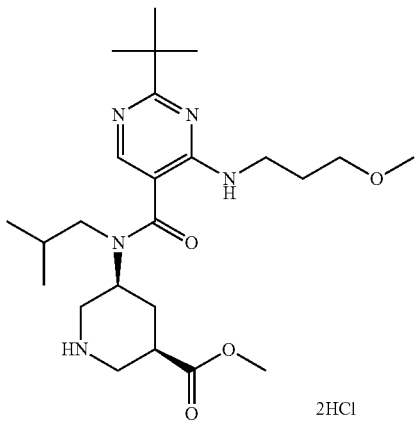

2HCl 1-tert-Butyl 3-methyl (3R*,5S*)-5-[({2-tert-butyl-4-[(3-methoxypropyl)amino]pyrimidin-5-yl}carbonyl)(2-s methylpropyl)amino]piperidine-1,3-dicarboxylate (144 mg) was dissolved in ethyl acetate (4.5 ml), 4 M hydrogen chloride-ethyl acetate solution (1.5 ml) was added, and the mixture was stirred at room temperature for 13 hr. The solvent was evaporated under reduced pressure, and the residue was dried under reduced pressure to give the object compound (129 mg).

MS (ESI+, m/e) 464 (M+1)

By a method similar to that of Example 177, the compounds of Examples 178 and 179 below were synthesized.

Example 178

2-tert-butyl-4-[(3-methoxypropyl)amino]-N-(2-methylpropyl)-N-[(3S*,5R*)-5-(morpholin-4-ylcarbonyl)piperidin-3-yl]pyrimidine-5-carboxamide dihydrochloride

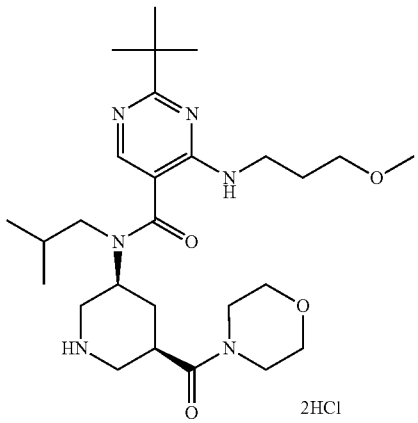

2HCl

MS (ESI+, m/e) 519 (M+1)

Example 179

2-tert-butyl-N-[(3S*,5R*)-5-carbamoylpiperidin-3-yl]-4-[(3-methoxypropyl)amino]-N-(2-methylpropyl)pyrimidine-5-carboxamide dihydrochloride

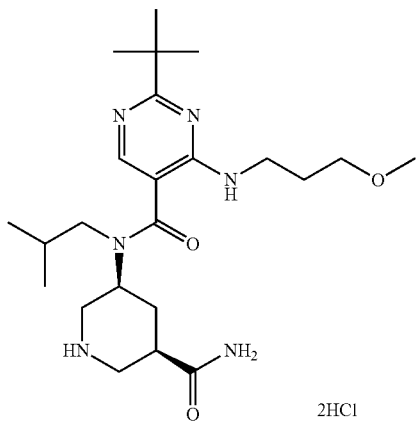

2HCl

MS (ESI+, m/e) 449 (M+1)

Example 180 methyl (3S*,5R*)-5-[({2-tert-butyl-4-[(thiophen-2-ylmethyl)amino]pyrimidin-5-yl}carbonyl)(2-methylpropyl)amino]piperidine-3-carboxylate

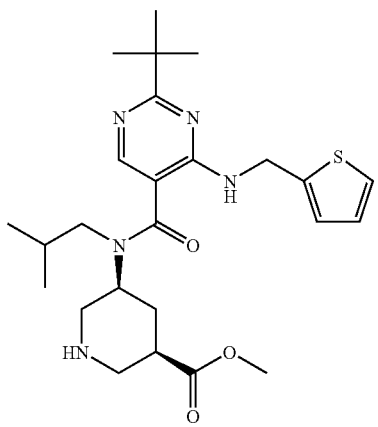

To a solution of 1-tert-butyl 3-methyl (3R*,5S*)-5-{[(2-tert-butyl-4-chloropyrimidin-5-yl)carbonyl](isobutyl)amino}piperidine-1,3-dicarboxylate (51.1 mg) and diisopropylethylamine (38 mg) in DMF (0.5 ml) was added a solution of 1-thiophen-2-ylmethanamine (23 mg) in DMF (0.5 ml) and the mixture was stirred at 80° C. overnight. 2% Aqueous sodium hydrogen carbonate was added to the reaction mixture and the mixture was extracted with ethyl acetate, and the extract was concentrated by a nitrogen gas blower. The residue was purified by reversed-phase preparative HPLC, and the object fraction was concentrated by a nitrogen gas blower. The residue was dissolved in trifluoroacetic acid/acetonitrile solution (20% (V/V), 1.0 ml), and the mixture was stirred at room temperature for 6 hr. The reaction mixture was concentrated by a nitrogen gas blower. The residue was neutralized with triethylamine (1 ml), and saturated aqueous sodium hydrogen carbonate was added. The mixture was extracted with ethyl acetate, and the extract was concentrated by a nitrogen gas blower. The residue was purified by reversed-phase preparative HPLC, and the object fraction was concentrated by a nitrogen gas blower to give the object compound (3.1 mg).

MS (ESI+, m/e) 488 (M+1)

By a method similar to that of the above-mentioned Example 180, the compounds of Examples 181 to 184 below were obtained. The compounds were isolated and purified as necessary by a known means such as phase transfer, pH conversion, solvent extraction, silica gel column chromatography, reversed-phase preparative HPLC and the like. The final products were isolated as a free form.

Example 181 methyl (3S*,5R*)-5-[({2-tert-butyl-4-[(thiophen-3-ylmethyl)amino]pyrimidin-5-yl}carbonyl)(2-methyl-propyl)amino]piperidine-3-carboxylate

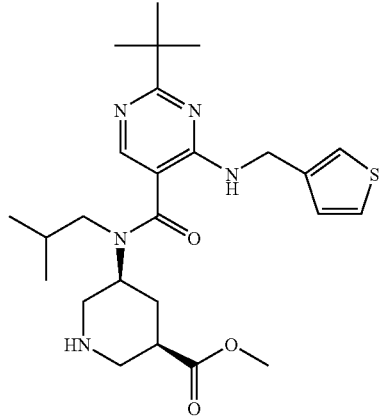

MS (ESI+, m/e) 488 (M+1)

Example 182 methyl (3R*,5S*)-5-[({2-tert-butyl-4-[(furan-2-ylmethyl)amino]pyrimidin-5-yl}carbonyl)(2-methylpropyl)amino]piperidine-3-carboxylate

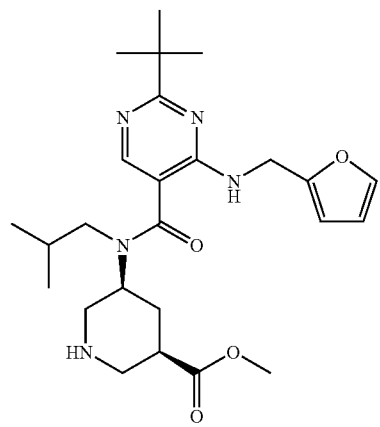

MS (ESI+, m/e) 472 (M+1)

Example 183 methyl (3S*,5R*)-5-[({2-tert-butyl-4-[(3-ethoxypropyl)amino]pyrimidin-5-yl}carbonyl)(2-methylpropyl)amino]piperidine-3-arboxylate

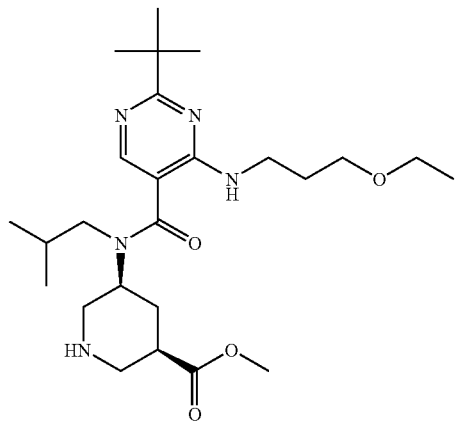

MS (ESI+, m/e) 478 (M+1)

Example 184 methyl (3S*,5R*)-5-[({2-tert-butyl-4-[(pyridin-3-ylmethyl)amino]pyrimidin-5-yl}carbonyl)(2-methyl-propyl)amino]piperidine-3-carboxylate

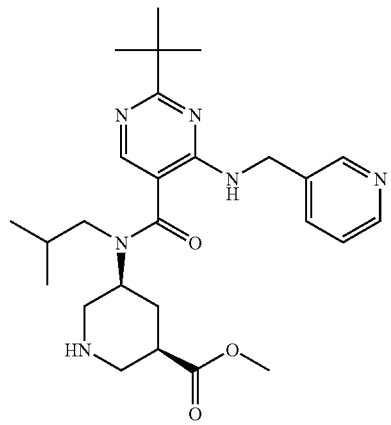

MS (ESI+, m/e) 483 (M+1)

Reference Example 221 tert-butyl (3S,5R)-3-[({2-tert-butyl-4-[(3-methoxypropyl)amino]pyrimidin-5-yl}carbonyl)(2-methylpropyl)amino]-5-{[(2R)-2-(methoxymethyl)pyrrolidin-1-yl]carbonyl}piperidine-1-carboxylate

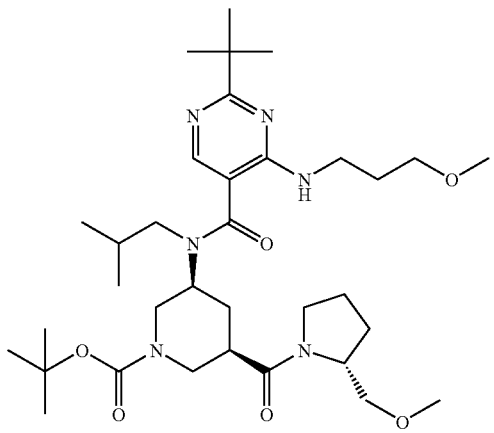

(3R,5S)-1-(tert-Butoxycarbonyl)-5-[({2-tert-butyl-4-[(3-methoxypropyl)amino]pyrimidin-5-yl}carbonyl)(isobutyl)amino]piperidine-3-carboxylic acid (102 mg), (2R)-2-(methoxymethyl)pyrrolidine (64 mg), HOBt (20 mg) and triethylamine (104 μl) were dissolved in DMF (5 ml), WSC.HCl (107 mg) was added, and the mixture was stirred at room temperature for 18 hr. The reaction mixture was concentrated under reduced pressure, and diluted with saturated aqueous sodium hydrogen carbonate, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane (0:1-1:0) was concentrated under reduced pressure to give the object compound (91 mg).

MS (ESI+, m/e) 647 (M+1)

By a method similar to that of the above-mentioned Reference Example 221, the compounds of Reference Examples 222 to 225 below were obtained.

Reference Example 222 tert-butyl (3S,5R)-3-[({2-tert-butyl-4-[(3-methoxypropyl)amino]pyrimidin-5-yl}carbonyl)(2-methylpropyl)amino]-5-{[(2S)-2-(methoxymethyl)pyrrolidin-1-yl]carbonyl}piperidine-1-carboxylate

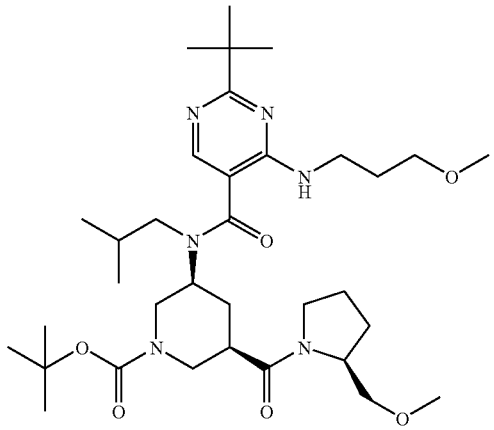

MS (ESI+, m/e) 647 (M+1)

Reference Example 223 tert-butyl (3S,5R)-3-[({2-tert-butyl-4-[(3-methoxypropyl)amino]pyrimidin-5-yl}carbonyl)(2-methylpropyl)amino]-5-(1,4-oxazepan-4-ylcarbonyl)piperidine-1-carboxylate

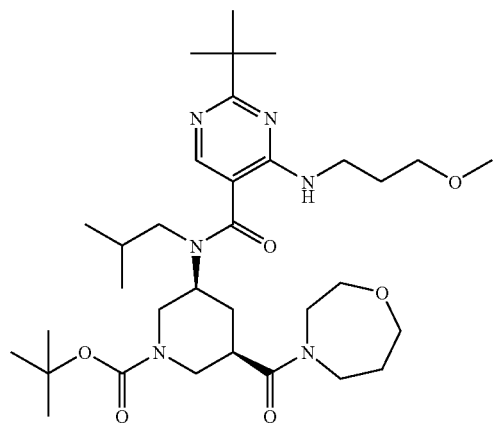

MS (ESI+, m/e) 633 (M+1)

Reference Example 224 tert-butyl (3S,5R)-3-[({2-tert-butyl-4-[(3-methoxypropyl)amino]pyrimidin-5-yl}carbonyl)(2-methylpropyl)amino]-5-[(4-hydroxy-4-methylpiperidin-1-yl)carbonyl]piperidine-1-carboxylate

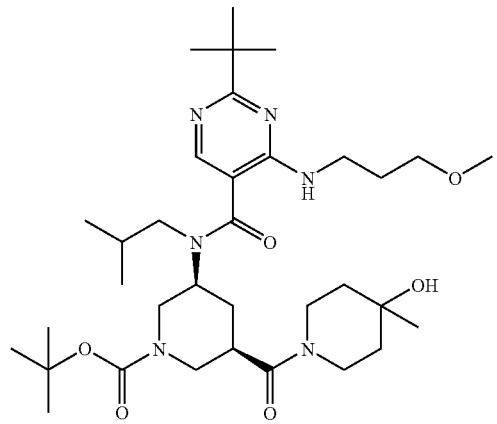

MS (ESI+, m/e) 647 (M+1)

Reference Example 225 tert-butyl (3S,5R)-3-[({2-tert-butyl-4-[(3-methoxypropyl)amino]pyrimidin-5-yl}carbonyl)(2-methylpropyl)amino]-5-[methoxy(methyl)carbamoyl]piperidine-1-carboxylate

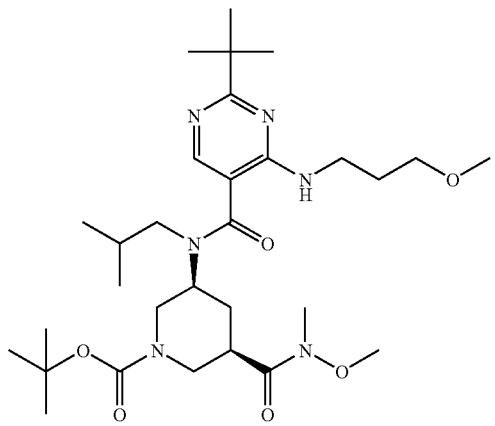

MS (ESI+, m/e) 593 (M+1)

Reference Example 226 tert-butyl (3S,5R)-3-[({2-tert-butyl-4-[(3-methoxypropyl)amino]pyrimidin-5-yl}carbonyl)(2-methylpropyl)amino]-5-(3,4-dihydroisoquinolin-2(1H)-ylcarbonyl)piperidine-1-carboxylate

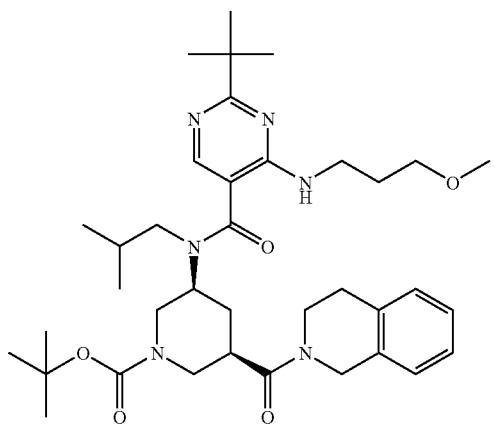

(3R,5S)-1-(tert-Butoxycarbonyl)-5-[({2-tert-butyl-4-[(3-methoxypropyl)amino]pyrimidin-5-yl}carbonyl)(isobutyl)amino]piperidine-3-carboxylic acid (97 mg), 1,2,3,4-tetrahydroisoquinoline (67 µl), HOBt (19 mg) and triethylamine (104 µl) were dissolved in 1,2-dichloroethane (5 ml), WSC.HCl (107 mg) was added, and the mixture was stirred at room temperature for 24 hr. The reaction mixture was concentrated under reduced pressure, and diluted with saturated aqueous sodium hydrogen carbonate, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane (0:1-1:1) was concentrated under reduced pressure to give the object compound (102 mg).

MS (ESI+, m/e) 665 (M+1)

By a method similar to that of the above-mentioned Reference Example 226, the compounds of Reference Examples 227 to 231 below were obtained.

Reference Example 227 tert-butyl (3S,5R)-3-[({2-tert-butyl-4-[(3-methoxypropyl)amino]pyrimidin-5-yl}carbonyl)(2-methylpropyl)amino]-5-(1,4-dioxa-8-azaspiro[4.5]dec-8-ylcarbonyl)piperidine-1-carboxylate

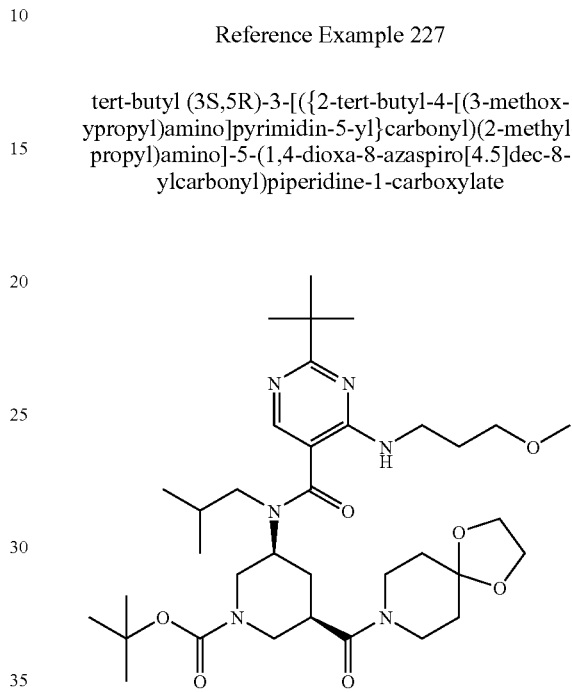

MS (ESI+, m/e) 675 (M+1)

Reference Example 228 tert-butyl (3S,5R)-3-[({2-tert-butyl-4-[(3-methoxypropyl)amino]pyrimidin-5-yl}carbonyl)(2-methylpropyl)amino]-5-(1,3-dihydro-2H-isoindol-2-ylcarbonyl)piperidine-1-carboxylate

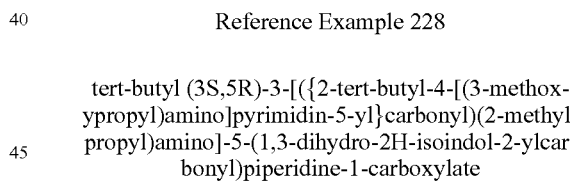

MS (ESI+, m/e) 651 (M+1)

Reference Example 229 tert-butyl (3S,5R)-3-[({2-tert-butyl-4-[(3-methoxypropyl)amino]pyrimidin-5-yl}carbonyl)(2-methylpropyl)amino]-5-[trans-(4a,8a)-octahydroquinolin-1(2H)-ylcarbonyl]piperidine-1-carboxylate

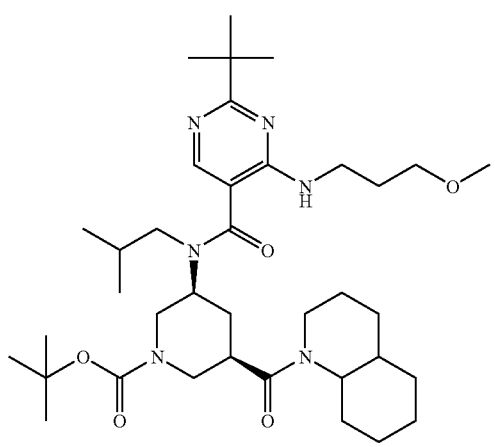

MS (ESI+, m/e) 671 (M+1)

Reference Example 230 tert-butyl (3S,5R)-3-[({2-tert-butyl-4-[(3-methoxypropyl)amino]pyrimidin-5-yl}carbonyl)(2-methylpropyl)amino]-5-[(2,6-dimethylmorpholin-4-yl)carbonyl]piperidine-1-carboxylate

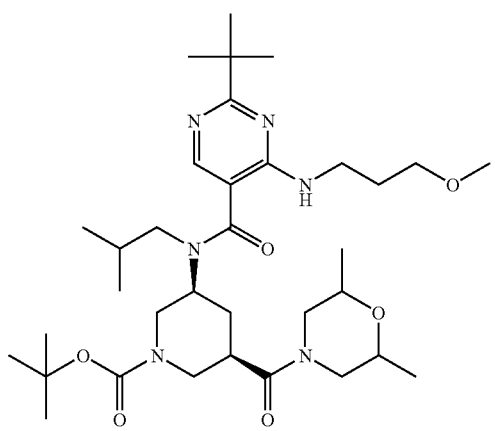

MS (ESI+, m/e) 647 (M+1)

Reference Example 231 tert-butyl (3S,5R)-3-[({2-tert-butyl-4-[(3-methoxypropyl)amino]pyrimidin-5-yl}carbonyl)(2-methylpropyl)amino]-5-[(2-methyl-6,7-dihydro[1,3]oxazolo[5,4-c]pyridin-5(4H)-yl)carbonyl]piperidine-1-carboxylate

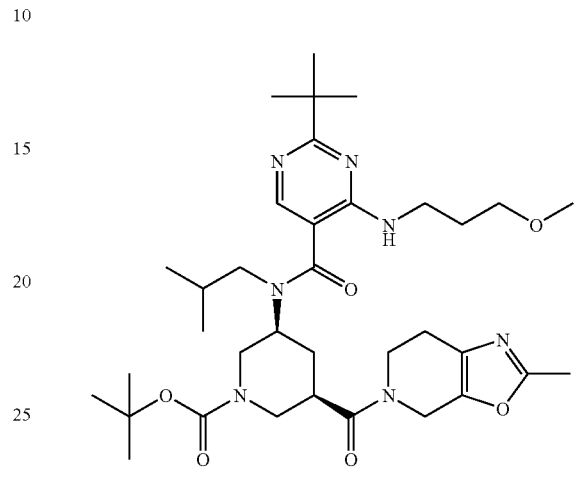

MS (ESI+, m/e) 670 (M+1)

Reference Example 232 tert-butyl (3S,5R)-3-[({2-tert-butyl-4-[(3-methoxypropyl)amino]pyrimidin-5-yl}carbonyl)(2-methylpropyl)amino]-5-(2,3-dihydro-1H-indol-1-ylcarbonyl)piperidine-1-carboxylate

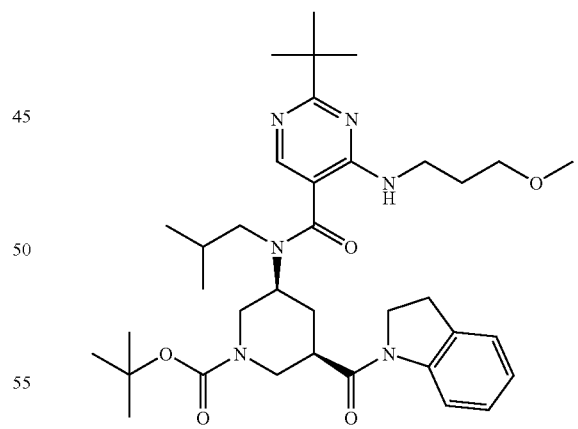

(3R,5S)-1-(tert-Butoxycarbonyl)-5-[({2-tert-butyl-4-[(3-methoxypropyl)amino]pyrimidin-5-yl}carbonyl)(isobutyl)amino]piperidine-3-carboxylic acid (100 mg), 2,3-dihydro-1H-indole (62 μl) and diisopropylethylamine (96 μl) were dissolved in 1,2-dichloroethane (5 ml), chloro-N,N,N',N'-tetramethylformamidinium hexafluorophosphate (155 mg) was added, and the mixture was stirred at room temperature for 3.5 hr. The reaction mixture was concentrated under reduced pressure, and diluted with saturated aqueous sodium hydrogen carbonate, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane (0:1-1:1) was concentrated under reduced pressure to give the object compound (100 mg).

MS (ESI+, m/e) 651 (M+1)

By a method similar to that of the above-mentioned Reference Example 232, the compounds of Reference Examples 233 to 235 below were obtained.

Reference Example 233 tert-butyl (3S,5R)-3-[({2-tert-butyl-4-[(3-methoxypropyl)amino]pyrimidin-5-yl}carbonyl)(2-methylpropyl)amino]-5-(3,4-dihydroquinolin-1(2H)-ylcarbonyl)piperidine-1-carboxylate

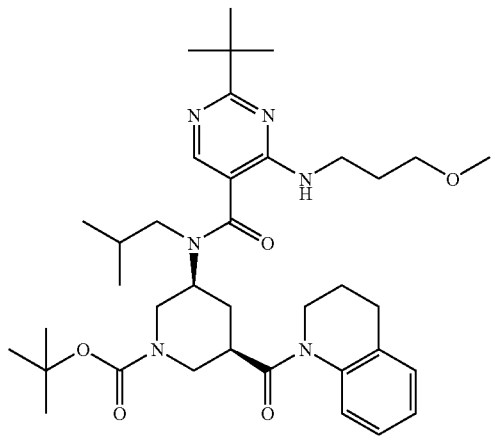

MS (ESI+, m/e) 665 (M+1)

Reference Example 234 tert-butyl (3S,5R)-3-[({2-tert-butyl-4-[(3-methoxypropyl)amino]pyrimidin-5-yl}carbonyl)(2-methylpropyl)amino]-5-[(5-fluoro-2,3-dihydro-1H-indol-1-yl)carbonyl]piperidine-1-carboxylate

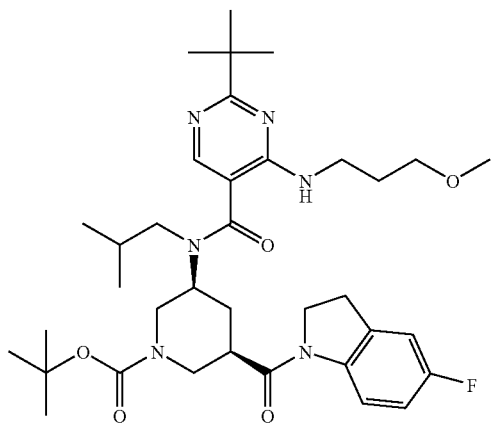

MS (ESI+, m/e) 669 (M+1)

Reference Example 235 tert-butyl (3S,5R)-3-[({2-tert-butyl-4-[(3-methoxypropyl)amino]pyrimidin-5-yl}carbonyl)(2-methylpropyl)amino]-5-[(6-fluoro-2,3-dihydro-1H-indol-1-yl)carbonyl]piperidine-1-carboxylate

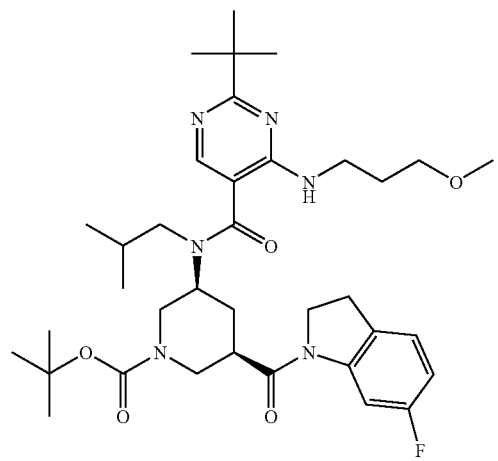

MS (ESI+, m/e) 669 (M+1)

Reference Example 236 tert-butyl (3R,5S)-3-acetyl-5-[({2-tert-butyl-4-[(3-methoxypropyl)amino]pyrimidin-5-yl}carbonyl)(2-methylpropyl)amino]piperidine-1-carboxylate

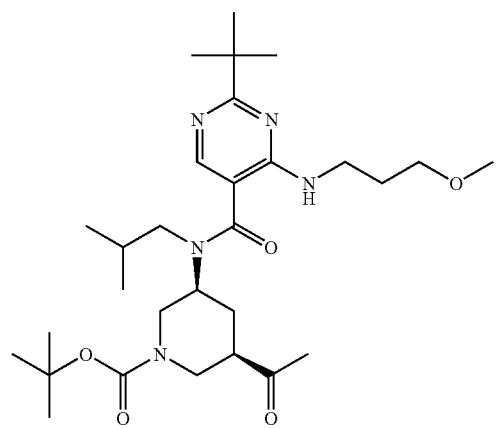

tert-Butyl (3S,5R)-3-[({2-tert-butyl-4-[(3-methoxypropyl)amino]pyrimidin-5-yl}carbonyl)(2-methylpropyl)amino]-5-[methoxy(methyl)carbamoyl]piperidine-1-carboxylate (75 mg) was dissolved in tetrahydrofuran (10 ml), 1 M methylmagnesium bromide in THF solution (1.3 ml) was added at 0° C., and the mixture was stirred at room temperature for 10 hr. Saturated aqueous ammonium chloride solution was added to the reaction mixture, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane (0:1-1:1) was concentrated under reduced pressure to give the object compound (38 mg).

MS (ESI+, m/e) 549(M+1)

By a method similar to that of the above-mentioned Reference Example 236, the compounds of Reference Examples 237 and 238 below were obtained.

Reference Example 237 tert-butyl (3S,5R)-3-[({2-tert-butyl-4-[(3-methoxypropyl)amino]pyrimidin-5-yl}carbonyl)(2-methylpropyl)amino]-5-(cyclopropylcarbonyl)piperidine-1-carboxylate

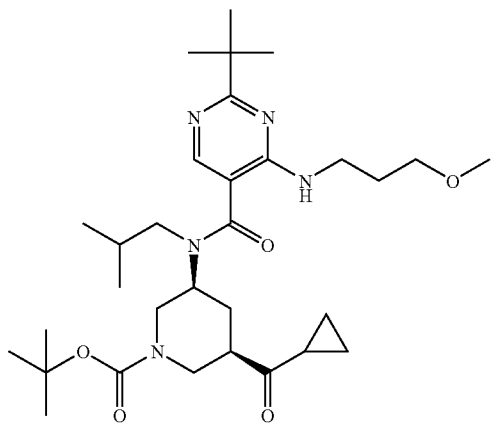

MS (ESI+, m/e) 574(M+1)

Reference Example 238 tert-butyl (3S,5R)-3-[({2-tert-butyl-4-[(3-methoxypropyl)amino]pyrimidin-5-yl}carbonyl)(2-methylpropyl)amino]-5-(2-methylpropanoyl)piperidine-1-carboxylate

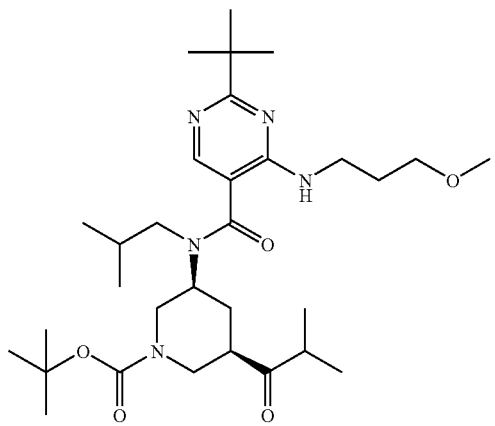

MS (ESI+, m/e) 576(M+1)

Reference Example 239 tert-butyl (3S,5R)-3-[({2-tert-butyl-4-[(3-methoxypropyl)amino]pyrimidin-5-yl}carbonyl)(2-methylpropyl)amino]-5-carbamoylpiperidine-1-carboxylate

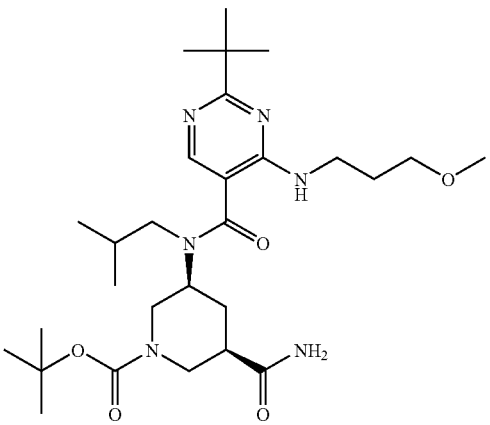

(3R,5S)-1-(tert-Butoxycarbonyl)-5-[({2-tert-butyl-4-[(3-methoxypropyl)amino]pyrimidin-5-yl}carbonyl)(isobutyl)amino]piperidine-3-carboxylic acid (301 mg), 1H-1,2,3-benzotriazol-1-ol ammoniate (167 mg) and triethylamine (230 µl) were dissolved in 1,2-dichloroethane (10 ml), WSC.HCl (210 mg) was added and the mixture was stirred at room temperature for 2 hr. The reaction mixture was concentrated under reduced pressure, and diluted with saturated aqueous sodium hydrogen carbonate, and the mixture was extracted with ethyl acetate. The extract was dried over anhydrous magnesium sulfate and the solvent was evaporated under reduced pressure. The residue was subjected to silica gel column chromatography, and the fraction eluted with ethyl acetate-hexane (1:1) to ethyl acetate was concentrated under reduced pressure to give the object compound (210 mg).

MS (ESI+, m/e) 549 (M+1)

Reference Example 240 tert-butyl (3S,5R)-3-[({2-tert-butyl-4-[(3-methoxypropyl)amino]pyrimidin-5-yl}carbonyl)(2-methylpropyl)amino]-5-(4H-1,2,4-triazol-3-yl)piperidine-1-carboxylate

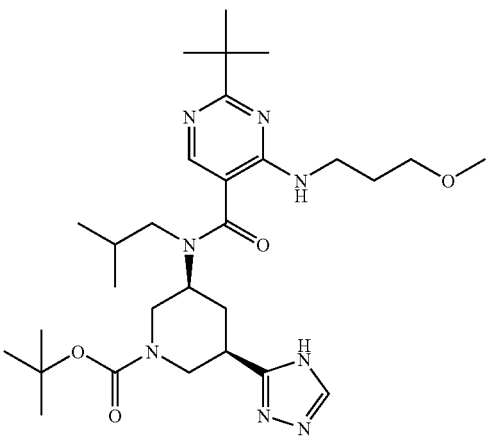

tert-Butyl (3S,5R)-3-[({2-tert-butyl-4-[(3-methoxypropyl)amino]pyrimidin-5-yl}carbonyl)(2-methylpropyl)amino]-5-carbamoylpiperidine-1-carboxylate (120 mg) was dissolved in N,N-dimethylformamide dimethyl acetal (4 ml), and the mixture was stirred at 100° C. for 12 hr. The reaction mixture was concentrated under reduced pressure, and the residue was dissolved in acetic acid (7 ml). Hydrazine monohydrate (32 μl) was added and the mixture was stirred at 80° C. for 3 hr. The reaction mixture was concentrated under reduced pressure, and diluted with 1 M aqueous sodium hydroxide solution, and the mixture was extracted with ethyl acetate. The extract was washed with saturated brine, and dried over anhydrous magnesium sulfate. The solvent was evaporated under reduced pressure. The residue was subjected to silica gel column chromatography, and the fraction eluted with ethyl acetate-hexane (1:1) to ethyl acetate was concentrated under reduced pressure to give the object compound (96 mg).

MS (ESI+, m/e) 573 (M+1)

By a method similar to that of Reference Examples 217 and 218, the compounds of Reference Examples 241 and 242 below were obtained.

Reference Example 241

1-tert-butyl 3-methyl (3R,5S)-5-[({2-tert-butyl-4-[(2-hydroxy-3-methoxypropyl)amino]pyrimidin-5-yl}carbonyl)(2-methylpropyl)amino]piperidine-1,3-dicarboxylate

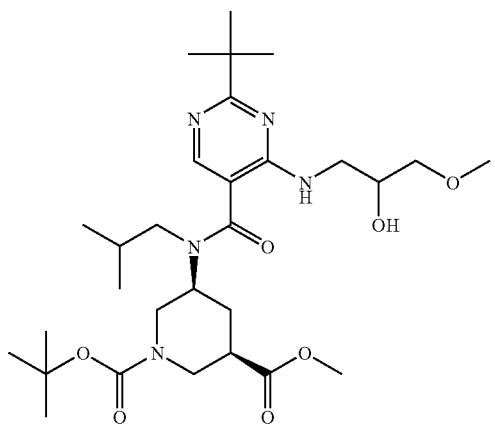

MS (ESI+, m/e) 580 (M+1)

Reference Example 242

(3R,5S)-1-(tert-butoxycarbonyl)-5-[({2-tert-butyl-4-[(2-hydroxy-3-methoxypropyl)amino]pyrimidin-5-yl}carbonyl)(2-methylpropyl)amino]piperidine-3-carboxylic acid

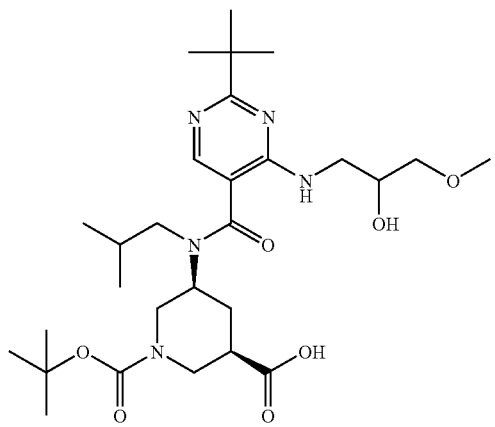

MS (ESI+, m/e) 566 (M+1)

By a method similar to that of Reference Example 226, the compound of Reference Example 243 below was obtained.

Reference Example 243 tert-butyl (3S,5R)-3-[({2-tert-butyl-4-[(2-hydroxy-3-methoxypropyl)amino]pyrimidin-5-yl}carbonyl)(2-methylpropyl)amino]-5-(morpholin-4-ylcarbonyl)piperidine-1-carboxylate

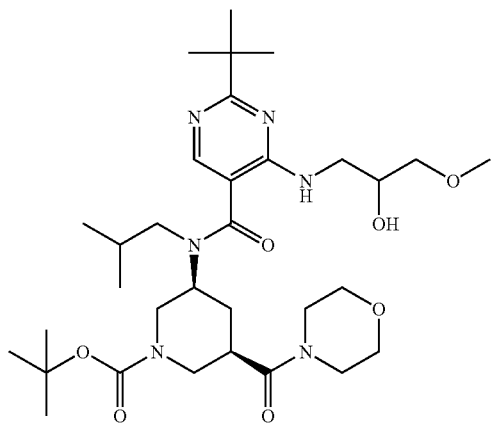

MS (ESI+, m/e) 635 (M+1)

305

By a method similar to that of Example 177, the compounds of Examples 185 to 201 below were synthesized.

Example 185

2-tert-butyl-N-[(3S,5R)-5-{[(2R)-2-(methoxymethyl)pyrrolidin-1-yl]carbonyl}piperidin-3-yl]-4-[(3-methoxypropyl)amino]-N-(2-methylpropyl)pyrimidine-5-carboxamide dihydrochloride

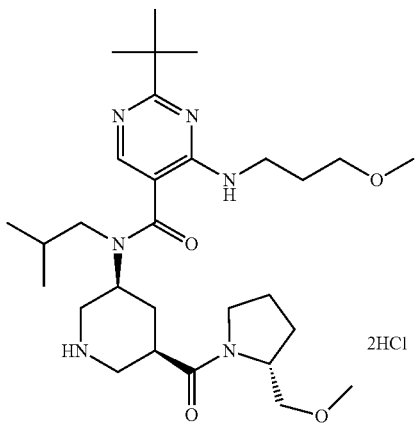

MS (ESI+, m/e) 547 (M+1)

Example 186

2-tert-butyl-N-[(3S,5R)-5-{[(2S)-2-(methoxymethyl)pyrrolidin-1-yl]carbonyl}piperidin-3-yl]-4-[(3-methoxypropyl)amino]-N-(2-methylpropyl)pyrimidine-5-carboxamide dihydrochloride

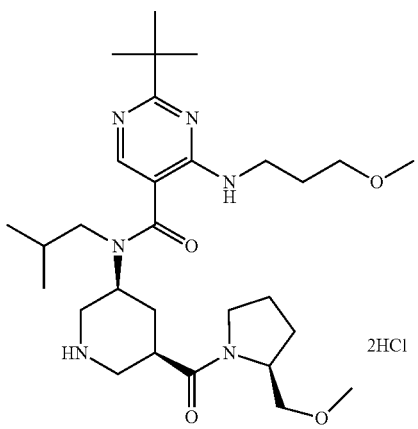

MS (ESI+, m/e) 547 (M+1)

306

Example 187

2-tert-butyl-4-[(3-methoxypropyl)amino]-N-(2-methylpropyl)-N-[(3S,5R)-5-(1,4-oxazepan-4-ylcarbonyl)piperidin-3-yl]pyrimidine-5-carboxamide dihydrochloride

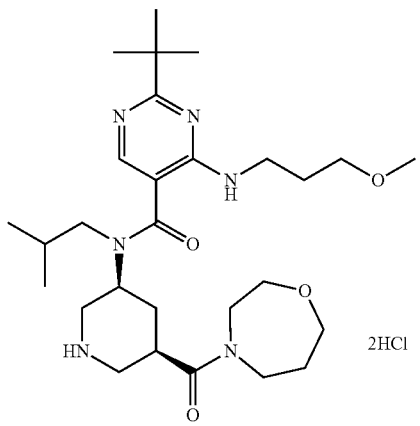

MS (ESI+, m/e) 533 (M+1)

Example 188

2-tert-butyl-N-[(3S,5R)-5-(3,4-dihydroquinolin-1(2H)-ylcarbonyl)piperidin-3-yl]-4-[(3-methoxypropyl)amino]-N-(2-methylpropyl)pyrimidine-5-carboxamide dihydrochloride

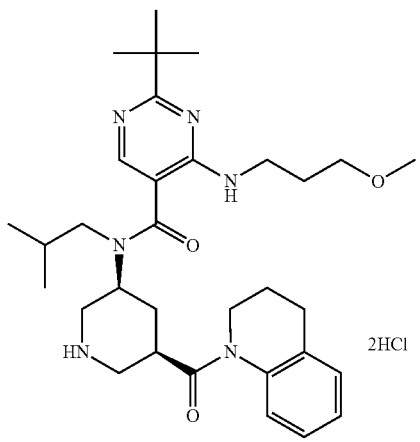

MS (ESI+, m/e) 565 (M+1)

Example 189

2-tert-butyl-N-[(3S,5R)-5-(3,4-dihydroisoquinolin-2 (1H)-ylcarbonylpiperidin-3-yl]-4-[(3-methoxypropyl)amino]-N-(2-methylpropyl)pyrimidine-5-carboxamide dihydrochloride

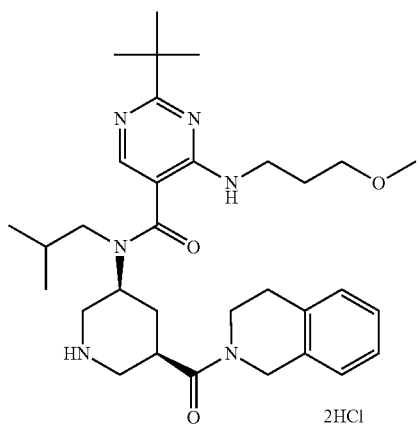

MS (ESI+, m/e) 565 (M+1)

Example 190

2-tert-butyl-N-[(3S,5R)-5-(1,3-dihydro-2H-isoindol-2-ylcarbonyl)piperidin-3-yl]-4-[(3-methoxypropyl)amino]-N-(2-methylpropyl)pyrimidine-5-carboxamide dihydrochloride

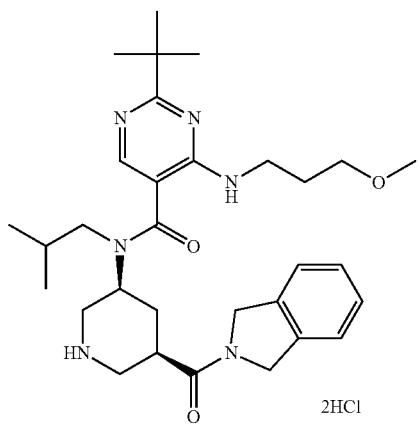

MS (ESI+, m/e) 551 (M+1)

Example 191

2-tert-butyl-N-[(3S,5R)-5-(2,3-dihydro-1H-indol-1-ylcarbonyl)piperidin-3-yl]-4-[(3-methoxypropyl)amino]-N-(2-methylpropyl)pyrimidine-5-carboxamide dihydrochloride

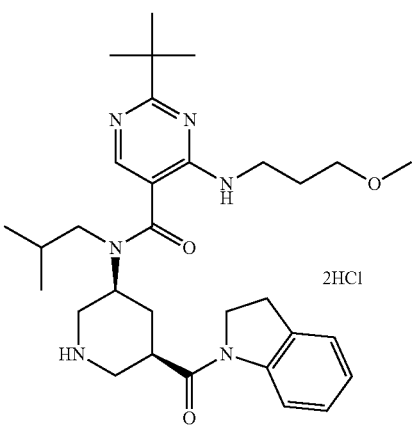

MS (ESI+, m/e) 551 (M+1)

Example 192

2-tert-butyl-N-{(3S,5R)-5-[(5-fluoro-2,3-dihydro-1H-indol-1-yl)carbonyl]piperidin-3-yl}-4-[(3-methoxypropyl)amino]-N-(2-methylpropyl)pyrimidine-5-carboxamide dihydrochloride

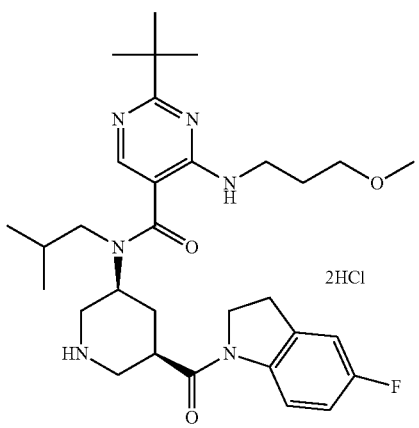

MS (ESI+, m/e) 569 (M+1)

Example 193

2-tert-butyl-N-{(3S,5R)-5-[(6-fluoro-2,3-dihydro-1H-indol-1-yl)carbonyl]piperidin-3-yl}-4-[(3-methoxypropyl)amino]-N-(2-methylpropyl)pyrimidine-5-carboxamide dihydrochloride

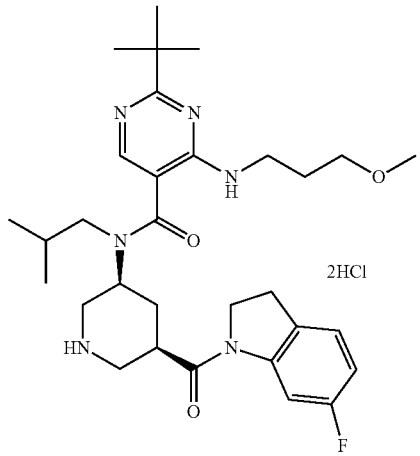

MS (ESI+, m/e) 569 (M+1)

Example 194

2-tert-butyl-4-[(3-methoxypropyl)amino]-N-(2-methylpropyl)-N-{(3S,5R)-5-[trans-(4a,8a)-octahydroquinolin-1(2H)-ylcarbonyl]piperidin-3-yl}pyrimidine-5-carboxamide dihydrochloride

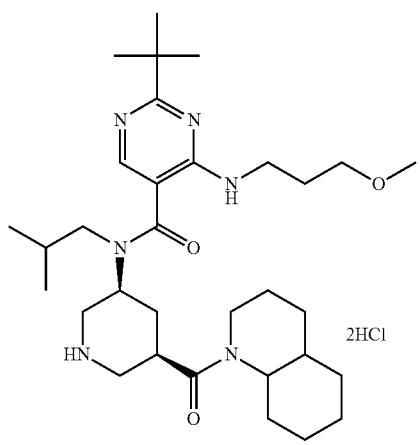

MS (ESI+, m/e) 571 (M+1)

Example 195

2-tert-butyl-N-{(3S,5R)-5-[(2,6-dimethylmorpholin-4-yl)carbonyl]piperidin-3-yl}-4-[(3-methoxypropyl)amino]-N-(2-methylpropyl)pyrimidine-5-carboxamide dihydrochloride

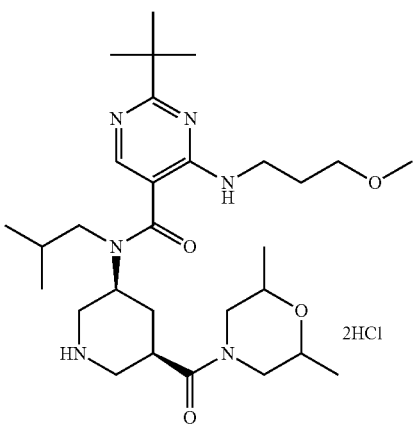

MS (ESI+, m/e) 547 (M+1)

Example 196

2-tert-butyl-4-[(3-methoxypropyl)amino]-N-{(3S,5R)-5-[(2-methyl-6,7-dihydro[1,3]oxazolo[5,4-c]pyridin-5(4H)-yl)carbonyl]piperidin-3-yl}-N-(2-methylpropyl)pyrimidine-5-carboxamide dihydrochloride

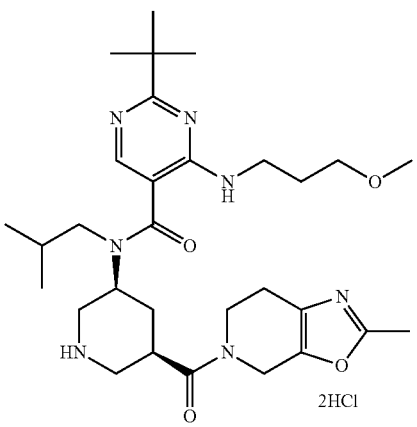

MS (ESI+, m/e) 570 (M+1)

311

Example 197

2-tert-butyl-N-{(3S,5R)-5-[methoxy(methyl)carbamoyl]piperidin-3-yl}-4-[(3-methoxypropyl)amino]-N-(2-methylpropyl)pyrimidine-5-carboxamide dihydrochloride

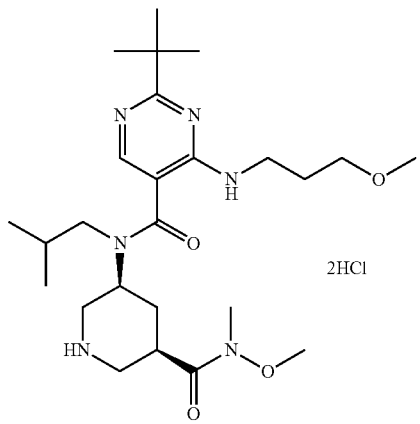

MS (ESI+, m/e) 493 (M+1)

Example 198

N-[(3S,5R)-5-acetylpiperidin-3-yl]-2-tert-butyl-4-[(3-methoxypropyl)amino]-N-(2-methylpropyl)pyrimidine-5-carboxamide dihydrochloride

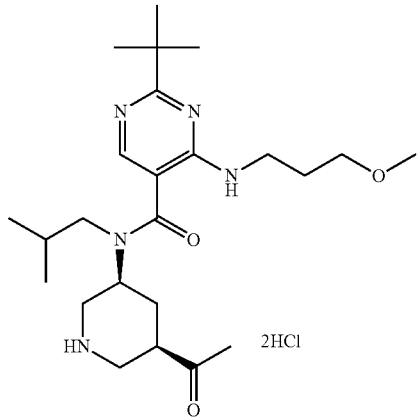

MS (ESI+, m/e) 448 (M+1)

312

Example 199

2-tert-butyl-4-[(3-methoxypropyl)amino]-N-[(3S,5R)-5-(2-methylpropanoyl)piperidin-3-yl]-N-(2-methylpropyl)pyrimidine-5-carboxamide dihydrochloride

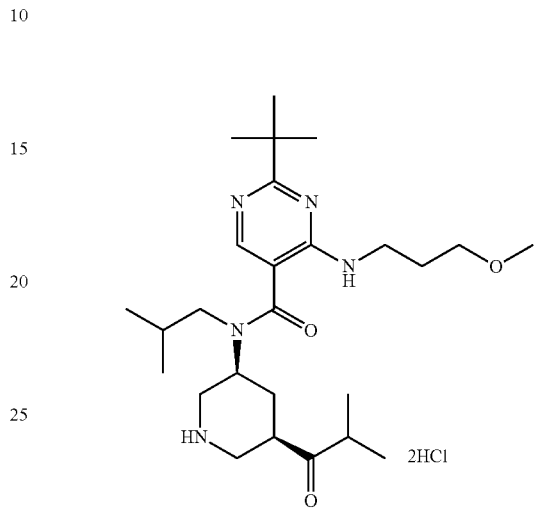

MS (ESI+, m/e) 476 (M+1)

Example 200

2-tert-butyl-N-[(3S,5R)-5-carbamoylpiperidin-3-yl]-4-[(3-methoxypropyl)amino]-N-(2-methylpropyl)pyrimidine-5-carboxamide dihydrochloride

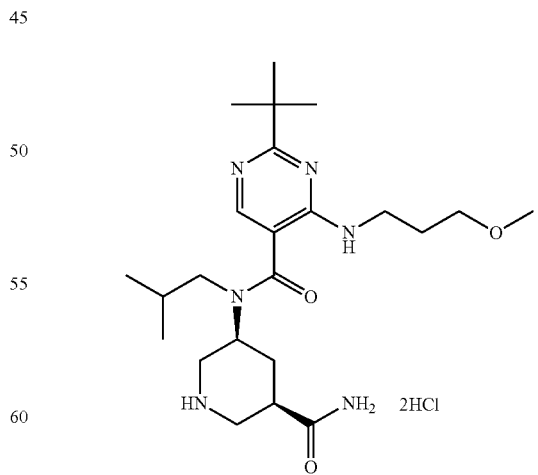

MS (ESI+, m/e) 449 (M+1)

Example 201

2-tert-butyl-4-[(3-methoxypropyl)amino]-N-(2-methylpropyl)-N-[(3S,5R)-5-(4H-1,2,4-triazol-3-yl)piperidin-3-yl]pyrimidine-5-carboxamide dihydrochloride

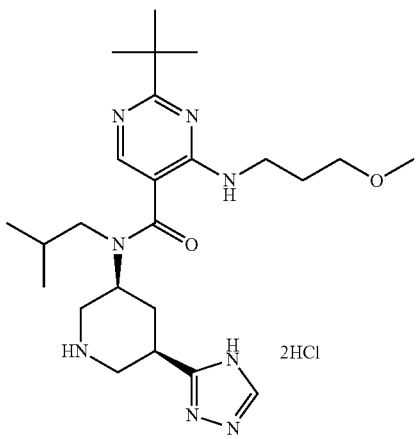

MS (ESI+, m/e) 473 (M+1)

Example 202

2-tert-butyl-N-{(3S,5R)-5-[(4-hydroxy-4-methylpiperidin-1-yl)carbonyl]piperidin-3-yl}-4-[(3-methoxypropyl)amino]-N-(2-methylpropyl)pyrimidine-5-carboxamide dihydrochloride

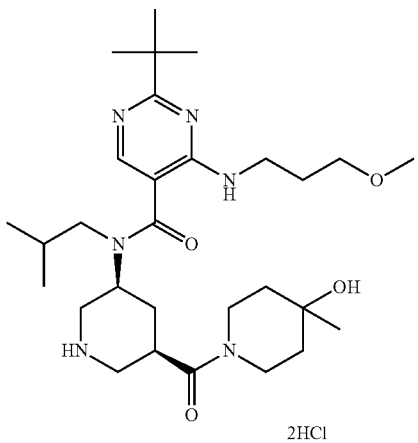

tert-Butyl (3S,5R)-3-[({2-tert-butyl-4-[(3-methoxypropyl)amino]pyrimidin-5-yl}carbonyl)(2-methylpropyl)amino]-5-[(4-hydroxy-4-methylpiperidin-1-yl)carbonyl]piperidine-1-carboxylate (113 mg) was dissolved in 10% hydrogen chloride-methanol solution (4.5 ml), and the mixture was stirred at room temperature for 18 hr. The solvent was evaporated under reduced pressure, and the residue was dried under reduced pressure to give the object compound (82 mg).

MS (ESI+, m/e) 547 (M+1)

By a method similar to that of the above-mentioned Example 202, the compound of Example 203 below was synthesized.

Example 203

2-tert-butyl-4-[(2-hydroxy-3-methoxypropyl)amino]-N-(2-methylpropyl)-N-[(3S,5R)-5-(morpholin-4-ylcarbonyl)piperidin-3-yl]pyrimidine-5-carboxamide dihydrochloride

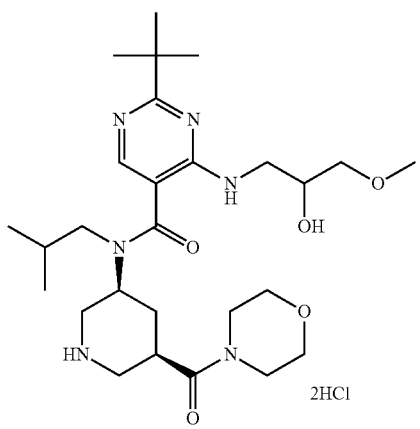

MS (ESI+, m/e) 535 (M+1)

Example 204

2-tert-butyl-N-[(3S,5R)-5-(1,4-dioxa-8-azaspiro[4.5]dec-8-ylcarbonyl)piperidin-3-yl]-4-[(3-methoxypropyl)amino]-N-(2-methylpropyl)pyrimidine-5-carboxamide

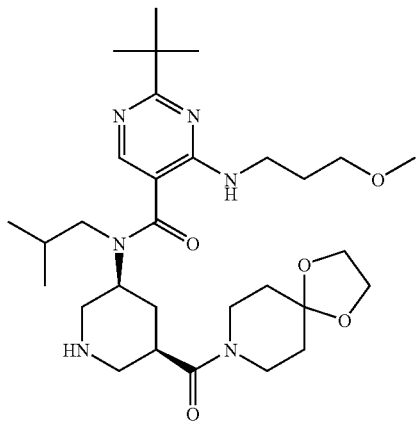

tert-Butyl (3S,5R)-3-[({2-tert-butyl-4-[(3-methoxypropyl)amino]pyrimidin-5-yl}carbonyl)(2-methylpropyl)amino]-5-(1,4-dioxa-8-azaspiro[4.5]dec-8-ylcarbonyl)piperidine-1-carboxylate (72 mg) was dissolved in acetonitrile (8 ml), TFA (2 ml) was added and the mixture stirred at room temperature for 3 hr. The reaction mixture was poured into 25% aqueous potassium carbonate solution at 0° C., and the mixture was extracted with ethyl acetate. The extract was washed with saturated brine, dried over anhydrous magnesium sulfate, and concentrated under reduced pressure. The residue was subjected to reversed-phase preparative HPLC, and fractions eluted with water-acetonitrile (9:1) to acetonitrile were collected. The mixture was basified (pH 10) with saturated aqueous potassium carbonate solution, and the mixture was extracted with ethyl acetate. The extract was dried over anhydrous magnesium sulfate, and concentrated under reduced pressure to give the object compound (29 mg).

MS (ESI+, m/e) 575 (M+1)

Example 205

2-tert-butyl-N-[(3S,5R)-5-(cyclopropylcarbonyl)piperidin-3-yl]-4-[(3-methoxypropyl)amino]-N-(2-methylpropyl)pyrimidine-5-carboxamide dihydrochloride

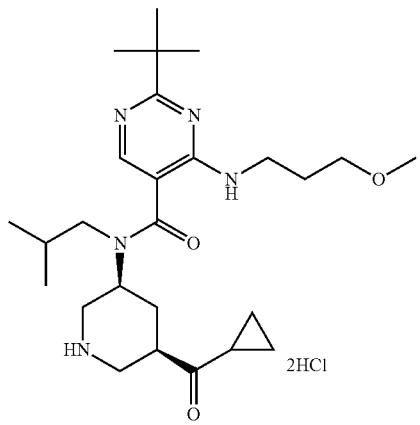

tert-Butyl (3S,5R)-3-[({2-tert-butyl-4-[(3-methoxypropyl)amino]pyrimidin-5-yl}carbonyl)(2-methylpropyl)amino]-5-(cyclopropylcarbonyl)piperidine-1-carboxylate (95 mg) was dissolved in ethyl acetate (3.2 ml), 4 M hydrogen chloride-ethyl acetate solution (0.8 ml) was added, and the mixture was stirred at room temperature for 16 hr. The solvent was evaporated under reduced pressure. The residue was subjected to reversed-phase preparative HPLC, and fractions eluted with water-acetonitrile (9:1) to acetonitrile were collected. The mixture was basified (pH 10) with saturated aqueous potassium carbonate solution, and the mixture was extracted with ethyl acetate. The extract was dried over anhydrous magnesium sulfate, and concentrated under reduced pressure. The residue was dissolved in ethyl acetate (5 ml), 4 M hydrogen chloride-ethyl acetate solution (75 μl) was added and the mixture was stirred for 1 min and concentrated under reduced pressure to give the object compound (48 mg).

MS (ESI+, m/e) 474 (M+1)

Example 206

(3R,5S)-5-[({2-tert-butyl-4-[(3-methoxypropyl)amino]pyrimidin-5-yl}carbonyl)(2-methylpropyl)amino]piperidine-3-carboxylic acid dihydrochloride

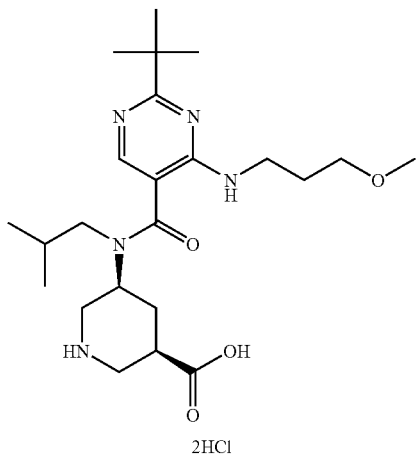

(3R,5S)-1-(tert-Butoxycarbonyl)-5-[({2-tert-butyl-4-[(3-methoxypropyl)amino]pyrimidin-5-yl}carbonyl)(isobutyl)amino]piperidine-3-carboxylic acid (102 mg) was dissolved in 1,4-dioxane (3 ml), water (100 μl) and 6 N hydrochloric acid (3 ml) were added and the mixture was stirred at room temperature for 3.5 hr. The reaction mixture was concentrated under reduced pressure to give the object compound (99 mg).

MS (ESI+, m/e) 449 (M+1)

Reference Example 244

2-tert-butyl-4-[(3-methoxypropyl)amino]-N-(2-methylpropyl)-N-[(3S,5R)-5-(morpholin-4-ylcarbonyl)piperidin-3-yl]pyrimidine-5-carboxamide

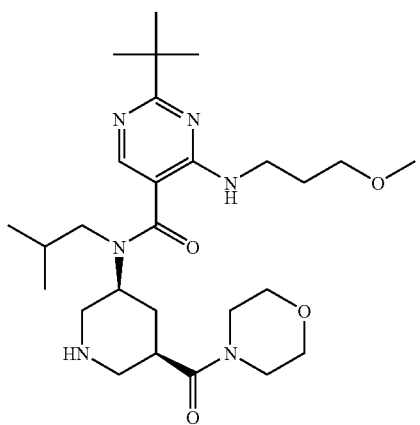

2-tert-Butyl-4-[(3-methoxypropyl)amino]-N-(2-methylpropyl)-N-[(3S,5R)-5-(morpholin-4-ylcarbonyl)piperidin-3-yl]pyrimidine-5-carboxamide dihydrochloride (2.58 g) was suspended in water (100 ml), saturated aqueous sodium hydrogen carbonate was added, and the mixture was extracted with ethyl acetate. The extract was dried over anhydrous magnesium sulfate, and concentrated under reduced pressure to give the object compound (2.15 g).

MS (ESI+, m/e) 519 (M+1)

Example 207

2-tert-butyl-4-[(3-methoxypropyl)amino]-N-(2-methylpropyl)-N-[(3S,5R)-5-(morpholin-4-ylcarbonyl)piperidin-3-yl]pyrimidine-5-carboxamide monofumarate

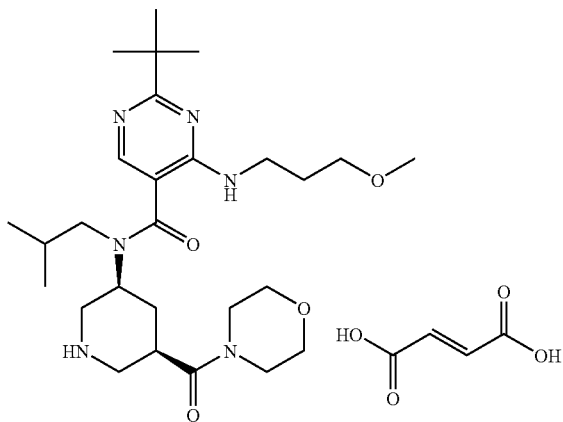

2-tert-Butyl-4-[(3-methoxypropyl)amino]-N-(2-methylpropyl)-N-[(3S,5R)-5-(morpholin-4-ylcarbonyl)piperidin-3-yl]pyrimidine-5-carboxamide (5.22 g) was dissolved in ethyl acetate (80 ml), and a solution of fumaric acid (1.17 g) in methanol (20 ml) was added. The mixture was heated to 70° C., stirred well and filtered. The filtrate was concentrated under reduced pressure, and the obtained white solid (6.40 g) was suspended in ethyl acetate (190 ml), and dissolved by heating to 70° C. Acetonitrile (190 ml) heated to 70° C. was added, and the mixture was allowed to cool to 50° C. Seed crystals (10 mg) were added, and the mixture was allowed to cool to room temperature with stirring. The mixture was further stirred at 0° C. for 2 hr, and the precipitated white solid was collected by filtration, and washed with ethyl acetate-acetonitrile (1:1). The obtained white crystals were dried under reduced pressure at 100° C. for 12 hr to give the object compound (4.16 g).

MS (ESI+, m/e) 519 (M+1)

Reference Example 245 methyl 3-[(tert-butoxycarbonyl)amino]-N-(2-methylpropyl)-L-alaninate

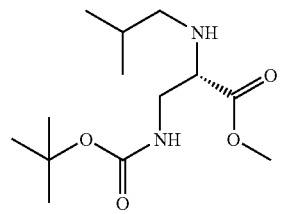

Methyl 3-[(tert-butoxycarbonyl)amino]-L-alaninate hydrochloride (2.00 g), 2-methylpropanal (860 µl) and acetic acid (450 µl) were dissolved in 1,2-dichloroethane-methanol (5:1, 60 ml), and the mixture was stirred at room temperature for 30 min. Sodium triacetoxyborohydride (4.00 g) was added and the mixture was stirred at room temperature for 2 hr. The reaction mixture was concentrated under reduced pressure, saturated aqueous sodium hydrogen carbonate was added, and the mixture was extracted with ethyl acetate. The extract was dried over anhydrous magnesium sulfate and the solvent was evaporated under reduced pressure. The residue was subjected to basic silica gel column chromatography, and the fraction eluted with ethyl acetate-hexane (0:1-1:0) was concentrated under reduced pressure to give the object compound (1.76 g).

$^1$H-NMR (CDCl$_3$) δ 0.90 (3H, d), 0.92 (3H, d), 1.44 (9H, s), 1.60-1.76 (1H, m), 2.28 (1H, dd), 2.44 (2H, dd), 3.24 (2H, dd), 3.29-3.36 (1H, m), 3.37-3.52 (1H, m), 3.74 (3H, s), 4.97 (1H, br s).

Reference Example 246 methyl 3-[(tert-butoxycarbonyl)amino]-N-({2-tert-butyl-4-[(furan-2-ylmethyl)amino]pyrimidin-5-yl}carbonyl)-N-(2-methylpropyl)-L-alaninate

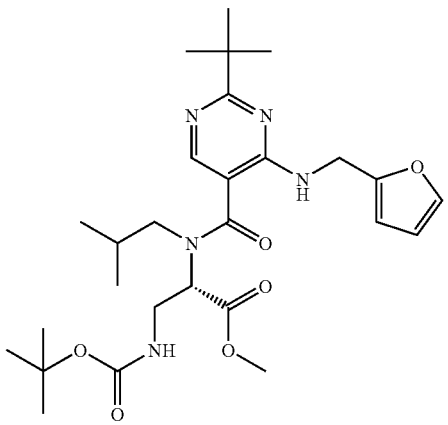

2-tert-Butyl-4-[(furan-2-ylmethyl)amino]pyrimidine-5-carboxylic acid (391 mg) was suspended in toluene (12 ml), thionyl chloride (260 µl) and DMF (1 drop) were added and the mixture was stirred at 90° C. for 2.5 hr. The reaction mixture was cooled to room temperature, and concentrated under reduced pressure, and the residue was subjected to azeotropic distillation with toluene. The obtained residue was suspended in acetonitrile (15 ml), and a solution of methyl 3-[(tert-butoxycarbonyl)amino]-N-(2-methylpropyl)-L-alaninate (368 mg) and diisopropylethylamine (745 μl) in acetonitrile (10 ml) was added. The mixture was stirred at room temperature for 22 hr. The reaction mixture was concentrated under reduced pressure, and diluted with saturated aqueous sodium hydrogen carbonate, and the mixture was extracted with ethyl acetate. The extract was dried over anhydrous magnesium sulfate, and the solvent was evaporated under reduced pressure. The residue was subjected to silica gel column chromatography, and the fraction eluted with ethyl acetate-hexane (0:1-1:2) was concentrated under reduced pressure to give the object compound (330 mg).

MS (ESI+, m/e) 532 (M+1)

By a method similar to that of the above-mentioned Reference Examples 245 and 246, the compounds of Reference Examples 247 and 248 below were synthesized.

Reference Example 247 methyl 3-[(tert-butoxycarbonyl)amino]-N-(2-methylpropyl)-D-alaninate

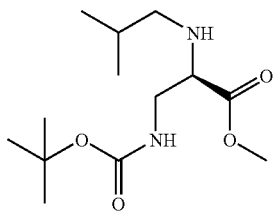

$^1$H-NMR (CDCl$_3$) δ 0.90 (3H, d), 0.92 (3H, d), 1.44 (9H, s), 1.60-1.75 (1H, m), 2.28 (1H, dd), 2.44 (1H, dd), 3.25 (1H, dd), 3.28-3.35 (1H, m), 3.36-3.51 (1H, m), 3.74 (3H, s), 4.99 (1H, br s).

Reference Example 248 methyl 3-[(tert-butoxycarbonyl)amino]-N-({2-tert-butyl-4-[(furan-2-ylmethyl)amino]pyrimidin-5-yl}carbonyl)-N-(2-methylpropyl)-D-alaninate

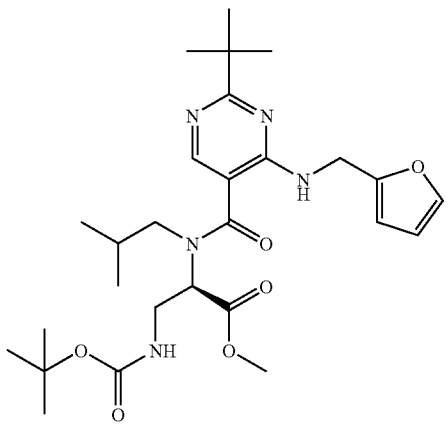

MS (ESI+, m/e) 532 (M+1)

Reference Example 249

3-[(tert-butoxycarbonyl)amino]-N-({2-tert-butyl-4-[(furan-2-ylmethyl)amino]pyrimidin-5-yl}carbonyl)-N-(2-methylpropyl)-L-alanine

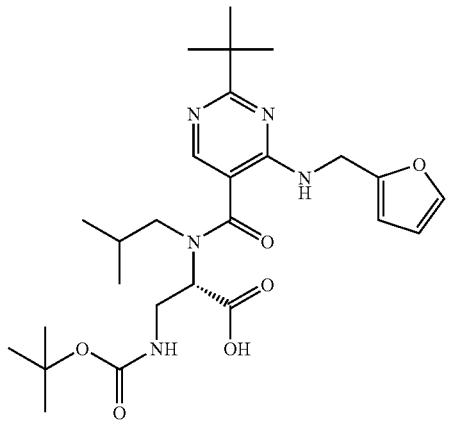

Methyl 3-[(tert-butoxycarbonyl)amino]-N-({2-tert-butyl-4-[(furan-2-ylmethyl)amino]pyrimidin-5-yl}carbonyl)-N-(2-methylpropyl)-L-alaninate (200 mg) was dissolved in tetrahydrofuran-methanol (1:2, 18 ml), 2 M aqueous sodium hydroxide solution (0.95 ml) was added and the mixture was stirred for 4 hr. The reaction mixture was concentrated under reduced pressure, and diluted with saturated aqueous ammonium chloride solution, and the mixture was extracted with ethyl acetate. The extract was dried over anhydrous magnesium sulfate, and solvent was evaporated under reduced pressure to give the object compound (240 mg).

MS (ESI+, m/e) 518 (M+1)

Reference Example 250 tert-butyl {(2S)-3-(benzylamino)-2-[({2-tert-butyl-4-[(furan-2-ylmethyl)amino]pyrimidin-5-yl}carbonyl)(2-methylpropyl)amino]-3-oxopropyl}carbamate

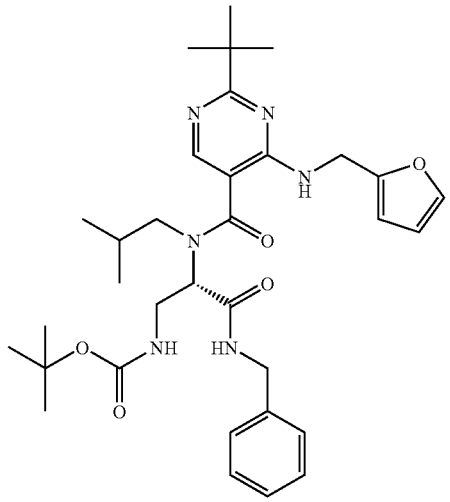

3-[(tert-Butoxycarbonyl)amino]-N-({2-tert-butyl-4-[(furan-2-ylmethyl)amino]pyrimidin-5-yl}carbonyl)-N-(2-methylpropyl)-L-alanine (27 mg), benzylamine (200 μl) and diisopropylethylamine (300 μl) were dissolved in 1,2-dichloroethane (5 ml), chloro-N,N,N',N'-tetramethylformamidinium hexafluorophosphate (100 mg) was added, and the mixture was stirred at room temperature for 3.5 hr. The reaction mixture was diluted with saturated aqueous sodium hydrogen carbonate, and the mixture was extracted with ethyl acetate. The extract was dried over anhydrous magnesium sulfate and the solvent was evaporated under reduced pressure. The residue was subjected to reversed-phase preparative HPLC, and fractions eluted with water-acetonitrile (9:1) to acetonitrile were collected. The mixture was basified (pH 10) with saturated aqueous potassium carbonate solution, and the mixture was extracted with ethyl acetate. The extract was dried over anhydrous magnesium sulfate, and concentrated under reduced pressure to give the object compound (19 mg).

MS (ESI+, m/e) 607 (M+1)

Reference Example 251 tert-butyl {(2S)-2-[({2-tert-butyl-4-[(furan-2-ylmethyl)amino]pyrimidin-5-yl}carbonyl)(2-methylpropyl)amino]-3-oxo-3-[(pyridin-2-ylmethyl)amino]propyl}carbamate

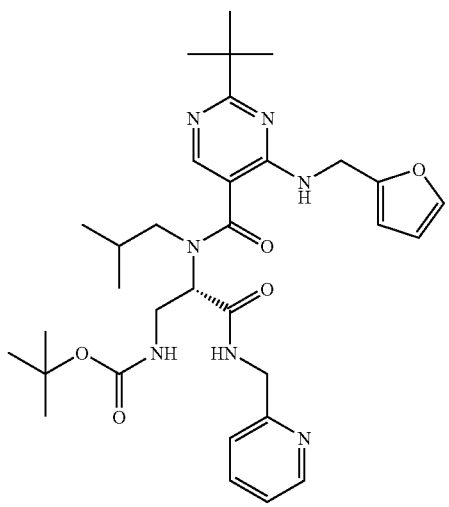

3-[(tert-Butoxycarbonyl)amino]-N-({2-tert-butyl-4-[(furan-2-ylmethyl)amino]pyrimidin-5-yl}carbonyl)-N-(2-methylpropyl)-L-alanine (40 mg), 1-pyridin-2-ylmethanamine (157 μl) and diisopropylethylamine (330 μl) were dissolved in 1,2-dichloroethane (5 ml), chloro-N,N,N',N'-tetramethylformamidinium hexafluorophosphate (200 mg) was added, and the mixture was stirred at room temperature for 2 hr. The reaction mixture was diluted with saturated aqueous sodium hydrogen carbonate, and the mixture was extracted with ethyl acetate. The extract was dried over anhydrous magnesium sulfate and the solvent was evaporated under reduced pressure. The residue was subjected to silica gel column chromatography, and the fraction eluted with ethyl acetate-hexane (1:9-1:0) was concentrated under reduced pressure to give the object compound (19 mg).

MS (ESI+, m/e) 608 (M+1)

By a method similar to that of the above-mentioned Reference Example 251, the compound of Reference Example 252 below was synthesized.

Reference Example 252 tert-butyl {(2S)-2-[({2-tert-butyl-4-[(furan-2-ylmethyl)amino]pyrimidin-5-yl}carbonyl)(2-methylpropyl)amino]-3-oxo-3-[(pyridin-3-ylmethyl)amino]propyl}carbamate

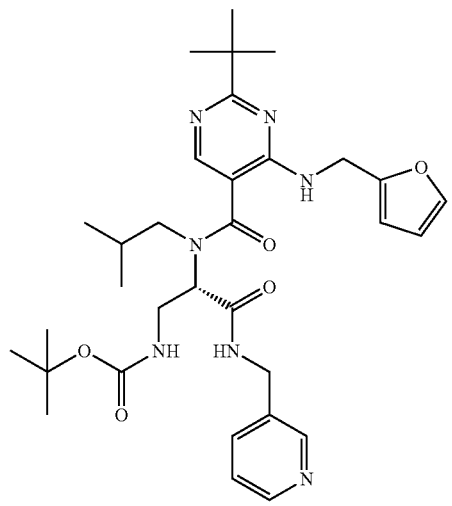

MS (ESI+, m/e) 608(M+1)

Reference Example 253 tert-butyl {(2S)-3-amino-2-[({2-tert-butyl-4-[(furan-2-ylmethyl)amino]pyrimidin-5-yl}carbonyl)(2-methylpropyl)amino]-3-oxopropyl}carbamate

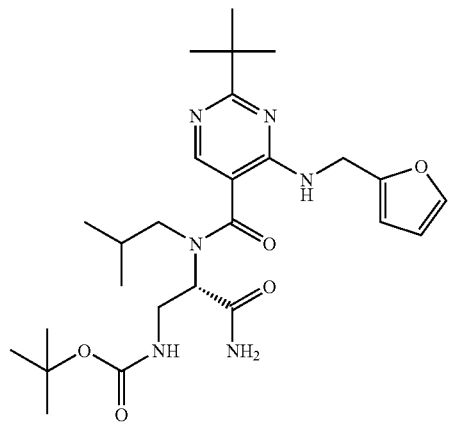

3-[(tert-Butoxycarbonyl)amino]-N-({2-tert-butyl-4-[(furan-2-ylmethyl)amino]pyrimidin-5-yl}carbonyl)-N-(2-methylpropyl)-L-alanine (147 mg), 1H-1,2,3-benzotriazol-1-ol ammoniate (130 mg) and triethylamine (160 μl) were dissolved in 1,2-dichloroethane-DMF (3:1, 15 ml), WSC.HCl (163 mg) was added and the mixture was stirred at room temperature for 21 hr. The reaction mixture was concentrated under reduced pressure, and diluted with saturated aqueous sodium hydrogen carbonate, and the mixture was extracted with ethyl acetate. The extract was dried over anhydrous magnesium sulfate and the solvent was evaporated under reduced pressure. The residue was subjected to silica gel column chromatography, and the fraction eluted with ethyl acetate-hexane (1:9) to ethyl acetate was concentrated under reduced pressure to give the object compound (90 mg).

MS (ESI+, m/e) 517 (M+1)

Reference Example 254 tert-butyl {(2S)-2-[({2-tert-butyl-4-[(furan-2-ylm-ethyl)amino]pyrimidin-5-yl}carbonyl)(2-methylpropyl)amino]-3-[(2-hydroxyethyl)amino]-3-oxopropyl}carbamate

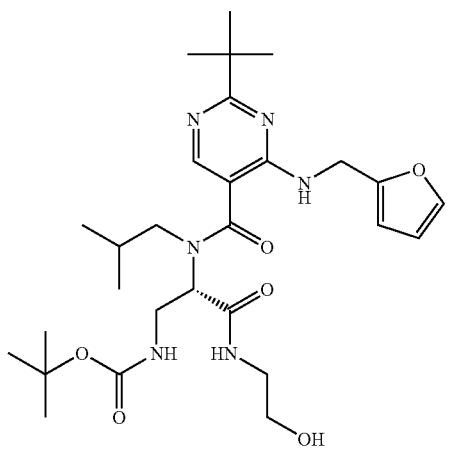

3-[(tert-Butoxycarbonyl)amino]-N-({2-tert-butyl-4-[(furan-2-ylmethyl)amino]pyrimidin-5-yl}carbonyl)-N-(2-methylpropyl)-L-alanine (125 mg), 2-aminoethanol (60 mg) and diisopropylethylamine (250 μl) were dissolved in DMF (10 ml), BOP reagent (500 mg) was added and the mixture was stirred at room temperature for 1.5 hr. The reaction mixture was diluted with saturated aqueous sodium hydrogen carbonate, and the mixture was extracted with ethyl acetate. The extract was dried over anhydrous magnesium sulfate and the solvent was evaporated under reduced pressure. The residue was subjected to silica gel column chromatography, and the fraction eluted with ethyl acetate-hexane (0:1-1:0) was concentrated under reduced pressure to give the object compound (110 mg).

MS (ESI+, m/e) 561 (M+1)

By a method similar to that of the above-mentioned Reference Example 254, the compounds of Reference Examples 255 and 256 below were synthesized.

Reference Example 255 tert-butyl {(2S)-2-[({2-tert-butyl-4-[(furan-2-ylm-ethyl)amino]pyrimidin-5-yl}carbonyl)(2-methylpropyl)amino]-3-[(3-hydroxy-2,2-dimethylpropyl)amino]-3-oxopropyl}carbamate

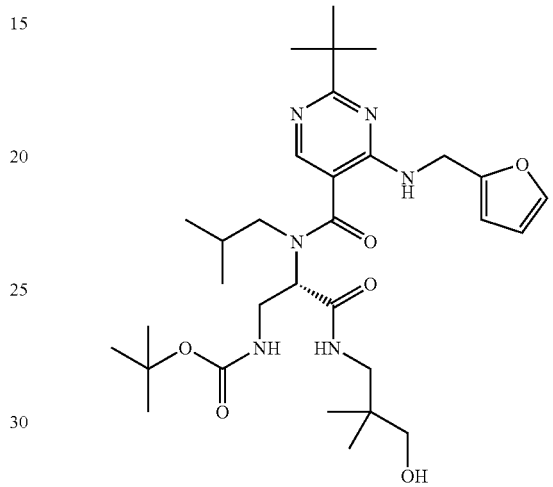

MS (ESI+, m/e) 603 (M+1)

Reference Example 256 tert-butyl {(2S)-2-[({2-tert-butyl-4-[(furan-2-ylm-ethyl)amino]pyrimidin-5-yl}carbonyl)(2-methylpropyl)amino]-3-[(2-morpholin-4-ylethyl)amino]-3-oxopropyl}carbamate

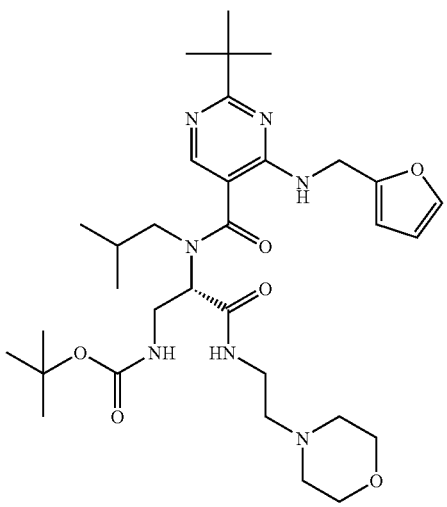

MS (ESI+, m/e) 630 (M+1)

Reference Example 257 tert-butyl {(2S)-2-[({2-tert-butyl-4-[(furan-2-ylmethyl)amino]pyrimidin-5-yl}carbonyl)(2-methylpropyl)amino]-3-hydroxypropyl}carbamate

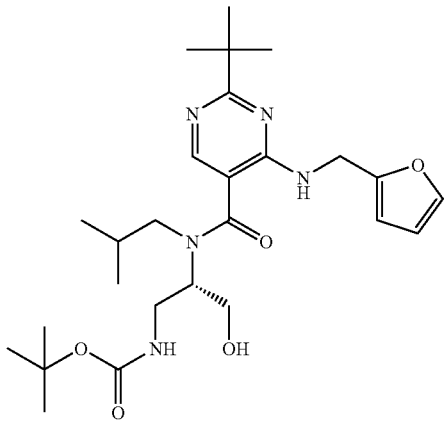

Calcium chloride (420 mg) was suspended in ethanol (5 ml), and sodium borohydride (286 mg) was added at 0° C. The mixture was stirred at 0° C. for 15 min, and a solution of methyl 3-[(tert-butoxycarbonyl)amino]-N-({2-tert-butyl-4-[(furan-2-ylmethyl)amino]pyrimidin-5-yl}carbonyl)-N-(2-methylpropyl)-L-alaninate (105 mg) in THF (5 ml) was added dropwise. The mixture was stirred at room temperature for 1.5 hr, the reaction mixture was diluted with 10% aqueous citric acid solution, and the mixture was extracted with ethyl acetate. The extract was washed with saturated aqueous sodium hydrogen carbonate, and dried over anhydrous magnesium sulfate. The solvent was evaporated under reduced pressure. The residue was subjected to reversed-phase preparative HPLC, and fractions eluted with water-acetonitrile (9:1) to acetonitrile were collected. The mixture was basified (pH 10) with saturated aqueous potassium carbonate solution, and the mixture was extracted with ethyl acetate. The extract was dried over anhydrous magnesium sulfate, and concentrated under reduced pressure to give the object compound (65 mg).

MS (ESI+, m/e) 504 (M+1)

By a method similar to that of Example 177, the compounds of Examples 208 to 211 below were synthesized.

Example 208 methyl 3-amino-N-({2-tert-butyl-4-[(furan-2-ylmethyl)amino]pyrimidin-5-yl}carbonyl)-N-(2-methylpropyl)-L-alaninate dihydrochloride

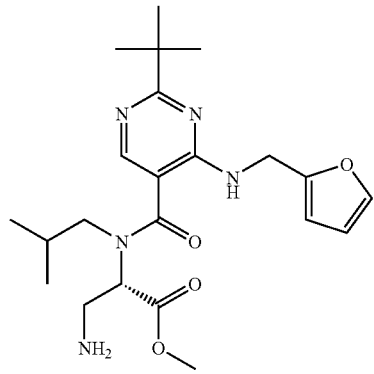

MS (ESI+, m/e) 432 (M+1)

Example 209 methyl 3-amino-N-({2-tert-butyl-4-[(furan-2-ylmethyl)amino]pyrimidin-5-yl}carbonyl)-N-(2-methylpropyl)-D-alaninate dihydrochloride

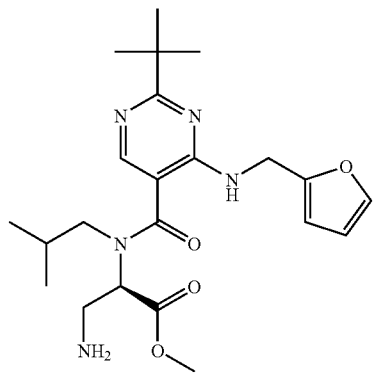

MS (ESI+, m/e) 432 (M+1)

Example 210

N-[(1S)-1-(aminomethyl)-2-(benzylamino)-2-oxoethyl]-2-tert-butyl-4-[(furan-2-ylmethyl)amino]-N-(2-methylpropyl)pyrimidine-5-carboxamide dihydrochloride

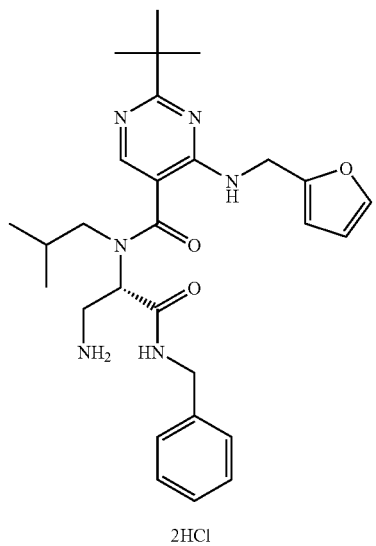

MS (ESI+, m/e) 507 (M+1)

Example 211

N-[(1S)-2-amino-1-(aminomethyl)-2-oxoethyl]-2-tert-butyl-4-[(furan-2-ylmethyl)amino]-N-(2-methylpropyl)pyrimidine-5-carboxamide dihydrochloride

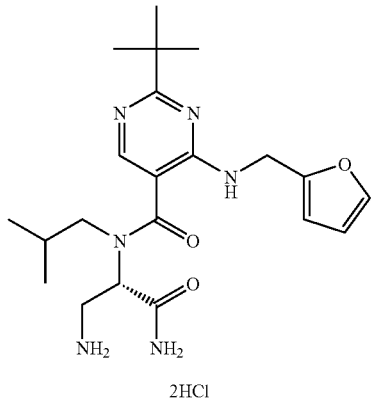

MS (ESI+, m/e) 417 (M+1)

By a method similar to that of Example 202, the compounds of Examples 212 to 214 below were synthesized.

Example 212

N-[(1S)-2-amino-1-(hydroxymethyl)ethyl]-2-tert-butyl-4-[(furan-2-ylmethyl)amino]-N-(2-methylpropyl)pyrimidine-5-carboxamide dihydrochloride

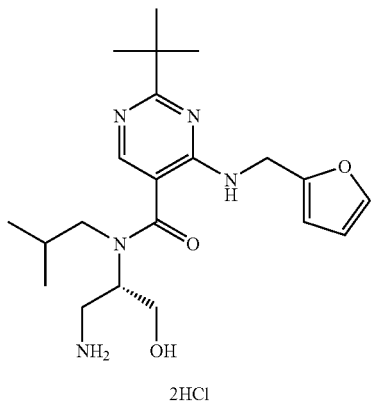

MS (ESI+, m/e) 404 (M+1)

Example 213

N-{(1S)-1-(aminomethyl)-2-[(2-hydroxyethyl)amino]-2-oxoethyl}-2-tert-butyl-4-[(furan-2-ylmethyl)amino]-N-(2-methylpropyl)pyrimidine-5-carboxamide dihydrochloride

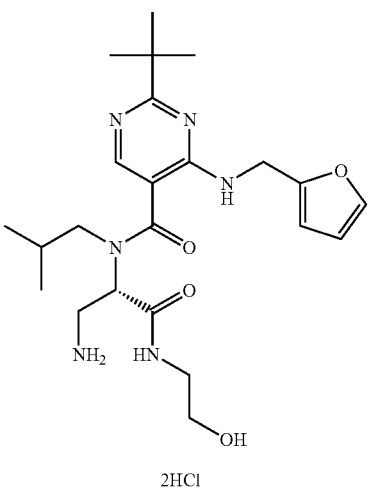

MS (ESI+, m/e) 461 (M+1)

Example 214

N-{(1S)-1-(aminomethyl)-2-[(3-hydroxy-2,2-dimethylpropyl)amino]-2-oxoethyl}-2-tert-butyl-4-[(furan-2-ylmethyl)amino]-N-(2-methylpropyl)pyrimidine-5-carboxamide dihydrochloride

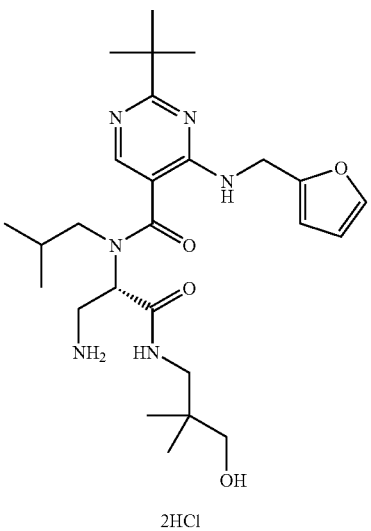

MS (ESI+, m/e) 503 (M+1)

Example 215

N-{(1S)-1-(aminomethyl)-2-oxo-2-[(pyridin-2-ylmethyl)amino]ethyl}-2-tert-butyl-4-[(furan-2-ylmethyl)amino]-N-(2-methylpropyl)pyrimidine-5-carboxamide trihydrochloride

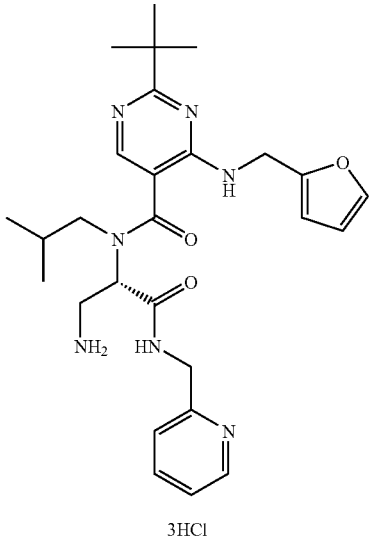

tert-Butyl {(2S)-2-[({2-tert-butyl-4-[(furan-2-ylmethyl)amino]pyrimidin-5-yl}carbonyl)(2-methylpropyl)amino]-3-oxo-3-[(pyridin-2-ylmethyl)amino]propyl}carbamate (19 mg) was dissolved in ethyl acetate (3 ml), 4 M hydrogen chloride-ethyl acetate solution (1.5 ml) was added, and the mixture was stirred at room temperature for 14 hr. The solvent was evaporated under reduced pressure. The residue was subjected to reversed-phase preparative HPLC, and fractions eluted with water-acetonitrile (9:1) to acetonitrile were collected. The mixture was basified (pH 10) with saturated aqueous potassium carbonate solution, and the mixture was extracted with ethyl acetate. The extract was dried over anhydrous magnesium sulfate, and concentrated under reduced pressure. The residue was dissolved in ethyl acetate (3 ml), 4 M hydrogen chloride-ethyl acetate solution (1.5 ml) was added and the mixture was stirred for 1 min and concentrated under reduced pressure to give the object compound (17 mg).

MS (ESI+, m/e) 508 (M+1)

By a method similar to that of the above-mentioned Example 215, the compounds of Examples 216 and 217 below were synthesized.

Example 216

N-{(1S)-1-(aminomethyl)-2-oxo-2-[(pyridin-3-ylmethyl)amino]ethyl}-2-tert-butyl-4-[(furan-2-ylmethyl)amino]-N-(2-methylpropyl)pyrimidine-5-carboxamide trihydrochloride

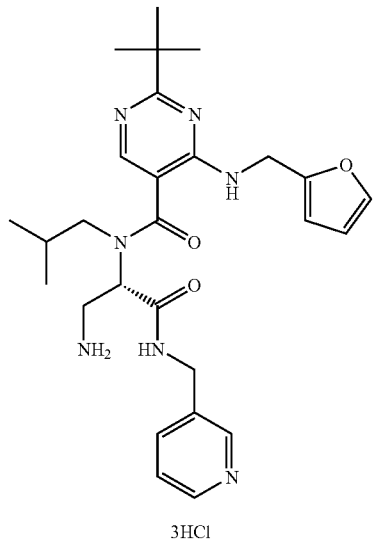

MS (ESI+, m/e) 508 (M+1)

Example 217

N-{(1S)-1-(aminomethyl)-2-[(2-morpholin-4-ylethyl)amino]-2-oxoethyl}-2-tert-butyl-4-[(furan-2-ylmethyl)amino]-N-(2-methylpropyl)pyrimidine-5-carboxamide trihydrochloride

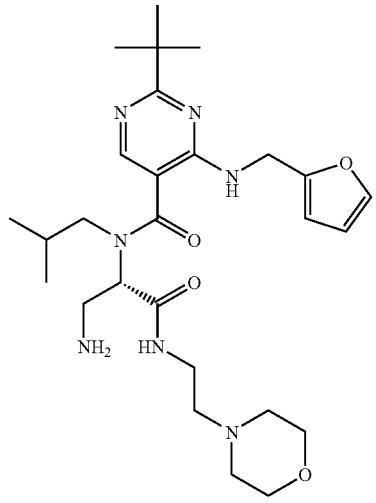

MS (ESI+, m/e) 530 (M+1)

Reference Example 258 tert-butyl (3S,5R)-3-[({2-tert-butyl-4-[(3-methoxypropyl)amino]pyrimidin-5-yl}carbonyl)(2-methylpropyl)amino]-5-[(4-methoxypiperidin-1-yl)carbonyl]piperidine-1-carboxylate

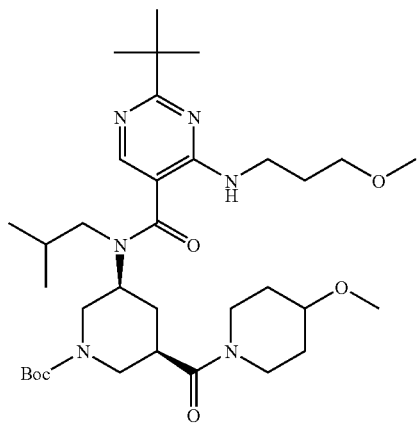

A solution of (3R,5S)-1-(tert-butoxycarbonyl)-5-[({2-tert-butyl-4-[(3-methoxypropyl)amino]pyrimidin-5-yl}carbonyl)(isobutyl)amino]piperidine-3-carboxylic acid (95 mg), WSC.HCl (50 mg), HOBt (34 g) and diisopropylethylamine (0.088 ml) in DMF (5 ml) was stirred at room temperature for 12 hr. The reaction mixture was poured into saturated aqueous sodium hydrogen carbonate, and the mixture was extracted with ethyl acetate. The extract was washed successively with 10% aqueous citric acid solution and saturated brine, and dried over anhydrous sodium sulfate. The solvent was evaporated under reduced pressure. The residue was subjected to silica gel column chromatography, and the fraction eluted with ethyl acetate-hexane (1:1-1:0) was concentrated under reduced pressure to give an amorphous solid (65 mg).

MS (ESI+, m/e) 647 (M+1)

By a method similar to that of Reference Example 258, the following compounds (Reference Examples 259 to 270) were obtained.

Reference Example 259 tert-butyl (3S,5R)-3-[({2-tert-butyl-4-[(3-methoxypropyl)amino]pyrimidin-5-yl}carbonyl)(2-methylpropyl)amino]-5-[(4-phenoxypiperidin-1-yl)carbonyl]piperidine-1-carboxylate

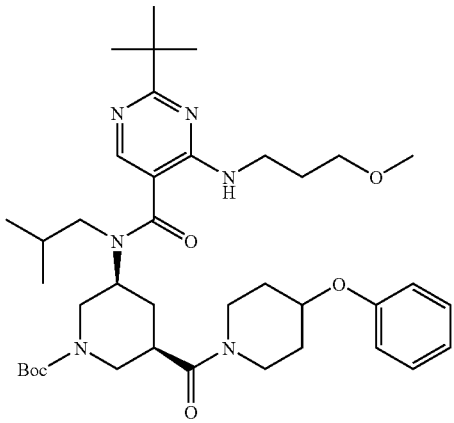

MS (ESI+, m/e) 709 (M+1)

Reference Example 260 tert-butyl (3R,5S)-3-{[4-(benzyloxy)piperidin-1-yl]carbonyl}-5-[({2-tert-butyl-4-[(3-methoxypropyl)amino]pyrimidin-5-yl}carbonyl)(2-methylpropyl)amino]piperidine-1-carboxylate

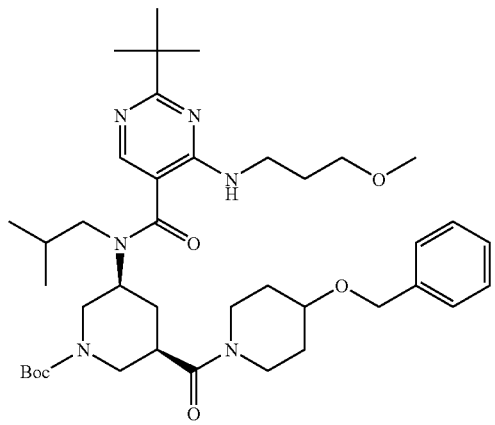

MS (ESI+, m/e) 723 (M+1)

Reference Example 261 tert-butyl (3S,5R)-3-[({2-tert-butyl-4-[(3-methoxypropyl)amino]pyrimidin-5-yl}carbonyl)(2-methylpropyl)amino]-5-(piperidin-1-ylcarbonyl)piperidine-1-carboxylate

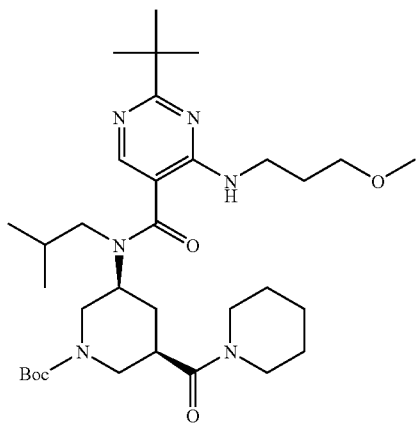

MS (ESI+, m/e) 617 (M+1)

333

Reference Example 262 tert-butyl (3S,5R)-3-[({2-tert-butyl-4-[(3-methoxypropyl)amino]pyrimidin-5-yl}carbonyl)(2-methylpropyl)amino]-5-[(4-hydroxy-4-phenylpiperidin-1-yl)carbonyl]piperidine-1-carboxylate

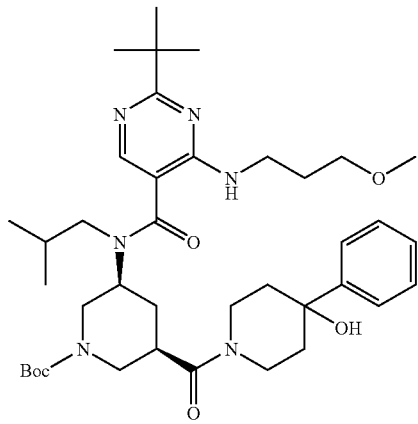

MS (ESI+, m/e) 709 (M+1)

Reference Example 263 tert-butyl (3S,5R)-3-[({2-tert-butyl-4-[(3-methoxypropyl)amino]pyrimidin-5-yl}carbonyl)(2-methylpropyl)amino]-5-[(4-phenylpiperidin-1-yl)carbonyl]piperidine-1-carboxylate

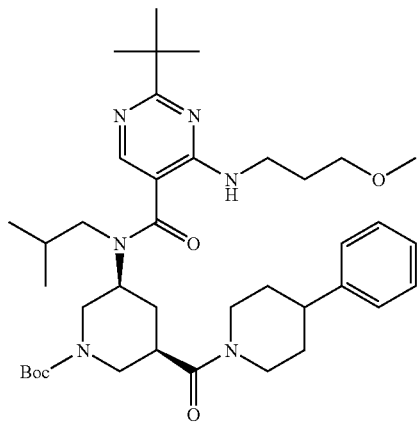

MS (ESI+, m/e) 693 (M+1)

334

Reference Example 264 tert-butyl (3S,5R)-3-[({2-tert-butyl-4-[(3-methoxypropyl)amino]pyrimidin-5-yl}carbonyl)(2-methylpropyl)amino]-5-(thiomorpholin-4-ylcarbonyl)piperidine-1-carboxylate

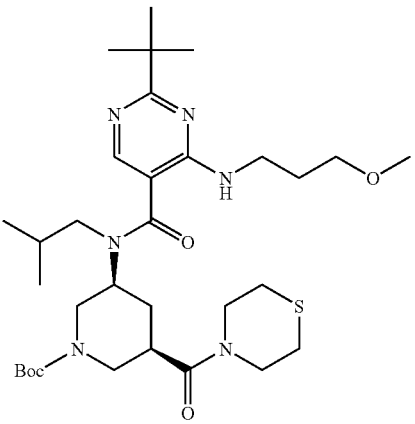

MS (ESI+, m/e) 635 (M+1)

Reference Example 265 tert-butyl (3S,5R)-3-[({2-tert-butyl-4-[(3-methoxypropyl)amino]pyrimidin-5-yl}carbonyl)(2-methylpropyl)amino]-5-[(1,1-dioxidothiomorpholin-4-yl)carbonyl]piperidine-1-carboxylate

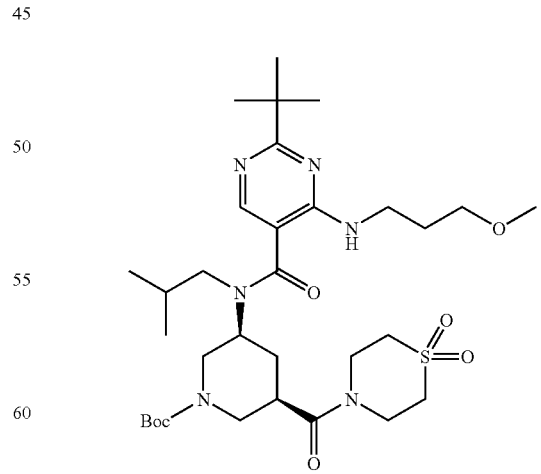

MS (ESI+, m/e) 667 (M+1)

Reference Example 266 tert-butyl (3S,5R)-3-[({2-tert-butyl-4-[(3-methoxypropyl)amino]pyrimidin-5-yl}carbonyl)(2-methylpropyl)amino]-5-[(1-oxidothiomorpholin-4-yl)carbonyl]piperidine-1-carboylate

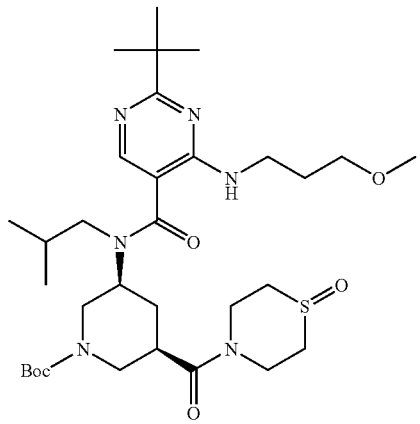

MS (ESI+, m/e) 651 (M+1)

Reference Example 267 tert-butyl (3S,5R)-3-[({2-tert-butyl-4-[(3-methoxypropyl)amino]pyrimidin-5-yl}carbonyl)(2-methylpropyl)amino]-5-[(4-pyridin-2-ylpiperidin-1-yl)carbonyl]piperidine-1-carboxylate

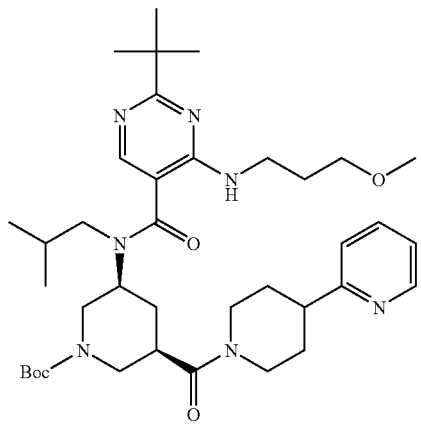

MS (ESI+, m/e) 694 (M+1)

Reference Example 268 tert-butyl (3S,5R)-3-[({2-tert-butyl-4-[(3-methoxypropyl)amino]pyrimidin-5-yl}carbonyl)(2-methylpropyl)amino]-5-[(4-fluoropiperidin-1-yl)carbonyl]piperidine-1-carboxylate

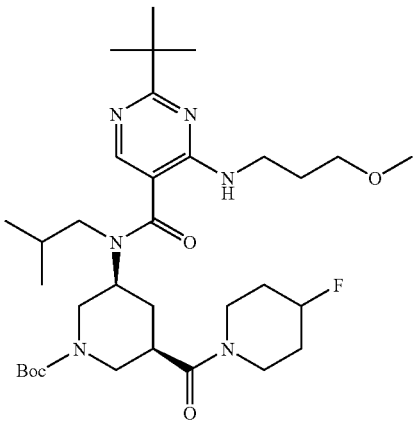

MS (ESI+, m/e) 635 (M+1)

Reference Example 269 tert-butyl (3S,5R)-3-[({2-tert-butyl-4-[(3-methoxypropyl)amino]pyrimidin-5-yl}carbonyl)(2-methylpropyl)amino]-5-[(4,4-difluoropiperidin-1-yl)carbonyl]piperidine-1-carboxylate

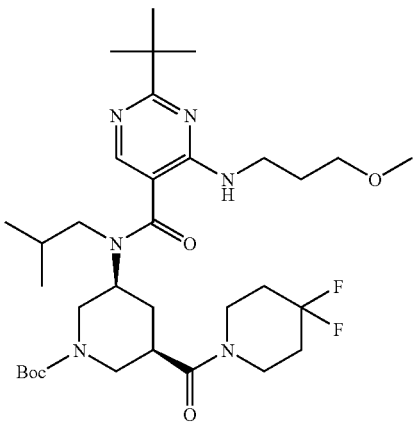

MS (ESI+, m/e) 653 (M+1)

Reference Example 270 tert-butyl (3S,5R)-3-[({2-tert-butyl-4-[(3-methoxypropyl)amino]pyrimidin-5-yl}carbonyl)(2-methylpropyl)amino]-5-{[4-(1-hydroxy-1-methylethyl)piperidin-1-yl]carbonyl}piperidine-1-carboxylate

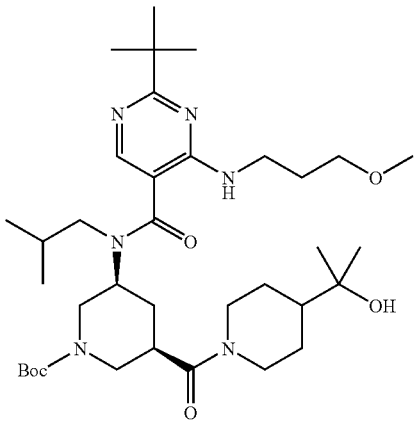

MS (ESI+, m/e) 675 (M+1)

Reference Example 271 tert-butyl (3S,5R)-3-{[(7-chlorothieno[3,2-b]pyridin-6-yl)carbonyl](2-methylpropyl)amino}-5-(morpholin-4-ylcarbonyl)piperidine-1-carboxylate

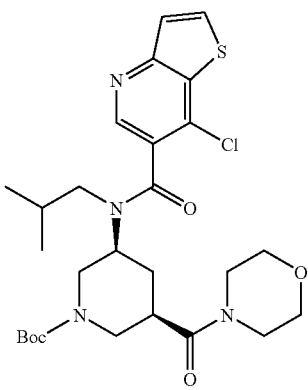

tert-Butyl (3S,5R)-3-[(2-methylpropyl)amino]-5-(morpholin-4-ylcarbonyl)piperidine-1-carboxylate (100 mg) and diisopropylethylamine (0.095 ml) were dissolved in dichloromethane (3 ml), a solution of 7-chlorothieno[3,2-b]pyridine-6-carbonyl chloride (70 mg) in dichloromethane (2 ml) was added dropwise, and the mixture was stirred at room temperature for 1 hr. The reaction mixture was poured into water, and the mixture was extracted with ethyl acetate. The extract was dried over anhydrous sodium sulfate and the solvent was evaporated under reduced pressure. The residue was subjected to silica gel column chromatography, and the fraction eluted with ethyl acetate was concentrated under reduced pressure to give the object compound (120 mg)

MS (ESI+, m/e) 565 (M+1).

Reference Example 272 tert-butyl (3S,5R)-3-[({7-[(3-methoxypropyl)amino]thieno[3,2-b]pyridin-6-yl}carbonyl)(2-methylpropyl)amino]-5-(morpholin-4-ylcarbonyl)piperidine-1-carboxylate

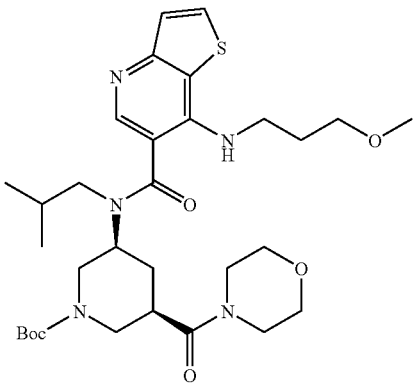

tert-Butyl (3S,5R)-3-{[(7-chlorothieno[3,2-b]pyridin-6-yl)carbonyl](2-methylpropyl)amino}-5-(morpholin-4-ylcarbonyl)piperidine-1-carboxylate (120 mg), 3-methoxypropan-1-amine (113 mg) and diisopropylethylamine (0.22 ml) were dissolved in 2-propanol (5 ml), and the mixture was stirred at 60° C. for 12 hr. The reaction mixture was poured into water, and the mixture was extracted with ethyl acetate. The extract was washed with brine, and dried over anhydrous sodium sulfate. The solvent was evaporated under reduced pressure. The residue was subjected to silica gel column chromatography, and the fraction eluted with ethyl acetate-methanol (1:0-9:1) was concentrated under reduced pressure to give the object compound (90 mg).

MS (ESI+, m/e) 618 (M+1)

Example 218

2-tert-butyl-N-{(3S,5R)-5-[(4-methoxypiperidin-1-yl)carbonyl]piperidin-3-yl}-4-[(3-methoxypropyl)amino]-N-(2-methylpropyl)pyrimidine-5-carboxamide dihydrochloride

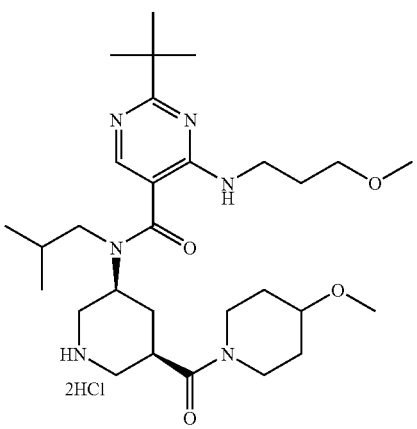

tert-Butyl (3S,5R)-3-[({2-tert-butyl-4-[(3-methoxypropyl)amino]pyrimidin-5-yl}carbonyl)(2-methylpropyl)amino]-5-[(4-methoxypiperidin-1-yl)carbonyl]piperidine-1-carboxylate (65 mg) was dissolved in ethyl acetate (5 ml), 4 N hydrogen chloride-ethyl acetate solution (7 ml) was added, and the mixture was stirred at room temperature for 1 hr. The solvent was evaporated under reduced pressure, and the residue was dried under reduced pressure to give the object compound (57 mg).

MS (ESI+, m/e) 547 (M+1)

By a method similar to that of Example 218, the following compounds (Examples 219 to 228) were obtained.

Example 219

2-tert-butyl-4-[(3-methoxypropyl)amino]-N-(2-methylpropyl)-N-{(3S,5R)-5-[(4-phenoxypiperidin-1-yl)carbonyl]piperidin-3-yl}pyrimidine-5-carboxamide dihydrochloride

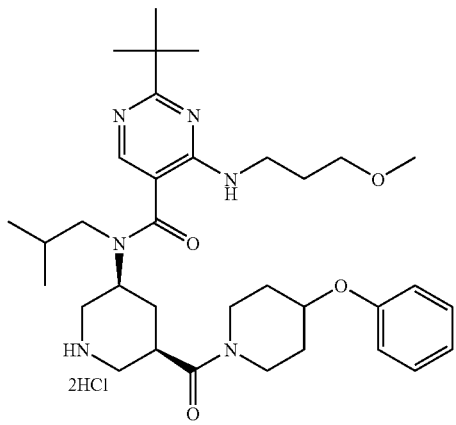

MS (ESI+, m/e) 609 (M+1)

Example 220

N-[(3S,5R)-5-{[4-(benzyloxy)piperidin-1-yl]carbonyl}piperidin-3-yl]-2-tert-butyl-4-[(3-methoxypropyl)amino]-N-(2-s methylpropyl)pyrimidine-5-carboxamide dihydrochloride

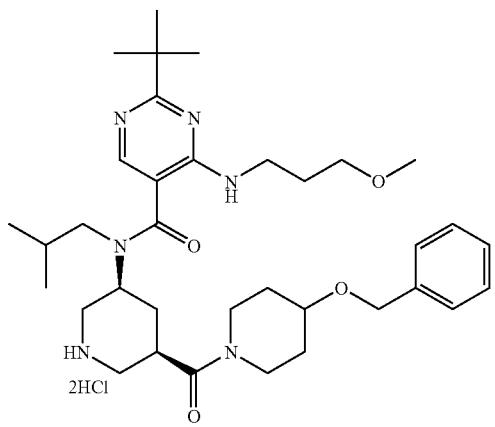

MS (ESI+, m/e) 623 (M+1)

Example 221

2-tert-butyl-4-[(3-methoxypropyl)amino]-N-(2-methylpropyl)-N-[(3S,5R)-5-(piperidin-1-ylcarbonyl)piperidin-3-yl]pyrimidine-5-carboxamide dihydrochloride

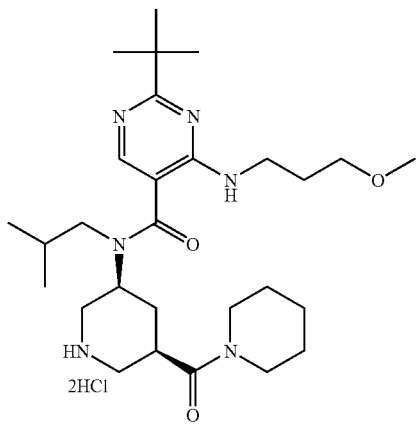

MS (ESI+, m/e) 517 (M+1)

Example 222

2-tert-butyl-4-[(3-methoxypropyl)amino]-N-(2-methylpropyl)-N-{(3S,5R)-5-[(4-phenylpiperidin-1-yl)carbonyl]piperidin-3-yl}pyrimidine-5-carboxamide dihydrochloride

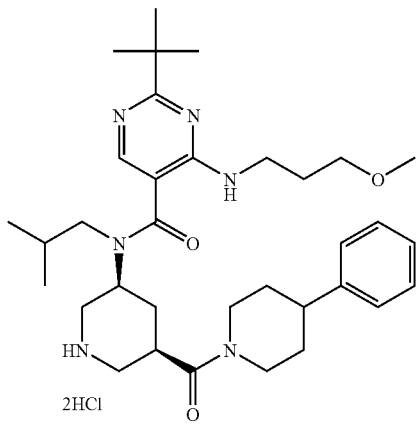

MS (ESI+, m/e) 593 (M+1)

Example 223

2-tert-butyl-4-[(3-methoxypropyl)amino]-N-(2-methylpropyl)-N-[(3S,5R)-5-(thiomorpholin-4-ylcarbonyl)piperidin-3-yl]pyrimidine-5-carboxamide dihydrochloride

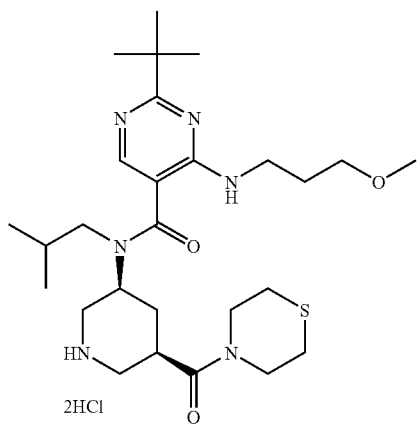

MS (ESI+, m/e) 535 (M+1)

Example 224

2-tert-butyl-N-{(3S,5R)-5-[(1,1-dioxidothiomorpholin-4-yl)carbonyl]piperidin-3-yl}-4-[(3-methoxypropyl)amino]-N-(2-methylpropyl)pyrimidine-5-carboxamide dihydrochloride

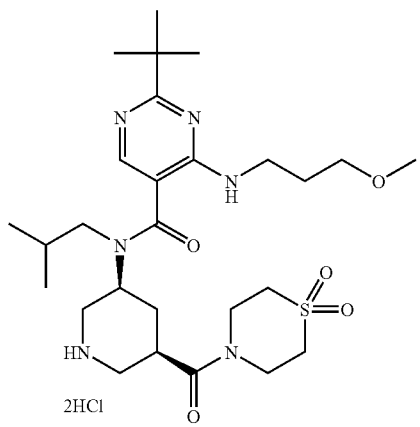

MS (ESI+, m/e) 567 (M+1)

Example 225

2-tert-butyl-4-[(3-methoxypropyl)amino]-N-(2-methylpropyl)-N-{(3S,5R)-5-[(4-pyridin-2-ylpiperidin-1-yl)carbonyl]piperidin-3-yl}pyrimidine-5-carboxamide trihydrochloride

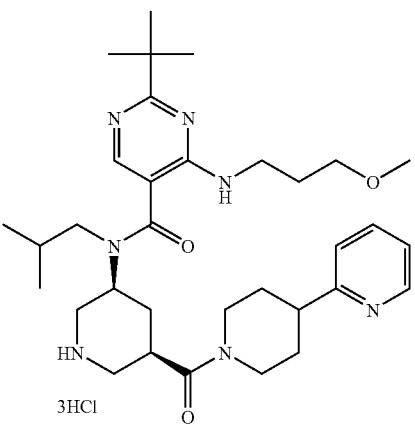

MS (ESI+, m/e) 694 (M+1)

Example 226

2-tert-butyl-N-{(3S,5R)-5-[(4-fluoropiperidin-1-yl)carbonyl]piperidin-3-yl}-4-[(3-methoxypropyl)amino]-N-(2-methylpropyl)pyrimidine-5-carboxamide dihydrochloride

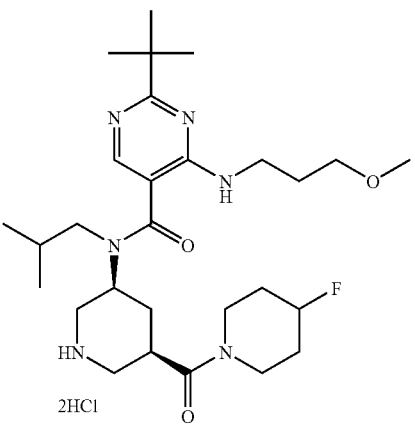

MS (ESI+, m/e) 535 (M+1)

Example 227

2-tert-butyl-N-{(3S,5R)-5-[(4,4-difluoropiperidin-1-yl)carbonyl]piperidin-3-yl}-4-[(3-methoxypropyl)amino]-N-(2-methylpropyl)pyrimidine-5-carboxamide dihydrochloride

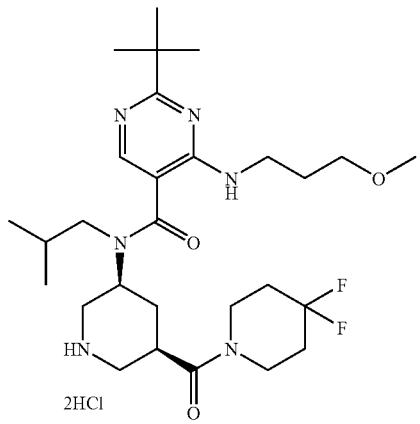

MS (ESI+, m/e) 553 (M+1)

Example 228

7-[(3-methoxypropyl)amino]-N-(2-methylpropyl)-N-[(3S,5R)-5-(morpholin-4-ylcarbonyl)piperidin-3-yl]thieno[3,2-b]pyridine-6-carboxamide dihydrochloride

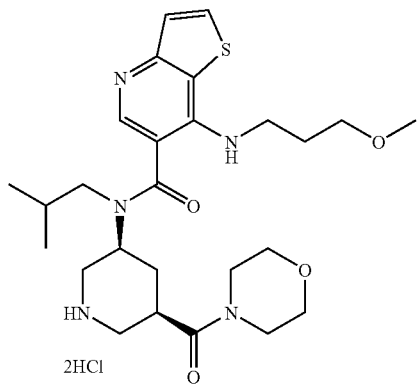

MS (ESI+, m/e) 507 (M+1)

Example 229

2-tert-butyl-4-[(3-methoxypropyl)amino]-N-(2-methylpropyl)-N-{(3S,5R)-5-[(4-phenyl-3,6-dihydropyridin-1(2H)-yl)carbonyl]piperidin-3-yl}pyrimidine-5-carboxamide dihydrochloride

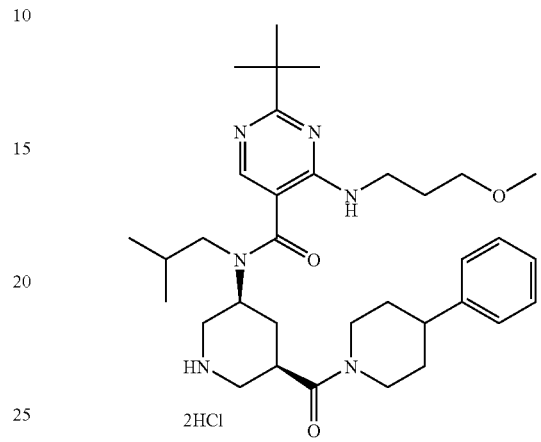

tert-Butyl (3S,5R)-3-[({2-tert-butyl-4-[(3-methoxypropyl)amino]pyrimidin-5-yl}carbonyl)(2-methylpropyl)amino]-5-[(4-hydroxy-4-phenylpiperidin-1-yl)carbonyl]piperidine-1-carboxylate (100 mg) was dissolved in ethyl acetate (5 ml), 4 N hydrogen chloride-ethyl acetate solution (7 ml) was added, and the mixture was stirred at room temperature for 1 hr. The solvent was evaporated under reduced pressure, and the residue was dried under reduced pressure to give the object compound (80 mg).

MS (ESI+, m/e) 591 (M+1)

Example 230

2-tert-butyl-4-[(3-methoxypropyl)amino]-N-(2-methylpropyl)-N-{(3S,5R)-5-[(1-oxidothiomorpholin-4-yl)carbonyl]piperidin-3-yl}pyrimidine-5-carboxamide

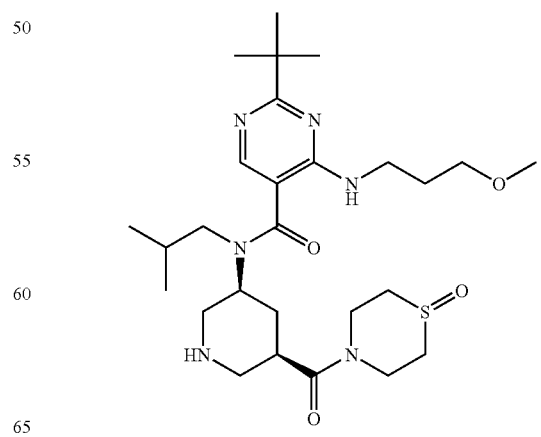

tert-Butyl (3S,5R)-3-[({2-tert-butyl-4-[(3-methoxypropyl)amino]pyrimidin-5-yl}carbonyl)(2-methylpropyl)amino]-5-[(1-oxidothiomorpholin-4-yl)carbonyl]piperidine-1-carboxylate (120 mg) was dissolved in chloroform (3 ml), TFA (1 ml) was added and the mixture was stirred for 1 hr. The reaction mixture was concentrated, and the residue was dissolved in ethyl acetate, washed successively with saturated aqueous sodium hydrogen carbonate and saturated brine, and dried over anhydrous sodium sulfate. The solvent was evaporated under reduced pressure to give the object compound (100 mg).

MS (ESI+, m/e) 551 (M+1)

Example 231

2-tert-butyl-N-[(3S,5R)-5-{[4-(1-hydroxy-1-methylethyl)piperidin-1-yl]carbonyl}piperidin-3-yl]-4-[(3-methoxypropyl)amino]-N-(2-methylpropyl)pyrimidine-5-carboxamide dihydrochloide

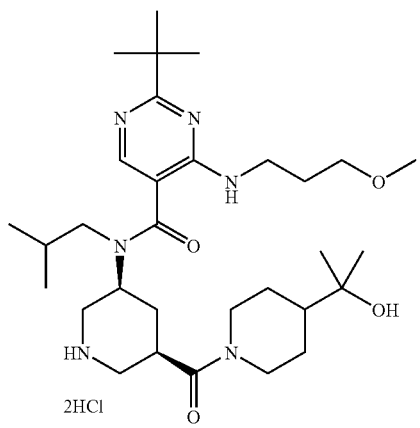

tert-Butyl (3S,5R)-3-[({2-tert-butyl-4-[(3-methoxypropyl)amino]pyrimidin-5-yl}carbonyl)(2-methylpropyl)amino]-5-{[4-(1-hydroxy-1-methylethyl)piperidin-1-yl]carbonyl}piperidine-1-carboxylate (120 mg) was dissolved in chloroform (3 ml), TFA (1 ml) was added and the mixture was stirred for 1 hr. The reaction mixture was concentrated, and the residue was dissolved in ethyl acetate, washed successively with saturated aqueous sodium hydrogen carbonate and saturated brine, and dried over anhydrous sodium sulfate. The solvent was evaporated under reduced pressure. The residue was dissolved in methanol (2 ml), hydrochloric acid-methanol (2 ml) was added, and the solvent was evaporated under reduced pressure to give the object compound (66 mg).

MS (ESI+, m/e) 575 (M+1)

Reference Example 273 tert-butyl (3S,5R)-3-[({2-tert-butyl-4-[(3-methoxypropyl)amino]pyrimidin-5-yl}carbonyl)(2-methylpropyl)amino]-5-[(4-methylpiperazin-1-yl)carbonyl]piperidine-1-carboxylate

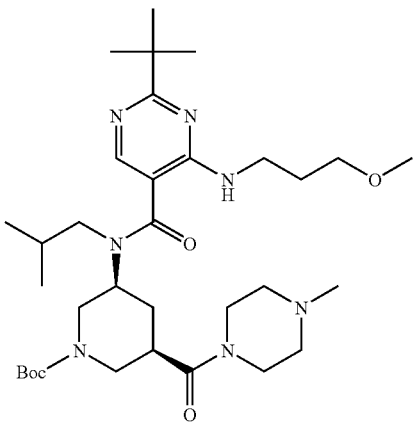

A solution of (3R,5S)-1-(tert-butoxycarbonyl)-5-[({2-tert-butyl-4-[(3-methoxypropyl)amino]pyrimidin-5-yl}carbonyl)(isobutyl)amino]piperidine-3-carboxylic acid (100 mg), WSC.HCl (52 mg), HOBt (36 g), diisopropylethylamine (0.094 ml) and 1-methylpiperazine (20 mg) in DMF (3 ml) was stirred at room temperature for 12 hr. The reaction mixture was poured into saturated aqueous sodium hydrogen carbonate, and the mixture was extracted with ethyl acetate. The extract was washed successively with 10% aqueous citric acid solution and saturated brine, and dried over anhydrous sodium sulfate. The solvent was evaporated under reduced pressure. The residue was subjected to silica gel column chromatography, and the fraction eluted with ethyl acetate-hexane (1:1-1:0) was concentrated under reduced pressure to give the object compound (87 mg).

MS (ESI+, m/e) 632 (M+1)

By a method similar to that of Reference Example 273, the compounds of Reference Examples 274 to 282 below were obtained.

Reference Example 274 tert-butyl (3S,5R)-3-[({2-tert-butyl-4-[(3-methoxypropyl)amino]pyrimidin-5-yl}carbonyl)(2-methylpropyl)amino]-5-[(4-phenylpiperazin-1-yl)carbonyl]piperidine-1-carboxylate

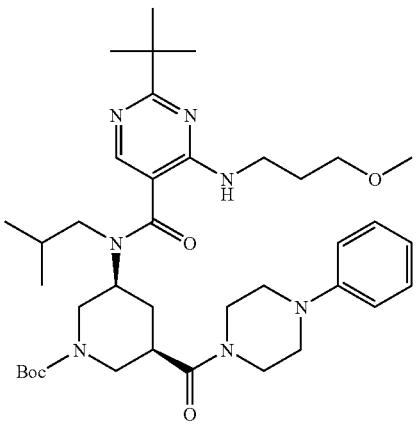

MS (ESI+, m/e) 694 (M+1)

Reference Example 275 tert-butyl (3R,5S)-3-[(4-acetylpiperazin-1-yl)carbonyl]-5-[({2-tert-btyl-4-[(3-methoxypropyl)amino]pyrimidin-5-yl}carbonyl)(2-methylpropyl)amino]piperidine-1-carboxylate

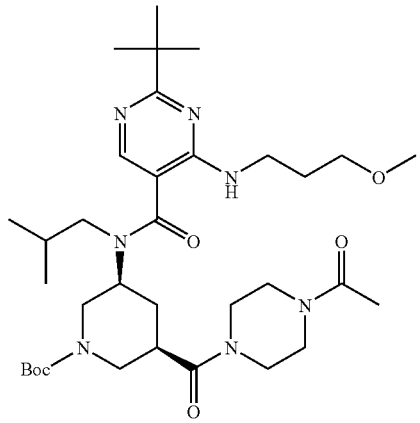

MS (ESI+, m/e) 660 (M+1)

Reference Example 276 tert-butyl (3S,5R)-3-[({2-tert-butyl-4-[(3-methoxypropyl)amino]pyrimidin-5-yl}carbonyl)(2-methylpropyl)amino]-5-{[4-(phenylcarbonyl)piperazin-1-yl]carbonyl}piperidine-1-carboxylate

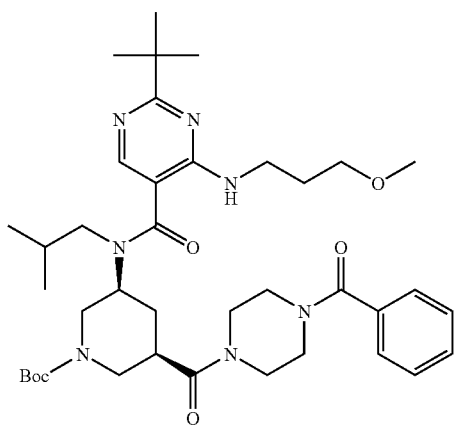

MS (ESI+, m/e) 722 (M+1)

Reference Example 277 tert-butyl (3S,5R)-3-[({2-tert-butyl-4-[(3-methoxypropyl)amino]pyrimidin-5-yl}carbonyl)(2-methylpropyl)amino]-5-{[4-(ethylsulfonyl)piperazin-1-yl]carbonyl}piperidine-1-carboxylate

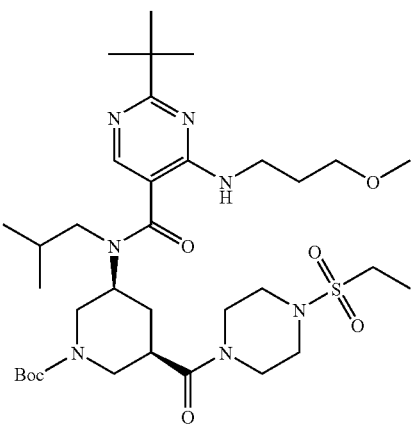

MS (ESI+, m/e) 710 (M+1)

Reference Example 278 tert-butyl (3S,5R)-3-[({2-tert-butyl-4-[(3-methoxypropyl)amino]pyrimidin-5-yl}carbonyl)(2-methylpropyl)amino]-5-[(4-pyridin-2-ylpiperazin-1-yl)carbonyl]piperidine-1-carboxylate

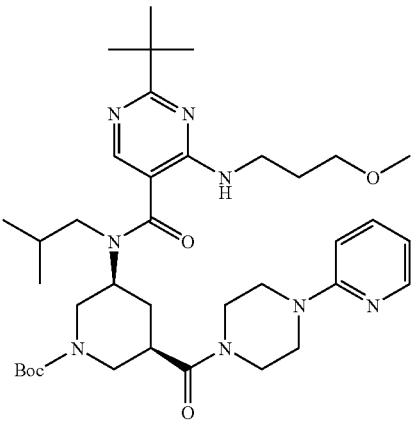

MS (ESI+, m/e) 695 (M+1)

Reference Example 279 tert-butyl (3S,5R)-3-[({2-tert-butyl-4-[(3-methoxypropyl)amino]pyrimidin-5-yl}carbonyl)(2-methylpropyl)amino]-5-[(3-oxo-4-phenylpiperazin-1-yl)carbonyl]piperidine-1-carboxylate

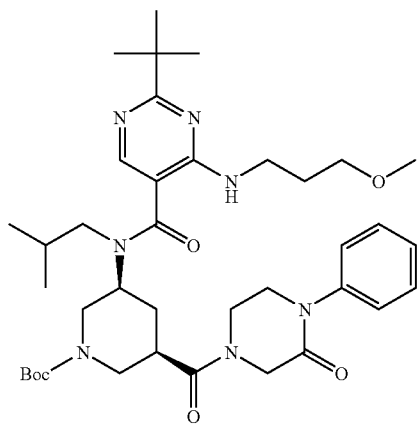

MS (ESI+, m/e) 708 (M+1)

Reference Example 280 tert-butyl (3S,5R)-3-[({2-tert-butyl-4-[(3-methoxypropyl)amino]pyrimidin-5-yl}carbonyl)(2-methylpropyl)amino]-5-{[4-(2-methoxyphenyl)piperazin-1-yl]carbonyl}piperidine-1-carboxylate

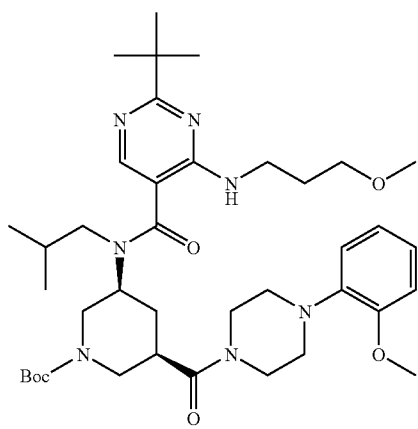

MS (ESI+, m/e) 724 (M+1)

Reference Example 281 tert-butyl (3S,5R)-3-[({2-tert-butyl-4-[(3-methoxypropyl)amino]pyrimidin-5-yl}carbonyl)(2-methylpropyl)amino]-5-{[4-(1,3-thiazol-2-yl)piperazin-1-yl]carbonyl}piperidine-1-carboxylate

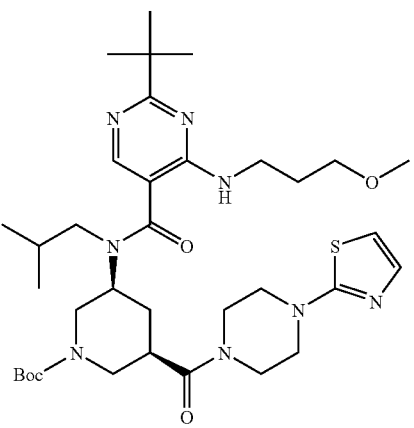

MS (ESI+, m/e) 701 (M+1)

Reference Example 282 tert-butyl (3S,5R)-3-[({2-tert-butyl-4-[(3-methoxypropyl)amino]pyrimidin-5-yl}carbonyl)(2-methylpropyl)amino]-5-{[4-(dimethylsulfamoyl)piperazin-1-yl]carbonyl}piperidie-1-carboxylate

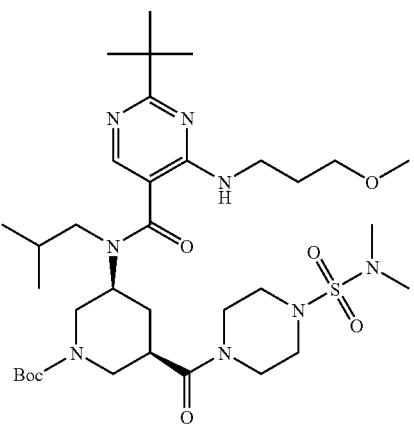

MS (ESI+, m/e) 725 (M+1)

Reference Example 283 tert-butyl 4-amino-3,4-dihydroisoquinoline-2(1H)-carboxylate

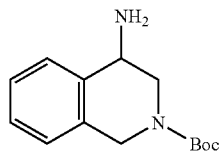

A solution of 2,2,2-trifluoro-N-(1,2,3,4-tetrahydroisoquinolin-4-yl)acetamide (1.34 g) and diisopropylethylamine (1.14 ml) in THF (20 ml) was cooled to 0 to 5° C., di-tert-butyl dicarbonate (1.2 g) was added and the mixture was stirred at room temperature for 1 hr. The solvent was evaporated under reduced pressure, methanol (25 ml) was added to the residue, and 20% aqueous potassium carbonate solution (10 ml) was added. The mixture was stirred at 60° C. for 5 hr. The solvent was evaporated under reduced pressure, saturated brine (20 ml) was added to the residue, and the mixture was extracted with chloroform (30 ml×2). The extract was dried over anhydrous sodium sulfate and the solvent was evaporated under reduced pressure. The residue was subjected to silica gel column chromatography, and the fraction eluted with ethyl acetate was concentrated under reduced pressure to give the object compound (840 mg) as a white powder.

MS (ESI+, m/e) 249 (M+1)

Reference Example 284 tert-butyl 4-[(trifluoroacetyl)amino]octahydroisoquinoline-2(1H)-carboxylate

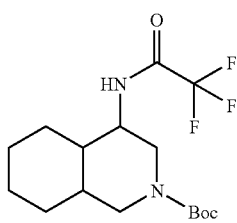

A solution of 2,2,2-trifluoro-N-isoquinolin-4-ylacetamide (1.57 g) and platinum oxide (150 mg) in acetic acid (25 ml) was subjected to hydrogenation (5 atm) at 60° C. for 8 hr. The catalyst was filtered off, and the filtrate was evaporated under reduced pressure. The residue was neutralized with saturated aqueous sodium hydrogen carbonate, and evaporated under reduced pressure. The residue was extracted with THF (30 ml×2), and the extract was dried over anhydrous sodium sulfate. The solvent was evaporated under reduced pressure. THF (25 ml) and diisopropylethylamine (1 g) were added to the residue, and the mixture was cooled to 0 to 5° C. Di-tert-butyl dicarbonate (1.42 g) was added and the mixture was stirred at room temperature for 15 hr. The solvent was evaporated under reduced pressure, and ethyl acetate (50 ml) was added to the residue. Insoluble material was filtered off, and the filtrate was concentrated under reduced pressure. The residue was subjected to silica gel column chromatography, and the fraction eluted with hexane-ethyl acetate (9:1-7:3) was concentrated under reduced pressure to give the object compound (1.8 g) as an oil.

MS (ESI+, m/e) 351 (M+1)

Reference Example 285 tert-butyl 4-aminooctahydroisoquinoline-2(1H)-carboxylate

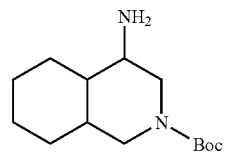

A solution of tert-butyl 4-[(trifluoroacetyl)amino]octahydroisoquinoline-2(1H)-carboxylate (1.75 g) and 20% aqueous potassium carbonate solution (10 ml) in methanol (25 ml) was stirred at 60° C. for 15 hr. The solvent was evaporated under reduced pressure, saturated brine (20 ml) was added to the residue, and the mixture was extracted with chloroform (30 ml×2). The extract was dried over anhydrous sodium sulfate and the solvent was evaporated under reduced pressure. The residue was subjected to silica gel column chromatography, and the fraction eluted with ethyl acetate-methanol (1:0-9:1) was concentrated under reduced pressure to give the object compound (1.12 g) as an oil.

MS (ESI+, m/e) 255 (M+1)

Reference Example 286 tert-butyl 4-[(2-methylpropyl)amino]-3,4-dihydroisoquinoline-2(1H)-carboxylate

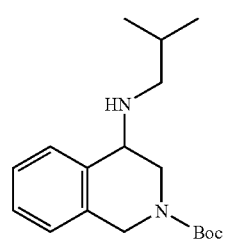

To a solution of tert-butyl 4-amino-3,4-dihydroisoquinoline-2(1H)-carboxylate (840 mg) and 2-methylpropanal (256 mg) in dichloroethane (10 ml) were added acetic acid (203 mg) and sodium triacetoxyborohydride (931 mg). The mixture was stirred at room temperature for 1 hr. The mixture was neutralized with 6% aqueous sodium hydrogen carbonate. After partitioning, the organic layer was dried over anhydrous magnesium sulfate. The solvent was evaporated under reduced pressure. The residue was subjected to silica gel column chromatography, and the fraction eluted with ethyl acetate-hexane (1:1) was concentrated under reduced pressure to give the object compound (940 mg) as an oil.

MS (ESI+, m/e) 305 (M+1)

By a method similar to that of Reference Example 286, the compound of Reference Example 287 below was obtained.

Reference Example 287 tert-butyl 4-[(2-methylpropyl)amino]octahydroiso-quinoline-2(1H)-carboxylate

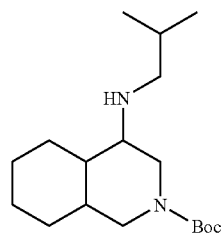

MS (ESI+, m/e) 311 (M+1)

Reference Example 288 tert-butyl 4-{[(2-tert-butyl-4-chloropyrimidin-5-yl)carbonyl](2-methylpropyl)amino}-3,4-dihydroiso-quinoline-2(1H)-carboxylate

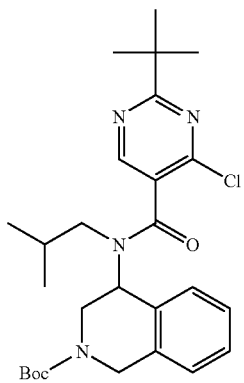

To a solution of 2-tert-butyl-6-oxo-1,6-dihydropyrimidine-5-carboxylic acid (245 mg) and DMF (1 to 2% drops) in THF (10 ml) was added thionyl chloride (520 mg) and the mixture was stirred at 65° C. for 3 hr. The solvent was evaporated under reduced pressure. The residue was dissolved in THF (1 ml). A solution of tert-butyl 4-[(2-methylpropyl)amino]-3,4-dihydroisoquinoline-2(1H)-carboxylate (304 mg) and diisopropylethylamine (0.7 ml) in THF (10 ml) was cooled to 0 to 5° C., and 2-tert-butyl-4-chloropyrimidine-5-carbonyl chloride/THF solution obtained in the above was added. The mixture was stirred at room temperature for 2 hr. The reaction mixture was poured into water, and the mixture was extracted with ethyl acetate. The extract was dried over anhydrous sodium sulfate and the solvent was evaporated under reduced pressure. The residue was subjected to silica gel column chromatography, and the fraction eluted with hexane-ethyl acetate (3:1) was concentrated under reduced pressure to give the object compound (450 mg).

MS (ESI+, m/e) 502 (M+1)

By a method similar to that of Reference Example 288, the compound of Reference Example 289 below was obtained.

Reference Example 289 tert-butyl 4-{[(2-tert-butyl-4-chloropyrimidin-5-yl)carbonyl](2-methylpropyl)amino}octahydroisoquinoline-2(1H)-carboxylate

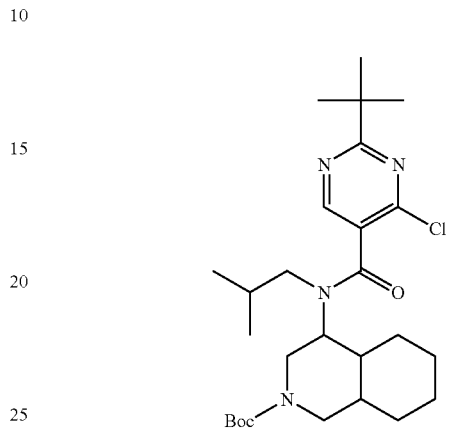

MS (ESI+, m/e) 508 (M+1)

Reference Example 290 tert-butyl 4-[({2-tert-butyl-4-[(1,3-oxazol-2-ylmethyl)amino]pyrimidin-5-yl}carbonyl)(2-methylpropyl)amino]-3,4-dihydroisoquinoline-2(1H)-carboxylate

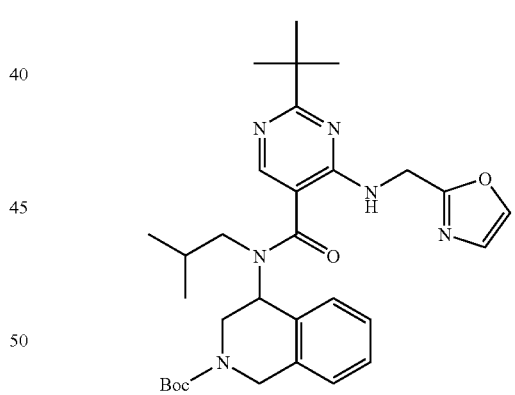

tert-Butyl 4-{[(2-tert-butyl-4-chloropyrimidin-5-yl)carbonyl](2-methylpropyl)amino}-3,4-dihydroisoquinoline-2(1H)-carboxylate (100 mg), 1-(1,3-oxazol-2-yl)methanamine hydrochloride (54 mg) and diisopropylethylamine (0.14 ml) were dissolved in 2-propanol (2 ml), and the mixture was stirred at 80° C. for 6 hr. The reaction mixture was poured into water, and the mixture was extracted with ethyl acetate. The extract was washed with brine, and dried over anhydrous sodium sulfate. The solvent was evaporated under reduced pressure. The residue was subjected to silica gel column chromatography, and the fraction eluted with hexane-ethyl acetate (3:1) was concentrated under reduced pressure to give the object compound (85 mg).

MS (ESI+, m/e) 563 (M+1)

By a method similar to that of Reference Example 290, the compound of Reference Example 291 below was obtained.

Reference Example 291 tert-butyl 4-[({2-tert-butyl-4-[(1,3-oxazol-2-ylmethyl)amino]pyrimidin-5-yl}carbonyl)(2-methylpropyl)amino]octahydroisoquinoline-2(1H)-carboxylate

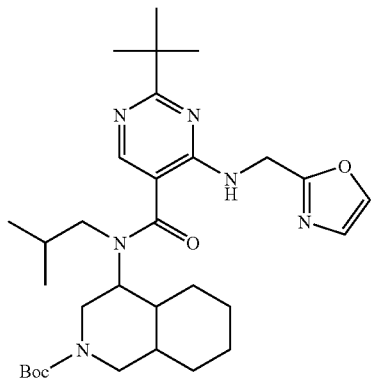

MS (ESI+, m/e) 569 (M+1)

Example 232

2-tert-butyl-4-[(3-methoxypropyl)amino]-N-{(3S,5R)-5-[(4-methylpiperazin-1-yl)carbonyl]piperidin-3-yl}-N-(2-methylpropyl)pyrimidine-5-carboxamide trihydrochloride

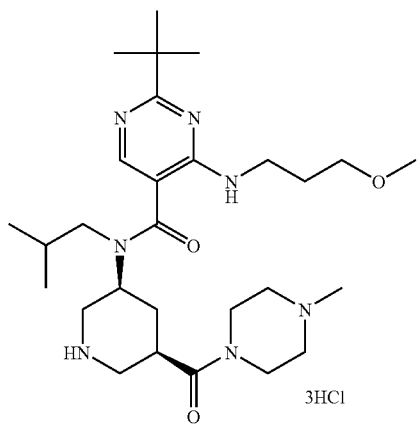

tert-Butyl (3S,5R)-3-[({2-tert-butyl-4-[(3-methoxypropyl)amino]pyrimidin-5-yl}carbonyl)(2-methylpropyl)amino]-5-[(4-methylpiperazin-1-yl)carbonyl]piperidine-1-carboxylate (87 mg) was dissolved in ethyl acetate (1 ml), 4 N hydrogen chloride-ethyl acetate solution (1 ml) was added, and the mixture was stirred at room temperature for 1 hr. The solvent was evaporated under reduced pressure, and the residue was dried under reduced pressure to give the object compound (87 mg).

MS (ESI+, m/e) 532 (M+1)

By a method similar to that of Example 232, the compounds of 233 to 243 below were obtained.

Example 233

2-tert-butyl-4-[(3-methoxypropyl)amino]-N-(2-methylpropyl)-N-{(3S,5R)-5-[(4-phenylpiperazin-1-yl)carbonyl]piperidin-3-yl}pyrimidine-5-carboxamide trihydrochloride

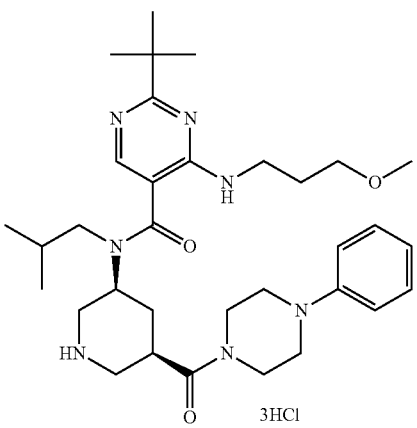

MS (ESI+, m/e) 594 (M+1)

Example 234

N-{(3S,5R)-5-[(4-acetylpiperazin-1-yl)carbonyl]piperidin-3-yl}-2-tert-butyl-4-[(3-methoxypropyl)amino]-N-(2-methylpropyl)pyrimidine-5-carboxamide dihydrochloride

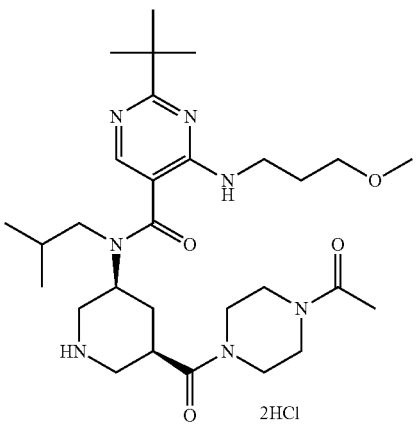

MS (ESI+, m/e) 560 (M+1)

Example 235

2-tert-butyl-4-[(3-methoxypropyl)amino]-N-(2-methylpropyl)-N-[(3S,5R)-5-{[4-(phenylcarbonyl)piperazin-1-yl]carbonyl}piperidin-3-yl]pyrimidine-5-carboxamide dihydrochloride

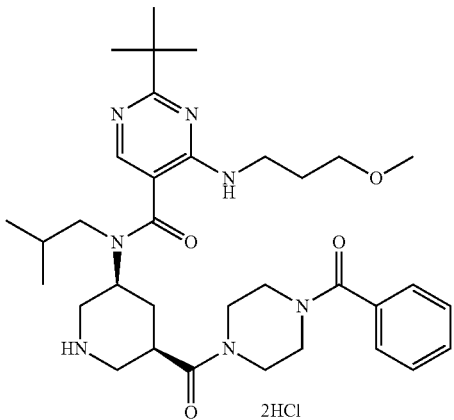

MS (ESI+, m/e) 622 (M+1)

Example 236

2-tert-butyl-N-[(3S,5R)-5-{[4-(ethylsulfonyl)piperazin-1-yl]carbonyl}piperidin-3-yl]-4-[(3-methoxypropyl)amino]-N-(2-methylpropyl)pyrimidine-5-carboxamide dihydrochloride

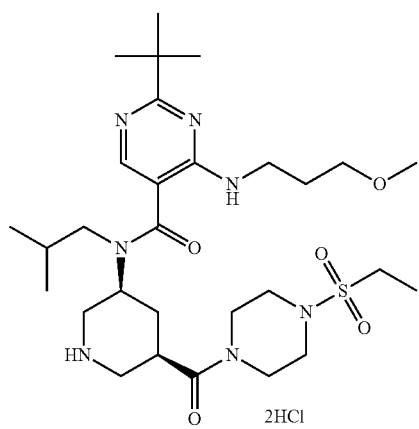

MS (ESI+, m/e) 610 (M+1)

Example 237

2-tert-butyl-4-[(3-methoxypropyl)amino]-N-(2-methylpropyl)-N-{(3S,5R)-5-[(4-pyridin-2-ylpiperazin-1-yl)carbonyl]piperidin-3-yl}pyrimidine-5-carboxamide trihydrochloride

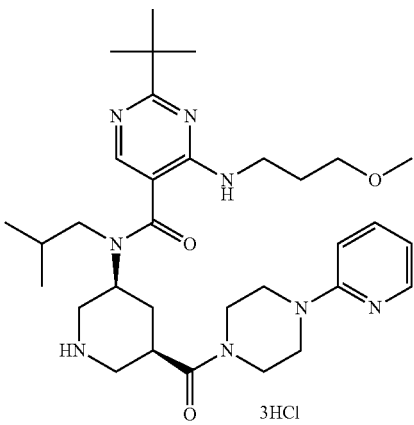

MS (ESI+, m/e) 595 (M+1)

Example 238

2-tert-butyl-4-[(3-methoxypropyl)amino]-N-(2-methylpropyl)-N-{(3S,5R)-5-[(3-oxo-4-phenylpiperazin-1-yl)carbonyl]piperidin-3-yl}pyrimiine-5-carboxamide dihydrochloride

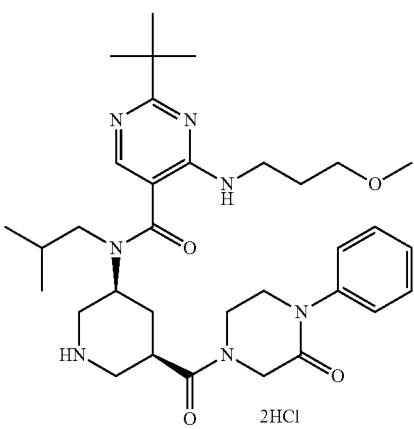

MS (ESI+, m/e) 608 (M+1)

Example 239

2-tert-butyl-N-[(3S,5R)-5-{[4-(2-methoxyphenyl)piperazin-1-yl]carbonyl}piperidin-3-yl]-4-[(3-methoxypropyl)amino]-N-(2-methylpropyl)pyrimidine-5-carboxamide trihydrochloride

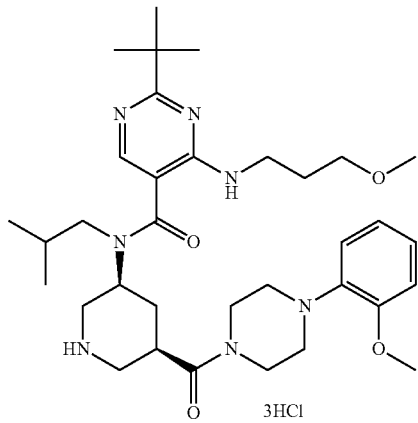

MS (ESI+, m/e) 624 (M+1)

Example 240

2-tert-butyl-4-[(3-methoxypropyl)amino]-N-(2-methylpropyl)-N-[(3S,5R)-5-{[4-(1,3-thiazol-2-yl)piperazin-1-yl]carbonyl}piperidin-3-yl]pyrimidine-5-carboxamide dihydrochloride

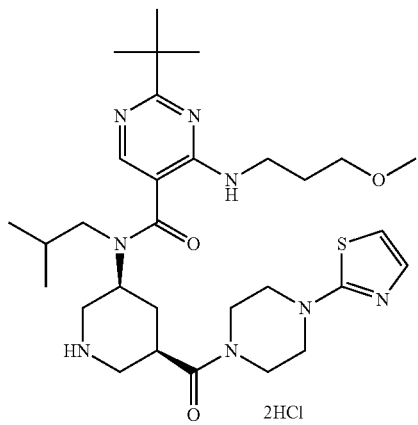

MS (ESI+, m/e) 601 (M+1)

Example 241

2-tert-butyl-N-[(3S,5R)-5-{[4-(dimethylsulfamoyl)piperazin-1-yl]carbonyl}piperidin-3-yl]-4-[(3-methoxypropyl)amino]-N-(2-methylpropyl)pyrimidine-5-carboxamide dihydrochloride

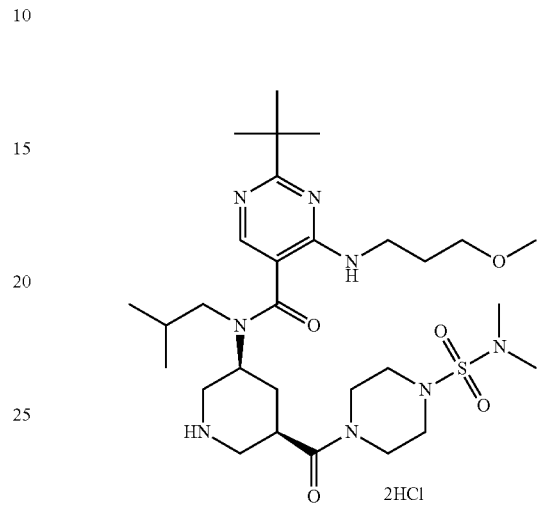

MS (ESI+, m/e) 625 (M+1)

Example 242

2-tert-butyl-N-(2-methylpropyl)-4-[(1,3-oxazol-2-ylmethyl)amino]-N-(1,2,3,4-tetrahydroisoquinolin-4-yl)pyrimidine-5-carboxamide dihydrochloride

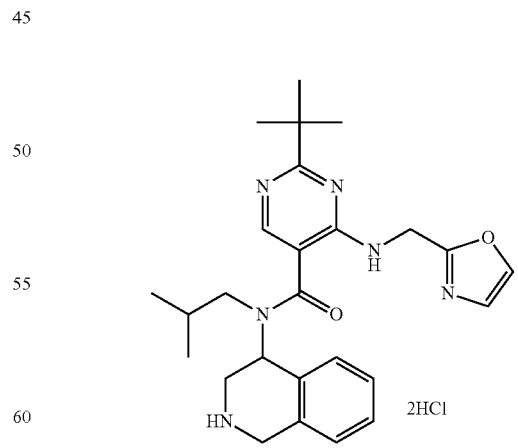

MS (ESI+, m/e) 463 (M+1)

Example 243

2-tert-butyl-N-(decahydroisoquinolin-4-yl)-N-(2-methylpropyl)-4-[(1,3-oxazol-2-ylmethyl)amino]pyrimidine-5-carboxamide dihydrochloride

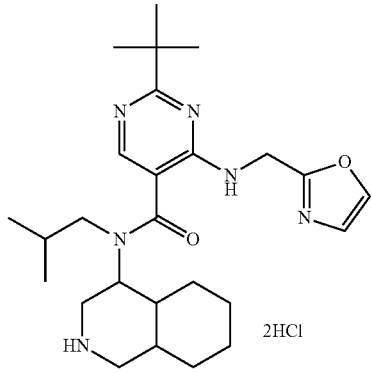

MS (ESI+, m/e) 469 (M+1)

By a method similar to that of Reference Example 46, the compound of Reference Example 292 below was obtained.

Reference Example 292 tert-butyl (3S,5R)-3-[{[2-chloro-6-(trifluoromethyl)pyridin-3-yl]carbonyl}(2-methylpropyl)amino]-5-(morpholin-4-ylcarbonyl)piperidine-1-carboxylate

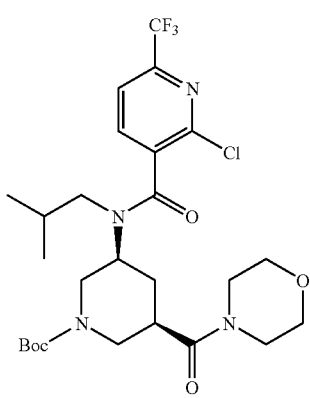

MS (ESI+, m/e) 577 (M+1)

Example 244

2-[(3-methoxypropyl)amino]-N-(2-methylpropyl)-N-[(3S,5R)-5-(morpholin-4-ylcarbonyl)piperidin-3-yl]-6-(trifluoromethyl)pyridine-3-carboxamide

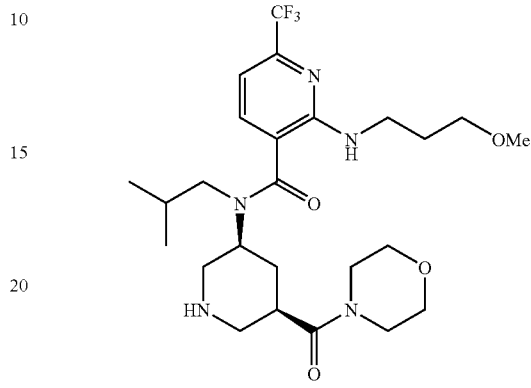

To a solution of tert-butyl (3S,5R)-3-[{[2-chloro-6-(trifluoromethyl)pyridin-3-yl]carbonyl}(2-methylpropyl)amino]-5-(morpholin-4-ylcarbonyl)piperidine-1-carboxylate (40 mg) and diisopropylethylamine (37 µl) in 2-propanol (3 ml) was added 3-methoxypropylamine (23 µl) and the mixture was stirred at 80° C. for 15 hr. The reaction mixture was concentrated under reduced pressure, saturated aqueous sodium hydrogen carbonate was added, and the mixture was extracted with ethyl acetate. The extract was dried over anhydrous magnesium sulfate, and concentrated under reduced pressure. The obtained residue was dissolved in methanol (2 ml), 4 M hydrogen chloride-ethyl acetate (2 ml) was added, and the mixture was stirred at room temperature for 15 hr. The reaction mixture was concentrated under reduced pressure, and the residue was subjected to reversed-phase preparative HPLC. Aqueous sodium hydrogen carbonate was added to the object fraction, and the mixture was extracted with ethyl acetate. The extract was washed with saturated brine, and dried over anhydrous sodium sulfate. The solvent was evaporated under reduced pressure to give the object compound (8.8 mg).

MS (ESI+, m/e) 530 (M+1)

Reference Example 293 ethyl 4-[(3-methoxypropyl)amino]-6-(1-methylethyl)pyridine-3-carboxylate

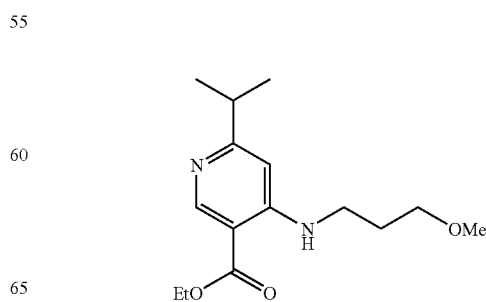

Ethyl 6-(1-methylethyl)-4-oxo-1,4-dihydropyridine-3-carboxylate (209 mg) was suspended in phosphorus oxychloride (2 ml), and the mixture was stirred at 120° C. for 3 hr. Phosphorus oxychloride was evaporated under reduced pressure, and the mixture was cooled to 0° C. The mixture was neutralized with saturated aqueous sodium hydrogen carbonate and water, and the mixture was extracted with ethyl acetate. The extract was washed with saturated brine, dried over anhydrous sodium sulfate and concentrated under reduced pressure. The obtained residue was dissolved in 2-propanol (5 ml), 3-methoxypropylamine (307 µl) and triethylamine (517 µl) were added, and the mixture was stirred with heating to reflux for 15 hr. The reaction mixture was concentrated under reduced pressure, saturated aqueous sodium hydrogen carbonate was added, and the mixture was extracted with ethyl acetate. The extract was washed with saturated brine, dried over anhydrous sodium sulfate and concentrated under reduced pressure. The obtained residue was subjected to silica gel chromatography, and the fraction eluted with acetic acid was concentrated under reduced pressure to give the object compound (263 mg).

MS (ESI+, m/e) 281 (M+1)

Reference Example 294

4-[(3-methoxypropyl)amino]-6-(1-methylethyl)pyridine-3-carboxylic acid

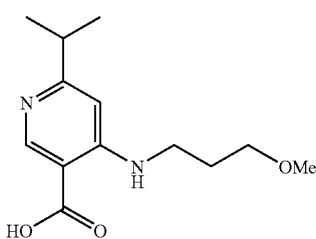

To a solution of ethyl 4-[(3-methoxypropyl)amino]-6-(1-methylethyl)pyridine-3-carboxylate (263 mg) in ethanol (5 ml) was added 2 M aqueous sodium hydroxide solution (0.94 ml) and the mixture was stirred at room temperature for 15 hr. The reaction mixture was adjusted to pH 7 with 1 M hydrochloric acid, and the solvent was evaporated under reduced pressure. The residue was suspended in ethanol, and the precipitated inorganic salt was filtered off. The filtrate was concentrated under reduced pressure to give the object compound (300 mg) as a mixture of inorganic salts.

MS (ESI+, m/e) 253 (M+1)

Reference Example 295 tert-butyl (3S,5R)-3-[({4-[(3-methoxypropyl)amino]-6-(1-methylethyl)pyridin-3-yl}carbonyl)(2-methylpropyl)amino]-5-(morpholin-4-ylcarbonyl)piperidine-1-carboxylate

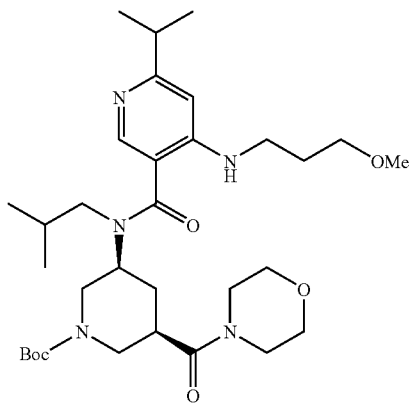

4-[(3-Methoxypropyl)amino]-6-(1-methylethyl)pyridine-3-carboxylic acid (160 mg), tert-butyl (3S,5R)-3-[(2-methylpropyl)amino]-5-(morpholin-4-ylcarbonyl)piperidine-1-carboxylate (185 mg) and diisopropylethylamine (431 µl) were dissolved in methylene chloride (10 ml), chloro-N,N,N',N'-tetramethylformamidinium hexafluorophosphate (168 mg) was added and the mixture was stirred at room temperature for 15 hr. Aqueous sodium hydrogen carbonate was added to the reaction mixture, and the mixture was extracted with ethyl acetate. The extract was washed with saturated brine, and dried over anhydrous sodium sulfate. The solvent was evaporated under reduced pressure. The residue was subjected to basic silica gel column chromatography, and the fraction eluted with ethyl acetate-hexane (7:3) was concentrated under reduced pressure to give the object compound (268 mg).

MS (ESI+, m/e) 604 (M+1)

Example 245

4-[(3-methoxypropyl)amino]-6-(1-methylethyl)-N-(2-methylpropyl)-N-[(3S,5R)-5-(morpholin-4-ylcarbonyl)piperidin-3-yl]pyridine-3-carboxamide dihydrochloride

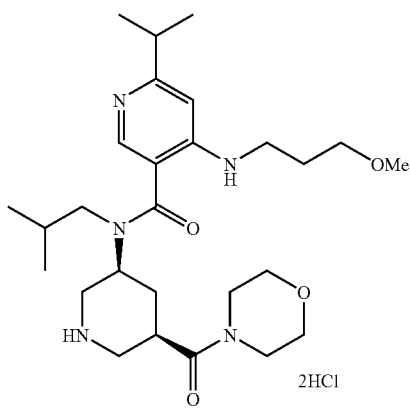

tert-Butyl (3S,5R)-3-[({4-[(3-methoxypropyl)amino]-6-(1-methylethyl)pyridin-3-yl}carbonyl)(2-methylpropyl)amino]-5-(morpholin-4-ylcarbonyl)piperidine-1-carboxylate (268 mg) was dissolved in 4 M hydrogen chloride-ethyl acetate (5 ml), and the mixture was stirred at room temperature for 15 hr. The reaction mixture was concentrated, the residue was purified by reversed-phase preparative HPLC, and the object fraction was concentrated under reduced pressure. Aqueous sodium hydrogen carbonate was added to the residue, and the mixture was extracted with ethyl acetate. The extract was washed with saturated brine, dried over anhydrous magnesium sulfate and concentrated under reduced pressure. 4 M Hydrogen chloride-ethyl acetate (1 ml) was added to the residue, and the mixture was stirred for 5 min and concentrated under reduced pressure to give the object compound (163 mg).

MS (ESI+, m/e) 504 (M+1)

By a method similar to that of Reference Example 258, the compounds of Reference Examples 296 to 303 below were obtained.

Reference Example 296 tert-butyl (3S,5R)-3-[({2-tert-butyl-4-[(3-methoxypropyl)amino]pyrimidin-5-yl}carbonyl)(2-methylpropyl)amino]-5-(pyrrolidin-1-ylcarbonyl)piperidine-1-carboxylate

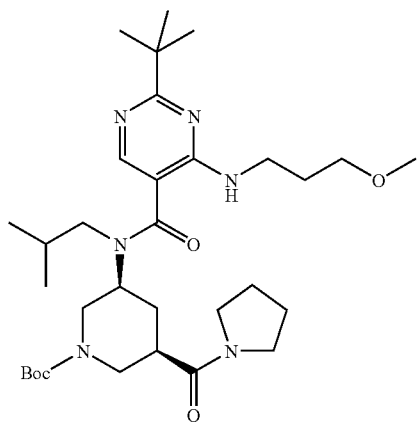

MS (ESI+, m/e) 503 (M+1)

Reference Example 297 tert-butyl (3R,5S)-3-(azetidin-1-ylcarbonyl)-5-[({2-tert-butyl-4-[(3-methoxypropyl)amino]pyrimidin-5-yl}carbonyl)(2-methylpropyl)amino]piperidine-1-carboxylate

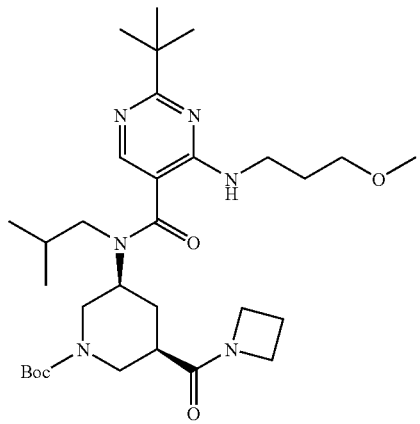

MS (ESI+, m/e) 589 (M+1)

Reference Example 298 tert-butyl (3S,5R)-3-[({2-tert-butyl-4-[(3-methoxypropyl)amino]pyrimidin-5-yl}carbonyl)(2-methylpropyl)amino]-5-[(2-phenylmorpholin-4-yl)carbonyl]piperidine-1-carboxylate

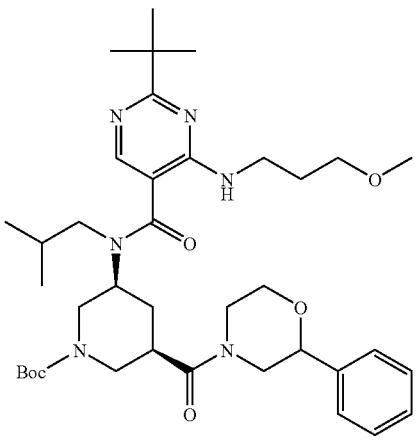

MS (ESI+, m/e) 695 (M+1)

Reference Example 299 tert-butyl (3R,5S)-3-[(2-benzylmorpholin-4-yl)carbonyl]-5-[({2-tert-butyl-4-[(3-methoxypropyl)amino]pyrimidin-5-yl}carbonyl)(2-methylpropyl)amino]piperidine-1-carboxylate

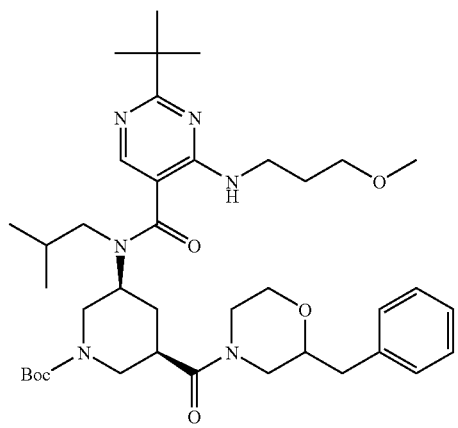

MS (ESI+, m/e) 709 (M+1)

Reference Example 300 tert-butyl (3S,5R)-3-[({2-tert-butyl-4-[(3-methoxypropyl)amino]pyrimidin-5-yl}carbonyl)(2-methylpropyl)amino]-5-[(3-phenylmorpholin-4-yl)carbonyl]piperidine-1-carboxylate

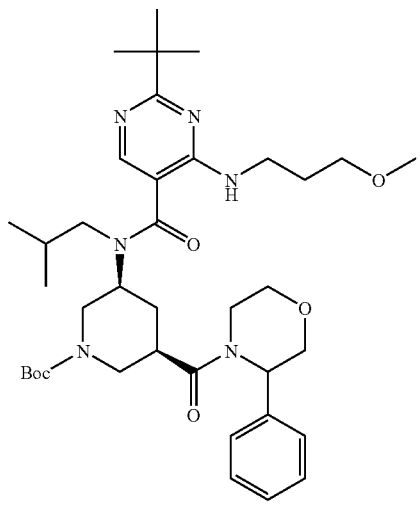

MS (ESI+, m/e) 695 (M+1)

Reference Example 301 tert-butyl (3R,5S)-3-[(3-benzylmorpholin-4-yl)carbonyl]-5-[({2-tert-butyl-4-[(3-methoxypropyl)amino]pyrimidin-5-yl}carbonyl)(2-methylpropyl)amino]piperidine-1-carboxylate

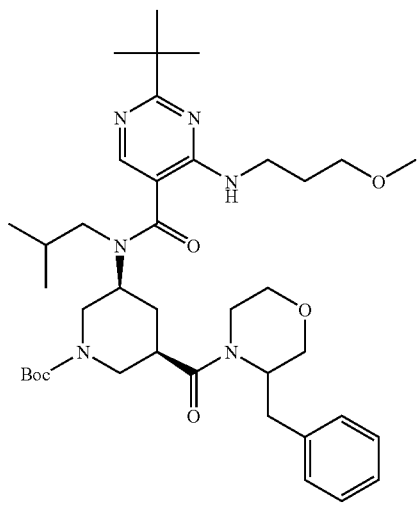

MS (ESI+, m/e) 709 (M+1)

Reference Example 302 tert-butyl (3S,5R)-3-[({2-tert-butyl-4-[(3-methoxypropyl)amino]pyrimidin-5-yl}carbonyl)(2-methylpropyl)amino]-5-[(3-pyridin-3-ylmorpholin-4-yl)carbonyl]piperidine-1-carboxylate

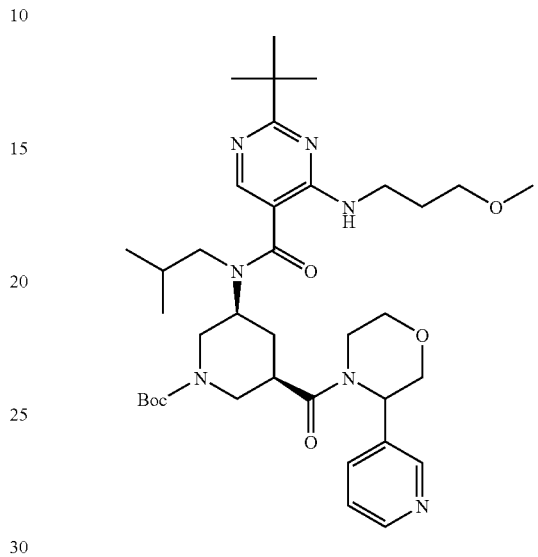

MS (ESI+, m/e) 696 (M+1)

Reference Example 303 tert-butyl (3S,5R)-3-[({2-tert-butyl-4-[(3-methoxypropyl)amino]pyrimidin-5-yl}carbonyl)(2-methylpropyl)amino]-5-[(2-pyridin-3-ylmorpholin-4-yl)carbonyl]piperidine-1-carboxylate

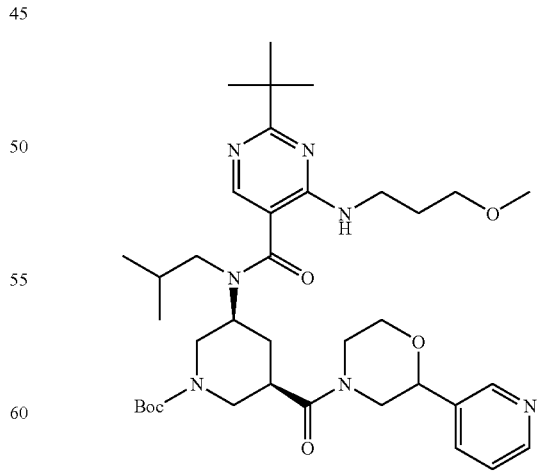

MS (ESI+, m/e) 696 (M+1)

By a method similar to that of Example 218, the compounds of Examples 246 to 251 below were obtained.

Example 246

2-tert-butyl-4-[(3-methoxypropyl)amino]-N-(2-methylpropyl)-N-[(3S,5R)-5-(pyrrolidin-1-ylcarbonyl)piperidin-3-yl]pyrimidine-5-carboxamide dihydrochloride

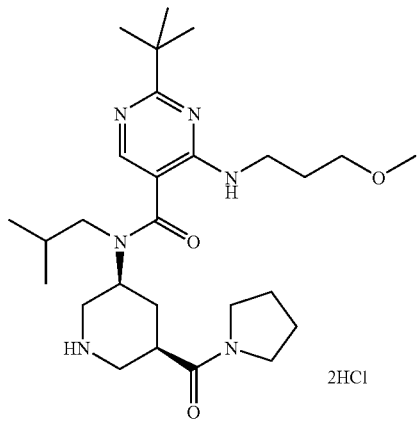

MS (ESI+, m/e) 503 (M+1)

Example 247

2-tert-butyl-4-[(3-methoxypropyl)amino]-N-(2-methylpropyl)-N-{(3S,5R)-5-[(2-phenylmorpholin-4-yl)carbonyl]piperidin-3-yl}pyrimidine-5-carboxamide dihydrochloride

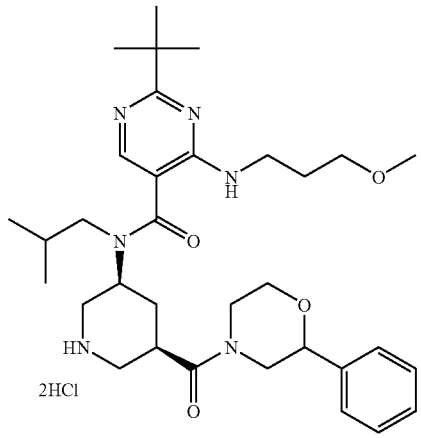

MS (ESI+, m/e) 595 (M+1)

Example 248

N-{(3S,5R)-5-[(2-benzylmorpholin-4-yl)carbonyl]piperidin-3-yl}-2-tert-butyl-4-[(3-methoxypropyl)amino]-N-(2-methylpropyl)pyrimidine-5-carboxamide dihydrochloride

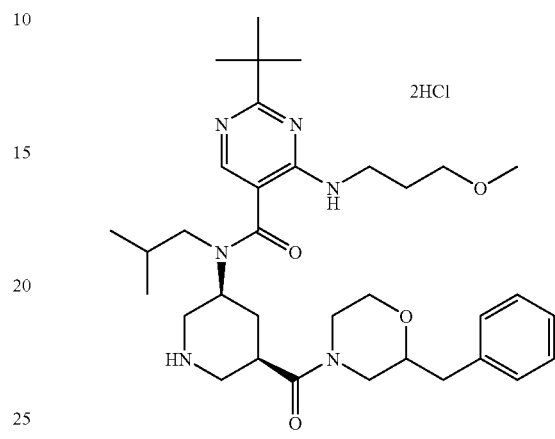

MS (ESI+, m/e) 609 (M+1)

Example 249

2-tert-butyl-4-[(3-methoxypropyl)amino]-N-(2-methylpropyl)-N-{(3S,5R)-5-[(3-phenylmorpholin-4-yl)carbonyl]piperidin-3-yl}pyrimidine-5-carboxamide dihydrochloride

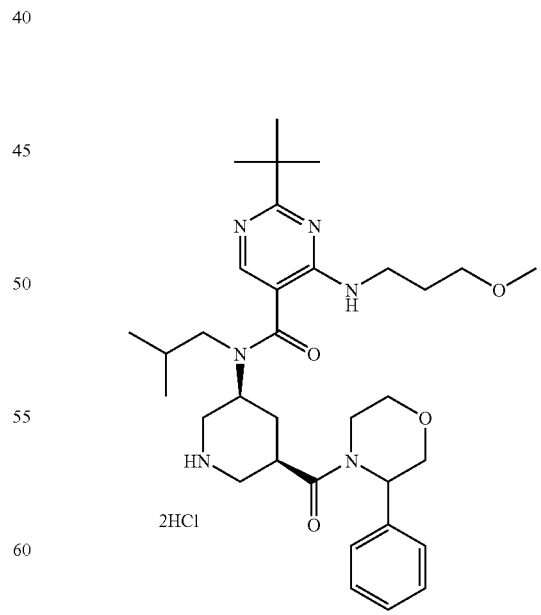

MS (ESI+, m/e) 595 (M+1)

Example 250

N-{(3S,5R)-5-[(3-benzylmorpholin-4-yl)carbonyl]piperidin-3-yl}-2-tert-butyl-4-[(3-methoxypropyl)amino]-N-(2-methylpropyl)pyrimidine-5-carboxamide dihydrochloride

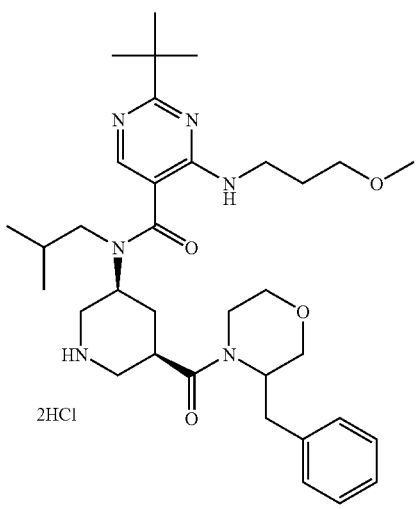

MS (ESI+, m/e) 609 (M+1)

Example 251

2-tert-butyl-4-[(3-methoxypropyl)amino]-N-(2-methylpropyl)-N-{(3S,5R)-5-[(3-pyridin-3-ylmorpholin-4-yl)carbonyl]piperidin-3-yl}pyrimidine-5-carboxamide trihydrochloride

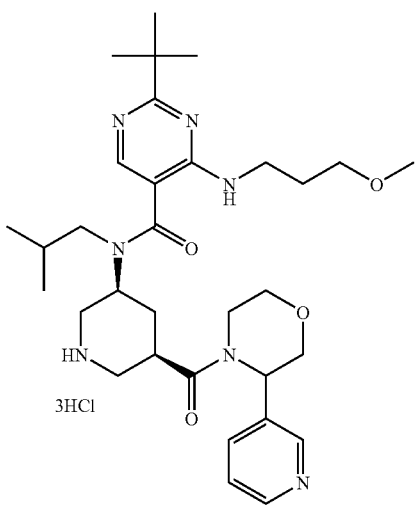

MS (ESI+, m/e) 596 (M+1)

Example 252

2-tert-butyl-4-[(3-methoxypropyl)amino]-N-(2-methylpropyl)-N-{(3S,5R)-5-[(2-pyridin-3-ylmorpholin-4-yl)carbonyl]piperidin-3-yl}pyrimidine-5-carboxamide trihydrochloride

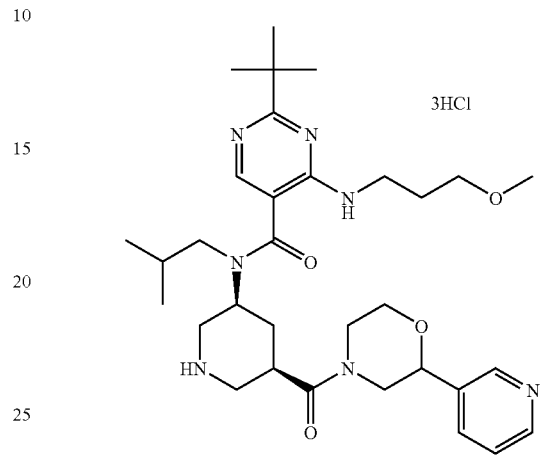

MS (ESI+, m/e) 596 (M+1)

Example 253

N-[(3S,5R)-5-(azetidin-1-ylcarbonyl)piperidin-3-yl]-2-tert-butyl-4-[(3-methoxypropyl)amino]-N-(2-methylpropyl)pyrimidine-5-carboxamide

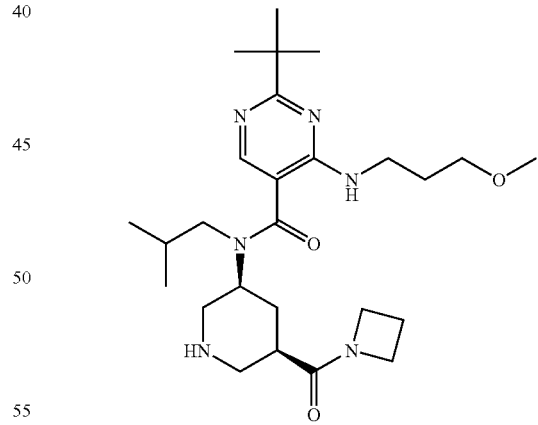

tert-Butyl (3R,5S)-3-(azetidin-1-ylcarbonyl)-5-[({2-tert-butyl-4-[(3-methoxypropyl)amino]pyrimidin-5-yl}carbonyl)(2-methylpropyl)amino]piperidine-1-carboxylate (94 mg) was dissolved in 4 M hydrogen chloride-ethyl acetate (3 ml), and the mixture was stirred at room temperature for 3 hr. The reaction mixture was concentrated under reduced pressure, and the residue was subjected to reversed-phase preparative HPLC. Aqueous sodium hydrogen carbonate was added to the object fraction, and the mixture was extracted with ethyl acetate. The extract was washed with saturated brine, and dried over anhydrous sodium sulfate. The solvent was evaporated under reduced pressure to give the object compound (33 mg).

MS (ESI+, m/e) 489 (M+1)

By a method similar to that of Reference Example 1, the compound of Reference Example 304 below was obtained.

Reference Example 304 ethyl 2-tert-butyl-4-methyl-6-oxo-1,6-dihydropyrimidine-5-carboxylate

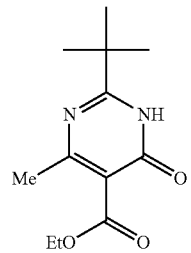

MS (ESI+, m/e) 239 (M+1)

By a method similar to that of Reference Example 293, the compound of Reference Example 305 below was obtained.

Reference Example 305 ethyl 2-tert-butyl-4-[(3-methoxypropyl)amino]-6-methylpyrimidine-5-carboxylate

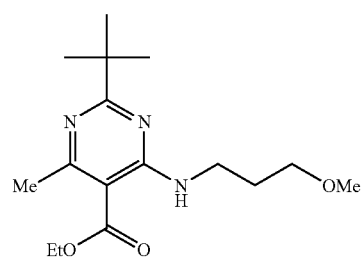

MS (ESI+, m/e) 310 (M+1)

By a method similar to that of Reference Example 294, the compound of Reference Example 306 below was obtained.

Reference Example 306

2-tert-butyl-4-[(3-methoxypropyl)amino]-6-methylpyrimidine-5-carboxylic acid

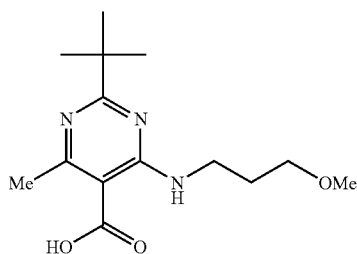

MS (ESI+, m/e) 282 (M+1)

By a method similar to that of Reference Example 295, the compound of Reference Example 307 below was obtained.

Reference Example 307 tert-butyl (3S,5R)-3-[({2-tert-butyl-4-[(3-methoxypropyl)amino]-6-methylpyrimidin-5-yl}carbonyl)(2-methylpropyl)amino]-5-(morpholin-4-ylcarbonyl)piperidine-1-carboxylate

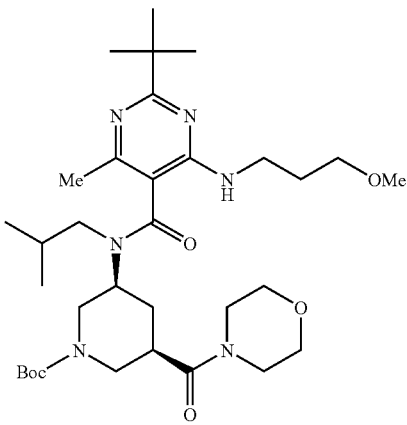

MS (ESI+, m/e) 633 (M+1)

By a method similar to that of Example 245, the compound of Example 254 below was obtained.

Example 254

2-tert-butyl-4-[(3-methoxypropyl)amino]-6-methyl-N-(2-methylpropyl)-N-[(3S,5R)-5-(morpholin-4-ylcarbonyl)piperidin-3-yl]pyrimidine-5-carboxamide dihydrochloride

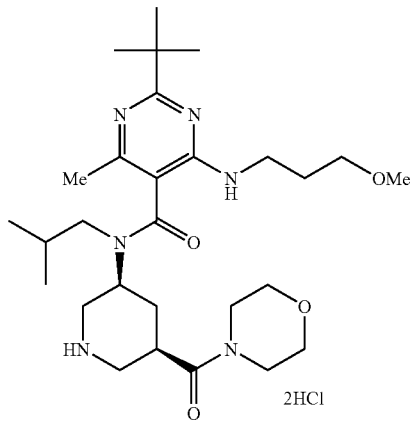

MS (ESI+, m/e) 533 (M+1)

Preparation Example 1

|     |                        |         |
| --- | ---------------------- | ------- |
| (1) | Compound of Example 1  | 10.0 g  |
| (2) | Lactose                | 70.0 g  |
| (3) | Cornstarch             | 50.0 g  |
| (4) | Soluble starch         | 7.0 g   |
| (5) | Magnesium stearate     | 3.0 g   |

10.0 g of the compound of Example 1 and 3.0 g of magnesium stearate are granulated with 70 ml of an aqueous solution of soluble starch (7.0 g as soluble starch), and the granules are dried and mixed with 70.0 g of lactose and 50.0 g of corn starch (all of lactose, corn starch, soluble starch and magnesium stearate are products in conformity to the 14$^{th}$ revision of the Japanese Pharmacopoeia). The mixture is compressed to give tablets.

Experimental Example 1

Human renin was obtained by expressing preprorenin (1-406) in an animal cell, treating the prorenin (24-406) contained in the culture supernatant with trypsin, and taking the active type (67-406).
(1) Construction of Renin-Expressing Vector
A plasmid DNA to express human renin in HEK293 cells was prepared as follows. PCR was carried out using human renal cDNA (Clontech Laboratories, Inc., Marathon Ready cDNA) as the template and using two synthetic DNAs (5'-AAGCTTATGGATGGATGGAGA-3'; SEQ ID NO:1, and 5'-GGATCCTCAGCGGGCCAAGGC-3'; SEQ ID NO:2), and the obtained fragments were cloned using a TOPO TA Cloning Kit (Invitrogen Corp.). The obtained fragments were subcloned into pcDNA3.1(+) that had been cleaved by HindIII and BamHI, thus to obtain a plasmid DNA for human preprorenin expression (pcDNA3.1(+)/hREN).
(2) Construction of Angiotensinogen-Expressing Vector
A plasmid DNA to express human angiotensinogen in HEK293 cells was prepared as follows. PCR was carried out using human liver cDNA (Clontech Laboratories, Inc., Marathon Ready cDNA) as the template and using two synthetic DNAs (5'-AAGCTTATGCGGAAGCGAGCAC-CCCAGTCT-3'; SEQ ID NO:3, and 5'-GGATCCTCACT-TGTCATCGTCGTCCTTGTAGTCTGCTGT-GCTCAGCGGGTTGGCCACGC-3'; SEQ ID NO:4), and the obtained fragments were cloned using a TOPO TA Cloning Kit (Invitrogen Corp.). The obtained fragments were subcloned into pcDNA3.1(+) that had been cleaved by HindIII and BamHI, thereby to give a plasmid DNA for expression of human angiotensinogen having a FLAG tag on the C-terminal (pcDNA3.1(+)/hAngiotensinogen-FLAG). Then, PCR was carried out using the pcDNA3.1(+)/hAngiotensinogen-FLAG as the template and using two synthetic DNAs (5'-CCTTAAGCTTCCACCATGCGGAAGCGAG-CACCCCAGTCT-3'; SEQ ID NO:5, and 5'-TTGGATCCTCATGCTGTGCTCAGCGGGT-TGGCCACGCGG-3'; SEQ ID NO:6), and the obtained fragments were cloned using a TOPO TA Cloning Kit (Invitrogen Corp.). The obtained fragments were subcloned into pcDNA3.1(+) that had been cleaved by HindIII and BamHI, thus to obtain a plasmid DNA for human angiotensinogen expression (pcDNA3.1(+)/hAngiotensinogen).
(3) Expression of Preprorenin and Purification of Prorenin (24-406)
Expression of human preprorenin was conducted using FreeStyle 293 Expression System (Invitrogen Corp.). According to the manual accompanying the FreeStyle 293 Expression System, the plasmid DNA for human preprorenin expression (pcDNA3.1(+)/hREN) constructed in the above-mentioned (1) was used to conduct transient expression by FreeStyle 293-F cells. After transfection of the plasmid DNA, the cells were subjected to shaking culture under the conditions of 37° C., 8% $CO_2$ and 125 rpm for 3 days. A 600-ml aliquot of the culture medium was centrifuged at 2,000 rpm for 10 min to recover the culture supernatant containing prorenin (24-406). The culture supernatant was concentrated by ultrafiltration using a PM10 membrane (Millipore, Inc.) to a volume of about 50 ml, and then was dialyzed against 20 mM Tris-hydrochloric acid (pH 8.0). The dialysate was fed to a 6-ml RESOURCE Q column (GE Healthcare) equilibrated with 20 mM Tris-hydrochloric acid (pH 8.0) at a flow rate of 3 ml/min to adsorb the prorenin (24-406). After washing the column with the buffer solution used in the equilibration, elution was carried out by means of a linear concentration gradient of sodium chloride from 0 M to 0.4 M. The fraction containing prorenin (24-406) was collected and concentrated using Vivaspin 20 (molecular weight cut off 10,000; Vivascience, Inc.) to a volume of about 2 ml.
The concentrated liquid was subjected to gel filtration chromatography using HiLoad 16/60 Superdex 200 pg (GE Healthcare) equilibrated with 20 mM Tris-hydrochloric acid (pH 8.0) containing 0.15 M sodium chloride, at a flow rate of 1.4 ml/min, thus to obtain 3.6 mg of purified prorenin (24-406).
(4) Purification of Active Type Renin (67-406)
To 3.6 mg of prorenin (24-406) dissolved in 5.2 ml of 0.1 M Tris-hydrochloric acid (pH 8.0), 12 μg of trypsin (Roche Diagnostics Corp.) was added, and the mixture was allowed to react at 28° C. for 55 min to carry out activation of renin. After the reaction, 0.4 ml of immobilized trypsin inhibitor (Pierce Biotechnology, Inc.) was added to remove the trypsin used in the activation by adsorption. The reaction liquid containing the active type renin was concentrated using Vivaspin 20 (molecular weight cut off 10,000, Vivascience, Inc.), and was diluted with 20 mM Tris-hydrochloric acid (pH 8.0). The diluted liquid was fed to a TSKgel DEAE-5PW column (7.5 mm I.D.×75 mm, Tosoh Corp.) equilibrated with 20 mM Tris-hydrochloric acid (pH 8.0) at a flow rate of 1 ml/min to adsorb the active type renin (67-406). The column was washed with the buffer solution used for the equilibration, and then elution was carried out by means of a sodium chloride linear concentration gradient from 0 M to 0.3 M, thus to obtain 1.5 mg of a purified product of active type renin (67-406).

(5) Purification of Angiotensinogen

Expression of human angiotensinogen was conducted using FreeStyle 293 Expression System (Invitrogen Corp.). According to the manual accompanying the FreeStyle 293 Expression System, the plasmid DNA for human angiotensinogen expression (pcDNA3.1(+)/hAngiotensinogen) constructed in the above-mentioned (2) was used to conduct transient expression by FreeStyle 293-F cells. After transfection of the plasmid DNA, the cells were subjected to shaking culture under the conditions of 37° C., 8% $CO_2$ and 125 rpm for 3 days. A 600-ml aliquot of the culture medium was centrifuged at 2,000 rpm for 10 min to recover the culture supernatant containing angiotensinogen. To the culture supernatant was added ammonium sulfate (30% saturated concentration), and the mixture was thoroughly stirred and centrifuged at 8,000 rpm for 20 min. The obtained supernatant was added to TOYO Pearl butyl 650M (2×5 cm, Tosoh Corporation) equilibrated with 50 mM tris-hydrochloric acid (pH 8.0) containing 30% saturated ammonium sulfate, at a flow rate of 25 ml/min to allow adsorption. After washing with equilibration buffer, angiotensinogen was eluted by linear concentration gradient from the buffer used for equilibration to 20 mM tris-hydrochloric acid (pH 8.0). The eluate containing angiotensinogen was applied to repeated concentration and dilution using Vivaspin 20 (molecular weight cut off 10,000, Vivascience, Inc.), and the buffer was changed to 20 mM tris-hydrochloric acid (pH 8.0). The eluate was fed to a 6-ml RESOURCE Q column (Amersham Biosciences, Inc.) equilibrated with 20 mM Tris-hydrochloric acid (pH 8.0) containing 50 mM sodium chloride at a flow rate of 6 ml/min to adsorb the angiotensinogen. After washing the column with the buffer solution used in the equilibration, elution was carried out by means of a linear concentration gradient of sodium chloride from 50 mM to 400 mM. The fractions containing angiotensinogen were collected and concentrated using Vivaspin 20 (molecular weight cut off 10,000, Vivascience, Inc.) to a volume of about 2 ml. The concentrated liquid was subjected to gel filtration chromatography using HiLoad 26/60 Superdex 200 pg (GE Healthcare) equilibrated with 20 mM Tris-hydrochloric acid (pH 8.0) containing 0.15 M sodium chloride, at a flow rate of 2.0 ml/min, thus to obtain 7.0 mg of purified angiotensinogen.

(6) Measurement of Renin Inhibition Value—A

As a substrate for renin activity measurement, a substrate peptide (FITC-Acp-Asp-Arg-Val-Tyr-Ile-His-Pro-Phe-His-Leu-Val-Ile-His-Gln-Arg-$NH_2$; SEQ ID NO:8) wherein the N-terminal of a peptide prepared in reference to a partial sequence (Asp-Arg-Val-Tyr-Ile-His-Pro-Phe-His-Leu-Val-Ile-His-Asn-Glu-$NH_2$; SEQ ID NO:7) of human angiotensinogen was bound with epsilon aminocaproic acid (Acp) as a linker and labeled with a fluorescence reagent Fluorescein isothiocyanate (FITC). 2 µl each of the test compound (containing 100% DMSO) was added to each well of a 384-well black plate (Nalge Nunc International Co., Ltd.). Renin was diluted with a buffer solution for reaction (20 mM citric acid-sodium citrate (pH 6.0)) to a concentration of 4.7 nM, and 30 µl each of the dilution was added to each well. The dilution was left to stand at 37° C. for 10 min, and then 8 µl of each of a 25 µM solution of substrate peptide was added to each well to initiate the reaction. The reaction mixture was left to stand at 37° C. for 30 min, and then 40 µl each of a reaction terminating solution [200 mM Tris-hydrochloric acid (pH 8.0), 0.04% Triton-X 100, 0.4% Coating 3 reagent (Caliper Life. Sciences Corp.) and 1 µM CGP-29287 (Bachem Holding AG)] was added to each well to terminate the reaction.

The substrate peptide and the product peptide were separated by a microchip type capillary electrophoresis system 250HTS (Caliper Life Sciences Co., Ltd.), and the rate of reaction [(peak height of product)/(peak height of product+peak height of substrate)×100 (%)] was calculated from the ratio of the respective peak height of the peptides obtained by fluorimetric detection (excitation wavelength 457 nm, measurement wavelength 530 nm), and was used as an index of the renin activity.

While the reaction rate of the well where 100% DMSO only was added was taken as 0% inhibition rate, and the reaction rate of the well where 10 µM of CGP-29287 was added was taken as 100% inhibition rate, the renin inhibitory activity of the wells where the test compound (containing 100% DMSO) was added was calculated.

(7) Measurement of Renin Inhibition Value—B

As a substrate for renin activity measurement, the angiotensinogen mentioned in (5) above was used. 1 µeach of the test compound (containing 100% DMSO) was added to each well of a 384-well plate (ABgene). Renin was diluted with a buffer solution for reaction (20 mM sodium phosphate (pH 7.4)) to a concentration of 57 pM, and 14 µl each of the dilution was added to each well. The dilution was left to stand at 37° C. for 10 min, and then 5 µl of each of a 6 µM solution of substrate angiotensinogen was added to each well to initiate the reaction. The reaction mixture was left to stand at 37° C. for 30 min, and then 20 µl each of a reaction terminating solution [20 mM Tris-hydrochloric acid (pH 7.4), 150 mM sodium chloride, 0.1% BSA, 0.05% Tween 20 and 1 µM CGP-29287] was added to each well to terminate the reaction, thus an enzyme reaction solution was obtained. The amount of angiotensin I produced by an enzyme reaction was quantified by Enzyme immunoassay (EIA) described below.

Anti-angiotensin I antibody (Peninsula Laboratories Inc.) diluted 5,000-fold with PBS was added to each well of a 384 well black plate (Nalge Nunc International Co., Ltd.) by 25 µl, and left standing overnight at 4° C. to immobilize the antibody in the plate. The antibody solution was removed, PBS solution (100 µl) containing 1% BSA was added to each well, and the mixture was left standing at room temperature for 2 hr for blocking. The blocking solution was removed, and each well was washed 5 times with 100 µl of 0.05% Tween20-PBS. An angiotensin I standard solution (Wako Pure Chemical Industries, Ltd.) prepared to 0.156-10 nM with an enzyme reaction solution or buffer [20 mM tris-hydrochloric acid (pH 7.4), 150 mM sodium chloride, 0.1% BSA, 0.05% Tween20] was dispensed to each well by 10 µl. Then, a biotinated angiotensin I solution (AnaSpec, 15 µl) prepared to 1.6 nM with a buffer [20 mM tris-hydrochloric acid (pH 7.4), 150 mM sodium chloride, 0.01% BSA, 0.05% Tween20] was added to each well, mixed with a plate mixer and left standing at room temperature for 1 hr. The solutions were removed from each well, and each well was washed 5 times with 100 µl of 0.05% Tween20-PBS. Horseradish peroxydase Streptavidin (PIERCE Biotecnology Inc., 25 µl) diluted to 100 ng/ml with a buffer [20 mM tris-hydrochloric acid (pH 7.4), 150 mM sodium chloride, 0.1% BSA, 0.05% Tween 20] was added to each well and the mixture was left standing at room temperature for 30 min. The solutions were removed from each well, and each well was washed 5 times with 100 µl of 0.05% Tween20-PBS. SuperSignal ELISA femto Maximum Sensitivity Substrate (PIERCE Biotecnology Inc.) was added by 25 µl and luminescence intensity was measured by EnVision (Perkin Elmer Inc.). An analytical curve was drawn from the luminescence intensity of a well containing an angiotensin I standard solution, and the amount of angiotensin I produced by an enzyme reaction was calculated and used as an index of renin activity.

While the reaction rate of the well where 100% DMSO only was added was taken as 0% inhibition rate, and the reaction rate of the well where angiotensin I was not contained was taken as 100% inhibition rate, the renin inhibitory activity of the wells where the test compound (containing 100% DMSO) was added was calculated.

(8) Results

The results of measurement by the method of the above-mentioned (7) are shown in Table 1.

TABLE 1

| human renin inhibitory activity | |
|---|---|
| Example No. | inhibitory activity (%) at 1 µM |
| 21 | 58 |
| 58 | 82 |
| 59 | 86 |
| 63 | 54 |
| 93 | 97 |

TABLE 1-continued

| human renin inhibitory activity | |
|---|---|
| Example No. | inhibitory activity (%) at 1 µM |
| 94 | 97 |
| 95 | 97 |
| 96 | 97 |
| 97 | 97 |
| 98 | 97 |
| 99 | 97 |
| 109 | 98 |
| 132 | 98 |
| 207 | 98 |

From the results of Table 1, it is clear that compound (1) of the present invention has a superior renin inhibitory activity.

Industrial Applicability

Compound (I) has superior renin inhibitory activity and thus is useful as an agent for the prophylaxis or treatment of hypertension, various organ damages attributable to hypertension, and the like.

This application is based on patent application No. 268100/2007 filed in Japan, the contents of which are hereby incorporated by reference.

Sequence Listing Free Text

[SEQ ID NO: 1] primer
[SEQ ID NO: 2] primer
[SEQ ID NO: 3] primer
[SEQ ID NO: 4] primer
[SEQ ID NO: 5] primer
[SEQ ID NO: 6] primer
[SEQ ID NO: 7] partial sequence of human angiotensinogen
[SEQ ID NO: 8] substrate peptide of renin

The invention claimed is:

1. A compound represented by the formula

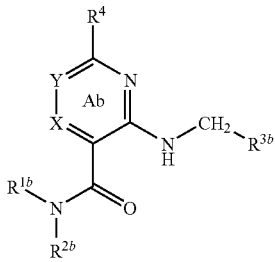

wherein $R^{1b}$ and $R^{2b}$ are each a hydrocarbon group optionally having substituent(s) or a heterocyclic group optionally having substituent(s), or
$R^{1b}$ and $R^{2b}$ optionally form, together with the nitrogen atom bonded thereto, a nitrogen-containing heterocycle optionally having substituent(s),
$R^{3b}$ is
(1) a 5- or 6-membered aromatic or nonaromatic heterocyclic group containing, as a ring-constituting atom besides carbon atom, 1 to 4 heteroatoms selected from the group consisting of an oxygen atom, a sulfur atom and a nitrogen atom, and optionally having 1 to 3 $C_{1-6}$ alkyl,
(2) $C_{6-14}$ aryl,
(3) $C_{3-10}$ cycloalkyl,
(4) $C_{1-6}$ alkyl optionally having 1 to 3 substituents selected from the group consisting of
  (a) hydroxy,
  (b) $C_{1-6}$ alkoxy,
  (c) $C_{1-6}$ alkylthio,
  (d) $C_{1-6}$ alkylsulfinyl, and
  (e) $C_{1-6}$ alkylsulfonyl, or
(5) $C_{1-6}$ alkoxy-carbonyl,
$R^4$ is
(1) a hydrocarbon group optionally having substituent(s),
(2) a heterocyclic group optionally having substituent(s), excluding a cyclic amino optionally having substituent(s),
(3) mercapto optionally having a substituent, or
(4) acyl,
X and Y are each C or N, and
ring Ab is a nitrogen-containing 6-membered ring optionally having substituent(s) in addition to $R^4$, or a salt thereof, excluding N-(2-chloro-3-pyridinyl)-2-(ethylamino)-N,6-dimethyl-3-pyridinecarboxamide.

2. The compound according to claim 1, wherein $R^{1b}$ and $R^{2b}$ are each (1) a hydrocarbon group optionally having substituent(s) or (2) pyrrolidinyl, imidazolidinyl, pyrazolidinyl, piperidinyl, piperazinyl, morpholinyl or thiomorpholinyl, each of which may have substituent(s).

3. The compound according to claim 1, wherein $R^{1b}$ and $R^{2b}$ form, together with the nitrogen atom bonded thereto, piperidine optionally having substituent(s) or piperazine optionally having substituent(s).

4. The compound according to claim 1, wherein $R^{3b}$ is
(1) a 5- or 6-membered aromatic or nonaromatic heterocyclic group containing, as a ring-constituting atom besides carbon atom, 1 to 4 heteroatoms selected from the group consisting of an oxygen atom, a sulfur atom and a nitrogen atom, and optionally having 1 to 3 $C_{1-6}$ alkyl,
(2) $C_{6-14}$ aryl,
(3) $C_{3-10}$ cycloalkyl,
(4) $C_{1-6}$ alkyl optionally having 1 to 3 $C_{1-6}$ alkoxy, or
(5) $C_{1-6}$ alkoxy-carbonyl.

5. The compound according to claim 1, wherein $R^4$ is a hydrocarbon group optionally having substituent(s) or a heterocyclic group optionally having substituent(s), excluding a cyclic amino optionally having substituent(s).

6. The compound according to claim 1, wherein $R^4$ is a hydrocarbon group optionally having substituent(s).

7. The compound according to claim 1, wherein ring Ab is a ring represented by the formula

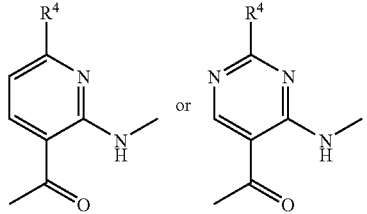

wherein $R^4$ is as defined in claim 1.

8. The compound according to claim 1, wherein $R^{1b}$ and $R^{2b}$ are each (1) a hydrocarbon group optionally having substituent(s) or (2) pyrrolidinyl, imidazolidinyl, pyrazolidinyl, piperidinyl, piperazinyl, morpholinyl or thiomorpholinyl, each of which may have substituent(s),
$R^{3b}$ is
(1) a 5- or 6-membered aromatic or nonaromatic heterocyclic group containing, as a ring-constituting atom besides carbon atom, 1 to 4 heteroatoms selected from the group consisting of an oxygen atom, a sulfur atom and a nitrogen atom, and optionally having 1 to 3 $C_{1-6}$ alkyl,
(2) $C_{6-14}$ aryl,
(3) $C_{3-10}$ cycloalkyl,
(4) $C_{1-6}$ alkyl optionally having 1 to 3 $C_{1-6}$ alkoxy, or
(5) $C_{1-6}$ alkoxy-carbonyl,
$R^4$ is a hydrocarbon group optionally having substituent(s), and
ring Ab is a ring represented by the formula

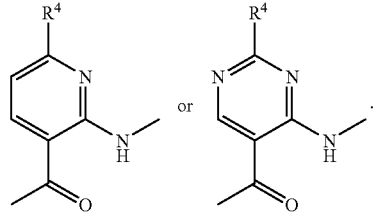

9. 2-tert-Butyl-N-[(3S,5R)-5-carbamoylpiperidin-3-yl]-4-[(furan-2-ylmethyl)amino]-N-(2-methylpropyl)pyrimidine-5-carboxamide or a salt thereof.

10. 2-tert-Butyl-4-[(3-methoxypropyl)amino]-N-(2-methylpropyl)-N-[(3S,5R)-5-(morpholin-4-ylcarbonyl)piperidin-3-yl]pyrimidine-5-carboxamide or a salt thereof.

11. 2-tert-Butyl-N-(2-methylpropyl)-N-[(3S,5R)-5-(morpholin-4-ylcarbonyl)piperidin-3-yl]-4-[(1,3-oxazol-2-ylmethyl)amino]pyrimidine-5-carboxamide or a salt thereof.

12. A pharmaceutical composition comprising the compound according to claim 1, and a pharmaceutically acceptable carrier.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial sequence
<220> FEATURE:
<223> OTHER INFORMATION: Synthetic construct; primer

<400> SEQUENCE: 1
aagcttatgg atggatggag a                                              21

<210> SEQ ID NO 2
<211> LENGTH: 21
<212> TYPE: DNA
<213> ORGANISM: Artificial sequence
<220> FEATURE:
<223> OTHER INFORMATION: Synthetic construct; primer

<400> SEQUENCE: 2
ggatcctcag cgggccaagg c                                              21

<210> SEQ ID NO 3
<211> LENGTH: 30
<212> TYPE: DNA
<213> ORGANISM: Artificial sequence
<220> FEATURE:
<223> OTHER INFORMATION: Synthetic construct; primer
```

```
<400> SEQUENCE: 3
aagcttatgc ggaagcgagc accccagtct                                    30

<210> SEQ ID NO 4
<211> LENGTH: 59
<212> TYPE: DNA
<213> ORGANISM: Artificial sequence
<220> FEATURE:
<223> OTHER INFORMATION: Synthetic construct; primer

<400> SEQUENCE: 4
ggatcctcac ttgtcatcgt cgtccttgta gtctgctgtg ctcagcgggt tggccacgc    59

<210> SEQ ID NO 5
<211> LENGTH: 39
<212> TYPE: DNA
<213> ORGANISM: Artificial sequence
<220> FEATURE:
<223> OTHER INFORMATION: Synthetic construct; primer

<400> SEQUENCE: 5
ccttaagctt ccaccatgcg gaagcgagca ccccagtct                          39

<210> SEQ ID NO 6
<211> LENGTH: 39
<212> TYPE: DNA
<213> ORGANISM: Artificial sequence
<220> FEATURE:
<223> OTHER INFORMATION: Synthetic construct; primer

<400> SEQUENCE: 6
ttggatcctc atgctgtgct cagcgggttg gccacgcgg                          39

<210> SEQ ID NO 7
<211> LENGTH: 15
<212> TYPE: PRT
<213> ORGANISM: Artificial sequence
<220> FEATURE:
<223> OTHER INFORMATION: Synthetic construct; partial sequence of human
      angiotensinogen
<220> FEATURE:
<221> NAME/KEY: MOD_RES
<222> LOCATION: (15)..(15)
<223> OTHER INFORMATION: AMIDATION

<400> SEQUENCE: 7

Asp Arg Val Tyr Ile His Pro Phe His Leu Val Ile His Asn Glu
1               5                   10                  15

<210> SEQ ID NO 8
<211> LENGTH: 16
<212> TYPE: PRT
<213> ORGANISM: Artificial sequence
<220> FEATURE:
<223> OTHER INFORMATION: Synthetic construct; substrate peptide for
      renin
<220> FEATURE:
<221> NAME/KEY: MISC_FEATURE
<222> LOCATION: (1)..(1)
<223> OTHER INFORMATION: FITC-labeled 6-aminocaproic acid
<220> FEATURE:
<221> NAME/KEY: MOD_RES
<222> LOCATION: (16)..(16)
<223> OTHER INFORMATION: AMIDATION

<400> SEQUENCE: 8

Xaa Asp Arg Val Tyr Ile His Pro Phe His Leu Val Ile His Gln Arg
1               5                   10                  15
```